United States Patent
Thorn et al.

(10) Patent No.: US 9,486,507 B2
(45) Date of Patent: Nov. 8, 2016

(54) PRO-COAGULANT COMPOUNDS AND METHODS OF USE THEREOF

(75) Inventors: Karina Thorn, Newmarket, NH (US); Garabet G. Toby, North Reading, MA (US); Adam R. Mezo, Needham, MA (US)

(73) Assignee: Biogen MA Inc., Cambridge, MA (US)

( * ) Notice: Subject to any disclaimer, the term of this patent is extended or adjusted under 35 U.S.C. 154(b) by 0 days.

(21) Appl. No.: 14/125,040

(22) PCT Filed: Jun. 9, 2012

(86) PCT No.: PCT/US2012/041777
§ 371 (c)(1),
(2), (4) Date: May 13, 2014

(87) PCT Pub. No.: WO2012/170969
PCT Pub. Date: Dec. 13, 2012

(65) Prior Publication Data
US 2014/0303084 A1   Oct. 9, 2014

Related U.S. Application Data

(60) Provisional application No. 61/495,818, filed on Jun. 10, 2011, provisional application No. 61/496,540, filed on Jun. 13, 2011, provisional application No. 61/496,543, filed on Jun. 13, 2011, provisional application No. 61/496,541, filed on Jun. 13, 2011, provisional application No. 61/496,542, filed on Jun. 13, 2011, provisional application No. 61/600,237, filed on Feb. 17, 2012, provisional application No. 61/605,540, filed on Mar. 1, 2012.

(51) Int. Cl.
| | | |
|---|---|---|
| *C12N 9/64* | (2006.01) | |
| *A61K 47/48* | (2006.01) | |
| *A61K 38/48* | (2006.01) | |
| *A61K 38/36* | (2006.01) | |
| *C07K 14/745* | (2006.01) | |
| *C07K 7/08* | (2006.01) | |
| *C07K 14/00* | (2006.01) | |
| *A61K 38/00* | (2006.01) | |

(52) U.S. Cl.
CPC ......... *A61K 38/36* (2013.01); *A61K 47/48246* (2013.01); *C07K 7/08* (2013.01); *C07K 14/001* (2013.01); *C07K 14/745* (2013.01); *A61K 38/00* (2013.01)

(58) Field of Classification Search
CPC ............... A61K 38/00; A61K 38/36; A61K 47/48246; C07K 14/001; C07K 14/745; C07K 7/08
See application file for complete search history.

(56) References Cited

U.S. PATENT DOCUMENTS

| | | |
|---|---|---|
| 4,179,337 A | 12/1979 | Davis et al. |
| 4,444,878 A | 4/1984 | Paulus |
| 4,694,778 A | 9/1987 | Learn et al. |
| 4,745,055 A | 5/1988 | Schenk et al. |
| 4,757,006 A | 7/1988 | Toole, Jr. et al. |
| 4,868,112 A | 9/1989 | Toole, Jr. |
| 4,965,199 A | 10/1990 | Capon et al. |
| 4,994,371 A | 2/1991 | Davie et al. |
| 5,004,803 A | 4/1991 | Kaufman et al. |
| 5,112,950 A | 5/1992 | Meulien et al. |
| 5,122,614 A | 6/1992 | Zalipsky |
| 5,171,844 A | 12/1992 | van Ooyen et al. |
| 5,364,771 A | 11/1994 | Lollar et al. |
| 5,439,686 A | 8/1995 | Desai et al. |
| 5,498,421 A | 3/1996 | Grinstaff et al. |
| 5,539,063 A | 7/1996 | Hakimi et al. |
| 5,543,502 A | 8/1996 | Nordfang et al. |
| 5,585,089 A | 12/1996 | Queen et al. |
| 5,589,369 A | 12/1996 | Seidman et al. |
| 5,591,669 A | 1/1997 | Krimpenfort et al. |

(Continued)

FOREIGN PATENT DOCUMENTS

| | | |
|---|---|---|
| EP | 0068763 A2 | 1/1983 |
| EP | 0097994 A2 | 1/1984 |

(Continued)

OTHER PUBLICATIONS

UniProt Protein Database, Protein Accession C6S498, Fish Virus Induced TRIM protein, accessed on Oct. 26, 2015.*
Lieke M van der Aa, A large new subset of TRIM genes highly diversified by duplication and positive selection in teleost fish, BMC Biology 2009, 7:7.*
Donald A. Yergeau, bloodthirsty, an RBCC/TRIM gene required for erythropoiesis in zebrafish, Developmental Biology 283 (2005) 97-112.*

(Continued)

*Primary Examiner* — James H Alstrum Acevedo
*Assistant Examiner* — Erinne Dabkowski
(74) *Attorney, Agent, or Firm* — Ji Eun Kim

(57) ABSTRACT

The present invention provides pro-coagulant compounds (e.g., pro-coagulant peptides or peptide derivatives) and methods of using and making those compounds. The present disclosure further provides conjugates between a pro-coagulant compound of the present disclosure (e.g., pro-coagulant peptide or peptide derivative) and a polypeptide selected from FIX, FVIIa, FVIII, and platelet targeting moieties (e.g., PDG-13), wherein the compound is linked to the polypeptide optionally via a linker. The compounds and conjugates of the present disclosure are useful for the treatment of coagulation disorders, such as hemophilia A and hemophilia B. The present disclosure further provides methods of using and making the conjugates.

21 Claims, 26 Drawing Sheets

(56) References Cited

U.S. PATENT DOCUMENTS

| | | |
|---|---|---|
| 5,595,886 A | 1/1997 | Chapman et al. |
| 5,610,278 A | 3/1997 | Nordfang et al. |
| 5,643,575 A | 7/1997 | Martinez et al. |
| 5,648,260 A | 7/1997 | Winter et al. |
| 5,658,570 A | 8/1997 | Newman et al. |
| 5,693,761 A | 12/1997 | Queen et al. |
| 5,693,762 A | 12/1997 | Queen et al. |
| 5,693,780 A | 12/1997 | Newman et al. |
| 5,712,122 A | 1/1998 | Boime et al. |
| 5,739,277 A | 4/1998 | Presta et al. |
| 5,756,096 A | 5/1998 | Newman et al. |
| 5,789,203 A | 8/1998 | Chapman et al. |
| 5,811,524 A | 9/1998 | Brams et al. |
| 5,834,250 A | 11/1998 | Wells et al. |
| 5,846,951 A | 12/1998 | Gregoriadis |
| 5,859,204 A | 1/1999 | Lollar |
| 5,869,046 A | 2/1999 | Presta et al. |
| 5,892,019 A | 4/1999 | Schlom et al. |
| 5,939,598 A | 8/1999 | Kucherlapati et al. |
| 5,972,885 A | 10/1999 | Spira et al. |
| 6,005,079 A | 12/1999 | Casterman et al. |
| 6,030,613 A | 2/2000 | Blumberg et al. |
| 6,048,720 A | 4/2000 | Dalborg et al. |
| 6,060,447 A | 5/2000 | Chapman et al. |
| 6,075,181 A | 6/2000 | Kucherlapati et al. |
| 6,086,875 A | 7/2000 | Blumberg et al. |
| 6,096,871 A | 8/2000 | Presta et al. |
| 6,121,022 A | 9/2000 | Presta et al. |
| 6,194,551 B1 | 2/2001 | Idusogie et al. |
| 6,228,620 B1 | 5/2001 | Chapman et al. |
| 6,242,195 B1 | 6/2001 | Idusogie et al. |
| 6,251,632 B1 | 6/2001 | Lillicrap et al. |
| 6,258,579 B1 | 7/2001 | Mercurio et al. |
| 6,277,375 B1 | 8/2001 | Ward |
| 6,316,226 B1 | 11/2001 | Van Ooyen et al. |
| 6,346,513 B1 | 2/2002 | Van Ooyen et al. |
| 6,376,463 B1 | 4/2002 | Lollar |
| 6,458,563 B1 | 10/2002 | Lollar |
| 6,485,726 B1 | 11/2002 | Blumberg et al. |
| 6,528,624 B1 | 3/2003 | Idusogie et al. |
| 6,538,124 B1 | 3/2003 | Idusogie et al. |
| 6,624,289 B1 | 9/2003 | Bajaj |
| 6,686,179 B2 | 2/2004 | Fleer et al. |
| 6,696,245 B2 | 2/2004 | Winter et al. |
| 6,703,491 B1 | 3/2004 | Homburger et al. |
| 6,737,056 B1 | 5/2004 | Presta |
| 6,765,087 B1 | 7/2004 | Casterman et al. |
| 6,821,505 B2 | 11/2004 | Ward |
| 6,998,253 B1 | 2/2006 | Presta et al. |
| 7,033,590 B1 | 4/2006 | Scheiflinger et al. |
| 7,041,635 B2 | 5/2006 | Kim et al. |
| 7,083,784 B2 | 8/2006 | Dall'Acqua et al. |
| 7,084,109 B2 | 8/2006 | Dennis et al. |
| 7,109,170 B2 | 9/2006 | Bajaj et al. |
| 7,317,091 B2 | 1/2008 | Lazar et al. |
| 7,348,004 B2 | 3/2008 | Peters et al. |
| 7,375,078 B2 | 5/2008 | Feng |
| 7,381,408 B2 | 6/2008 | Mezo et al. |
| 7,404,956 B2 | 7/2008 | Peters et al. |
| 7,589,178 B2 | 9/2009 | Le Bonniec et al. |
| 7,592,010 B2 | 9/2009 | Rosen et al. |
| 7,754,681 B2 | 7/2010 | Feng |
| 2001/0014456 A1 | 8/2001 | Yu et al. |
| 2003/0069395 A1 | 4/2003 | Sato et al. |
| 2003/0138769 A1 | 7/2003 | Birkett |
| 2003/0165996 A1 | 9/2003 | Halkier et al. |
| 2003/0170850 A1 | 9/2003 | Cardone et al. |
| 2003/0211094 A1 | 11/2003 | Nelsestuen |
| 2003/0235536 A1 | 12/2003 | Blumberg et al. |
| 2004/0043446 A1 | 3/2004 | DeFrees et al. |
| 2004/0063911 A1 | 4/2004 | DeFrees et al. |
| 2004/0132028 A1 | 7/2004 | Stumpp et al. |
| 2004/0132640 A1 | 7/2004 | DeFrees et al. |
| 2004/0137557 A1 | 7/2004 | DeFrees et al. |
| 2004/0142856 A1 | 7/2004 | DeFrees et al. |
| 2005/0100990 A1 | 5/2005 | Saenko et al. |
| 2005/0267017 A1 | 12/2005 | Gilon et al. |
| 2006/0115876 A1 | 6/2006 | Pan et al. |
| 2007/0191597 A1 | 8/2007 | Jain et al. |
| 2007/0218067 A1 | 9/2007 | Buttner et al |
| 2007/0231329 A1 | 10/2007 | Lazar et al. |
| 2007/0237765 A1 | 10/2007 | Lazar et al. |
| 2007/0237766 A1 | 10/2007 | Lazar et al. |
| 2007/0237767 A1 | 10/2007 | Lazar et al. |
| 2007/0243188 A1 | 10/2007 | Lazar et al. |
| 2007/0248603 A1 | 10/2007 | Lazar et al. |
| 2007/0286859 A1 | 12/2007 | Lazar et al. |
| 2008/0004206 A1 | 1/2008 | Rosen et al. |
| 2008/0050370 A1 | 2/2008 | Glaser et al. |
| 2008/0057056 A1 | 3/2008 | Lazar et al. |
| 2008/0069838 A1 | 3/2008 | Peiris et al. |
| 2008/0153751 A1 | 6/2008 | Rosen et al. |
| 2008/0161243 A1 | 7/2008 | Rosen et al. |
| 2008/0194481 A1 | 8/2008 | Rosen et al. |
| 2008/0261877 A1 | 10/2008 | Ballance et al. |
| 2008/0318276 A1 | 12/2008 | Persson et al. |
| 2009/0041744 A1 | 2/2009 | Ostergaard et al. |
| 2009/0087411 A1 | 4/2009 | Fares et al. |
| 2009/0087878 A9 | 4/2009 | La Rosa et al. |
| 2009/0092582 A1 | 4/2009 | Bogin et al. |
| 2009/0131306 A1 | 5/2009 | Gupta et al. |
| 2009/0291890 A1 | 11/2009 | Madison et al. |
| 2009/0305297 A1 | 12/2009 | Hornbeck et al. |
| 2010/0022445 A1 | 1/2010 | Scheiflinger et al. |
| 2010/0189682 A1 | 7/2010 | Schellenberger et al. |
| 2010/0239554 A1 | 9/2010 | Schellenberger et al. |
| 2010/0260706 A1 | 10/2010 | Bogin et al. |
| 2010/0292130 A1 | 11/2010 | Skerra et al. |
| 2010/0323956 A1 | 12/2010 | Schellenberger et al. |
| 2011/0046060 A1 | 2/2011 | Schellenberger et al. |
| 2011/0046061 A1 | 2/2011 | Schellenberger et al. |
| 2011/0077199 A1 | 3/2011 | Schellenberger et al. |
| 2011/0172146 A1 | 7/2011 | Schellenberger et al. |

FOREIGN PATENT DOCUMENTS

| | | | |
|---|---|---|---|
| EP | 0120694 A2 | 10/1984 | |
| EP | 0125023 A1 | 11/1984 | |
| EP | 0255694 A1 | 2/1988 | |
| EP | 0256654 A2 | 2/1988 | |
| EP | 0266663 A1 | 5/1988 | |
| EP | 0280576 A2 | 8/1988 | |
| EP | 0295597 A2 | 12/1988 | |
| EP | 1339006 A1 | 8/2003 | |
| GB | WO 9923222 A1 * | 5/1999 | ......... C07K 14/7158 |
| JP | 2008289374 A | 12/2008 | |
| WO | WO-8704187 A1 | 7/1987 | |
| WO | WO-8803558 A1 | 5/1988 | |
| WO | WO-8803559 A1 | 5/1988 | |
| WO | WO-8803565 A1 | 5/1988 | |
| WO | WO-8807089 A1 | 9/1988 | |
| WO | WO-8808035 A1 | 10/1988 | |
| WO | WO-9109122 A1 | 6/1991 | |
| WO | WO-9320093 A1 | 10/1993 | |
| WO | WO-9411503 A2 | 5/1994 | |
| WO | WO-9614339 A1 | 5/1996 | |
| WO | WO-9805787 A1 | 2/1998 | |
| WO | WO-9823289 A1 | 6/1998 | |
| WO | WO-9951642 A1 | 10/1999 | |
| WO | WO-9958572 A1 | 11/1999 | |
| WO | WO-0009560 A2 | 2/2000 | |
| WO | WO-0032767 A1 | 6/2000 | |
| WO | WO-0040602 A1 | 7/2000 | |
| WO | WO-0042072 A2 | 7/2000 | |
| WO | WO-0101749 A2 | 1/2001 | |
| WO | WO-0104287 A1 | 1/2001 | |
| WO | WO-0131019 A2 | 5/2001 | |
| WO | WO-0158935 A2 | 8/2001 | |
| WO | WO-0183725 A1 | 11/2001 | |
| WO | WO-0187922 A2 | 11/2001 | |
| WO | WO-0202764 A2 | 1/2002 | |
| WO | WO-0202781 A1 | 1/2002 | |
| WO | WO-0222776 A2 | 3/2002 | |
| WO | WO-0238162 A1 | 5/2002 | |

(56) References Cited

FOREIGN PATENT DOCUMENTS

| | | |
|---|---|---|
| WO | WO-0240544 A3 | 5/2002 |
| WO | WO-0244215 A2 | 6/2002 |
| WO | WO-02060919 A2 | 8/2002 |
| WO | WO-02077218 A1 | 10/2002 |
| WO | WO-03020764 A2 | 3/2003 |
| WO | WO-03027147 A2 | 4/2003 |
| WO | WO-03031464 A2 | 4/2003 |
| WO | WO-03074569 A2 | 9/2003 |
| WO | WO-03077834 A2 | 9/2003 |
| WO | WO-03093465 A1 | 11/2003 |
| WO | WO-2004016750 A2 | 2/2004 |
| WO | WO-2004029090 A1 | 4/2004 |
| WO | WO-2004029207 A2 | 4/2004 |
| WO | WO-2004035752 A2 | 4/2004 |
| WO | WO-2004063351 A2 | 7/2004 |
| WO | WO-2004074455 A2 | 9/2004 |
| WO | WO-2004099249 A2 | 11/2004 |
| WO | WO-2005035003 A2 | 4/2005 |
| WO | WO-2005040217 A2 | 5/2005 |
| WO | WO-2005070963 A1 | 8/2005 |
| WO | WO-2005077981 A2 | 8/2005 |
| WO | WO-2005092925 A2 | 10/2005 |
| WO | WO-2005123780 A2 | 12/2005 |
| WO | WO-2006019447 A1 | 2/2006 |
| WO | WO-2006047350 A2 | 5/2006 |
| WO | WO-2006085967 A2 | 8/2006 |
| WO | WO-2006138479 A2 | 12/2006 |
| WO | WO-2007021494 A2 | 2/2007 |
| WO | WO-2007077561 A2 | 7/2007 |
| WO | WO-2007103515 A2 | 9/2007 |
| WO | WO-2007149406 A2 | 12/2007 |
| WO | WO-2008033413 A2 | 3/2008 |
| WO | WO-2008118507 A2 | 10/2008 |
| WO | WO-2008155134 A1 | 12/2008 |
| WO | WO-2009023270 A2 | 2/2009 |
| WO | WO-2009051717 A2 | 4/2009 |
| WO | WO-2009058322 A1 | 5/2009 |
| WO | WO-2009130198 A2 | 10/2009 |
| WO | WO-2009137254 A2 | 11/2009 |
| WO | WO-2009140015 A2 | 11/2009 |
| WO | WO-2010040024 A2 | 4/2010 |
| WO | WO-2010091122 A1 | 8/2010 |
| WO | WO-2010144502 A2 | 12/2010 |
| WO | WO-2010144508 A1 | 12/2010 |
| WO | WO-2011028228 A1 | 3/2011 |
| WO | WO-2011028229 A1 | 3/2011 |
| WO | WO-2011028344 A2 | 3/2011 |
| WO | WO-2011069164 A2 | 6/2011 |
| WO | WO-2011149909 A2 | 12/2011 |
| WO | WO-2012006623 A1 | 1/2012 |
| WO | WO-2012006633 A1 | 1/2012 |
| WO | WO-2012006635 A1 | 1/2012 |
| WO | WO-2013151663 A1 | 10/2013 |
| WO | WO-2013185113 A1 | 12/2013 |
| WO | WO-2013185114 A2 | 12/2013 |

OTHER PUBLICATIONS

Aljamali, M.N., et al., "Thrombin Generation and Platelet Activation Induced by rFVIIa (NovoSeven®) and NN1731 in a Reconstituted Cell-Based Model Mimicking Haemophilia Conditions," Haemophilia 15(5):1318-1326, Blackwell Publishing Ltd., England (2009).

Andersen, M.H., et al., "Phosphorylated Peptides can be Transported by TAP Molecules, Presented by Class I MHC Molecules, and Recognized by PHosphopeptide-Specific CTL", Journal of Immunology 163:3812-3818, American Association of Immuologists, Inc., United States (1999).

Andersson, L.O., et al., "Purificaiton and Characterization of Human Factor IX," Thrombosis Research 7(3):451-459, Pergamon Press, Inc., United States (1975).

Bajaj, S.P., etal., "Factor IXa:Factor VIIIa Interaction: Helix 330-338 of Factor IXa Interacts wth Residues 558-565 and Spatially Adjacent Regions of the A2 Subunit of Factor VIIIa," The Journal of Biological Chemistry 276(19):16302-16309, American Society for Biochemistry and Molecular Biology, United States (2001).

Benard, S.A., et al., "Identification of Peptide Antagonists to Glycoprotein Ibα that Selectively Inhibit von Willebrand Factor Dependent Platelet Aggregation," Biochemistry 47(16): 4674-4682, American Chemical Society, United States (2008).

Berge, S.M., et al., "Pharmaceutical Salts," Journal of Pharmaceutical Sciences 66(1):1-19, Wiley-Liss, United States (1977).

Better, M., et al., "*Escherichia coli* Secretion of an Active Chimeric Antibody Fragment," Science 240(4855):1041-1043, Association for the Advancement of Science, United States (1988).

Bird, R.E., et al., "Single-Chain Antigen-Binding Proteins," Science 242(4877):423-426, Association for the Advancement of Science, United States (1988).

Blanchette, P., et al., "A Survey of Factor Prophylaxis in the Canadian Haemophilia A Population," Haemophilia 10(6):679-683, Blackwell Publishing Ltd., England (2004).

Blanchette, V.S., et al., "Plasma and Albumin-Free Recombinant Factor VIII: Pharmacokinetics, Efficacy and Safety in Previously Treated Pediatric Patients," Journal of Thrombosis and Haemostasis 6(8):1319-1326, International Society on Thrombosis and Haemostasis, England (2008).

Blostein, M.D., et al., "Amphipathic Helices Support Function of Blood Coagulation Factor IXa," Biochemistry 39(39):12000-12006, American Chemical Society, United States (2000).

Bovenschen, N., et al., "LDL Receptor Cooperates with LDL Receptor-Related Protein in Regulating Plasma Levels of Coagulation Factor VIII in Vivo," Blood 106(3):906-912, The American Society of Hematology, United States (2005).

Bovenschen, N., "LDL Receptor Polymorphisms Revisited," Blood 116(25):5439-5440, The American Society of Hematology, United States (2010).

Brutlag, D.L., et al., "Improved Sensitivity of Biological Sequence Database Searches," Computer Applications in the Biosciences 6(3):237-245, Oxford University Press, England (1990).

Caliceti, P., et al., "Biopharmaceutical Properties of Uricase Conjugated to Neutral and Amphiphilic Polymers," Bioconjugate Chemistry 10(4):638-646, American Chemical Society, United States (1999).

Cameron, C., et al., "The Canine Factor VIII cDNA and 5' Flanking Sequence," Thrombosis and Haemostasis 79(2):317-322, Schattauer Verlag, Germany (1998).

Capon, D.J., et al., "Designing CD4 Immunoadhesins for AIDS Therapy," Nature 337(6207):525-531, Nature Publishing Group, England (1989).

Cargile, B.J., et al., "Immobilized pH Gradients as a first Dimension in Shotgun Proteomics and Analysis of the Accuracy of pI Predictability of Peptides," Electrophoresis 25(6):936-945, Wiley-VCH Verlag GmbH & Co. KGaA, Germany (2004).

Cho, J.W. and Troy, F.A. II, "Polysialic Acid Engineering: Synthesis of Polysialylated Neoglycosphingolipids by using the Polysialyltransferase from Neuroinvasive *Escherichia coli* K1," Proceedings of the National Academy of Sciences 91(24):11427-11431, National Academy of Sciences, United States (1994).

Christiansen, M.L., et al., "Functional Characteristics of N8, a New Recombinant FVIII," Haemophilia 16(6):878-887, Blackwell Publishing Ltd., England (2010).

Cutler, J.A., et al., "The Identification and Classification of 41 novel Mutations in the Factor VIII Gene (F8C)," Human Mutation 19(3):274-278, Wiley-Liss, Inc., England (2002).

Davies, J. and Riechmann, L., "Single Antibody Domains as Small Recognition Units: Design and in Vitro Antigen Selection of Camelized, Human VH Domains with Improved Protein Stability," Protein Engineering 9(6):531-537, Oxford University Press, England (1996).

Dawson, P.E. and Kent, S.B., "Synthesis of Native Proteins by Chemical Ligation," Annual Review of Biochemistry 69:923-960, Annula Review, United States (2000).

(56) References Cited

OTHER PUBLICATIONS

Döbeli, H., et al., "Role of the Carboxy-Terminal Sequence on the Biological Activity of Human Immune Interferon (IFN-γ)," Journal of Biotechnology 7:199-216, Elsevier Science Publishers B.V., Netherlands (1988).

Decanniere, K., et al., "A Single-Domain Antibody Fragment in Complex with RNase A: Non-Canonical Loop Structural and Nanomolar Affinity using Two CDR Loops," Structure 7(4):361-370, Elsevier Science Ltd., United States (1999).

Delgado, C., et al., "The Uses and Properties of PEG-Linked Proteins," Critical Reviews in Therapeutic Drug Carrier Sytems 9(3,4):249-304, CRC Press, Inc., United States (1992).

Dennis, M.S., et al., "Albumin Binding as a General Strategy for Improving the Pharmacokinetics of Proteins," The Journal of Biological Chemistry 277(38):35035-35043, The American Society for Biochemistry and Molecular Biology, Inc., United States, (2002).

Desmyter, A., et al., "Crystal Structure of a Camel Single-Domain VH Antibody Fragment in Complex with Lysozyme," Nature Structural Biology 3(9):803-811, Nature Publishing Group, England (1996).

Diness, V. and Ostergaard, P.B., "Neutralization of a Low Molecular Weight Heparin (LHN-1) and Conventional Heparin by Protamine Sulfate in Rats," Thrombosis and Haemostasis 56(3):318-322, F.K. Schattauer Verlag GmbH, Germany (1986).

Dumont, J.A., et al., "Prolonged Activity of a Recombinant Factor VIII-Fc Fusion Protein in Hemophilia A Mice and Dogs," Blood 119(13):3024-3030, The American Society of Hameatology, United States (Jan. 2012).

Dumoulin, M., et al., "Single-Domain Antibody Fragments with High Conformational Stability," Protein Science 11(3):500-515, Cold Spring Harbor Laboratory Press, United States (2002).

Eaton, D.L., et al., "Construction and Characterization of an Active Factor VIII Variant Lacking the Central One-Third of the Molecule," Biochemistry 25(26):8343-8347, American Chemical Society, United States (1986).

El Ridi, R., et al., "Immunogenicity and Vaccine Potential of Dipeptidic Multiple Antigen Peptides from Schistosoma Mansoni Glyceraldhyde 3-Phosphate Dehydrogenase," Scaninavian Journal of Immunology 60(4):392-402, Blackwell Publishing Ltd., England (2004).

Engen, J.R. and Smith, D.L., "Investigating Protein Structure and Dynamics by Hydrogen Exchange MS," Analytical Chemistry 73(9):256A-265A, American Chemical Society, United States (2001).

European Search Report for EP Application No. 12797036.6 , Munich, Germany, mailed on Oct. 28, 2014.

Ewenstein, B.M., et al., "Pharmacokinetic Analysis of Plasma-Derived and Recombinant F IX Concentrates in Previously Treated Patients with Moderate or Severe Hemophilia B," Transfusion 42:190-197, American Assoication of Blood Banks, United States (2002).

Falkner, F.G. and Zachau, H.G., "Expression of Mouse Immunoglobulin Genes in Monkey Cells," Nature 298(5871):286-288, Nature Publishing Group, England (1982).

Frank, R., "Spot-Synthesis: an Easy Technique for the Positionally Addressable, Parallel Chemical Synthesis on a Membrane Support," Tetrahedron 48(42):9217-9232, Pergamon Press Ltd., England (1992).

Gayle, R.B., III., et al., "Identification of Regions in Interleukin-1α Important for Activity," The Journal of Biological Chemsitry 268(29:22105-22111, The American Society for Biochemistry and Molecular Biology, Inc., United States (1993).

GenBank, "Coagulation Factor VII Isoform a Preproprotein [*Homo sapiens*]," Accession No. NP_000122.1 accessed at https://www.ncbi.nlm.nih.gov/protein/NP_000122, accessed on Jan. 15, 2015, 4 pages.

GenBank, "Predicted: hypothetical protein [Saccoglossus kowalevskii]," Accession No. XP002730889, Entry Date Mar. 19, 2010, accessed at https://www.ncbi.nlm.nih.gov/protein/XP_00273889.1?report=genpept, accessed on Dec. 23, 2014.

GenBank, "*Homo sapiens* Transferrin (TF), mRNA", Accession No. NM001063.1, accessed at http://www.ncbi.nlm.nih.gov/nuccore/NM_001063, accessedon Sep. 24, 2014, 5 pages.

GenBank, "*Homo sapiens* Transferrin (TF), mRNA," Accession No. XM002793 published on May 13, 2002, accessed at https://www.ncbi.nlm.nih.gov/nuccore/XM_002793.7?report=genbank, accessed on Sep. 24, 2014, 2 pages.

GenBank, "*Homo sapiens* Transferrin (TF), mRNA," Accession No. XM039847 published on Jul. 16, 2001, accessed at http://www.ncbi.nlm.nih.gov/nuccore/XM_039847.1?report=genbank, accessed on Sep. 24, 2014, 2 pages.

GenBank, "*Homo sapiens* Transferrin (TF), mRNA," Accession No. XM039845 published Jul. 16, 2001, accesed at https://www.ncbi.nlm.nih.gov/nuccore/XM_039845.1?report=genbank, accessed on Sep. 24, 2014, 2 pages.

GenBank, "Human Transferrin: cDNA Characterization and Chromosomal Localization", Accession No. AAA61140.1, published on Jan. 14, 1995, accessed at https://www.ncbi.nlm.nih.gov/protein/AAA61140, accessed on Jan 15, 2015, 1 page.

GenBank, "Human Transferrin mRNA, Complete cds", Accession No. M12530.1, published on Jan. 14, 1995, accessed at http://www.ncbi.nlm.nih.gov/nuccore/M1253014, acceswsed on Jan. 15, 2015, 2 pages.

GenBank, "Hypothetical Protein Sph21_4515 [*Sphingobacterium sp. 21*]," Accession No. ADZ81032.1, Entry Date Nov. 21, 2011, accessed at https//www.ncbi.nlm.nih.gov/protein/ADZ81032, accessed on Dec. 23, 2014, 1 page.

GenBank, "Transferrin [human, liver, mRNA, 2347 nt]", Accession No. S95936.1, published on May 7, 1993, accessed at http://www.ncbi.nlm.nih.gov/nuccore/S95936, accessed on Sep. 24, 2014, 2 pages.

Gitschier, J., et al., "Characterization of the Human Factor VIII Gene," Nature 312(5992):326-330, Nature Publishing Group, England (1984).

Graham, J.B., et al., "Canine Hemophilia: Observations on the Course, the Clotting Anomaly, and the Effect of Blood Transfusions," The Journal of Experimental Medicine 90(2):97-111, The Rockefeller University Press, United States (1949).

Guichard, G., et al., "Antigenic Mimicry of Natural L-Peptides with Retro-Inverso-Peptidomimetics," Proceedings of the National Academy of Sciences 91(21):9765-9769, National Academy of Sciences, United States (1994).

Hamers-Casterman, C., et al., "Naturally Occurring Antibodies Devoid of Light Chains," Nature 363(6428):446-448, Nature Publishing Group, England (1993).

Hartmann, R., et al., "Factor IX Mutants with Enhanced Catalytic Activity," Journal of Thrombosis and Haemostasis 7(10):1656-1662, International Society on Thrombosis and Haemostasis, England (2009).

Healey, J.F., et al., "The cDNA and Derived Amino Acid Sequence of Porcine Factor VIII," Blood 88(11):4209-4214, The American Society of Hematology, United States (1996).

Ho, S.N., et al., "Site-Directed Mutagenesis by Overlap Extension Using the Polymerase Chain Reaction," Gene 77(1):51-59, Elsevier Science Publishers B.V., Netherlands (1989).

Hoeben, R.C., et al., "Expression of Functional Factor VIII in Primary Human Skin Fibroblasts after Retrovirus-mediated Gene Transfer," The Journal of Biological Chemistry 265(13):7318-7323, The American Society for Biochemistry and Molecular Biology, United States (1990).

Holland-Nell, K. and Meldal, M., "Maintaining Biological Activity by using Triazoles as Disulfide Bond Mimetics," Angew Chem Int Ed 50(22):5204-5206, Wiley-VCH Verlag GmbH & Co. KGaA, Germany (2011).

Holt, L.J., et al., "Anti-Serum Albumin Domain Antibodies for Extending the Half-Lives of Short Lived Drugs," Protein Engineering, Design and Selectin 21(5):283-288, Oxford University Press, England (2008).

Houde, D., et al., "Post-Translational Modifications Differentially Affect IgG1 Conformation and Receptor Binding," Molecular and Cellular Proteomics 9(8):1716-1728, American Society for Biochemistry and Molecular Biology, Inc., United States (2010).

(56) References Cited

OTHER PUBLICATIONS

Huston, J.S., et al., "Protein Engineering of Antibody Binding Sites: Recovery of Specific Activity in an Anit-Digoxin Single-Chain Fv Analogue Produced in *Escherichia coli*," Proceedings of the National Academy of Sciences 85(16):5879-5883, National Academy of Sciences, United States (1988).
International Search Report for International Application No. PCT/US2012/41777, European Patent Office, Netherlands, mailed on Jun. 20, 2013, 6 pages.
Jendreyko, N., et al., "Protein Synthesis, Post-Translation Modification, and Degradation: Intradiabodies, Bispecific, Tetravalent Antibodies for the Simultaneous Functional Knockout of Two Cell Surface Receptors," The Journal of Biological Chemistry 278(48):47812-47819, The American Society of Biochemistry and Molecular Biology, Inc., United States (2003).
Johnson, D.J.D., et al., "Molecular Basis of Factor IXa Recognition by Heparin-Activated Antithrombin Revealed by a 1.7-A Structure of the Ternary Complex," Proceedings of the National Academy of Sciences 107(2):645-650, National Academy of Sciences, United States (2010).
Jones, E.W., et al., "Proteinase Mutants of *Saccharomyces cerevisiae*," Genetics 85:23-33, Genetics Society of America, United States (1977).
Kandrotas, R.J., "Heparin Pharmocokinetics and Pharmacodynamics," Clinical Pharmacokinetics 22(5):359-374, Adis International Ltd., New Zealand (1992).
Kasper, C.K., et al., "A More Uniform Measurement of Factor VIII Inhibitors," Thrombosis ET Diathesis Haemorhagica 34(1):612, F.K. Schattauer Verlag, New York (1975) (Abstract).
Kingsman, A.J., et al., "Replication in *Saccharomyces cerevisiae* of Plasmid pBR313 Carrying DNA from Yeast Trpl Region," Gene 7(2):141-152, Elsevier/North-Holland Biomedical Press, Netherlands (1979).
Kohler, G., "Immunoglobulin chain loss in hybridoma lines," Proceedings of the National Academy of Sciences USA 77(4):2197-2199, National Academy of Sciences, United States, (1980).
Konig, T. and Skerra, A., "Use of an Albumin-Binding Domain for the Selective Immobilisation of Recombinant Capture Antibody Fragments on ELISA Plates," Journal of Immunological Methods 218(1-2):73-83, Elsevier Science B.V., Netherlands (1998).
Kortt, A.A., et al., "Solution Properties of *Escherichia coli*-Expressed VH Domain of Anti-Neuraminidase Antibody NC41," Journal of Protein Chemistry 14(3):167-178, Plenum Publishing Corporation, United States (1995).
Kraulis, P.J., et al., "The Serum Albumin-Binding Domain of Streptococcal Protein G is a Three-Helical Bundle: a Heteronuclear NMR study," FEBS Letters 378(2):190-194, Federation of European Biochemical Societies, England (1996).
Lai, E., et al., "Conserved organization of the human and murine T-cell receptor β-gene families," Nature 331(6156):543-546, Nature Publishing Group, England (1988).
Langner, K-D., et al., "Synthesis of Biologically Active Deletion Mutants of Human Factor VIII:C," Behring Institute Mitteilungen 82:16-25, Behringwerke AG, Germany (1988).
Lauritzen, B., et al., "rFVIIa and a New Enhanced rFVIIa-Analogue, NN1731, Reduce Bleeding in Clopidogrel-Treated and in Thrombocytopenic Rats," Journal of Thrombosis and Haemostasis 7(4):651-657, International Society on Thrombosis and Haemostasis, England (2009).
Lehninger, A. L., Biochemistry Edition 2, pp. 71-92, Worth Publishers, Inc., United States (1975).
Lenting, P.J., et al., "Biochemistry of FVIII and INhibitors: The Disappearing Act of Factor VIII," Haemophilia 16(102):6-15, Blackwell Publishing Ltd, England (2010).
Liles, D.K., et at., "The Factor VIII Peptide Consisting of Amino Acids 698 to 712 Enhances Factor IXa cleavage of factor X," Blood 90(Suppl. 1):463a, The American Society of Hematology, United States (1997) (Abstract 2054).

Linhult, M., et al., "Mutational Analysis of the Interaction Between Albumin-Binding Domain from Streptococcal Protein G and Human Serum Albumin," Protein Science 11(2):206-213, Cold Spring Harbor Laboratory Press, United States (2002).
Lozier, J.N., et al., "The Chapel Hill Hemophilia A Dog Colony Exhibits a Factor VIII Gene Inversion," Proceedings of the National Academy of Sciences USA 99(20):12991-12996, National Academy of Sciences, United States (2002).
Manco-Johnson, M.J., et al., "Prophylaxis versus Episodic Treatment to Prevent Joint Disease in Boys with Severe Hemophilia," New England Journal of Medicine 357(6):535-544, Massachusetts Medical Society, United States (2007).
Mannucci, P.M. and Tuddenham, E.G.D., "The Hemophilias—from Royal Genes to Gene Therapy," New England Journal of Medicine 344(23):1773-1779, Massachusetts Medical Society, United States (2001).
Martinelli, N., et al., "Polymorphisms at LDLR Locus may be Associated with Coronary Artery Disease through Modulation of coagulation Factor VIII Activity and Independently from Lipid Profile," Blood 116(25):5688-5697, The American Society of Hematology, United States (2010).
Medzihradszky, K.F., et al., "O-Sulfonation of Serine and Threonine: Mass Spectrometric Detection and Characterization of a New Posttransistion Modification in Diverse Proteins Throughout the Eukaryotes," Molecular & Cellular Proteomics 3(5):429-440, American Society for Biochemistry and Molecular Biology, Inc., United States (2004).
Mei, B., et al., "Expression of Human Coagulation Factor VIII in a Human Hybrid Cell Line, HKB11," Molecular Biotechnology 34(2):165-178, Humana Press Inc., United States (2006).
Mei, B., et al., "Rational Design of a Fully active, Long-Acting PEGylated Factor VIII for Hemophilia A Treatment," Blood 116(2):270-279, The American Society of Hematology, United States, (2010).
Meulien, P., et al., "A new Recombinant Procoagulant Protein Derived from the cDNA Encoding Human Factor VIII," Protein Engineering 2(4):301-306, IRL Press Ltd., England (1988).
Milenic, D.E., et al., "Construction, Binding Properties, Metabolism, and Tumor Targeting of a Single-Chain Fv Derived from the Pancarcinoma Monoclonal Antibody CC49," Cancer Research 51:6363-6371, American Association of Cancer Research, United States (1991).
Morfini, M., "Pharmacokinetics of Factor VIII and Factor IX," Haemophilia 9(Suppl. 1):94-100, Blackwell Publishing Ltd., England (2003).
Morpurgo, M., et al., "Covalent modification of mushroom tyrosinase with different amphiphic polymers for pharmaceutical and biocatalysis applications," Applied Biochemistry and Biotechnology 56(1):59-72, Human Press, Inc., United States (1996).
Morrison, S.L., "Sequentially Derived Mutants of the Constant Region of the Heavy Chain of Murine Immunoglobulins," The Journal of Immunology 123(2):793-800, The Williams & Wilkins Co., United States (1979).
Morrison, S.L., et al., "Chimeric Human Antibody Molecules: Mouse Antigen-Binding Domains with Human Constant Region Domains," Proceedings of the National Academy of Sciences USA 81(21):6851-6855, National Academy of Sciences, United States (1984).
Morrison, S.L., "Transfectomas Provide Novel Chimeric Antibodies," Science 229(4719):1202-1207, Association for the Advancement of Science, United States (1985).
Morrison S.L., "Transfer and Expression of Immunoglobulin Genes," Annual Review of Immunology 2:239-256, Annual Reviews, Inc. United States (1984).
Muller, D. and Kontermann, R.E., "Recombinant Bispecific Antibodies for Cellular Cancer Immunotherapy," Current Opinion in Molecular Therapeutics 9(4):319-326, Current Drugs Ltd. England (2007).
Mullinax, R.L., et al., "Identification of Human Antibody Fragment Clones Specific for Tetanus Toxoid in a Bacteriophage λ Immunoexpression Library," Proceedings of the National Academy of Sciences USA 87(20):8095-8099, National Academy of Sciences, United States (1990).

(56) References Cited

OTHER PUBLICATIONS

Mézière, C., et al., "In Vivo T Helper Cell Response to Retro-Inverso Peptidomimetics," The Journal of Immunology 159(7):3230-3237, American Association of Immunologists, United States (1997).

Neumann, E., et al., "Gene Transfer into Mouse Lyoma Cells By Electroporation in High Electric Fields," The EMBO Journal 1(7):841-845, IRL Press Limited, England (1982).

Newman, R., et al., "'Primatization' of Recombinant Antibodies for Immunotherapy of Human Diseases: a Macaque/Human Chimeric Antibody Against Human CD4," Biotechnology 10(11):1455-1460, Nature Publishing Group, England (1992).

Pan, J., et al., "Enhanced Efficacy of Recombinant FVIII in Noncovalent Complex with PEGylated Liposome in Hemophilia a Mice," Blood 114(13):2802-2811, The American Society of Hematology, United States (2009).

Pantoliano, M.W., et al., "Conformational Stability, Folding, and Ligand-Binding Affinity of Single-Chain Fv Immunoglobulin Fragments Expressed in *Escherichia coli*," Biochemistry 30(42):10117-10125, American Chemical Society, United States (1991).

Raso, V. and Griffin, T., "Hybrid Antibodies with Dual Specificity for the Delivery of Ricin to Immunoglobulin-Bearing Target Cells," Cancer Research 41(6):2073-2078, American Association of Cancer Research, United States (1981).

Rodriguez-Merchan, E.C., "Management of Musculoskeletal Complications of Hemophilia," Seminars in Thrombosis and Hemostasis 29(1):87-95, Thieme, United States (2003).

Ron, D., et al., "Expression of Biologically Active Recombinant Keratinocyte Growth Factor: Structure/Function Analysis of Amino-Terminal Truncation Mutants," The Journal of Biological Chemistry 268(4):2984-2988, American Society of Biochemistry and Molecular Biology, United States (1993).

Roovers, R.C., et al., "Efficient Inhibition of EGFR Signaling and of Tumour Growth by Antagonistic Anti-EGFR Nanobodies," Cancer Immunology, Immunotherapy 56(3):303-317, Springer Verlag, Germany (2007).

Rostin, J., et al., "B-Domain Deleted Recombinant Coagulation Factor VIII Modified with Monomethoxy Polyethylene Glycol," Bioconjugate Chemistry 11(3):387-396, American Chemical Society, United States (2000).

Roth, J. et al., "From Microbes to Man" in Polysialic Acid, Roth J., Rutishauser U., Troy F.A., eds., pp. 335-348, BirkhauserVerlag, Basel, Switzerland (1993).

Sarver, N., et al., "Stable Expression of Recombinant Factor VIII Molecules Using a Bovine Papillomavirus Vector," DNA 6(6):553-564, Mary Ann Liebert, Inc., United States (1987).

Scheiflinger, F., et al., "Enhancement of the Enzymatic Activity of Activated Coagulation Factor IX by Anti-Factor IX Antibodies," Journal of Thrombosis and Haemostasis 6(2):315-322, International Society on Thrombosis and Haemostasis, England (2008).

Schellenberger, V., et al., "A Recombinant Polypeptide Extends the in Vivo Half-Life of Peptides and Proteins in a Tunable Manner," Nature Biotechnology 27(12):1186-1190, Nature America, Inc., United States (2009).

Schulte, S., "Half-life Extension Through Albumin Fusion Technologies," Thrombosis Research 124(Suppl. 2):S6-S8, Elsevier Ltd, United States (2009).

Schulte, S., "Use of Albumin Fusion Technology to Prolong the Half-Life of Recombinant Factor VIIa," Thrombosis Research 122(Suppl 4):S14-S19, Elsevier Ltd, United States (2008).

Silva, J.C., et al., "Absolute Quantification of Proteins by LCMSE: a Virtue of Parallel MS Acquisition," Molecular and Cellular Proteomics 5(1):144-156, American Society for Biochemistry and Molecular Biology, Inc., United States (2006).

Skerra, A. and Plückthun, A., "Assembly of a Functional Immunoglobulin Fv Fragment in *Escherichia coli*," Science 240(4855):1038-1041, Association for the Advancement of Science, United States (1988).

Sommermeyer, V.K., et al., "Klinisch Verwendete Hydroxyethylstarke: Physikalisch-Chemische Charakterisierung," Krankenhauspharmazie 8(8):271-278, Deutscher Apotheker Verlag, Birkenwaldstr, Germany (1987).

Spira, J., et al., "Prolonged Bleeding-Free Period Following Prophylactic Infusion of Recombinant Factor VIII Reconstituted With Pegylated Liposomes," Blood 108(12):3668-3673, The American Society of Hematology, United States (2006).

Stennicke, H.R., et al., "Generation and Biochemical Characterization of GlycoPEGylated Factor VIIa Derivatives," Thrombosis and Haemostasis 100(5):920-928, Schattauer GmbH, Germany (2008).

Stinchcomb, D.T., et al., "Isolation and Characterisation of a Yeast Chromosomal Replicator," Nature 282(5734):39-43, Nature Publishing Group, England (1979).

Strickland, D.K. and Medved, L., "Low-Density Lipoprotein Receptor-Related Protein (LRP)-Mediated Clearance of Activated Blood Coagulation Co-Factors and Proteases Clearance Mechanism or Regulation?" Journal of Thrombosis and Haemostasis 4(7):1484-1486, International Society on Thrombosis and Haemostasis, England (2006).

Takkinen, K., et al., "An Active Single-Chain Antibody Containing a Cellulase linker Domain is Secreted by *Escherichia coli*," Protein Engineering Design and Selection 4(7):837-841, Oxford University Press, England (1991).

Tan, L., et al., "An Improved Assembly Assay for Peptide Binding to HLA-B*2705 and H-2K(k) Class I MHC Molecules," Journal of Immunological Methods 209(1):25-36, Elsevier Science B.V., Netherlands (1997).

Toole, J.J., et al., "A large region (95 kDa) of human factor VIII is dispensable for in vitro procoagulant activity," Proceedings of the National Academy of Sciences USA 83(16):5939-5942, National Academy of Sciences, United States (1986).

Toole, J.J., et al., "Molecular Cloning of cDNA Encoding Human Antihaemophilic Factor," Nature 312(5992):342-347, Nature Publishing Group, England (1984).

Tranholm, M., et al., "Improved Hemostasis with Superactive Analogs of Factor VIIa in a Mouse Model of Hemophilia A," Blod 102(10):3615-3620, American Society of Hematology, United States (2003).

Tranholm, M., et al., "Recombinant Factor Vila Reduces Bleeding in Severely Thrombocytopenic Rabbits," Thrombosis Research 109(4):217-223, Elsevier Science B.V., Netherlands (2003).

Trussel, S., et al., "New Strategy for the Extension of the Serum Half-Life of Antibody Fragments," Bioconjugate Chemistry 20(12):2286-2292, American Chemical Society, United States (2009).

Tschumper, G. and Carbon, J., "Sequence of a Yeast DNA Fragment Containing a Chromosomal Replicator and the TRP1 Gene," Gene 10(2):157-166, Elsevier/North-Holland Biomedical Press, Netherlands (1980).

UniProt, "Chromosome undetermined SCAF15069, whole genome shotgun sequence," Accession No. Q4RH68, Entry Date Jul. 19, 2005, accessed at https://www.ncbi.nih.gov/protein/Q4RH68, accessed on Dec. 23, 2014.

UniProt, "Predicted: CG15439-like [Saccoglossus kowalevskii]," Accession No. XP002730886.1, published Mar. 19, 2010, accessed at https://www.ncbi.nlm.nih.gov/protein/XP_002730886.1?report=genpept, accessed on Dec. 23, 2014.

UniProt, "Proteolipid c subunit (Chromosome undetermined scaffold_37, whole genome shotgun sequence," Accession No. QZ1Q5, Entry Dated Oct. 1, 2003, accessed at https://www.ncbi.nlm.nih.gov/protein/Q7Z105, accessed on Dec. 23, 2014.

UnitProtKB, Accession No. P00541.1, accessed at https://www.ncbi.nlm.nih.gov/protein/P00541, accessed on Jan. 15, 2015, 88 pages.

Van Ryn-McKenna, J., et al., "Neutralization of Enoxaparine-Induced Bleeding by Protamine Sulfate," Thrombosis and Haemostasis 63(2):271-274, F.K. Schattauer Verlagsgesellschaft mbH, Germany (1990).

Vehar, G.A., et al., "Structure of Human Factor VIII," Nature 312(5992):337-342, Nature Publishing Group, England (1984).

(56) References Cited

OTHER PUBLICATIONS

Vorobjev, P.E., et al., "Oligonucleotide Conjugated to Linear and Branched High Molecular Weight Polyethylene Glycol as Substrates for RNase H," Nucleosides & Nucleotides 18(11-12):2745-2750, Marcel Dekker, Inc., United States (1999).

Wakefield, T.W., et al., "A [+18RGD] Protamine Variant for Nontoxic and Effective Reversal of Conventional Heparin and Low-Molecular-Weight Heparin Anticoagulation," The Journal of Surgical Research 63(1):280-286, Academic Press, Inc., United States (1996).

Wales, T.E. and Engen, J.R., "Hydrogen Exchange Mass Spectrometry for the Analysis of Protein Dynamics," Mass Spectrometry Reviews 25(1):158-170, Wiley Periodicals, Inc., United States (2006).

Wales, T.E., et al., "High-Speed and High-Resolution UPLC Separation at Zero Degrees Celsius," Analytical Chemistry 80(17):6815-6820, American Chemical Society, United States (2008).

Ward, E.S. et al., "Binding Activities of a Repertoire of Single Immunoglobulin Variable Domains Secreted from *Escherichia coli*," Nature 331:544-554, Nature Publishing Group, England (1989).

Weidler, B., et al., "Pharmakokinetische Merkmale als Kriterien fur den klinischen Einsatz von Hydroxyethylstarke," Arzneimittel-Forschung 41(5):494-498, Editio Cantor, Germany (1991).

White, G.C. II, et al., "A Multicenter Study of Recombinant Factor VIII (Recombinate(TM)) in Previously Treated Patients with Hemophilia A," Thrombosis and Haemostasis 78(1):261-265, F.K. Schattauer Verlagsgesellshaft mbH, Germany (1997).

White, G.C. II., et al., "Recombinant Factor IX," Thrombosis and Haemostasis 78(1):261-265, F.K. Schattauer Verlagsgesellschaft mbH, Germany (1997).

Wiebe, E.M., et al., "Enzyme Catalysis and Regulation: Mechanism of Catalysis of Inhibitionof Factor IXa by Antithrombin in the Presence of Heparin or Pentasaccharide," The Journal of Biological Chemistry 278*37:35767-35774, American Society for Biochemistry and Molecular Biology, United States (2003).

Wigler, M., et al., "Biochemical Transfer of Single-Copy Eurcaryotic Genes Using Total Cellular DNA as Donor," Cell 14(3):725-731, MIT, United States (1978).

Wong, P.C., et al., "Nonpeptide Factor Xa Inhibitors: I. Studies with SF303 and SK549, a New Class of Potent Antithrombotics," The Journal of Pharmacology and Experimental Therpeutics 291(1):351-357, American Soceity for Pharmacology and Experimental Therapeutics, United States (2000).

Wood, W.I., et al., "Expression of Active Human Factor VIII from Recombinant DNA Clones," Nature 312(5992):330-337, Nature Publishing Group, England (1984).

Yang, L., et al., "Protein Structure and Folding: Localization of the Heparin Binding Exosite of Factor IXa," The Journal of Biological Chemistry 277(52):50756-50760, American Soceity for Biochemstry and Molecular Biology, United States (2002).

GenBank, "Oncorhynchus mykiss clone B32 Vhsv-induced protein mRNA, complete cds," Accession No. AF483536.1, accessed at http://www.ncbi.nlm.nih.gov/nuccore/AF483536.1, accessed on Apr. 13, 2016, 2 pp.

\* cited by examiner

```
                          SEQUENCE LISTING

<160> NUMBER OF SEQ ID NOS: 904

<210> SEQ ID NO 1
<211> LENGTH: 5
<212> TYPE: PRT
<213> ORGANISM: Artificial Sequence
<220> FEATURE:
<223> OTHER INFORMATION: compound binding site

<400> SEQUENCE: 1

Met Phe Cys Ala Gly
1               5

<210> SEQ ID NO 2
<211> LENGTH: 11
<212> TYPE: PRT
<213> ORGANISM: Artificial Sequence
<220> FEATURE:
<223> OTHER INFORMATION: compound binding site

<400> SEQUENCE: 2

Tyr Asn Asn Met Phe Cys Ala Gly Phe His Glu
1               5                   10

<210> SEQ ID NO 3
<211> LENGTH: 26
<212> TYPE: PRT
<213> ORGANISM: Artificial Sequence
<220> FEATURE:
<223> OTHER INFORMATION: compound binding site

<400> SEQUENCE: 3

Arg Ser Thr Lys Phe Thr Ile Tyr Asn Asn Met Phe Cys Ala Gly Phe
1               5                   10                  15

His Glu Gly Gly Arg Asp Ser Cys Gln Gly
            20                  25

<210> SEQ ID NO 4
<211> LENGTH: 22
<212> TYPE: PRT
<213> ORGANISM: Artificial Sequence
<220> FEATURE:
<223> OTHER INFORMATION: synthetic

<400> SEQUENCE: 4

Arg Arg Ala Pro Gly Lys Leu Gln Cys Leu Ala Ser Tyr Cys Trp Leu
1               5                   10                  15

Phe Trp Thr Gly Ile Ala
            20

<210> SEQ ID NO 5
<211> LENGTH: 22
<212> TYPE: PRT
<213> ORGANISM: Artificial Sequence
<220> FEATURE:
<223> OTHER INFORMATION: synthetic
```

```
<400> SEQUENCE: 5

Pro Leu Lys Trp Thr Ala Ser Gly Cys Arg Trp Leu Gly Cys Ile Gln
1               5                   10                  15

Leu Ala Arg Phe Ala Tyr
            20

<210> SEQ ID NO 6
<211> LENGTH: 22
<212> TYPE: PRT
<213> ORGANISM: Artificial Sequence
<220> FEATURE:
<223> OTHER INFORMATION: synthetic

<400> SEQUENCE: 6

Leu Tyr Thr Ala Trp Ile Lys Cys Gln Phe Ala Arg Leu Pro Gly Cys
1               5                   10                  15

Ala Leu Ser Gly Arg Trp
            20

<210> SEQ ID NO 7
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Biotin-PEG2

<400> SEQUENCE: 7

Leu Tyr Thr Ala Trp Ile Lys Cys Gln Phe Ala Arg Leu Pro Gly Cys
1               5                   10                  15

Ala Leu Ser Gly Arg Trp
            20

<210> SEQ ID NO 8

<400> SEQUENCE: 8

000

<210> SEQ ID NO 9
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (6)..(6)
<223> OTHER INFORMATION: D-amino acid
<220> FEATURE:
<221> NAME/KEY: MOD_RES
<222> LOCATION: (7)..(7)
<223> OTHER INFORMATION: N-METHYLATION

<400> SEQUENCE: 9

Arg Arg Ala Pro Gly Lys Leu Thr Cys Leu Ala Ser Tyr Cys Trp Leu
1               5                   10                  15

Phe Trp Thr Gly Ile Ala
            20
```

```
<210> SEQ ID NO 10
<211> LENGTH: 17
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (2)..(2)
<223> OTHER INFORMATION: N-Methylated

<400> SEQUENCE: 10

Lys Leu Thr Cys Leu Ala Ser Tyr Cys Trp Leu Phe Trp Thr Gly Ile
1               5                   10                  15

Ala

<210> SEQ ID NO 11
<211> LENGTH: 22
<212> TYPE: PRT
<213> ORGANISM: Artificial Sequence
<220> FEATURE:
<223> OTHER INFORMATION: synthetic

<400> SEQUENCE: 11

Arg Arg Ala Pro Gly Lys Leu Gln Cys Leu Ala Ser Tyr Cys Trp Leu
1               5                   10                  15

Phe Trp Thr Gly Ala Ala
            20

<210> SEQ ID NO 12
<211> LENGTH: 22
<212> TYPE: PRT
<213> ORGANISM: Artificial Sequence
<220> FEATURE:
<223> OTHER INFORMATION: synthetic

<400> SEQUENCE: 12

Arg Arg Ala Pro Gly Lys Leu Gln Cys Leu Ala Ser Tyr Cys Trp Leu
1               5                   10                  15

Phe Trp Thr Ala Ile Ala
            20

<210> SEQ ID NO 13
<211> LENGTH: 22
<212> TYPE: PRT
<213> ORGANISM: Artificial Sequence
<220> FEATURE:
<223> OTHER INFORMATION: synthetic

<400> SEQUENCE: 13

Arg Arg Ala Pro Gly Lys Leu Gln Cys Leu Ala Ser Tyr Cys Trp Leu
1               5                   10                  15

Phe Trp Ala Gly Ile Ala
            20

<210> SEQ ID NO 14
<211> LENGTH: 22
<212> TYPE: PRT
<213> ORGANISM: Artificial Sequence
<220> FEATURE:
<223> OTHER INFORMATION: synthetic
```

```
<400> SEQUENCE: 14

Arg Arg Ala Pro Gly Lys Leu Gln Cys Leu Ala Ser Tyr Cys Trp Leu
1               5                   10                  15

Phe Ala Thr Ala Ile Ala
            20

<210> SEQ ID NO 15
<211> LENGTH: 22
<212> TYPE: PRT
<213> ORGANISM: Artificial Sequence
<220> FEATURE:
<223> OTHER INFORMATION: synthetic

<400> SEQUENCE: 15

Arg Arg Ala Pro Ala Lys Leu Gln Cys Leu Ala Ser Tyr Cys Trp Leu
1               5                   10                  15

Phe Trp Thr Gly Ile Ala
            20

<210> SEQ ID NO 16
<211> LENGTH: 22
<212> TYPE: PRT
<213> ORGANISM: Artificial Sequence
<220> FEATURE:
<223> OTHER INFORMATION: synthetic

<400> SEQUENCE: 16

Arg Arg Ala Ala Gly Lys Leu Gln Cys Leu Ala Ser Tyr Cys Trp Leu
1               5                   10                  15

Phe Trp Thr Gly Ile Ala
            20

<210> SEQ ID NO 17
<211> LENGTH: 22
<212> TYPE: PRT
<213> ORGANISM: Artificial Sequence
<220> FEATURE:
<223> OTHER INFORMATION: synthetic

<400> SEQUENCE: 17

Arg Ala Ala Pro Gly Lys Leu Gln Cys Leu Ala Ser Tyr Cys Trp Leu
1               5                   10                  15

Phe Trp Thr Gly Ile Ala
            20

<210> SEQ ID NO 18
<211> LENGTH: 22
<212> TYPE: PRT
<213> ORGANISM: Artificial Sequence
<220> FEATURE:
<223> OTHER INFORMATION: synthetic

<400> SEQUENCE: 18

Ala Arg Ala Pro Gly Lys Leu Gln Cys Leu Ala Ser Tyr Cys Trp Leu
1               5                   10                  15

Phe Trp Thr Gly Ile Ala
            20

<210> SEQ ID NO 19
<211> LENGTH: 21
<212> TYPE: PRT
<213> ORGANISM: Artificial Sequence
<220> FEATURE:
<223> OTHER INFORMATION: synthetic
```

<400> SEQUENCE: 19

Arg Arg Ala Pro Gly Lys Leu Gln Cys Leu Ala Ser Tyr Cys Trp Leu
1               5                   10                  15

Phe Trp Thr Gly Ile
            20

<210> SEQ ID NO 20
<211> LENGTH: 20
<212> TYPE: PRT
<213> ORGANISM: Artificial Sequence
<220> FEATURE:
<223> OTHER INFORMATION: synthetic

<400> SEQUENCE: 20

Arg Arg Ala Pro Gly Lys Leu Gln Cys Leu Ala Ser Tyr Cys Trp Leu
1               5                   10                  15

Phe Trp Thr Gly
            20

<210> SEQ ID NO 21
<211> LENGTH: 19
<212> TYPE: PRT
<213> ORGANISM: Artificial Sequence
<220> FEATURE:
<223> OTHER INFORMATION: synthetic

<400> SEQUENCE: 21

Arg Arg Ala Pro Gly Lys Leu Gln Cys Leu Ala Ser Tyr Cys Trp Leu
1               5                   10                  15

Phe Trp Thr

<210> SEQ ID NO 22
<211> LENGTH: 18
<212> TYPE: PRT
<213> ORGANISM: Artificial Sequence
<220> FEATURE:
<223> OTHER INFORMATION: synthetic

<400> SEQUENCE: 22

Arg Arg Ala Pro Gly Lys Leu Gln Cys Leu Ala Ser Tyr Cys Trp Leu
1               5                   10                  15

Phe Trp

<210> SEQ ID NO 23
<211> LENGTH: 17
<212> TYPE: PRT
<213> ORGANISM: Artificial Sequence
<220> FEATURE:
<223> OTHER INFORMATION: synthetic

<400> SEQUENCE: 23

Arg Arg Ala Pro Gly Lys Leu Gln Cys Leu Ala Ser Tyr Cys Trp Leu
1               5                   10                  15

Phe

<210> SEQ ID NO 24
<211> LENGTH: 21
<212> TYPE: PRT
<213> ORGANISM: Artificial Sequence
<220> FEATURE:
<223> OTHER INFORMATION: synthetic

<400> SEQUENCE: 24

```
Arg Ala Pro Gly Lys Leu Gln Cys Leu Ala Ser Tyr Cys Trp Leu Phe
1               5                   10                  15

Trp Thr Gly Ile Ala
            20

<210> SEQ ID NO 25
<211> LENGTH: 20
<212> TYPE: PRT
<213> ORGANISM: Artificial Sequence
<220> FEATURE:
<223> OTHER INFORMATION: synthetic

<400> SEQUENCE: 25

Ala Pro Gly Lys Leu Gln Cys Leu Ala Ser Tyr Cys Trp Leu Phe Trp
1               5                   10                  15

Thr Gly Ile Ala
            20

<210> SEQ ID NO 26
<211> LENGTH: 19
<212> TYPE: PRT
<213> ORGANISM: Artificial Sequence
<220> FEATURE:
<223> OTHER INFORMATION: synthetic

<400> SEQUENCE: 26

Pro Gly Lys Leu Gln Cys Leu Ala Ser Tyr Cys Trp Leu Phe Trp Thr
1               5                   10                  15

Gly Ile Ala

<210> SEQ ID NO 27
<211> LENGTH: 18
<212> TYPE: PRT
<213> ORGANISM: Artificial Sequence
<220> FEATURE:
<223> OTHER INFORMATION: synthetic

<400> SEQUENCE: 27

Gly Lys Leu Gln Cys Leu Ala Ser Tyr Cys Trp Leu Phe Trp Thr Gly
1               5                   10                  15

Ile Ala

<210> SEQ ID NO 28
<211> LENGTH: 17
<212> TYPE: PRT
<213> ORGANISM: Artificial Sequence
<220> FEATURE:
<223> OTHER INFORMATION: synthetic

<400> SEQUENCE: 28

Lys Leu Gln Cys Leu Ala Ser Tyr Cys Trp Leu Phe Trp Thr Gly Ile
1               5                   10                  15

Ala

<210> SEQ ID NO 29
<211> LENGTH: 22
<212> TYPE: PRT
<213> ORGANISM: Artificial Sequence
<220> FEATURE:
<223> OTHER INFORMATION: synthetic

<400> SEQUENCE: 29

Arg Arg Ala Pro Gly Lys Leu Thr Cys Leu Ala Ser Tyr Cys Trp Leu
```

```
1               5                   10                  15

Phe Trp Thr Gly Ile Ala
            20

<210> SEQ ID NO 30
<211> LENGTH: 22
<212> TYPE: PRT
<213> ORGANISM: Artificial Sequence
<220> FEATURE:
<223> OTHER INFORMATION: synthetic

<400> SEQUENCE: 30

Arg Arg Ala Pro Gly Lys Leu Gln Cys Leu Ala Ser Tyr Cys Trp Leu
1               5                   10                  15

Phe Trp Thr Gly Leu Ala
            20

<210> SEQ ID NO 31
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (21)..(21)
<223> OTHER INFORMATION: Xaa is Nle

<400> SEQUENCE: 31

Arg Arg Ala Pro Gly Lys Leu Gln Cys Leu Ala Ser Tyr Cys Trp Leu
1               5                   10                  15

Phe Trp Thr Gly Xaa Ala
            20

<210> SEQ ID NO 32
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (21)..(21)
<223> OTHER INFORMATION: Xaa is Tle

<400> SEQUENCE: 32

Arg Arg Ala Pro Gly Lys Leu Gln Cys Leu Ala Ser Tyr Cys Trp Leu
1               5                   10                  15

Phe Trp Thr Gly Xaa Ala
            20

<210> SEQ ID NO 33
<211> LENGTH: 22
<212> TYPE: PRT
<213> ORGANISM: Artificial Sequence
<220> FEATURE:
<223> OTHER INFORMATION: synthetic

<400> SEQUENCE: 33

Arg Arg Ala Pro Gly Lys Leu Gln Cys Leu Ala Ser Tyr Cys Trp Leu
1               5                   10                  15

Phe Trp Thr Gly Phe Ala
            20

<210> SEQ ID NO 34
```

-continued

```
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (21)..(21)
<223> OTHER INFORMATION: Xaa is Cha

<400> SEQUENCE: 34

Arg Arg Ala Pro Gly Lys Leu Gln Cys Leu Ala Ser Tyr Cys Trp Leu
1               5                   10                  15

Phe Trp Thr Gly Xaa Ala
            20

<210> SEQ ID NO 35
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (21)..(21)
<223> OTHER INFORMATION: Xaa is 1-Nal

<400> SEQUENCE: 35

Arg Arg Ala Pro Gly Lys Leu Gln Cys Leu Ala Ser Tyr Cys Trp Leu
1               5                   10                  15

Phe Trp Thr Gly Xaa Ala
            20

<210> SEQ ID NO 36
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (20)..(20)
<223> OTHER INFORMATION: Xaa is Aib

<400> SEQUENCE: 36

Arg Arg Ala Pro Gly Lys Leu Gln Cys Leu Ala Ser Tyr Cys Trp Leu
1               5                   10                  15

Phe Trp Thr Xaa Ile Ala
            20

<210> SEQ ID NO 37
<211> LENGTH: 28
<212> TYPE: PRT
<213> ORGANISM: Artificial Sequence
<220> FEATURE:
<223> OTHER INFORMATION: synthetic

<400> SEQUENCE: 37

Arg Arg Ala Pro Gly Lys Leu Gln Cys Leu Ala Ser Tyr Cys Trp Leu
1               5                   10                  15

Phe Trp Thr Gly Ile Ala Ala Ala Ala Gly Ala Pro
            20                  25

<210> SEQ ID NO 38
<211> LENGTH: 22
<212> TYPE: PRT
<213> ORGANISM: Artificial Sequence
```

<220> FEATURE:
<223> OTHER INFORMATION: synthetic

<400> SEQUENCE: 38

Arg Arg Ala Pro Gly Lys Leu Gln Cys Leu Ala Ser Tyr Cys Trp Leu
1               5                   10                  15

Phe Trp Thr Gly Ile Lys
            20

<210> SEQ ID NO 39
<211> LENGTH: 22
<212> TYPE: PRT
<213> ORGANISM: Artificial Sequence
<220> FEATURE:
<223> OTHER INFORMATION: synthetic

<400> SEQUENCE: 39

Arg Arg Ala Pro Gly Lys Leu Gln Cys Leu Ala Ser Tyr Cys Trp Leu
1               5                   10                  15

Phe Trp Thr Gly Lys Ala
            20

<210> SEQ ID NO 40
<211> LENGTH: 22
<212> TYPE: PRT
<213> ORGANISM: Artificial Sequence
<220> FEATURE:
<223> OTHER INFORMATION: synthetic

<400> SEQUENCE: 40

Arg Arg Ala Pro Gly Lys Leu Gln Cys Leu Ala Ser Tyr Cys Trp Leu
1               5                   10                  15

Phe Trp Thr Lys Ile Ala
            20

<210> SEQ ID NO 41
<211> LENGTH: 22
<212> TYPE: PRT
<213> ORGANISM: Artificial Sequence
<220> FEATURE:
<223> OTHER INFORMATION: synthetic

<400> SEQUENCE: 41

Arg Arg Ala Pro Gly Lys Leu Gln Cys Leu Ala Ser Tyr Cys Trp Leu
1               5                   10                  15

Phe Trp Lys Gly Ile Ala
            20

<210> SEQ ID NO 42
<211> LENGTH: 22
<212> TYPE: PRT
<213> ORGANISM: Artificial Sequence
<220> FEATURE:
<223> OTHER INFORMATION: synthetic

<400> SEQUENCE: 42

Arg Arg Ala Pro Gly Lys Leu Gln Cys Leu Ala Ser Tyr Cys Trp Leu
1               5                   10                  15

Phe Lys Thr Gly Ile Ala
            20

<210> SEQ ID NO 43
<211> LENGTH: 22
<212> TYPE: PRT

<213> ORGANISM: Artificial Sequence
<220> FEATURE:
<223> OTHER INFORMATION: synthetic

<400> SEQUENCE: 43

Arg Arg Ala Pro Lys Lys Leu Gln Cys Leu Ala Ser Tyr Cys Trp Leu
1               5                   10                  15

Phe Trp Thr Gly Ile Ala
            20

<210> SEQ ID NO 44
<211> LENGTH: 22
<212> TYPE: PRT
<213> ORGANISM: Artificial Sequence
<220> FEATURE:
<223> OTHER INFORMATION: synthetic

<400> SEQUENCE: 44

Arg Arg Ala Lys Gly Lys Leu Gln Cys Leu Ala Ser Tyr Cys Trp Leu
1               5                   10                  15

Phe Trp Thr Gly Ile Ala
            20

<210> SEQ ID NO 45
<211> LENGTH: 22
<212> TYPE: PRT
<213> ORGANISM: Artificial Sequence
<220> FEATURE:
<223> OTHER INFORMATION: synthetic

<400> SEQUENCE: 45

Arg Arg Lys Pro Gly Lys Leu Gln Cys Leu Ala Ser Tyr Cys Trp Leu
1               5                   10                  15

Phe Trp Thr Gly Ile Ala
            20

<210> SEQ ID NO 46
<211> LENGTH: 22
<212> TYPE: PRT
<213> ORGANISM: Artificial Sequence
<220> FEATURE:
<223> OTHER INFORMATION: synthetic

<400> SEQUENCE: 46

Arg Lys Ala Pro Gly Lys Leu Gln Cys Leu Ala Ser Tyr Cys Trp Leu
1               5                   10                  15

Phe Trp Thr Gly Ile Ala
            20

<210> SEQ ID NO 47
<211> LENGTH: 22
<212> TYPE: PRT
<213> ORGANISM: Artificial Sequence
<220> FEATURE:
<223> OTHER INFORMATION: synthetic

<400> SEQUENCE: 47

Lys Arg Ala Pro Gly Lys Leu Gln Cys Leu Ala Ser Tyr Cys Trp Leu
1               5                   10                  15

Phe Trp Thr Gly Ile Ala
            20

<210> SEQ ID NO 48
<211> LENGTH: 22

```
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (1)..(1)
<223> OTHER INFORMATION: METHYLATION

<400> SEQUENCE: 48

Arg Arg Ala Pro Gly Lys Leu Thr Cys Leu Ala Ser Tyr Cys Trp Leu
1               5                   10                  15

Phe Trp Thr Gly Ile Ala
            20

<210> SEQ ID NO 49
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (2)..(2)
<223> OTHER INFORMATION: METHYLATION

<400> SEQUENCE: 49

Arg Arg Ala Pro Gly Lys Leu Thr Cys Leu Ala Ser Tyr Cys Trp Leu
1               5                   10                  15

Phe Trp Thr Gly Ile Ala
            20

<210> SEQ ID NO 50
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (3)..(3)
<223> OTHER INFORMATION: METHYLATION

<400> SEQUENCE: 50

Arg Arg Ala Pro Gly Lys Leu Thr Cys Leu Ala Ser Tyr Cys Trp Leu
1               5                   10                  15

Phe Trp Thr Gly Ile Ala
            20

<210> SEQ ID NO 51
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (5)..(5)
<223> OTHER INFORMATION: Xaa is Sar

<400> SEQUENCE: 51

Arg Arg Ala Pro Xaa Lys Leu Thr Cys Leu Ala Ser Tyr Cys Trp Leu
1               5                   10                  15

Phe Trp Thr Gly Ile Ala
            20

<210> SEQ ID NO 52
```

```
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (6)..(6)
<223> OTHER INFORMATION: METHYLATION

<400> SEQUENCE: 52

Arg Arg Ala Pro Gly Lys Leu Thr Cys Leu Ala Ser Tyr Cys Trp Leu
1               5                   10                  15

Phe Trp Thr Gly Ile Ala
            20

<210> SEQ ID NO 53
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (7)..(7)
<223> OTHER INFORMATION: METHYLATION

<400> SEQUENCE: 53

Arg Arg Ala Pro Gly Lys Leu Thr Cys Leu Ala Ser Tyr Cys Trp Leu
1               5                   10                  15

Phe Trp Thr Gly Ile Ala
            20

<210> SEQ ID NO 54
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (8)..(8)
<223> OTHER INFORMATION: METHYLATION

<400> SEQUENCE: 54

Arg Arg Ala Pro Gly Lys Leu Thr Cys Leu Ala Ser Tyr Cys Trp Leu
1               5                   10                  15

Phe Trp Thr Gly Ile Ala
            20

<210> SEQ ID NO 55
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (10)..(10)
<223> OTHER INFORMATION: METHYLATION

<400> SEQUENCE: 55

Arg Arg Ala Pro Gly Lys Leu Thr Cys Leu Ala Ser Tyr Cys Trp Leu
1               5                   10                  15

Phe Trp Thr Gly Ile Ala
            20
```

```
<210> SEQ ID NO 56
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (11)..(11)
<223> OTHER INFORMATION: METHYLATION

<400> SEQUENCE: 56

Arg Arg Ala Pro Gly Lys Leu Thr Cys Leu Ala Ser Tyr Cys Trp Leu
1               5                   10                  15

Phe Trp Thr Gly Ile Ala
            20

<210> SEQ ID NO 57
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (12)..(12)
<223> OTHER INFORMATION: METHYLATION

<400> SEQUENCE: 57

Arg Arg Ala Pro Gly Lys Leu Thr Cys Leu Ala Ser Tyr Cys Trp Leu
1               5                   10                  15

Phe Trp Thr Gly Ile Ala
            20

<210> SEQ ID NO 58
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (13)..(13)
<223> OTHER INFORMATION: METHYLATION

<400> SEQUENCE: 58

Arg Arg Ala Pro Gly Lys Leu Thr Cys Leu Ala Ser Tyr Cys Trp Leu
1               5                   10                  15

Phe Trp Thr Gly Ile Ala
            20

<210> SEQ ID NO 59
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (15)..(15)
<223> OTHER INFORMATION: METHYLATION

<400> SEQUENCE: 59

Arg Arg Ala Pro Gly Lys Leu Thr Cys Leu Ala Ser Tyr Cys Trp Leu
1               5                   10                  15

Phe Trp Thr Gly Ile Ala
            20
```

<210> SEQ ID NO 60
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (16)..(16)
<223> OTHER INFORMATION: METHYLATION

<400> SEQUENCE: 60

Arg Arg Ala Pro Gly Lys Leu Thr Cys Leu Ala Ser Tyr Cys Trp Leu
1               5                   10                  15

Phe Trp Thr Gly Ile Ala
            20

<210> SEQ ID NO 61
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (17)..(17)
<223> OTHER INFORMATION: METHYLATION

<400> SEQUENCE: 61

Arg Arg Ala Pro Gly Lys Leu Thr Cys Leu Ala Ser Tyr Cys Trp Leu
1               5                   10                  15

Phe Trp Thr Gly Ile Ala
            20

<210> SEQ ID NO 62
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (18)..(18)
<223> OTHER INFORMATION: METHYLATION

<400> SEQUENCE: 62

Arg Arg Ala Pro Gly Lys Leu Thr Cys Leu Ala Ser Tyr Cys Trp Leu
1               5                   10                  15

Phe Trp Thr Gly Ile Ala
            20

<210> SEQ ID NO 63
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (19)..(19)
<223> OTHER INFORMATION: METHYLATION

<400> SEQUENCE: 63

Arg Arg Ala Pro Gly Lys Leu Thr Cys Leu Ala Ser Tyr Cys Trp Leu
1               5                   10                  15

Phe Trp Thr Gly Ile Ala
            20

```
<210> SEQ ID NO 64
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (20)..(20)
<223> OTHER INFORMATION: Xaa is Sar

<400> SEQUENCE: 64

Arg Arg Ala Pro Gly Lys Leu Thr Cys Leu Ala Ser Tyr Cys Trp Leu
1               5                   10                  15

Phe Trp Thr Xaa Ile Ala
            20

<210> SEQ ID NO 65
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (21)..(21)
<223> OTHER INFORMATION: METHYLATION

<400> SEQUENCE: 65

Arg Arg Ala Pro Gly Lys Leu Thr Cys Leu Ala Ser Tyr Cys Trp Leu
1               5                   10                  15

Phe Trp Thr Gly Ile Ala
            20

<210> SEQ ID NO 66
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (22)..(22)
<223> OTHER INFORMATION: METHYLATION

<400> SEQUENCE: 66

Arg Arg Ala Pro Gly Lys Leu Thr Cys Leu Ala Ser Tyr Cys Trp Leu
1               5                   10                  15

Phe Trp Thr Gly Ile Ala
            20

<210> SEQ ID NO 67
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 67

Arg Arg Ala Pro Gly Lys Leu Thr Cys Leu Ala Ser Tyr Cys Trp Leu
1               5                   10                  15

Phe Trp Thr Gly Ile Ala
```

```
<210> SEQ ID NO 68
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (2)..(2)
<223> OTHER INFORMATION: D-AMINO ACID

<400> SEQUENCE: 68

Arg Arg Ala Pro Gly Lys Leu Thr Cys Leu Ala Ser Tyr Cys Trp Leu
1               5                   10                  15

Phe Trp Thr Gly Ile Ala
            20

<210> SEQ ID NO 69
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (3)..(3)
<223> OTHER INFORMATION: D-AMINO ACID

<400> SEQUENCE: 69

Arg Arg Ala Pro Gly Lys Leu Thr Cys Leu Ala Ser Tyr Cys Trp Leu
1               5                   10                  15

Phe Trp Thr Gly Ile Ala
            20

<210> SEQ ID NO 70
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (4)..(4)
<223> OTHER INFORMATION: D-AMINO ACID

<400> SEQUENCE: 70

Arg Arg Ala Pro Gly Lys Leu Thr Cys Leu Ala Ser Tyr Cys Trp Leu
1               5                   10                  15

Phe Trp Thr Gly Ile Ala
            20

<210> SEQ ID NO 71
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (6)..(6)
<223> OTHER INFORMATION: D-AMINO ACID

<400> SEQUENCE: 71

Arg Arg Ala Pro Gly Lys Leu Thr Cys Leu Ala Ser Tyr Cys Trp Leu
1               5                   10                  15
```

Phe Trp Thr Gly Ile Ala
            20

<210> SEQ ID NO 72
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (7)..(7)
<223> OTHER INFORMATION: D-AMINO ACID

<400> SEQUENCE: 72

Arg Arg Ala Pro Gly Lys Leu Thr Cys Leu Ala Ser Tyr Cys Trp Leu
1               5                   10                  15

Phe Trp Thr Gly Ile Ala
            20

<210> SEQ ID NO 73
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (8)..(8)
<223> OTHER INFORMATION: D-AMINO ACID

<400> SEQUENCE: 73

Arg Arg Ala Pro Gly Lys Leu Thr Cys Leu Ala Ser Tyr Cys Trp Leu
1               5                   10                  15

Phe Trp Thr Gly Ile Ala
            20

<210> SEQ ID NO 74
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (9)..(9)
<223> OTHER INFORMATION: D-AMINO ACID

<400> SEQUENCE: 74

Arg Arg Ala Pro Gly Lys Leu Thr Cys Leu Ala Ser Tyr Cys Trp Leu
1               5                   10                  15

Phe Trp Thr Gly Ile Ala
            20

<210> SEQ ID NO 75
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (10)..(10)
<223> OTHER INFORMATION: D-AMINO ACID

<400> SEQUENCE: 75

Arg Arg Ala Pro Gly Lys Leu Thr Cys Leu Ala Ser Tyr Cys Trp Leu
1               5                   10                  15

-continued

Phe Trp Thr Gly Ile Ala
            20

<210> SEQ ID NO 76
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (11)..(11)
<223> OTHER INFORMATION: D-AMINO ACID

<400> SEQUENCE: 76

Arg Arg Ala Pro Gly Lys Leu Thr Cys Leu Ala Ser Tyr Cys Trp Leu
1               5                   10                  15

Phe Trp Thr Gly Ile Ala
            20

<210> SEQ ID NO 77
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (12)..(12)
<223> OTHER INFORMATION: D-AMINO ACID

<400> SEQUENCE: 77

Arg Arg Ala Pro Gly Lys Leu Thr Cys Leu Ala Ser Tyr Cys Trp Leu
1               5                   10                  15

Phe Trp Thr Gly Ile Ala
            20

<210> SEQ ID NO 78
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (13)..(13)
<223> OTHER INFORMATION: D-AMINO ACID

<400> SEQUENCE: 78

Arg Arg Ala Pro Gly Lys Leu Thr Cys Leu Ala Ser Tyr Cys Trp Leu
1               5                   10                  15

Phe Trp Thr Gly Ile Ala
            20

<210> SEQ ID NO 79
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (14)..(14)
<223> OTHER INFORMATION: D-AMINO ACID

<400> SEQUENCE: 79

Arg Arg Ala Pro Gly Lys Leu Thr Cys Leu Ala Ser Tyr Cys Trp Leu

```
1               5                   10                  15

Phe Trp Thr Gly Ile Ala
            20

<210> SEQ ID NO 80
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (15)..(15)
<223> OTHER INFORMATION: D-AMINO ACID

<400> SEQUENCE: 80

Arg Arg Ala Pro Gly Lys Leu Thr Cys Leu Ala Ser Tyr Cys Trp Leu
1               5                   10                  15

Phe Trp Thr Gly Ile Ala
            20

<210> SEQ ID NO 81
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (16)..(16)
<223> OTHER INFORMATION: D-AMINO ACID

<400> SEQUENCE: 81

Arg Arg Ala Pro Gly Lys Leu Thr Cys Leu Ala Ser Tyr Cys Trp Leu
1               5                   10                  15

Phe Trp Thr Gly Ile Ala
            20

<210> SEQ ID NO 82
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (17)..(17)
<223> OTHER INFORMATION: D-AMINO ACID

<400> SEQUENCE: 82

Arg Arg Ala Pro Gly Lys Leu Thr Cys Leu Ala Ser Tyr Cys Trp Leu
1               5                   10                  15

Phe Trp Thr Gly Ile Ala
            20

<210> SEQ ID NO 83
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (18)..(18)
<223> OTHER INFORMATION: D-AMINO ACID

<400> SEQUENCE: 83
```

Arg Arg Ala Pro Gly Lys Leu Thr Cys Leu Ala Ser Tyr Cys Trp Leu
1               5                   10                  15

Phe Trp Thr Gly Ile Ala
            20

<210> SEQ ID NO 84
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (19)..(19)
<223> OTHER INFORMATION: D-AMINO ACID

<400> SEQUENCE: 84

Arg Arg Ala Pro Gly Lys Leu Thr Cys Leu Ala Ser Tyr Cys Trp Leu
1               5                   10                  15

Phe Trp Thr Gly Ile Ala
            20

<210> SEQ ID NO 85
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (21)..(21)
<223> OTHER INFORMATION: D-AMINO ACID

<400> SEQUENCE: 85

Arg Arg Ala Pro Gly Lys Leu Thr Cys Leu Ala Ser Tyr Cys Trp Leu
1               5                   10                  15

Phe Trp Thr Gly Ile Ala
            20

<210> SEQ ID NO 86
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (22)..(22)
<223> OTHER INFORMATION: D-AMINO ACID

<400> SEQUENCE: 86

Arg Arg Ala Pro Gly Lys Leu Thr Cys Leu Ala Ser Tyr Cys Trp Leu
1               5                   10                  15

Phe Trp Thr Gly Ile Ala
            20

<210> SEQ ID NO 87
<211> LENGTH: 24
<212> TYPE: PRT
<213> ORGANISM: Artificial Sequence
<220> FEATURE:
<223> OTHER INFORMATION: synthetic

<400> SEQUENCE: 87

Cys Arg Arg Ala Pro Gly Lys Leu Gln Cys Leu Ala Ser Tyr Cys Trp
1               5                   10                  15

Leu Phe Trp Thr Gly Ile Ala Cys
            20

<210> SEQ ID NO 88
<211> LENGTH: 29
<212> TYPE: PRT
<213> ORGANISM: Artificial Sequence
<220> FEATURE:
<223> OTHER INFORMATION: Synthetic

<400> SEQUENCE: 88

Cys Gly Gly Ser Gly Gly Arg Arg Ala Pro Gly Lys Leu Gln Cys Leu
1               5                   10                  15

Ala Ser Tyr Cys Trp Leu Phe Trp Thr Gly Ile Ala Cys
            20                  25

<210> SEQ ID NO 89
<211> LENGTH: 29
<212> TYPE: PRT
<213> ORGANISM: Artificial Sequence
<220> FEATURE:
<223> OTHER INFORMATION: synthetic

<400> SEQUENCE: 89

Cys Arg Arg Ala Pro Gly Lys Leu Gln Cys Leu Ala Ser Tyr Cys Trp
1               5                   10                  15

Leu Phe Trp Thr Gly Ile Ala Gly Gly Ser Gly Gly Cys
            20                  25

<210> SEQ ID NO 90
<211> LENGTH: 34
<212> TYPE: PRT
<213> ORGANISM: Artificial Sequence
<220> FEATURE:
<223> OTHER INFORMATION: synthetic

<400> SEQUENCE: 90

Cys Gly Gly Ser Gly Gly Arg Arg Ala Pro Gly Lys Leu Gln Cys Leu
1               5                   10                  15

Ala Ser Tyr Cys Trp Leu Phe Trp Thr Gly Ile Ala Gly Gly Ser Gly
            20                  25                  30

Gly Cys

<210> SEQ ID NO 91
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (1)..(1)
<223> OTHER INFORMATION: PEG4

<400> SEQUENCE: 91

Arg Arg Ala Pro Gly Lys Leu Thr Cys Leu Ala Ser Tyr Cys Trp Leu
1               5                   10                  15

Phe Trp Thr Gly Ile Ala
            20

<210> SEQ ID NO 92
<211> LENGTH: 22
<212> TYPE: PRT
<213> ORGANISM: Artificial Sequence
<220> FEATURE:

```
<223> OTHER INFORMATION: synthetic
<220> FEATURE:
<221> NAME/KEY: MOD_RES
<222> LOCATION: (1)..(1)
<223> OTHER INFORMATION: BIOTINYL-PEG

<400> SEQUENCE: 92

Glu Arg Ala Pro Gly Lys Leu Thr Cys Leu Ala Ser Tyr Cys Trp Leu
1               5                   10                  15
Phe Trp Thr Gly Ile Ala
            20

<210> SEQ ID NO 93
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (2)..(2)
<223> OTHER INFORMATION: PEG2-BIOTIN

<400> SEQUENCE: 93

Arg Lys Ala Pro Gly Lys Leu Thr Cys Leu Ala Ser Tyr Cys Trp Leu
1               5                   10                  15
Phe Trp Thr Gly Ile Ala
            20

<210> SEQ ID NO 94
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (3)..(3)
<223> OTHER INFORMATION: PEG2-BIOTIN

<400> SEQUENCE: 94

Arg Arg Lys Pro Gly Lys Leu Thr Cys Leu Ala Ser Tyr Cys Trp Leu
1               5                   10                  15
Phe Trp Thr Gly Ile Ala
            20

<210> SEQ ID NO 95
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (4)..(4)
<223> OTHER INFORMATION: PEG2-BIOTIN

<400> SEQUENCE: 95

Arg Arg Ala Lys Gly Lys Leu Thr Cys Leu Ala Ser Tyr Cys Trp Leu
1               5                   10                  15
Phe Trp Thr Gly Ile Ala
            20

<210> SEQ ID NO 96
<211> LENGTH: 22
<212> TYPE: PRT
<213> ORGANISM: Artificial Sequence
```

```
<220> FEATURE:
<223> OTHER INFORMATION: synthetic
<220> FEATURE:
<221> NAME/KEY: MOD_RES
<222> LOCATION: (5)..(5)
<223> OTHER INFORMATION: PEG2-BIOTIN

<400> SEQUENCE: 96

Arg Arg Ala Pro Lys Lys Leu Thr Cys Leu Ala Ser Tyr Cys Trp Leu
1               5                   10                  15

Phe Trp Thr Gly Ile Ala
            20

<210> SEQ ID NO 97
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (6)..(6)
<223> OTHER INFORMATION: PEG2-BIOTIN

<400> SEQUENCE: 97

Arg Arg Ala Pro Gly Lys Leu Thr Cys Leu Ala Ser Tyr Cys Trp Leu
1               5                   10                  15

Phe Trp Thr Gly Ile Ala
            20

<210> SEQ ID NO 98
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (7)..(7)
<223> OTHER INFORMATION: PEG2-BIOTIN

<400> SEQUENCE: 98

Arg Arg Ala Pro Gly Lys Lys Thr Cys Leu Ala Ser Tyr Cys Trp Leu
1               5                   10                  15

Phe Trp Thr Gly Ile Ala
            20

<210> SEQ ID NO 99
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (8)..(8)
<223> OTHER INFORMATION: PEG2-BIOTIN

<400> SEQUENCE: 99

Arg Arg Ala Pro Gly Lys Leu Lys Cys Leu Ala Ser Tyr Cys Trp Leu
1               5                   10                  15

Phe Trp Thr Gly Ile Ala
            20

<210> SEQ ID NO 100
<211> LENGTH: 22
<212> TYPE: PRT
```

```
<213> ORGANISM: Artificial Sequence
<220> FEATURE:
<223> OTHER INFORMATION: synthetic
<220> FEATURE:
<221> NAME/KEY: MOD_RES
<222> LOCATION: (10)..(10)
<223> OTHER INFORMATION: PEG2-BIOTIN

<400> SEQUENCE: 100

Arg Arg Ala Pro Gly Lys Leu Thr Cys Lys Ala Ser Tyr Cys Trp Leu
1               5                   10                  15

Phe Trp Thr Gly Ile Ala
            20

<210> SEQ ID NO 101
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (11)..(11)
<223> OTHER INFORMATION: PEG2-BIOTIN

<400> SEQUENCE: 101

Arg Arg Ala Pro Gly Lys Leu Thr Cys Leu Lys Ser Tyr Cys Trp Leu
1               5                   10                  15

Phe Trp Thr Gly Ile Ala
            20

<210> SEQ ID NO 102
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (12)..(12)
<223> OTHER INFORMATION: PEG2-BIOTIN

<400> SEQUENCE: 102

Arg Arg Ala Pro Gly Lys Leu Thr Cys Leu Ala Lys Tyr Cys Trp Leu
1               5                   10                  15

Phe Trp Thr Gly Ile Ala
            20

<210> SEQ ID NO 103
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (13)..(13)
<223> OTHER INFORMATION: PEG2-BIOTIN

<400> SEQUENCE: 103

Arg Arg Ala Pro Gly Lys Leu Thr Cys Leu Ala Ser Lys Cys Trp Leu
1               5                   10                  15

Phe Trp Thr Gly Ile Ala
            20

<210> SEQ ID NO 104
<211> LENGTH: 22
```

```
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (15)..(15)
<223> OTHER INFORMATION: PEG2-BIOTIN

<400> SEQUENCE: 104
```

Arg Arg Ala Pro Gly Lys Leu Thr Cys Leu Ala Ser Tyr Cys Lys Leu
1               5                   10                  15

Phe Trp Thr Gly Ile Ala
            20

```
<210> SEQ ID NO 105
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (16)..(16)
<223> OTHER INFORMATION: PEG2-BIOTIN

<400> SEQUENCE: 105
```

Arg Arg Ala Pro Gly Lys Leu Thr Cys Leu Ala Ser Tyr Cys Trp Lys
1               5                   10                  15

Phe Trp Thr Gly Ile Ala
            20

```
<210> SEQ ID NO 106
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (17)..(17)
<223> OTHER INFORMATION: PEG2-BIOTIN

<400> SEQUENCE: 106
```

Arg Arg Ala Pro Gly Lys Leu Thr Cys Leu Ala Ser Tyr Cys Trp Leu
1               5                   10                  15

Lys Trp Thr Gly Ile Ala
            20

```
<210> SEQ ID NO 107
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (18)..(18)
<223> OTHER INFORMATION: PEG2-BIOTIN

<400> SEQUENCE: 107
```

Arg Arg Ala Pro Gly Lys Leu Thr Cys Leu Ala Ser Tyr Cys Trp Leu
1               5                   10                  15

Phe Lys Thr Gly Ile Ala
            20

```
<210> SEQ ID NO 108
```

```
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (19)..(19)
<223> OTHER INFORMATION: PEG2-BIOTIN

<400> SEQUENCE: 108

Arg Arg Ala Pro Gly Lys Leu Thr Cys Leu Ala Ser Tyr Cys Trp Leu
1               5                   10                  15

Phe Trp Lys Gly Ile Ala
            20

<210> SEQ ID NO 109
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (20)..(20)
<223> OTHER INFORMATION: PEG2-BIOTIN

<400> SEQUENCE: 109

Arg Arg Ala Pro Gly Lys Leu Thr Cys Leu Ala Ser Tyr Cys Trp Leu
1               5                   10                  15

Phe Trp Thr Lys Ile Ala
            20

<210> SEQ ID NO 110
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (21)..(21)
<223> OTHER INFORMATION: PEG2-BIOTIN

<400> SEQUENCE: 110

Arg Arg Ala Pro Gly Lys Leu Thr Cys Leu Ala Ser Tyr Cys Trp Leu
1               5                   10                  15

Phe Trp Thr Gly Lys Ala
            20

<210> SEQ ID NO 111
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (22)..(22)
<223> OTHER INFORMATION: PEG2-BIOTIN

<400> SEQUENCE: 111

Arg Arg Ala Pro Gly Lys Leu Thr Cys Leu Ala Ser Tyr Cys Trp Leu
1               5                   10                  15

Phe Trp Thr Gly Ile Lys
            20
```

```
<210> SEQ ID NO 112
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (22)..(22)
<223> OTHER INFORMATION: PEG4

<400> SEQUENCE: 112

Arg Arg Ala Pro Gly Lys Leu Thr Cys Leu Ala Ser Tyr Cys Trp Leu
1               5                   10                  15

Phe Trp Thr Gly Ile Ala
            20

<210> SEQ ID NO 113
<211> LENGTH: 32
<212> TYPE: PRT
<213> ORGANISM: Artificial Sequence
<220> FEATURE:
<223> OTHER INFORMATION: synthetic

<400> SEQUENCE: 113

Gln Trp Gln Ile Ala Gly Gln Val Leu Lys Arg Arg Ala Pro Ala Lys
1               5                   10                  15

Leu Thr Cys Leu Ala Ser Tyr Cys Trp Leu Phe Trp Thr Gly Ile Ala
            20                  25                  30

<210> SEQ ID NO 114
<211> LENGTH: 32
<212> TYPE: PRT
<213> ORGANISM: Artificial Sequence
<220> FEATURE:
<223> OTHER INFORMATION: synthetic

<400> SEQUENCE: 114

Leu Gln Leu Ser Tyr Gly Glu Gln Arg Gln Ser Arg Ala Pro Gly Lys
1               5                   10                  15

Leu Thr Cys Leu Ala Ser Tyr Cys Trp Leu Phe Trp Thr Gly Ile Ala
            20                  25                  30

<210> SEQ ID NO 115
<211> LENGTH: 32
<212> TYPE: PRT
<213> ORGANISM: Artificial Sequence
<220> FEATURE:
<223> OTHER INFORMATION: synthetic

<400> SEQUENCE: 115

Trp Met Ser Ala Glu Gly Ile Val Gly Val Arg Arg Ala Thr Gly Lys
1               5                   10                  15

Leu Thr Cys Leu Ala Ser Tyr Cys Trp Leu Phe Trp Thr Gly Ile Ala
            20                  25                  30

<210> SEQ ID NO 116
<211> LENGTH: 32
<212> TYPE: PRT
<213> ORGANISM: Artificial Sequence
<220> FEATURE:
<223> OTHER INFORMATION: synthetic

<400> SEQUENCE: 116

Thr Ser Gly Pro Phe Gly Phe Gly Gly Ser Ser Arg Ala Gln Gly Lys
1               5                   10                  15
```

```
Leu Thr Cys Leu Ala Ser Tyr Cys Trp Leu Phe Trp Thr Gly Ile Ala
            20                  25                  30
```

<210> SEQ ID NO 117
<211> LENGTH: 32
<212> TYPE: PRT
<213> ORGANISM: Artificial Sequence
<220> FEATURE:
<223> OTHER INFORMATION: synthetic

<400> SEQUENCE: 117

```
His Leu Phe Gly Ala Asp Trp Leu Gly Ala Arg Thr Ala Pro Gly Lys
1               5                   10                  15

Leu Thr Cys Leu Ala Ser Tyr Cys Trp Leu Phe Trp Thr Gly Ile Ala
            20                  25                  30
```

<210> SEQ ID NO 118
<211> LENGTH: 32
<212> TYPE: PRT
<213> ORGANISM: Artificial Sequence
<220> FEATURE:
<223> OTHER INFORMATION: synthetic

<400> SEQUENCE: 118

```
Gln Arg Ala Gly Arg Val Ala Arg Leu His Arg Arg Ala Pro Asn Lys
1               5                   10                  15

Leu Thr Cys Leu Ala Ser Tyr Cys Trp Leu Phe Trp Thr Gly Ile Ala
            20                  25                  30
```

<210> SEQ ID NO 119
<211> LENGTH: 32
<212> TYPE: PRT
<213> ORGANISM: Artificial Sequence
<220> FEATURE:
<223> OTHER INFORMATION: synthetic

<400> SEQUENCE: 119

```
Trp Arg Ala Gly Leu Asp Glu Ser Gln Arg Asp Arg Ala Pro Gly Lys
1               5                   10                  15

Leu Thr Cys Leu Ala Ser Tyr Cys Trp Leu Phe Trp Thr Gly Ile Ala
            20                  25                  30
```

<210> SEQ ID NO 120
<211> LENGTH: 32
<212> TYPE: PRT
<213> ORGANISM: Artificial Sequence
<220> FEATURE:
<223> OTHER INFORMATION: synthetic

<400> SEQUENCE: 120

```
Pro Ser Gly Trp Ala Gly Trp Ala Pro Gly Arg Arg Glu Pro Gly Lys
1               5                   10                  15

Leu Thr Cys Leu Ala Ser Tyr Cys Trp Leu Phe Trp Thr Gly Ile Ala
            20                  25                  30
```

<210> SEQ ID NO 121
<211> LENGTH: 32
<212> TYPE: PRT
<213> ORGANISM: Artificial Sequence
<220> FEATURE:
<223> OTHER INFORMATION: synthetic

<400> SEQUENCE: 121

```
Ala Val Asp Ser Leu Pro Leu Tyr Gly Ala Arg Ser Ala Pro Ser Lys
```

```
                1               5                   10                  15
Leu Thr Cys Leu Ala Ser Tyr Cys Trp Leu Phe Trp Thr Gly Ile Ala
                20                  25                  30
```

<210> SEQ ID NO 122
<211> LENGTH: 32
<212> TYPE: PRT
<213> ORGANISM: Artificial Sequence
<220> FEATURE:
<223> OTHER INFORMATION: synthetic

<400> SEQUENCE: 122

```
Ala Ser Val Trp Gly Ala Leu Ala Leu Val Arg Arg Ala Ser Gly Lys
1               5                   10                  15
Leu Thr Cys Leu Ala Ser Tyr Cys Trp Leu Phe Trp Thr Gly Ile Ala
                20                  25                  30
```

<210> SEQ ID NO 123
<211> LENGTH: 32
<212> TYPE: PRT
<213> ORGANISM: Artificial Sequence
<220> FEATURE:
<223> OTHER INFORMATION: synthetic

<400> SEQUENCE: 123

```
Gly Tyr Arg Val Pro Val Gly Leu Val Arg Arg Ala His Gly Lys
1               5                   10                  15
Leu Thr Cys Leu Ala Ser Tyr Cys Trp Leu Phe Trp Thr Gly Ile Ala
                20                  25                  30
```

<210> SEQ ID NO 124
<211> LENGTH: 32
<212> TYPE: PRT
<213> ORGANISM: Artificial Sequence
<220> FEATURE:
<223> OTHER INFORMATION: synthetic

<400> SEQUENCE: 124

```
Thr Gln Trp Ala Gln Val Gly Pro Arg Gly Arg Arg Ala Gln Gly Lys
1               5                   10                  15
Leu Thr Cys Leu Ala Ser Tyr Cys Trp Leu Phe Trp Thr Gly Ile Ala
                20                  25                  30
```

<210> SEQ ID NO 125
<211> LENGTH: 32
<212> TYPE: PRT
<213> ORGANISM: Artificial Sequence
<220> FEATURE:
<223> OTHER INFORMATION: synthetic

<400> SEQUENCE: 125

```
Val Gly Ser Gly Asp Glu Arg Ala Leu Pro Ser Arg Ala Ser Gly Lys
1               5                   10                  15
Leu Thr Cys Leu Ala Ser Tyr Cys Trp Leu Phe Trp Thr Gly Ile Ala
                20                  25                  30
```

<210> SEQ ID NO 126
<211> LENGTH: 32
<212> TYPE: PRT
<213> ORGANISM: Artificial Sequence
<220> FEATURE:
<223> OTHER INFORMATION: synthetic

<400> SEQUENCE: 126

Thr Leu Trp Pro Trp Gly Gly Gln Gly Gly Arg Asn Ala Pro Gly Lys
1               5                   10                  15

Leu Thr Cys Leu Ala Ser Tyr Cys Trp Leu Phe Trp Thr Gly Ile Ala
            20                  25                  30

<210> SEQ ID NO 127
<211> LENGTH: 32
<212> TYPE: PRT
<213> ORGANISM: Artificial Sequence
<220> FEATURE:
<223> OTHER INFORMATION: synthetic

<400> SEQUENCE: 127

Thr Gly Leu Leu Gln Gly Arg Arg Asp Glu Arg Ala Arg Pro Pro Lys
1               5                   10                  15

Leu Thr Cys Leu Ala Ser Tyr Cys Trp Leu Phe Trp Thr Gly Ile Ala
            20                  25                  30

<210> SEQ ID NO 128
<211> LENGTH: 32
<212> TYPE: PRT
<213> ORGANISM: Artificial Sequence
<220> FEATURE:
<223> OTHER INFORMATION: synthetic

<400> SEQUENCE: 128

Arg Gly Gly Phe Phe Val Trp Phe Leu Ser Arg Ile Ala Pro Gly Lys
1               5                   10                  15

Leu Thr Cys Leu Ala Ser Tyr Cys Trp Leu Phe Trp Thr Gly Ile Ala
            20                  25                  30

<210> SEQ ID NO 129
<211> LENGTH: 32
<212> TYPE: PRT
<213> ORGANISM: Artificial Sequence
<220> FEATURE:
<223> OTHER INFORMATION: synthetic

<400> SEQUENCE: 129

Arg Arg Ala Pro Gly Lys Leu Thr Cys Leu Ala Ser Tyr Cys Trp Leu
1               5                   10                  15

Phe Ser Thr Gly Val Ala Thr His Ala Asn Thr Thr Ala Thr Ala Gln
            20                  25                  30

<210> SEQ ID NO 130
<211> LENGTH: 32
<212> TYPE: PRT
<213> ORGANISM: Artificial Sequence
<220> FEATURE:
<223> OTHER INFORMATION: synthetic

<400> SEQUENCE: 130

Arg Arg Ala Pro Gly Lys Leu Thr Cys Leu Ala Ser Tyr Cys Trp Leu
1               5                   10                  15

Phe Trp Ala Gly Phe Ala Ala Ser Thr Leu Ala Pro Ala His His Gln
            20                  25                  30

<210> SEQ ID NO 131
<211> LENGTH: 32
<212> TYPE: PRT
<213> ORGANISM: Artificial Sequence
<220> FEATURE:
<223> OTHER INFORMATION: synthetic

<400> SEQUENCE: 131

Arg Arg Ala Pro Gly Lys Leu Thr Cys Leu Ala Ser Tyr Cys Trp Leu
1               5                   10                  15

Phe Trp Ser Gly Phe Ala Ser Leu Gly Gly Leu Leu Trp Pro Val Ala
            20                  25                  30

<210> SEQ ID NO 132
<211> LENGTH: 32
<212> TYPE: PRT
<213> ORGANISM: Artificial Sequence
<220> FEATURE:
<223> OTHER INFORMATION: synthetic

<400> SEQUENCE: 132

Arg Arg Ala Pro Gly Lys Leu Thr Cys Leu Ala Ser Tyr Cys Trp Leu
1               5                   10                  15

Phe Trp Thr Gly Tyr Ala Ser Gly Lys Pro Ser Arg Val Tyr Val Ile
            20                  25                  30

<210> SEQ ID NO 133
<211> LENGTH: 32
<212> TYPE: PRT
<213> ORGANISM: Artificial Sequence
<220> FEATURE:
<223> OTHER INFORMATION: synthetic

<400> SEQUENCE: 133

Arg Arg Ala Pro Gly Lys Leu Thr Cys Leu Ala Ser Tyr Cys Trp Leu
1               5                   10                  15

Phe Trp Thr Gly Leu Ser Arg Tyr Gln Trp Gln Ala Gln Glu Asp Val
            20                  25                  30

<210> SEQ ID NO 134
<211> LENGTH: 32
<212> TYPE: PRT
<213> ORGANISM: Artificial Sequence
<220> FEATURE:
<223> OTHER INFORMATION: synthetic

<400> SEQUENCE: 134

Arg Arg Ala Pro Gly Lys Leu Thr Cys Leu Ala Ser Tyr Cys Trp Leu
1               5                   10                  15

Phe Gly Ser Gly Ile Ser Leu Ser Arg Ala Pro Glu Ser Ala Ala Pro
            20                  25                  30

<210> SEQ ID NO 135
<211> LENGTH: 32
<212> TYPE: PRT
<213> ORGANISM: Artificial Sequence
<220> FEATURE:
<223> OTHER INFORMATION: synthetic

<400> SEQUENCE: 135

Arg Arg Ala Pro Gly Lys Leu Thr Cys Leu Ala Ser Tyr Cys Trp Leu
1               5                   10                  15

Phe Trp Thr Gly Trp Ala Val Leu Ala Arg Val Pro Val Gly Trp Thr
            20                  25                  30

<210> SEQ ID NO 136
<211> LENGTH: 32
<212> TYPE: PRT
<213> ORGANISM: Artificial Sequence
<220> FEATURE:
<223> OTHER INFORMATION: synthetic

<400> SEQUENCE: 136

Arg Arg Ala Pro Gly Lys Leu Thr Cys Leu Ala Ser Tyr Cys Trp Leu
1               5                   10                  15

Phe Trp Thr Gly Leu Ala Pro Gly Arg Gly Gln Gly Gly Val Ala Gly
            20                  25                  30

<210> SEQ ID NO 137
<211> LENGTH: 32
<212> TYPE: PRT
<213> ORGANISM: Artificial Sequence
<220> FEATURE:
<223> OTHER INFORMATION: synthetic

<400> SEQUENCE: 137

Arg Arg Ala Pro Gly Lys Leu Thr Cys Leu Ala Ser Tyr Cys Trp Leu
1               5                   10                  15

Phe Trp Thr Gly Ile Ala Asp Arg Leu Val Trp Gly Val Ile Ser Thr
            20                  25                  30

<210> SEQ ID NO 138
<211> LENGTH: 32
<212> TYPE: PRT
<213> ORGANISM: Artificial Sequence
<220> FEATURE:
<223> OTHER INFORMATION: synthetic

<400> SEQUENCE: 138

Arg Arg Ala Pro Gly Lys Leu Thr Cys Leu Ala Ser Tyr Cys Trp Leu
1               5                   10                  15

Phe Trp Thr Gly Phe Ala Phe Arg Val Gly Leu Ala Ser Ser Leu Tyr
            20                  25                  30

<210> SEQ ID NO 139
<211> LENGTH: 32
<212> TYPE: PRT
<213> ORGANISM: Artificial Sequence
<220> FEATURE:
<223> OTHER INFORMATION: synthetic

<400> SEQUENCE: 139

Arg Arg Ala Pro Gly Lys Leu Thr Cys Leu Ala Ser Tyr Cys Trp Leu
1               5                   10                  15

Phe Trp Thr Gly Leu Ala Ser Thr Leu Tyr Lys Thr Tyr Thr Arg Glu
            20                  25                  30

<210> SEQ ID NO 140
<211> LENGTH: 32
<212> TYPE: PRT
<213> ORGANISM: Artificial Sequence
<220> FEATURE:
<223> OTHER INFORMATION: synthetic

<400> SEQUENCE: 140

Arg Arg Ala Pro Gly Lys Leu Thr Cys Leu Ala Ser Tyr Cys Trp Leu
1               5                   10                  15

Phe Arg Thr Gln Ile Ala Thr Pro Glu Ser Glu Tyr Arg Gln Gln Ala
            20                  25                  30

<210> SEQ ID NO 141
<211> LENGTH: 32
<212> TYPE: PRT
<213> ORGANISM: Artificial Sequence
<220> FEATURE:
<223> OTHER INFORMATION: synthetic

<400> SEQUENCE: 141

Arg Arg Ala Pro Gly Lys Leu Thr Cys Leu Ala Ser Tyr Cys Trp Leu
1               5                   10                  15

Phe Trp Ala Gly Tyr Pro Ser Leu Arg Gly Ser Leu Leu Val Gly Val
            20                  25                  30

<210> SEQ ID NO 142
<211> LENGTH: 32
<212> TYPE: PRT
<213> ORGANISM: Artificial Sequence
<220> FEATURE:
<223> OTHER INFORMATION: synthetic

<400> SEQUENCE: 142

Arg Arg Ala Pro Gly Lys Leu Thr Cys Leu Ala Ser Tyr Cys Trp Leu
1               5                   10                  15

Phe Gln Thr Gly Trp Ala Tyr Trp Gly Tyr Arg Gln His Pro Gly Ser
            20                  25                  30

<210> SEQ ID NO 143
<211> LENGTH: 32
<212> TYPE: PRT
<213> ORGANISM: Artificial Sequence
<220> FEATURE:
<223> OTHER INFORMATION: synthetic

<400> SEQUENCE: 143

Arg Arg Ala Pro Gly Lys Leu Thr Cys Leu Ala Ser Tyr Cys Trp Leu
1               5                   10                  15

Phe Trp Thr Gly Trp Cys Arg Asp Thr Ala Ser His Ala Cys Asp Ser
            20                  25                  30

<210> SEQ ID NO 144
<211> LENGTH: 32
<212> TYPE: PRT
<213> ORGANISM: Artificial Sequence
<220> FEATURE:
<223> OTHER INFORMATION: synthetic

<400> SEQUENCE: 144

Arg Arg Ala Pro Gly Lys Leu Thr Cys Leu Ala Ser Tyr Cys Trp Leu
1               5                   10                  15

Phe Trp Thr Gly Trp Ser Arg Asp Thr Ala Ser His Ala Ser Asp Ser
            20                  25                  30

<210> SEQ ID NO 145
<211> LENGTH: 32
<212> TYPE: PRT
<213> ORGANISM: Artificial Sequence
<220> FEATURE:
<223> OTHER INFORMATION: synthetic

<400> SEQUENCE: 145

Arg Arg Ala Pro Gly Lys Leu Thr Cys Leu Ala Ser Tyr Cys Trp Leu
1               5                   10                  15

Phe Trp Arg Gly Phe Ala Glu Arg Ala Ser Glu Asp Thr Asn Gln Gly
            20                  25                  30

<210> SEQ ID NO 146
<211> LENGTH: 32
<212> TYPE: PRT
<213> ORGANISM: Artificial Sequence
<220> FEATURE:

<223> OTHER INFORMATION: synthetic

<400> SEQUENCE: 146

Arg Arg Ala Pro Gly Lys Leu Thr Cys Leu Ala Ser Tyr Cys Trp Leu
1               5                   10                  15

Phe Glu Pro Gly Ile Ala Gln Pro Tyr Ala Lys Ser Pro Thr Arg Asn
            20                  25                  30

<210> SEQ ID NO 147
<211> LENGTH: 32
<212> TYPE: PRT
<213> ORGANISM: Artificial Sequence
<220> FEATURE:
<223> OTHER INFORMATION: synthetic

<400> SEQUENCE: 147

Arg Arg Ala Pro Gly Lys Leu Thr Cys Leu Ala Ser Tyr Cys Trp Leu
1               5                   10                  15

Phe Ser Thr Pro Val Ala Arg Lys Ser Leu Arg Arg His Gln Pro Thr
            20                  25                  30

<210> SEQ ID NO 148
<211> LENGTH: 32
<212> TYPE: PRT
<213> ORGANISM: Artificial Sequence
<220> FEATURE:
<223> OTHER INFORMATION: synthetic

<400> SEQUENCE: 148

Pro Arg Ile Arg Thr Val Gly Pro Gly Ser Arg Ser Ala Ser Gly Lys
1               5                   10                  15

Leu Thr Cys Leu Ala Ser Tyr Cys Trp Leu Phe Trp Thr Gly Ile Ala
            20                  25                  30

<210> SEQ ID NO 149
<211> LENGTH: 32
<212> TYPE: PRT
<213> ORGANISM: Artificial Sequence
<220> FEATURE:
<223> OTHER INFORMATION: synthetic

<400> SEQUENCE: 149

Pro Thr Asp Thr Gly Pro Val Ile Ser Gly Leu Arg Ala Pro Gly Lys
1               5                   10                  15

Leu Thr Cys Leu Ala Ser Tyr Cys Trp Leu Phe Trp Thr Gly Ile Ala
            20                  25                  30

<210> SEQ ID NO 150
<211> LENGTH: 32
<212> TYPE: PRT
<213> ORGANISM: Artificial Sequence
<220> FEATURE:
<223> OTHER INFORMATION: synthetic

<400> SEQUENCE: 150

Gly Ser Val Arg Arg Ala Leu Phe Val Ala Ala Arg Ala Pro Ala Lys
1               5                   10                  15

Leu Thr Cys Leu Ala Ser Tyr Cys Trp Leu Phe Trp Thr Gly Ile Ala
            20                  25                  30

<210> SEQ ID NO 151
<211> LENGTH: 32
<212> TYPE: PRT
<213> ORGANISM: Artificial Sequence

```
<220> FEATURE:
<223> OTHER INFORMATION: synthetic

<400> SEQUENCE: 151

Arg Arg Phe Val Gly Gly Ser Leu Ser Gln Arg Arg Ala Pro Gly Lys
1               5                   10                  15

Leu Thr Cys Leu Ala Ser Tyr Cys Trp Leu Phe Trp Thr Gly Ile Ala
            20                  25                  30

<210> SEQ ID NO 152
<211> LENGTH: 32
<212> TYPE: PRT
<213> ORGANISM: Artificial Sequence
<220> FEATURE:
<223> OTHER INFORMATION: synthetic

<400> SEQUENCE: 152

Ser Lys Gln Gly Arg Pro Ile Ser Pro Asp Arg Arg Ala Ala Gly Lys
1               5                   10                  15

Leu Thr Cys Leu Ala Ser Tyr Cys Trp Leu Phe Trp Thr Gly Ile Ala
            20                  25                  30

<210> SEQ ID NO 153
<211> LENGTH: 32
<212> TYPE: PRT
<213> ORGANISM: Artificial Sequence
<220> FEATURE:
<223> OTHER INFORMATION: synthetic

<400> SEQUENCE: 153

Arg Pro Arg Ser Ser Ala His Asp Arg Pro Arg Ala Ala Gly Lys
1               5                   10                  15

Leu Thr Cys Leu Ala Ser Tyr Cys Trp Leu Phe Trp Thr Gly Ile Ala
            20                  25                  30

<210> SEQ ID NO 154
<211> LENGTH: 32
<212> TYPE: PRT
<213> ORGANISM: Artificial Sequence
<220> FEATURE:
<223> OTHER INFORMATION: synthetic

<400> SEQUENCE: 154

Thr Ala Leu Ser Arg Gly Leu Val Thr Met Arg Thr Ala Pro Asp Lys
1               5                   10                  15

Leu Thr Cys Leu Ala Ser Tyr Cys Trp Leu Phe Trp Thr Gly Ile Ala
            20                  25                  30

<210> SEQ ID NO 155
<211> LENGTH: 32
<212> TYPE: PRT
<213> ORGANISM: Artificial Sequence
<220> FEATURE:
<223> OTHER INFORMATION: synthetic

<400> SEQUENCE: 155

Pro Ala Arg Gly Lys Glu Arg Glu Leu Met Arg Arg Ala Pro Gly Lys
1               5                   10                  15

Leu Thr Cys Leu Ala Ser Tyr Cys Trp Leu Phe Trp Thr Gly Ile Ala
            20                  25                  30

<210> SEQ ID NO 156
<211> LENGTH: 32
<212> TYPE: PRT
```

<210> SEQ ID NO 156
<211> LENGTH: 32
<212> TYPE: PRT
<213> ORGANISM: Artificial Sequence
<220> FEATURE:
<223> OTHER INFORMATION: synthetic

<400> SEQUENCE: 156

Gly Arg Ala Met Ala Ala Glu Pro Trp Pro Arg Gln Ala Pro Gly Lys
1               5                   10                  15

Leu Thr Cys Leu Ala Ser Tyr Cys Trp Leu Phe Trp Thr Gly Ile Ala
            20                  25                  30

<210> SEQ ID NO 157
<211> LENGTH: 32
<212> TYPE: PRT
<213> ORGANISM: Artificial Sequence
<220> FEATURE:
<223> OTHER INFORMATION: synthetic

<400> SEQUENCE: 157

Leu Tyr Pro Arg Leu Tyr Thr Pro Gly Ser Arg Arg Ala Tyr Gly Lys
1               5                   10                  15

Leu Thr Cys Leu Ala Ser Tyr Cys Trp Leu Phe Trp Thr Gly Ile Ala
            20                  25                  30

<210> SEQ ID NO 158
<211> LENGTH: 32
<212> TYPE: PRT
<213> ORGANISM: Artificial Sequence
<220> FEATURE:
<223> OTHER INFORMATION: synthetic

<400> SEQUENCE: 158

Ala Gln Trp Val Gly Arg Gly Gln Trp Ala Ile Arg Ala Pro Gly Lys
1               5                   10                  15

Leu Thr Cys Leu Ala Ser Tyr Cys Trp Leu Phe Trp Thr Gly Ile Ala
            20                  25                  30

<210> SEQ ID NO 159
<211> LENGTH: 32
<212> TYPE: PRT
<213> ORGANISM: Artificial Sequence
<220> FEATURE:
<223> OTHER INFORMATION: synthetic

<400> SEQUENCE: 159

Met Gln Ile Arg Gln Ala His Gln Pro Arg Arg Ser Ala Pro Gln Lys
1               5                   10                  15

Leu Thr Cys Leu Ala Ser Tyr Cys Trp Leu Phe Trp Thr Gly Ile Ala
            20                  25                  30

<210> SEQ ID NO 160
<211> LENGTH: 32
<212> TYPE: PRT
<213> ORGANISM: Artificial Sequence
<220> FEATURE:
<223> OTHER INFORMATION: synthetic

<400> SEQUENCE: 160

Pro Arg Thr Thr Ala Asn Arg Arg Ser Ser Arg Arg Ala Pro Ala Lys
1               5                   10                  15

Leu Thr Cys Leu Ala Ser Tyr Cys Trp Leu Phe Trp Thr Gly Ile Ala
            20                  25                  30

<210> SEQ ID NO 161
<211> LENGTH: 32

<212> TYPE: PRT
<213> ORGANISM: Artificial Sequence
<220> FEATURE:
<223> OTHER INFORMATION: synthetic

<400> SEQUENCE: 161

Pro Asn Leu Leu Arg Val Arg Thr Ser Glu Val Arg Asn Pro Gly Lys
1               5                   10                  15

Leu Thr Cys Leu Ala Ser Tyr Cys Trp Leu Phe Trp Thr Gly Ile Ala
            20                  25                  30

<210> SEQ ID NO 162
<211> LENGTH: 32
<212> TYPE: PRT
<213> ORGANISM: Artificial Sequence
<220> FEATURE:
<223> OTHER INFORMATION: synthetic

<400> SEQUENCE: 162

Ser Leu Ile Ser Met Thr Asn Pro Ser Gly Arg Arg Val Pro Gly Lys
1               5                   10                  15

Leu Thr Cys Leu Ala Ser Tyr Cys Trp Leu Phe Trp Thr Gly Ile Ala
            20                  25                  30

<210> SEQ ID NO 163
<211> LENGTH: 32
<212> TYPE: PRT
<213> ORGANISM: Artificial Sequence
<220> FEATURE:
<223> OTHER INFORMATION: synthetic

<400> SEQUENCE: 163

Asn Gly Ala Leu Gly Phe Arg Ser Val Val Pro Arg Ala Ala Gly Lys
1               5                   10                  15

Leu Thr Cys Leu Ala Ser Tyr Cys Trp Leu Phe Trp Thr Gly Ile Ala
            20                  25                  30

<210> SEQ ID NO 164
<211> LENGTH: 32
<212> TYPE: PRT
<213> ORGANISM: Artificial Sequence
<220> FEATURE:
<223> OTHER INFORMATION: synthetic

<400> SEQUENCE: 164

Arg Ser His Ser Leu Asp Arg Met Ala Gly Arg Arg Ala Pro Gly Lys
1               5                   10                  15

Leu Thr Cys Leu Ala Ser Tyr Cys Trp Leu Phe Trp Thr Gly Ile Ala
            20                  25                  30

<210> SEQ ID NO 165
<211> LENGTH: 32
<212> TYPE: PRT
<213> ORGANISM: Artificial Sequence
<220> FEATURE:
<223> OTHER INFORMATION: synthetic

<400> SEQUENCE: 165

Ala Val Val Arg Gly Gln Glu Pro Thr His Arg Arg Thr Pro Gly Lys
1               5                   10                  15

Leu Thr Cys Leu Ala Ser Tyr Cys Trp Leu Phe Trp Thr Gly Ile Ala
            20                  25                  30

<210> SEQ ID NO 166

```
<211> LENGTH: 32
<212> TYPE: PRT
<213> ORGANISM: Artificial Sequence
<220> FEATURE:
<223> OTHER INFORMATION: synthetic

<400> SEQUENCE: 166

Pro Gln Thr Arg Asp Pro Ser Ser Arg Asp Arg Ala Pro Gly Lys
1               5                   10                  15

Leu Thr Cys Leu Ala Ser Tyr Cys Trp Leu Phe Trp Thr Gly Ile Ala
            20                  25                  30

<210> SEQ ID NO 167
<211> LENGTH: 32
<212> TYPE: PRT
<213> ORGANISM: Artificial Sequence
<220> FEATURE:
<223> OTHER INFORMATION: synthetic

<400> SEQUENCE: 167

Arg Arg Ala Pro Gly Lys Leu Thr Cys Leu Ala Ser Tyr Cys Trp Leu
1               5                   10                  15

Phe Leu Gly Gly Ile Ala Pro Glu Gly Ala Ser Thr Arg Thr Ala Asn
            20                  25                  30

<210> SEQ ID NO 168
<211> LENGTH: 32
<212> TYPE: PRT
<213> ORGANISM: Artificial Sequence
<220> FEATURE:
<223> OTHER INFORMATION: synthetic

<400> SEQUENCE: 168

Arg Arg Ala Pro Gly Lys Leu Thr Cys Leu Ala Ser Tyr Cys Trp Leu
1               5                   10                  15

Phe Val Thr Gly Thr Ala His Ala Pro Arg Val Ala Pro Ala Pro Ala
            20                  25                  30

<210> SEQ ID NO 169
<211> LENGTH: 32
<212> TYPE: PRT
<213> ORGANISM: Artificial Sequence
<220> FEATURE:
<223> OTHER INFORMATION: synthetic

<400> SEQUENCE: 169

Arg Arg Ala Pro Gly Lys Leu Thr Cys Leu Ala Ser Tyr Cys Trp Leu
1               5                   10                  15

Phe Trp Thr Ala Val Gly Gly Gln Pro Tyr Met Leu Leu Ala Trp Arg
            20                  25                  30

<210> SEQ ID NO 170
<211> LENGTH: 32
<212> TYPE: PRT
<213> ORGANISM: Artificial Sequence
<220> FEATURE:
<223> OTHER INFORMATION: synthetic

<400> SEQUENCE: 170

Arg Arg Ala Pro Gly Lys Leu Thr Cys Leu Ala Ser Tyr Cys Trp Leu
1               5                   10                  15

Phe Trp Ala Gly Ile Ala Pro His Arg Pro Leu Lys Glu Arg Val Arg
            20                  25                  30
```

-continued

<210> SEQ ID NO 171
<211> LENGTH: 32
<212> TYPE: PRT
<213> ORGANISM: Artificial Sequence
<220> FEATURE:
<223> OTHER INFORMATION: synthetic

<400> SEQUENCE: 171

Arg Arg Ala Pro Gly Lys Leu Thr Cys Leu Ala Ser Tyr Cys Trp Leu
1               5                   10                  15

Phe Trp Ala Val Ile Ala Pro Pro Lys Val Lys Gly Thr Arg Gln Ser
            20                  25                  30

<210> SEQ ID NO 172
<211> LENGTH: 32
<212> TYPE: PRT
<213> ORGANISM: Artificial Sequence
<220> FEATURE:
<223> OTHER INFORMATION: synthetic

<400> SEQUENCE: 172

Arg Arg Ala Pro Gly Lys Leu Thr Cys Leu Ala Ser Tyr Cys Trp Leu
1               5                   10                  15

Phe Ala Thr Gly Val Thr Phe Pro Gln Ile Trp Ala Ile Pro Ser Pro
            20                  25                  30

<210> SEQ ID NO 173
<211> LENGTH: 32
<212> TYPE: PRT
<213> ORGANISM: Artificial Sequence
<220> FEATURE:
<223> OTHER INFORMATION: synthetic

<400> SEQUENCE: 173

Arg Arg Ala Pro Gly Lys Leu Thr Cys Leu Ala Ser Tyr Cys Trp Leu
1               5                   10                  15

Phe Tyr Thr Gly Ile Ala His Gly His Pro Met Glu His Arg Lys Ser
            20                  25                  30

<210> SEQ ID NO 174
<211> LENGTH: 32
<212> TYPE: PRT
<213> ORGANISM: Artificial Sequence
<220> FEATURE:
<223> OTHER INFORMATION: synthetic

<400> SEQUENCE: 174

Arg Arg Ala Pro Gly Lys Leu Thr Cys Leu Ala Ser Tyr Cys Trp Leu
1               5                   10                  15

Phe Leu Thr Gly Trp Ala Arg Val Pro Leu Pro Pro Arg Pro His Pro
            20                  25                  30

<210> SEQ ID NO 175
<211> LENGTH: 32
<212> TYPE: PRT
<213> ORGANISM: Artificial Sequence
<220> FEATURE:
<223> OTHER INFORMATION: synthetic

<400> SEQUENCE: 175

Arg Arg Ala Pro Gly Lys Leu Thr Cys Leu Ala Ser Tyr Cys Trp Leu
1               5                   10                  15

Phe Trp Thr Gly Ile Ala Arg Trp Pro Ser His Arg Ser Gly Pro Ser
            20                  25                  30

<210> SEQ ID NO 176
<211> LENGTH: 32
<212> TYPE: PRT
<213> ORGANISM: Artificial Sequence
<220> FEATURE:
<223> OTHER INFORMATION: synthetic

<400> SEQUENCE: 176

Arg Arg Ala Pro Gly Lys Leu Thr Cys Leu Ala Ser Tyr Cys Trp Leu
1               5                   10                  15

Phe Trp Thr Thr Tyr Ala Ser Tyr Ala Thr Lys Pro Ala Asp Thr Thr
            20                  25                  30

<210> SEQ ID NO 177
<211> LENGTH: 32
<212> TYPE: PRT
<213> ORGANISM: Artificial Sequence
<220> FEATURE:
<223> OTHER INFORMATION: synthetic

<400> SEQUENCE: 177

Arg Arg Ala Pro Gly Lys Leu Thr Cys Leu Ala Ser Tyr Cys Trp Leu
1               5                   10                  15

Phe Phe Thr Gly Val Ala Arg Ser Thr Ala Thr Thr Asn Thr Gln
            20                  25                  30

<210> SEQ ID NO 178
<211> LENGTH: 32
<212> TYPE: PRT
<213> ORGANISM: Artificial Sequence
<220> FEATURE:
<223> OTHER INFORMATION: synthetic

<400> SEQUENCE: 178

Arg Arg Ala Pro Gly Lys Leu Thr Cys Leu Ala Ser Tyr Cys Trp Leu
1               5                   10                  15

Phe Trp Ser Gly Ile Ala Pro Gln Pro Pro Asn Met Arg Pro Ser Val
            20                  25                  30

<210> SEQ ID NO 179
<211> LENGTH: 32
<212> TYPE: PRT
<213> ORGANISM: Artificial Sequence
<220> FEATURE:
<223> OTHER INFORMATION: synthetic

<400> SEQUENCE: 179

Arg Arg Ala Pro Gly Lys Leu Thr Cys Leu Ala Ser Tyr Cys Trp Leu
1               5                   10                  15

Phe Trp Thr Thr Phe Ala Trp Val Phe Val Val Ala Val Tyr Gly Ser
            20                  25                  30

<210> SEQ ID NO 180
<211> LENGTH: 32
<212> TYPE: PRT
<213> ORGANISM: Artificial Sequence
<220> FEATURE:
<223> OTHER INFORMATION: synthetic

<400> SEQUENCE: 180

Arg Arg Ala Pro Gly Lys Leu Thr Cys Leu Ala Ser Tyr Cys Trp Leu
1               5                   10                  15

Phe Trp Thr Ala Leu Ala Thr Leu Ser Val Ser Met Arg Ser Pro Phe
            20                  25                  30

<210> SEQ ID NO 181
<211> LENGTH: 32
<212> TYPE: PRT
<213> ORGANISM: Artificial Sequence
<220> FEATURE:
<223> OTHER INFORMATION: synthetic

<400> SEQUENCE: 181

Arg Arg Ala Pro Gly Lys Leu Thr Cys Leu Ala Ser Tyr Cys Trp Leu
1               5                   10                  15

Phe Trp Thr Thr Trp Thr Thr Ala Pro Thr Thr Pro Leu Thr Thr
            20                  25                  30

<210> SEQ ID NO 182
<211> LENGTH: 32
<212> TYPE: PRT
<213> ORGANISM: Artificial Sequence
<220> FEATURE:
<223> OTHER INFORMATION: synthetic

<400> SEQUENCE: 182

Arg Arg Ala Pro Gly Lys Leu Thr Cys Leu Ala Ser Tyr Cys Trp Leu
1               5                   10                  15

Phe Trp Thr Gly Leu Leu Asp Tyr Pro Thr Pro Gln Ser His Glu Pro
            20                  25                  30

<210> SEQ ID NO 183
<211> LENGTH: 32
<212> TYPE: PRT
<213> ORGANISM: Artificial Sequence
<220> FEATURE:
<223> OTHER INFORMATION: synthetic

<400> SEQUENCE: 183

Arg Arg Ala Pro Gly Lys Leu Thr Cys Leu Ala Ser Tyr Cys Trp Leu
1               5                   10                  15

Phe Trp Thr Gly Ile Ala Leu Gly His Pro Pro Arg Pro Ala Pro Lys
            20                  25                  30

<210> SEQ ID NO 184
<211> LENGTH: 22
<212> TYPE: PRT
<213> ORGANISM: Artificial Sequence
<220> FEATURE:
<223> OTHER INFORMATION: synthetic

<400> SEQUENCE: 184

Arg Arg Ala Pro Gly Lys Leu Cys Ala Leu Ala Ser Tyr Cys Trp Leu
1               5                   10                  15

Phe Trp Thr Gly Ile Ala
            20

<210> SEQ ID NO 185
<211> LENGTH: 22
<212> TYPE: PRT
<213> ORGANISM: Artificial Sequence
<220> FEATURE:
<223> OTHER INFORMATION: synthetic

<400> SEQUENCE: 185

Arg Arg Ala Pro Gly Lys Cys Thr Ala Leu Ala Ser Tyr Cys Trp Leu
1               5                   10                  15

Phe Trp Thr Gly Ile Ala

```
                        20

<210> SEQ ID NO 186
<211> LENGTH: 22
<212> TYPE: PRT
<213> ORGANISM: Artificial Sequence
<220> FEATURE:
<223> OTHER INFORMATION: synthetic

<400> SEQUENCE: 186

Arg Arg Ala Pro Gly Cys Leu Thr Ala Leu Ala Ser Tyr Cys Trp Leu
1               5                   10                  15

Phe Trp Thr Gly Ile Ala
            20

<210> SEQ ID NO 187
<211> LENGTH: 22
<212> TYPE: PRT
<213> ORGANISM: Artificial Sequence
<220> FEATURE:
<223> OTHER INFORMATION: synthetic

<400> SEQUENCE: 187

Arg Arg Ala Pro Gly Lys Leu Thr Cys Leu Ala Ser Tyr Ala Cys Leu
1               5                   10                  15

Phe Trp Thr Gly Ile Ala
            20

<210> SEQ ID NO 188
<211> LENGTH: 22
<212> TYPE: PRT
<213> ORGANISM: Artificial Sequence
<220> FEATURE:
<223> OTHER INFORMATION: synthetic

<400> SEQUENCE: 188

Arg Arg Ala Pro Gly Lys Leu Thr Cys Leu Ala Ser Tyr Ala Trp Cys
1               5                   10                  15

Phe Trp Thr Gly Ile Ala
            20

<210> SEQ ID NO 189
<211> LENGTH: 22
<212> TYPE: PRT
<213> ORGANISM: Artificial Sequence
<220> FEATURE:
<223> OTHER INFORMATION: synthetic

<400> SEQUENCE: 189

Arg Arg Ala Pro Gly Lys Leu Thr Cys Leu Ala Ser Tyr Ala Trp Leu
1               5                   10                  15

Cys Trp Thr Gly Ile Ala
            20

<210> SEQ ID NO 190
<211> LENGTH: 22
<212> TYPE: PRT
<213> ORGANISM: Artificial Sequence
<220> FEATURE:
<223> OTHER INFORMATION: synthetic

<400> SEQUENCE: 190

Arg Arg Ala Pro Gly Lys Leu Cys Ala Leu Ala Ser Tyr Ala Cys Leu
1               5                   10                  15
```

Phe Trp Thr Gly Ile Ala
            20

<210> SEQ ID NO 191
<211> LENGTH: 22
<212> TYPE: PRT
<213> ORGANISM: Artificial Sequence
<220> FEATURE:
<223> OTHER INFORMATION: synthetic

<400> SEQUENCE: 191

Arg Arg Ala Pro Gly Lys Cys Thr Ala Leu Ala Ser Tyr Ala Trp Cys
1               5                   10                  15

Phe Trp Thr Gly Ile Ala
            20

<210> SEQ ID NO 192
<211> LENGTH: 22
<212> TYPE: PRT
<213> ORGANISM: Artificial Sequence
<220> FEATURE:
<223> OTHER INFORMATION: synthetic

<400> SEQUENCE: 192

Arg Arg Ala Pro Gly Cys Leu Thr Ala Leu Ala Ser Tyr Ala Trp Leu
1               5                   10                  15

Cys Trp Thr Gly Ile Ala
            20

<210> SEQ ID NO 193
<211> LENGTH: 22
<212> TYPE: PRT
<213> ORGANISM: Artificial Sequence
<220> FEATURE:
<223> OTHER INFORMATION: synthetic

<400> SEQUENCE: 193

Arg Arg Ala Pro Gly Lys Leu Thr Lys Leu Ala Ser Tyr Asp Trp Leu
1               5                   10                  15

Phe Trp Thr Gly Ile Ala
            20

<210> SEQ ID NO 194
<211> LENGTH: 22
<212> TYPE: PRT
<213> ORGANISM: Artificial Sequence
<220> FEATURE:
<223> OTHER INFORMATION: synthetic

<400> SEQUENCE: 194

Arg Arg Ala Pro Gly Lys Leu Thr Asp Leu Ala Ser Tyr Lys Trp Leu
1               5                   10                  15

Phe Trp Thr Gly Ile Ala
            20

<210> SEQ ID NO 195
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (9)..(9)
<223> OTHER INFORMATION: Xaa is Orn

```
<400> SEQUENCE: 195

Arg Arg Ala Pro Gly Lys Leu Thr Xaa Leu Ala Ser Tyr Asp Trp Leu
1               5                   10                  15

Phe Trp Thr Gly Ile Ala
            20

<210> SEQ ID NO 196
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (14)..(14)
<223> OTHER INFORMATION: Xaa is Orn

<400> SEQUENCE: 196

Arg Arg Ala Pro Gly Lys Leu Thr Asp Leu Ala Ser Tyr Xaa Trp Leu
1               5                   10                  15

Phe Trp Thr Gly Ile Ala
            20

<210> SEQ ID NO 197
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (14)..(14)
<223> OTHER INFORMATION: Xaa is Dab

<400> SEQUENCE: 197

Arg Arg Ala Pro Gly Lys Leu Thr Asp Leu Ala Ser Tyr Xaa Trp Leu
1               5                   10                  15

Phe Trp Thr Gly Ile Ala
            20

<210> SEQ ID NO 198
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (9)..(9)
<223> OTHER INFORMATION: Xaa is Dap

<400> SEQUENCE: 198

Arg Arg Ala Pro Gly Lys Leu Thr Xaa Leu Ala Ser Tyr Asp Trp Leu
1               5                   10                  15

Phe Trp Thr Gly Ile Ala
            20

<210> SEQ ID NO 199
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (14)..(14)
<223> OTHER INFORMATION: Xaa is Dap
```

```
<400> SEQUENCE: 199

Arg Arg Ala Pro Gly Lys Leu Thr Asp Leu Ala Ser Tyr Xaa Trp Leu
1               5                   10                  15

Phe Trp Thr Gly Ile Ala
            20

<210> SEQ ID NO 200
<211> LENGTH: 12
<212> TYPE: PRT
<213> ORGANISM: Artificial Sequence
<220> FEATURE:
<223> OTHER INFORMATION: synthetic

<400> SEQUENCE: 200

Lys Leu Thr Cys Leu Ala Ser Tyr Cys Trp Leu Phe
1               5                   10

<210> SEQ ID NO 201
<211> LENGTH: 18
<212> TYPE: PRT
<213> ORGANISM: Artificial Sequence
<220> FEATURE:
<223> OTHER INFORMATION: synthetic

<400> SEQUENCE: 201

Arg Arg Arg Lys Leu Thr Cys Leu Ala Ser Tyr Cys Trp Leu Phe Arg
1               5                   10                  15

Arg Arg

<210> SEQ ID NO 202
<211> LENGTH: 22
<212> TYPE: PRT
<213> ORGANISM: Artificial Sequence
<220> FEATURE:
<223> OTHER INFORMATION: synthetic

<400> SEQUENCE: 202

Arg Arg Arg Arg Arg Lys Leu Thr Cys Leu Ala Ser Tyr Cys Trp Leu
1               5                   10                  15

Phe Arg Arg Arg Arg Arg
            20

<210> SEQ ID NO 203
<211> LENGTH: 18
<212> TYPE: PRT
<213> ORGANISM: Artificial Sequence
<220> FEATURE:
<223> OTHER INFORMATION: synthetic

<400> SEQUENCE: 203

Lys Lys Lys Lys Leu Thr Cys Leu Ala Ser Tyr Cys Trp Leu Phe Lys
1               5                   10                  15

Lys Lys

<210> SEQ ID NO 204
<211> LENGTH: 13
<212> TYPE: PRT
<213> ORGANISM: Artificial Sequence
<220> FEATURE:
<223> OTHER INFORMATION: synthetic

<400> SEQUENCE: 204

Lys Leu Thr Cys Leu Ala Ser Tyr Cys Trp Leu Phe Lys
```

```
<210> SEQ ID NO 205
<211> LENGTH: 13
<212> TYPE: PRT
<213> ORGANISM: Artificial Sequence
<220> FEATURE:
<223> OTHER INFORMATION: synthetic

<400> SEQUENCE: 205

Lys Lys Leu Thr Cys Leu Ala Ser Tyr Cys Trp Leu Phe
1               5                   10

<210> SEQ ID NO 206
<211> LENGTH: 12
<212> TYPE: PRT
<213> ORGANISM: Artificial Sequence
<220> FEATURE:
<223> OTHER INFORMATION: synthetic

<400> SEQUENCE: 206

Ala Leu Thr Cys Leu Ala Ser Tyr Cys Trp Leu Phe
1               5                   10

<210> SEQ ID NO 207
<211> LENGTH: 12
<212> TYPE: PRT
<213> ORGANISM: Artificial Sequence
<220> FEATURE:
<223> OTHER INFORMATION: synthetic

<400> SEQUENCE: 207

Lys Ala Thr Cys Leu Ala Ser Tyr Cys Trp Leu Phe
1               5                   10

<210> SEQ ID NO 208
<211> LENGTH: 12
<212> TYPE: PRT
<213> ORGANISM: Artificial Sequence
<220> FEATURE:
<223> OTHER INFORMATION: synthetic

<400> SEQUENCE: 208

Lys Leu Ala Cys Leu Ala Ser Tyr Cys Trp Leu Phe
1               5                   10

<210> SEQ ID NO 209
<211> LENGTH: 12
<212> TYPE: PRT
<213> ORGANISM: Artificial Sequence
<220> FEATURE:
<223> OTHER INFORMATION: synthetic

<400> SEQUENCE: 209

Lys Leu Thr Ala Leu Ala Ser Tyr Cys Trp Leu Phe
1               5                   10

<210> SEQ ID NO 210
<211> LENGTH: 12
<212> TYPE: PRT
<213> ORGANISM: Artificial Sequence
<220> FEATURE:
<223> OTHER INFORMATION: synthetic

<400> SEQUENCE: 210

Lys Leu Thr Cys Ala Ala Ser Tyr Cys Trp Leu Phe
1               5                   10
```

<210> SEQ ID NO 211
<211> LENGTH: 12
<212> TYPE: PRT
<213> ORGANISM: Artificial Sequence
<220> FEATURE:
<223> OTHER INFORMATION: synthetic

<400> SEQUENCE: 211

Lys Leu Thr Cys Leu Ala Ala Tyr Cys Trp Leu Phe
1               5                   10

<210> SEQ ID NO 212
<211> LENGTH: 12
<212> TYPE: PRT
<213> ORGANISM: Artificial Sequence
<220> FEATURE:
<223> OTHER INFORMATION: synthetic

<400> SEQUENCE: 212

Lys Leu Thr Cys Leu Ala Ser Ala Cys Trp Leu Phe
1               5                   10

<210> SEQ ID NO 213
<211> LENGTH: 12
<212> TYPE: PRT
<213> ORGANISM: Artificial Sequence
<220> FEATURE:
<223> OTHER INFORMATION: synthetic

<400> SEQUENCE: 213

Lys Leu Thr Cys Leu Ala Ser Tyr Ala Trp Leu Phe
1               5                   10

<210> SEQ ID NO 214
<211> LENGTH: 12
<212> TYPE: PRT
<213> ORGANISM: Artificial Sequence
<220> FEATURE:
<223> OTHER INFORMATION: synthetic

<400> SEQUENCE: 214

Lys Leu Thr Cys Leu Ala Ser Tyr Cys Ala Leu Phe
1               5                   10

<210> SEQ ID NO 215
<211> LENGTH: 12
<212> TYPE: PRT
<213> ORGANISM: Artificial Sequence
<220> FEATURE:
<223> OTHER INFORMATION: synthetic

<400> SEQUENCE: 215

Lys Leu Thr Cys Leu Ala Ser Tyr Cys Trp Ala Phe
1               5                   10

<210> SEQ ID NO 216
<211> LENGTH: 12
<212> TYPE: PRT
<213> ORGANISM: Artificial Sequence
<220> FEATURE:
<223> OTHER INFORMATION: synthetic

<400> SEQUENCE: 216

Lys Leu Thr Cys Leu Ala Ser Tyr Cys Trp Leu Ala
1               5                   10

```
<210> SEQ ID NO 217
<211> LENGTH: 12
<212> TYPE: PRT
<213> ORGANISM: Artificial Sequence
<220> FEATURE:
<223> OTHER INFORMATION: synthetic

<400> SEQUENCE: 217

Ala Leu Thr Cys Leu Ala Ala Tyr Cys Ala Leu Phe
1               5                   10

<210> SEQ ID NO 218
<211> LENGTH: 12
<212> TYPE: PRT
<213> ORGANISM: Artificial Sequence
<220> FEATURE:
<223> OTHER INFORMATION: synthetic

<400> SEQUENCE: 218

Lys Ala Ala Cys Leu Ala Ser Ala Cys Trp Leu Ala
1               5                   10

<210> SEQ ID NO 219
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 219

Lys Leu Thr Cys Leu Ala Ser Tyr Cys Trp Leu Phe
1               5                   10

<210> SEQ ID NO 220
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (2)..(2)
<223> OTHER INFORMATION: D-AMINO ACID

<400> SEQUENCE: 220

Lys Leu Thr Cys Leu Ala Ser Tyr Cys Trp Leu Phe
1               5                   10

<210> SEQ ID NO 221
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (3)..(3)
<223> OTHER INFORMATION: D-AMINO ACID

<400> SEQUENCE: 221

Lys Leu Thr Cys Leu Ala Ser Tyr Cys Trp Leu Phe
1               5                   10

<210> SEQ ID NO 222
```

```
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (4)..(4)
<223> OTHER INFORMATION: D-AMINO ACID

<400> SEQUENCE: 222

Lys Leu Thr Cys Leu Ala Ser Tyr Cys Trp Leu Phe
1               5                   10

<210> SEQ ID NO 223
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (5)..(5)
<223> OTHER INFORMATION: D-AMINO ACID

<400> SEQUENCE: 223

Lys Leu Thr Cys Leu Ala Ser Tyr Cys Trp Leu Phe
1               5                   10

<210> SEQ ID NO 224
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (6)..(6)
<223> OTHER INFORMATION: D-AMINO ACID

<400> SEQUENCE: 224

Lys Leu Thr Cys Leu Ala Ser Tyr Cys Trp Leu Phe
1               5                   10

<210> SEQ ID NO 225
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (7)..(7)
<223> OTHER INFORMATION: D-AMINO ACID

<400> SEQUENCE: 225

Lys Leu Thr Cys Leu Ala Ser Tyr Cys Trp Leu Phe
1               5                   10

<210> SEQ ID NO 226
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (8)..(8)
<223> OTHER INFORMATION: D-AMINO ACID

<400> SEQUENCE: 226
```

Lys Leu Thr Cys Leu Ala Ser Tyr Cys Trp Leu Phe
1               5                   10

<210> SEQ ID NO 227
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (9)..(9)
<223> OTHER INFORMATION: D-AMINO ACID

<400> SEQUENCE: 227

Lys Leu Thr Cys Leu Ala Ser Tyr Cys Trp Leu Phe
1               5                   10

<210> SEQ ID NO 228
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (10)..(10)
<223> OTHER INFORMATION: D-AMINO ACID

<400> SEQUENCE: 228

Lys Leu Thr Cys Leu Ala Ser Tyr Cys Trp Leu Phe
1               5                   10

<210> SEQ ID NO 229
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (11)..(11)
<223> OTHER INFORMATION: D-AMINO ACID

<400> SEQUENCE: 229

Lys Leu Thr Cys Leu Ala Ser Tyr Cys Trp Leu Phe
1               5                   10

<210> SEQ ID NO 230
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (12)..(12)
<223> OTHER INFORMATION: D-AMINO ACID

<400> SEQUENCE: 230

Lys Leu Thr Cys Leu Ala Ser Tyr Cys Trp Leu Phe
1               5                   10

<210> SEQ ID NO 231
<211> LENGTH: 12
<212> TYPE: PRT
<213> ORGANISM: Artificial Sequence
<220> FEATURE:
<223> OTHER INFORMATION: synthetic

```
<220> FEATURE:
<221> NAME/KEY: MOD_RES
<222> LOCATION: (1)..(1)
<223> OTHER INFORMATION: METHYLATION

<400> SEQUENCE: 231

Lys Leu Thr Cys Leu Ala Ser Tyr Cys Trp Leu Phe
1               5                   10

<210> SEQ ID NO 232
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (2)..(2)
<223> OTHER INFORMATION: METHYLATION

<400> SEQUENCE: 232

Lys Leu Thr Cys Leu Ala Ser Tyr Cys Trp Leu Phe
1               5                   10

<210> SEQ ID NO 233
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (3)..(3)
<223> OTHER INFORMATION: METHYLATION

<400> SEQUENCE: 233

Lys Leu Thr Cys Leu Ala Ser Tyr Cys Trp Leu Phe
1               5                   10

<210> SEQ ID NO 234
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (5)..(5)
<223> OTHER INFORMATION: METHYLATION

<400> SEQUENCE: 234

Lys Leu Thr Cys Leu Ala Ser Tyr Cys Trp Leu Phe
1               5                   10

<210> SEQ ID NO 235
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (6)..(6)
<223> OTHER INFORMATION: METHYLATION

<400> SEQUENCE: 235

Lys Leu Thr Cys Leu Ala Ser Tyr Cys Trp Leu Phe
1               5                   10
```

```
<210> SEQ ID NO 236
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (7)..(7)
<223> OTHER INFORMATION: METHYLATION

<400> SEQUENCE: 236

Lys Leu Thr Cys Leu Ala Ser Tyr Cys Trp Leu Phe
1               5                   10

<210> SEQ ID NO 237
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (8)..(8)
<223> OTHER INFORMATION: METHYLATION

<400> SEQUENCE: 237

Lys Leu Thr Cys Leu Ala Ser Tyr Cys Trp Leu Phe
1               5                   10

<210> SEQ ID NO 238
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (10)..(10)
<223> OTHER INFORMATION: METHYLATION

<400> SEQUENCE: 238

Lys Leu Thr Cys Leu Ala Ser Tyr Cys Trp Leu Phe
1               5                   10

<210> SEQ ID NO 239
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (11)..(11)
<223> OTHER INFORMATION: METHYLATION

<400> SEQUENCE: 239

Lys Leu Thr Cys Leu Ala Ser Tyr Cys Trp Leu Phe
1               5                   10

<210> SEQ ID NO 240
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (12)..(12)
<223> OTHER INFORMATION: METHYLATION
```

```
<400> SEQUENCE: 240

Lys Leu Thr Cys Leu Ala Ser Tyr Cys Trp Leu Phe
1               5                   10

<210> SEQ ID NO 241
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID
<220> FEATURE:
<221> NAME/KEY: MOD_RES
<222> LOCATION: (2)..(2)
<223> OTHER INFORMATION: METHYLATION

<400> SEQUENCE: 241

Lys Leu Thr Cys Leu Ala Ser Tyr Cys Trp Leu Phe
1               5                   10

<210> SEQ ID NO 242
<211> LENGTH: 11
<212> TYPE: PRT
<213> ORGANISM: Artificial Sequence
<220> FEATURE:
<223> OTHER INFORMATION: synthetic

<400> SEQUENCE: 242

Lys Leu Thr Cys Leu Ala Ser Tyr Cys Trp Leu
1               5                   10

<210> SEQ ID NO 243
<211> LENGTH: 10
<212> TYPE: PRT
<213> ORGANISM: Artificial Sequence
<220> FEATURE:
<223> OTHER INFORMATION: synthetic

<400> SEQUENCE: 243

Lys Leu Thr Cys Leu Ala Ser Tyr Cys Trp
1               5                   10

<210> SEQ ID NO 244
<211> LENGTH: 9
<212> TYPE: PRT
<213> ORGANISM: Artificial Sequence
<220> FEATURE:
<223> OTHER INFORMATION: synthetic

<400> SEQUENCE: 244

Lys Leu Thr Cys Leu Ala Ser Tyr Cys
1               5

<210> SEQ ID NO 245
<211> LENGTH: 11
<212> TYPE: PRT
<213> ORGANISM: Artificial Sequence
<220> FEATURE:
<223> OTHER INFORMATION: synthetic

<400> SEQUENCE: 245

Leu Thr Cys Leu Ala Ser Tyr Cys Trp Leu Phe
1               5                   10
```

```
<210> SEQ ID NO 246
<211> LENGTH: 10
<212> TYPE: PRT
<213> ORGANISM: Artificial Sequence
<220> FEATURE:
<223> OTHER INFORMATION: synthetic

<400> SEQUENCE: 246

Thr Cys Leu Ala Ser Tyr Cys Trp Leu Phe
1               5                   10

<210> SEQ ID NO 247
<211> LENGTH: 9
<212> TYPE: PRT
<213> ORGANISM: Artificial Sequence
<220> FEATURE:
<223> OTHER INFORMATION: synthetic

<400> SEQUENCE: 247

Cys Leu Ala Ser Tyr Cys Trp Leu Phe
1               5

<210> SEQ ID NO 248
<211> LENGTH: 12
<212> TYPE: PRT
<213> ORGANISM: Artificial Sequence
<220> FEATURE:
<223> OTHER INFORMATION: synthetic

<400> SEQUENCE: 248

Trp Ser Leu Cys Phe Lys Leu Thr Cys Ala Tyr Leu
1               5                   10

<210> SEQ ID NO 249
<211> LENGTH: 12
<212> TYPE: PRT
<213> ORGANISM: Artificial Sequence
<220> FEATURE:
<223> OTHER INFORMATION: synthetic

<400> SEQUENCE: 249

Lys Leu Thr Ala Leu Ala Ser Tyr Ala Trp Leu Phe
1               5                   10

<210> SEQ ID NO 250
<211> LENGTH: 12
<212> TYPE: PRT
<213> ORGANISM: Artificial Sequence
<220> FEATURE:
<223> OTHER INFORMATION: synthetic

<400> SEQUENCE: 250

Lys Leu Thr Ser Leu Ala Ser Tyr Ser Trp Leu Phe
1               5                   10

<210> SEQ ID NO 251
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (4)..(4)
<223> OTHER INFORMATION: Xaa is Pen

<400> SEQUENCE: 251

Lys Leu Thr Xaa Leu Ala Ser Tyr Cys Trp Leu Phe
```

<210> SEQ ID NO 252
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (9)..(9)
<223> OTHER INFORMATION: Xaa is Pen

<400> SEQUENCE: 252

Lys Leu Thr Cys Leu Ala Ser Tyr Xaa Trp Leu Phe
1               5                   10

<210> SEQ ID NO 253
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (4)..(4)
<223> OTHER INFORMATION: Xaa is HCy

<400> SEQUENCE: 253

Lys Leu Thr Xaa Leu Ala Ser Tyr Cys Trp Leu Phe
1               5                   10

<210> SEQ ID NO 254
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (9)..(9)
<223> OTHER INFORMATION: Xaa is HCy

<400> SEQUENCE: 254

Lys Leu Thr Cys Leu Ala Ser Tyr Xaa Trp Leu Phe
1               5                   10

<210> SEQ ID NO 255
<211> LENGTH: 12
<212> TYPE: PRT
<213> ORGANISM: Artificial Sequence
<220> FEATURE:
<223> OTHER INFORMATION: synthetic

<400> SEQUENCE: 255

Lys Leu Thr Lys Leu Ala Ser Tyr Glu Trp Leu Phe
1               5                   10

<210> SEQ ID NO 256
<211> LENGTH: 12
<212> TYPE: PRT
<213> ORGANISM: Artificial Sequence
<220> FEATURE:
<223> OTHER INFORMATION: synthetic

<400> SEQUENCE: 256

Lys Leu Thr Glu Leu Ala Ser Tyr Lys Trp Leu Phe
1               5                   10

```
<210> SEQ ID NO 257
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (9)..(9)
<223> OTHER INFORMATION: Xaa is Orn

<400> SEQUENCE: 257

Lys Leu Thr Glu Leu Ala Ser Tyr Xaa Trp Leu Phe
1               5                   10

<210> SEQ ID NO 258
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (4)..(4)
<223> OTHER INFORMATION: Xaa is Orn

<400> SEQUENCE: 258

Lys Leu Thr Xaa Leu Ala Ser Tyr Glu Trp Leu Phe
1               5                   10

<210> SEQ ID NO 259
<211> LENGTH: 12
<212> TYPE: PRT
<213> ORGANISM: Artificial Sequence
<220> FEATURE:
<223> OTHER INFORMATION: synthetic

<400> SEQUENCE: 259

Lys Lys Thr Cys Leu Ala Ser Tyr Cys Trp Leu Phe
1               5                   10

<210> SEQ ID NO 260
<211> LENGTH: 12
<212> TYPE: PRT
<213> ORGANISM: Artificial Sequence
<220> FEATURE:
<223> OTHER INFORMATION: synthetic

<400> SEQUENCE: 260

Lys Leu Lys Cys Leu Ala Ser Tyr Cys Trp Leu Phe
1               5                   10

<210> SEQ ID NO 261
<211> LENGTH: 12
<212> TYPE: PRT
<213> ORGANISM: Artificial Sequence
<220> FEATURE:
<223> OTHER INFORMATION: synthetic

<400> SEQUENCE: 261

Lys Leu Thr Cys Lys Ala Ser Tyr Cys Trp Leu Phe
1               5                   10

<210> SEQ ID NO 262
<211> LENGTH: 12
<212> TYPE: PRT
<213> ORGANISM: Artificial Sequence
<220> FEATURE:
```

<223> OTHER INFORMATION: synthetic

<400> SEQUENCE: 262

Lys Leu Thr Cys Leu Lys Ser Tyr Cys Trp Leu Phe
1               5                   10

<210> SEQ ID NO 263
<211> LENGTH: 12
<212> TYPE: PRT
<213> ORGANISM: Artificial Sequence
<220> FEATURE:
<223> OTHER INFORMATION: synthetic

<400> SEQUENCE: 263

Lys Leu Thr Cys Leu Ala Ser Lys Cys Trp Leu Phe
1               5                   10

<210> SEQ ID NO 264
<211> LENGTH: 12
<212> TYPE: PRT
<213> ORGANISM: Artificial Sequence
<220> FEATURE:
<223> OTHER INFORMATION: synthetic

<400> SEQUENCE: 264

Lys Leu Thr Cys Leu Ala Ser Tyr Cys Trp Leu Lys
1               5                   10

<210> SEQ ID NO 265
<211> LENGTH: 12
<212> TYPE: PRT
<213> ORGANISM: Artificial Sequence
<220> FEATURE:
<223> OTHER INFORMATION: synthetic

<400> SEQUENCE: 265

Arg Leu Thr Cys Leu Ala Ser Tyr Cys Trp Leu Phe
1               5                   10

<210> SEQ ID NO 266
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (1)..(1)
<223> OTHER INFORMATION: Xaa is Dpr

<400> SEQUENCE: 266

Xaa Leu Thr Cys Leu Ala Ser Tyr Cys Trp Leu Phe
1               5                   10

<210> SEQ ID NO 267
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (1)..(1)
<223> OTHER INFORMATION: Xaa is Dab

<400> SEQUENCE: 267

Xaa Leu Thr Cys Leu Ala Ser Tyr Cys Trp Leu Phe
1               5                   10

<210> SEQ ID NO 268
<211> LENGTH: 12
<212> TYPE: PRT
<213> ORGANISM: Artificial Sequence
<220> FEATURE:
<223> OTHER INFORMATION: synthetic

<400> SEQUENCE: 268

Gln Leu Thr Cys Leu Ala Ser Tyr Cys Trp Leu Phe
1               5                   10

<210> SEQ ID NO 269
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (1)..(1)
<223> OTHER INFORMATION: Xaa is Orn

<400> SEQUENCE: 269

Xaa Leu Thr Cys Leu Ala Ser Tyr Cys Trp Leu Phe
1               5                   10

<210> SEQ ID NO 270
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (1)..(1)
<223> OTHER INFORMATION: METHYLATION

<400> SEQUENCE: 270

Lys Leu Thr Cys Leu Ala Ser Tyr Cys Trp Leu Phe
1               5                   10

<210> SEQ ID NO 271
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (1)..(1)
<223> OTHER INFORMATION: METHYLATION (Me2)

<400> SEQUENCE: 271

Lys Leu Thr Cys Leu Ala Ser Tyr Cys Trp Leu Phe
1               5                   10

<210> SEQ ID NO 272
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (1)..(1)
<223> OTHER INFORMATION: METHYLATION (Me3)

<400> SEQUENCE: 272

```
Lys Leu Thr Cys Leu Ala Ser Tyr Cys Trp Leu Phe
1               5                   10
```

<210> SEQ ID NO 273
<211> LENGTH: 12
<212> TYPE: PRT
<213> ORGANISM: Artificial Sequence
<220> FEATURE:
<223> OTHER INFORMATION: synthetic

<400> SEQUENCE: 273

```
Lys Leu Thr Cys Leu Ser Ser Tyr Cys Trp Leu Phe
1               5                   10
```

<210> SEQ ID NO 274
<211> LENGTH: 12
<212> TYPE: PRT
<213> ORGANISM: Artificial Sequence
<220> FEATURE:
<223> OTHER INFORMATION: synthetic

<400> SEQUENCE: 274

```
Lys Leu Thr Cys Leu Val Ser Tyr Cys Trp Leu Phe
1               5                   10
```

<210> SEQ ID NO 275
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (6)..(6)
<223> OTHER INFORMATION: Xaa is Dpr

<400> SEQUENCE: 275

```
Lys Leu Thr Cys Leu Xaa Ser Tyr Cys Trp Leu Phe
1               5                   10
```

<210> SEQ ID NO 276
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (6)..(6)
<223> OTHER INFORMATION: Xaa is Abu

<400> SEQUENCE: 276

```
Lys Leu Thr Cys Leu Xaa Ser Tyr Cys Trp Leu Phe
1               5                   10
```

<210> SEQ ID NO 277
<211> LENGTH: 12
<212> TYPE: PRT
<213> ORGANISM: Artificial Sequence
<220> FEATURE:
<223> OTHER INFORMATION: synthetic

<400> SEQUENCE: 277

```
Lys Leu Thr Cys Leu Gly Ser Tyr Cys Trp Leu Phe
1               5                   10
```

<210> SEQ ID NO 278
<211> LENGTH: 12

```
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (6)..(6)
<223> OTHER INFORMATION: Xaa is Aib

<400> SEQUENCE: 278

Lys Leu Thr Cys Leu Xaa Ser Tyr Cys Trp Leu Phe
1               5                   10

<210> SEQ ID NO 279
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (7)..(7)
<223> OTHER INFORMATION: Xaa is Hse

<400> SEQUENCE: 279

Lys Leu Thr Cys Leu Ala Xaa Tyr Cys Trp Leu Phe
1               5                   10

<210> SEQ ID NO 280
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (7)..(7)
<223> OTHER INFORMATION: Xaa is Dpr

<400> SEQUENCE: 280

Lys Leu Thr Cys Leu Ala Xaa Tyr Cys Trp Leu Phe
1               5                   10

<210> SEQ ID NO 281
<211> LENGTH: 12
<212> TYPE: PRT
<213> ORGANISM: Artificial Sequence
<220> FEATURE:
<223> OTHER INFORMATION: synthetic

<400> SEQUENCE: 281

Lys Leu Thr Cys Leu Ala Thr Tyr Cys Trp Leu Phe
1               5                   10

<210> SEQ ID NO 282
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (10)..(10)
<223> OTHER INFORMATION: Xaa is Nal

<400> SEQUENCE: 282

Lys Leu Thr Cys Leu Ala Ser Tyr Cys Xaa Leu Phe
1               5                   10
```

```
<210> SEQ ID NO 283
<211> LENGTH: 12
<212> TYPE: PRT
<213> ORGANISM: Artificial Sequence
<220> FEATURE:
<223> OTHER INFORMATION: synthetic

<400> SEQUENCE: 283

Lys Leu Thr Cys Leu Ala Ser Tyr Cys Phe Leu Phe
1               5                   10

<210> SEQ ID NO 284
<211> LENGTH: 12
<212> TYPE: PRT
<213> ORGANISM: Artificial Sequence
<220> FEATURE:
<223> OTHER INFORMATION: synthetic

<400> SEQUENCE: 284

Lys Leu Thr Cys Leu Ala Ser Tyr Cys Leu Leu Phe
1               5                   10

<210> SEQ ID NO 285
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (11)..(11)
<223> OTHER INFORMATION: Xaa is Nle

<400> SEQUENCE: 285

Lys Leu Thr Cys Leu Ala Ser Tyr Cys Trp Xaa Phe
1               5                   10

<210> SEQ ID NO 286
<211> LENGTH: 12
<212> TYPE: PRT
<213> ORGANISM: Artificial Sequence
<220> FEATURE:
<223> OTHER INFORMATION: synthetic

<400> SEQUENCE: 286

Lys Leu Thr Cys Leu Ala Ser Tyr Cys Trp Tyr Phe
1               5                   10

<210> SEQ ID NO 287
<211> LENGTH: 12
<212> TYPE: PRT
<213> ORGANISM: Artificial Sequence
<220> FEATURE:
<223> OTHER INFORMATION: synthetic

<400> SEQUENCE: 287

Lys Leu Thr Cys Leu Ala Ser Tyr Cys Trp Ile Phe
1               5                   10

<210> SEQ ID NO 288
<211> LENGTH: 18
<212> TYPE: PRT
<213> ORGANISM: Artificial Sequence
<220> FEATURE:
<223> OTHER INFORMATION: synthetic

<400> SEQUENCE: 288

Thr Gly Ser Lys Leu Thr Cys Leu Ala Ser Tyr Cys Trp Leu Phe Ala
```

-continued

```
1               5                   10                  15

Pro Gly

<210> SEQ ID NO 289
<211> LENGTH: 12
<212> TYPE: PRT
<213> ORGANISM: Artificial Sequence
<220> FEATURE:
<223> OTHER INFORMATION: synthetic

<400> SEQUENCE: 289

Lys Leu Thr Cys Leu Ala Ser Tyr Cys Trp Leu Phe
1               5                   10

<210> SEQ ID NO 290
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (1)..(1)
<223> OTHER INFORMATION: ACETYLATION

<400> SEQUENCE: 290

Lys Leu Thr Cys Leu Ala Ser Tyr Cys Trp Leu Phe
1               5                   10

<210> SEQ ID NO 291
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (12)..(12)
<223> OTHER INFORMATION: PEG4-CONH2

<400> SEQUENCE: 291

Lys Leu Thr Cys Leu Ala Ser Tyr Cys Trp Leu Phe
1               5                   10

<210> SEQ ID NO 292
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: PEG27

<400> SEQUENCE: 292

Lys Leu Thr Cys Leu Ala Ser Tyr Cys Trp Leu Phe
1               5                   10

<210> SEQ ID NO 293
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: PEG27-PEG27
```

```
<400> SEQUENCE: 293

Lys Leu Thr Cys Leu Ala Ser Tyr Cys Trp Leu Phe
1               5                   10

<210> SEQ ID NO 294
<211> LENGTH: 12
<212> TYPE: PRT
<213> ORGANISM: Artificial Sequence
<220> FEATURE:
<223> OTHER INFORMATION: synthetic

<400> SEQUENCE: 294

Lys Leu Thr Cys Gln Ala Ser Tyr Cys Trp Leu Phe
1               5                   10

<210> SEQ ID NO 295
<211> LENGTH: 12
<212> TYPE: PRT
<213> ORGANISM: Artificial Sequence
<220> FEATURE:
<223> OTHER INFORMATION: synthetic

<400> SEQUENCE: 295

Lys Leu Thr Cys Leu Ala Ser Gln Cys Trp Leu Phe
1               5                   10

<210> SEQ ID NO 296
<211> LENGTH: 12
<212> TYPE: PRT
<213> ORGANISM: Artificial Sequence
<220> FEATURE:
<223> OTHER INFORMATION: synthetic

<400> SEQUENCE: 296

Lys Leu Thr Cys Leu Ala Ser Tyr Cys Gln Leu Phe
1               5                   10

<210> SEQ ID NO 297
<211> LENGTH: 12
<212> TYPE: PRT
<213> ORGANISM: Artificial Sequence
<220> FEATURE:
<223> OTHER INFORMATION: synthetic

<400> SEQUENCE: 297

Gln Gln Thr Cys Gln Ala Ser Gln Cys Gln Leu Phe
1               5                   10

<210> SEQ ID NO 298
<211> LENGTH: 12
<212> TYPE: PRT
<213> ORGANISM: Artificial Sequence
<220> FEATURE:
<223> OTHER INFORMATION: synthetic

<400> SEQUENCE: 298

Asn Pro Thr Cys Gln Ala Ser Tyr Cys Gln Leu Phe
1               5                   10

<210> SEQ ID NO 299
<211> LENGTH: 12
<212> TYPE: PRT
<213> ORGANISM: Artificial Sequence
<220> FEATURE:
<223> OTHER INFORMATION: synthetic
```

<400> SEQUENCE: 299

Gln Leu Thr Cys Leu Ala Ser Glu Cys Gly Leu Ser
1               5                   10

<210> SEQ ID NO 300
<211> LENGTH: 12
<212> TYPE: PRT
<213> ORGANISM: Artificial Sequence
<220> FEATURE:
<223> OTHER INFORMATION: synthetic

<400> SEQUENCE: 300

Ala Gln Thr Arg Val Ala Arg Cys Cys Gln Leu Phe
1               5                   10

<210> SEQ ID NO 301
<211> LENGTH: 12
<212> TYPE: PRT
<213> ORGANISM: Artificial Sequence
<220> FEATURE:
<223> OTHER INFORMATION: synthetic

<400> SEQUENCE: 301

Lys Lys Thr Cys Val Ala Ser Phe Cys Gln Met Ile
1               5                   10

<210> SEQ ID NO 302
<211> LENGTH: 12
<212> TYPE: PRT
<213> ORGANISM: Artificial Sequence
<220> FEATURE:
<223> OTHER INFORMATION: synthetic

<400> SEQUENCE: 302

Asn Leu Thr Gly Arg Ala Ser Tyr Gly Trp Leu Pro
1               5                   10

<210> SEQ ID NO 303
<211> LENGTH: 12
<212> TYPE: PRT
<213> ORGANISM: Artificial Sequence
<220> FEATURE:
<223> OTHER INFORMATION: synthetic

<400> SEQUENCE: 303

Lys Gly Arg Cys Leu Thr Ser His Cys Trp Leu Phe
1               5                   10

<210> SEQ ID NO 304
<211> LENGTH: 12
<212> TYPE: PRT
<213> ORGANISM: Artificial Sequence
<220> FEATURE:
<223> OTHER INFORMATION: synthetic

<400> SEQUENCE: 304

Thr Leu Thr Cys Arg Ala Ser Tyr Cys Gln Leu Phe
1               5                   10

<210> SEQ ID NO 305
<211> LENGTH: 12
<212> TYPE: PRT
<213> ORGANISM: Artificial Sequence
<220> FEATURE:
<223> OTHER INFORMATION: synthetic

<400> SEQUENCE: 305

```
Lys Leu Thr Cys Arg Ala Ser Tyr Cys Gln Leu Phe
1               5                   10
```

<210> SEQ ID NO 306
<211> LENGTH: 12
<212> TYPE: PRT
<213> ORGANISM: Artificial Sequence
<220> FEATURE:
<223> OTHER INFORMATION: synthetic

<400> SEQUENCE: 306

```
Lys Leu Ser Cys Gln Ala Gly Gln Cys Trp Val Phe
1               5                   10
```

<210> SEQ ID NO 307
<211> LENGTH: 12
<212> TYPE: PRT
<213> ORGANISM: Artificial Sequence
<220> FEATURE:
<223> OTHER INFORMATION: synthetic

<400> SEQUENCE: 307

```
Lys Leu Thr Cys Leu Ala Ser Tyr Cys Gln Leu Val
1               5                   10
```

<210> SEQ ID NO 308
<211> LENGTH: 12
<212> TYPE: PRT
<213> ORGANISM: Artificial Sequence
<220> FEATURE:
<223> OTHER INFORMATION: synthetic

<400> SEQUENCE: 308

```
Lys Leu Lys Cys Leu Ser Ser Glu Cys Gln Leu Leu
1               5                   10
```

<210> SEQ ID NO 309
<211> LENGTH: 12
<212> TYPE: PRT
<213> ORGANISM: Artificial Sequence
<220> FEATURE:
<223> OTHER INFORMATION: synthetic

<400> SEQUENCE: 309

```
Gln Leu Thr Cys Leu Ala Ser Tyr Cys Gly Gly Val
1               5                   10
```

<210> SEQ ID NO 310
<211> LENGTH: 12
<212> TYPE: PRT
<213> ORGANISM: Artificial Sequence
<220> FEATURE:
<223> OTHER INFORMATION: synthetic

<400> SEQUENCE: 310

```
Glu Gln Thr Cys Leu Ala Ser Tyr Cys Trp Leu Phe
1               5                   10
```

<210> SEQ ID NO 311
<211> LENGTH: 12
<212> TYPE: PRT
<213> ORGANISM: Artificial Sequence
<220> FEATURE:
<223> OTHER INFORMATION: synthetic

<400> SEQUENCE: 311

Gln Leu Pro Cys Leu Ala Ser Tyr Cys Gly Leu Phe
1               5                   10

<210> SEQ ID NO 312
<211> LENGTH: 12
<212> TYPE: PRT
<213> ORGANISM: Artificial Sequence
<220> FEATURE:
<223> OTHER INFORMATION: synthetic

<400> SEQUENCE: 312

Met Leu Thr Cys Ile Ala Ser Tyr Cys Gln Leu Gly
1               5                   10

<210> SEQ ID NO 313
<211> LENGTH: 22
<212> TYPE: PRT
<213> ORGANISM: Artificial Sequence
<220> FEATURE:
<223> OTHER INFORMATION: synthetic

<400> SEQUENCE: 313

Ser Leu Ala Asp Thr Gln Leu Thr Trp Leu Ala Arg Gln Tyr Trp Leu
1               5                   10                  15

Ser Val Ser Glu Gly Ser
            20

<210> SEQ ID NO 314
<211> LENGTH: 22
<212> TYPE: PRT
<213> ORGANISM: Artificial Sequence
<220> FEATURE:
<223> OTHER INFORMATION: synthetic

<400> SEQUENCE: 314

Arg Arg Cys Pro Gly Lys Leu Gln Ala Leu Ala Ser Tyr Cys Trp Leu
1               5                   10                  15

Phe Trp Thr Gly Ile Ala
            20

<210> SEQ ID NO 315
<211> LENGTH: 22
<212> TYPE: PRT
<213> ORGANISM: Artificial Sequence
<220> FEATURE:
<223> OTHER INFORMATION: synthetic

<400> SEQUENCE: 315

Arg Arg Ala Pro Gly Lys Leu Gln Cys Leu Ala Ser Tyr Cys Trp Leu
1               5                   10                  15

Phe Trp Thr Gly Ile Ala
            20

<210> SEQ ID NO 316
<211> LENGTH: 22
<212> TYPE: PRT
<213> ORGANISM: Artificial Sequence
<220> FEATURE:
<223> OTHER INFORMATION: synthetic

<400> SEQUENCE: 316

Asp Ser Arg Ser Ala Lys Arg Lys Cys Leu Ala Ser Tyr Cys Trp Leu
1               5                   10                  15

Phe Gly Ile Gly Gln Ala
            20

```
<210> SEQ ID NO 317
<211> LENGTH: 22
<212> TYPE: PRT
<213> ORGANISM: Artificial Sequence
<220> FEATURE:
<223> OTHER INFORMATION: synthetic

<400> SEQUENCE: 317

Gly Ala Ser Ser Asp Lys Leu Thr Cys Arg Thr Arg His Cys Ser Met
1               5                   10                  15

Phe Gln Pro Leu Ser Val
            20

<210> SEQ ID NO 318
<211> LENGTH: 22
<212> TYPE: PRT
<213> ORGANISM: Artificial Sequence
<220> FEATURE:
<223> OTHER INFORMATION: synthetic

<400> SEQUENCE: 318

Gly Cys Ser Ser Asp Lys Leu Thr Ala Arg Thr Arg His Cys Ser Met
1               5                   10                  15

Phe Gln Pro Leu Ser Val
            20

<210> SEQ ID NO 319
<211> LENGTH: 22
<212> TYPE: PRT
<213> ORGANISM: Artificial Sequence
<220> FEATURE:
<223> OTHER INFORMATION: synthetic

<400> SEQUENCE: 319

Gly Ser Cys Arg Asp Gln Leu Thr Cys Leu Ser Ser Asp Arg Trp Gln
1               5                   10                  15

Phe Phe Arg Arg Val Ser
            20

<210> SEQ ID NO 320
<211> LENGTH: 22
<212> TYPE: PRT
<213> ORGANISM: Artificial Sequence
<220> FEATURE:
<223> OTHER INFORMATION: synthetic

<400> SEQUENCE: 320

Lys Glu Gly Phe Ala Gln Leu Pro Cys Leu Val Cys Gln Gly Gly Leu
1               5                   10                  15

Phe Ser Pro Arg Ala Ile
            20

<210> SEQ ID NO 321
<211> LENGTH: 22
<212> TYPE: PRT
<213> ORGANISM: Artificial Sequence
<220> FEATURE:
<223> OTHER INFORMATION: synthetic

<400> SEQUENCE: 321

Leu Arg Thr Gln Pro Lys Val Thr Gly Leu Ala Ser Cys Ser Gly Leu
1               5                   10                  15

Val Asn Cys Ser Arg Asp
```

20

<210> SEQ ID NO 322
<211> LENGTH: 22
<212> TYPE: PRT
<213> ORGANISM: Artificial Sequence
<220> FEATURE:
<223> OTHER INFORMATION: synthetic

<400> SEQUENCE: 322

Arg Cys Ala Gln Ser Arg Leu Pro Trp Leu Val Ser Tyr Cys Trp Leu
1               5                   10                  15

Phe Ser Pro Tyr Gly Met
        20

<210> SEQ ID NO 323
<211> LENGTH: 22
<212> TYPE: PRT
<213> ORGANISM: Artificial Sequence
<220> FEATURE:
<223> OTHER INFORMATION: synthetic

<400> SEQUENCE: 323

Leu Gln Glu Leu Thr Lys Leu Thr Cys Leu Ala Arg Ser Gly Trp Leu
1               5                   10                  15

Val Cys Asn Pro Gly Tyr
        20

<210> SEQ ID NO 324
<211> LENGTH: 22
<212> TYPE: PRT
<213> ORGANISM: Artificial Sequence
<220> FEATURE:
<223> OTHER INFORMATION: synthetic

<400> SEQUENCE: 324

Trp Val Pro Gln Trp Lys Val Thr Cys Leu Ala Ser Cys Ser Arg Leu
1               5                   10                  15

Phe His Gly Phe Asp Ala
        20

<210> SEQ ID NO 325
<211> LENGTH: 22
<212> TYPE: PRT
<213> ORGANISM: Artificial Sequence
<220> FEATURE:
<223> OTHER INFORMATION: synthetic

<400> SEQUENCE: 325

Ser Cys Val Lys His Glu Leu Lys Cys Leu Ser Ser Asp Ser Arg Leu
1               5                   10                  15

Phe Ser Ala Val Gln Arg
        20

<210> SEQ ID NO 326
<211> LENGTH: 22
<212> TYPE: PRT
<213> ORGANISM: Artificial Sequence
<220> FEATURE:
<223> OTHER INFORMATION: synthetic

<400> SEQUENCE: 326

Val Ala His Tyr Gly Lys Val Thr Cys Leu Ala Ser Tyr Cys Gln Pro
1               5                   10                  15

Leu Pro Ser Val Gly Ala
            20

<210> SEQ ID NO 327
<211> LENGTH: 22
<212> TYPE: PRT
<213> ORGANISM: Artificial Sequence
<220> FEATURE:
<223> OTHER INFORMATION: synthetic

<400> SEQUENCE: 327

Met Glu Gly Thr Arg Gln Pro Thr Cys Leu Ala Ser Tyr Cys Ser Pro
1               5                   10                  15

Phe Gln Tyr Val Ala Pro
            20

<210> SEQ ID NO 328
<211> LENGTH: 22
<212> TYPE: PRT
<213> ORGANISM: Artificial Sequence
<220> FEATURE:
<223> OTHER INFORMATION: synthetic

<400> SEQUENCE: 328

Arg Pro Gly Gly Gly Lys Val Thr Cys Gln Ala Ser Tyr Cys Trp Pro
1               5                   10                  15

Phe Leu Ala Arg Ala Gly
            20

<210> SEQ ID NO 329
<211> LENGTH: 22
<212> TYPE: PRT
<213> ORGANISM: Artificial SequencE
<220> FEATURE:
<223> OTHER INFORMATION: synthetic

<400> SEQUENCE: 329

Glu Arg Tyr Arg Leu Asp Met Thr Cys Met Ala Ser Gln Cys Trp Gln
1               5                   10                  15

Phe Pro Pro Ala Ala Gly
            20

<210> SEQ ID NO 330
<211> LENGTH: 22
<212> TYPE: PRT
<213> ORGANISM: Artificial Sequence
<220> FEATURE:
<223> OTHER INFORMATION: synthetic

<400> SEQUENCE: 330

Val Gly Glu His Arg Lys Ile Ser Cys Val Ala Ser Asn Cys Gln Leu
1               5                   10                  15

Leu Arg Ser Gly Leu Ala
            20

<210> SEQ ID NO 331
<211> LENGTH: 22
<212> TYPE: PRT
<213> ORGANISM: Artificial Sequence
<220> FEATURE:
<223> OTHER INFORMATION: synthetic

<400> SEQUENCE: 331

Ser Ile Ser Gly Gln Gln Leu Thr Cys Arg Ala Ser His Cys Trp Leu
1               5                   10                  15

Asn Leu Pro Trp His Ser
            20

<210> SEQ ID NO 332
<211> LENGTH: 22
<212> TYPE: PRT
<213> ORGANISM: Artificial Sequence
<220> FEATURE:
<223> OTHER INFORMATION: synthetic

<400> SEQUENCE: 332

Thr Leu Asp Ser Lys Asn Leu Gln Cys Leu Gly Ser Ser Cys Trp Leu
1               5                   10                  15

Phe Ser Ser Gly Leu Ser
            20

<210> SEQ ID NO 333
<211> LENGTH: 22
<212> TYPE: PRT
<213> ORGANISM: Artificial Sequence
<220> FEATURE:
<223> OTHER INFORMATION: synthetic

<400> SEQUENCE: 333

Val Gln Arg Ser Thr Gln Leu Thr Cys Leu Tyr Gly Gly Cys Arg Leu
1               5                   10                  15

Phe Gly Trp Asn Tyr His
            20

<210> SEQ ID NO 334
<211> LENGTH: 22
<212> TYPE: PRT
<213> ORGANISM: Artificial Sequence
<220> FEATURE:
<223> OTHER INFORMATION: synthetic

<400> SEQUENCE: 334

Val Ser Gly Thr Gly Arg Leu Thr Cys Val Ala Ser Tyr Cys Trp Met
1               5                   10                  15

Phe Gln Leu Gly Ser Phe
            20

<210> SEQ ID NO 335
<211> LENGTH: 22
<212> TYPE: PRT
<213> ORGANISM: Artificial Sequence
<220> FEATURE:
<223> OTHER INFORMATION: synthetic

<400> SEQUENCE: 335

Met Ala Gly Met Leu Lys Leu Thr Cys Phe Ala Ser Tyr Cys Gly Leu
1               5                   10                  15

Phe Pro Leu Val Ser Ser
            20

<210> SEQ ID NO 336
<211> LENGTH: 22
<212> TYPE: PRT
<213> ORGANISM: Artificial Sequence
<220> FEATURE:
<223> OTHER INFORMATION: synthetic

<400> SEQUENCE: 336

Gly Ala Gln Leu Asp Lys Glu Thr Cys Leu Ala Ser Tyr Cys Gln Leu

```
1               5                   10                  15
Phe Ser Thr Val Arg Arg
            20
```

<210> SEQ ID NO 337
<211> LENGTH: 22
<212> TYPE: PRT
<213> ORGANISM: Artificial Sequence
<220> FEATURE:
<223> OTHER INFORMATION: synthetic

<400> SEQUENCE: 337

```
His Met Gln Trp Gly Lys Leu Pro Cys Leu Ala Ser Tyr Cys Trp Leu
1               5                   10                  15
Phe Trp Tyr Gly Ile Gly
            20
```

<210> SEQ ID NO 338
<211> LENGTH: 22
<212> TYPE: PRT
<213> ORGANISM: Artificial Sequence
<220> FEATURE:
<223> OTHER INFORMATION: synthetic

<400> SEQUENCE: 338

```
Leu Arg Gln Arg Leu Ala Lys Thr Cys Val Ala Ser Tyr Cys Trp Leu
1               5                   10                  15
Phe Ser Leu Val Ala Ser
            20
```

<210> SEQ ID NO 339
<211> LENGTH: 22
<212> TYPE: PRT
<213> ORGANISM: Artificial Sequence
<220> FEATURE:
<223> OTHER INFORMATION: synthetic

<400> SEQUENCE: 339

```
Trp His Glu Arg Gln Gln Leu Thr Cys Leu Ala Ser Tyr Cys Gly Leu
1               5                   10                  15
Phe Val Gly Gln Val Ala
            20
```

<210> SEQ ID NO 340
<211> LENGTH: 22
<212> TYPE: PRT
<213> ORGANISM: Artificial Sequence
<220> FEATURE:
<223> OTHER INFORMATION: synthetic

<400> SEQUENCE: 340

```
Arg Tyr Gln Arg Ala Arg Leu Thr Cys Leu Ala Ser Tyr Cys Gly Leu
1               5                   10                  15
Leu Phe Ser Met Ser Ala
            20
```

<210> SEQ ID NO 341
<211> LENGTH: 22
<212> TYPE: PRT
<213> ORGANISM: Artificial Sequence
<220> FEATURE:
<223> OTHER INFORMATION: synthetic

<400> SEQUENCE: 341

```
Ala Val Ala Ile Asn Lys Val Pro Cys Val Ala Ser Tyr Cys Gln Leu
1               5                   10                  15

Phe Glu Ser Lys Ile His
            20
```

<210> SEQ ID NO 342
<211> LENGTH: 22
<212> TYPE: PRT
<213> ORGANISM: Artificial Sequence
<220> FEATURE:
<223> OTHER INFORMATION: synthetic

<400> SEQUENCE: 342

```
Ala Trp Pro Tyr His Lys Pro Thr Cys Leu Ala Ser Gln Cys Trp Gln
1               5                   10                  15

Phe Leu Ala Gln Gly Ser
            20
```

<210> SEQ ID NO 343
<211> LENGTH: 22
<212> TYPE: PRT
<213> ORGANISM: Artificial Sequence
<220> FEATURE:
<223> OTHER INFORMATION: synthetic

<400> SEQUENCE: 343

```
Ser Tyr Gly Arg Thr Lys Leu Thr Cys Leu Ala Ser Ser Cys Trp Leu
1               5                   10                  15

Phe Gly Gln Val His Gly
            20
```

<210> SEQ ID NO 344
<211> LENGTH: 22
<212> TYPE: PRT
<213> ORGANISM: Artificial Sequence
<220> FEATURE:
<223> OTHER INFORMATION: synthetic

<400> SEQUENCE: 344

```
Gly Val Glu Asp Arg Gln Leu Thr Cys Leu Ala Ser Ser Cys Trp Val
1               5                   10                  15

Phe Ser Arg His Ser Val
            20
```

<210> SEQ ID NO 345
<211> LENGTH: 22
<212> TYPE: PRT
<213> ORGANISM: Artificial Sequence
<220> FEATURE:
<223> OTHER INFORMATION: synthetic

<400> SEQUENCE: 345

```
Arg Ser Phe Thr Ser Glu Leu Thr Cys Leu Ala Ser Ser Cys Arg Arg
1               5                   10                  15

Phe His His Val Pro Pro
            20
```

<210> SEQ ID NO 346
<211> LENGTH: 22
<212> TYPE: PRT
<213> ORGANISM: Artificial Sequence
<220> FEATURE:
<223> OTHER INFORMATION: synthetic

<400> SEQUENCE: 346

```
Ala Gln Leu Arg Arg Lys Leu Thr Cys Leu Ala Ser Tyr Cys Trp Leu
1               5                   10                  15

Phe Gly Phe Phe Ser Pro
            20

<210> SEQ ID NO 347
<211> LENGTH: 22
<212> TYPE: PRT
<213> ORGANISM: Artificial Sequence
<220> FEATURE:
<223> OTHER INFORMATION: synthetic

<400> SEQUENCE: 347

His Met Gln Trp Gly Lys Leu Pro Cys Leu Ala Ser Tyr Cys Trp Leu
1               5                   10                  15

Phe Trp Tyr Gly Ile Gly
            20

<210> SEQ ID NO 348
<211> LENGTH: 22
<212> TYPE: PRT
<213> ORGANISM: Artificial Sequence
<220> FEATURE:
<223> OTHER INFORMATION: synthetic

<400> SEQUENCE: 348

Gln Gln Arg Gln Ile Lys Met Ser Cys Leu Ala Ser Tyr Cys Trp Leu
1               5                   10                  15

Phe Gly Ser Ile Pro Trp
            20

<210> SEQ ID NO 349
<211> LENGTH: 22
<212> TYPE: PRT
<213> ORGANISM: Artificial Sequence
<220> FEATURE:
<223> OTHER INFORMATION: synthetic

<400> SEQUENCE: 349

Gly Gly Ala Leu Gln Gln Leu Thr Cys Pro Ala Ser Tyr Cys Trp Leu
1               5                   10                  15

Phe Pro Met Glu His Ser
            20

<210> SEQ ID NO 350
<211> LENGTH: 22
<212> TYPE: PRT
<213> ORGANISM: Artificial Sequence
<220> FEATURE:
<223> OTHER INFORMATION: synthetic

<400> SEQUENCE: 350

His Tyr Ala Arg Val Gln Leu Arg Cys Leu Asp Gly Tyr Cys Trp Leu
1               5                   10                  15

Leu Thr Lys Ser Arg Met
            20

<210> SEQ ID NO 351
<211> LENGTH: 22
<212> TYPE: PRT
<213> ORGANISM: Artificial Sequence
<220> FEATURE:
<223> OTHER INFORMATION: synthetic
```

-continued

<400> SEQUENCE: 351

Tyr Ala Arg Asp Ser Thr Leu Thr Cys Gln Ala Arg Thr Cys Gln Leu
1               5                   10                  15

Val Asp Tyr Leu Gly Pro
            20

<210> SEQ ID NO 352
<211> LENGTH: 22
<212> TYPE: PRT
<213> ORGANISM: Artificial Sequence
<220> FEATURE:
<223> OTHER INFORMATION: synthetic

<400> SEQUENCE: 352

Gln Gly Gln Ala Arg Lys Leu Ala Cys Leu Ala Ser Tyr Cys Trp Leu
1               5                   10                  15

Phe Pro Ser Ser Ala Gly
            20

<210> SEQ ID NO 353
<211> LENGTH: 22
<212> TYPE: PRT
<213> ORGANISM: Artificial Sequence
<220> FEATURE:
<223> OTHER INFORMATION: synthetic

<400> SEQUENCE: 353

Ala Pro Pro Gly Gly Lys Arg Met Cys Leu Val Ser Gly Cys Gln Leu
1               5                   10                  15

Phe Pro Trp Ser Ala Ser
            20

<210> SEQ ID NO 354
<211> LENGTH: 22
<212> TYPE: PRT
<213> ORGANISM: Artificial Sequence
<220> FEATURE:
<223> OTHER INFORMATION: synthetic

<400> SEQUENCE: 354

Gln Asp Gly Asp Gly Lys Leu Thr Cys Arg Ala Ser Tyr Cys Arg Arg
1               5                   10                  15

Phe Leu Val Gly Val His
            20

<210> SEQ ID NO 355
<211> LENGTH: 22
<212> TYPE: PRT
<213> ORGANISM: Artificial Sequence
<220> FEATURE:
<223> OTHER INFORMATION: synthetic

<400> SEQUENCE: 355

Gly Ile Gln Gly Ser Glu Val Ala Cys Arg Ala Ser Phe Cys Arg Leu
1               5                   10                  15

Phe Glu Gln Gly His Val
            20

<210> SEQ ID NO 356
<211> LENGTH: 22
<212> TYPE: PRT
<213> ORGANISM: Artificial Sequence
<220> FEATURE:
<223> OTHER INFORMATION: synthetic

<400> SEQUENCE: 356

Arg Phe Gln Thr Thr Gln Leu Thr Cys Leu Gly Ser Ala Ser Cys Leu
1               5                   10                  15

Phe Asn Leu Ser Val Arg
            20

<210> SEQ ID NO 357
<211> LENGTH: 22
<212> TYPE: PRT
<213> ORGANISM: Artificial Sequence
<220> FEATURE:
<223> OTHER INFORMATION: synthetic

<400> SEQUENCE: 357

Ala Trp Pro Tyr His Lys Pro Thr Cys Leu Ala Ser Gln Cys Trp Gln
1               5                   10                  15

Phe Leu Ala Gln Gly Ser
            20

<210> SEQ ID NO 358
<211> LENGTH: 22
<212> TYPE: PRT
<213> ORGANISM: Artificial Sequence
<220> FEATURE:
<223> OTHER INFORMATION: synthetic

<400> SEQUENCE: 358

Gly Phe Gly Ser Arg Lys Leu Thr Ser Leu Ala Ser Tyr Gly Trp Leu
1               5                   10                  15

Ile Gln Asp Arg Leu Pro
            20

<210> SEQ ID NO 359
<211> LENGTH: 22
<212> TYPE: PRT
<213> ORGANISM: Artificial Sequence
<220> FEATURE:
<223> OTHER INFORMATION: synthetic

<400> SEQUENCE: 359

Ser Gly Arg Gly Gly Lys Leu Thr Cys Gln Ala Ser Phe Cys Gln Leu
1               5                   10                  15

Phe Gly Asn Gly Leu Ser
            20

<210> SEQ ID NO 360
<211> LENGTH: 22
<212> TYPE: PRT
<213> ORGANISM: Artificial Sequence
<220> FEATURE:
<223> OTHER INFORMATION: synthetic

<400> SEQUENCE: 360

Arg Ser Gln Gly Arg Lys Leu Thr Cys Leu Ala Ser Tyr Cys Trp Leu
1               5                   10                  15

Phe Leu Val Val His Arg
            20

<210> SEQ ID NO 361
<211> LENGTH: 22
<212> TYPE: PRT
<213> ORGANISM: Artificial Sequence
<220> FEATURE:

<223> OTHER INFORMATION: synthetic

<400> SEQUENCE: 361

Glu Gly Arg Arg Asp Lys Leu Thr Cys Leu Ala Ser Tyr Cys Trp Leu
1               5                   10                  15

Val Gly His Gly Gln His
            20

<210> SEQ ID NO 362
<211> LENGTH: 22
<212> TYPE: PRT
<213> ORGANISM: Artificial Sequence
<220> FEATURE:
<223> OTHER INFORMATION: synthetic

<400> SEQUENCE: 362

Arg Gly Arg Ser Ala Lys Leu Arg Cys Leu Ala Ser Tyr Cys Trp Leu
1               5                   10                  15

Phe Phe Gly Val Ile Leu
            20

<210> SEQ ID NO 363
<211> LENGTH: 22
<212> TYPE: PRT
<213> ORGANISM: Artificial Sequence
<220> FEATURE:
<223> OTHER INFORMATION: synthetic

<400> SEQUENCE: 363

Leu Leu Gln Ile Pro Asn Leu Thr Cys Leu Gly Ser Tyr Cys Trp Leu
1               5                   10                  15

Asp Asn Gly Val Tyr Ala
            20

<210> SEQ ID NO 364
<211> LENGTH: 22
<212> TYPE: PRT
<213> ORGANISM: Artificial Sequence
<220> FEATURE:
<223> OTHER INFORMATION: synthetic

<400> SEQUENCE: 364

Phe Gly Gln Pro Ser Arg Leu Thr Cys Leu Ala Ser Tyr Cys Trp Leu
1               5                   10                  15

Phe Gly Asn Leu Val Thr
            20

<210> SEQ ID NO 365
<211> LENGTH: 22
<212> TYPE: PRT
<213> ORGANISM: Artificial Sequence
<220> FEATURE:
<223> OTHER INFORMATION: synthetic

<400> SEQUENCE: 365

Gly Glu Gly Gly Gly Lys Leu Ser Cys Val Ala Ile Gln Cys Gly Leu
1               5                   10                  15

Phe Lys Gly Leu Gly Arg
            20

<210> SEQ ID NO 366
<211> LENGTH: 22
<212> TYPE: PRT
<213> ORGANISM: Artificial Sequence
<220> FEATURE:
<223> OTHER INFORMATION: synthetic

<400> SEQUENCE: 366

Val Asp Lys Gly His Gln Leu Arg Cys Gln Ala Gly Tyr Cys Trp Leu
1               5                   10                  15
Leu Gly Tyr Asn Arg Glu
            20

<210> SEQ ID NO 367
<211> LENGTH: 22
<212> TYPE: PRT
<213> ORGANISM: Artificial Sequence
<220> FEATURE:
<223> OTHER INFORMATION: synthetic

<400> SEQUENCE: 367

Ser Gly Phe Gly Met Lys Leu Thr Cys Leu Ala Ser Tyr Cys Gly Leu
1               5                   10                  15
Phe Gln Gly Glu Ile Gly
            20

<210> SEQ ID NO 368
<211> LENGTH: 22
<212> TYPE: PRT
<213> ORGANISM: Artificial Sequence
<220> FEATURE:
<223> OTHER INFORMATION: synthetic

<400> SEQUENCE: 368

Leu Leu His Ala Gln Lys Leu Ser Cys Leu Ala Ser Tyr Cys Trp Val
1               5                   10                  15
Phe Asp Ala Glu Trp Asp
            20

<210> SEQ ID NO 369
<211> LENGTH: 22
<212> TYPE: PRT
<213> ORGANISM: Artificial Sequence
<220> FEATURE:
<223> OTHER INFORMATION: synthetic

<400> SEQUENCE: 369

Ser Gly Gly Ser Gly Lys Leu Thr Cys Leu Ala Ser Tyr Cys Trp Pro
1               5                   10                  15
Phe Gly Ser Gln Val Arg
            20

<210> SEQ ID NO 370
<211> LENGTH: 22
<212> TYPE: PRT
<213> ORGANISM: Artificial Sequence
<220> FEATURE:
<223> OTHER INFORMATION: synthetic

<400> SEQUENCE: 370

Gln Asp Gly Val Glu Lys Leu Thr Cys Leu Ala Ser Tyr Cys Trp Arg
1               5                   10                  15
Phe Gly Asp His Gly Ala
            20

<210> SEQ ID NO 371
<211> LENGTH: 22
<212> TYPE: PRT

<213> ORGANISM: Artificial Sequence
<220> FEATURE:
<223> OTHER INFORMATION: synthetic

<400> SEQUENCE: 371

Asp Ala Gly Pro Asn Lys Leu Arg Cys Leu Ala Ser Tyr Cys Gln Leu
1               5                   10                  15
Phe Gly Gly Gly His Ala
            20

<210> SEQ ID NO 372
<211> LENGTH: 22
<212> TYPE: PRT
<213> ORGANISM: Artificial Sequence
<220> FEATURE:
<223> OTHER INFORMATION: synthetic

<400> SEQUENCE: 372

Thr Leu Leu Tyr Gln Asn Arg Thr Cys Leu Ala Ser Tyr Cys Trp Leu
1               5                   10                  15
Phe Asp Lys Arg Ser Val
            20

<210> SEQ ID NO 373
<211> LENGTH: 22
<212> TYPE: PRT
<213> ORGANISM: Artificial Sequence
<220> FEATURE:
<223> OTHER INFORMATION: synthetic

<400> SEQUENCE: 373

Leu Thr Trp Arg Glu Lys Leu Ala Cys Leu Ala Ser Tyr Cys Trp Leu
1               5                   10                  15
Phe Leu Trp Gly Ala Pro
            20

<210> SEQ ID NO 374
<211> LENGTH: 22
<212> TYPE: PRT
<213> ORGANISM: Artificial Sequence
<220> FEATURE:
<223> OTHER INFORMATION: synthetic

<400> SEQUENCE: 374

Arg Gln Leu Trp Asn Lys Leu Thr Cys Leu Ala Ser Tyr Cys Ala Leu
1               5                   10                  15
Ile Gly Leu Ser Gly Thr
            20

<210> SEQ ID NO 375
<211> LENGTH: 22
<212> TYPE: PRT
<213> ORGANISM: Artificial Sequence
<220> FEATURE:
<223> OTHER INFORMATION: synthetic

<400> SEQUENCE: 375

Lys Gly Ala Tyr Gln Lys Leu Thr Cys Leu Ala Ser Tyr Cys Leu Leu
1               5                   10                  15
Phe Leu Leu Thr Ala Gln
            20

<210> SEQ ID NO 376
<211> LENGTH: 22

```
<212> TYPE: PRT
<213> ORGANISM: Artificial Sequence
<220> FEATURE:
<223> OTHER INFORMATION: synthetic

<400> SEQUENCE: 376

Gln Glu Gln Pro Ala Lys Leu Thr Cys Arg Gly Ser Tyr Cys Trp Leu
1               5                   10                  15

Phe Lys Arg Gly Asp Gln
            20

<210> SEQ ID NO 377
<211> LENGTH: 22
<212> TYPE: PRT
<213> ORGANISM: Artificial Sequence
<220> FEATURE:
<223> OTHER INFORMATION: synthetic

<400> SEQUENCE: 377

His Asp Ser Leu Asp Gln Leu Thr Cys Leu Ala Ser Val Cys Gln Leu
1               5                   10                  15

Ala Ser Met Gly Ala Arg
            20

<210> SEQ ID NO 378
<211> LENGTH: 22
<212> TYPE: PRT
<213> ORGANISM: Artificial Sequence
<220> FEATURE:
<223> OTHER INFORMATION: synthetic

<400> SEQUENCE: 378

Ser Arg Gln Ser Asp Lys Pro Thr Cys Leu Ala Ile Ser Cys Ser Leu
1               5                   10                  15

Leu Thr Ser Asn Val Arg
            20

<210> SEQ ID NO 379
<211> LENGTH: 22
<212> TYPE: PRT
<213> ORGANISM: Artificial Sequence
<220> FEATURE:
<223> OTHER INFORMATION: synthetic

<400> SEQUENCE: 379

His Gly Leu Ala Asp Arg Leu Thr Cys Leu Ser Ser Asp Cys Trp Leu
1               5                   10                  15

Gln Pro Phe Gly Thr Ser
            20

<210> SEQ ID NO 380
<211> LENGTH: 22
<212> TYPE: PRT
<213> ORGANISM: Artificial Sequence
<220> FEATURE:
<223> OTHER INFORMATION: synthetic

<400> SEQUENCE: 380

Val Ala Arg Ala Ser Lys Val Glu Cys Leu Ala Ser Tyr Cys Gln Leu
1               5                   10                  15

Phe Val Gly Gly Glu Val
            20

<210> SEQ ID NO 381
```

```
<211> LENGTH: 22
<212> TYPE: PRT
<213> ORGANISM: Artificial Sequence
<220> FEATURE:
<223> OTHER INFORMATION: synthetic

<400> SEQUENCE: 381

Gly Ala Ser Gly Arg Arg Arg Thr Cys Val Ala Ser Tyr Cys Leu Leu
1               5                   10                  15

Phe Gln Ser Gly Leu Pro
            20

<210> SEQ ID NO 382
<211> LENGTH: 22
<212> TYPE: PRT
<213> ORGANISM: Artificial Sequence
<220> FEATURE:
<223> OTHER INFORMATION: synthetic

<400> SEQUENCE: 382

Phe Pro Ile Gln His Lys Leu Thr Cys Leu Ser Ser Asp Cys Trp Leu
1               5                   10                  15

Phe Pro Ser His Ser Tyr
            20

<210> SEQ ID NO 383
<211> LENGTH: 22
<212> TYPE: PRT
<213> ORGANISM: Artificial Sequence
<220> FEATURE:
<223> OTHER INFORMATION: synthetic

<400> SEQUENCE: 383

Gln Ala Lys Met Leu Lys Leu Thr Cys Leu Ala Ser Tyr Cys Trp Leu
1               5                   10                  15

Phe Trp Val Thr Arg Ser
            20

<210> SEQ ID NO 384
<211> LENGTH: 22
<212> TYPE: PRT
<213> ORGANISM: Artificial Sequence
<220> FEATURE:
<223> OTHER INFORMATION: synthetic

<400> SEQUENCE: 384

Arg Gly Arg Ser Ala Lys Leu Arg Cys Leu Ala Ser Tyr Cys Trp Leu
1               5                   10                  15

Phe Phe Gly Val Ile Leu
            20

<210> SEQ ID NO 385
<211> LENGTH: 22
<212> TYPE: PRT
<213> ORGANISM: Artificial Sequence
<220> FEATURE:
<223> OTHER INFORMATION: synthetic

<400> SEQUENCE: 385

Arg Gly Arg Ser Ala Lys Leu Thr Cys Leu Ala Ser Tyr Cys Trp Leu
1               5                   10                  15

Phe Phe Gly Val Ile Leu
            20
```

```
<210> SEQ ID NO 386
<211> LENGTH: 22
<212> TYPE: PRT
<213> ORGANISM: Artificial Sequence
<220> FEATURE:
<223> OTHER INFORMATION: synthetic

<400> SEQUENCE: 386

Arg Gly Arg Ser Ala Lys Leu Arg Cys Leu Ala Ser Tyr Cys Trp Leu
1               5                   10                  15

Phe Phe Thr Val Ile Leu
            20

<210> SEQ ID NO 387
<211> LENGTH: 22
<212> TYPE: PRT
<213> ORGANISM: Artificial Sequence
<220> FEATURE:
<223> OTHER INFORMATION: synthetic

<400> SEQUENCE: 387

Val Ser Gly Thr Gly Arg Leu Thr Cys Val Ala Ser Tyr Cys Trp Met
1               5                   10                  15

Phe Gln Leu Gly Ser Phe
            20

<210> SEQ ID NO 388
<211> LENGTH: 22
<212> TYPE: PRT
<213> ORGANISM: Artificial Sequence
<220> FEATURE:
<223> OTHER INFORMATION: synthetic

<400> SEQUENCE: 388

Val Ser Gly Thr Gly Arg Leu Thr Cys Val Ala Ser Tyr Cys Trp Met
1               5                   10                  15

Phe Gln Leu Gly Ile Phe
            20

<210> SEQ ID NO 389
<211> LENGTH: 22
<212> TYPE: PRT
<213> ORGANISM: Artificial Sequence
<220> FEATURE:
<223> OTHER INFORMATION: synthetic

<400> SEQUENCE: 389

Val Ser Gly Thr Gly Lys Leu Thr Cys Leu Ala Ser Tyr Cys Trp Leu
1               5                   10                  15

Phe Gln Leu Gly Ser Phe
            20

<210> SEQ ID NO 390
<211> LENGTH: 22
<212> TYPE: PRT
<213> ORGANISM: Artificial Sequence
<220> FEATURE:
<223> OTHER INFORMATION: synthetic

<400> SEQUENCE: 390

His Gln Gln Arg Arg Lys Leu Thr Cys Leu Ala Gly Tyr Cys Trp Leu
1               5                   10                  15

Phe Val Leu Gly Pro Ser
            20
```

```
<210> SEQ ID NO 391
<211> LENGTH: 22
<212> TYPE: PRT
<213> ORGANISM: Artificial Sequence
<220> FEATURE:
<223> OTHER INFORMATION: synthetic

<400> SEQUENCE: 391

Gly Asp Ser Gly Arg Lys Leu Ser Cys Leu Gly Ser Tyr Cys Trp Leu
1               5                   10                  15

Ser Val Gln Phe Met Ala
            20

<210> SEQ ID NO 392
<211> LENGTH: 22
<212> TYPE: PRT
<213> ORGANISM: Artificial Sequence
<220> FEATURE:
<223> OTHER INFORMATION: synthetic

<400> SEQUENCE: 392

Arg Ser Thr Val Ser Gln Met Arg Cys Leu Ala Ser Tyr Cys Trp Leu
1               5                   10                  15

Phe Pro Ala Leu Val Ser
            20

<210> SEQ ID NO 393
<211> LENGTH: 22
<212> TYPE: PRT
<213> ORGANISM: Artificial Sequence
<220> FEATURE:
<223> OTHER INFORMATION: synthetic

<400> SEQUENCE: 393

Asn Gly Gly Met Gln Lys Pro Ala Cys Leu Ala Ser Gln Cys Trp Leu
1               5                   10                  15

Phe Ala Asn Pro Leu Pro
            20

<210> SEQ ID NO 394
<211> LENGTH: 22
<212> TYPE: PRT
<213> ORGANISM: Artificial Sequence
<220> FEATURE:
<223> OTHER INFORMATION: synthetic

<400> SEQUENCE: 394

Arg His Ser Asn His Asn Leu Thr Cys Gln Ala Ser Tyr Cys Trp Leu
1               5                   10                  15

Leu Pro Ala Gly Leu Gln
            20

<210> SEQ ID NO 395
<211> LENGTH: 22
<212> TYPE: PRT
<213> ORGANISM: Artificial Sequence
<220> FEATURE:
<223> OTHER INFORMATION: synthetic

<400> SEQUENCE: 395

His Leu Gly Ser Pro Lys Leu Thr Cys Gly Ala Ser Gln Cys Trp Leu
1               5                   10                  15

Leu Asn His Glu Val Ser
            20
```

<210> SEQ ID NO 396
<211> LENGTH: 22
<212> TYPE: PRT
<213> ORGANISM: Artificial Sequence
<220> FEATURE:
<223> OTHER INFORMATION: synthetic

<400> SEQUENCE: 396

Asp Ala Lys Val Ala Lys Leu Arg Cys Leu Gly Ser Gln Cys Trp Leu
1               5                   10                  15

Leu Gln Tyr Ala Pro Gly
            20

<210> SEQ ID NO 397
<211> LENGTH: 22
<212> TYPE: PRT
<213> ORGANISM: Artificial Sequence
<220> FEATURE:
<223> OTHER INFORMATION: synthetic

<400> SEQUENCE: 397

Ser Lys Trp Glu His Gln Arg Gly Cys Leu Ala Asn Asn Cys Trp Leu
1               5                   10                  15

Phe Thr Leu Ala Pro Gly
            20

<210> SEQ ID NO 398
<211> LENGTH: 22
<212> TYPE: PRT
<213> ORGANISM: Artificial Sequence
<220> FEATURE:
<223> OTHER INFORMATION: synthetic

<400> SEQUENCE: 398

Arg Gly Ser Val His Gln Pro Thr Cys Leu Gly Gly Tyr Cys Gly Arg
1               5                   10                  15

Leu His Ser Ser Trp Val
            20

<210> SEQ ID NO 399
<211> LENGTH: 22
<212> TYPE: PRT
<213> ORGANISM: Artificial Sequence
<220> FEATURE:
<223> OTHER INFORMATION: synthetic

<400> SEQUENCE: 399

Lys Arg Tyr Val Tyr Arg Gln Met Cys Leu Val Ser Ala Cys Trp Leu
1               5                   10                  15

Leu Gln Leu Gly Tyr Ala
            20

<210> SEQ ID NO 400
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID
<220> FEATURE:
<221> NAME/KEY: MOD_RES
<222> LOCATION: (2)..(2)

<223> OTHER INFORMATION: METHYLATION

<400> SEQUENCE: 400

Lys Leu Thr Cys Leu Ala Ser Tyr Cys Trp Leu Phe
1               5                   10

<210> SEQ ID NO 401
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (2)..(2)
<223> OTHER INFORMATION: D-AMINO ACID
<220> FEATURE:
<221> NAME/KEY: MOD_RES
<222> LOCATION: (3)..(3)
<223> OTHER INFORMATION: METHYLATION

<400> SEQUENCE: 401

Lys Lys Leu Thr Cys Leu Ala Ser Tyr Cys Trp Leu Phe
1               5                   10

<210> SEQ ID NO 402
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: D-AMINO ACID
<220> FEATURE:
<221> NAME/KEY: MOD_RES
<222> LOCATION: (3)..(3)
<223> OTHER INFORMATION: METHYLATION

<400> SEQUENCE: 402

Lys Lys Leu Thr Cys Leu Ala Ser Tyr Cys Trp Leu Phe
1               5                   10

<210> SEQ ID NO 403
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (3)..(3)
<223> OTHER INFORMATION: D-AMINO ACID
<220> FEATURE:
<221> NAME/KEY: MOD_RES
<222> LOCATION: (4)..(4)
<223> OTHER INFORMATION: METHYLATION

<400> SEQUENCE: 403

Lys Lys Lys Leu Thr Cys Leu Ala Ser Tyr Cys Trp Leu Phe
1               5                   10

<210> SEQ ID NO 404
<211> LENGTH: 15
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (4)..(4)
<223> OTHER INFORMATION: D-AMINO ACID
<220> FEATURE:
<221> NAME/KEY: MOD_RES
<222> LOCATION: (5)..(5)
<223> OTHER INFORMATION: METHYLATION

<400> SEQUENCE: 404

Lys Lys Lys Lys Leu Thr Cys Leu Ala Ser Tyr Cys Trp Leu Phe
1               5                   10                  15

<210> SEQ ID NO 405
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(2)
<223> OTHER INFORMATION: D-AMINO ACIDS
<220> FEATURE:
<221> NAME/KEY: MOD_RES
<222> LOCATION: (3)..(3)
<223> OTHER INFORMATION: METHYLATION

<400> SEQUENCE: 405

Lys Lys Leu Thr Cys Leu Ala Ser Tyr Cys Trp Leu Phe
1               5                   10

<210> SEQ ID NO 406
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (2)..(2)
<223> OTHER INFORMATION: D-AMINO ACID
<220> FEATURE:
<221> NAME/KEY: MOD_RES
<222> LOCATION: (3)..(3)
<223> OTHER INFORMATION: METHYLATION

<400> SEQUENCE: 406

Arg Lys Leu Thr Cys Leu Ala Ser Tyr Cys Trp Leu Phe
1               5                   10

<210> SEQ ID NO 407
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID
<220> FEATURE:
<221> NAME/KEY: MOD_RES
<222> LOCATION: (2)..(2)
<223> OTHER INFORMATION: METHYLATION

<400> SEQUENCE: 407

Lys Leu Thr Cys Leu Ala Ser Phe Cys Trp Leu Phe
1               5                   10

<210> SEQ ID NO 408
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID
<220> FEATURE:
<221> NAME/KEY: MOD_RES
<222> LOCATION: (2)..(2)
<223> OTHER INFORMATION: METHYLATION
<220> FEATURE:
<221> NAME/KEY: MOD_RES
<222> LOCATION: (8)..(8)
<223> OTHER INFORMATION: METHYLATION

<400> SEQUENCE: 408

Lys Leu Thr Cys Leu Ala Ser Tyr Cys Trp Leu Phe
1               5                   10

<210> SEQ ID NO 409
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID
<220> FEATURE:
<221> NAME/KEY: MOD_RES
<222> LOCATION: (2)..(2)
<223> OTHER INFORMATION: METHYLATION

<400> SEQUENCE: 409

Lys Leu Thr Cys Leu Ala Ser Tyr Cys Gln Leu Phe
1               5                   10

<210> SEQ ID NO 410
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID
<220> FEATURE:
<221> NAME/KEY: MOD_RES
<222> LOCATION: (2)..(2)
<223> OTHER INFORMATION: METHYLATION

<400> SEQUENCE: 410

Lys Leu Thr Cys Leu Ala Ser Tyr Cys Trp Leu Ala
1               5                   10

<210> SEQ ID NO 411
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (12)..(12)
<223> OTHER INFORMATION: dimer with linker 1

-continued

<400> SEQUENCE: 411

Lys Leu Thr Cys Leu Ala Ser Tyr Cys Trp Leu Phe
1               5                   10

<210> SEQ ID NO 412
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (13)..(13)
<223> OTHER INFORMATION: dimer with linker 1

<400> SEQUENCE: 412

Lys Leu Thr Cys Leu Ala Ser Tyr Cys Trp Leu Phe Gly
1               5                   10

<210> SEQ ID NO 413
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: dimer with linker 2
<220> FEATURE:
<221> NAME/KEY: MOD_RES
<222> LOCATION: (12)..(12)
<223> OTHER INFORMATION: AMIDATION

<400> SEQUENCE: 413

Lys Leu Thr Cys Leu Ala Ser Tyr Cys Trp Leu Phe
1               5                   10

<210> SEQ ID NO 414
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 414

Arg Arg Ala Ala Gly Lys Leu Thr Cys Leu Ala Ser Tyr Cys Trp Leu
1               5                   10                  15

Phe Ala Thr Gly Ile Ala
            20

<210> SEQ ID NO 415
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 415

Arg Arg Ala Ala Gly Lys Ala Thr Cys Leu Ala Ser Tyr Cys Trp Leu
1               5                   10                  15

Phe Ala Thr Gly Ile Ala
            20

<210> SEQ ID NO 416
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 416

Arg Arg Ala Ala Gly Lys Leu Thr Cys Leu Ala Ser Ala Cys Trp Leu
1               5                   10                  15

Phe Ala Thr Gly Ile Ala
            20

<210> SEQ ID NO 417
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 417

Arg Arg Ala Ala Gly Lys Leu Thr Cys Leu Ala Ser Tyr Cys Trp Leu
1               5                   10                  15

Ala Ala Thr Gly Ile Ala
            20

<210> SEQ ID NO 418
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 418

Arg Arg Ala Ala Gly Lys Ala Thr Cys Leu Ala Ser Ala Cys Trp Leu
1               5                   10                  15

Ala Ala Thr Gly Ile Ala
            20

<210> SEQ ID NO 419
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 419

Arg Arg Ala Ser Gly Lys Leu Thr Cys Leu Ala Ser Tyr Cys Trp Leu

Phe Trp Thr Gly Ile Ala
        20

<210> SEQ ID NO 420
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 420

Arg Arg Ala Pro Gly Lys Leu Thr Cys Leu Ala Ser Tyr Cys Trp Leu
1               5                   10                  15

Phe Ser Thr Gly Ile Ala
        20

<210> SEQ ID NO 421
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 421

Arg Arg Ala Pro Gly Lys Ser Thr Cys Leu Ala Ser Tyr Cys Trp Leu
1               5                   10                  15

Phe Trp Thr Gly Ile Ala
        20

<210> SEQ ID NO 422
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 422

Arg Arg Ala Pro Gly Lys Leu Thr Cys Leu Ala Ser Ser Cys Trp Leu
1               5                   10                  15

Phe Trp Thr Gly Ile Ala
        20

<210> SEQ ID NO 423
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 423

Arg Arg Ala Pro Gly Lys Leu Thr Cys Leu Ala Ser Tyr Cys Trp Leu
1               5                   10                  15

Ser Trp Thr Gly Ile Ala
            20

<210> SEQ ID NO 424
<211> LENGTH: 28
<212> TYPE: PRT
<213> ORGANISM: Artificial Sequence
<220> FEATURE:
<223> OTHER INFORMATION: synthetic

<400> SEQUENCE: 424

Thr Val Gly Pro Gly Ser Arg Ser Ala Ser Gly Lys Leu Thr Cys Leu
1               5                   10                  15

Ala Ser Tyr Cys Trp Leu Phe Trp Thr Gly Ile Ala
            20                  25

<210> SEQ ID NO 425
<211> LENGTH: 32
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (4)..(4)
<223> OTHER INFORMATION: D-AMINO ACID

<400> SEQUENCE: 425

Pro Arg Ile Arg Thr Val Gly Pro Gly Ser Arg Ser Ala Ser Gly Lys
1               5                   10                  15

Leu Thr Cys Leu Ala Ser Tyr Cys Trp Leu Phe Trp Thr Gly Ile Ala
            20                  25                  30

<210> SEQ ID NO 426
<211> LENGTH: 32
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (4)..(4)
<223> OTHER INFORMATION: D-AMINO ACID
<220> FEATURE:
<221> NAME/KEY: MISC_FEATURE
<222> LOCATION: (11)..(11)
<223> OTHER INFORMATION: D-AMINO ACID

<400> SEQUENCE: 426

Pro Arg Ile Arg Thr Val Gly Pro Gly Ser Arg Ser Ala Ser Gly Lys
1               5                   10                  15

Leu Thr Cys Leu Ala Ser Tyr Cys Trp Leu Phe Trp Thr Gly Ile Ala
            20                  25                  30

<210> SEQ ID NO 427
<211> LENGTH: 32
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (32)..(32)
<223> OTHER INFORMATION: PEG4

<400> SEQUENCE: 427

```
Pro Arg Ile Arg Thr Val Gly Pro Gly Ser Arg Ser Ala Ser Gly Lys
1               5                   10                  15

Leu Thr Cys Leu Ala Ser Tyr Cys Trp Leu Phe Trp Thr Gly Ile Ala
            20                  25                  30
```

<210> SEQ ID NO 428
<211> LENGTH: 32
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: PEG4

<400> SEQUENCE: 428

```
Pro Arg Ile Arg Thr Val Gly Pro Gly Ser Arg Ser Ala Ser Gly Lys
1               5                   10                  15

Leu Thr Cys Leu Ala Ser Tyr Cys Trp Leu Phe Trp Thr Gly Ile Ala
            20                  25                  30
```

<210> SEQ ID NO 429
<211> LENGTH: 33
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (32)..(33)
<223> OTHER INFORMATION: PEG4
<220> FEATURE:
<221> NAME/KEY: MOD_RES
<222> LOCATION: (33)..(33)
<223> OTHER INFORMATION: Xaa is Pra

<400> SEQUENCE: 429

```
Pro Arg Ile Arg Thr Val Gly Pro Gly Ser Arg Ser Ala Ser Gly Lys
1               5                   10                  15

Leu Thr Cys Leu Ala Ser Tyr Cys Trp Leu Phe Trp Thr Gly Ile Ala
            20                  25                  30

Xaa
```

<210> SEQ ID NO 430
<211> LENGTH: 33
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (1)..(1)
<223> OTHER INFORMATION: Xaa is Pra
<220> FEATURE:
<221> NAME/KEY: MISC_FEATURE
<222> LOCATION: (1)..(2)
<223> OTHER INFORMATION: PEG4

<400> SEQUENCE: 430

```
Xaa Pro Arg Ile Arg Thr Val Gly Pro Gly Ser Arg Ser Ala Ser Gly
1               5                   10                  15

Lys Leu Thr Cys Leu Ala Ser Tyr Cys Trp Leu Phe Trp Thr Gly Ile
            20                  25                  30

Ala
```

<210> SEQ ID NO 431
<211> LENGTH: 32
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (1)..(1)
<223> OTHER INFORMATION: ACETYLATION

<400> SEQUENCE: 431

Pro Arg Ile Arg Thr Val Gly Pro Gly Ser Arg Ser Ala Ser Gly Lys
1               5                   10                  15

Leu Thr Cys Leu Ala Ser Tyr Cys Trp Leu Phe Trp Thr Gly Ile Ala
            20                  25                  30

<210> SEQ ID NO 432
<211> LENGTH: 32
<212> TYPE: PRT
<213> ORGANISM: Artificial Sequence
<220> FEATURE:
<223> OTHER INFORMATION: synthetic

<400> SEQUENCE: 432

Ser Arg Ile Arg Thr Val Gly Pro Gly Ser Arg Ser Ala Ser Gly Lys
1               5                   10                  15

Leu Thr Cys Leu Ala Ser Tyr Cys Trp Leu Phe Trp Thr Gly Ile Ala
            20                  25                  30

<210> SEQ ID NO 433
<211> LENGTH: 32
<212> TYPE: PRT
<213> ORGANISM: Artificial Sequence
<220> FEATURE:
<223> OTHER INFORMATION: synthetic

<400> SEQUENCE: 433

Pro Ser Ile Arg Thr Val Gly Pro Gly Ser Arg Ser Ala Ser Gly Lys
1               5                   10                  15

Leu Thr Cys Leu Ala Ser Tyr Cys Trp Leu Phe Trp Thr Gly Ile Ala
            20                  25                  30

<210> SEQ ID NO 434
<211> LENGTH: 32
<212> TYPE: PRT
<213> ORGANISM: Artificial Sequence
<220> FEATURE:
<223> OTHER INFORMATION: synthetic

<400> SEQUENCE: 434

Pro Arg Ser Arg Thr Val Gly Pro Gly Ser Arg Ser Ala Ser Gly Lys
1               5                   10                  15

Leu Thr Cys Leu Ala Ser Tyr Cys Trp Leu Phe Trp Thr Gly Ile Ala
            20                  25                  30

<210> SEQ ID NO 435
<211> LENGTH: 32
<212> TYPE: PRT
<213> ORGANISM: Artificial Sequence
<220> FEATURE:
<223> OTHER INFORMATION: synthetic

<400> SEQUENCE: 435

Pro Arg Ile Ser Thr Val Gly Pro Gly Ser Arg Ser Ala Ser Gly Lys

```
                1               5                  10                  15
Leu Thr Cys Leu Ala Ser Tyr Cys Trp Leu Phe Trp Thr Gly Ile Ala
            20                  25              30
```

<210> SEQ ID NO 436
<211> LENGTH: 32
<212> TYPE: PRT
<213> ORGANISM: Artificial Sequence
<220> FEATURE:
<223> OTHER INFORMATION: synthetic

<400> SEQUENCE: 436

```
Pro Arg Ile Arg Ser Val Gly Pro Gly Ser Arg Ser Ala Ser Gly Lys
1               5                  10                  15
Leu Thr Cys Leu Ala Ser Tyr Cys Trp Leu Phe Trp Thr Gly Ile Ala
            20                  25              30
```

<210> SEQ ID NO 437
<211> LENGTH: 32
<212> TYPE: PRT
<213> ORGANISM: Artificial Sequence
<220> FEATURE:
<223> OTHER INFORMATION: synthetic

<400> SEQUENCE: 437

```
Pro Arg Ile Arg Thr Ser Gly Pro Gly Ser Arg Ser Ala Ser Gly Lys
1               5                  10                  15
Leu Thr Cys Leu Ala Ser Tyr Cys Trp Leu Phe Trp Thr Gly Ile Ala
            20                  25              30
```

<210> SEQ ID NO 438
<211> LENGTH: 32
<212> TYPE: PRT
<213> ORGANISM: Artificial Sequence
<220> FEATURE:
<223> OTHER INFORMATION: synthetic

<400> SEQUENCE: 438

```
Pro Arg Ile Arg Thr Val Ser Pro Gly Ser Arg Ser Ala Ser Gly Lys
1               5                  10                  15
Leu Thr Cys Leu Ala Ser Tyr Cys Trp Leu Phe Trp Thr Gly Ile Ala
            20                  25              30
```

<210> SEQ ID NO 439
<211> LENGTH: 32
<212> TYPE: PRT
<213> ORGANISM: Artificial Sequence
<220> FEATURE:
<223> OTHER INFORMATION: synthetic

<400> SEQUENCE: 439

```
Pro Arg Ile Arg Thr Val Gly Ser Gly Ser Arg Ser Ala Ser Gly Lys
1               5                  10                  15
Leu Thr Cys Leu Ala Ser Tyr Cys Trp Leu Phe Trp Thr Gly Ile Ala
            20                  25              30
```

<210> SEQ ID NO 440
<211> LENGTH: 32
<212> TYPE: PRT
<213> ORGANISM: Artificial Sequence
<220> FEATURE:
<223> OTHER INFORMATION: synthetic

<400> SEQUENCE: 440

```
Pro Arg Ile Arg Thr Val Gly Pro Ser Ser Arg Ser Ala Ser Gly Lys
1               5                   10                  15

Leu Thr Cys Leu Ala Ser Tyr Cys Trp Leu Phe Trp Thr Gly Ile Ala
            20                  25                  30
```

<210> SEQ ID NO 441
<211> LENGTH: 32
<212> TYPE: PRT
<213> ORGANISM: Artificial Sequence
<220> FEATURE:
<223> OTHER INFORMATION: synthetic

<400> SEQUENCE: 441

```
Pro Arg Ile Arg Thr Val Gly Pro Gly Ser Arg Ser Ala Ser Gly Lys
1               5                   10                  15

Ser Thr Cys Leu Ala Ser Tyr Cys Trp Leu Phe Trp Thr Gly Ile Ala
            20                  25                  30
```

<210> SEQ ID NO 442
<211> LENGTH: 32
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (4)..(4)
<223> OTHER INFORMATION: D-AMINO ACID
<220> FEATURE:
<221> NAME/KEY: MISC_FEATURE
<222> LOCATION: (11)..(11)
<223> OTHER INFORMATION: D-AMINO ACID

<400> SEQUENCE: 442

```
Pro Arg Ile Arg Thr Val Gly Pro Gly Ser Arg Ser Ala Ser Gly Lys
1               5                   10                  15

Ser Thr Cys Leu Ala Ser Tyr Cys Trp Leu Phe Trp Thr Gly Ile Ala
            20                  25                  30
```

<210> SEQ ID NO 443
<211> LENGTH: 33
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (4)..(4)
<223> OTHER INFORMATION: D-AMINO ACID
<220> FEATURE:
<221> NAME/KEY: MISC_FEATURE
<222> LOCATION: (11)..(11)
<223> OTHER INFORMATION: D-AMINO ACID
<220> FEATURE:
<221> NAME/KEY: MISC_FEATURE
<222> LOCATION: (32)..(33)
<223> OTHER INFORMATION: PEG4
<220> FEATURE:
<221> NAME/KEY: MOD_RES
<222> LOCATION: (33)..(33)
<223> OTHER INFORMATION: Xaa is Pra

<400> SEQUENCE: 443

```
Pro Arg Ile Arg Thr Val Gly Pro Gly Ser Arg Ser Ala Ser Gly Lys
1               5                   10                  15

Ser Thr Cys Leu Ala Ser Tyr Cys Trp Leu Phe Trp Thr Gly Ile Ala
            20                  25                  30

Xaa
```

<210> SEQ ID NO 444
<211> LENGTH: 33
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (1)..(1)
<223> OTHER INFORMATION: Xaa is Pra
<220> FEATURE:
<221> NAME/KEY: MISC_FEATURE
<222> LOCATION: (1)..(2)
<223> OTHER INFORMATION: PEG4
<220> FEATURE:
<221> NAME/KEY: MOD_RES
<222> LOCATION: (5)..(5)
<223> OTHER INFORMATION: D-AMINO ACID
<220> FEATURE:
<221> NAME/KEY: MOD_RES
<222> LOCATION: (12)..(12)
<223> OTHER INFORMATION: D-AMINO ACID

<400> SEQUENCE: 444

Xaa Pro Arg Ile Arg Thr Val Gly Pro Gly Ser Arg Ser Ala Ser Gly
1               5                   10                  15

Lys Ser Thr Cys Leu Ala Ser Tyr Cys Trp Leu Phe Trp Thr Gly Ile
            20                  25                  30

Ala

<210> SEQ ID NO 445
<211> LENGTH: 32
<212> TYPE: PRT
<213> ORGANISM: Artificial Sequence
<220> FEATURE:
<223> OTHER INFORMATION: synthetic

<400> SEQUENCE: 445

Ser Arg Ile Arg Thr Val Gly Pro Gly Ser Arg Ser Ala Ser Gly Lys
1               5                   10                  15

Ser Thr Cys Leu Ala Ser Tyr Cys Trp Leu Phe Trp Thr Gly Ile Ala
            20                  25                  30

<210> SEQ ID NO 446
<211> LENGTH: 32
<212> TYPE: PRT
<213> ORGANISM: Artificial Sequence
<220> FEATURE:
<223> OTHER INFORMATION: synthetic

<400> SEQUENCE: 446

Pro Arg Ile Arg Thr Val Ser Pro Gly Ser Arg Ser Ala Ser Gly Lys
1               5                   10                  15

Ser Thr Cys Leu Ala Ser Tyr Cys Trp Leu Phe Trp Thr Gly Ile Ala
            20                  25                  30

<210> SEQ ID NO 447
<211> LENGTH: 32
<212> TYPE: PRT
<213> ORGANISM: Artificial Sequence
<220> FEATURE:
<223> OTHER INFORMATION: synthetic

<400> SEQUENCE: 447

Ser Arg Ile Arg Thr Val Ser Pro Gly Ser Arg Ser Ala Ser Gly Lys
1               5                   10                  15

Ser Thr Cys Leu Ala Ser Tyr Cys Trp Leu Phe Trp Thr Gly Ile Ala
            20                  25                  30

<210> SEQ ID NO 448
<211> LENGTH: 32
<212> TYPE: PRT
<213> ORGANISM: Artificial Sequence
<220> FEATURE:
<223> OTHER INFORMATION: synthetic

<400> SEQUENCE: 448

Pro Arg Ser Arg Thr Val Gly Pro Gly Ser Arg Ser Ala Ser Gly Lys
1               5                   10                  15

Ser Thr Cys Leu Ala Ser Tyr Cys Trp Leu Phe Trp Thr Gly Ile Ala
            20                  25                  30

<210> SEQ ID NO 449
<211> LENGTH: 32
<212> TYPE: PRT
<213> ORGANISM: Artificial Sequence
<220> FEATURE:
<223> OTHER INFORMATION: synthetic

<400> SEQUENCE: 449

Ser Arg Ser Arg Thr Val Ser Pro Gly Ser Arg Ser Ala Ser Gly Lys
1               5                   10                  15

Ser Thr Cys Leu Ala Ser Tyr Cys Trp Leu Phe Trp Thr Gly Ile Ala
            20                  25                  30

<210> SEQ ID NO 450
<211> LENGTH: 33
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (1)..(1)
<223> OTHER INFORMATION: PEG2-BIOTIN
<220> FEATURE:
<221> NAME/KEY: MISC_FEATURE
<222> LOCATION: (1)..(2)
<223> OTHER INFORMATION: PEG4

<400> SEQUENCE: 450

Lys Pro Arg Ile Arg Thr Val Gly Pro Gly Ser Arg Ser Ala Ser Gly
1               5                   10                  15

Lys Leu Thr Cys Leu Ala Ser Tyr Cys Trp Leu Phe Trp Thr Gly Ile
            20                  25                  30

Ala

<210> SEQ ID NO 451
<211> LENGTH: 32
<212> TYPE: PRT
<213> ORGANISM: Artificial Sequence
<220> FEATURE:
<223> OTHER INFORMATION: synthetic

<400> SEQUENCE: 451

Pro Arg Ile Arg Thr Val Gly Pro Gly Ser Arg Ser Ala Ser Gly Lys
1               5                   10                  15

Leu Thr Cys Leu Ala Ser Tyr Cys Trp Leu Ala Trp Thr Gly Ile Ala
            20                  25                  30

<210> SEQ ID NO 452
<211> LENGTH: 32
<212> TYPE: PRT
<213> ORGANISM: Artificial Sequence
<220> FEATURE:
<223> OTHER INFORMATION: synthetic

<400> SEQUENCE: 452

Pro Arg Ile Arg Thr Val Gly Pro Gly Ser Arg Ser Ala Ser Gly Lys
1               5                   10                  15

Leu Thr Cys Leu Ala Ser Tyr Cys Trp Leu Leu Trp Thr Gly Ile Ala
            20                  25                  30

<210> SEQ ID NO 453
<211> LENGTH: 32
<212> TYPE: PRT
<213> ORGANISM: Artificial Sequence
<220> FEATURE:
<223> OTHER INFORMATION: synthetic

<400> SEQUENCE: 453

Pro Arg Ile Arg Thr Val Gly Pro Gly Ser Arg Ser Ala Ser Gly Lys
1               5                   10                  15

Leu Thr Cys Leu Ala Ser Tyr Cys Trp Leu Phe Ala Thr Gly Ile Ala
            20                  25                  30

<210> SEQ ID NO 454
<211> LENGTH: 32
<212> TYPE: PRT
<213> ORGANISM: Artificial Sequence
<220> FEATURE:
<223> OTHER INFORMATION: synthetic

<400> SEQUENCE: 454

Pro Arg Ile Arg Thr Val Gly Pro Gly Ser Arg Ser Ala Ser Gly Lys
1               5                   10                  15

Leu Thr Cys Leu Ala Ser Tyr Cys Trp Leu Phe Phe Thr Gly Ile Ala
            20                  25                  30

<210> SEQ ID NO 455
<211> LENGTH: 32
<212> TYPE: PRT
<213> ORGANISM: Artificial Sequence
<220> FEATURE:
<223> OTHER INFORMATION: synthetic

<400> SEQUENCE: 455

Pro Arg Ile Arg Thr Val Gly Pro Gly Ser Arg Ser Ala Ser Gly Lys
1               5                   10                  15

Leu Thr Cys Leu Ala Ser Tyr Cys Trp Leu Phe Leu Thr Gly Ile Ala
            20                  25                  30

<210> SEQ ID NO 456
<211> LENGTH: 32
<212> TYPE: PRT
<213> ORGANISM: Artificial Sequence
<220> FEATURE:
<223> OTHER INFORMATION: synthetic

<400> SEQUENCE: 456

Pro Arg Ile Arg Thr Val Gly Pro Gly Ser Arg Ser Ala Ser Gly Lys
1               5                   10                  15

Leu Thr Cys Leu Ala Ser Tyr Cys Trp Leu Phe Trp Ser Gly Ile Ala
            20                  25                  30

<210> SEQ ID NO 457
<211> LENGTH: 32
<212> TYPE: PRT
<213> ORGANISM: Artificial Sequence
<220> FEATURE:
<223> OTHER INFORMATION: synthetic

<400> SEQUENCE: 457

Pro Arg Ile Arg Thr Val Gly Pro Gly Ser Arg Ser Ala Ser Gly Lys
1               5                   10                  15
Leu Thr Cys Leu Ala Ser Tyr Cys Trp Leu Phe Trp Thr Leu Ile Ala
            20                  25                  30

<210> SEQ ID NO 458
<211> LENGTH: 32
<212> TYPE: PRT
<213> ORGANISM: Artificial Sequence
<220> FEATURE:
<223> OTHER INFORMATION: synthetic

<400> SEQUENCE: 458

Pro Arg Ile Arg Thr Val Gly Pro Gly Ser Arg Ser Ala Ser Gly Lys
1               5                   10                  15
Leu Thr Cys Leu Ala Ser Tyr Cys Trp Leu Phe Trp Thr Phe Ile Ala
            20                  25                  30

<210> SEQ ID NO 459
<211> LENGTH: 32
<212> TYPE: PRT
<213> ORGANISM: Artificial Sequence
<220> FEATURE:
<223> OTHER INFORMATION: synthetic

<400> SEQUENCE: 459

Pro Arg Ile Arg Thr Val Gly Pro Gly Ser Arg Ser Ala Ser Gly Lys
1               5                   10                  15
Leu Thr Cys Leu Ala Ser Tyr Cys Trp Leu Phe Trp Thr Ser Ile Ala
            20                  25                  30

<210> SEQ ID NO 460
<211> LENGTH: 31
<212> TYPE: PRT
<213> ORGANISM: Artificial Sequence
<220> FEATURE:
<223> OTHER INFORMATION: synthetic

<400> SEQUENCE: 460

Pro Arg Ile Arg Thr Val Gly Pro Gly Ser Arg Ser Ala Ser Gly Lys
1               5                   10                  15
Leu Thr Cys Leu Ala Ser Tyr Cys Trp Leu Phe Trp Thr Gly Ile
            20                  25                  30

<210> SEQ ID NO 461
<211> LENGTH: 32
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (4)..(4)
<223> OTHER INFORMATION: D-AMINO ACID
<220> FEATURE:
<221> NAME/KEY: MISC_FEATURE
<222> LOCATION: (11)..(11)
<223> OTHER INFORMATION: D-AMINO ACID

```
<400> SEQUENCE: 461

Ser Arg Ile Arg Thr Val Ser Pro Gly Ser Arg Ala Ser Gly Lys
1               5                   10                  15

Ser Thr Cys Leu Ala Ser Tyr Cys Trp Leu Phe Trp Thr Gly Ile Ala
            20                  25                  30

<210> SEQ ID NO 462
<211> LENGTH: 32
<212> TYPE: PRT
<213> ORGANISM: Artificial Sequence
<220> FEATURE:
<223> OTHER INFORMATION: synthetic

<400> SEQUENCE: 462

Pro Arg Ile Arg Thr Val Gly Pro Gly Ser Arg Ala Ser Gly Lys
1               5                   10                  15

Leu Thr Cys Leu Ala Ser Tyr Cys Trp Leu Phe Trp Thr Gly Ile Ala
            20                  25                  30

<210> SEQ ID NO 463
<211> LENGTH: 32
<212> TYPE: PRT
<213> ORGANISM: Artificial Sequence
<220> FEATURE:
<223> OTHER INFORMATION: synthetic

<400> SEQUENCE: 463

Pro Arg Ile Arg Thr Val Gly Pro Gly Ser Ser Ala Ser Gly Lys
1               5                   10                  15

Leu Ser Cys Leu Ala Ser Tyr Cys Trp Leu Phe Trp Thr Gly Ile Ala
            20                  25                  30

<210> SEQ ID NO 464
<211> LENGTH: 32
<212> TYPE: PRT
<213> ORGANISM: Artificial Sequence
<220> FEATURE:
<223> OTHER INFORMATION: synthetic

<400> SEQUENCE: 464

Pro Arg Ile Arg Thr Val Gly Pro Gly Ser Arg Ser Ala Ser Gly Lys
1               5                   10                  15

Leu Thr Cys Ala Ala Ser Tyr Cys Trp Leu Phe Trp Thr Gly Ile Ala
            20                  25                  30

<210> SEQ ID NO 465
<211> LENGTH: 32
<212> TYPE: PRT
<213> ORGANISM: Artificial Sequence
<220> FEATURE:
<223> OTHER INFORMATION: synthetic

<400> SEQUENCE: 465

Pro Arg Ile Arg Thr Val Gly Pro Gly Ser Arg Ser Ala Ser Gly Lys
1               5                   10                  15

Leu Thr Cys Ser Ala Ser Tyr Cys Trp Leu Phe Trp Thr Gly Ile Ala
            20                  25                  30

<210> SEQ ID NO 466
<211> LENGTH: 32
<212> TYPE: PRT
<213> ORGANISM: Artificial Sequence
<220> FEATURE:
```

<223> OTHER INFORMATION: synthetic

<400> SEQUENCE: 466

Pro Arg Ile Arg Thr Val Gly Pro Gly Ser Arg Ser Ala Ser Gly Lys
1               5                   10                  15

Leu Thr Cys Ile Ala Ser Tyr Cys Trp Leu Phe Trp Thr Gly Ile Ala
            20                  25                  30

<210> SEQ ID NO 467
<211> LENGTH: 32
<212> TYPE: PRT
<213> ORGANISM: Artificial Sequence
<220> FEATURE:
<223> OTHER INFORMATION: synthetic

<400> SEQUENCE: 467

Pro Arg Ile Arg Thr Val Gly Pro Gly Ser Arg Ser Ala Ser Gly Lys
1               5                   10                  15

Leu Thr Cys Val Ala Ser Tyr Cys Trp Leu Phe Trp Thr Gly Ile Ala
            20                  25                  30

<210> SEQ ID NO 468
<211> LENGTH: 32
<212> TYPE: PRT
<213> ORGANISM: Artificial Sequence
<220> FEATURE:
<223> OTHER INFORMATION: synthetic

<400> SEQUENCE: 468

Pro Arg Ile Arg Thr Val Gly Pro Gly Ser Arg Ser Ala Ser Gly Lys
1               5                   10                  15

Leu Thr Cys Phe Ala Ser Tyr Cys Trp Leu Phe Trp Thr Gly Ile Ala
            20                  25                  30

<210> SEQ ID NO 469
<211> LENGTH: 32
<212> TYPE: PRT
<213> ORGANISM: Artificial Sequence
<220> FEATURE:
<223> OTHER INFORMATION: synthetic

<400> SEQUENCE: 469

Pro Arg Ile Arg Thr Val Gly Pro Gly Ser Arg Ser Ala Ser Gly Lys
1               5                   10                  15

Leu Thr Cys Leu Ala Ser Phe Cys Trp Leu Phe Trp Thr Gly Ile Ala
            20                  25                  30

<210> SEQ ID NO 470
<211> LENGTH: 32
<212> TYPE: PRT
<213> ORGANISM: Artificial Sequence
<220> FEATURE:
<223> OTHER INFORMATION: synthetic

<400> SEQUENCE: 470

Pro Arg Ile Arg Thr Val Gly Pro Gly Ser Arg Ser Ala Ser Gly Lys
1               5                   10                  15

Leu Thr Cys Leu Ala Ser Ala Cys Trp Leu Phe Trp Thr Gly Ile Ala
            20                  25                  30

<210> SEQ ID NO 471
<211> LENGTH: 32
<212> TYPE: PRT
<213> ORGANISM: Artificial Sequence

```
<220> FEATURE:
<223> OTHER INFORMATION: synthetic
<220> FEATURE:
<221> NAME/KEY: MISC_FEATURE
<222> LOCATION: (11)..(11)
<223> OTHER INFORMATION: D-AMINO ACID

<400> SEQUENCE: 471

Ser Lys Gln Gly Arg Pro Ile Ser Pro Asp Arg Arg Ala Ala Gly Lys
1               5                   10                  15

Leu Thr Cys Leu Ala Ser Tyr Cys Trp Leu Phe Trp Thr Gly Ile Ala
            20                  25                  30

<210> SEQ ID NO 472
<211> LENGTH: 33
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (32)..(33)
<223> OTHER INFORMATION: PEG2
<220> FEATURE:
<221> NAME/KEY: MOD_RES
<222> LOCATION: (33)..(33)
<223> OTHER INFORMATION: PEG2-BIOTIN

<400> SEQUENCE: 472

Ser Lys Gln Gly Arg Pro Ile Ser Pro Asp Arg Arg Ala Ala Gly Lys
1               5                   10                  15

Leu Thr Cys Leu Ala Ser Tyr Cys Trp Leu Phe Trp Thr Gly Ile Ala
            20                  25                  30

Lys

<210> SEQ ID NO 473
<211> LENGTH: 31
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (11)..(11)
<223> OTHER INFORMATION: D-AMINO ACID

<400> SEQUENCE: 473

Ser Lys Gln Gly Arg Pro Ile Ser Pro Asp Arg Arg Ala Ala Gly Lys
1               5                   10                  15

Leu Thr Cys Leu Ala Ser Tyr Cys Trp Leu Phe Trp Thr Gly Ile
            20                  25                  30

<210> SEQ ID NO 474
<211> LENGTH: 30
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (11)..(11)
<223> OTHER INFORMATION: D-AMINO ACID

<400> SEQUENCE: 474

Ser Lys Gln Gly Arg Pro Ile Ser Pro Asp Arg Arg Ala Ala Gly Lys
1               5                   10                  15

Leu Thr Cys Leu Ala Ser Tyr Cys Trp Leu Phe Trp Thr Gly
            20                  25                  30
```

-continued

```
                 20                  25                  30
```

```
<210> SEQ ID NO 475
<211> LENGTH: 29
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (11)..(11)
<223> OTHER INFORMATION: D-AMINO ACID

<400> SEQUENCE: 475

Ser Lys Gln Gly Arg Pro Ile Ser Pro Asp Arg Arg Ala Ala Gly Lys
1               5                   10                  15

Leu Thr Cys Leu Ala Ser Tyr Cys Trp Leu Phe Trp Thr
            20                  25

<210> SEQ ID NO 476
<211> LENGTH: 28
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (11)..(11)
<223> OTHER INFORMATION: D-AMINO ACID

<400> SEQUENCE: 476

Ser Lys Gln Gly Arg Pro Ile Ser Pro Asp Arg Arg Ala Ala Gly Lys
1               5                   10                  15

Leu Thr Cys Leu Ala Ser Tyr Cys Trp Leu Phe Trp
            20                  25

<210> SEQ ID NO 477
<211> LENGTH: 27
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (11)..(11)
<223> OTHER INFORMATION: D-AMINO ACID

<400> SEQUENCE: 477

Ser Lys Gln Gly Arg Pro Ile Ser Pro Asp Arg Arg Ala Ala Gly Lys
1               5                   10                  15

Leu Thr Cys Leu Ala Ser Tyr Cys Trp Leu Phe
            20                  25

<210> SEQ ID NO 478
<211> LENGTH: 32
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (11)..(11)
<223> OTHER INFORMATION: D-AMINO ACID

<400> SEQUENCE: 478

Ala Lys Gln Gly Arg Pro Ile Ser Pro Asp Arg Arg Ala Ala Gly Lys
1               5                   10                  15
```

```
Leu Thr Cys Leu Ala Ser Tyr Cys Trp Leu Phe Trp Thr Gly Ile Ala
            20                  25                  30
```

<210> SEQ ID NO 479
<211> LENGTH: 32
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (11)..(11)
<223> OTHER INFORMATION: D-AMINO ACID

<400> SEQUENCE: 479

```
Ser Ala Gln Gly Arg Pro Ile Ser Pro Asp Arg Arg Ala Ala Gly Lys
1               5                   10                  15
Leu Thr Cys Leu Ala Ser Tyr Cys Trp Leu Phe Trp Thr Gly Ile Ala
            20                  25                  30
```

<210> SEQ ID NO 480
<211> LENGTH: 32
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (11)..(11)
<223> OTHER INFORMATION: D-AMINO ACID

<400> SEQUENCE: 480

```
Ser Lys Ala Gly Arg Pro Ile Ser Pro Asp Arg Arg Ala Ala Gly Lys
1               5                   10                  15
Leu Thr Cys Leu Ala Ser Tyr Cys Trp Leu Phe Trp Thr Gly Ile Ala
            20                  25                  30
```

<210> SEQ ID NO 481
<211> LENGTH: 32
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (11)..(11)
<223> OTHER INFORMATION: D-AMINO ACID

<400> SEQUENCE: 481

```
Ser Lys Gln Ala Arg Pro Ile Ser Pro Asp Arg Arg Ala Ala Gly Lys
1               5                   10                  15
Leu Thr Cys Leu Ala Ser Tyr Cys Trp Leu Phe Trp Thr Gly Ile Ala
            20                  25                  30
```

<210> SEQ ID NO 482
<211> LENGTH: 32
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (11)..(11)
<223> OTHER INFORMATION: D-AMINO ACID

<400> SEQUENCE: 482

```
Ser Lys Gln Gly Ala Pro Ile Ser Pro Asp Arg Arg Ala Ala Gly Lys
1               5                   10                  15
```

Leu Thr Cys Leu Ala Ser Tyr Cys Trp Leu Phe Trp Thr Gly Ile Ala
            20                  25                  30

<210> SEQ ID NO 483
<211> LENGTH: 32
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (11)..(11)
<223> OTHER INFORMATION: D-AMINO ACID

<400> SEQUENCE: 483

Ser Lys Gln Gly Arg Ala Ile Ser Pro Asp Arg Arg Ala Ala Gly Lys
1               5                   10                  15
Leu Thr Cys Leu Ala Ser Tyr Cys Trp Leu Phe Trp Thr Gly Ile Ala
            20                  25                  30

<210> SEQ ID NO 484
<211> LENGTH: 32
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (11)..(11)
<223> OTHER INFORMATION: D-AMINO ACID

<400> SEQUENCE: 484

Ser Lys Gln Gly Arg Pro Ala Ser Pro Asp Arg Arg Ala Ala Gly Lys
1               5                   10                  15
Leu Thr Cys Leu Ala Ser Tyr Cys Trp Leu Phe Trp Thr Gly Ile Ala
            20                  25                  30

<210> SEQ ID NO 485
<211> LENGTH: 32
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (11)..(11)
<223> OTHER INFORMATION: D-AMINO ACID

<400> SEQUENCE: 485

Ser Lys Gln Gly Arg Pro Ile Ala Pro Asp Arg Arg Ala Ala Gly Lys
1               5                   10                  15
Leu Thr Cys Leu Ala Ser Tyr Cys Trp Leu Phe Trp Thr Gly Ile Ala
            20                  25                  30

<210> SEQ ID NO 486
<211> LENGTH: 32
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (11)..(11)
<223> OTHER INFORMATION: D-AMINO ACID

<400> SEQUENCE: 486

Ser Lys Gln Gly Arg Pro Ile Ser Ala Asp Arg Arg Ala Ala Gly Lys

```
                1               5                  10                  15
Leu Thr Cys Leu Ala Ser Tyr Cys Trp Leu Phe Trp Thr Gly Ile Ala
            20                  25                  30

<210> SEQ ID NO 487
<211> LENGTH: 32
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (11)..(11)
<223> OTHER INFORMATION: D-AMINO ACID

<400> SEQUENCE: 487

Ser Lys Gln Gly Arg Pro Ile Ser Pro Ala Arg Arg Ala Ala Gly Lys
1               5                   10                  15

Leu Thr Cys Leu Ala Ser Tyr Cys Trp Leu Phe Trp Thr Gly Ile Ala
            20                  25                  30

<210> SEQ ID NO 488
<211> LENGTH: 32
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (11)..(11)
<223> OTHER INFORMATION: D-AMINO ACID
<220> FEATURE:
<221> NAME/KEY: MISC_FEATURE
<222> LOCATION: (21)..(21)
<223> OTHER INFORMATION: D-AMINO ACID

<400> SEQUENCE: 488

Ser Lys Gln Gly Arg Pro Ile Ser Pro Asp Arg Arg Ala Ala Gly Lys
1               5                   10                  15

Leu Thr Cys Leu Ala Ser Tyr Cys Trp Leu Phe Trp Thr Gly Ile Ala
            20                  25                  30

<210> SEQ ID NO 489
<211> LENGTH: 32
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (11)..(11)
<223> OTHER INFORMATION: D-AMINO ACID

<400> SEQUENCE: 489

Ser Lys Gln Gly Arg Pro Ile Ser Pro Asp Arg Arg Ala Ala Gly Lys
1               5                   10                  15

Leu Thr Cys Leu Ala Ser Tyr Cys Trp Leu Phe Trp Thr Gly Ile Ala
            20                  25                  30

<210> SEQ ID NO 490
<211> LENGTH: 32
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (11)..(11)
```

```
<223> OTHER INFORMATION: D-AMINO ACID
<220> FEATURE:
<221> NAME/KEY: MOD_RES
<222> LOCATION: (23)..(23)
<223> OTHER INFORMATION: N-METHYLATION

<400> SEQUENCE: 490

Ser Lys Gln Gly Arg Pro Ile Ser Pro Asp Arg Arg Ala Ala Gly Lys
1               5                   10                  15
Leu Thr Cys Leu Ala Ser Tyr Cys Trp Leu Phe Trp Thr Gly Ile Ala
            20                  25                  30

<210> SEQ ID NO 491
<211> LENGTH: 32
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (11)..(11)
<223> OTHER INFORMATION: D-AMINO ACID
<220> FEATURE:
<221> NAME/KEY: MOD_RES
<222> LOCATION: (26)..(26)
<223> OTHER INFORMATION: N-METHYLATION

<400> SEQUENCE: 491

Ser Lys Gln Gly Arg Pro Ile Ser Pro Asp Arg Arg Ala Ala Gly Lys
1               5                   10                  15
Leu Thr Cys Leu Ala Ser Tyr Cys Trp Leu Phe Trp Thr Gly Ile Ala
            20                  25                  30

<210> SEQ ID NO 492
<211> LENGTH: 32
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (11)..(11)
<223> OTHER INFORMATION: D-AMINO ACID

<400> SEQUENCE: 492

Ser Lys Gln Gly Arg Pro Ile Ser Ser Asp Arg Arg Ala Ala Gly Lys
1               5                   10                  15
Leu Thr Cys Leu Ala Ser Tyr Cys Trp Leu Phe Trp Thr Gly Ile Ala
            20                  25                  30

<210> SEQ ID NO 493
<211> LENGTH: 32
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (11)..(11)
<223> OTHER INFORMATION: D-AMINO ACID

<400> SEQUENCE: 493

Ser Lys Gln Gly Arg Pro Ile Ser Ser Asp Arg Arg Ala Ala Gly Lys
1               5                   10                  15
Ser Thr Cys Leu Ala Ser Tyr Cys Trp Leu Phe Trp Thr Gly Ile Ala
            20                  25                  30
```

<210> SEQ ID NO 494
<211> LENGTH: 32
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (11)..(11)
<223> OTHER INFORMATION: D-AMINO ACID

<400> SEQUENCE: 494

Ser Lys Gln Gly Arg Pro Ile Ser Ser Asp Arg Arg Ala Ser Gly Lys
1               5                   10                  15

Leu Thr Cys Leu Ala Ser Tyr Cys Trp Leu Phe Trp Thr Gly Ile Ala
            20                  25                  30

<210> SEQ ID NO 495
<211> LENGTH: 32
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (11)..(11)
<223> OTHER INFORMATION: D-AMINO ACID

<400> SEQUENCE: 495

Ser Lys Gln Gly Arg Pro Ile Ser Ser Asp Arg Arg Ala Ser Gly Lys
1               5                   10                  15

Ser Thr Cys Leu Ala Ser Tyr Cys Trp Leu Phe Trp Thr Gly Ile Ala
            20                  25                  30

<210> SEQ ID NO 496
<211> LENGTH: 42
<212> TYPE: PRT
<213> ORGANISM: Artificial Sequence
<220> FEATURE:
<223> OTHER INFORMATION: synthetic

<400> SEQUENCE: 496

Ser Lys Gln Gly Arg Pro Ile Ser Pro Asp Arg Arg Ala Ala Gly Lys
1               5                   10                  15

Leu Thr Cys Leu Ala Ser Tyr Cys Trp Leu Phe Gly Ser Gly Ile Ser
            20                  25                  30

Leu Ser Arg Ala Pro Glu Ser Ala Ala Pro
            35                  40

<210> SEQ ID NO 497
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (22)..(22)
<223> OTHER INFORMATION: AMIDATION

<400> SEQUENCE: 497

Arg Arg Ala Pro Gly Lys Leu Cys Ala Leu Ala Ser Tyr Cys Trp Leu
1               5                   10                  15

Phe Trp Thr Gly Ile Ala
            20

<210> SEQ ID NO 498
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (22)..(22)
<223> OTHER INFORMATION: AMIDATION

<400> SEQUENCE: 498

Arg Arg Ala Pro Gly Lys Cys Thr Ala Leu Ala Ser Tyr Cys Trp Leu
1               5                   10                  15

Phe Trp Thr Gly Ile Ala
            20

<210> SEQ ID NO 499
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (22)..(22)
<223> OTHER INFORMATION: AMIDATION

<400> SEQUENCE: 499

Arg Arg Ala Pro Gly Cys Leu Thr Ala Leu Ala Ser Tyr Cys Trp Leu
1               5                   10                  15

Phe Trp Thr Gly Ile Ala
            20

<210> SEQ ID NO 500
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (22)..(22)
<223> OTHER INFORMATION: AMIDATION

<400> SEQUENCE: 500

Arg Arg Ala Pro Gly Lys Leu Thr Cys Leu Ala Ser Tyr Ala Cys Leu
1               5                   10                  15

Phe Trp Thr Gly Ile Ala
            20

<210> SEQ ID NO 501
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (22)..(22)
<223> OTHER INFORMATION: AMIDATION

<400> SEQUENCE: 501

Arg Arg Ala Pro Gly Lys Leu Thr Cys Leu Ala Ser Tyr Ala Trp Cys
1               5                   10                  15

Phe Trp Thr Gly Ile Ala
            20

<210> SEQ ID NO 502
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (22)..(22)
<223> OTHER INFORMATION: AMIDATION

<400> SEQUENCE: 502

Arg Arg Ala Pro Gly Lys Leu Thr Cys Leu Ala Ser Tyr Ala Trp Leu
1               5                   10                  15

Cys Trp Thr Gly Ile Ala
            20

<210> SEQ ID NO 503
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (22)..(22)
<223> OTHER INFORMATION: AMIDATION

<400> SEQUENCE: 503

Arg Arg Ala Pro Gly Lys Leu Cys Ala Leu Ala Ser Tyr Ala Cys Leu
1               5                   10                  15

Phe Trp Thr Gly Ile Ala
            20

<210> SEQ ID NO 504
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (22)..(22)
<223> OTHER INFORMATION: AMIDATION

<400> SEQUENCE: 504

Arg Arg Ala Pro Gly Lys Cys Thr Ala Leu Ala Ser Tyr Ala Trp Cys
1               5                   10                  15

Phe Trp Thr Gly Ile Ala
            20

<210> SEQ ID NO 505
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (22)..(22)
<223> OTHER INFORMATION: AMIDATION

<400> SEQUENCE: 505

Arg Arg Ala Pro Gly Cys Leu Thr Ala Leu Ala Ser Tyr Ala Trp Leu
1               5                   10                  15

Cys Trp Thr Gly Ile Ala
            20

```
<210> SEQ ID NO 506
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (9)..(9)
<223> OTHER INFORMATION: Xaa is Dab

<400> SEQUENCE: 506

Arg Arg Ala Pro Gly Lys Leu Thr Xaa Leu Ala Ser Tyr Asp Trp Leu
1               5                  10                  15

Phe Trp Thr Gly Ile Ala
            20

<210> SEQ ID NO 507
<211> LENGTH: 22
<212> TYPE: PRT
<213> ORGANISM: Artificial Sequence
<220> FEATURE:
<223> OTHER INFORMATION: synthetic

<400> SEQUENCE: 507

Arg Arg Ala Pro Gly Lys Leu Thr Lys Leu Ala Ser Tyr Glu Trp Leu
1               5                  10                  15

Phe Trp Thr Gly Ile Ala
            20

<210> SEQ ID NO 508
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (22)..(22)
<223> OTHER INFORMATION: AMIDATION

<400> SEQUENCE: 508

Arg Arg Ala Pro Gly Lys Leu Thr Lys Leu Ala Ser Tyr Asp Trp Leu
1               5                  10                  15

Phe Trp Thr Gly Ile Ala
            20

<210> SEQ ID NO 509
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (22)..(22)
<223> OTHER INFORMATION: AMIDATION

<400> SEQUENCE: 509

Arg Arg Ala Pro Gly Lys Leu Thr Asp Leu Ala Ser Tyr Lys Trp Leu
1               5                  10                  15

Phe Trp Thr Gly Ile Ala
            20

<210> SEQ ID NO 510
```

```
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (9)..(9)
<223> OTHER INFORMATION: Xaa is Orn
<220> FEATURE:
<221> NAME/KEY: MOD_RES
<222> LOCATION: (22)..(22)
<223> OTHER INFORMATION: AMIDATION

<400> SEQUENCE: 510

Arg Arg Ala Pro Gly Lys Leu Thr Xaa Leu Ala Ser Tyr Asp Trp Leu
1               5                   10                  15

Phe Trp Thr Gly Ile Ala
            20

<210> SEQ ID NO 511
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (14)..(14)
<223> OTHER INFORMATION: Xaa is Orn
<220> FEATURE:
<221> NAME/KEY: MOD_RES
<222> LOCATION: (22)..(22)
<223> OTHER INFORMATION: AMIDATION

<400> SEQUENCE: 511

Arg Arg Ala Pro Gly Lys Leu Thr Asp Leu Ala Ser Tyr Xaa Trp Leu
1               5                   10                  15

Phe Trp Thr Gly Ile Ala
            20

<210> SEQ ID NO 512
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (9)..(9)
<223> OTHER INFORMATION: Xaa is Dab
<220> FEATURE:
<221> NAME/KEY: MOD_RES
<222> LOCATION: (22)..(22)
<223> OTHER INFORMATION: AMIDATION

<400> SEQUENCE: 512

Arg Arg Ala Pro Gly Lys Leu Thr Xaa Leu Ala Ser Tyr Asp Trp Leu
1               5                   10                  15

Phe Trp Thr Gly Ile Ala
            20

<210> SEQ ID NO 513
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MOD_RES
```

```
<222> LOCATION: (9)..(9)
<223> OTHER INFORMATION: Xaa is Dap
<220> FEATURE:
<221> NAME/KEY: MOD_RES
<222> LOCATION: (22)..(22)
<223> OTHER INFORMATION: AMIDATION

<400> SEQUENCE: 513

Arg Arg Ala Pro Gly Lys Leu Thr Xaa Leu Ala Ser Tyr Asp Trp Leu
1               5                   10                  15

Phe Trp Thr Gly Ile Ala
            20

<210> SEQ ID NO 514
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (14)..(14)
<223> OTHER INFORMATION: Xaa is Dap
<220> FEATURE:
<221> NAME/KEY: MOD_RES
<222> LOCATION: (22)..(22)
<223> OTHER INFORMATION: AMIDATION

<400> SEQUENCE: 514

Arg Arg Ala Pro Gly Lys Leu Thr Asp Leu Ala Ser Tyr Xaa Trp Leu
1               5                   10                  15

Phe Trp Thr Gly Ile Ala
            20

<210> SEQ ID NO 515
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (22)..(22)
<223> OTHER INFORMATION: AMIDATION

<400> SEQUENCE: 515

Arg Arg Ala Pro Gly Lys Leu Thr Lys Leu Ala Ser Tyr Glu Trp Leu
1               5                   10                  15

Phe Trp Thr Gly Ile Ala
            20

<210> SEQ ID NO 516
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (14)..(14)
<223> OTHER INFORMATION: Xaa is Dab

<400> SEQUENCE: 516

Arg Arg Ala Pro Gly Lys Leu Thr Asp Leu Ala Ser Tyr Xaa Trp Leu
1               5                   10                  15

Phe Trp Thr Gly Ile Ala
            20
```

<210> SEQ ID NO 517
<211> LENGTH: 32
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (24)..(24)
<223> OTHER INFORMATION: Xaa is Orn

<400> SEQUENCE: 517

Ser Lys Gln Gly Arg Pro Ile Ser Pro Asp Arg Arg Ala Ala Gly Lys
1               5                   10                  15

Leu Thr Asp Leu Ala Ser Tyr Xaa Trp Leu Phe Trp Thr Gly Ile Ala
            20                  25                  30

<210> SEQ ID NO 518
<211> LENGTH: 32
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (14)..(14)
<223> OTHER INFORMATION: Xaa is Orn

<400> SEQUENCE: 518

Arg Arg Ala Pro Gly Lys Leu Thr Asp Leu Ala Ser Tyr Xaa Trp Leu
1               5                   10                  15

Phe Gly Ser Gly Ile Ser Leu Ser Arg Ala Pro Glu Ser Ala Ala Pro
            20                  25                  30

<210> SEQ ID NO 519
<211> LENGTH: 32
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (24)..(24)
<223> OTHER INFORMATION: Xaa is Orn

<400> SEQUENCE: 519

Pro Arg Ile Arg Thr Val Gly Pro Gly Ser Arg Ser Ala Ser Gly Lys
1               5                   10                  15

Leu Thr Asp Leu Ala Ser Tyr Xaa Trp Leu Phe Trp Thr Gly Ile Ala
            20                  25                  30

<210> SEQ ID NO 520
<211> LENGTH: 32
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (24)..(24)
<223> OTHER INFORMATION: Xaa is Orn

<400> SEQUENCE: 520

Arg Arg Phe Val Gly Gly Ser Leu Ser Gln Arg Arg Ala Pro Gly Lys
1               5                   10                  15

Leu Thr Asp Leu Ala Ser Tyr Xaa Trp Leu Phe Trp Thr Gly Ile Ala
            20                  25                  30

<210> SEQ ID NO 521
<211> LENGTH: 32
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (24)..(24)
<223> OTHER INFORMATION: Xaa is Orn

<400> SEQUENCE: 521

Pro Gln Thr Arg Asp Pro Ser Ser Arg Asp Arg Ala Pro Gly Lys
1               5                   10                  15
Leu Thr Asp Leu Ala Ser Tyr Xaa Trp Leu Phe Trp Thr Gly Ile Ala
            20                  25                  30

<210> SEQ ID NO 522
<211> LENGTH: 26
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (1)..(1)
<223> OTHER INFORMATION: PEG(5K)

<400> SEQUENCE: 522

Cys Gly Gly Gly Arg Arg Ala Pro Gly Lys Leu Thr Asp Leu Ala Ser
1               5                   10                  15
Tyr Lys Trp Leu Phe Trp Thr Gly Ile Ala
            20                  25

<210> SEQ ID NO 523
<211> LENGTH: 26
<212> TYPE: PRT
<213> ORGANISM: Artificial Sequence
<220> FEATURE:
<223> OTHER INFORMATION: synthetic

<400> SEQUENCE: 523

Cys Gly Gly Gly Arg Arg Ala Pro Gly Lys Leu Thr Asp Leu Ala Ser
1               5                   10                  15
Tyr Lys Trp Leu Phe Trp Thr Gly Ile Ala
            20                  25

<210> SEQ ID NO 524
<211> LENGTH: 33
<212> TYPE: PRT
<213> ORGANISM: Artificial Sequence
<220> FEATURE:
<223> OTHER INFORMATION: synthetic

<400> SEQUENCE: 524

Cys Gly Gly Gly Leu Val Pro Arg Gly Gly Arg Arg Ala Pro Gly
1               5                   10                  15
Lys Leu Thr Asp Leu Ala Ser Tyr Lys Trp Leu Phe Trp Thr Gly Ile
            20                  25                  30
Ala

<210> SEQ ID NO 525
<211> LENGTH: 33
<212> TYPE: PRT

```
<213> ORGANISM: Artificial Sequence
<220> FEATURE:
<223> OTHER INFORMATION: synthetic
<220> FEATURE:
<221> NAME/KEY: MOD_RES
<222> LOCATION: (1)..(1)
<223> OTHER INFORMATION: PEG(5K)

<400> SEQUENCE: 525

Cys Gly Gly Gly Leu Val Pro Arg Gly Gly Arg Arg Ala Pro Gly
1               5                   10                  15

Lys Leu Thr Asp Leu Ala Ser Tyr Lys Trp Leu Phe Trp Thr Gly Ile
                20                  25                  30

Ala

<210> SEQ ID NO 526
<211> LENGTH: 27
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (1)..(1)
<223> OTHER INFORMATION: N-ETHyLMALEIMIDE
<220> FEATURE:
<221> NAME/KEY: MISC_FEATURE
<222> LOCATION: (1)..(2)
<223> OTHER INFORMATION: PEG4
<220> FEATURE:
<221> NAME/KEY: MISC_FEATURE
<222> LOCATION: (5)..(6)
<223> OTHER INFORMATION: PEG4
<220> FEATURE:
<221> NAME/KEY: MISC_FEATURE
<222> LOCATION: (6)..(6)
<223> OTHER INFORMATION: D-AMINO ACID

<400> SEQUENCE: 526

Cys Leu Val Pro Arg Arg Arg Ala Pro Gly Lys Leu Thr Cys Leu Ala
1               5                   10                  15

Ser Tyr Cys Trp Leu Phe Trp Thr Gly Ile Ala
                20                  25

<210> SEQ ID NO 527
<211> LENGTH: 23
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID
<220> FEATURE:
<221> NAME/KEY: MISC_FEATURE
<222> LOCATION: (22)..(23)
<223> OTHER INFORMATION: PEG4
<220> FEATURE:
<221> NAME/KEY: MOD_RES
<222> LOCATION: (23)..(23)
<223> OTHER INFORMATION: N-PEG5K MALEIMIDE

<400> SEQUENCE: 527

Arg Arg Ala Pro Gly Lys Leu Thr Cys Leu Ala Ser Tyr Cys Trp Leu
1               5                   10                  15

Phe Trp Thr Gly Ile Ala Cys
                20
```

```
<210> SEQ ID NO 528
<211> LENGTH: 27
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (1)..(1)
<223> OTHER INFORMATION: N-PEG(5K)MALEIMIDE
<220> FEATURE:
<221> NAME/KEY: MISC_FEATURE
<222> LOCATION: (1)..(2)
<223> OTHER INFORMATION: PEG4
<220> FEATURE:
<221> NAME/KEY: MISC_FEATURE
<222> LOCATION: (5)..(6)
<223> OTHER INFORMATION: PEG4
<220> FEATURE:
<221> NAME/KEY: MISC_FEATURE
<222> LOCATION: (6)..(6)
<223> OTHER INFORMATION: D-AMINO ACID

<400> SEQUENCE: 528

Cys Leu Val Pro Arg Arg Arg Ala Pro Gly Lys Leu Thr Cys Leu Ala
1               5                   10                  15
Ser Tyr Cys Trp Leu Phe Trp Thr Gly Ile Ala
            20                  25

<210> SEQ ID NO 529
<211> LENGTH: 33
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (1)..(1)
<223> OTHER INFORMATION: N-PEG(5K)MALEIMIDE
<220> FEATURE:
<221> NAME/KEY: MISC_FEATURE
<222> LOCATION: (1)..(2)
<223> OTHER INFORMATION: PEG-4
<220> FEATURE:
<221> NAME/KEY: MISC_FEATURE
<222> LOCATION: (12)..(12)
<223> OTHER INFORMATION: D-AMINO ACID

<400> SEQUENCE: 529

Cys Ser Lys Gln Gly Arg Pro Ile Ser Pro Asp Arg Arg Ala Ala Gly
1               5                   10                  15
Lys Leu Thr Cys Leu Ala Ser Tyr Cys Trp Leu Phe Trp Thr Gly Ile
            20                  25                  30
Ala

<210> SEQ ID NO 530
<211> LENGTH: 33
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (11)..(11)
<223> OTHER INFORMATION: D-AMINO ACID
<220> FEATURE:
<221> NAME/KEY: MISC_FEATURE
<222> LOCATION: (32)..(33)
<223> OTHER INFORMATION: PEG4
<220> FEATURE:
<221> NAME/KEY: MOD_RES
<222> LOCATION: (33)..(33)
```

<223> OTHER INFORMATION: N-PEG(5K)MALEIMIDE

<400> SEQUENCE: 530

Ser Lys Gln Gly Arg Pro Ile Ser Pro Asp Arg Arg Ala Ala Gly Lys
1               5                   10                  15

Leu Thr Cys Leu Ala Ser Tyr Cys Trp Leu Phe Trp Thr Gly Ile Ala
            20                  25                  30

Cys

<210> SEQ ID NO 531
<211> LENGTH: 30
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (1)..(1)
<223> OTHER INFORMATION: Acm (acetamidomethyl)
<220> FEATURE:
<221> NAME/KEY: MISC_FEATURE
<222> LOCATION: (6)..(6)
<223> OTHER INFORMATION: D-AMINO ACID
<220> FEATURE:
<221> NAME/KEY: MOD_RES
<222> LOCATION: (7)..(7)
<223> OTHER INFORMATION: Xaa is Pip
<220> FEATURE:
<221> NAME/KEY: MISC_FEATURE
<222> LOCATION: (8)..(9)
<223> OTHER INFORMATION: PEG5
<220> FEATURE:
<221> NAME/KEY: MISC_FEATURE
<222> LOCATION: (9)..(9)
<223> OTHER INFORMATION: D-AMINO ACID

<400> SEQUENCE: 531

Cys Gly Gly Gly Gly Phe Xaa Arg Arg Arg Ala Pro Gly Lys Leu Thr
1               5                   10                  15

Cys Leu Ala Ser Tyr Cys Trp Leu Phe Trp Thr Gly Ile Ala
            20                  25                  30

<210> SEQ ID NO 532
<211> LENGTH: 39
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (8)..(8)
<223> OTHER INFORMATION: D-AMINO ACID
<220> FEATURE:
<221> NAME/KEY: MISC_FEATURE
<222> LOCATION: (16)..(17)
<223> OTHER INFORMATION: PEG12
<220> FEATURE:
<221> NAME/KEY: MOD_RES
<222> LOCATION: (17)..(17)
<223> OTHER INFORMATION: PEG2-BIOTIN
<220> FEATURE:
<221> NAME/KEY: MISC_FEATURE
<222> LOCATION: (17)..(18)
<223> OTHER INFORMATION: PEG12
<220> FEATURE:
<221> NAME/KEY: MISC_FEATURE
<222> LOCATION: (18)..(18)
<223> OTHER INFORMATION: D-AMINO ACID

<400> SEQUENCE: 532

Cys Lys Thr Tyr Phe Trp Lys Pro Gly Asn Ile Met Val Thr Phe Cys

```
1               5                   10                  15
Lys Arg Arg Ala Pro Gly Lys Leu Thr Cys Leu Ala Ser Tyr Cys Trp
        20                  25                  30

Leu Phe Trp Thr Gly Ile Ala
            35
```

<210> SEQ ID NO 533
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(22)
<223> OTHER INFORMATION: D-AMINO ACIDS

<400> SEQUENCE: 533

```
Arg Arg Ala Pro Gly Lys Leu Thr Cys Leu Ala Ser Tyr Cys Trp Leu
1               5                   10                  15

Phe Trp Thr Gly Ile Ala
            20
```

<210> SEQ ID NO 534
<211> LENGTH: 22
<212> TYPE: PRT
<213> ORGANISM: Artificial Sequence
<220> FEATURE:
<223> OTHER INFORMATION: synthetic

<400> SEQUENCE: 534

```
Ala Ile Gly Thr Trp Phe Leu Trp Cys Tyr Ser Ala Leu Cys Thr Leu
1               5                   10                  15

Lys Gly Pro Ala Arg Arg
            20
```

<210> SEQ ID NO 535
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(22)
<223> OTHER INFORMATION: D-AMINO ACIDS

<400> SEQUENCE: 535

```
Ala Ile Gly Thr Trp Phe Leu Trp Cys Tyr Ser Ala Leu Cys Thr Leu
1               5                   10                  15

Lys Gly Pro Ala Arg Arg
            20
```

<210> SEQ ID NO 536
<211> LENGTH: 22
<212> TYPE: PRT
<213> ORGANISM: Artificial Sequence
<220> FEATURE:
<223> OTHER INFORMATION: synthetic

<400> SEQUENCE: 536

```
Arg Arg Ala Pro Gly Lys Leu Thr Cys Leu Ala Ser Tyr Cys Trp Leu
1               5                   10                  15

Phe Trp Thr Gly Ile Ala
            20
```

<210> SEQ ID NO 537
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 537

Arg Arg Ala Pro Gly Lys Leu Thr Cys Leu Ala Ser Tyr Cys Trp Leu
1               5                   10                  15

Phe Trp Thr Gly Ile Ala
            20

<210> SEQ ID NO 538
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (4)..(4)
<223> OTHER INFORMATION: Xaa is Orn
<220> FEATURE:
<221> NAME/KEY: MOD_RES
<222> LOCATION: (12)..(12)
<223> OTHER INFORMATION: AMIDATION

<400> SEQUENCE: 538

Lys Leu Thr Xaa Leu Ala Ser Tyr Glu Trp Leu Phe
1               5                   10

<210> SEQ ID NO 539
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (9)..(9)
<223> OTHER INFORMATION: Xaa is Dab

<400> SEQUENCE: 539

Lys Leu Thr Glu Leu Ala Ser Tyr Xaa Trp Leu Phe
1               5                   10

<210> SEQ ID NO 540
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (4)..(4)
<223> OTHER INFORMATION: Xaa is Dab

<400> SEQUENCE: 540

Lys Leu Thr Xaa Leu Ala Ser Tyr Glu Trp Leu Phe
1               5                   10

<210> SEQ ID NO 541
<211> LENGTH: 12

```
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (9)..(9)
<223> OTHER INFORMATION: Xaa is Dap

<400> SEQUENCE: 541

Lys Leu Thr Glu Leu Ala Ser Tyr Xaa Trp Leu Phe
1               5                   10

<210> SEQ ID NO 542
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (4)..(4)
<223> OTHER INFORMATION: Xaa is Dap

<400> SEQUENCE: 542

Lys Leu Thr Xaa Leu Ala Ser Tyr Glu Trp Leu Phe
1               5                   10

<210> SEQ ID NO 543
<211> LENGTH: 27
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (16)..(16)
<223> OTHER INFORMATION: D-AMINO ACID
<220> FEATURE:
<221> NAME/KEY: MOD_RES
<222> LOCATION: (17)..(17)
<223> OTHER INFORMATION: METHYLATION

<400> SEQUENCE: 543

Lys Leu Leu Lys Leu Leu Leu Lys Leu Leu Lys Leu Leu Lys Lys
1               5                   10                  15

Leu Thr Cys Leu Ala Ser Tyr Cys Trp Leu Phe
            20                  25

<210> SEQ ID NO 544
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (9)..(9)
<223> OTHER INFORMATION: D-AMINO ACID
<220> FEATURE:
<221> NAME/KEY: MOD_RES
<222> LOCATION: (10)..(10)
<223> OTHER INFORMATION: METHYLATION

<400> SEQUENCE: 544

Phe Ala Met Gly Gly Ser Gly Gly Lys Leu Thr Cys Leu Ala Ser Tyr
1               5                   10                  15

Cys Trp Leu Phe
            20
```

<210> SEQ ID NO 545
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: PALMITOYL-(PEG)27

<400> SEQUENCE: 545

Lys Leu Thr Cys Leu Ala Ser Tyr Cys Trp Leu Phe
1               5                   10

<210> SEQ ID NO 546
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: PALMITOYL-(PEG)27(PEG)27

<400> SEQUENCE: 546

Lys Leu Thr Cys Leu Ala Ser Tyr Cys Trp Leu Phe
1               5                   10

<210> SEQ ID NO 547
<211> LENGTH: 22
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (13)..(14)
<223> OTHER INFORMATION: =N-O-CH2-CO-PEG27
<220> FEATURE:
<221> NAME/KEY: MISC_FEATURE
<222> LOCATION: (20)..(20)
<223> OTHER INFORMATION: OEt

<400> SEQUENCE: 547

Lys Leu Thr Cys Leu Ala Ser Tyr Cys Trp Leu Phe Gly Cys Asn Pro
1               5                   10                  15

Arg Gly Asp Tyr Arg Cys
            20

<210> SEQ ID NO 548
<211> LENGTH: 21
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (7)..(7)
<223> OTHER INFORMATION: OEt
<220> FEATURE:
<221> NAME/KEY: MISC_FEATURE
<222> LOCATION: (9)..(10)
<223> OTHER INFORMATION: -PEG27-CO-CH2-O-N=CH2NHCOCH2CH2CO-

<400> SEQUENCE: 548

Cys Asn Pro Arg Gly Asp Tyr Arg Cys Lys Leu Thr Cys Leu Ala Ser
1               5                   10                  15

Tyr Cys Trp Leu Phe
            20

<210> SEQ ID NO 549
<211> LENGTH: 9
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: 5-FAM (5-carboxy-fluorescein)
<220> FEATURE:
<221> NAME/KEY: MISC_FEATURE
<222> LOCATION: (7)..(7)
<223> OTHER INFORMATION: OEt

<400> SEQUENCE: 549

Cys Asn Pro Arg Gly Asp Tyr Arg Cys
1               5

<210> SEQ ID NO 550
<211> LENGTH: 24
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID
<220> FEATURE:
<221> NAME/KEY: MISC_FEATURE
<222> LOCATION: (22)..(23)
<223> OTHER INFORMATION: PEG-16
<220> FEATURE:
<221> NAME/KEY: MOD_RES
<222> LOCATION: (23)..(23)
<223> OTHER INFORMATION: PEG2-BIOTIN
<220> FEATURE:
<221> NAME/KEY: MISC_FEATURE
<222> LOCATION: (23)..(24)
<223> OTHER INFORMATION: PEG-16
<220> FEATURE:
<221> NAME/KEY: MOD_RES
<222> LOCATION: (24)..(24)
<223> OTHER INFORMATION: palmitoyl

<400> SEQUENCE: 550

Arg Arg Ala Pro Gly Lys Leu Thr Cys Leu Ala Ser Tyr Cys Trp Leu
1               5                   10                  15

Phe Trp Thr Gly Ile Ala Lys Lys
            20

<210> SEQ ID NO 551
<211> LENGTH: 24
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(2)
<223> OTHER INFORMATION: PEG-16
<220> FEATURE:
<221> NAME/KEY: MISC_FEATURE
<222> LOCATION: (1)..(2)
<223> OTHER INFORMATION: PEG-16
<220> FEATURE:
<221> NAME/KEY: MOD_RES
<222> LOCATION: (1)..(1)
<223> OTHER INFORMATION: palmitoyl

```
<220> FEATURE:
<221> NAME/KEY: MOD_RES
<222> LOCATION: (2)..(2)
<223> OTHER INFORMATION: PEG2-BIOTIN
<220> FEATURE:
<221> NAME/KEY: MISC_FEATURE
<222> LOCATION: (2)..(3)
<223> OTHER INFORMATION: PEG-16
<220> FEATURE:
<221> NAME/KEY: MISC_FEATURE
<222> LOCATION: (3)..(3)
<223> OTHER INFORMATION: D-AMINO ACID

<400> SEQUENCE: 551

Lys Lys Arg Arg Ala Pro Gly Lys Leu Thr Cys Leu Ala Ser Tyr Cys
1               5                   10                  15

Trp Leu Phe Trp Thr Gly Ile Ala
            20

<210> SEQ ID NO 552
<211> LENGTH: 23
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID
<220> FEATURE:
<221> NAME/KEY: MISC_FEATURE
<222> LOCATION: (22)..(23)
<223> OTHER INFORMATION: PEG-16
<220> FEATURE:
<221> NAME/KEY: MOD_RES
<222> LOCATION: (23)..(23)
<223> OTHER INFORMATION: PEG2-BIOTIN
<220> FEATURE:
<221> NAME/KEY: MISC_FEATURE
<222> LOCATION: (23)..(23)
<223> OTHER INFORMATION: PEG-16

<400> SEQUENCE: 552

Arg Arg Ala Pro Gly Lys Leu Thr Cys Leu Ala Ser Tyr Cys Trp Leu
1               5                   10                  15

Phe Trp Thr Gly Ile Ala Lys
            20

<210> SEQ ID NO 553
<211> LENGTH: 32
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID
<220> FEATURE:
<221> NAME/KEY: MISC_FEATURE
<222> LOCATION: (22)..(23)
<223> OTHER INFORMATION: PEG-16
<220> FEATURE:
<221> NAME/KEY: MOD_RES
<222> LOCATION: (23)..(23)
<223> OTHER INFORMATION: PEG2-BIOTIN
<220> FEATURE:
<221> NAME/KEY: MISC_FEATURE
<222> LOCATION: (23)..(24)
<223> OTHER INFORMATION: PEG-16
<220> FEATURE:
<221> NAME/KEY: MOD_RES
<222> LOCATION: (30)..(30)
```

<223> OTHER INFORMATION: OEt

<400> SEQUENCE: 553

Arg Arg Ala Pro Gly Lys Leu Thr Cys Leu Ala Ser Tyr Cys Trp Leu
1               5                   10                  15

Phe Trp Thr Gly Ile Ala Lys Cys Asn Pro Arg Gly Asp Tyr Arg Cys
            20                  25                  30

<210> SEQ ID NO 554
<211> LENGTH: 23
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: PEG-16
<220> FEATURE:
<221> NAME/KEY: MOD_RES
<222> LOCATION: (1)..(1)
<223> OTHER INFORMATION: PEG2-BIOTIN
<220> FEATURE:
<221> NAME/KEY: MISC_FEATURE
<222> LOCATION: (1)..(2)
<223> OTHER INFORMATION: PEG-16
<220> FEATURE:
<221> NAME/KEY: MISC_FEATURE
<222> LOCATION: (2)..(2)
<223> OTHER INFORMATION: D-AMINO ACID

<400> SEQUENCE: 554

Lys Arg Arg Ala Pro Gly Lys Leu Thr Cys Leu Ala Ser Tyr Cys Trp
1               5                   10                  15

Leu Phe Trp Thr Gly Ile Ala
            20

<210> SEQ ID NO 555
<211> LENGTH: 32
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (7)..(7)
<223> OTHER INFORMATION: OEt
<220> FEATURE:
<221> NAME/KEY: MISC_FEATURE
<222> LOCATION: (9)..(10)
<223> OTHER INFORMATION: PEG-16
<220> FEATURE:
<221> NAME/KEY: MISC_FEATURE
<222> LOCATION: (10)..(11)
<223> OTHER INFORMATION: PEG-16
<220> FEATURE:
<221> NAME/KEY: MOD_RES
<222> LOCATION: (10)..(10)
<223> OTHER INFORMATION: PEG2-BIOTIN
<220> FEATURE:
<221> NAME/KEY: MISC_FEATURE
<222> LOCATION: (11)..(11)
<223> OTHER INFORMATION: D-AMINO ACID

<400> SEQUENCE: 555

Cys Asn Pro Arg Gly Asp Tyr Arg Cys Lys Arg Arg Ala Pro Gly Lys
1               5                   10                  15

Leu Thr Cys Leu Ala Ser Tyr Cys Trp Leu Phe Trp Thr Gly Ile Ala
            20                  25                  30

```
<210> SEQ ID NO 556

<400> SEQUENCE: 556

000

<210> SEQ ID NO 557

<400> SEQUENCE: 557

000

<210> SEQ ID NO 558

<400> SEQUENCE: 558

000

<210> SEQ ID NO 559

<400> SEQUENCE: 559

000

<210> SEQ ID NO 560
<211> LENGTH: 6
<212> TYPE: PRT
<213> ORGANISM: Artificial Sequence
<220> FEATURE:
<223> OTHER INFORMATION: synthetic

<400> SEQUENCE: 560

Lys Gly Ala Ser Tyr Glu
1               5

<210> SEQ ID NO 561
<211> LENGTH: 6
<212> TYPE: PRT
<213> ORGANISM: Artificial Sequence
<220> FEATURE:
<223> OTHER INFORMATION: synthetic

<400> SEQUENCE: 561

Lys Leu Gly Ser Tyr Glu
1               5

<210> SEQ ID NO 562
<211> LENGTH: 6
<212> TYPE: PRT
<213> ORGANISM: Artificial Sequence
<220> FEATURE:
<223> OTHER INFORMATION: synthetic

<400> SEQUENCE: 562

Lys Leu Ala Ser Gly Glu
1               5

<210> SEQ ID NO 563
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 563
```

```
Lys Gly Ala Ser Tyr Glu
1               5

<210> SEQ ID NO 564
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 564

Lys Leu Gly Ser Tyr Glu
1               5

<210> SEQ ID NO 565
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 565

Lys Leu Ala Ser Gly Glu
1               5

<210> SEQ ID NO 566
<211> LENGTH: 6
<212> TYPE: PRT
<213> ORGANISM: Artificial Sequence
<220> FEATURE:
<223> OTHER INFORMATION: synthetic

<400> SEQUENCE: 566

Lys Ala Ala Ser Tyr Glu
1               5

<210> SEQ ID NO 567
<211> LENGTH: 6
<212> TYPE: PRT
<213> ORGANISM: Artificial Sequence
<220> FEATURE:
<223> OTHER INFORMATION: synthetic

<400> SEQUENCE: 567

Lys Leu Ala Ser Ala Glu
1               5

<210> SEQ ID NO 568
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 568

Lys Ala Ala Ser Tyr Glu
```

1               5

<210> SEQ ID NO 569
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 569

Lys Leu Ala Ser Ala Glu
1               5

<210> SEQ ID NO 570
<211> LENGTH: 6
<212> TYPE: PRT
<213> ORGANISM: Artificial Sequence
<220> FEATURE:
<223> OTHER INFORMATION: synthetic

<400> SEQUENCE: 570

Lys Val Ala Ser Tyr Glu
1               5

<210> SEQ ID NO 571
<211> LENGTH: 6
<212> TYPE: PRT
<213> ORGANISM: Artificial Sequence
<220> FEATURE:
<223> OTHER INFORMATION: synthetic

<400> SEQUENCE: 571

Lys Leu Val Ser Tyr Glu
1               5

<210> SEQ ID NO 572
<211> LENGTH: 6
<212> TYPE: PRT
<213> ORGANISM: Artificial Sequence
<220> FEATURE:
<223> OTHER INFORMATION: synthetic

<400> SEQUENCE: 572

Lys Leu Ala Ser Val Glu
1               5

<210> SEQ ID NO 573
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 573

Lys Val Ala Ser Tyr Glu
1               5

<210> SEQ ID NO 574
<211> LENGTH: 6
<212> TYPE: PRT

```
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 574

Lys Leu Val Ser Tyr Glu
1               5

<210> SEQ ID NO 575
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 575

Lys Leu Ala Ser Val Glu
1               5

<210> SEQ ID NO 576
<211> LENGTH: 6
<212> TYPE: PRT
<213> ORGANISM: Artificial Sequence
<220> FEATURE:
<223> OTHER INFORMATION: synthetic

<400> SEQUENCE: 576

Lys Ile Ala Ser Tyr Glu
1               5

<210> SEQ ID NO 577
<211> LENGTH: 6
<212> TYPE: PRT
<213> ORGANISM: Artificial Sequence
<220> FEATURE:
<223> OTHER INFORMATION: synthetic

<400> SEQUENCE: 577

Lys Leu Ile Ser Tyr Glu
1               5

<210> SEQ ID NO 578
<211> LENGTH: 6
<212> TYPE: PRT
<213> ORGANISM: Artificial Sequence
<220> FEATURE:
<223> OTHER INFORMATION: synthetic

<400> SEQUENCE: 578

Lys Leu Ala Ser Ile Glu
1               5

<210> SEQ ID NO 579
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
```

```
<223> OTHER INFORMATION: D-AMINO ACID

<400> SEQUENCE: 579

Lys Ile Ala Ser Tyr Glu
1               5

<210> SEQ ID NO 580
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 580

Lys Leu Ile Ser Tyr Glu
1               5

<210> SEQ ID NO 581
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 581

Lys Leu Ala Ser Ile Glu
1               5

<210> SEQ ID NO 582
<211> LENGTH: 6
<212> TYPE: PRT
<213> ORGANISM: Artificial Sequence
<220> FEATURE:
<223> OTHER INFORMATION: synthetic

<400> SEQUENCE: 582

Lys Leu Ala Ser Tyr Glu
1               5

<210> SEQ ID NO 583
<211> LENGTH: 6
<212> TYPE: PRT
<213> ORGANISM: Artificial Sequence
<220> FEATURE:
<223> OTHER INFORMATION: synthetic

<400> SEQUENCE: 583

Lys Leu Leu Ser Tyr Glu
1               5

<210> SEQ ID NO 584
<211> LENGTH: 6
<212> TYPE: PRT
<213> ORGANISM: Artificial Sequence
<220> FEATURE:
<223> OTHER INFORMATION: synthetic

<400> SEQUENCE: 584

Lys Leu Ala Ser Leu Glu
1               5
```

```
<210> SEQ ID NO 585
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 585

Lys Leu Ala Ser Tyr Glu
1               5

<210> SEQ ID NO 586
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 586

Lys Leu Leu Ser Tyr Glu
1               5

<210> SEQ ID NO 587
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 587

Lys Leu Ala Ser Leu Glu
1               5

<210> SEQ ID NO 588
<211> LENGTH: 6
<212> TYPE: PRT
<213> ORGANISM: Artificial Sequence
<220> FEATURE:
<223> OTHER INFORMATION: synthetic

<400> SEQUENCE: 588

Lys Phe Ala Ser Tyr Glu
1               5

<210> SEQ ID NO 589
<211> LENGTH: 6
<212> TYPE: PRT
<213> ORGANISM: Artificial Sequence
<220> FEATURE:
<223> OTHER INFORMATION: synthetic

<400> SEQUENCE: 589

Lys Leu Phe Ser Tyr Glu
1               5
```

-continued

```
<210> SEQ ID NO 590
<211> LENGTH: 6
<212> TYPE: PRT
<213> ORGANISM: Artificial Sequence
<220> FEATURE:
<223> OTHER INFORMATION: synthetic

<400> SEQUENCE: 590

Lys Leu Ala Ser Phe Glu
1               5

<210> SEQ ID NO 591
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 591

Lys Phe Ala Ser Tyr Glu
1               5

<210> SEQ ID NO 592
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 592

Lys Leu Phe Ser Tyr Glu
1               5

<210> SEQ ID NO 593
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 593

Lys Leu Ala Ser Phe Glu
1               5

<210> SEQ ID NO 594
<211> LENGTH: 6
<212> TYPE: PRT
<213> ORGANISM: Artificial Sequence
<220> FEATURE:
<223> OTHER INFORMATION: synthetic

<400> SEQUENCE: 594

Lys Trp Ala Ser Tyr Glu
1               5

<210> SEQ ID NO 595
<211> LENGTH: 6
```

```
<212> TYPE: PRT
<213> ORGANISM: Artificial Sequence
<220> FEATURE:
<223> OTHER INFORMATION: synthetic

<400> SEQUENCE: 595

Lys Leu Trp Ser Tyr Glu
1               5

<210> SEQ ID NO 596
<211> LENGTH: 6
<212> TYPE: PRT
<213> ORGANISM: Artificial Sequence
<220> FEATURE:
<223> OTHER INFORMATION: synthetic

<400> SEQUENCE: 596

Lys Leu Ala Ser Trp Glu
1               5

<210> SEQ ID NO 597
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 597

Lys Trp Ala Ser Tyr Glu
1               5

<210> SEQ ID NO 598
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 598

Lys Leu Trp Ser Tyr Glu
1               5

<210> SEQ ID NO 599
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 599

Lys Leu Ala Ser Trp Glu
1               5

<210> SEQ ID NO 600
<211> LENGTH: 6
<212> TYPE: PRT
<213> ORGANISM: Artificial Sequence
```

```
<220> FEATURE:
<223> OTHER INFORMATION: synthetic

<400> SEQUENCE: 600

Lys Tyr Ala Ser Tyr Glu
1               5

<210> SEQ ID NO 601
<211> LENGTH: 6
<212> TYPE: PRT
<213> ORGANISM: Artificial Sequence
<220> FEATURE:
<223> OTHER INFORMATION: synthetic

<400> SEQUENCE: 601

Lys Leu Tyr Ser Tyr Glu
1               5

<210> SEQ ID NO 602
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 602

Lys Tyr Ala Ser Tyr Glu
1               5

<210> SEQ ID NO 603
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 603

Lys Leu Tyr Ser Tyr Glu
1               5

<210> SEQ ID NO 604
<211> LENGTH: 6
<212> TYPE: PRT
<213> ORGANISM: Artificial Sequence
<220> FEATURE:
<223> OTHER INFORMATION: synthetic

<400> SEQUENCE: 604

Lys Gln Ala Ser Tyr Glu
1               5

<210> SEQ ID NO 605
<211> LENGTH: 6
<212> TYPE: PRT
<213> ORGANISM: Artificial Sequence
<220> FEATURE:
<223> OTHER INFORMATION: synthetic

<400> SEQUENCE: 605

Lys Leu Gln Ser Tyr Glu
```

```
1               5

<210> SEQ ID NO 606
<211> LENGTH: 6
<212> TYPE: PRT
<213> ORGANISM: Artificial Sequence
<220> FEATURE:
<223> OTHER INFORMATION: synthetic

<400> SEQUENCE: 606

Lys Leu Ala Ser Gln Glu
1               5

<210> SEQ ID NO 607
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 607

Lys Gln Ala Ser Tyr Glu
1               5

<210> SEQ ID NO 608
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 608

Lys Leu Gln Ser Tyr Glu
1               5

<210> SEQ ID NO 609
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 609

Lys Leu Ala Ser Gln Glu
1               5

<210> SEQ ID NO 610
<211> LENGTH: 6
<212> TYPE: PRT
<213> ORGANISM: Artificial Sequence
<220> FEATURE:
<223> OTHER INFORMATION: synthetic

<400> SEQUENCE: 610

Glu Gly Ala Ser Tyr Lys
1               5
```

```
<210> SEQ ID NO 611
<211> LENGTH: 6
<212> TYPE: PRT
<213> ORGANISM: Artificial Sequence
<220> FEATURE:
<223> OTHER INFORMATION: synthetic

<400> SEQUENCE: 611

Glu Leu Gly Ser Tyr Lys
1               5

<210> SEQ ID NO 612
<211> LENGTH: 6
<212> TYPE: PRT
<213> ORGANISM: Artificial Sequence
<220> FEATURE:
<223> OTHER INFORMATION: synthetic

<400> SEQUENCE: 612

Glu Leu Ala Ser Gly Lys
1               5

<210> SEQ ID NO 613
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 613

Glu Gly Ala Ser Tyr Lys
1               5

<210> SEQ ID NO 614
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 614

Glu Leu Gly Ser Tyr Lys
1               5

<210> SEQ ID NO 615
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 615

Glu Leu Ala Ser Gly Lys
1               5

<210> SEQ ID NO 616
```

```
<211> LENGTH: 6
<212> TYPE: PRT
<213> ORGANISM: Artificial Sequence
<220> FEATURE:
<223> OTHER INFORMATION: synthetic

<400> SEQUENCE: 616

Glu Ala Ala Ser Tyr Lys
1               5

<210> SEQ ID NO 617
<211> LENGTH: 6
<212> TYPE: PRT
<213> ORGANISM: Artificial Sequence
<220> FEATURE:
<223> OTHER INFORMATION: synthetic

<400> SEQUENCE: 617

Glu Leu Ala Ser Ala Lys
1               5

<210> SEQ ID NO 618
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 618

Glu Ala Ala Ser Tyr Lys
1               5

<210> SEQ ID NO 619
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 619

Glu Leu Ala Ser Ala Lys
1               5

<210> SEQ ID NO 620
<211> LENGTH: 6
<212> TYPE: PRT
<213> ORGANISM: Artificial Sequence
<220> FEATURE:
<223> OTHER INFORMATION: synthetic

<400> SEQUENCE: 620

Glu Val Ala Ser Tyr Lys
1               5

<210> SEQ ID NO 621
<211> LENGTH: 6
<212> TYPE: PRT
<213> ORGANISM: Artificial Sequence
<220> FEATURE:
<223> OTHER INFORMATION: synthetic
```

```
<400> SEQUENCE: 621

Glu Leu Val Ser Tyr Lys
1               5

<210> SEQ ID NO 622
<211> LENGTH: 6
<212> TYPE: PRT
<213> ORGANISM: Artificial Sequence
<220> FEATURE:
<223> OTHER INFORMATION: synthetic

<400> SEQUENCE: 622

Glu Leu Ala Ser Val Lys
1               5

<210> SEQ ID NO 623
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 623

Glu Val Ala Ser Tyr Lys
1               5

<210> SEQ ID NO 624
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 624

Glu Leu Val Ser Tyr Lys
1               5

<210> SEQ ID NO 625
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 625

Glu Leu Ala Ser Val Lys
1               5

<210> SEQ ID NO 626
<211> LENGTH: 6
<212> TYPE: PRT
<213> ORGANISM: Artificial Sequence
<220> FEATURE:
<223> OTHER INFORMATION: synthetic

<400> SEQUENCE: 626
```

```
Glu Ile Ala Ser Tyr Lys
1               5

<210> SEQ ID NO 627
<211> LENGTH: 6
<212> TYPE: PRT
<213> ORGANISM: Artificial Sequence
<220> FEATURE:
<223> OTHER INFORMATION: synthetic

<400> SEQUENCE: 627

Glu Leu Ile Ser Tyr Lys
1               5

<210> SEQ ID NO 628
<211> LENGTH: 6
<212> TYPE: PRT
<213> ORGANISM: Artificial Sequence
<220> FEATURE:
<223> OTHER INFORMATION: synthetic

<400> SEQUENCE: 628

Glu Leu Ala Ser Ile Lys
1               5

<210> SEQ ID NO 629
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 629

Glu Ile Ala Ser Tyr Lys
1               5

<210> SEQ ID NO 630
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 630

Glu Leu Ile Ser Tyr Lys
1               5

<210> SEQ ID NO 631
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 631

Glu Leu Ala Ser Ile Lys
1               5
```

```
<210> SEQ ID NO 632
<211> LENGTH: 6
<212> TYPE: PRT
<213> ORGANISM: Artificial Sequence
<220> FEATURE:
<223> OTHER INFORMATION: synthetic

<400> SEQUENCE: 632

Glu Leu Ala Ser Tyr Lys
1               5

<210> SEQ ID NO 633
<211> LENGTH: 6
<212> TYPE: PRT
<213> ORGANISM: Artificial Sequence
<220> FEATURE:
<223> OTHER INFORMATION: synthetic

<400> SEQUENCE: 633

Glu Leu Leu Ser Tyr Lys
1               5

<210> SEQ ID NO 634
<211> LENGTH: 6
<212> TYPE: PRT
<213> ORGANISM: Artificial Sequence
<220> FEATURE:
<223> OTHER INFORMATION: synthetic

<400> SEQUENCE: 634

Glu Leu Ala Ser Leu Lys
1               5

<210> SEQ ID NO 635
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 635

Glu Leu Ala Ser Tyr Lys
1               5

<210> SEQ ID NO 636
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 636

Glu Leu Leu Ser Tyr Lys
1               5

<210> SEQ ID NO 637
<211> LENGTH: 6
<212> TYPE: PRT
<213> ORGANISM: Artificial Sequence
```

```
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 637

Glu Leu Ala Ser Leu Lys
1               5

<210> SEQ ID NO 638
<211> LENGTH: 6
<212> TYPE: PRT
<213> ORGANISM: Artificial Sequence
<220> FEATURE:
<223> OTHER INFORMATION: synthetic

<400> SEQUENCE: 638

Glu Phe Ala Ser Tyr Lys
1               5

<210> SEQ ID NO 639
<211> LENGTH: 6
<212> TYPE: PRT
<213> ORGANISM: Artificial Sequence
<220> FEATURE:
<223> OTHER INFORMATION: synthetic

<400> SEQUENCE: 639

Glu Leu Phe Ser Tyr Lys
1               5

<210> SEQ ID NO 640
<211> LENGTH: 6
<212> TYPE: PRT
<213> ORGANISM: Artificial Sequence
<220> FEATURE:
<223> OTHER INFORMATION: synthetic

<400> SEQUENCE: 640

Glu Leu Ala Ser Phe Lys
1               5

<210> SEQ ID NO 641
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 641

Glu Phe Ala Ser Tyr Lys
1               5

<210> SEQ ID NO 642
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID
```

```
<400> SEQUENCE: 642

Glu Leu Phe Ser Tyr Lys
1               5

<210> SEQ ID NO 643
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 643

Glu Leu Ala Ser Phe Lys
1               5

<210> SEQ ID NO 644
<211> LENGTH: 6
<212> TYPE: PRT
<213> ORGANISM: Artificial Sequence
<220> FEATURE:
<223> OTHER INFORMATION: synthetic

<400> SEQUENCE: 644

Glu Trp Ala Ser Tyr Lys
1               5

<210> SEQ ID NO 645
<211> LENGTH: 6
<212> TYPE: PRT
<213> ORGANISM: Artificial Sequence
<220> FEATURE:
<223> OTHER INFORMATION: synthetic

<400> SEQUENCE: 645

Glu Leu Trp Ser Tyr Lys
1               5

<210> SEQ ID NO 646
<211> LENGTH: 6
<212> TYPE: PRT
<213> ORGANISM: Artificial Sequence
<220> FEATURE:
<223> OTHER INFORMATION: synthetic

<400> SEQUENCE: 646

Glu Leu Ala Ser Trp Lys
1               5

<210> SEQ ID NO 647
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 647

Glu Trp Ala Ser Tyr Lys
1               5
```

<210> SEQ ID NO 648
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 648

Glu Leu Trp Ser Tyr Lys
1               5

<210> SEQ ID NO 649
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 649

Glu Leu Ala Ser Trp Lys
1               5

<210> SEQ ID NO 650
<211> LENGTH: 6
<212> TYPE: PRT
<213> ORGANISM: Artificial Sequence
<220> FEATURE:
<223> OTHER INFORMATION: synthetic

<400> SEQUENCE: 650

Glu Tyr Ala Ser Tyr Lys
1               5

<210> SEQ ID NO 651
<211> LENGTH: 6
<212> TYPE: PRT
<213> ORGANISM: Artificial Sequence
<220> FEATURE:
<223> OTHER INFORMATION: synthetic

<400> SEQUENCE: 651

Glu Leu Tyr Ser Tyr Lys
1               5

<210> SEQ ID NO 652
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 652

Glu Tyr Ala Ser Tyr Lys
1               5

<210> SEQ ID NO 653

```
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 653

Glu Leu Tyr Ser Tyr Lys
1               5

<210> SEQ ID NO 654
<211> LENGTH: 6
<212> TYPE: PRT
<213> ORGANISM: Artificial Sequence
<220> FEATURE:
<223> OTHER INFORMATION: synthetic

<400> SEQUENCE: 654

Glu Gln Ala Ser Tyr Lys
1               5

<210> SEQ ID NO 655
<211> LENGTH: 6
<212> TYPE: PRT
<213> ORGANISM: Artificial Sequence
<220> FEATURE:
<223> OTHER INFORMATION: synthetic

<400> SEQUENCE: 655

Glu Leu Gln Ser Tyr Lys
1               5

<210> SEQ ID NO 656
<211> LENGTH: 6
<212> TYPE: PRT
<213> ORGANISM: Artificial Sequence
<220> FEATURE:
<223> OTHER INFORMATION: synthetic

<400> SEQUENCE: 656

Glu Leu Ala Ser Gln Lys
1               5

<210> SEQ ID NO 657
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 657

Glu Gln Ala Ser Tyr Lys
1               5

<210> SEQ ID NO 658
<211> LENGTH: 6
<212> TYPE: PRT
<213> ORGANISM: Artificial Sequence
<220> FEATURE:
<223> OTHER INFORMATION: synthetic
<220> FEATURE:
```

```
<221> NAME/KEY: MISC_FEATURE
<222> LOCATION: (1)..(1)
<223> OTHER INFORMATION: D-AMINO ACID

<400> SEQUENCE: 658

Glu Leu Gln Ser Tyr Lys
1               5

<210> SEQ ID NO 659
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 659

Glu Leu Ala Ser Gln Lys
1               5

<210> SEQ ID NO 660
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (1)..(1)
<223> OTHER INFORMATION: Xaa is Orn

<400> SEQUENCE: 660

Xaa Leu Ala Ser Tyr Glu
1               5

<210> SEQ ID NO 661
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (6)..(6)
<223> OTHER INFORMATION: Xaa is Orn

<400> SEQUENCE: 661

Glu Leu Ala Ser Tyr Xaa
1               5

<210> SEQ ID NO 662
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (1)..(1)
<223> OTHER INFORMATION: Xaa is Dab

<400> SEQUENCE: 662

Xaa Leu Ala Ser Tyr Glu
1               5

<210> SEQ ID NO 663
```

```
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (1)..(1)
<223> OTHER INFORMATION: Xaa is Dap

<400> SEQUENCE: 663

Xaa Leu Ala Ser Tyr Glu
1               5

<210> SEQ ID NO 664
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (6)..(6)
<223> OTHER INFORMATION: Xaa is Dap

<400> SEQUENCE: 664

Glu Leu Ala Ser Tyr Xaa
1               5

<210> SEQ ID NO 665
<211> LENGTH: 6
<212> TYPE: PRT
<213> ORGANISM: Artificial Sequence
<220> FEATURE:
<223> OTHER INFORMATION: synthetic

<400> SEQUENCE: 665

Asp Leu Ala Ser Tyr Lys
1               5

<210> SEQ ID NO 666
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (6)..(6)
<223> OTHER INFORMATION: Xaa is Orn

<400> SEQUENCE: 666

Asp Leu Ala Ser Tyr Xaa
1               5

<210> SEQ ID NO 667
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (6)..(6)
<223> OTHER INFORMATION: Xaa is Dpr

<400> SEQUENCE: 667

Asp Leu Ala Ser Tyr Xaa
1               5
```

<210> SEQ ID NO 668
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (1)..(1)
<223> OTHER INFORMATION: Xaa is Dab

<400> SEQUENCE: 668

Xaa Leu Ala Ser Tyr Asp
1               5

<210> SEQ ID NO 669
<211> LENGTH: 4
<212> TYPE: PRT
<213> ORGANISM: Artificial Sequence
<220> FEATURE:
<223> OTHER INFORMATION: C-Terminal amino acids

<400> SEQUENCE: 669

Thr Gly Ile Ala
1

<210> SEQ ID NO 670
<211> LENGTH: 5
<212> TYPE: PRT
<213> ORGANISM: Artificial Sequence
<220> FEATURE:
<223> OTHER INFORMATION: C-Terminal amino acids

<400> SEQUENCE: 670

Trp Thr Gly Ile Ala
1               5

<210> SEQ ID NO 671
<211> LENGTH: 6
<212> TYPE: PRT
<213> ORGANISM: Artificial Sequence
<220> FEATURE:
<223> OTHER INFORMATION: C-Terminal amino acids

<400> SEQUENCE: 671

Phe Trp Thr Gly Ile Ala
1               5

<210> SEQ ID NO 672
<211> LENGTH: 5
<212> TYPE: PRT
<213> ORGANISM: Artificial Sequence
<220> FEATURE:
<223> OTHER INFORMATION: Peptide Linker polymer

<400> SEQUENCE: 672

Gly Gly Ser Gly Gly
1               5

<210> SEQ ID NO 673
<211> LENGTH: 3
<212> TYPE: PRT
<213> ORGANISM: Artificial Sequence
<220> FEATURE:
<223> OTHER INFORMATION: Peptide Linker polymer

<400> SEQUENCE: 673

Gly Gly Ser
1

<210> SEQ ID NO 674
<211> LENGTH: 4
<212> TYPE: PRT
<213> ORGANISM: Artificial Sequence
<220> FEATURE:
<223> OTHER INFORMATION: Peptide Linker polymer

<400> SEQUENCE: 674

Gly Gly Gly Ser
1

<210> SEQ ID NO 675
<211> LENGTH: 5
<212> TYPE: PRT
<213> ORGANISM: Artificial Sequence
<220> FEATURE:
<223> OTHER INFORMATION: Peptide Linker polymer

<400> SEQUENCE: 675

Gly Gly Gly Gly Ser
1               5

<210> SEQ ID NO 676
<211> LENGTH: 9
<212> TYPE: PRT
<213> ORGANISM: Artificial Sequence
<220> FEATURE:
<223> OTHER INFORMATION: FXIa cleavage site

<400> SEQUENCE: 676

Thr Gln Ser Phe Asn Asp Phe Thr Arg
1               5

<210> SEQ ID NO 677
<211> LENGTH: 10
<212> TYPE: PRT
<213> ORGANISM: Artificial Sequence
<220> FEATURE:
<223> OTHER INFORMATION: FXIa cleavage site

<400> SEQUENCE: 677

Ser Val Ser Gln Thr Ser Lys Leu Thr Arg
1               5                   10

<210> SEQ ID NO 678
<211> LENGTH: 10
<212> TYPE: PRT
<213> ORGANISM: Artificial Sequence
<220> FEATURE:
<223> OTHER INFORMATION: Thrombin cleavage site

<400> SEQUENCE: 678

Asp Phe Leu Ala Glu Gly Gly Gly Val Arg
1               5                   10

<210> SEQ ID NO 679
<211> LENGTH: 11
<212> TYPE: PRT
<213> ORGANISM: Artificial Sequence
<220> FEATURE:
<223> OTHER INFORMATION: Thrombin cleavage site

<400> SEQUENCE: 679

Asp Phe Leu Ala Glu Glu Gly Gly Gly Val Arg

```
1               5              10
```

<210> SEQ ID NO 680
<211> LENGTH: 7
<212> TYPE: PRT
<213> ORGANISM: Artificial Sequence
<220> FEATURE:
<223> OTHER INFORMATION: Thrombin cleavage site

<400> SEQUENCE: 680

```
Thr Thr Lys Ile Lys Pro Arg
1               5
```

<210> SEQ ID NO 681
<211> LENGTH: 5
<212> TYPE: PRT
<213> ORGANISM: Artificial Sequence
<220> FEATURE:
<223> OTHER INFORMATION: Thrombin cleavage site

<400> SEQUENCE: 681

```
Ala Leu Val Pro Arg
1               5
```

<210> SEQ ID NO 682
<211> LENGTH: 5
<212> TYPE: PRT
<213> ORGANISM: Artificial Sequence
<220> FEATURE:
<223> OTHER INFORMATION: Thrombin cleavage site

<400> SEQUENCE: 682

```
Ala Leu Arg Pro Arg
1               5
```

<210> SEQ ID NO 683
<211> LENGTH: 10
<212> TYPE: PRT
<213> ORGANISM: Artificial Sequence
<220> FEATURE:
<223> OTHER INFORMATION: Thrombin cleavage site

<400> SEQUENCE: 683

```
Ala Leu Arg Pro Arg Val Val Gly Gly Ala
1               5                   10
```

<210> SEQ ID NO 684
<211> LENGTH: 32
<212> TYPE: PRT
<213> ORGANISM: Artificial Sequence
<220> FEATURE:
<223> OTHER INFORMATION: CTP peptide

<400> SEQUENCE: 684

```
Asp Pro Arg Phe Gln Asp Ser Ser Ser Lys Ala Pro Pro Pro Ser
1               5                   10                  15

Leu Pro Ser Pro Ser Arg Leu Pro Gly Pro Ser Asp Thr Pro Ile Leu
                20                  25                  30
```

<210> SEQ ID NO 685
<211> LENGTH: 28
<212> TYPE: PRT
<213> ORGANISM: Artificial Sequence
<220> FEATURE:
<223> OTHER INFORMATION: CTP peptide

<400> SEQUENCE: 685

```
Ser Ser Ser Ser Lys Ala Pro Pro Ser Leu Pro Ser Pro Ser Arg
1               5                   10                  15

Leu Pro Gly Pro Ser Asp Thr Pro Ile Leu Pro Gln
            20                  25
```

<210> SEQ ID NO 686
<211> LENGTH: 20
<212> TYPE: PRT
<213> ORGANISM: Artificial Sequence
<220> FEATURE:
<223> OTHER INFORMATION: PAS Sequence

<400> SEQUENCE: 686

```
Ala Ser Pro Ala Ala Pro Ala Pro Ala Ser Pro Ala Ala Pro Ala Pro
1               5                   10                  15

Ser Ala Pro Ala
            20
```

<210> SEQ ID NO 687
<211> LENGTH: 20
<212> TYPE: PRT
<213> ORGANISM: Artificial Sequence
<220> FEATURE:
<223> OTHER INFORMATION: PAS Sequence

<400> SEQUENCE: 687

```
Ala Ala Pro Ala Ser Pro Ala Pro Ala Ala Pro Ser Ala Pro Ala Pro
1               5                   10                  15

Ala Ala Pro Ser
            20
```

<210> SEQ ID NO 688
<211> LENGTH: 20
<212> TYPE: PRT
<213> ORGANISM: Artificial Sequence
<220> FEATURE:
<223> OTHER INFORMATION: PAS Sequence

<400> SEQUENCE: 688

```
Ala Pro Ser Ser Pro Ser Pro Ser Ala Pro Ser Ser Pro Ser Pro Ala
1               5                   10                  15

Ser Pro Ser Ser
            20
```

<210> SEQ ID NO 689
<211> LENGTH: 19
<212> TYPE: PRT
<213> ORGANISM: Artificial Sequence
<220> FEATURE:
<223> OTHER INFORMATION: PAS Sequence

<400> SEQUENCE: 689

```
Ala Pro Ser Ser Pro Ser Pro Ser Ala Pro Ser Ser Pro Ser Pro Ala
1               5                   10                  15

Ser Pro Ser
```

<210> SEQ ID NO 690
<211> LENGTH: 20
<212> TYPE: PRT
<213> ORGANISM: Artificial Sequence
<220> FEATURE:
<223> OTHER INFORMATION: PAS Sequence

<400> SEQUENCE: 690

-continued

Ser Ser Pro Ser Ala Pro Ser Pro Ser Pro Ala Ser Pro Ser Pro
1               5                   10                  15

Ser Ser Pro Ala
            20

<210> SEQ ID NO 691
<211> LENGTH: 24
<212> TYPE: PRT
<213> ORGANISM: Artificial Sequence
<220> FEATURE:
<223> OTHER INFORMATION: PAS Sequence

<400> SEQUENCE: 691

Ala Ala Ser Pro Ala Ala Pro Ser Ala Pro Pro Ala Ala Ala Ser Pro
1               5                   10                  15

Ala Ala Pro Ser Ala Pro Pro Ala
            20

<210> SEQ ID NO 692
<211> LENGTH: 20
<212> TYPE: PRT
<213> ORGANISM: Artificial Sequence
<220> FEATURE:
<223> OTHER INFORMATION: PAS Sequence

<400> SEQUENCE: 692

Ala Ser Ala Ala Ala Pro Ala Ala Ala Ser Ala Ala Ala Ser Ala Pro
1               5                   10                  15

Ser Ala Ala Ala
            20

<210> SEQ ID NO 693
<211> LENGTH: 20
<212> TYPE: PRT
<213> ORGANISM: Artificial Sequence
<220> FEATURE:
<223> OTHER INFORMATION: scFv linker

<400> SEQUENCE: 693

Gly Gly Gly Gly Ser Gly Gly Gly Ser Gly Gly Gly Gly Ser Gly
1               5                   10                  15

Gly Gly Gly Ser
            20

<210> SEQ ID NO 694
<211> LENGTH: 7
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 694

Lys Cys Leu Ala Ser Tyr Cys
1               5

<210> SEQ ID NO 695
<211> LENGTH: 7
<212> TYPE: PRT
<213> ORGANISM: Artificial Sequence
<220> FEATURE:
<223> OTHER INFORMATION: synthetic

```
<220> FEATURE:
<221> NAME/KEY: MISC_FEATURE
<222> LOCATION: (2)..(7)
<223> OTHER INFORMATION: D-AMINO ACIDS

<400> SEQUENCE: 695

Lys Cys Leu Ala Ser Tyr Cys
1               5

<210> SEQ ID NO 696
<211> LENGTH: 7
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (7)..(7)
<223> OTHER INFORMATION: D-AMINO ACID

<400> SEQUENCE: 696

Cys Tyr Ser Ala Leu Cys Lys
1               5

<210> SEQ ID NO 697
<211> LENGTH: 7
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(6)
<223> OTHER INFORMATION: D-AMINO ACID

<400> SEQUENCE: 697

Cys Tyr Ser Ala Leu Cys Lys
1               5

<210> SEQ ID NO 698
<211> LENGTH: 21
<212> TYPE: PRT
<213> ORGANISM: Artificial Sequence
<220> FEATURE:
<223> OTHER INFORMATION: Compound 7

<400> SEQUENCE: 698

Gly Trp Lys Pro Phe Leu Trp Asp Pro Arg Val Leu Leu Ser Ser Gly
1               5                   10                  15

Trp Tyr Gly Arg Gly
            20

<210> SEQ ID NO 699
<211> LENGTH: 24
<212> TYPE: PRT
<213> ORGANISM: Artificial Sequence
<220> FEATURE:
<223> OTHER INFORMATION: Compound 8

<400> SEQUENCE: 699

Pro Trp Arg Arg Phe Trp Ala Trp Asn Pro Arg Ser Leu Ala Leu Ser
1               5                   10                  15

Thr Trp Phe Gly Arg Gly Cys Asp
            20

<210> SEQ ID NO 700
<211> LENGTH: 5052
```

```
<212> TYPE: DNA
<213> ORGANISM: Artificial Sequence
<220> FEATURE:
<223> OTHER INFORMATION: B-Domain Deleted FVIII-Fc Chain DNA Sequence
<220> FEATURE:
<221> NAME/KEY: sig_peptide
<222> LOCATION: (1)..(57)
<223> OTHER INFORMATION: FVIII signal peptide
<220> FEATURE:
<221> NAME/KEY: misc_feature
<222> LOCATION: (4372)..(5052)
<223> OTHER INFORMATION: Fc region

<400> SEQUENCE: 700
```

| | | | | |
|---|---|---|---|---|
| atgcaaatag | agctctccac | ctgcttcttt | ctgtgccttt | tgcgattctg | ctttagtgcc | 60 |
| accagaagat | actacctggg | tgcagtggaa | ctgtcatggg | actatatgca | aagtgatctc | 120 |
| ggtgagctgc | ctgtggacgc | aagatttcct | cctagagtgc | caaaatcttt | tccattcaac | 180 |
| acctcagtcg | tgtacaaaaa | gactctgttt | gtagaattca | cggatcacct | tttcaacatc | 240 |
| gctaagccaa | ggccaccctg | gatgggtctg | ctaggtccta | ccatccaggc | tgaggtttat | 300 |
| gatacagtgg | tcattacact | taagaacatg | gcttcccatc | ctgtcagtct | tcatgctgtt | 360 |
| ggtgtatcct | actggaaagc | ttctgaggga | gctgaatatg | atgatcagac | cagtcaaagg | 420 |
| gagaaagaag | atgataaagt | cttccctggt | ggaagccata | catatgtctg | gcaggtcctg | 480 |
| aaagagaatg | gtccaatggc | ctctgaccca | ctgtgcctta | cctactcata | tctttctcat | 540 |
| gtggacctgg | taaagacttt | gaattcaggc | ctcattggag | ccctactagt | atgtagagaa | 600 |
| gggagtctgg | ccaaggaaaa | gacacagacc | ttgcacaaat | ttatactact | ttttgctgta | 660 |
| tttgatgaag | ggaaaagttg | gcactcagaa | acaaagaact | ccttgatgca | ggatagggat | 720 |
| gctgcatctg | ctcgggcctg | gcctaaaatg | cacacagtca | atggttatgt | aaacaggtct | 780 |
| ctgccaggtc | tgattggatg | ccacaggaaa | tcagtctatt | ggcatgtgat | tggaatgggc | 840 |
| accactcctg | aagtgcactc | aatattcctc | gaaggtcaca | catttcttgt | gaggaaccat | 900 |
| cgccaggcgt | ccttggaaat | ctcgccaata | actttcctta | ctgctcaaac | actcttgatg | 960 |
| gaccttggac | agtttctact | gtttttgtcat | atctcttccc | accaacatga | tggcatggaa | 1020 |
| gcttatgtca | aagtagacag | ctgtccagag | gaaccccaac | tacgaatgaa | aaataatgaa | 1080 |
| gaagcggaag | actatgatga | tgatcttact | gattctgaaa | tggatgtggt | caggtttgat | 1140 |
| gatgacaact | ctccttcctt | tatccaaatt | cgctcagttg | ccaagaagca | tcctaaaact | 1200 |
| tgggtacatt | acattgctgc | tgaagaggag | gactgggact | atgctcccct | agtcctcgcc | 1260 |
| cccgatgaca | gaagttataa | aagtcaatat | ttgaacaatg | ccctcagcg | gattggtagg | 1320 |
| aagtacaaaa | aagtccgatt | tatggcatac | acagatgaaa | cctttaagac | tcgtgaagct | 1380 |
| attcagcatg | aatcaggaat | cttgggacct | tactttatgg | ggaagttgg | agacacactg | 1440 |
| ttgattatat | ttaagaatca | agcaagcaga | ccatataaca | tctaccctca | cggaatcact | 1500 |
| gatgtccgtc | ctttgtattc | aaggagatta | ccaaaaggtg | taaaacattt | gaaggatttt | 1560 |
| ccaattctgc | caggagaaat | attcaaatat | aaatggacag | tgactgtaga | agatgggcca | 1620 |
| actaaatcag | atcctcggtg | cctgacccgc | tattactcta | gtttcgttaa | tatggagaga | 1680 |
| gatctagctt | caggactcat | tggccctctc | ctcatctgct | acaaagaatc | tgtagatcaa | 1740 |
| agaggaaacc | agataatgtc | agacaagagg | aatgtcatcc | tgttttctgt | atttgatgag | 1800 |
| aaccgaagct | ggtacctcac | agagaatata | caacgctttc | tccccaatcc | agctggagtg | 1860 |
| cagcttgagg | atccagagtt | ccaagcctcc | aacatcatgc | acagcatcaa | tggctatgtt | 1920 |

```
tttgatagtt tgcagttgtc agtttgtttg catgaggtgg catactggta cattctaagc    1980
attggagcac agactgactt cctttctgtc ttcttctctg gatatacctt caaacacaaa    2040
atggtctatg aagacacact caccctattc ccattctcag agaaactgt cttcatgtcg     2100 atggaaaacc caggtctatg gattctgggg tgccacaact cagactttcg gaacagaggc    2160
atgaccgcct tactgaaggt ttctagttgt gacaagaaca ctggtgatta ttacgaggac    2220
agttatgaag atatttcagc atacttgctg agtaaaaaca atgccattga accaagaagc    2280
ttctctcaaa acccaccagt cttgaaacgc catcaacggg aaataactcg tactactctt    2340
cagtcagatc aagaggaaat tgactatgat gataccatat cagttgaaat gaagaaggaa    2400
gattttgaca tttatgatga ggatgaaaat cagagccccc gcagctttca aaagaaaaca    2460
cgacactatt ttattgctgc agtggagagg ctctgggatt atgggatgag tagctcccca    2520
catgttctaa gaaacagggc tcagagtggc agtgtccctc agttcaagaa agttgttttc    2580
caggaattta ctgatggctc ctttactcag cccttatacc gtggagaact aaatgaacat    2640
ttgggactcc tggggccata tataagagca gaagttgaag ataatatcat ggtaactttc    2700
agaaatcagg cctctcgtcc ctattccttc tattctagcc ttatttctta tgaggaagat    2760
cagaggcaag agcagaacc tagaaaaaac tttgtcaagc ctaatgaaac caaaacttac    2820
ttttggaaag tgcaacatca tatggcaccc actaaagatg agtttgactg caaagcctgg    2880
gcttatttct ctgatgttga cctggaaaaa gatgtgcact caggcctgat ggaccccctt    2940
ctggtctgcc acactaacac actgaaccct gctcatggga gacaagtgac agtacaggaa    3000
tttgctctgt ttttcaccat ctttgatgag accaaaagct ggtacttcac tgaaaatatg    3060
gaaagaaact gcagggctcc ctgcaatatc cagatggaag atcccacttt taaagagaat    3120
tatcgcttcc atgcaatcaa tggctacata atggatacac tacctggctt agtaatggct    3180
caggatcaaa ggattcgatg gtatctgctc agcatgggca gcaatgaaaa catccattct    3240
attcatttca gtggacatgt gttcactgta cgaaaaaaag aggagtataa aatggcactg    3300
tacaatctct atccaggtgt ttttgagaca gtggaaatgt taccatccaa agctggaatt    3360
tggcgggtgg aatgccttat tggcgagcat ctacatgctg ggatgagcac acttttctg    3420 gtgtacagca ataagtgtca gactcccctg ggaatggctt ctggacacat tagagatttt    3480
cagattacag cttcaggaca atatggacag tgggcccaa agctggccag acttcattat    3540
tccggatcaa tcaatgcctg gagcaccaag gagccctttt cttggatcaa ggtggatctg    3600
ttggcaccaa tgattattca cggcatcaag acccagggtg cccgtcagaa gttctccagc    3660
ctctacatct ctcagtttat catcatgtat agtcttgatg ggaagaagtg gcagacttat    3720
cgaggaaatt ccactggaac cttaatggtc ttctttggca atgtggattc atctgggata    3780
aaacacaata ttttttaaccc tccaattatt gctcgataca tccgtttgca cccaactcat    3840
tatagcattc gcagcactct tcgcatggag ttgatgggct gtgatttaaa tagttgcagc    3900
atgccattgg gaatggagag taaagcaata tcagatgcac agattactgc ttcatcctac    3960
tttaccaata tgtttgccac ctggtctcct tcaaaagctc gacttcacct caagggagg    4020 agtaatgcct ggagacctca ggtgaataat ccaaaagagt ggctgcaagt ggacttccag    4080
aagacaatga agtcacagg agtaactact cagggagtaa aatctctgct taccagcatg    4140
tatgtgaagg agttcctcat ctccagcagt caagatggcc atcagtggac tctctttttt    4200
cagaatggca agtaaaggt ttttcaggga aatcaagact ccttcacacc tgtggtgaac    4260
tctctagacc caccgttact gactcgctac cttcgaattc accccagag ttgggtgcac    4320
```

```
cagattgccc tgaggatgga ggttctgggc tgcgaggcac aggacctcta cgacaaaact   4380
cacacatgcc caccgtgccc agctccagaa ctcctgggcg gaccgtcagt cttcctcttc   4440
cccccaaaac ccaaggacac cctcatgatc tcccggaccc ctgaggtcac atgcgtggtg   4500
gtggacgtga gccacgaaga ccctgaggtc aagttcaact ggtacgtgga cggcgtggag   4560
gtgcataatg ccaagacaaa gccgcgggag gagcagtaca acagcacgta ccgtgtggtc   4620
agcgtcctca ccgtcctgca ccaggactgg ctgaatggca aggagtacaa gtgcaaggtc   4680
tccaacaaag ccctcccagc ccccatcgag aaaaccatct ccaaagccaa agggcagccc   4740
cgagaaccac aggtgtacac cctgccccca tcccgggatg agctgaccaa gaaccaggtc   4800
agcctgacct gcctggtcaa aggcttctat cccagcgaca tcgccgtgga gtgggagagc   4860
aatgggcagc cggagaacaa ctacaagacc acgcctcccg tgttggactc cgacggctcc   4920
ttcttcctct acagcaagct caccgtggac aagagcaggt ggcagcaggg gaacgtcttc   4980
tcatgctccg tgatgcatga ggctctgcac aaccactaca cgcagaagag cctctccctg   5040
tctccgggta aa                                                      5052
```

<210> SEQ ID NO 701
<211> LENGTH: 1684
<212> TYPE: PRT
<213> ORGANISM: Artificial Sequence
<220> FEATURE:
<223> OTHER INFORMATION: B domain deleted FVIII-Fc chain polypeptide
<220> FEATURE:
<221> NAME/KEY: SIGNAL
<222> LOCATION: (1)..(19)
<220> FEATURE:
<221> NAME/KEY: MISC_FEATURE
<222> LOCATION: (20)..(759)
<223> OTHER INFORMATION: HC Sequence
<220> FEATURE:
<221> NAME/KEY: DOMAIN
<222> LOCATION: (760)..(772)
<223> OTHER INFORMATION: B Domain Sequence
<220> FEATURE:
<221> NAME/KEY: MISC_FEATURE
<222> LOCATION: (1458)..(1684)
<223> OTHER INFORMATION: Fc Sequence

<400> SEQUENCE: 701

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
                20                  25                  30

Trp Asp Tyr Met Gln Ser Asp Leu Gly Glu Leu Pro Val Asp Ala Arg
            35                  40                  45

Phe Pro Pro Arg Val Pro Lys Ser Phe Pro Phe Asn Thr Ser Val Val
        50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140
```

```
Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
```

-continued

```
                565                 570                 575
Ser Val Asp Gln Arg Gly Asn Gln Ile Met Ser Asp Lys Arg Asn Val
            580                 585                 590
Ile Leu Phe Ser Val Phe Asp Glu Asn Arg Ser Trp Tyr Leu Thr Glu
            595                 600                 605
Asn Ile Gln Arg Phe Leu Pro Asn Pro Ala Gly Val Gln Leu Glu Asp
            610                 615                 620
Pro Glu Phe Gln Ala Ser Asn Ile Met His Ser Ile Asn Gly Tyr Val
625                 630                 635                 640
Phe Asp Ser Leu Gln Leu Ser Val Cys Leu His Glu Val Ala Tyr Trp
                645                 650                 655
Tyr Ile Leu Ser Ile Gly Ala Gln Thr Asp Phe Leu Ser Val Phe Phe
                660                 665                 670
Ser Gly Tyr Thr Phe Lys His Lys Met Val Tyr Glu Asp Thr Leu Thr
                675                 680                 685
Leu Phe Pro Phe Ser Gly Glu Thr Val Phe Met Ser Met Glu Asn Pro
            690                 695                 700
Gly Leu Trp Ile Leu Gly Cys His Asn Ser Asp Phe Arg Asn Arg Gly
705                 710                 715                 720
Met Thr Ala Leu Leu Lys Val Ser Ser Cys Asp Lys Asn Thr Gly Asp
                725                 730                 735
Tyr Tyr Glu Asp Ser Tyr Glu Asp Ile Ser Ala Tyr Leu Leu Ser Lys
                740                 745                 750
Asn Asn Ala Ile Glu Pro Arg Ser Phe Ser Gln Asn Pro Pro Val Leu
            755                 760                 765
Lys Arg His Gln Arg Glu Ile Thr Arg Thr Thr Leu Gln Ser Asp Gln
770                 775                 780
Glu Glu Ile Asp Tyr Asp Asp Thr Ile Ser Val Glu Met Lys Lys Glu
785                 790                 795                 800
Asp Phe Asp Ile Tyr Asp Glu Asp Glu Asn Gln Ser Pro Arg Ser Phe
                805                 810                 815
Gln Lys Lys Thr Arg His Tyr Phe Ile Ala Ala Val Glu Arg Leu Trp
                820                 825                 830
Asp Tyr Gly Met Ser Ser Ser Pro His Val Leu Arg Asn Arg Ala Gln
            835                 840                 845
Ser Gly Ser Val Pro Gln Phe Lys Lys Val Val Phe Gln Glu Phe Thr
            850                 855                 860
Asp Gly Ser Phe Thr Gln Pro Leu Tyr Arg Gly Glu Leu Asn Glu His
865                 870                 875                 880
Leu Gly Leu Leu Gly Pro Tyr Ile Arg Ala Glu Val Glu Asp Asn Ile
                885                 890                 895
Met Val Thr Phe Arg Asn Gln Ala Ser Arg Pro Tyr Ser Phe Tyr Ser
                900                 905                 910
Ser Leu Ile Ser Tyr Glu Glu Asp Gln Arg Gln Gly Ala Glu Pro Arg
                915                 920                 925
Lys Asn Phe Val Lys Pro Asn Glu Thr Lys Thr Tyr Phe Trp Lys Val
            930                 935                 940
Gln His His Met Ala Pro Thr Lys Asp Glu Phe Asp Cys Lys Ala Trp
945                 950                 955                 960
Ala Tyr Phe Ser Asp Val Asp Leu Glu Lys Asp Val His Ser Gly Leu
                965                 970                 975
Ile Gly Pro Leu Leu Val Cys His Thr Asn Thr Leu Asn Pro Ala His
            980                 985                 990
```

-continued

Gly Arg Gln Val Thr Val Gln Glu Phe Ala Leu Phe Phe Thr Ile Phe
    995                 1000                    1005

Asp Glu Thr Lys Ser Trp Tyr Phe Thr Glu Asn Met Glu Arg Asn
    1010                1015                    1020

Cys Arg Ala Pro Cys Asn Ile Gln Met Glu Asp Pro Thr Phe Lys
    1025                1030                    1035

Glu Asn Tyr Arg Phe His Ala Ile Asn Gly Tyr Ile Met Asp Thr
    1040                1045                    1050

Leu Pro Gly Leu Val Met Ala Gln Asp Gln Arg Ile Arg Trp Tyr
    1055                1060                    1065

Leu Leu Ser Met Gly Ser Asn Glu Asn Ile His Ser Ile His Phe
    1070                1075                    1080

Ser Gly His Val Phe Thr Val Arg Lys Lys Glu Glu Tyr Lys Met
    1085                1090                    1095

Ala Leu Tyr Asn Leu Tyr Pro Gly Val Phe Glu Thr Val Glu Met
    1100                1105                    1110

Leu Pro Ser Lys Ala Gly Ile Trp Arg Val Glu Cys Leu Ile Gly
    1115                1120                    1125

Glu His Leu His Ala Gly Met Ser Thr Leu Phe Leu Val Tyr Ser
    1130                1135                    1140

Asn Lys Cys Gln Thr Pro Leu Gly Met Ala Ser Gly His Ile Arg
    1145                1150                    1155

Asp Phe Gln Ile Thr Ala Ser Gly Gln Tyr Gly Gln Trp Ala Pro
    1160                1165                    1170

Lys Leu Ala Arg Leu His Tyr Ser Gly Ser Ile Asn Ala Trp Ser
    1175                1180                    1185

Thr Lys Glu Pro Phe Ser Trp Ile Lys Val Asp Leu Leu Ala Pro
    1190                1195                    1200

Met Ile Ile His Gly Ile Lys Thr Gln Gly Ala Arg Gln Lys Phe
    1205                1210                    1215

Ser Ser Leu Tyr Ile Ser Gln Phe Ile Ile Met Tyr Ser Leu Asp
    1220                1225                    1230

Gly Lys Lys Trp Gln Thr Tyr Arg Gly Asn Ser Thr Gly Thr Leu
    1235                1240                    1245

Met Val Phe Phe Gly Asn Val Asp Ser Ser Gly Ile Lys His Asn
    1250                1255                    1260

Ile Phe Asn Pro Pro Ile Ile Ala Arg Tyr Ile Arg Leu His Pro
    1265                1270                    1275

Thr His Tyr Ser Ile Arg Ser Thr Leu Arg Met Glu Leu Met Gly
    1280                1285                    1290

Cys Asp Leu Asn Ser Cys Ser Met Pro Leu Gly Met Glu Ser Lys
    1295                1300                    1305

Ala Ile Ser Asp Ala Gln Ile Thr Ala Ser Ser Tyr Phe Thr Asn
    1310                1315                    1320

Met Phe Ala Thr Trp Ser Pro Ser Lys Ala Arg Leu His Leu Gln
    1325                1330                    1335

Gly Arg Ser Asn Ala Trp Arg Pro Gln Val Asn Asn Pro Lys Glu
    1340                1345                    1350

Trp Leu Gln Val Asp Phe Gln Lys Thr Met Lys Val Thr Gly Val
    1355                1360                    1365

Thr Thr Gln Gly Val Lys Ser Leu Leu Thr Ser Met Tyr Val Lys
    1370                1375                    1380

```
Glu Phe Leu Ile Ser Ser Ser Gln Asp Gly His Gln Trp Thr Leu
    1385                1390                1395

Phe Phe Gln Asn Gly Lys Val Lys Val Phe Gln Gly Asn Gln Asp
    1400                1405                1410

Ser Phe Thr Pro Val Val Asn Ser Leu Asp Pro Pro Leu Leu Thr
    1415                1420                1425

Arg Tyr Leu Arg Ile His Pro Gln Ser Trp Val His Gln Ile Ala
    1430                1435                1440

Leu Arg Met Glu Val Leu Gly Cys Glu Ala Gln Asp Leu Tyr Asp
    1445                1450                1455

Lys Thr His Thr Cys Pro Pro Cys Pro Ala Pro Glu Leu Leu Gly
    1460                1465                1470

Gly Pro Ser Val Phe Leu Phe Pro Pro Lys Pro Lys Asp Thr Leu
    1475                1480                1485

Met Ile Ser Arg Thr Pro Glu Val Thr Cys Val Val Val Asp Val
    1490                1495                1500

Ser His Glu Asp Pro Glu Val Lys Phe Asn Trp Tyr Val Asp Gly
    1505                1510                1515

Val Glu Val His Asn Ala Lys Thr Lys Pro Arg Glu Glu Gln Tyr
    1520                1525                1530

Asn Ser Thr Tyr Arg Val Val Ser Val Leu Thr Val Leu His Gln
    1535                1540                1545

Asp Trp Leu Asn Gly Lys Glu Tyr Lys Cys Lys Val Ser Asn Lys
    1550                1555                1560

Ala Leu Pro Ala Pro Ile Glu Lys Thr Ile Ser Lys Ala Lys Gly
    1565                1570                1575

Gln Pro Arg Glu Pro Gln Val Tyr Thr Leu Pro Pro Ser Arg Asp
    1580                1585                1590

Glu Leu Thr Lys Asn Gln Val Ser Leu Thr Cys Leu Val Lys Gly
    1595                1600                1605

Phe Tyr Pro Ser Asp Ile Ala Val Glu Trp Glu Ser Asn Gly Gln
    1610                1615                1620

Pro Glu Asn Asn Tyr Lys Thr Thr Pro Pro Val Leu Asp Ser Asp
    1625                1630                1635

Gly Ser Phe Phe Leu Tyr Ser Lys Leu Thr Val Asp Lys Ser Arg
    1640                1645                1650

Trp Gln Gln Gly Asn Val Phe Ser Cys Ser Val Met His Glu Ala
    1655                1660                1665

Leu His Asn His Tyr Thr Gln Lys Ser Leu Ser Leu Ser Pro Gly
    1670                1675                1680

Lys

<210> SEQ ID NO 702
<211> LENGTH: 741
<212> TYPE: DNA
<213> ORGANISM: Artificial Sequence
<220> FEATURE:
<223> OTHER INFORMATION: Fc DNA sequence
<220> FEATURE:
<221> NAME/KEY: sig_peptide
<222> LOCATION: (1)..(60)
<223> OTHER INFORMATION: mouse Igk signal peptide

<400> SEQUENCE: 702
atggagacag acacactcct gctatgggta ctgctgctct gggttccagg ttccactggt      60
gacaaaactc acacatgccc accgtgccca gcacctgaac tcctgggagg accgtcagtc     120
```

-continued

```
ttcctcttcc ccccaaaacc caaggacacc ctcatgatct cccggacccc tgaggtcaca    180
tgcgtggtgg tggacgtgag ccacgaagac cctgaggtca agttcaactg gtacgtggac    240
ggcgtggagg tgcataatgc caagacaaag ccgcgggagg agcagtacaa cagcacgtac    300
cgtgtggtca gcgtcctcac cgtcctgcac caggactggc tgaatggcaa ggagtacaag    360
tgcaaggtct ccaacaaagc cctcccagcc cccatcgaga aaaccatctc caaagccaaa    420
gggcagcccc gagaaccaca ggtgtacacc ctgcccccat cccgcgatga gctgaccaag    480
aaccaggtca gcctgacctg cctggtcaaa ggcttctatc ccagcgacat cgccgtggag    540
tgggagagca atgggcagcc ggagaacaac tacaagacca cgcctcccgt gttggactcc    600
gacggctcct tcttcctcta cagcaagctc accgtggaca gagcaggtg gcagcagggg    660 aacgtcttct catgctccgt gatgcatgag gctctgcaca accactacac gcagaagagc    720
ctctccctgt ctccgggtaa a                                              741
```

<210> SEQ ID NO 703
<211> LENGTH: 247
<212> TYPE: PRT
<213> ORGANISM: Artificial Sequence
<220> FEATURE:
<223> OTHER INFORMATION: Fc chain polypeptide
<220> FEATURE:
<221> NAME/KEY: SIGNAL
<222> LOCATION: (1)..(20)
<223> OTHER INFORMATION: mouse Igk signal peptide

<400> SEQUENCE: 703

```
Met Glu Thr Asp Thr Leu Leu Leu Trp Val Leu Leu Leu Trp Val Pro
 1               5                  10                  15

Gly Ser Thr Gly Asp Lys Thr His Thr Cys Pro Pro Cys Pro Ala Pro
            20                  25                  30

Glu Leu Leu Gly Gly Pro Ser Val Phe Leu Phe Pro Pro Lys Pro Lys
        35                  40                  45

Asp Thr Leu Met Ile Ser Arg Thr Pro Glu Val Thr Cys Val Val Val
    50                  55                  60

Asp Val Ser His Glu Asp Pro Glu Val Lys Phe Asn Trp Tyr Val Asp
65                  70                  75                  80

Gly Val Glu Val His Asn Ala Lys Thr Lys Pro Arg Glu Glu Gln Tyr
                85                  90                  95

Asn Ser Thr Tyr Arg Val Val Ser Val Leu Thr Val Leu His Gln Asp
            100                 105                 110

Trp Leu Asn Gly Lys Glu Tyr Lys Cys Lys Val Ser Asn Lys Ala Leu
        115                 120                 125

Pro Ala Pro Ile Glu Lys Thr Ile Ser Lys Ala Lys Gly Gln Pro Arg
    130                 135                 140

Glu Pro Gln Val Tyr Thr Leu Pro Pro Ser Arg Asp Glu Leu Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
    210                 215                 220
```

-continued

```
Cys Ser Val Met His Glu Ala Leu His Asn His Tyr Thr Gln Lys Ser
225                 230                 235                 240

Leu Ser Leu Ser Pro Gly Lys
            245
```

<210> SEQ ID NO 704
<211> LENGTH: 7734
<212> TYPE: DNA
<213> ORGANISM: Artificial Sequence
<220> FEATURE:
<223> OTHER INFORMATION: Full Length FVIII-Fc DNA Sequence
<220> FEATURE:
<221> NAME/KEY: sig_peptide
<222> LOCATION: (1)..(57)
<223> OTHER INFORMATION: FVIII signal peptide
<220> FEATURE:
<221> NAME/KEY: misc_feature
<222> LOCATION: (7054)..(7734)
<223> OTHER INFORMATION: Fc region

<400> SEQUENCE: 704

| | |
|---|---:|
| atgcaaatag agctctccac ctgcttcttt ctgtgccttt gcgattctg ctttagtgcc | 60 |
| accagaagat actacctggg tgcagtggaa ctgtcatggg actatatgca aagtgatctc | 120 |
| ggtgagctgc ctgtggacgc aagatttcct cctagagtgc caaaatcttt tccattcaac | 180 |
| acctcagtcg tgtacaaaaa gactctgttt gtagaattca cggatcacct tttcaacatc | 240 |
| gctaagccaa ggccaccctg gatgggtctg ctaggtccta ccatccaggc tgaggtttat | 300 |
| gatacagtgg tcattacact taagaacatg gcttcccatc ctgtcagtct tcatgctgtt | 360 |
| ggtgtatcct actggaaagc ttctgaggga gctgaatatg atgatcagac cagtcaaagg | 420 |
| gagaaagaag atgataaagt cttccctggt ggaagccata catatgtctg gcaggtcctg | 480 |
| aaagagaatg gtccaatggc ctctgaccca ctgtgcctta cctactcata tctttctcat | 540 |
| gtggacctgg taaagacttt gaattcaggc ctcattggag ccctactagt atgtagagaa | 600 |
| gggagtctgg ccaaggaaaa gacacagacc ttgcacaaat ttatactact ttttgctgta | 660 |
| tttgatgaag ggaaaagttg gcactcagaa acaaagaact ccttgatgca ggatagggat | 720 |
| gctgcatctg ctcgggcctg gcctaaaatg cacacagtca atggttatgt aaacaggtct | 780 |
| ctgccaggtc tgattggatg ccacaggaaa tcagtctatt ggcatgtgat tggaatgggc | 840 |
| accactcctg aagtgcactc aatattcctc gaaggtcaca cattcttgtg gaggaaccat | 900 |
| cgccaggcgt ccttggaaat ctcgccaata actttcctta ctgctcaaac actcttgatg | 960 |
| gaccttggac agtttctact gttttgtcat atctcttccc accaacatga tggcatggaa | 1020 |
| gcttatgtca agtagacag ctgtccagag gaaccccaac tacgaatgaa aaataatgaa | 1080 |
| gaagcggaag actatgatga tgatcttact gattctgaaa tggatgtggt caggtttgat | 1140 |
| gatgacaact ctccttcctt tatccaaatt cgctcagttg ccaagaagca tcctaaaact | 1200 |
| tgggtacatt acattgctgc tgaagaggag gactgggact atgctccctt agtcctcgcc | 1260 |
| cccgatgaca gaagttataa aagtcaatat ttgaacaatg gccctcagcg gattggtagg | 1320 |
| aagtacaaaa aagtccgatt tatggcatac acagatgaaa cctttaagac tcgtgaagct | 1380 |
| attcagcatg aatcaggaat cttgggacct tactttatg gggaagttgg agacacactg | 1440 |
| ttgattatat ttaagaatca agcaagcaga ccatataaca tctaccctca cggaatcact | 1500 |
| gatgtccgtc ctttgtattc aaggagatta ccaaaaggtg taaaacattt gaaggatttt | 1560 |
| ccaattctgc caggagaaat attcaaatat aaatggacag tgactgtaga agatgggcca | 1620 |
| actaaatcag atcctcggtg cctgacccgc tattactcta gtttcgttaa tatggagaga | 1680 |

```
gatctagctt caggactcat tggccctctc ctcatctgct acaaagaatc tgtagatcaa    1740
agaggaaacc agataatgtc agacaagagg aatgtcatcc tgttttctgt atttgatgag    1800
aaccgaagct ggtacctcac agagaatata caacgctttc tccccaatcc agctggagtg    1860
cagcttgagg atccagagtt ccaagcctcc aacatcatgc acagcatcaa tggctatgtt    1920
tttgatagtt tgcagttgtc agtttgtttg catgaggtgg catactggta cattctaagc    1980
attggagcac agactgactt cctttctgtc ttcttctctg gatataccttc aaacacaaa    2040 atggtctatg aagacacact caccctattc ccattctcag agaaactgt cttcatgtcg    2100 atggaaaacc caggtctatg gattctgggg tgccacaact cagactttcg gaacagaggc    2160
atgaccgcct tactgaaggt ttctagttgt gacaagaaca ctggtgatta ttacgaggac    2220
agttatgaag atatttcagc atacttgctg agtaaaaaca atgccattga accaagaagc    2280
ttctcccaga attcaagaca ccctagcact aggcaaaagc aatttaatgc caccacaatt    2340
ccagaaaatg acatagagaa gactgaccct tggtttgcac acagaacacc tatgcctaaa    2400
atacaaaatg tctcctctag tgatttgttg atgctcttgc gacagagtcc tactccacat    2460
gggctatcct tatctgatct ccaagaagcc aaatatgaga ctttttctga tgatccatca    2520
cctggagcaa tagacagtaa taacagcctg tctgaaatga cacacttcag gccacagctc    2580
catcacagtg gggacatggt atttacccct gagtcaggcc tccaattaag attaaatgag    2640
aaactgggga caactgcagc aacagagttg aagaaacttg atttcaaagt ttctagtaca    2700
tcaaataatc tgatttcaac aattccatca gacaatttgg cagcaggtac tgataataca    2760
agttccttag ccccccaag tatgccagtt cattatgata gtcaattaga taccactcta    2820
tttggcaaaa agtcatctcc ccttactgag tctggtggac ctctgagctt gagtgaagaa    2880
aataatgatt caaagttgtt agaatcaggt ttaatgaata gccaagaaag ttcatgggga    2940
aaaaatgtat cgtcaacaga gagtggtagg ttatttaaag ggaaaagagc tcatggacct    3000
gctttgttga ctaaagataa tgccttattc aaagttagca tctctttgtt aaagacaaac    3060
aaaacttcca ataattcagc aactaataga aagactcaca ttgatggccc atcattatta    3120
attgagaata gtccatcagt ctggcaaaat atattagaaa gtgacactga gtttaaaaaa    3180
gtgacacctt tgattcatga cagaatgctt atggacaaaa atgctacagc tttgaggcta    3240
aatcatatgt caaataaaac tacttcatca aaaaacatgg aaatggtcca acagaaaaaa    3300
gagggcccca ttccaccaga tgcacaaaat ccagatatgt cgttctttaa gatgctattc    3360
ttgccagaat cagcaaggtg gatacaaagg actcatggaa agaactctct gaactctggg    3420
caaggcccca gtccaaagca attagtatcc ttaggaccag aaaaatctgt ggaaggtcag    3480
aatttcttgt ctgagaaaaa caaagtggta gtaggaaagg gtgaatttac aaaggacgta    3540
ggactcaaag agatggtttt tccaagcagc agaaacctat ttcttactaa cttggataat    3600
ttacatgaaa ataatacaca caatcaagaa aaaaaaattc aggaagaaat agaaaagaag    3660
gaaacattaa tccaagagaa tgtagttttg cctcagatac atacagtgac tggcactaag    3720
aatttcatga agaacctttt cttactgagc actaggcaaa atgtagaagg ttcatatgac    3780
ggggcatatg ctccagtact tcaagatttt aggtcattaa atgattcaac aaatagaaca    3840
aagaaacaca cagctcattt ctcaaaaaaa ggggaggaag aaaacttgga aggcttggga    3900
aatcaaacca agcaaattgt agagaaatat gcatgcacca caaggatatc tcctaataca    3960
agccagcaga attttgtcac gcaacgtagt aagagagctt tgaaacaatt cagactccca    4020
```

```
ctagaagaaa cagaacttga aaaaaggata attgtggatg acacctcaac ccagtggtcc    4080
aaaaacatga aacatttgac cccgagcacc ctcacacaga tagactacaa tgagaaggag    4140
aaagggggcca ttactcagtc tcccttatca gattgcctta cgaggagtca tagcatccct   4200
caagcaaata gatctccatt acccattgca aaggtatcat catttccatc tattagacct    4260
atatatctga ccagggtcct attccaagac aactcttctc atcttccagc agcatcttat    4320
agaaagaaag attctggggt ccaagaaagc agtcatttct tacaaggagc aaaaaaaat    4380
aacctttctt tagccattct aaccttggag atgactggtg atcaaagaga ggttggctcc    4440
ctggggacaa gtgccacaaa ttcagtcaca tacaagaaag ttgagaacac tgttctcccg    4500
aaaccagact tgcccaaaac atctggcaaa gttgaattgc ttccaaaagt tcacatttat    4560
cagaaggacc tattccctac ggaaactagc aatgggtctc ctggccatct ggatctcgtg    4620
gaagggagcc ttcttcaggg aacagaggga gcgattaagt ggaatgaagc aaacagacct    4680
ggaaaagttc cctttctgag agtagcaaca gaaagctctg caaagactcc ctccaagcta    4740
ttggatcctc ttgcttggga taaccactat ggtactcaga taccaaaaga agagtggaaa    4800
tcccaagaga agtcaccaga aaaaacagct tttaagaaaa aggataccat tttgtccctg    4860
aacgcttgtg aaagcaatca tgcaatagca gcaataaatg agggacaaaa taagcccgaa    4920
atagaagtca cctgggcaaa gcaaggtagg actgaaaggc tgtgctctca aaacccacca    4980
gtcttgaaac gccatcaacg ggaaataact cgtactactc ttcagtcaga tcaagaggaa    5040
attgactatg atgataccat atcagttgaa atgaagaagg aagattttga catttatgat    5100
gaggatgaaa atcagagccc ccgcagcttt caaaagaaaa cacgcacacta ttttattgct    5160
gcagtggaga ggctctggga ttatgggatg agtagctccc cacatgttct aagaaacagg    5220
gctcagagtg gcagtgtccc tcagttcaag aaagttgttt tccaggaatt tactgatggc    5280
tcctttactc agcccttata ccgtggagaa ctaaatgaac atttgggact cctggggcca    5340
tatataagag cagaagttga agataatatc atggtaactt tcagaaatca ggcctctcgt    5400
ccctattcct tctattctag ccttatttct tatgaggaag atcagaggca aggagcagaa    5460
cctagaaaaa actttgtcaa gcctaatgaa accaaaactt acttttggaa agtgcaaacat   5520
catatggcac ccactaaaga tgagtttgac tgcaaagcct gggcttattt ctctgatgtt    5580
gacctggaaa aagatgtgca ctcaggcctg attggacccc ttctggtctg ccacactaac    5640
acactgaacc ctgctcatgg gagacaagtg acagtacagg aatttgctct gtttttcacc    5700
atctttgatg agaccaaaag ctggtacttc actgaaaata tggaaagaaa ctgcagggct    5760
ccctgcaata tccagatgga agatcccact tttaaagaga attatcgctt ccatgcaatc    5820
aatggctaca taatggatac actacctggc ttagtaatgg ctcaggatca aaggattcga    5880
tggtatctgc tcagcatggg cagcaatgaa aacatccatt ctattcattt cagtggacat    5940
gtgttcactg tacgaaaaaa agaggagtat aaaatggcac tgtacaatct ctatccaggt    6000
gttttttgaga cagtggaaat gttaccatcc aaagctggaa tttggcgggt ggaatgcctt    6060
attggcgagc atctacatgc tgggatgagc acacttttc tggtgtacag caataagtgt    6120
cagactcccc tggaatggc ttctggacac attagagatt tcagattac agcttcagga    6180
caatatggac agtgggcccc aaagctggcc agacttcatt attccggatc aatcaatgcc    6240
tggagcacca aggagccctt ttcttggatc aaggtggatc tgttggcacc aatgattatt    6300
cacggcatca gacccagggg tgcccgtcag aagttctcca gcctctacat ctctcagttt    6360
atcatcatgt atagtcttga tgggaagaag tggcagactt atcgaggaaa ttccactgga    6420
```

-continued

```
accttaatgg tcttctttgg caatgtggat tcatctggga taaaacacaa tatttttaac    6480
cctccaatta ttgctcgata catccgtttg cacccaactc attatagcat tcgcagcact    6540
cttcgcatgg agttgatggg ctgtgattta aatagttgca gcatgccatt gggaatggag    6600
agtaaagcaa tatcagatgc acagattact gcttcatcct actttaccaa tatgtttgcc    6660
acctggtctc cttcaaaagc tcgacttcac ctccaaggga ggagtaatgc ctggagacct    6720
caggtgaata atccaaaaga gtggctgcaa gtggacttcc agaagacaat gaaagtcaca    6780
ggagtaacta ctcagggagt aaaatctctg cttaccagca tgtatgtgaa ggagttcctc    6840
atctccagca gtcaagatgg ccatcagtgg actctctttt ttcagaatgg caaagtaaag    6900
gtttttcagg gaaatcaaga ctccttcaca cctgtggtga actctctaga cccaccgtta    6960
ctgactcgct accttcgaat tcaccccag agttgggtgc accagattgc cctgaggatg    7020
gaggttctgg gctgcgaggc acaggacctc tacgacaaaa ctcacacatg cccaccgtgc    7080
ccagctccag aactcctggg cggaccgtca gtcttcctct tccccccaaa acccaaggac    7140
accctcatga tctcccggac ccctgaggtc acatgcgtgg tggtggacgt gagccacgaa    7200
gaccctgagg tcaagttcaa ctggtacgtg gacggcgtgg aggtgcataa tgccaagaca    7260
aagccgcggg aggagcagta acagcacg taccgtgtgg tcagcgtcct caccgtcctg    7320
caccaggact ggctgaatgg caaggagtac aagtgcaagg tctccaacaa agccctccca    7380
gcccccatcg agaaaaccat ctccaaagcc aagggcagc ccgagaacc acaggtgtac    7440 accctgcccc catcccggga tgagctgacc aagaaccagg tcagcctgac ctgcctggtc    7500
aaaggcttct atcccagcga catcgccgtg gagtgggaga gcaatgggca gccggagaac    7560
aactacaaga ccacgcctcc cgtgttggac tccgacggct ccttcttcct ctacagcaag    7620
ctcaccgtgg acaagagcag gtggcagcag gggaacgtct tctcatgctc cgtgatgcat    7680
gaggctctgc acaaccacta cacgcagaag agcctctccc tgtctccggg taaa           7734
```

<210> SEQ ID NO 705
<211> LENGTH: 2578
<212> TYPE: PRT
<213> ORGANISM: Artificial Sequence
<220> FEATURE:
<223> OTHER INFORMATION: Full length FVIII-Fc chain polypeptide
<220> FEATURE:
<221> NAME/KEY: SIGNAL
<222> LOCATION: (1)..(19)
<223> OTHER INFORMATION: FVIII signal peptide
<220> FEATURE:
<221> NAME/KEY: MISC_FEATURE
<222> LOCATION: (20)..(759)
<223> OTHER INFORMATION: HC Sequence
<220> FEATURE:
<221> NAME/KEY: DOMAIN
<222> LOCATION: (760)..(1167)
<223> OTHER INFORMATION: B Domain Sequence
<220> FEATURE:
<221> NAME/KEY: MISC_FEATURE
<222> LOCATION: (2352)..(2578)
<223> OTHER INFORMATION: Fc Sequence

<400> SEQUENCE: 705

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
                20                  25                  30

Trp Asp Tyr Met Gln Ser Asp Leu Gly Glu Leu Pro Val Asp Ala Arg
        35                  40                  45
```

-continued

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

```
Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Ser Arg His Pro
        755                 760                 765

Ser Thr Arg Gln Lys Gln Phe Asn Ala Thr Thr Ile Pro Glu Asn Asp
    770                 775                 780

Ile Glu Lys Thr Asp Pro Trp Phe Ala His Arg Thr Pro Met Pro Lys
785                 790                 795                 800

Ile Gln Asn Val Ser Ser Ser Asp Leu Leu Met Leu Leu Arg Gln Ser
                805                 810                 815

Pro Thr Pro His Gly Leu Ser Leu Ser Asp Leu Gln Glu Ala Lys Tyr
            820                 825                 830

Glu Thr Phe Ser Asp Asp Pro Ser Pro Gly Ala Ile Asp Ser Asn Asn
        835                 840                 845

Ser Leu Ser Glu Met Thr His Phe Arg Pro Gln Leu His His Ser Gly
    850                 855                 860

Asp Met Val Phe Thr Pro Glu Ser Gly Leu Gln Leu Arg Leu Asn Glu
865                 870                 875                 880

Lys Leu Gly Thr Thr Ala Ala Thr Glu Leu Lys Lys Leu Asp Phe Lys
```

-continued

```
                    885                 890                 895
Val Ser Ser Thr Ser Asn Asn Leu Ile Ser Thr Ile Pro Ser Asp Asn
                900                 905                 910

Leu Ala Ala Gly Thr Asp Asn Thr Ser Ser Leu Gly Pro Pro Ser Met
                915                 920                 925

Pro Val His Tyr Asp Ser Gln Leu Asp Thr Thr Leu Phe Gly Lys Lys
                930                 935                 940

Ser Ser Pro Leu Thr Glu Ser Gly Gly Pro Leu Ser Leu Ser Glu Glu
945                 950                 955                 960

Asn Asn Asp Ser Lys Leu Leu Glu Ser Gly Leu Met Asn Ser Gln Glu
                965                 970                 975

Ser Ser Trp Gly Lys Asn Val Ser Ser Thr Glu Ser Gly Arg Leu Phe
                980                 985                 990

Lys Gly Lys Arg Ala His Gly Pro Ala Leu Leu Thr Lys Asp Asn Ala
                995                1000                1005

Leu Phe Lys Val Ser Ile Ser Leu Leu Lys Thr Asn Lys Thr Ser
        1010                1015                1020

Asn Asn Ser Ala Thr Asn Arg Lys Thr His Ile Asp Gly Pro Ser
        1025                1030                1035

Leu Leu Ile Glu Asn Ser Pro Ser Val Trp Gln Asn Ile Leu Glu
        1040                1045                1050

Ser Asp Thr Glu Phe Lys Lys Val Thr Pro Leu Ile His Asp Arg
        1055                1060                1065

Met Leu Met Asp Lys Asn Ala Thr Ala Leu Arg Leu Asn His Met
        1070                1075                1080

Ser Asn Lys Thr Thr Ser Ser Lys Asn Met Glu Met Val Gln Gln
        1085                1090                1095

Lys Lys Glu Gly Pro Ile Pro Pro Asp Ala Gln Asn Pro Asp Met
        1100                1105                1110

Ser Phe Phe Lys Met Leu Phe Leu Pro Glu Ser Ala Arg Trp Ile
        1115                1120                1125

Gln Arg Thr His Gly Lys Asn Ser Leu Asn Ser Gly Gln Gly Pro
        1130                1135                1140

Ser Pro Lys Gln Leu Val Ser Leu Gly Pro Glu Lys Ser Val Glu
        1145                1150                1155

Gly Gln Asn Phe Leu Ser Glu Lys Asn Lys Val Val Val Gly Lys
        1160                1165                1170

Gly Glu Phe Thr Lys Asp Val Gly Leu Lys Glu Met Val Phe Pro
        1175                1180                1185

Ser Ser Arg Asn Leu Phe Leu Thr Asn Leu Asp Asn Leu His Glu
        1190                1195                1200

Asn Asn Thr His Asn Gln Glu Lys Lys Ile Gln Glu Glu Ile Glu
        1205                1210                1215

Lys Lys Glu Thr Leu Ile Gln Glu Asn Val Val Leu Pro Gln Ile
        1220                1225                1230

His Thr Val Thr Gly Thr Lys Asn Phe Met Lys Asn Leu Phe Leu
        1235                1240                1245

Leu Ser Thr Arg Gln Asn Val Glu Gly Ser Tyr Asp Gly Ala Tyr
        1250                1255                1260

Ala Pro Val Leu Gln Asp Phe Arg Ser Leu Asn Asp Ser Thr Asn
        1265                1270                1275

Arg Thr Lys Lys His Thr Ala His Phe Ser Lys Lys Gly Glu Glu
        1280                1285                1290
```

```
Glu Asn Leu Glu Gly Leu Gly Asn Gln Thr Lys Gln Ile Val Glu
1295                1300                1305

Lys Tyr Ala Cys Thr Thr Arg Ile Ser Pro Asn Thr Ser Gln Gln
1310                1315                1320

Asn Phe Val Thr Gln Arg Ser Lys Arg Ala Leu Lys Gln Phe Arg
1325                1330                1335

Leu Pro Leu Glu Glu Thr Glu Leu Glu Lys Arg Ile Ile Val Asp
1340                1345                1350

Asp Thr Ser Thr Gln Trp Ser Lys Asn Met Lys His Leu Thr Pro
1355                1360                1365

Ser Thr Leu Thr Gln Ile Asp Tyr Asn Glu Lys Glu Lys Gly Ala
1370                1375                1380

Ile Thr Gln Ser Pro Leu Ser Asp Cys Leu Thr Arg Ser His Ser
1385                1390                1395

Ile Pro Gln Ala Asn Arg Ser Pro Leu Pro Ile Ala Lys Val Ser
1400                1405                1410

Ser Phe Pro Ser Ile Arg Pro Ile Tyr Leu Thr Arg Val Leu Phe
1415                1420                1425

Gln Asp Asn Ser Ser His Leu Pro Ala Ala Ser Tyr Arg Lys Lys
1430                1435                1440

Asp Ser Gly Val Gln Glu Ser Ser His Phe Leu Gln Gly Ala Lys
1445                1450                1455

Lys Asn Asn Leu Ser Leu Ala Ile Leu Thr Leu Glu Met Thr Gly
1460                1465                1470

Asp Gln Arg Glu Val Gly Ser Leu Gly Thr Ser Ala Thr Asn Ser
1475                1480                1485

Val Thr Tyr Lys Lys Val Glu Asn Thr Val Leu Pro Lys Pro Asp
1490                1495                1500

Leu Pro Lys Thr Ser Gly Lys Val Glu Leu Leu Pro Lys Val His
1505                1510                1515

Ile Tyr Gln Lys Asp Leu Phe Pro Thr Glu Thr Ser Asn Gly Ser
1520                1525                1530

Pro Gly His Leu Asp Leu Val Glu Gly Ser Leu Leu Gln Gly Thr
1535                1540                1545

Glu Gly Ala Ile Lys Trp Asn Glu Ala Asn Arg Pro Gly Lys Val
1550                1555                1560

Pro Phe Leu Arg Val Ala Thr Glu Ser Ser Ala Lys Thr Pro Ser
1565                1570                1575

Lys Leu Leu Asp Pro Leu Ala Trp Asp Asn His Tyr Gly Thr Gln
1580                1585                1590

Ile Pro Lys Glu Glu Trp Lys Ser Gln Glu Lys Ser Pro Glu Lys
1595                1600                1605

Thr Ala Phe Lys Lys Lys Asp Thr Ile Leu Ser Leu Asn Ala Cys
1610                1615                1620

Glu Ser Asn His Ala Ile Ala Ala Ile Asn Glu Gly Gln Asn Lys
1625                1630                1635

Pro Glu Ile Glu Val Thr Trp Ala Lys Gln Gly Arg Thr Glu Arg
1640                1645                1650

Leu Cys Ser Gln Asn Pro Pro Val Leu Lys Arg His Gln Arg Glu
1655                1660                1665

Ile Thr Arg Thr Thr Leu Gln Ser Asp Gln Glu Glu Ile Asp Tyr
1670                1675                1680
```

```
Asp Asp Thr Ile Ser Val Glu Met Lys Lys Glu Asp Phe Asp Ile
    1685                1690                1695

Tyr Asp Glu Asp Glu Asn Gln Ser Pro Arg Ser Phe Gln Lys Lys
    1700                1705                1710

Thr Arg His Tyr Phe Ile Ala Ala Val Glu Arg Leu Trp Asp Tyr
    1715                1720                1725

Gly Met Ser Ser Ser Pro His Val Leu Arg Asn Arg Ala Gln Ser
    1730                1735                1740

Gly Ser Val Pro Gln Phe Lys Lys Val Val Phe Gln Glu Phe Thr
    1745                1750                1755

Asp Gly Ser Phe Thr Gln Pro Leu Tyr Arg Gly Glu Leu Asn Glu
    1760                1765                1770

His Leu Gly Leu Leu Gly Pro Tyr Ile Arg Ala Glu Val Glu Asp
    1775                1780                1785

Asn Ile Met Val Thr Phe Arg Asn Gln Ala Ser Arg Pro Tyr Ser
    1790                1795                1800

Phe Tyr Ser Ser Leu Ile Ser Tyr Glu Glu Asp Gln Arg Gln Gly
    1805                1810                1815

Ala Glu Pro Arg Lys Asn Phe Val Lys Pro Asn Glu Thr Lys Thr
    1820                1825                1830

Tyr Phe Trp Lys Val Gln His His Met Ala Pro Thr Lys Asp Glu
    1835                1840                1845

Phe Asp Cys Lys Ala Trp Ala Tyr Phe Ser Asp Val Asp Leu Glu
    1850                1855                1860

Lys Asp Val His Ser Gly Leu Ile Gly Pro Leu Leu Val Cys His
    1865                1870                1875

Thr Asn Thr Leu Asn Pro Ala His Gly Arg Gln Val Thr Val Gln
    1880                1885                1890

Glu Phe Ala Leu Phe Phe Thr Ile Phe Asp Glu Thr Lys Ser Trp
    1895                1900                1905

Tyr Phe Thr Glu Asn Met Glu Arg Asn Cys Arg Ala Pro Cys Asn
    1910                1915                1920

Ile Gln Met Glu Asp Pro Thr Phe Lys Glu Asn Tyr Arg Phe His
    1925                1930                1935

Ala Ile Asn Gly Tyr Ile Met Asp Thr Leu Pro Gly Leu Val Met
    1940                1945                1950

Ala Gln Asp Gln Arg Ile Arg Trp Tyr Leu Leu Ser Met Gly Ser
    1955                1960                1965

Asn Glu Asn Ile His Ser Ile His Phe Ser Gly His Val Phe Thr
    1970                1975                1980

Val Arg Lys Lys Glu Glu Tyr Lys Met Ala Leu Tyr Asn Leu Tyr
    1985                1990                1995

Pro Gly Val Phe Glu Thr Val Glu Met Leu Pro Ser Lys Ala Gly
    2000                2005                2010

Ile Trp Arg Val Glu Cys Leu Ile Gly Glu His Leu His Ala Gly
    2015                2020                2025

Met Ser Thr Leu Phe Leu Val Tyr Ser Asn Lys Cys Gln Thr Pro
    2030                2035                2040

Leu Gly Met Ala Ser Gly His Ile Arg Asp Phe Gln Ile Thr Ala
    2045                2050                2055

Ser Gly Gln Tyr Gly Gln Trp Ala Pro Lys Leu Ala Arg Leu His
    2060                2065                2070

Tyr Ser Gly Ser Ile Asn Ala Trp Ser Thr Lys Glu Pro Phe Ser
```

```
                2075                2080                2085
Trp Ile Lys Val Asp Leu Leu Ala Pro Met Ile Ile His Gly Ile
        2090                2095                2100
Lys Thr Gln Gly Ala Arg Gln Lys Phe Ser Ser Leu Tyr Ile Ser
        2105                2110                2115
Gln Phe Ile Ile Met Tyr Ser Leu Asp Gly Lys Lys Trp Gln Thr
        2120                2125                2130
Tyr Arg Gly Asn Ser Thr Gly Thr Leu Met Val Phe Phe Gly Asn
        2135                2140                2145
Val Asp Ser Ser Gly Ile Lys His Asn Ile Phe Asn Pro Pro Ile
        2150                2155                2160
Ile Ala Arg Tyr Ile Arg Leu His Pro Thr His Tyr Ser Ile Arg
        2165                2170                2175
Ser Thr Leu Arg Met Glu Leu Met Gly Cys Asp Leu Asn Ser Cys
        2180                2185                2190
Ser Met Pro Leu Gly Met Glu Ser Lys Ala Ile Ser Asp Ala Gln
        2195                2200                2205
Ile Thr Ala Ser Ser Tyr Phe Thr Asn Met Phe Ala Thr Trp Ser
        2210                2215                2220
Pro Ser Lys Ala Arg Leu His Leu Gln Gly Arg Ser Asn Ala Trp
        2225                2230                2235
Arg Pro Gln Val Asn Asn Pro Lys Glu Trp Leu Gln Val Asp Phe
        2240                2245                2250
Gln Lys Thr Met Lys Val Thr Gly Val Thr Thr Gln Gly Val Lys
        2255                2260                2265
Ser Leu Leu Thr Ser Met Tyr Val Lys Glu Phe Leu Ile Ser Ser
        2270                2275                2280
Ser Gln Asp Gly His Gln Trp Thr Leu Phe Phe Gln Asn Gly Lys
        2285                2290                2295
Val Lys Val Phe Gln Gly Asn Gln Asp Ser Phe Thr Pro Val Val
        2300                2305                2310
Asn Ser Leu Asp Pro Pro Leu Leu Thr Arg Tyr Leu Arg Ile His
        2315                2320                2325
Pro Gln Ser Trp Val His Gln Ile Ala Leu Arg Met Glu Val Leu
        2330                2335                2340
Gly Cys Glu Ala Gln Asp Leu Tyr Asp Lys Thr His Thr Cys Pro
        2345                2350                2355
Pro Cys Pro Ala Pro Glu Leu Leu Gly Gly Pro Ser Val Phe Leu
        2360                2365                2370
Phe Pro Pro Lys Pro Lys Asp Thr Leu Met Ile Ser Arg Thr Pro
        2375                2380                2385
Glu Val Thr Cys Val Val Val Asp Val Ser His Glu Asp Pro Glu
        2390                2395                2400
Val Lys Phe Asn Trp Tyr Val Asp Gly Val Glu Val His Asn Ala
        2405                2410                2415
Lys Thr Lys Pro Arg Glu Glu Gln Tyr Asn Ser Thr Tyr Arg Val
        2420                2425                2430
Val Ser Val Leu Thr Val Leu His Gln Asp Trp Leu Asn Gly Lys
        2435                2440                2445
Glu Tyr Lys Cys Lys Val Ser Asn Lys Ala Leu Pro Ala Pro Ile
        2450                2455                2460
Glu Lys Thr Ile Ser Lys Ala Lys Gly Gln Pro Arg Glu Pro Gln
        2465                2470                2475
```

| | | | | | | | | | | |
|---|---|---|---|---|---|---|---|---|---|---|
| Val | Tyr | Thr | Leu | Pro | Pro | Ser | Arg | Asp | Glu | Leu | Thr | Lys | Asn | Gln |
| | 2480 | | | | | 2485 | | | | 2490 |

Val Ser Leu Thr Cys Leu Val Lys Gly Phe Tyr Pro Ser Asp Ile
　　　2495　　　　　　　　　　　2500　　　　　　　　　　　2505

Ala Val Glu Trp Glu Ser Asn Gly Gln Pro Glu Asn Asn Tyr Lys
　　　2510　　　　　　　　　　　2515　　　　　　　　　　　2520

Thr Thr Pro Pro Val Leu Asp Ser Asp Gly Ser Phe Phe Leu Tyr
　　　2525　　　　　　　　　　　2530　　　　　　　　　　　2535

Ser Lys Leu Thr Val Asp Lys Ser Arg Trp Gln Gln Gly Asn Val
　　　2540　　　　　　　　　　　2545　　　　　　　　　　　2550

Phe Ser Cys Ser Val Met His Glu Ala Leu His Asn His Tyr Thr
　　　2555　　　　　　　　　　　2560　　　　　　　　　　　2565

Gln Lys Ser Leu Ser Leu Ser Pro Gly Lys
　　　2570　　　　　　　　　　　2575

<210> SEQ ID NO 706
<211> LENGTH: 2958
<212> TYPE: DNA
<213> ORGANISM: Artificial Sequence
<220> FEATURE:
<223> OTHER INFORMATION: FVIII Heavy Chain (HC)-Fc DNA sequence (no
      linker between HC and Fc)
<220> FEATURE:
<221> NAME/KEY: sig_peptide
<222> LOCATION: (1)..(57)
<220> FEATURE:
<221> NAME/KEY: misc_feature
<222> LOCATION: (2278)..(2958)
<223> OTHER INFORMATION: Fc region

<400> SEQUENCE: 706

| | |
|---|---|
| atgcaaatag agctctccac ctgcttcttt ctgtgccttt tgcgattctg ctttagtgcc | 60 |
| accagaagat actacctggg tgcagtggaa ctgtcatggg actatatgca agtgatctc | 120 |
| ggtgagctgc ctgtggacgc aagatttcct cctagagtgc aaaatctttt ccattcaac | 180 |
| acctcagtcg tgtacaaaaa gactctgttt gtagaattca cggatcacct tttcaacatc | 240 |
| gctaagccaa ggccaccctg gatgggtctg ctaggtccta ccatccaggc tgaggtttat | 300 |
| gatacagtgg tcattacact taagaacatg gcttcccatc ctgtcagtct tcatgctgtt | 360 |
| ggtgtatcct actggaaagc ttctgaggga gctgaatatg atgatcagac cagtcaaagg | 420 |
| gagaaagaag atgataaagt cttccctggt ggaagccata catatgtctg gcaggtcctg | 480 |
| aaagagaatg gtccaatggc ctctgaccca ctgtgcctta cctactcata tctttctcat | 540 |
| gtggacctgg taaagactt gaattcaggc ctcattggag ccctactagt atgtagagaa | 600 |
| gggagtctgg ccaaggaaaa gacacagacc ttgcacaaat ttatactact ttttgctgta | 660 |
| tttgatgaag ggaaaagttg gcactcagaa acaaagaact ccttgatgca ggataggat | 720 |
| gctgcatctg ctcgggcctg gcctaaaatg cacacagtca atggttatgt aaacaggtct | 780 |
| ctgccaggtc tgattggatg ccacaggaaa tcagtctatt ggcatgtgat tggaatgggc | 840 |
| accactcctg aagtgcactc aatattcctc gaaggtcaca catttcttgt gaggaaccat | 900 |
| cgccaggcgt cctggaaat ctcgccaata actttcctta ctgctcaaac actcttgatg | 960 |
| gaccttggac agtttctact gttttgtcat atctcttccc accaacatga tggcatggaa | 1020 |
| gcttatgtca agtagacag ctgtccagag gaacccaac tacgaatgaa aaataatgaa | 1080 |
| gaagcggaag actatgatga tgatcttact gattctgaaa tggatgtggt caggtttgat | 1140 |
| gatgacaact ctccttcctt tatccaaatt cgctcagttg ccaagaagca tcctaaaact | 1200 |

-continued

```
tgggtacatt acattgctgc tgaagaggag gactgggact atgctccctt agtcctcgcc    1260
cccgatgaca gaagttataa aagtcaatat ttgaacaatg ccctcagcg gattggtagg     1320
aagtacaaaa aagtccgatt tatggcatac acagatgaaa cctttaagac tcgtgaagct    1380
attcagcatg aatcaggaat cttgggacct ttactttatg gggaagttgg agacacactg    1440
ttgattatat ttaagaatca agcaagcaga ccatataaca tctaccctca cggaatcact    1500
gatgtccgtc ctttgtattc aaggagatta ccaaaaggtg taaaacattt gaaggatttt    1560
ccaattctgc caggagaaat attcaaatat aaatggacag tgactgtaga agatgggcca    1620
actaaatcag atcctcggtg cctgacccgc tattactcta gtttcgttaa tatggagaga    1680
gatctagctt caggactcat tggccctctc ctcatctgct acaaagaatc tgtagatcaa    1740
agaggaaacc agataatgtc agacaagagg aatgtcatcc tgttttctgt atttgatgag    1800
aaccgaagct ggtacctcac agagaatata caacgctttc tccccaatcc agctggagtg    1860
cagcttgagg atccagagtt ccaagcctcc aacatcatgc acagcatcaa tggctatgtt    1920
tttgatagtt tgcagttgtc agtttgtttg catgaggtgg catactggta cattctaagc    1980
attggagcac agactgactt cctttctgtc ttcttctctg gatataccct caaacacaaa    2040
atggtctatg aagacacact caccctattc ccattctcag gagaaactgt cttcatgtcg    2100
atggaaaacc caggtctatg gattctgggg tgccacaact cagactttcg aacagaggc    2160
atgaccgcct tactgaaggt ttctagttgt gacaagaaca ctggtgatta ttacgaggac    2220
agttatgaag atatttcagc atacttgctg agtaaaaaca atgccattga accaagagac    2280
aaaactcaca catgcccacc gtgcccagct ccagaactcc tgggcggacc gtcagtcttc    2340
ctcttccccc caaaacccaa ggacaccctc atgatctccc ggaccctga ggtcacatgc     2400
gtggtggtgg acgtgagcca cgaagaccct gaggtcaagt tcaactggta cgtggacggc    2460
gtggaggtgc ataatgccaa gacaaagccg cgggaggagc agtacaacag cacgtaccgt    2520
gtggtcagcg tcctcaccgt cctgcaccag gactggctga atggcaagga gtacaagtgc    2580
aaggtctcca acaaagccct cccagccccc atcgagaaaa ccatctccaa agccaaaggg    2640
cagccccgag aaccacaggt gtacaccctg cccccatccc gggatgagct gaccaagaac    2700
caggtcagcc tgacctgcct ggtcaaaggc ttctatccca gcgacatcgc cgtggagtgg    2760
gagagcaatg ggcagccgga gaacaactac aagaccacgc ctcccgtgtt ggactccgac    2820
ggctccttct tcctctacag caagctcacc gtggacaaga gcaggtggca gcaggggaac    2880
gtcttctcat gctccgtgat gcatgaggct ctgcacaacc actacacgca gaagagcctc    2940
tccctgtctc cgggtaaa                                                  2958
```

<210> SEQ ID NO 707
<211> LENGTH: 986
<212> TYPE: PRT
<213> ORGANISM: Artificial Sequence
<220> FEATURE:
<223> OTHER INFORMATION: FVIII Heavy Chain (HC)-Fc polypeptide (no
      linker between HC and Fc)
<220> FEATURE:
<221> NAME/KEY: SIGNAL
<222> LOCATION: (1)..(19)
<223> OTHER INFORMATION: FVIII signal peptide
<220> FEATURE:
<221> NAME/KEY: MISC_FEATURE
<222> LOCATION: (760)..(986)
<223> OTHER INFORMATION: Fc Sequence

<400> SEQUENCE: 707

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
                35                  40                  45

Phe Pro Pro Arg Val Pro Lys Ser Phe Pro Phe Asn Thr Ser Val Val
50                      55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Gly Pro Thr Ile Gln
                85                  90                  95

Ala Glu Val Tyr Asp Thr Val Val Ile Thr Leu Lys Asn Met Ala Ser
                100                 105                 110

His Pro Val Ser Leu His Ala Val Gly Val Ser Tyr Trp Lys Ala Ser
            115                 120                 125

Glu Gly Ala Glu Tyr Asp Asp Gln Thr Ser Gln Arg Glu Lys Glu Asp
        130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
        340                 345                 350

Gln Leu Arg Met Lys Asn Asn Glu Glu Ala Glu Asp Tyr Asp Asp Asp
            355                 360                 365

Leu Thr Asp Ser Glu Met Asp Val Val Arg Phe Asp Asp Asp Asn Ser
370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415
```

```
Leu Val Leu Ala Pro Asp Asp Arg Ser Tyr Lys Ser Gln Tyr Leu Asn
                420                 425                 430

Asn Gly Pro Gln Arg Ile Gly Arg Lys Tyr Lys Val Arg Phe Met
        435                 440                 445

Ala Tyr Thr Asp Glu Thr Phe Lys Thr Arg Glu Ala Ile Gln His Glu
450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
        530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
        610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
        690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Asp Lys Thr His Thr Cys Pro Pro Cys
        755                 760                 765

Pro Ala Pro Glu Leu Leu Gly Gly Pro Ser Val Phe Leu Phe Pro Pro
        770                 775                 780

Lys Pro Lys Asp Thr Leu Met Ile Ser Arg Thr Pro Glu Val Thr Cys
785                 790                 795                 800

Val Val Val Asp Val Ser His Glu Asp Pro Glu Val Lys Phe Asn Trp
                805                 810                 815

Tyr Val Asp Gly Val Glu Val His Asn Ala Lys Thr Lys Pro Arg Glu
            820                 825                 830

Glu Gln Tyr Asn Ser Thr Tyr Arg Val Val Ser Val Leu Thr Val Leu
```

```
                    835                 840                 845
His Gln Asp Trp Leu Asn Gly Lys Glu Tyr Lys Cys Lys Val Ser Asn
                850                 855                 860

Lys Ala Leu Pro Ala Pro Ile Glu Lys Thr Ile Ser Lys Ala Lys Gly
865                 870                 875                 880

Gln Pro Arg Glu Pro Gln Val Tyr Thr Leu Pro Pro Ser Arg Asp Glu
                    885                 890                 895

Leu Thr Lys Asn Gln Val Ser Leu Thr Cys Leu Val Lys Gly Phe Tyr
                900                 905                 910

Pro Ser Asp Ile Ala Val Glu Trp Glu Ser Asn Gly Gln Pro Glu Asn
                915                 920                 925

Asn Tyr Lys Thr Thr Pro Pro Val Leu Asp Ser Asp Gly Ser Phe Phe
            930                 935                 940

Leu Tyr Ser Lys Leu Thr Val Asp Lys Ser Arg Trp Gln Gln Gly Asn
945                 950                 955                 960

Val Phe Ser Cys Ser Val Met His Glu Ala Leu His Asn His Tyr Thr
                965                 970                 975

Gln Lys Ser Leu Ser Leu Ser Pro Gly Lys
                980                 985

<210> SEQ ID NO 708
<211> LENGTH: 2973
<212> TYPE: DNA
<213> ORGANISM: Artificial Sequence
<220> FEATURE:
<223> OTHER INFORMATION: FVIII Heavy Chain (HC)-Fc DNA sequence (5 amino
      acid linker between HC and Fc)
<220> FEATURE:
<221> NAME/KEY: sig_peptide
<222> LOCATION: (1)..(58)
<220> FEATURE:
<221> NAME/KEY: misc_feature
<222> LOCATION: (2278)..(2292)
<223> OTHER INFORMATION: 5 amino acid linker
<220> FEATURE:
<221> NAME/KEY: misc_feature
<222> LOCATION: (2293)..(2973)
<223> OTHER INFORMATION: Fc region

<400> SEQUENCE: 708
atgcaaatag agctctccac ctgcttcttt ctgtgccttt tgcgattctg ctttagtgcc      60
accagaagat actacctggg tgcagtggaa ctgtcatggg actatatgca aagtgatctc     120
ggtgagctgc ctgtggacgc aagatttcct cctagagtgc aaaatctttt ccattcaac      180 acctcagtcg tgtacaaaaa gactctgttt gtagaattca cggatcacct tttcaacatc     240
gctaagccaa ggccaccctg gatgggtctg ctaggtccta ccatccaggc tgaggtttat     300
gatacagtgt cattacact aagaacatg gcttcccatc ctgtcagtct tcatgctgtt      360
ggtgtatcct actggaaagc ttctgaggga gctgaatatg atgatcagac cagtcaaagg     420
gagaaagaag atgataaagt cttccctggt ggaagccata catatgtctg gcaggtcctg     480
aaagagaatg gtccaatggc ctctgaccca ctgtgcctta cctactcata tctttctcat     540
gtggacctgg taaagacttt gaattcaggc ctcattggag ccctactagt atgtagagaa     600
gggagtctgg ccaaggaaaa gacacagacc ttgcacaaat ttatactact ttttgctgta     660
tttgatgaag ggaaaagttg gcactcagaa acaagaact ccttgatgca ggatagggat     720
gctgcatctg ctcgggcctg gcctaaaatg cacacagtca atggttatgt aaacaggtct     780
ctgccaggtc tgattggatg ccacaggaaa tcagtctatt ggcatgtgat tggaatgggc     840
```

```
accactcctg aagtgcactc aatattcctc gaaggtcaca catttcttgt gaggaaccat    900
cgccaggcgt ccttggaaat ctcgccaata actttcctta ctgctcaaac actcttgatg    960
gaccttggac agtttctact gttttgtcat atctcttccc accaacatga tggcatggaa   1020
gcttatgtca aagtagacag ctgtccagag aaccccaac tacgaatgaa aaataatgaa   1080
gaagcggaag actatgatga tgatcttact gattctgaaa tggatgtggt caggtttgat   1140
gatgacaact ctccttcctt tatccaaatt cgctcagttg ccaagaagca tcctaaaact   1200
tgggtacatt acattgctgc tgaagaggag gactgggact atgctccctt agtcctcgcc   1260
cccgatgaca gaagttataa aagtcaatat ttgaacaatg gccctcagcg gattggtagg   1320
aagtacaaaa aagtccgatt tatggcatac acagatgaaa cctttaagac tcgtgaagct   1380
attcagcatg aatcaggaat cttgggacct ttactttatg gggaagttgg agacacactg   1440
ttgattatat ttaagaatca agcaagcaga ccatataaca tctaccctca cggaatcact   1500
gatgtccgtc ctttgtattc aaggagatta ccaaaaggtg taaaacattt gaaggatttt   1560
ccaattctgc caggagaaat attcaaatat aaatggacag tgactgtaga agatgggcca   1620
actaaatcag atcctcggtg cctgacccgc tattactcta gtttcgttaa tatggagaga   1680
gatctagctt caggactcat tggccctctc ctcatctgct acaaagaatc tgtagatcaa   1740
agaggaaacc agataatgtc agacaagagg aatgtcatcc tgttttctgt atttgatgag   1800
aaccgaagct ggtacctcac agagaatata caacgctttc tccccaatcc agctggagtg   1860
cagcttgagg atccagagtt ccaagcctcc aacatcatgc acagcatcaa tggctatgtt   1920
tttgatagtt tgcagttgtc agtttgtttg catgaggtgg catactggta cattctaagc   1980
attggagcac agactgactt cctttctgtc ttcttctctg gatataccct caaacacaaa   2040
atggtctatg aagacacact caccctattc ccattctcag agaaactgt cttcatgtcg   2100 atggaaaacc caggtctatg gattctgggg tgccacaact cagactttcg gaacagaggc   2160
atgaccgcct tactgaaggt ttctagttgt gacaagaaca ctggtgatta ttacgaggac   2220
agttatgaag atatttcagc atacttgctg agtaaaaaca atgccattga accaagaagc   2280
ttctcccaga tgacaaaaac tcacacatgc ccaccgtgcc cagctccaga actcctgggc   2340
ggaccgtcag tcttcctctt ccccccaaaa cccaaggaca cctcatgat ctcccggacc   2400 cctgaggtca catgcgtggt ggtggacgtg agccacgaag accctgaggt caagttcaac   2460
tggtacgtgg acggcgtgga ggtgcataat gccaagacaa agccgcggga ggagcagtac   2520
aacagcacgt accgtgtggt cagcgtcctc accgtcctgc accaggactg gctgaatggc   2580
aaggagtaca agtgcaaggt ctccaacaaa gccctcccag cccccatcga gaaaaccatc   2640
tccaaagcca agggcagccc cgagaaccca caggtgtaca ccctgccccc atcccgggat   2700
gagctgacca agaaccaggt cagcctgacc tgcctggtca aaggcttcta tcccagcgac   2760
atcgccgtgg agtgggagag caatgggcag ccggagaaca actacaagac cacgcctccc   2820
gtgttggact ccgacggctc cttcttcctc tacagcaagc tcaccgtgga caagagcagg   2880
tggcagcagg ggaacgtctt ctcatgctcc gtgatgcatg aggctctgca caaccactac   2940
acgcagaaga gcctctccct gtctccgggt aaa   2973
```

<210> SEQ ID NO 709
<211> LENGTH: 991
<212> TYPE: PRT
<213> ORGANISM: Artificial Sequence
<220> FEATURE:
<223> OTHER INFORMATION: FVIII Heavy Chain (HC)-Fc polypeptide (5 amino -continued

```
        acid linker between HC and Fc)
<220> FEATURE:
<221> NAME/KEY: SIGNAL
<222> LOCATION: (1)..(19)
<223> OTHER INFORMATION: FVIII signal peptide
<220> FEATURE:
<221> NAME/KEY: MISC_FEATURE
<222> LOCATION: (760)..(764)
<223> OTHER INFORMATION: amino acid linker sequence
<220> FEATURE:
<221> NAME/KEY: MISC_FEATURE
<222> LOCATION: (765)..(991)
<223> OTHER INFORMATION: Fc region

<400> SEQUENCE: 709
```

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

```
Asp Gly Met Glu Ala Tyr Val Lys Val Asp Ser Cys Pro Glu Pro
            340                 345                 350

Gln Leu Arg Met Lys Asn Asn Glu Glu Ala Glu Asp Tyr Asp Asp
            355                 360                 365

Leu Thr Asp Ser Glu Met Asp Val Val Arg Phe Asp Asp Asn Ser
            370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Asp Trp Asp Tyr Ala Pro
            405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
            435                 440                 445

Ala Tyr Thr Asp Glu Thr Phe Lys Thr Arg Glu Ala Ile Gln His Glu
            450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
            485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
            515                 520                 525

Lys Tyr Lys Trp Thr Val Thr Val Glu Asp Gly Pro Thr Lys Ser Asp
            530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
            565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
            595                 600                 605

Asn Ile Gln Arg Phe Leu Pro Asn Pro Ala Gly Val Gln Leu Glu Asp
            610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
            645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
            675                 680                 685

Leu Phe Pro Phe Ser Gly Glu Thr Val Phe Met Ser Met Glu Asn Pro
            690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
            725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Asp Lys Thr His
```

```
                        755                 760                 765
Thr Cys Pro Pro Cys Pro Ala Pro Glu Leu Leu Gly Gly Pro Ser Val
        770                 775                 780

Phe Leu Phe Pro Pro Lys Pro Lys Asp Thr Leu Met Ile Ser Arg Thr
785                 790                 795                 800

Pro Glu Val Thr Cys Val Val Val Asp Val Ser His Glu Asp Pro Glu
                805                 810                 815

Val Lys Phe Asn Trp Tyr Val Asp Gly Val Glu Val His Asn Ala Lys
            820                 825                 830

Thr Lys Pro Arg Glu Glu Gln Tyr Asn Ser Thr Tyr Arg Val Val Ser
        835                 840                 845

Val Leu Thr Val Leu His Gln Asp Trp Leu Asn Gly Lys Glu Tyr Lys
    850                 855                 860

Cys Lys Val Ser Asn Lys Ala Leu Pro Ala Pro Ile Glu Lys Thr Ile
865                 870                 875                 880

Ser Lys Ala Lys Gly Gln Pro Arg Glu Pro Gln Val Tyr Thr Leu Pro
                885                 890                 895

Pro Ser Arg Asp Glu Leu Thr Lys Asn Gln Val Ser Leu Thr Cys Leu
            900                 905                 910

Val Lys Gly Phe Tyr Pro Ser Asp Ile Ala Val Glu Trp Glu Ser Asn
        915                 920                 925

Gly Gln Pro Glu Asn Asn Tyr Lys Thr Thr Pro Pro Val Leu Asp Ser
    930                 935                 940

Asp Gly Ser Phe Phe Leu Tyr Ser Lys Leu Thr Val Asp Lys Ser Arg
945                 950                 955                 960

Trp Gln Gln Gly Asn Val Phe Ser Cys Ser Val Met His Glu Ala Leu
                965                 970                 975

His Asn His Tyr Thr Gln Lys Ser Leu Ser Leu Ser Pro Gly Lys
            980                 985                 990
```

<210> SEQ ID NO 710
<211> LENGTH: 2793
<212> TYPE: DNA
<213> ORGANISM: Artificial Sequence
<220> FEATURE:
<223> OTHER INFORMATION: FVIII Light Chain (LC)-Fc DNA sequence
<220> FEATURE:
<221> NAME/KEY: sig_peptide
<222> LOCATION: (1)..(60)
<220> FEATURE:
<221> NAME/KEY: misc_feature
<222> LOCATION: (2113)..(2793)
<223> OTHER INFORMATION: Fc region

<400> SEQUENCE: 710

```
atggagacag acacactcct gctatgggta ctgctgctct ggttccagg ttccactggt      60 gaaataactc gtactactct tcagtcagat caagaggaaa ttgactatga tgataccata     120
tcagttgaaa tgaagaagga agattttgac atttatgatg aggatgaaaa tcagagcccc     180
cgcagctttc aaaagaaaac acgacactat tttattgctg cagtggagag gctctgggat     240
tatgggatga gtagctcccc acatgttcta gaaacagggg ctcagagtgg cagtgtccct     300
cagttcaaga agttgttttt ccaggaattt actgatggcc ctttactca gcccttatac     360 cgtggagaac taaatgaaca tttgggactc ctggggccat atataagagc agaagttgaa     420
gataatatca tggtaacttt cagaaatcag gcctctcgtc cctattcctt ctattctagc     480
cttatttctt atgaggaaga tcagaggcaa ggagcagaac ctagaaaaaa ctttgtcaag     540
```

-continued

```
cctaatgaaa ccaaaactta cttttggaaa gtgcaacatc atatggcacc cactaaagat    600
gagtttgact gcaaagcctg ggcttatttc tctgatgttg acctggaaaa agatgtgcac    660
tcaggcctga ttggacccct tctggtctgc cacactaaca cactgaaccc tgctcatggg    720
agacaagtga cagtacagga atttgctctg tttttcacca tctttgatga gaccaaaagc    780
tggtacttca ctgaaaatat ggaaagaaac tgcagggctc cctgcaatat ccagatggaa    840
gatcccactt ttaaagagaa ttatcgcttc catgcaatca atggctacat aatggataca    900
ctacctggct tagtaatggc tcaggatcaa aggattcgat ggtatctgct cagcatgggc    960
agcaatgaaa acatccattc tattcatttc agtggacatg tgttcactgt acgaaaaaaa   1020
gaggagtata aaatggcact gtacaatctc tatccaggtg ttttttgagac agtggaaatg   1080
ttaccatcca aagctggaat ttggcgggtg gaatgcctta ttggcgagca tctacatgct   1140
gggatgagca cacttttttct ggtgtacagc aataagtgtc agactcccct gggaatggct   1200
tctggacaca ttagagattt tcagattaca gcttcaggac aatatggaca gtgggcccca   1260
aagctggcca gacttcatta ttccggatca atcaatgcct ggagcaccaa ggagcccttt   1320
tcttggatca aggtggatct gttggcacca atgattattc acggcatcaa gacccagggt   1380
gcccgtcaga agttctccag cctctacatc tctcagttta tcatcatgta tagtcttgat   1440
gggaagaagt ggcagactta tcgaggaaat tccactggaa ccttaatggt cttctttggc   1500
aatgtggatt catctgggat aaaacacaat attttttaacc ctccaattat tgctcgatac   1560
atccgtttgc acccaactca ttatagcatt cgcagcactc ttcgcatgga gttgatgggc   1620
tgtgatttaa atagttgcag catgccattg ggaatggaga gtaaagcaat atcagatgca   1680
cagattactg cttcatccta ctttaccaat atgtttgcca cctggtctcc ttcaaaagct   1740
cgacttcacc tccaagggag gagtaatgcc tggagacctc aggtgaataa tccaaaagag   1800
tggctgcaag tggacttcca aagacaatg aaagtcacag gagtaactac tcagggagta   1860
aaatctctgc ttaccagcat gtatgtgaag gagttcctca tctccagcag tcaagatggc   1920
catcagtgga ctctctttttt tcagaatggc aaagtaaagg ttttttcaggg aaatcaagac   1980
tccttcacac ctgtggtgaa ctctctagac ccaccgttac tgactcgcta ccttcgaatt   2040
caccccccaga gttgggtgca ccagattgcc ctgaggatgg aggttctggg ctgcgaggca   2100
caggacctct acgacaaaac tcacacatgc ccaccgtgcc cagctccaga actcctgggc   2160
ggaccgtcag tcttcctctt ccccccaaaa cccaaggaca cctcatgat ctccccggacc   2220
cctgaggtca catgcgtggt ggtggacgtg agccacgaag accctgaggt caagttcaac   2280
tggtacgtgg acggcgtgga ggtgcataat gccaagacaa agccgcggga ggagcagtac   2340
aacagcacgt accgtgtggt cagcgtcctc accgtcctgc accaggactg gctgaatggc   2400
aaggagtaca agtgcaaggt ctccaacaaa gccctcccag cccccatcga gaaaaccatc   2460
tccaaagcca agggcagcc ccgagaacca caggtgtaca ccctgccccc atccgggat    2520
gagctgacca agaaccaggt cagcctgacc tgcctggtca aaggcttcta tcccagcgac   2580
atcgccgtgg agtgggagag caatgggcag ccggagaaca actacaagac cacgcctccc   2640
gtgttggact ccgacggctc cttcttcctc tacagcaagc tcaccgtgga caagagcagg   2700
tggcagcagg ggaacgtctt ctcatgctcc gtgatgcatg aggctctgca caaccactac   2760
acgcagaaga gcctctccct gtctccgggt aaa                                 2793
```

<210> SEQ ID NO 711
<211> LENGTH: 931

```
<212> TYPE: PRT
<213> ORGANISM: Artificial Sequence
<220> FEATURE:
<223> OTHER INFORMATION: FVIII Light Chain (LC)-Fc polypeptide
<220> FEATURE:
<221> NAME/KEY: SIGNAL
<222> LOCATION: (1)..(20)
<223> OTHER INFORMATION: mouse Igk signal
<220> FEATURE:
<221> NAME/KEY: MISC_FEATURE
<222> LOCATION: (705)..(931)
<223> OTHER INFORMATION: Fc Sequence

<400> SEQUENCE: 711
```

Met Glu Thr Asp Thr Leu Leu Leu Trp Val Leu Leu Leu Trp Val Pro
1               5                   10                  15

Gly Ser Thr Gly Glu Ile Thr Arg Thr Thr Leu Gln Ser Asp Gln Glu
            20                  25                  30

Glu Ile Asp Tyr Asp Asp Thr Ile Ser Val Glu Met Lys Lys Glu Asp
        35                  40                  45

Phe Asp Ile Tyr Asp Glu Asp Glu Asn Gln Ser Pro Arg Ser Phe Gln
    50                  55                  60

Lys Lys Thr Arg His Tyr Phe Ile Ala Ala Val Glu Arg Leu Trp Asp
65                  70                  75                  80

Tyr Gly Met Ser Ser Ser Pro His Val Leu Arg Asn Arg Ala Gln Ser
                85                  90                  95

Gly Ser Val Pro Gln Phe Lys Lys Val Val Phe Gln Glu Phe Thr Asp
            100                 105                 110

Gly Ser Phe Thr Gln Pro Leu Tyr Arg Gly Glu Leu Asn Glu His Leu
        115                 120                 125

Gly Leu Leu Gly Pro Tyr Ile Arg Ala Glu Val Glu Asp Asn Ile Met
    130                 135                 140

Val Thr Phe Arg Asn Gln Ala Ser Arg Pro Tyr Ser Phe Tyr Ser Ser
145                 150                 155                 160

Leu Ile Ser Tyr Glu Glu Asp Gln Arg Gln Gly Ala Glu Pro Arg Lys
                165                 170                 175

Asn Phe Val Lys Pro Asn Glu Thr Lys Thr Tyr Phe Trp Lys Val Gln
            180                 185                 190

His His Met Ala Pro Thr Lys Asp Glu Phe Asp Cys Lys Ala Trp Ala
        195                 200                 205

Tyr Phe Ser Asp Val Asp Leu Glu Lys Asp Val His Ser Gly Leu Ile
    210                 215                 220

Gly Pro Leu Leu Val Cys His Thr Asn Thr Leu Asn Pro Ala His Gly
225                 230                 235                 240

Arg Gln Val Thr Val Gln Glu Phe Ala Leu Phe Phe Thr Ile Phe Asp
                245                 250                 255

Glu Thr Lys Ser Trp Tyr Phe Thr Glu Asn Met Glu Arg Asn Cys Arg
            260                 265                 270

Ala Pro Cys Asn Ile Gln Met Glu Asp Pro Thr Phe Lys Glu Asn Tyr
        275                 280                 285

Arg Phe His Ala Ile Asn Gly Tyr Ile Met Asp Thr Leu Pro Gly Leu
    290                 295                 300

Val Met Ala Gln Asp Gln Arg Ile Arg Trp Tyr Leu Leu Ser Met Gly
305                 310                 315                 320

Ser Asn Glu Asn Ile His Ser Ile His Phe Ser Gly His Val Phe Thr
                325                 330                 335

Val Arg Lys Lys Glu Glu Tyr Lys Met Ala Leu Tyr Asn Leu Tyr Pro

-continued

```
                340                 345                 350
Gly Val Phe Glu Thr Val Glu Met Leu Pro Ser Lys Ala Gly Ile Trp
            355                 360                 365
Arg Val Glu Cys Leu Ile Gly Glu His Leu His Ala Gly Met Ser Thr
        370                 375                 380
Leu Phe Leu Val Tyr Ser Asn Lys Cys Gln Thr Pro Leu Gly Met Ala
385                 390                 395                 400
Ser Gly His Ile Arg Asp Phe Gln Ile Thr Ala Ser Gly Gln Tyr Gly
                405                 410                 415
Gln Trp Ala Pro Lys Leu Ala Arg Leu His Tyr Ser Gly Ser Ile Asn
            420                 425                 430
Ala Trp Ser Thr Lys Glu Pro Phe Ser Trp Ile Lys Val Asp Leu Leu
        435                 440                 445
Ala Pro Met Ile Ile His Gly Ile Lys Thr Gln Gly Ala Arg Gln Lys
    450                 455                 460
Phe Ser Ser Leu Tyr Ile Ser Gln Phe Ile Ile Met Tyr Ser Leu Asp
465                 470                 475                 480
Gly Lys Lys Trp Gln Thr Tyr Arg Gly Asn Ser Thr Gly Thr Leu Met
                485                 490                 495
Val Phe Phe Gly Asn Val Asp Ser Ser Gly Ile Lys His Asn Ile Phe
            500                 505                 510
Asn Pro Pro Ile Ile Ala Arg Tyr Ile Arg Leu His Pro Thr His Tyr
        515                 520                 525
Ser Ile Arg Ser Thr Leu Arg Met Glu Leu Met Gly Cys Asp Leu Asn
    530                 535                 540
Ser Cys Ser Met Pro Leu Gly Met Glu Ser Lys Ala Ile Ser Asp Ala
545                 550                 555                 560
Gln Ile Thr Ala Ser Ser Tyr Phe Thr Asn Met Phe Ala Thr Trp Ser
                565                 570                 575
Pro Ser Lys Ala Arg Leu His Leu Gln Gly Arg Ser Asn Ala Trp Arg
            580                 585                 590
Pro Gln Val Asn Asn Pro Lys Glu Trp Leu Gln Val Asp Phe Gln Lys
        595                 600                 605
Thr Met Lys Val Thr Gly Val Thr Thr Gln Gly Val Lys Ser Leu Leu
    610                 615                 620
Thr Ser Met Tyr Val Lys Glu Phe Leu Ile Ser Ser Ser Gln Asp Gly
625                 630                 635                 640
His Gln Trp Thr Leu Phe Phe Gln Asn Gly Lys Val Lys Val Phe Gln
                645                 650                 655
Gly Asn Gln Asp Ser Phe Thr Pro Val Val Asn Ser Leu Asp Pro Pro
            660                 665                 670
Leu Leu Thr Arg Tyr Leu Arg Ile His Pro Gln Ser Trp Val His Gln
        675                 680                 685
Ile Ala Leu Arg Met Glu Val Leu Gly Cys Glu Ala Gln Asp Leu Tyr
    690                 695                 700
Asp Lys Thr His Thr Cys Pro Pro Cys Pro Ala Pro Glu Leu Leu Gly
705                 710                 715                 720
Gly Pro Ser Val Phe Leu Phe Pro Pro Lys Pro Lys Asp Thr Leu Met
                725                 730                 735
Ile Ser Arg Thr Pro Glu Val Thr Cys Val Val Val Asp Val Ser His
            740                 745                 750
Glu Asp Pro Glu Val Lys Phe Asn Trp Tyr Val Asp Gly Val Glu Val
        755                 760                 765
```

```
His Asn Ala Lys Thr Lys Pro Arg Glu Glu Gln Tyr Asn Ser Thr Tyr
    770                 775                 780
Arg Val Val Ser Val Leu Thr Val Leu His Gln Asp Trp Leu Asn Gly
785                 790                 795                 800
Lys Glu Tyr Lys Cys Lys Val Ser Asn Lys Ala Leu Pro Ala Pro Ile
                805                 810                 815
Glu Lys Thr Ile Ser Lys Ala Lys Gly Gln Pro Arg Glu Pro Gln Val
            820                 825                 830
Tyr Thr Leu Pro Pro Ser Arg Asp Glu Leu Thr Lys Asn Gln Val Ser
        835                 840                 845
Leu Thr Cys Leu Val Lys Gly Phe Tyr Pro Ser Asp Ile Ala Val Glu
    850                 855                 860
Trp Glu Ser Asn Gly Gln Pro Glu Asn Asn Tyr Lys Thr Thr Pro Pro
865                 870                 875                 880
Val Leu Asp Ser Asp Gly Ser Phe Phe Leu Tyr Ser Lys Leu Thr Val
                885                 890                 895
Asp Lys Ser Arg Trp Gln Gln Gly Asn Val Phe Ser Cys Ser Val Met
            900                 905                 910
His Glu Ala Leu His Asn His Tyr Thr Gln Lys Ser Leu Ser Leu Ser
        915                 920                 925
Pro Gly Lys
    930

<210> SEQ ID NO 712
<211> LENGTH: 7583
<212> TYPE: DNA
<213> ORGANISM: Artificial Sequence
<220> FEATURE:
<223> OTHER INFORMATION: FIX-Fc Chain DNA Sequence
<220> FEATURE:
<221> NAME/KEY: sig_peptide
<222> LOCATION: (690)..(777)
<223> OTHER INFORMATION: FIX signal peptide
<220> FEATURE:
<221> NAME/KEY: misc_feature
<222> LOCATION: (1077)..(2371)
<223> OTHER INFORMATION: FIX sequence
<220> FEATURE:
<221> NAME/KEY: misc_feature
<222> LOCATION: (2372)..(3052)
<223> OTHER INFORMATION: Fc region

<400> SEQUENCE: 712
gcgcgcgttg acattgatta ttgactagtt attaatagta atcaattacg gggtcattag       60
ttcatagccc atatatggag ttccgcgtta cataacttac ggtaaatggc ccgcctggct      120
gaccgcccaa cgaccccccgc ccattgacgt caataatgac gtatgttccc atagtaacgc      180
caatagggac tttccattga cgtcaatggg tggagtattt acggtaaact gcccacttgg      240
cagtacatca agtgtatcat atgccaagta cgccccctat tgacgtcaat gacggtaaat      300
ggcccgcctg gcattatgcc cagtacatga ccttatggga ctttcctact tggcagtaca      360
tctacgtatt agtcatcgct attaccatgg tgatgcggtt ttggcagtac atcaatgggc      420
gtggatagcg gtttgactca cggggatttc caagtctcca ccccattgac gtcaatggga      480
gtttgttttg gcaccaaaat caacgggact ttccaaaatg tcgtaacaac tccgccccat      540
tgacgcaaat gggcggtagg cgtgtacggt gggaggtcta taagcagag ctctctggc      600 taactagaga acccactgct tactggctta tcgaaattaa tacgactcac tatagggaga      660
cccaagcttc gcgacgtacg gccgccacca tgcagcgcgt gaacatgatc atggcagaat      720
```

-continued

```
caccaggcct catcaccatc tgccttttag gatatctact cagtgctgaa tgtacaggtt      780
tgtttccttt tttaaaatac attgagtatg cttgccttt agatatagaa atatctgatg       840
ctgtcttctt cactaaattt tgattacatg atttgacagc aatattgaag agtctaacag      900
ccagcacgca ggttggtaag tactgtggga acatcacaga ttttggctcc atgccctaaa      960
gagaaattgg ctttcagatt atttggatta aaaacaaaga ctttcttaag agatgtaaaa     1020
ttttcatgat gttttctttt ttgctaaaac taaagaatta ttcttttaca tttcagtttt     1080
tcttgatcat gaaaacgcca acaaaattct gaatcggcca agaggtata attcaggtaa      1140 attggaagag tttgttcaag ggaatctaga gagagaatgt atggaagaaa agtgtagttt     1200
tgaagaagca cgagaagttt ttgaaaacac tgaaagaaca actgaatttt ggaagcagta     1260
tgttgatgga gatcagtgtg agtccaatcc atgtttaaat ggcggcagtt gcaaggatga     1320
cattaattcc tatgaatgtt ggtgtcccct tggatttgaa ggaaagaact gtgaattaga     1380
tgtaacatgt aacattaaga atggcagatg cgagcagttt tgtaaaaata gtgctgataa     1440
caaggtggtt tgctcctgta ctgagggata tcgacttgca gaaaaccaga agtcctgtga     1500
accagcagtg ccatttccat gtggaagagt ttctgtttca caaacttcta agctcacccg     1560
tgctgagact gttttccctg atgtggacta tgtaaattct actgaagctg aaaccatttt     1620
ggataacatc actcaaagca cccaatcatt taatgacttc actcggggttg ttggtggaga     1680 agatgccaaa ccaggtcaat tcccttggca ggttgttttg aatggtaaag ttgatgcatt     1740
ctgtggaggc tctatcgtta tgaaaaatg gattgtaact gctgcccact gtgttgaaac     1800
tggtgttaaa attacagttg tcgcaggtga acataatatt gaggagacag aacatacaga     1860
gcaaaagcga aatgtgattc gaattattcc tcaccacaac tacaatgcag ctattaataa     1920
gtacaaccat gacattgccc ttctggaact ggacgaaccc ttagtgctaa acagctacgt     1980
tacacctatt tgcattgctg acaaggaata cacgaacatc ttcctcaaat ttggatctgg     2040
ctatgtaagt ggctggggaa gagtcttcca caaagggaga tcagctttag ttcttcagta     2100
ccttagagtt ccacttgttg accgagccac atgtcttcga tctacaaagt tcaccatcta     2160
taacaacatg ttctgtgctg gcttccatga aggaggtaga gattcatgtc aaggagatag     2220
tggggacccc catgttactg aagtggaagg gaccagtttc ttaactggaa ttattagctg     2280
gggtgaagag tgtgcaatga aaggcaaata tggaatatat accaaggtgt cccgtgtatgt     2340 caactggatt aaggaaaaaa caaagctcac tgacaaaact cacacatgcc caccgtgccc     2400
agctccggaa ctcctgggcg gaccgtcagt cttcctcttc cccccaaaac ccaaggacac     2460
cctcatgatc tcccggaccc ctgaggtcac atgcgtggtg gtggacgtga gccacgaaga     2520
ccctgaggtc aagttcaact ggtacgtgga cggcgtggag gtgcataatg ccaagacaaa     2580
gccgcgggag gagcagtaca acagcacgta ccgtgtggtc agcgtcctca ccgtcctgca     2640
ccaggactgg ctgaatggca aggagtacaa gtgcaaggtc tccaacaaag ccctcccagc     2700
ccccatcgag aaaaccatct ccaaagccaa agggcagccc cgagaaccac aggtgtacac     2760
cctgccccca tcccgggatg agctgaccaa gaaccaggtc agcctgacct gcctggtcaa     2820
aggcttctat cccagcgaca tcgccgtgga gtgggagagc aatgggcagc cggagaacaa     2880
ctacaagacc acgcctcccg tgttggactc cgacggctcc ttcttcctct acagcaagct     2940
caccgtggac aagagcaggt ggcagcaggg gaacgtcttc tcatgctccg tgatgcatga     3000
ggctctgcac aaccactaca cgcagaagag cctctccctg tctccgggta aatgagaatt     3060
```

```
cagacatgat aagatacatt gatgagtttg acaaaccac aactagaatg cagtgaaaaa    3120
aatgctttat ttgtgaaatt tgtgatgcta ttgctttatt tgtaaccatt ataagctgca    3180
ataaacaagt tggggtgggc gaagaactcc agcatgagat ccccgcgctg gaggatcatc    3240
cagccggcgt cccggaaaac gattccgaag cccaaccttt catagaaggc ggcggtggaa    3300
tcgaaatctc gtagcacgtg tcagtcctgc tcctcggcca cgaagtgcac gcagttgccg    3360
gccgggtcgc gcagggcgaa ctcccgcccc cacggctgct cgccgatctc ggtcatggcc    3420
ggcccggagg cgtcccggaa gttcgtggac acgacctccg accactcggc gtacagctcg    3480
tccaggccgc gcacccacac ccaggccagg gtgttgtccg gcaccacctg gtcctggacc    3540
gcgctgatga acagggtcac gtcgtcccgg accacaccgg cgaagtcgtc ctccacgaag    3600
tcccgggaga cccgagccg gtcggtccag aactcgaccg ctccggcgac gtcgcgcgcg    3660
gtgagcaccg gaacggcact ggtcaacttg gccatggttt agttcctcac cttgtcgtat    3720
tatactatgc cgatatacta tgccgatgat taattgtcaa cacgtgctga tcagatccga    3780
aaatggatat acaagctccc gggagctttt tgcaaaagcc taggcctcca aaaaagcctc    3840
ctcactactt ctggaatagc tcagaggcag aggcggcctc ggcctctgca taaataaaaa    3900
aaattagtca gccatggggc ggagaatggg cggaactggg cggagttagg ggcgggatgg    3960
gcggagttag gggcgggact atggttgctg actaattgag atgcatgctt tgcatacttc    4020
tgcctgctgg ggagcctggg gactttccac acctggttgc tgactaattg agatgcatgc    4080
tttgcatact tctgcctgct ggggagcctg gggactttcc acaccctcgt cgagctagct    4140
tcgtgaggct ccggtgcccg tcagtgggca gagcgcacat cgcccacagt ccccgagaag    4200 ttgggggag gggtcggcaa ttgaaccggt gcctagagaa ggtggcgcgg ggtaaactgg    4260
gaaagtgatg tcgtgtactg gctccgcctt tttcccgagg gtgggggaga accgtatata    4320
agtgcagtag tcgccgtgaa cgttcttttt cgcaacgggt ttgccgccag aacacaggta    4380
agtgccgtgt gtggttcccg cgggcctggc ctctttacgg gttatggccc ttgcgtgcct    4440
tgaattactt ccacctggct ccagtacgtg attcttgatc ccgagctgga gccaggggcg    4500
ggccttgcgc tttaggagcc ccttcgcctc gtgcttgagt tgaggcctgg cctgggcgct    4560
ggggccgccg cgtgcgaatc tggtggcacc ttcgcgcctg tctcgctgct ttcgataagt    4620
ctctagccat ttaaaatttt tgatgacctg ctgcgacgct ttttttctgg caagatagtc    4680
ttgtaaatgc gggccaggat ctgcacactg gtatttcggt ttttggggcc gcgggcggcg    4740
acggggcccg tgcgtcccag cgcacatgtt cggcgaggcg gggcctgcga gcgcggccac    4800
cgagaatcgg acggggtag tctcaagctg gccggcctgc tctggtgcct ggcctcgcgc    4860
cgccgtgtat cgccccgccc tgggcggcaa ggctggcccg tcggcacca gttgcgtgag    4920 cggaaagatg gccgcttccc ggccctgctc caggggctc aaaatggagg acgcggcgct    4980
cgggagagcg ggcgggtgag tcacccacac aaaggaaagg ggccttccg tcctcagccg    5040 tcgcttcatg tgactccacg gagtaccggg cgccgtccag gcacctcgat tagttctgga    5100
gcttttggag tacgtcgtct ttaggttggg gggagggtt ttatgcgatg gagtttcccc    5160
acactgagtg ggtggagact gaagttaggc cagcttggca cttgatgtaa ttctccttgg    5220
aatttgccct ttttgagttt ggatcttggt tcattctcaa gcctcagaca gtggttcaaa    5280 gttttttttct tccatttcag gtgtcgtgaa cacgtggtcg cggccgcgcc gccaccatgg    5340
agacagacac actcctgcta tgggtactgc tgctctgggt tccaggttcc actggtgaca    5400
aaactcacac atgcccaccg tgcccagcac ctgaactcct gggaggaccg tcagtcttcc    5460
```

```
tcttcccccc aaaacccaag gacaccctca tgatctcccg gacccctgag gtcacatgcg    5520
tggtggtgga cgtgagccac gaagaccctg aggtcaagtt caactggtac gtggacggcg    5580
tggaggtgca taatgccaag acaaagccgc gggaggagca gtacaacagc acgtaccgtg    5640
tggtcagcgt cctcaccgtc ctgcaccagg actggctgaa tggcaaggag tacaagtgca    5700
aggtctccaa caaagccctc ccagccccca tcgagaaaac catctccaaa gccaaagggc    5760
agccccgaga accacaggtg tacaccctgc cccatcccg cgatgagctg accaagaacc    5820
aggtcagcct gacctgcctg gtcaaaggct tctatcccag cgacatcgcc gtggagtggg    5880
agagcaatgg gcagccggag aacaactaca agaccacgcc tcccgtgttg gactccgacg    5940
gctccttctt cctctacagc aagctcaccg tggacaagag caggtggcag caggggaacg    6000
tcttctcatg ctccgtgatg catgaggctc tgcacaacca ctacacgcag aagagcctct    6060
ccctgtctcc gggtaaatga ctcgagagat ctggccggct gggcccgttt cgaaggtaag    6120
cctatcccta accctctcct cggtctcgat tctacgcgta ccggtcatca tcaccatcac    6180
cattgagttt aaacccgctg atcagcctcg actgtgcctt ctagttgcca gccatctgtt    6240
gtttgcccct cccccgtgcc ttccttgacc ctggaaggtg ccactcccac tgtcctttcc    6300
taataaaatg aggaaattgc atcgcattgt ctgagtaggt gtcattctat tctggggggt    6360
ggggtggggc aggacagcaa gggggaggat tgggaagaca atagcaggca tgctggggat    6420
gcggtgggct ctatggcttc tgaggcggaa agaaccagtg gcggtaatac ggttatccac    6480
agaatcaggg gataacgcag gaaagaacat gtgagcaaaa ggccagcaaa aggccaggaa    6540
ccgtaaaaag gccgcgttgc tggcgttttt ccataggctc cgcccccctg acgagcatca    6600
caaaaatcga cgctcaagtc agaggtggcg aaacccgaca ggactataaa gataccaggc    6660
gtttccccct agaagctccc tcgtgcgctc tcctgttccg accctgccgc ttaccggata    6720
cctgtccgcc tttctccctt cgggaagcgt ggcgctttct catagctcac gctgtaggta    6780
tctcagttcg gtgtaggtcg ttcgctccaa gctgggctgt gtgcacgaac cccccgttca    6840
gcccgaccgc tgcgccttat ccggtaacta tcgtcttgag tccaacccgg taagacacga    6900
cttatcgcca ctggcagcag ccactggtaa caggattagc agagcgaggt atgtaggcgg    6960
tgctacagag ttcttgaagt ggtggcctaa ctacggctac actagaagaa cagtatttgg    7020
tatctgcgct ctgctgaagc cagttacctt cggaaaaaga gttggtagct cttgatccgg    7080
caaacaaacc accgctggta gcggtggttt ttttgtttgc aagcagcaga ttacgcgcag    7140
aaaaaaagga tctcaagaag atcctttgat cttttctacg gggtctgacg ctcagtggaa    7200
cgaaaactca cgttaaggga ttttggtcat gacattaacc tataaaaata ggcgtatcac    7260
gaggcccttt cgtctcgcgc gtttcggtga tgacggtgaa aacctctgac acatgcagct    7320
cccggagacg gtcacagctt gtctgtaagc ggatgccggg agcagacaag cccgtcaggg    7380
cgcgtcagcg ggtgttggcg ggtgtcgggg ctggcttaac tatgcggcat cagagcagat    7440
tgtactgaga gtgcaccata tatgcggtgt gaaataccgc acagatgcgt aaggagaaaa    7500
taccgcatca ggcgccattc gccattcagg ctgcgcaact gttgggaagg gcgatcggtg    7560
cgggcctctt cgctattacg cca                                           7583
```

<210> SEQ ID NO 713
<211> LENGTH: 688
<212> TYPE: PRT
<213> ORGANISM: Artificial Sequence
<220> FEATURE:

```
<223> OTHER INFORMATION: FIX-Fc Chain polypeptide
<220> FEATURE:
<221> NAME/KEY: SIGNAL
<222> LOCATION: (1)..(46)
<220> FEATURE:
<221> NAME/KEY: MISC_FEATURE
<222> LOCATION: (462)..(688)
<223> OTHER INFORMATION: Fc Sequence

<400> SEQUENCE: 713
```

| Met | Gln | Arg | Val | Asn | Met | Ile | Met | Ala | Glu | Ser | Pro | Ser | Leu | Ile | Thr |
|---|---|---|---|---|---|---|---|---|---|---|---|---|---|---|---|
| 1 | | | | 5 | | | | | 10 | | | | | 15 | |

| Ile | Cys | Leu | Leu | Gly | Tyr | Leu | Leu | Ser | Ala | Glu | Cys | Thr | Val | Phe | Leu |
|---|---|---|---|---|---|---|---|---|---|---|---|---|---|---|---|
| | | | 20 | | | | | 25 | | | | | 30 | | |

| Asp | His | Glu | Asn | Ala | Asn | Lys | Ile | Leu | Asn | Arg | Pro | Lys | Arg | Tyr | Asn |
|---|---|---|---|---|---|---|---|---|---|---|---|---|---|---|---|
| | | 35 | | | | | 40 | | | | | 45 | | | |

| Ser | Gly | Lys | Leu | Glu | Glu | Phe | Val | Gln | Gly | Asn | Leu | Glu | Arg | Glu | Cys |
|---|---|---|---|---|---|---|---|---|---|---|---|---|---|---|---|
| | 50 | | | | | 55 | | | | | 60 | | | | |

| Met | Glu | Glu | Lys | Cys | Ser | Phe | Glu | Glu | Ala | Arg | Glu | Val | Phe | Glu | Asn |
|---|---|---|---|---|---|---|---|---|---|---|---|---|---|---|---|
| 65 | | | | | 70 | | | | | 75 | | | | | 80 |

| Thr | Glu | Arg | Thr | Thr | Glu | Phe | Trp | Lys | Gln | Tyr | Val | Asp | Gly | Asp | Gln |
|---|---|---|---|---|---|---|---|---|---|---|---|---|---|---|---|
| | | | | 85 | | | | | 90 | | | | | 95 | |

| Cys | Glu | Ser | Asn | Pro | Cys | Leu | Asn | Gly | Gly | Ser | Cys | Lys | Asp | Asp | Ile |
|---|---|---|---|---|---|---|---|---|---|---|---|---|---|---|---|
| | | | 100 | | | | | 105 | | | | | 110 | | |

| Asn | Ser | Tyr | Glu | Cys | Trp | Cys | Pro | Phe | Gly | Phe | Glu | Gly | Lys | Asn | Cys |
|---|---|---|---|---|---|---|---|---|---|---|---|---|---|---|---|
| | | 115 | | | | | 120 | | | | | 125 | | | |

| Glu | Leu | Asp | Val | Thr | Cys | Asn | Ile | Lys | Asn | Gly | Arg | Cys | Glu | Gln | Phe |
|---|---|---|---|---|---|---|---|---|---|---|---|---|---|---|---|
| | 130 | | | | | 135 | | | | | 140 | | | | |

| Cys | Lys | Asn | Ser | Ala | Asp | Asn | Lys | Val | Val | Cys | Ser | Cys | Thr | Glu | Gly |
|---|---|---|---|---|---|---|---|---|---|---|---|---|---|---|---|
| 145 | | | | | 150 | | | | | 155 | | | | | 160 |

| Tyr | Arg | Leu | Ala | Glu | Asn | Gln | Lys | Ser | Cys | Glu | Pro | Ala | Val | Pro | Phe |
|---|---|---|---|---|---|---|---|---|---|---|---|---|---|---|---|
| | | | | 165 | | | | | 170 | | | | | 175 | |

| Pro | Cys | Gly | Arg | Val | Ser | Val | Ser | Gln | Thr | Ser | Lys | Leu | Thr | Arg | Ala |
|---|---|---|---|---|---|---|---|---|---|---|---|---|---|---|---|
| | | | 180 | | | | | 185 | | | | | 190 | | |

| Glu | Thr | Val | Phe | Pro | Asp | Val | Asp | Tyr | Val | Asn | Ser | Thr | Glu | Ala | Glu |
|---|---|---|---|---|---|---|---|---|---|---|---|---|---|---|---|
| | | 195 | | | | | 200 | | | | | 205 | | | |

| Thr | Ile | Leu | Asp | Asn | Ile | Thr | Gln | Ser | Thr | Gln | Ser | Phe | Asn | Asp | Phe |
|---|---|---|---|---|---|---|---|---|---|---|---|---|---|---|---|
| | 210 | | | | | 215 | | | | | 220 | | | | |

| Thr | Arg | Val | Val | Gly | Gly | Glu | Asp | Ala | Lys | Pro | Gly | Gln | Phe | Pro | Trp |
|---|---|---|---|---|---|---|---|---|---|---|---|---|---|---|---|
| 225 | | | | | 230 | | | | | 235 | | | | | 240 |

| Gln | Val | Val | Leu | Asn | Gly | Lys | Val | Asp | Ala | Phe | Cys | Gly | Gly | Ser | Ile |
|---|---|---|---|---|---|---|---|---|---|---|---|---|---|---|---|
| | | | | 245 | | | | | 250 | | | | | 255 | |

| Val | Asn | Glu | Lys | Trp | Ile | Val | Thr | Ala | Ala | His | Cys | Val | Glu | Thr | Gly |
|---|---|---|---|---|---|---|---|---|---|---|---|---|---|---|---|
| | | | 260 | | | | | 265 | | | | | 270 | | |

| Val | Lys | Ile | Thr | Val | Val | Ala | Gly | Glu | His | Asn | Ile | Glu | Glu | Thr | Glu |
|---|---|---|---|---|---|---|---|---|---|---|---|---|---|---|---|
| | | 275 | | | | | 280 | | | | | 285 | | | |

| His | Thr | Glu | Gln | Lys | Arg | Asn | Val | Ile | Arg | Ile | Ile | Pro | His | His | Asn |
|---|---|---|---|---|---|---|---|---|---|---|---|---|---|---|---|
| | 290 | | | | | 295 | | | | | 300 | | | | |

| Tyr | Asn | Ala | Ala | Ile | Asn | Lys | Tyr | Asn | His | Asp | Ile | Ala | Leu | Leu | Glu |
|---|---|---|---|---|---|---|---|---|---|---|---|---|---|---|---|
| 305 | | | | | 310 | | | | | 315 | | | | | 320 |

| Leu | Asp | Glu | Pro | Leu | Val | Leu | Asn | Ser | Tyr | Val | Thr | Pro | Ile | Cys | Ile |
|---|---|---|---|---|---|---|---|---|---|---|---|---|---|---|---|
| | | | | 325 | | | | | 330 | | | | | 335 | |

| Ala | Asp | Lys | Glu | Tyr | Thr | Asn | Ile | Phe | Leu | Lys | Phe | Gly | Ser | Gly | Tyr |
|---|---|---|---|---|---|---|---|---|---|---|---|---|---|---|---|
| | | | 340 | | | | | 345 | | | | | 350 | | |

| Val | Ser | Gly | Trp | Gly | Arg | Val | Phe | His | Lys | Gly | Arg | Ser | Ala | Leu | Val |
|---|---|---|---|---|---|---|---|---|---|---|---|---|---|---|---|
| | | 355 | | | | | 360 | | | | | 365 | | | |

-continued

```
Leu Gln Tyr Leu Arg Val Pro Leu Val Asp Arg Ala Thr Cys Leu Arg
        370                 375                 380

Ser Thr Lys Phe Thr Ile Tyr Asn Asn Met Phe Cys Ala Gly Phe His
385                 390                 395                 400

Glu Gly Gly Arg Asp Ser Cys Gln Gly Asp Ser Gly Gly Pro His Val
                405                 410                 415

Thr Glu Val Glu Gly Thr Ser Phe Leu Thr Gly Ile Ile Ser Trp Gly
            420                 425                 430

Glu Glu Cys Ala Met Lys Gly Lys Tyr Gly Ile Tyr Thr Lys Val Ser
        435                 440                 445

Arg Tyr Val Asn Trp Ile Lys Glu Lys Thr Lys Leu Thr Asp Lys Thr
450                 455                 460

His Thr Cys Pro Pro Cys Pro Ala Pro Glu Leu Leu Gly Gly Pro Ser
465                 470                 475                 480

Val Phe Leu Phe Pro Pro Lys Pro Lys Asp Thr Leu Met Ile Ser Arg
                485                 490                 495

Thr Pro Glu Val Thr Cys Val Val Val Asp Val Ser His Glu Asp Pro
            500                 505                 510

Glu Val Lys Phe Asn Trp Tyr Val Asp Gly Val Glu Val His Asn Ala
        515                 520                 525

Lys Thr Lys Pro Arg Glu Glu Gln Tyr Asn Ser Thr Tyr Arg Val Val
530                 535                 540

Ser Val Leu Thr Val Leu His Gln Asp Trp Leu Asn Gly Lys Glu Tyr
545                 550                 555                 560

Lys Cys Lys Val Ser Asn Lys Ala Leu Pro Ala Pro Ile Glu Lys Thr
                565                 570                 575

Ile Ser Lys Ala Lys Gly Gln Pro Arg Glu Pro Gln Val Tyr Thr Leu
            580                 585                 590

Pro Pro Ser Arg Asp Glu Leu Thr Lys Asn Gln Val Ser Leu Thr Cys
        595                 600                 605

Leu Val Lys Gly Phe Tyr Pro Ser Asp Ile Ala Val Glu Trp Glu Ser
610                 615                 620

Asn Gly Gln Pro Glu Asn Asn Tyr Lys Thr Thr Pro Pro Val Leu Asp
625                 630                 635                 640

Ser Asp Gly Ser Phe Phe Leu Tyr Ser Lys Leu Thr Val Asp Lys Ser
                645                 650                 655

Arg Trp Gln Gln Gly Asn Val Phe Ser Cys Ser Val Met His Glu Ala
            660                 665                 670

Leu His Asn His Tyr Thr Gln Lys Ser Leu Ser Leu Ser Pro Gly Lys
        675                 680                 685

<210> SEQ ID NO 714
<211> LENGTH: 2082
<212> TYPE: DNA
<213> ORGANISM: Artificial Sequence
<220> FEATURE:
<223> OTHER INFORMATION: Full Length FVII-Fc DNA Sequence
<220> FEATURE:
<221> NAME/KEY: sig_peptide
<222> LOCATION: (1)..(180)
<223> OTHER INFORMATION: FVII signal
<220> FEATURE:
<221> NAME/KEY: misc_feature
<222> LOCATION: (1402)..(2082)
<223> OTHER INFORMATION: Fc region

<400> SEQUENCE: 714
```

| | |
|---|---|
| atggtctccc aggccctcag gctcctctgc cttctgcttg ggcttcaggg ctgcctggct | 60 |
| gcaggcgggg tcgctaaggc ctcaggagga gaaacacggg acatgccgtg aagccgggg | 120 |
| cctcacagag tcttcgtaac ccaggaggaa gcccacggcg tcctgcaccg cgccggcgc | 180 |
| gccaacgcgt tcctggagga gctgcggccg ggctccctgg agagggagtg caaggaggag | 240 |
| cagtgctcct tcgaggaggc ccgggagatc ttcaaggacg cggagaggac gaagctgttc | 300 |
| tggatttctt acagtgatgg ggaccagtgt gcctcaagtc catgccagaa tgggggctcc | 360 |
| tgcaaggacc agctccagtc ctatatctgc ttctgcctcc ctgccttcga gggccggaac | 420 |
| tgtgagacgc acaaggatga ccagctgatc tgtgtgaacg agaacggcgg ctgtgagcag | 480 |
| tactgcagtg accacacggg caccaagcgc tcctgtcggt gccacgaggg gtactctctg | 540 |
| ctggcagacg gggtgtcctg cacacccaca gttgaatatc catgtggaaa aataccattt | 600 |
| ctagaaaaaa gaaatgccag caaaccccaa ggccgaattg tggggggcaa ggtgtgcccc | 660 |
| aaaggggagt gtccatggca ggtcctgttg ttggtgaatg gagctcagtt gtgtgggggg | 720 |
| accctgatca acaccatctg ggtggtctcc gcggcccact gtttcgacaa aatcaagaac | 780 |
| tggaggaacc tgatcgcggt gctgggcgag cacgacctca gcgagcacga cggggatgag | 840 |
| cagagccggc gggtggcgca ggtcatcatc cccagcacgt acgtcccggg caccaccaac | 900 |
| cacgacatcg cgctgctccg cctgcaccag cccgtggtcc tcactgacca tgtggtgccc | 960 |
| ctctgcctgc ccgaacggac gttctctgag aggacgctgg ccttcgtgcg cttctcattg | 1020 |
| gtcagcggct ggggccagct gctggaccgt ggcgccacgg ccctggagct catggtcctc | 1080 |
| aacgtgcccc ggctgatgac ccaggactgc ctgcagcagt cacggaaggt gggagactcc | 1140 |
| ccaaatatca cggagtacat gttctgtgcc ggctactcgg atggcagcaa ggactcctgc | 1200 |
| aaggggdaca gtgaggccc acatgccacc cactaccggg gcacgtggta cctgacgggc | 1260 |
| atcgtcagct ggggccaggg ctgcgcaacc gtgggccact ttggggtgta caccagggtc | 1320 |
| tcccagtaca tcgagtggct gcaaaagctc atgcgctcag agccacgccc aggagtcctc | 1380 |
| ctgcgagccc catttcccta ggacaaaact cacacatgcc caccgtgccc agctccagaa | 1440 |
| ctcctgggcg gaccgtcagt cttcctcttc cccccaaaac ccaaggacac cctcatgatc | 1500 |
| tcccggaccc ctgaggtcac atgcgtggtg gtggacgtga gccacgaaga ccctgaggtc | 1560 |
| aagttcaact ggtacgtgga cggcgtggag gtgcataatg ccaagacaaa gccgcgggag | 1620 |
| gagcagtaca acagcacgta ccgtgtggtc agcgtcctca ccgtcctgca ccaggactgg | 1680 |
| ctgaatggca aggagtacaa gtgcaaggtc tccaacaaag ccctcccagc ccccatcgag | 1740 |
| aaaaccatct ccaaagccaa agggcagccc cgagaaccac aggtgtacac cctgcccca | 1800 |
| tcccgggatg agctgaccaa gaaccaggtc agcctgacct gcctggtcaa aggcttctat | 1860 |
| cccagcgaca tcgccgtgga gtgggagagc aatgggcagc cggagaacaa ctacaagacc | 1920 |
| acgcctcccg tgttggactc cgacggctcc ttcttcctct acagcaagct caccgtggac | 1980 |
| aagagcaggt ggcagcaggg gaacgtcttc tcatgctccg tgatgcatga ggctctgcac | 2040 |
| aaccactaca cgcagaagag cctctccctg tctccgggta aa | 2082 |

<210> SEQ ID NO 715
<211> LENGTH: 693
<212> TYPE: PRT
<213> ORGANISM: Artificial Sequence
<220> FEATURE:
<223> OTHER INFORMATION: Full Length FVII-Fc polypeptide
<220> FEATURE:
<221> NAME/KEY: SIGNAL

```
<222> LOCATION: (1)..(60)
<220> FEATURE:
<221> NAME/KEY: MISC_FEATURE
<222> LOCATION: (467)..(693)
<223> OTHER INFORMATION: Fc Sequence

<400> SEQUENCE: 715
```

| | | | | | | | | | | | | | | |
|---|---|---|---|---|---|---|---|---|---|---|---|---|---|---|
| Met | Val | Ser | Gln | Ala | Leu | Arg | Leu | Leu | Cys | Leu | Leu | Leu | Gly | Leu | Gln |
| 1 | | | | 5 | | | | | 10 | | | | | 15 | |
| Gly | Cys | Leu | Ala | Ala | Gly | Gly | Val | Ala | Lys | Ala | Ser | Gly | Gly | Glu | Thr |
| | | | 20 | | | | | 25 | | | | | 30 | | |
| Arg | Asp | Met | Pro | Trp | Lys | Pro | Gly | Pro | His | Arg | Val | Phe | Val | Thr | Gln |
| | | 35 | | | | | 40 | | | | | 45 | | | |
| Glu | Glu | Ala | His | Gly | Val | Leu | His | Arg | Arg | Arg | Ala | Asn | Ala | Phe |
| | 50 | | | | | 55 | | | | | 60 | | | |
| Leu | Glu | Glu | Leu | Arg | Pro | Gly | Ser | Leu | Glu | Arg | Glu | Cys | Lys | Glu | Glu |
| 65 | | | | | 70 | | | | | 75 | | | | | 80 |
| Gln | Cys | Ser | Phe | Glu | Glu | Ala | Arg | Glu | Ile | Phe | Lys | Asp | Ala | Glu | Arg |
| | | | | 85 | | | | | 90 | | | | | 95 | |
| Thr | Lys | Leu | Phe | Trp | Ile | Ser | Tyr | Ser | Asp | Gly | Asp | Gln | Cys | Ala | Ser |
| | | | 100 | | | | | 105 | | | | | 110 | | |
| Ser | Pro | Cys | Gln | Asn | Gly | Gly | Ser | Cys | Lys | Asp | Gln | Leu | Gln | Ser | Tyr |
| | | 115 | | | | | 120 | | | | | 125 | | | |
| Ile | Cys | Phe | Cys | Leu | Pro | Ala | Phe | Glu | Gly | Arg | Asn | Cys | Glu | Thr | His |
| | 130 | | | | | 135 | | | | | 140 | | | | |
| Lys | Asp | Asp | Gln | Leu | Ile | Cys | Val | Asn | Glu | Asn | Gly | Gly | Cys | Glu | Gln |
| 145 | | | | | 150 | | | | | 155 | | | | | 160 |
| Tyr | Cys | Ser | Asp | His | Thr | Gly | Thr | Lys | Arg | Ser | Cys | Arg | Cys | His | Glu |
| | | | | 165 | | | | | 170 | | | | | 175 | |
| Gly | Tyr | Ser | Leu | Leu | Ala | Asp | Gly | Val | Ser | Cys | Thr | Pro | Thr | Val | Glu |
| | | | 180 | | | | | 185 | | | | | 190 | | |
| Tyr | Pro | Cys | Gly | Lys | Ile | Pro | Ile | Leu | Glu | Lys | Arg | Asn | Ala | Ser | Lys |
| | | 195 | | | | | 200 | | | | | 205 | | | |
| Pro | Gln | Gly | Arg | Ile | Val | Gly | Gly | Lys | Val | Cys | Pro | Lys | Gly | Glu | Cys |
| | 210 | | | | | 215 | | | | | 220 | | | | |
| Pro | Trp | Gln | Val | Leu | Leu | Leu | Val | Asn | Gly | Ala | Gln | Leu | Cys | Gly | Gly |
| 225 | | | | | 230 | | | | | 235 | | | | | 240 |
| Thr | Leu | Ile | Asn | Thr | Ile | Trp | Val | Val | Ser | Ala | Ala | His | Cys | Phe | Asp |
| | | | | 245 | | | | | 250 | | | | | 255 | |
| Lys | Ile | Lys | Asn | Trp | Arg | Asn | Leu | Ile | Ala | Val | Leu | Gly | Glu | His | Asp |
| | | | 260 | | | | | 265 | | | | | 270 | | |
| Leu | Ser | Glu | His | Asp | Gly | Asp | Glu | Gln | Ser | Arg | Arg | Val | Ala | Gln | Val |
| | | 275 | | | | | 280 | | | | | 285 | | | |
| Ile | Ile | Pro | Ser | Thr | Tyr | Val | Pro | Gly | Thr | Thr | Asn | His | Asp | Ile | Ala |
| | 290 | | | | | 295 | | | | | 300 | | | | |
| Leu | Leu | Arg | Leu | His | Gln | Pro | Val | Val | Leu | Thr | Asp | His | Val | Val | Pro |
| 305 | | | | | 310 | | | | | 315 | | | | | 320 |
| Leu | Cys | Leu | Pro | Glu | Arg | Thr | Phe | Ser | Glu | Arg | Thr | Leu | Ala | Phe | Val |
| | | | | 325 | | | | | 330 | | | | | 335 | |
| Arg | Phe | Ser | Leu | Val | Ser | Gly | Trp | Gly | Gln | Leu | Leu | Asp | Arg | Gly | Ala |
| | | | 340 | | | | | 345 | | | | | 350 | | |
| Thr | Ala | Leu | Glu | Leu | Met | Val | Leu | Asn | Val | Pro | Arg | Leu | Met | Thr | Gln |
| | | 355 | | | | | 360 | | | | | 365 | | | |
| Asp | Cys | Leu | Gln | Gln | Ser | Arg | Lys | Val | Gly | Asp | Ser | Pro | Asn | Ile | Thr |
| | 370 | | | | | 375 | | | | | 380 | | | | |

```
Glu Tyr Met Phe Cys Ala Gly Tyr Ser Asp Gly Ser Lys Asp Ser Cys
385                 390                 395                 400

Lys Gly Asp Ser Gly Pro His Ala Thr His Tyr Arg Gly Thr Trp
            405                 410                 415

Tyr Leu Thr Gly Ile Val Ser Trp Gly Gln Gly Cys Ala Thr Val Gly
            420                 425                 430

His Phe Gly Val Tyr Thr Arg Val Ser Gln Tyr Ile Glu Trp Leu Gln
            435                 440                 445

Lys Leu Met Arg Ser Glu Pro Arg Pro Gly Val Leu Leu Arg Ala Pro
            450                 455                 460

Phe Pro Asp Lys Thr His Thr Cys Pro Pro Cys Pro Ala Pro Glu Leu
465                 470                 475                 480

Leu Gly Gly Pro Ser Val Phe Leu Phe Pro Pro Lys Pro Lys Asp Thr
            485                 490                 495

Leu Met Ile Ser Arg Thr Pro Glu Val Thr Cys Val Val Val Asp Val
            500                 505                 510

Ser His Glu Asp Pro Glu Val Lys Phe Asn Trp Tyr Val Asp Gly Val
            515                 520                 525

Glu Val His Asn Ala Lys Thr Lys Pro Arg Glu Glu Gln Tyr Asn Ser
            530                 535                 540

Thr Tyr Arg Val Val Ser Val Leu Thr Val Leu His Gln Asp Trp Leu
545                 550                 555                 560

Asn Gly Lys Glu Tyr Lys Cys Lys Val Ser Asn Lys Ala Leu Pro Ala
            565                 570                 575

Pro Ile Glu Lys Thr Ile Ser Lys Ala Lys Gly Gln Pro Arg Glu Pro
            580                 585                 590

Gln Val Tyr Thr Leu Pro Pro Ser Arg Asp Glu Leu Thr Lys Asn Gln
            595                 600                 605

Val Ser Leu Thr Cys Leu Val Lys Gly Phe Tyr Pro Ser Asp Ile Ala
            610                 615                 620

Val Glu Trp Glu Ser Asn Gly Gln Pro Glu Asn Asn Tyr Lys Thr Thr
625                 630                 635                 640

Pro Pro Val Leu Asp Ser Asp Gly Ser Phe Phe Leu Tyr Ser Lys Leu
            645                 650                 655

Thr Val Asp Lys Ser Arg Trp Gln Gln Gly Asn Val Phe Ser Cys Ser
            660                 665                 670

Val Met His Glu Ala Leu His Asn His Tyr Thr Gln Lys Ser Leu Ser
            675                 680                 685

Leu Ser Pro Gly Lys
            690

<210> SEQ ID NO 716

<400> SEQUENCE: 716

000

<210> SEQ ID NO 717
<211> LENGTH: 45
<212> TYPE: PRT
<213> ORGANISM: Artificial Sequence
<220> FEATURE:
<223> OTHER INFORMATION: Compound 9

<400> SEQUENCE: 717

Gly Trp Lys Pro Phe Leu Trp Asp Pro Arg Val Leu Leu Ser Ser Gly
```

```
 1               5                   10                  15
Trp Tyr Gly Arg Gly Gly Gly Gly Trp Lys Pro Phe Leu Trp Asp
        20                  25                  30
Pro Arg Val Leu Leu Ser Ser Gly Trp Tyr Gly Arg Gly
        35                  40                  45
```

<210> SEQ ID NO 718
<211> LENGTH: 105
<212> TYPE: DNA
<213> ORGANISM: Artificial Sequence
<220> FEATURE:
<223> OTHER INFORMATION: phage
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (74)..(75)
<223> OTHER INFORMATION: n is a, c, g, or t
<220> FEATURE:
<221> NAME/KEY: misc_feature
<222> LOCATION: (77)..(78)
<223> OTHER INFORMATION: n is a, c, g, or t
<220> FEATURE:
<221> NAME/KEY: misc_feature
<222> LOCATION: (80)..(81)
<223> OTHER INFORMATION: n is a, c, g, or t
<220> FEATURE:
<221> NAME/KEY: misc_feature
<222> LOCATION: (83)..(84)
<223> OTHER INFORMATION: n is a, c, g, or t
<220> FEATURE:
<221> NAME/KEY: misc_feature
<222> LOCATION: (86)..(87)
<223> OTHER INFORMATION: n is a, c, g, or t

<400> SEQUENCE: 718
atgggcccag ccggccatgg cannbnnbnn bnnbnnbaag ctgacgtgtc tggccagtta      60
ttgttggctg ttcnnbnnbn nbnnbnnbgc ggccgcaggt agcta                    105

<210> SEQ ID NO 719
<211> LENGTH: 19
<212> TYPE: DNA
<213> ORGANISM: Artificial Sequence
<220> FEATURE:
<223> OTHER INFORMATION: oligo A

<400> SEQUENCE: 719
atgggcccag ccggccatg                                                  19

<210> SEQ ID NO 720
<211> LENGTH: 17
<212> TYPE: DNA
<213> ORGANISM: Artificial Sequence
<220> FEATURE:
<223> OTHER INFORMATION: oligo B

<400> SEQUENCE: 720
tagctacctg cggccgc                                                    17

<210> SEQ ID NO 721

<400> SEQUENCE: 721

000

<210> SEQ ID NO 722

<400> SEQUENCE: 722

000

<210> SEQ ID NO 723

<400> SEQUENCE: 723

000

<210> SEQ ID NO 724

<400> SEQUENCE: 724

000

<210> SEQ ID NO 725

<400> SEQUENCE: 725

000

<210> SEQ ID NO 726

<400> SEQUENCE: 726

000

<210> SEQ ID NO 727

<400> SEQUENCE: 727

000

<210> SEQ ID NO 728
<211> LENGTH: 30
<212> TYPE: PRT
<213> ORGANISM: Artificial Sequence
<220> FEATURE:
<223> OTHER INFORMATION: thrombin cleavable linker
<220> FEATURE:
<221> NAME/KEY: misc_feature
<222> LOCATION: (1)..(1)
<223> OTHER INFORMATION: Acm
<220> FEATURE:
<221> NAME/KEY: MOD_RES
<222> LOCATION: (6)..(6)
<223> OTHER INFORMATION: Xaa is Dphe
<220> FEATURE:
<221> NAME/KEY: MOD_RES
<222> LOCATION: (7)..(7)
<223> OTHER INFORMATION: Xaa is Pip
<220> FEATURE:
<221> NAME/KEY: misc_feature
<222> LOCATION: (8)..(9)
<223> OTHER INFORMATION: PABC

```
<220> FEATURE:
<221> NAME/KEY: misc_feature
<222> LOCATION: (9)..(9)
<223> OTHER INFORMATION: D-AMINO ACID
<220> FEATURE:
<221> NAME/KEY: misc_feature
<222> LOCATION: (30)..(30)
<223> OTHER INFORMATION: AMIDATION

<400> SEQUENCE: 728

Cys Gly Gly Gly Xaa Xaa Arg Arg Arg Ala Pro Gly Lys Leu Thr
1               5                   10                  15

Cys Leu Ala Ser Tyr Cys Trp Leu Phe Trp Thr Gly Ile Ala
            20                  25                  30

<210> SEQ ID NO 729

<400> SEQUENCE: 729

000

<210> SEQ ID NO 730

<400> SEQUENCE: 730

000

<210> SEQ ID NO 731
<211> LENGTH: 4
<212> TYPE: PRT
<213> ORGANISM: Artificial Sequence
<220> FEATURE:
<223> OTHER INFORMATION: cleavage site

<400> SEQUENCE: 731

Arg Arg Arg Arg
1

<210> SEQ ID NO 732
<211> LENGTH: 6
<212> TYPE: PRT
<213> ORGANISM: Artificial Sequence
<220> FEATURE:
<223> OTHER INFORMATION: cleavage site

<400> SEQUENCE: 732

Arg Lys Arg Arg Lys Arg
1               5

<210> SEQ ID NO 733

<400> SEQUENCE: 733

000

<210> SEQ ID NO 734

<400> SEQUENCE: 734

000

<210> SEQ ID NO 735

<400> SEQUENCE: 735

000
```

<210> SEQ ID NO 736

<400> SEQUENCE: 736

000

<210> SEQ ID NO 737

<400> SEQUENCE: 737

000

<210> SEQ ID NO 738

<400> SEQUENCE: 738

000

<210> SEQ ID NO 739

<400> SEQUENCE: 739

000

<210> SEQ ID NO 740

<400> SEQUENCE: 740

000

<210> SEQ ID NO 741

<400> SEQUENCE: 741

000

<210> SEQ ID NO 742

<400> SEQUENCE: 742

000

<210> SEQ ID NO 743

<400> SEQUENCE: 743

000

<210> SEQ ID NO 744

<400> SEQUENCE: 744

000

<210> SEQ ID NO 745

<400> SEQUENCE: 745

000

<210> SEQ ID NO 746

<400> SEQUENCE: 746

000

<210> SEQ ID NO 747

```
<400> SEQUENCE: 747
000

<210> SEQ ID NO 748
<400> SEQUENCE: 748
000

<210> SEQ ID NO 749
<400> SEQUENCE: 749
000

<210> SEQ ID NO 750
<400> SEQUENCE: 750
000

<210> SEQ ID NO 751
<400> SEQUENCE: 751
000

<210> SEQ ID NO 752
<400> SEQUENCE: 752
000

<210> SEQ ID NO 753
<400> SEQUENCE: 753
000

<210> SEQ ID NO 754
<400> SEQUENCE: 754
000

<210> SEQ ID NO 755
<400> SEQUENCE: 755
000

<210> SEQ ID NO 756
<400> SEQUENCE: 756
000

<210> SEQ ID NO 757
<400> SEQUENCE: 757
000

<210> SEQ ID NO 758
<400> SEQUENCE: 758
```

000

<210> SEQ ID NO 759

<400> SEQUENCE: 759

000

<210> SEQ ID NO 760
<211> LENGTH: 6
<212> TYPE: PRT
<213> ORGANISM: Artificial Sequence
<220> FEATURE:
<223> OTHER INFORMATION: synthetic

<400> SEQUENCE: 760

Cys Gly Ala Ser Tyr Cys
1               5

<210> SEQ ID NO 761
<211> LENGTH: 6
<212> TYPE: PRT
<213> ORGANISM: Artificial Sequence
<220> FEATURE:
<223> OTHER INFORMATION: synthetic

<400> SEQUENCE: 761

Cys Leu Gly Ser Tyr Cys
1               5

<210> SEQ ID NO 762
<211> LENGTH: 6
<212> TYPE: PRT
<213> ORGANISM: Artificial Sequence
<220> FEATURE:
<223> OTHER INFORMATION: synthetic

<400> SEQUENCE: 762

Cys Leu Ala Ser Gly Cys
1               5

<210> SEQ ID NO 763
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 763

Cys Gly Ala Ser Tyr Cys
1               5

<210> SEQ ID NO 764
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 764

Cys Leu Gly Ser Tyr Cys
1               5

<210> SEQ ID NO 765
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 765

Cys Leu Ala Ser Gly Cys
1               5

<210> SEQ ID NO 766
<211> LENGTH: 6
<212> TYPE: PRT
<213> ORGANISM: Artificial Sequence
<220> FEATURE:
<223> OTHER INFORMATION: synthetic

<400> SEQUENCE: 766

Cys Ala Ala Ser Tyr Cys
1               5

<210> SEQ ID NO 767
<211> LENGTH: 6
<212> TYPE: PRT
<213> ORGANISM: Artificial Sequence
<220> FEATURE:
<223> OTHER INFORMATION: synthetic

<400> SEQUENCE: 767

Cys Leu Ala Ser Ala Cys
1               5

<210> SEQ ID NO 768
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 768

Cys Ala Ala Ser Tyr Cys
1               5

<210> SEQ ID NO 769
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 769

Cys Leu Ala Ser Ala Cys
1               5

<210> SEQ ID NO 770
<211> LENGTH: 6
<212> TYPE: PRT
<213> ORGANISM: Artificial Sequence
<220> FEATURE:
<223> OTHER INFORMATION: synthetic

<400> SEQUENCE: 770

Cys Val Ala Ser Tyr Cys
1               5

<210> SEQ ID NO 771
<211> LENGTH: 6
<212> TYPE: PRT
<213> ORGANISM: Artificial Sequence
<220> FEATURE:
<223> OTHER INFORMATION: synthetic

<400> SEQUENCE: 771

Cys Leu Val Ser Tyr Cys
1               5

<210> SEQ ID NO 772
<211> LENGTH: 6
<212> TYPE: PRT
<213> ORGANISM: Artificial Sequence
<220> FEATURE:
<223> OTHER INFORMATION: synthetic

<400> SEQUENCE: 772

Cys Leu Ala Ser Val Cys
1               5

<210> SEQ ID NO 773
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 773

Cys Val Ala Ser Tyr Cys
1               5

<210> SEQ ID NO 774
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 774

Cys Leu Val Ser Tyr Cys
1               5

<210> SEQ ID NO 775
<211> LENGTH: 6
<212> TYPE: PRT
<213> ORGANISM: Artificial Sequence

```
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 775

Cys Leu Ala Ser Val Cys
1               5

<210> SEQ ID NO 776
<211> LENGTH: 6
<212> TYPE: PRT
<213> ORGANISM: Artificial Sequence
<220> FEATURE:
<223> OTHER INFORMATION: synthetic

<400> SEQUENCE: 776

Cys Ile Ala Ser Tyr Cys
1               5

<210> SEQ ID NO 777
<211> LENGTH: 6
<212> TYPE: PRT
<213> ORGANISM: Artificial Sequence
<220> FEATURE:
<223> OTHER INFORMATION: synthetic

<400> SEQUENCE: 777

Cys Leu Ile Ser Tyr Cys
1               5

<210> SEQ ID NO 778
<211> LENGTH: 6
<212> TYPE: PRT
<213> ORGANISM: Artificial Sequence
<220> FEATURE:
<223> OTHER INFORMATION: synthetic

<400> SEQUENCE: 778

Cys Leu Ala Ser Ile Cys
1               5

<210> SEQ ID NO 779
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 779

Cys Ile Ala Ser Tyr Cys
1               5

<210> SEQ ID NO 780
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID
```

```
<400> SEQUENCE: 780

Cys Leu Ile Ser Tyr Cys
1               5

<210> SEQ ID NO 781
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 781

Cys Leu Ala Ser Ile Cys
1               5

<210> SEQ ID NO 782
<211> LENGTH: 6
<212> TYPE: PRT
<213> ORGANISM: Artificial Sequence
<220> FEATURE:
<223> OTHER INFORMATION: synthetic

<400> SEQUENCE: 782

Cys Leu Ala Ser Tyr Cys
1               5

<210> SEQ ID NO 783
<211> LENGTH: 6
<212> TYPE: PRT
<213> ORGANISM: Artificial Sequence
<220> FEATURE:
<223> OTHER INFORMATION: synthetic

<400> SEQUENCE: 783

Cys Leu Leu Ser Tyr Cys
1               5

<210> SEQ ID NO 784
<211> LENGTH: 6
<212> TYPE: PRT
<213> ORGANISM: Artificial Sequence
<220> FEATURE:
<223> OTHER INFORMATION: synthetic

<400> SEQUENCE: 784

Cys Leu Ala Ser Leu Cys
1               5

<210> SEQ ID NO 785
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 785

Cys Leu Ala Ser Tyr Cys
1               5
```

```
<210> SEQ ID NO 786
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 786

Cys Leu Leu Ser Tyr Cys
1               5

<210> SEQ ID NO 787
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 787

Cys Leu Ala Ser Leu Cys
1               5

<210> SEQ ID NO 788
<211> LENGTH: 5
<212> TYPE: PRT
<213> ORGANISM: Artificial Sequence
<220> FEATURE:
<223> OTHER INFORMATION: synthetic

<400> SEQUENCE: 788

Phe Ala Ser Tyr Cys
1               5

<210> SEQ ID NO 789
<211> LENGTH: 6
<212> TYPE: PRT
<213> ORGANISM: Artificial Sequence
<220> FEATURE:
<223> OTHER INFORMATION: synthetic

<400> SEQUENCE: 789

Cys Leu Phe Ser Tyr Cys
1               5

<210> SEQ ID NO 790
<211> LENGTH: 6
<212> TYPE: PRT
<213> ORGANISM: Artificial Sequence
<220> FEATURE:
<223> OTHER INFORMATION: synthetic

<400> SEQUENCE: 790

Cys Leu Ala Ser Phe Cys
1               5

<210> SEQ ID NO 791
<211> LENGTH: 6
<212> TYPE: PRT
<213> ORGANISM: Artificial Sequence
<220> FEATURE:
```

<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 791

Cys Phe Ala Ser Tyr Cys
1               5

<210> SEQ ID NO 792
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 792

Cys Leu Phe Ser Tyr Cys
1               5

<210> SEQ ID NO 793
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 793

Cys Leu Ala Ser Phe Cys
1               5

<210> SEQ ID NO 794
<211> LENGTH: 6
<212> TYPE: PRT
<213> ORGANISM: Artificial Sequence
<220> FEATURE:
<223> OTHER INFORMATION: synthetic

<400> SEQUENCE: 794

Cys Trp Ala Ser Tyr Cys
1               5

<210> SEQ ID NO 795
<211> LENGTH: 6
<212> TYPE: PRT
<213> ORGANISM: Artificial Sequence
<220> FEATURE:
<223> OTHER INFORMATION: synthetic

<400> SEQUENCE: 795

Cys Leu Trp Ser Tyr Cys
1               5

<210> SEQ ID NO 796
<211> LENGTH: 6
<212> TYPE: PRT
<213> ORGANISM: Artificial Sequence
<220> FEATURE:
<223> OTHER INFORMATION: synthetic

```
<400> SEQUENCE: 796

Cys Leu Ala Ser Trp Cys
1               5

<210> SEQ ID NO 797
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 797

Cys Trp Ala Ser Tyr Cys
1               5

<210> SEQ ID NO 798
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 798

Cys Leu Trp Ser Tyr Cys
1               5

<210> SEQ ID NO 799
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 799

Cys Leu Ala Ser Trp Cys
1               5

<210> SEQ ID NO 800
<211> LENGTH: 6
<212> TYPE: PRT
<213> ORGANISM: Artificial Sequence
<220> FEATURE:
<223> OTHER INFORMATION: synthetic

<400> SEQUENCE: 800

Cys Tyr Ala Ser Tyr Cys
1               5

<210> SEQ ID NO 801
<211> LENGTH: 6
<212> TYPE: PRT
<213> ORGANISM: Artificial Sequence
<220> FEATURE:
<223> OTHER INFORMATION: synthetic

<400> SEQUENCE: 801
```

Cys Leu Tyr Ser Tyr Cys
1               5

<210> SEQ ID NO 802
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 802

Cys Tyr Ala Ser Tyr Cys
1               5

<210> SEQ ID NO 803
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 803

Cys Leu Tyr Ser Tyr Cys
1               5

<210> SEQ ID NO 804
<211> LENGTH: 6
<212> TYPE: PRT
<213> ORGANISM: Artificial Sequence
<220> FEATURE:
<223> OTHER INFORMATION: synthetic

<400> SEQUENCE: 804

Cys Gln Ala Ser Tyr Cys
1               5

<210> SEQ ID NO 805
<211> LENGTH: 6
<212> TYPE: PRT
<213> ORGANISM: Artificial Sequence
<220> FEATURE:
<223> OTHER INFORMATION: synthetic

<400> SEQUENCE: 805

Cys Leu Gln Ser Tyr Cys
1               5

<210> SEQ ID NO 806
<211> LENGTH: 6
<212> TYPE: PRT
<213> ORGANISM: Artificial Sequence
<220> FEATURE:
<223> OTHER INFORMATION: synthetic

<400> SEQUENCE: 806

Cys Leu Ala Ser Gln Cys
1               5

<210> SEQ ID NO 807
<211> LENGTH: 6

```
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 807

Cys Gln Ala Ser Tyr Cys
1               5

<210> SEQ ID NO 808
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 808

Cys Leu Gln Ser Tyr Cys
1               5

<210> SEQ ID NO 809
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-AMINO ACID

<400> SEQUENCE: 809

Cys Leu Ala Ser Gln Cys
1               5

<210> SEQ ID NO 810
<211> LENGTH: 6
<212> TYPE: PRT
<213> ORGANISM: Artificial Sequence
<220> FEATURE:
<223> OTHER INFORMATION: synthetic

<400> SEQUENCE: 810

Cys Leu Ala Ser Ser Cys
1               5

<210> SEQ ID NO 811
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (4)..(4)
<223> OTHER INFORMATION: D-AMINO ACID

<400> SEQUENCE: 811

Cys Leu Ala Ser Tyr Cys
1               5
```

```
<210> SEQ ID NO 812
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (5)..(5)
<223> OTHER INFORMATION: D-AMINO ACID

<400> SEQUENCE: 812

Cys Leu Ala Ser Tyr Cys
1               5

<210> SEQ ID NO 813

<400> SEQUENCE: 813

000

<210> SEQ ID NO 814

<400> SEQUENCE: 814

000

<210> SEQ ID NO 815

<400> SEQUENCE: 815

000

<210> SEQ ID NO 816

<400> SEQUENCE: 816

000

<210> SEQ ID NO 817

<400> SEQUENCE: 817

000

<210> SEQ ID NO 818

<400> SEQUENCE: 818

000

<210> SEQ ID NO 819

<400> SEQUENCE: 819

000

<210> SEQ ID NO 820

<400> SEQUENCE: 820

000

<210> SEQ ID NO 821

<400> SEQUENCE: 821

000
```

<210> SEQ ID NO 822

<400> SEQUENCE: 822

000

<210> SEQ ID NO 823

<400> SEQUENCE: 823

000

<210> SEQ ID NO 824

<400> SEQUENCE: 824

000

<210> SEQ ID NO 825

<400> SEQUENCE: 825

000

<210> SEQ ID NO 826

<400> SEQUENCE: 826

000

<210> SEQ ID NO 827

<400> SEQUENCE: 827

000

<210> SEQ ID NO 828

<400> SEQUENCE: 828

000

<210> SEQ ID NO 829

<400> SEQUENCE: 829

000

<210> SEQ ID NO 830
<211> LENGTH: 3117
<212> TYPE: DNA
<213> ORGANISM: Artificial Sequence
<220> FEATURE:
<223> OTHER INFORMATION: FVII-171

<400> SEQUENCE: 830

| | | | | | |
|---|---|---|---|---|---|
| atggtctccc | aggccctcag | gctcctctgc | cttctgcttg | ggcttcaggg | ctgcctggct | 60 |
| gcagtcttcg | taacccagga | ggaagcccac | ggcgtcctgc | accggcgccg | gcgcgccaac | 120 |
| gcgttcctgg | aggagctgcg | gccgggctcc | ctggagaggg | agtgcaagga | ggagcagtgc | 180 |
| tccttcgagg | aggcccggga | gatcttcaag | gacgcggaga | ggacgaagct | gttctggatt | 240 |
| tcttacagtg | atggggacca | gtgtgcctca | gtccatgcc | agaatggggg | ctcctgcaag | 300 |
| gaccagctcc | agtcctatat | ctgcttctgc | ctccctgcct | tcgagggccg | gaactgtgag | 360 |
| acgcacaagg | atgaccagct | gatctgtgtg | aacgagaacg | gcggctgtga | gcagtactgc | 420 |

-continued

```
agtgaccaca cgggcaccaa gcgctcctgt cggtgccacg aggggtactc tctgctggca    480
gacgggtgt cctgcacacc cacagttgaa tatccatgtg gaaaaatacc tattctagaa     540
aaaagaaatg ccagcaaacc ccaaggccga aggaagagga ggaagaggat tgtgggggc     600
aaggtgtgcc ccaaagggga gtgtccatgg caggtcctgt tgttggtgaa tggagctcag    660
ttgtgtgggg ggaccctgat caacaccatc tgggtggtct ccgcggccca ctgtttcgac    720
aaaatcaaga actggaggaa cctgatcgcg gtgctgggcg agcacgacct cagcgagcac    780
gacggggatg agcagagccg gcgggtggcg caggtcatca tccccagcac gtacgtcccg    840
ggcaccacca accacgacat cgcgctgctc cgcctgcacc agcccgtggt cctcactgac    900
catgtggtgc ccctctgcct gcccgaacgg acgttctctg agaggacgct ggccttcgtg    960
cgcttctcat tggtcagcgg ctggggccag ctgctggacc gtggcgccac ggccctggag    1020
ctcatggtcc tcaacgtgcc ccggctgatg acccaggact gcctgcagca gtcacggaag    1080
gtgggagact ccccaaatat cacgagtac atgttctgtg ccggctactc ggatggcagc     1140
aaggactcct gcaaggggga cagtggaggc ccacatgcca cccactaccg ggcacgtgg     1200
tacctgacgg gcatcgtcag ctggggccag ggctgcgcaa ccgtgggcca ctttggggtg    1260
tacaccaggg tctcccagta catcgagtgg ctgcaaaagc tcatgcgctc agagccacgc    1320
ccaggagtcc tcctgcgagc cccatttccc ggtggcggtg gctccggcgg aggtgggtcc    1380
ggtggcggcg gatcaggtgg gggtggatca ggcggtggag gttccggtgg cggggctcc    1440
gacaaaactc acacatgccc accgtgccca gctccggaac tcctgggagg accgtcagtc    1500
ttcctcttcc ccccaaaacc caaggacacc ctcatgatct cccggacccc tgaggtcaca    1560
tgcgtggtgg tggacgtgag ccacgaagac cctgaggtca agttcaactg gtacgtggac    1620
ggcgtggagg tgcataatgc caagacaaag ccgcgggagg agcagtacaa cagcacgtac    1680
cgtgtggtca gcgtcctcac cgtcctgcac caggactggc tgaatggcaa ggagtacaag    1740
tgcaaggtct ccaacaaagc cctcccagcc cccatcgaga aaaccatctc caaagccaaa    1800
gggcagcccc gagaaccaca ggtgtacacc ctgcccccat cccgggatga gctgaccaag    1860
aaccaggtca gcctgacctg cctggtcaaa ggcttctatc ccagcgacat cgccgtggag    1920
tgggagagca atgggcagcc ggagaacaac tacaagacca cgcctcccgt gttggactcc    1980
gacggctcct tcttcctcta cagcaagctc accgtcgaca gagcaggtg gcagcagggg     2040
aacgtcttct catgctccgt gatgcatgag gctctgcaca accactacac gcagaagagc    2100
ctctccctgt ctccgggtaa acggcgccgc cggagcggtg gcggcggatc aggtgggggt    2160
ggatcaggcg gtggaggttc cggtggcggg ggatctggcg gtggaggttc cggtgggggt    2220
ggatccagga agaggaggaa gaggggcccc ggatccggac agtgggccc cggcagccgg    2280
agcgccagcg gcaagctgac ctgcctggcc agctactgct ggctgttctg gaccggcatc    2340
gccggtggcg gtggatccgg cggaggtggg tccggtggcg gcggatcagg tggggtgga    2400
tcaggcggtg gaggttccgg tgcgggga tcagacaaaa ctcacacatg cccaccgtgc     2460
ccagcaccgg aactcctggg cggaccgtca gtcttcctct tccccccaaa acccaaggac    2520
accctcatga tctccccggac ccctgaggtc acatgcgtgg tggtggacgt gagccacgaa    2580
gaccctgagg tcaagttcaa ctggtacgtg gacggcgtgg aggtgcataa tgccaagaca    2640
aagccgcggg aggagcagta caacagcacg taccgtgtgg tcagcgtcct caccgtcctg    2700
caccaggact ggctgaatgg caaggagtac aagtgcaagg tctccaacaa agccctccca    2760
```

-continued

```
gcccccatcg agaaaaccat ctccaaagcc aaagggcagc cccgagaacc acaggtgtac    2820
accctgcccc catcccggga tgagctgacc aagaaccagg tcagcctgac ctgcctggtc    2880
aaaggcttct atcccagcga catcgccgtg gagtgggaga gcaatgggca gccggagaac    2940
aactacaaga ccacgcctcc cgtgttggac tccgacggct ccttcttcct ctacagcaag    3000
ctcaccgtgg acaagagcag gtggcagcag gggaacgtct tctcatgctc cgtgatgcat    3060
gaggctctgc acaaccacta cacgcagaag agcctctccc tgtctccggg taaatga       3117
```

```
<210> SEQ ID NO 831
<211> LENGTH: 1038
<212> TYPE: PRT
<213> ORGANISM: Artificial Sequence
<220> FEATURE:
<223> OTHER INFORMATION: FVII-171
<220> FEATURE:
<221> NAME/KEY: SIGNAL
<222> LOCATION: (1)..(20)
<220> FEATURE:
<221> NAME/KEY: PROPEP
<222> LOCATION: (20)..(40)
<220> FEATURE:
<221> NAME/KEY: SITE
<222> LOCATION: (190)..(196)
<223> OTHER INFORMATION: FURIN CLEAVAGE SITE
<220> FEATURE:
<221> NAME/KEY: SITE
<222> LOCATION: (451)..(480)
<223> OTHER INFORMATION: LINKER
<220> FEATURE:
<221> NAME/KEY: SITE
<222> LOCATION: (708)..(711)
<223> OTHER INFORMATION: FURIN CLEAVAGE SITE
<220> FEATURE:
<221> NAME/KEY: SITE
<222> LOCATION: (743)..(748)
<223> OTHER INFORMATION: FURIN CLEAVAGE SITE
<220> FEATURE:
<221> NAME/KEY: SITE
<222> LOCATION: (782)..(811)
<223> OTHER INFORMATION: LINKER

<400> SEQUENCE: 831

Met Val Ser Gln Ala Leu Arg Leu Leu Cys Leu Leu Leu Gly Leu Gln
1               5                  10                  15

Gly Cys Leu Ala Ala Val Phe Val Thr Gln Glu Glu Ala His Gly Val
            20                  25                  30

Leu His Arg Arg Arg Arg Ala Asn Ala Phe Leu Glu Glu Leu Arg Pro
        35                  40                  45

Gly Ser Leu Glu Arg Glu Cys Lys Glu Glu Gln Cys Ser Phe Glu Glu
    50                  55                  60

Ala Arg Glu Ile Phe Lys Asp Ala Glu Arg Thr Lys Leu Phe Trp Ile
65                  70                  75                  80

Ser Tyr Ser Asp Gly Asp Gln Cys Ala Ser Ser Pro Cys Gln Asn Gly
                85                  90                  95

Gly Ser Cys Lys Asp Gln Leu Gln Ser Tyr Ile Cys Phe Cys Leu Pro
            100                 105                 110

Ala Phe Glu Gly Arg Asn Cys Glu Thr His Lys Asp Asp Gln Leu Ile
        115                 120                 125

Cys Val Asn Glu Asn Gly Gly Cys Glu Gln Tyr Cys Ser Asp His Thr
    130                 135                 140

Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
```

```
                    165                 170                 175
Pro Ile Leu Glu Lys Arg Asn Ala Ser Lys Pro Gln Gly Arg Arg Lys
                180                 185                 190

Arg Arg Lys Arg Ile Val Gly Lys Val Cys Pro Lys Gly Glu Cys
            195                 200                 205

Pro Trp Gln Val Leu Leu Leu Val Asn Gly Ala Gln Leu Cys Gly Gly
        210                 215                 220

Thr Leu Ile Asn Thr Ile Trp Val Val Ser Ala Ala His Cys Phe Asp
225                 230                 235                 240

Lys Ile Lys Asn Trp Arg Asn Leu Ile Ala Val Leu Gly Glu His Asp
                245                 250                 255

Leu Ser Glu His Asp Gly Asp Glu Gln Ser Arg Arg Val Ala Gln Val
            260                 265                 270

Ile Ile Pro Ser Thr Tyr Val Pro Gly Thr Thr Asn His Asp Ile Ala
        275                 280                 285

Leu Leu Arg Leu His Gln Pro Val Val Leu Thr Asp His Val Val Pro
        290                 295                 300

Leu Cys Leu Pro Glu Arg Thr Phe Ser Glu Arg Thr Leu Ala Phe Val
305                 310                 315                 320

Arg Phe Ser Leu Val Ser Gly Trp Gly Gln Leu Leu Asp Arg Gly Ala
                325                 330                 335

Thr Ala Leu Glu Leu Met Val Leu Asn Val Pro Arg Leu Met Thr Gln
            340                 345                 350

Asp Cys Leu Gln Gln Ser Arg Lys Val Gly Asp Ser Pro Asn Ile Thr
        355                 360                 365

Glu Tyr Met Phe Cys Ala Gly Tyr Ser Asp Gly Ser Lys Asp Ser Cys
        370                 375                 380

Lys Gly Asp Ser Gly Gly Pro His Ala Thr His Tyr Arg Gly Thr Trp
385                 390                 395                 400

Tyr Leu Thr Gly Ile Val Ser Trp Gly Gln Gly Cys Ala Thr Val Gly
                405                 410                 415

His Phe Gly Val Tyr Thr Arg Val Ser Gln Tyr Ile Glu Trp Leu Gln
            420                 425                 430

Lys Leu Met Arg Ser Glu Pro Arg Pro Gly Val Leu Leu Arg Ala Pro
        435                 440                 445

Phe Pro Gly Gly Gly Ser Gly Gly Gly Ser Gly Gly Gly Gly
        450                 455                 460

Ser Gly Gly Gly Ser Gly Gly Gly Gly Ser Gly Gly Gly Gly Ser
465                 470                 475                 480

Asp Lys Thr His Thr Cys Pro Pro Cys Pro Ala Pro Glu Leu Leu Gly
            485                 490                 495

Gly Pro Ser Val Phe Leu Phe Pro Pro Lys Pro Lys Asp Thr Leu Met
        500                 505                 510

Ile Ser Arg Thr Pro Glu Val Thr Cys Val Val Val Asp Val Ser His
        515                 520                 525

Glu Asp Pro Glu Val Lys Phe Asn Trp Tyr Val Asp Gly Val Glu Val
        530                 535                 540

His Asn Ala Lys Thr Lys Pro Arg Glu Glu Gln Tyr Asn Ser Thr Tyr
545                 550                 555                 560

Arg Val Val Ser Val Leu Thr Val Leu His Gln Asp Trp Leu Asn Gly
                565                 570                 575

Lys Glu Tyr Lys Cys Lys Val Ser Asn Lys Ala Leu Pro Ala Pro Ile
            580                 585                 590
```

```
Glu Lys Thr Ile Ser Lys Ala Lys Gly Gln Pro Arg Glu Pro Gln Val
            595                 600                 605

Tyr Thr Leu Pro Pro Ser Arg Asp Glu Leu Thr Lys Asn Gln Val Ser
610                 615                 620

Leu Thr Cys Leu Val Lys Gly Phe Tyr Pro Ser Asp Ile Ala Val Glu
625                 630                 635                 640

Trp Glu Ser Asn Gly Gln Pro Glu Asn Asn Tyr Lys Thr Thr Pro Pro
                645                 650                 655

Val Leu Asp Ser Asp Gly Ser Phe Phe Leu Tyr Ser Lys Leu Thr Val
            660                 665                 670

Asp Lys Ser Arg Trp Gln Gln Gly Asn Val Phe Ser Cys Ser Val Met
            675                 680                 685

His Glu Ala Leu His Asn His Tyr Thr Gln Lys Ser Leu Ser Leu Ser
690                 695                 700

Pro Gly Lys Arg Arg Arg Ser Gly Gly Gly Ser Gly Gly Gly
705                 710                 715                 720

Gly Ser Gly Gly Gly Ser Gly Gly Gly Ser Gly Gly Gly
                    725                 730                 735

Ser Gly Gly Gly Ser Arg Lys Arg Arg Lys Arg Gly Pro Arg Ile
            740                 745                 750

Arg Thr Val Gly Pro Gly Ser Arg Ser Ala Ser Gly Lys Leu Thr Cys
            755                 760                 765

Leu Ala Ser Tyr Cys Trp Leu Phe Trp Thr Gly Ile Ala Gly Gly Gly
770                 775                 780

Gly Ser Gly Gly Gly Ser Gly Gly Gly Ser Gly Gly Gly
785                 790                 795                 800

Ser Gly Gly Gly Ser Gly Gly Gly Ser Asp Lys Thr His Thr
                    805                 810                 815

Cys Pro Pro Cys Pro Ala Pro Glu Leu Leu Gly Gly Pro Ser Val Phe
                820                 825                 830

Leu Phe Pro Pro Lys Pro Lys Asp Thr Leu Met Ile Ser Arg Thr Pro
            835                 840                 845

Glu Val Thr Cys Val Val Val Asp Val Ser His Glu Asp Pro Glu Val
            850                 855                 860

Lys Phe Asn Trp Tyr Val Asp Gly Val Glu Val His Asn Ala Lys Thr
865                 870                 875                 880

Lys Pro Arg Glu Glu Gln Tyr Asn Ser Thr Tyr Arg Val Val Ser Val
                885                 890                 895

Leu Thr Val Leu His Gln Asp Trp Leu Asn Gly Lys Glu Tyr Lys Cys
            900                 905                 910

Lys Val Ser Asn Lys Ala Leu Pro Ala Pro Ile Glu Lys Thr Ile Ser
            915                 920                 925

Lys Ala Lys Gly Gln Pro Arg Glu Pro Gln Val Tyr Thr Leu Pro Pro
            930                 935                 940

Ser Arg Asp Glu Leu Thr Lys Asn Gln Val Ser Leu Thr Cys Leu Val
945                 950                 955                 960

Lys Gly Phe Tyr Pro Ser Asp Ile Ala Val Glu Trp Glu Ser Asn Gly
                965                 970                 975

Gln Pro Glu Asn Asn Tyr Lys Thr Thr Pro Pro Val Leu Asp Ser Asp
                980                 985                 990

Gly Ser Phe Phe Leu Tyr Ser Lys  Leu Thr Val Asp Lys Ser Arg Trp
            995                 1000                 1005
```

| | | | | | | | | | | |
|---|---|---|---|---|---|---|---|---|---|---|
|Gln|Gln|Gly|Asn|Val|Phe|Ser|Cys|Ser|Val|Met|His|Glu|Ala|Leu|
|1010| | | | |1015| | | | |1020|

His Asn His Tyr Thr Gln Lys Ser Leu Ser Leu Ser Pro Gly Lys
    1025                1030                1035

<210> SEQ ID NO 832
<211> LENGTH: 3060
<212> TYPE: DNA
<213> ORGANISM: Artificial Sequence
<220> FEATURE:
<223> OTHER INFORMATION: FIX-124

<400> SEQUENCE: 832

```
atgcagcgcg tgaacatgat catggcagaa tcaccaggcc tcatcaccat ctgccttta      60
ggatatctac tcagtgctga atgtacagtt tttcttgatc atgaaaacgc caacaaaatt    120
ctgaatcggc caaagaggta taattcaggt aaattggaag agtttgttca agggaatcta    180
gagagagaat gtatgaagaa aagtgtagt tttgaagaag cacgagaagt ttttgaaaac    240
actgaaagaa caactgaatt tggaagcag atgttgatg gagatcagtg tgagtccaat    300
ccatgtttaa atggcggcag ttgcaaggat gacattaatt cctatgaatg ttggtgtccc    360
tttggatttg aaggaagaa ctgtgaatta gatgtaacat gtaacattaa gaatggcaga    420
tgcgagcagt tttgtaaaaa tagtgctgat aacaaggtgg tttgctcctg tactgaggga    480
tatcgacttg cagaaaacca gaagtcctgt gaaccagcag tgccatttcc atgtggaaga    540
gtttctgttt cacaaacttc taagctcacc cgtgctgaga ctgttttttcc tgatgtggac    600
tatgtaaatt ctactgaagc tgaaaccatt ttggataaca tcactcaaag cacccaatca    660
tttaatgact tcactcgggt tgttggtgga agatgcca aaccaggtca attccttgg    720
caggttgtt tgaatggtaa agttgatgca ttctgtggag gctctatcgt taatgaaaaa    780
tggattgtaa ctgctgccca ctgtgttgaa actggtgtta aaattacagt tgtcgcaggt    840
gaacataata ttgaggagac agaacataca gagcaaaagc gaaatgtgat tcgaattatt    900
cctcaccaca actacaatgc agctattaat aagtacaacc atgacattgc ccttctggaa    960
ctggacgaac cctagtgct aaacagctac gttacaccta tttgcattgc tgacaaggaa   1020
tacacgaaca tcttcctcaa atttggatct ggctatgtaa gtggctgggg aagagtcttc   1080
cacaaaggga tcagctttt agttcttcag taccttagag ttccacttgt tgaccgagcc   1140
acatgtcttc gatctacaaa gttcaccatc tataacaaca tgttctgtgc tggcttccat   1200
gaaggaggta gagattcatg tcaaggagat agtgggggac ccatgttac tgaagtggaa   1260
gggaccagtt tcttaactgg aattattagc tggggtgaag agtgtgcaat gaaaggcaaa   1320
tatggaatat ataccaaggt gtcccggtat gtcaactgga ttaaggaaaa aacaaagctc   1380
actgacaaaa ctcacacatg cccaccgtgc ccagctccgg aactcctggg aggaccgtca   1440
gtcttcctct ccccccaaaa acccaaggac accctcatga tctcccggac ccctgaggtc   1500
acatgcgtgg tggtggacgt gagccacgaa gaccctgagg tcaagttcaa ctggtacgtg   1560
gacggcgtgg aggtgcataa tgccaagaca aagccgcggg aggagcagta caacagcacg   1620
taccgtgtgg tcagcgtcct caccgtcctg caccaggact ggctgaatgg caaggagtac   1680
aagtgcaagg tctccaacaa agccctccca gccccatcg agaaaaccat ctccaaagcc   1740
aaagggcagc cccgagaacc acaggtgtac accctgcccc catcccggga tgagctgacc   1800
aagaaccagg tcagcctgac ctgcctggtc aaaggcttct atcccagcga catcgccgtg   1860
gagtgggaga gcaatgggca gccggagaac aactacaaga ccacgcctcc cgtgttggac   1920
```

-continued

```
tccgacggct ccttcttcct ctacagcaag ctcaccgtcg acaagagcag gtggcagcag      1980
gggaacgtct tctcatgctc cgtgatgcat gaggctctgc acaaccacta cacgcagaag      2040
agcctctccc tgtctccggg taaacggcgc cgccggagcg gtggcggcgg atcaggtggg      2100
ggtggatcag gcggtggagg ttccggtggc gggggatctg gcggtggagg ttccggtggg      2160
ggtggatcca ggaagaggag gaagaggggc ccccggatcc ggacagtggg ccccggcagc      2220
cggagcgcca gcggcaagct gacctgcctg gccagctact gctggctgtt ctggaccggc      2280
atcgccggtg gcggtggatc cggcggaggt gggtccggtg gcggcggatc aggtgggggt      2340
ggatcaggcg gtggaggttc cggtggcggg ggatcagaca aaactcacac atgcccaccg      2400
tgcccagcac cggaactcct gggcggaccg tcagtcttcc tcttcccccc aaaacccaag      2460
gacaccctca tgatctcccg gacccctgag gtcacatgcg tggtggtgga cgtgagccac      2520
gaagaccctg aggtcaagtt caactggtac gtggacggcg tggaggtgca taatgccaag      2580
acaaagccgc gggaggagca gtacaacagc acgtaccgtg tggtcagcgt cctcaccgtc      2640
ctgcaccagg actggctgaa tggcaaggag tacaagtgca aggtctccaa caaagccctc      2700
ccagccccca tcgagaaaac catctccaaa gccaaagggc agccccgaga accacaggtg      2760
tacaccctgc cccatcccg ggatgagctg accaagaacc aggtcagcct gacctgcctg      2820
gtcaaaggct tctatcccag cgacatcgcc gtggagtggg agagcaatgg gcagccggag      2880
aacaactaca agaccacgcc tcccgtgttg gactccgacg gctccttctt cctctacagc      2940
aagctcaccg tggacaagag caggtggcag caggggaacg tcttctcatg ctccgtgatg      3000
catgaggctc tgcacaacca ctacacgcag aagagcctct ccctgtctcc gggtaaatga      3060
```

<210> SEQ ID NO 833
<211> LENGTH: 1019
<212> TYPE: PRT
<213> ORGANISM: Artificial Sequence
<220> FEATURE:
<223> OTHER INFORMATION: FIX-124
<220> FEATURE:
<221> NAME/KEY: SIGNAL
<222> LOCATION: (1)..(28)
<220> FEATURE:
<221> NAME/KEY: PROPEP
<222> LOCATION: (29)..(46)
<220> FEATURE:
<221> NAME/KEY: SITE
<222> LOCATION: (462)..(688)
<223> OTHER INFORMATION: Fc Site
<220> FEATURE:
<221> NAME/KEY: SITE
<222> LOCATION: (693)..(723)
<223> OTHER INFORMATION: LINKER
<220> FEATURE:
<221> NAME/KEY: SITE
<222> LOCATION: (730)..(762)
<223> OTHER INFORMATION: Compound 21
<220> FEATURE:
<221> NAME/KEY: SITE
<222> LOCATION: (793)..(1019)
<223> OTHER INFORMATION: Fc Site

<400> SEQUENCE: 833

```
Met Gln Arg Val Asn Met Ile Met Ala Glu Ser Pro Gly Leu Ile Thr
 1               5                  10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45
```

```
Ser Gly Lys Leu Glu Glu Phe Val Gln Gly Asn Leu Glu Arg Glu Cys
 50                  55                  60

Met Glu Glu Lys Cys Ser Phe Glu Glu Ala Arg Glu Val Phe Glu Asn
 65                  70                  75                  80

Thr Glu Arg Thr Thr Glu Phe Trp Lys Gln Tyr Val Asp Gly Asp Gln
                 85                  90                  95

Cys Glu Ser Asn Pro Cys Leu Asn Gly Gly Ser Cys Lys Asp Asp Ile
                100                 105                 110

Asn Ser Tyr Glu Cys Trp Cys Pro Phe Gly Phe Glu Gly Lys Asn Cys
            115                 120                 125

Glu Leu Asp Val Thr Cys Asn Ile Lys Asn Gly Arg Cys Glu Gln Phe
            130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
                180                 185                 190

Glu Thr Val Phe Pro Asp Val Asp Tyr Val Asn Ser Thr Glu Ala Glu
                195                 200                 205

Thr Ile Leu Asp Asn Ile Thr Gln Ser Thr Gln Ser Phe Asn Asp Phe
210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
                260                 265                 270

Val Lys Ile Thr Val Val Ala Gly Glu His Asn Ile Glu Glu Thr Glu
                275                 280                 285

His Thr Glu Gln Lys Arg Asn Val Ile Arg Ile Ile Pro His His Asn
                290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
                325                 330                 335

Ala Asp Lys Glu Tyr Thr Asn Ile Phe Leu Lys Phe Gly Ser Gly Tyr
                340                 345                 350

Val Ser Gly Trp Gly Arg Val Phe His Lys Gly Arg Ser Ala Leu Val
                355                 360                 365

Leu Gln Tyr Leu Arg Val Pro Leu Val Asp Arg Ala Thr Cys Leu Arg
                370                 375                 380

Ser Thr Lys Phe Thr Ile Tyr Asn Asn Met Phe Cys Ala Gly Phe His
385                 390                 395                 400

Glu Gly Gly Arg Asp Ser Cys Gln Gly Asp Ser Gly Gly Pro His Val
                405                 410                 415

Thr Glu Val Glu Gly Thr Ser Phe Leu Thr Gly Ile Ile Ser Trp Gly
                420                 425                 430

Glu Glu Cys Ala Met Lys Gly Lys Tyr Gly Ile Tyr Thr Lys Val Ser
                435                 440                 445

Arg Tyr Val Asn Trp Ile Lys Glu Lys Thr Lys Leu Thr Asp Lys Thr
450                 455                 460
```

-continued

His Thr Cys Pro Pro Cys Pro Ala Pro Glu Leu Leu Gly Gly Pro Ser
465                 470                 475                 480

Val Phe Leu Phe Pro Lys Pro Lys Asp Thr Leu Met Ile Ser Arg
            485                 490                 495

Thr Pro Glu Val Thr Cys Val Val Val Asp Val Ser His Glu Asp Pro
            500                 505                 510

Glu Val Lys Phe Asn Trp Tyr Val Asp Gly Val Glu Val His Asn Ala
            515                 520                 525

Lys Thr Lys Pro Arg Glu Glu Gln Tyr Asn Ser Thr Tyr Arg Val Val
    530                 535                 540

Ser Val Leu Thr Val Leu His Gln Asp Trp Leu Asn Gly Lys Glu Tyr
545                 550                 555                 560

Lys Cys Lys Val Ser Asn Lys Ala Leu Pro Ala Pro Ile Glu Lys Thr
                565                 570                 575

Ile Ser Lys Ala Lys Gly Gln Pro Arg Glu Pro Gln Val Tyr Thr Leu
            580                 585                 590

Pro Pro Ser Arg Asp Glu Leu Thr Lys Asn Gln Val Ser Leu Thr Cys
        595                 600                 605

Leu Val Lys Gly Phe Tyr Pro Ser Asp Ile Ala Val Glu Trp Glu Ser
610                 615                 620

Asn Gly Gln Pro Glu Asn Asn Tyr Lys Thr Thr Pro Pro Val Leu Asp
625                 630                 635                 640

Ser Asp Gly Ser Phe Phe Leu Tyr Ser Lys Leu Thr Val Asp Lys Ser
                645                 650                 655

Arg Trp Gln Gln Gly Asn Val Phe Ser Cys Ser Val Met His Glu Ala
            660                 665                 670

Leu His Asn His Tyr Thr Gln Lys Ser Leu Ser Leu Ser Pro Gly Lys
        675                 680                 685

Arg Arg Arg Arg Ser Gly Gly Gly Ser Gly Gly Gly Ser Gly
690                 695                 700

Gly Gly Gly Ser Gly Gly Gly Gly Ser Gly Gly Gly Gly Ser Gly Gly
705                 710                 715                 720

Gly Gly Ser Arg Lys Arg Arg Lys Arg Gly Pro Arg Ile Arg Thr Val
            725                 730                 735

Gly Pro Gly Ser Arg Ser Ala Ser Gly Lys Leu Thr Cys Leu Ala Ser
            740                 745                 750

Tyr Cys Trp Leu Phe Trp Thr Gly Ile Ala Gly Gly Gly Ser Gly
        755                 760                 765

Gly Gly Gly Ser Gly Gly Gly Ser Gly Gly Gly Gly Ser Gly Gly
    770                 775                 780

Gly Gly Ser Gly Gly Gly Gly Ser Asp Lys Thr His Thr Cys Pro Pro
785                 790                 795                 800

Cys Pro Ala Pro Glu Leu Leu Gly Gly Pro Ser Val Phe Leu Phe Pro
            805                 810                 815

Pro Lys Pro Lys Asp Thr Leu Met Ile Ser Arg Thr Pro Glu Val Thr
        820                 825                 830

Cys Val Val Val Asp Val Ser His Glu Asp Pro Glu Val Lys Phe Asn
            835                 840                 845

Trp Tyr Val Asp Gly Val Glu Val His Asn Ala Lys Thr Lys Pro Arg
        850                 855                 860

Glu Glu Gln Tyr Asn Ser Thr Tyr Arg Val Val Ser Val Leu Thr Val
865                 870                 875                 880

Leu His Gln Asp Trp Leu Asn Gly Lys Glu Tyr Lys Cys Lys Val Ser

```
                        885                 890                 895
Asn Lys Ala Leu Pro Ala Pro Ile Glu Lys Thr Ile Ser Lys Ala Lys
                    900                 905                 910
Gly Gln Pro Arg Glu Pro Gln Val Tyr Thr Leu Pro Pro Ser Arg Asp
                915                 920                 925
Glu Leu Thr Lys Asn Gln Val Ser Leu Thr Cys Leu Val Lys Gly Phe
            930                 935                 940
Tyr Pro Ser Asp Ile Ala Val Glu Trp Glu Ser Asn Gly Gln Pro Glu
945                 950                 955                 960
Asn Asn Tyr Lys Thr Thr Pro Pro Val Leu Asp Ser Asp Gly Ser Phe
                965                 970                 975
Phe Leu Tyr Ser Lys Leu Thr Val Asp Lys Ser Arg Trp Gln Gln Gly
            980                 985                 990
Asn Val Phe Ser Cys Ser Val Met His Glu Ala Leu His Asn His Tyr
        995                1000                1005
Thr Gln  Lys Ser Leu Ser Leu  Ser Pro Gly Lys
    1010                1015
```

<210> SEQ ID NO 834
<211> LENGTH: 2589
<212> TYPE: DNA
<213> ORGANISM: Artificial Sequence
<220> FEATURE:
<223> OTHER INFORMATION: Fc-046

<400> SEQUENCE: 834

| | |
|---|---:|
| atggagacag acacactcct gctatgggta ctgctgctct gggttccagg ttccactggt | 60 |
| ggcccccgga ttcggacagt gggcccggc agccggagcg ccagcggcaa gctgacctgc | 120 |
| ctggccagct actgctggct gttctggacc ggcatcgccg gtggcggtgg atccggcgga | 180 |
| ggtgggtccg gtggcggcgg atcaggtggg ggtggatcag gcggtggagg ttccggtggc | 240 |
| gggggatcag acaaaactca cacatgccca ccgtgcccag ctccggaact cctgggagga | 300 |
| ccgtcagtct tcctcttccc cccaaaaccc aaggacaccc tcatgatctc ccggacccct | 360 |
| gaggtcacat gcgtggtggt ggacgtgagc cacgaagacc ctgaggtcaa gttcaactgg | 420 |
| tacgtggacg gcgtggaggt gcataatgcc aagacaaagc cgcgggagga gcagtacaac | 480 |
| agcacgtacc gtgtggtcag cgtcctcacc gtcctgcacc aggactggct gaatggcaag | 540 |
| gagtacaagt gcaaggtctc caacaaagcc ctcccagccc ccatcgagaa aaccatctcc | 600 |
| aaagccaaag gcagccccg agaaccacag gtgtacaccc tgcccccatc ccgggatgag | 660 |
| ctgaccaaga accaggtcag cctgacctgc ctggtcaaag gcttctatcc cagcgacatc | 720 |
| gccgtggagt gggagagcaa tgggcagccg gagaacaact acaagaccac gcctcccgtg | 780 |
| ttggactccg acggctcctt cttcctctac agcaagctca ccgtcgacaa gagcaggtgg | 840 |
| cagcagggga acgtcttctc atgctccgtg atgcatgagg ctctgcacaa ccactacacg | 900 |
| cagaagagcc tctccctgtc tccgggtaaa cggcgccgcc ggagcggtgg cggcggatca | 960 |
| ggtggggtg atcaggcgg tggaggttcc ggtggcgggg gatccggcgg tggaggttcc | 1020 |
| ggtggggtg atcaaggaa gaggaggaag aggcaggtga aactgctcga gtctggggga | 1080 |
| ggcgtggtcc agcctgggag gtccctgaga ctctcctgtg cagcctctgg attcaccttc | 1140 |
| agtagctatg ctatgcactg ggtccgccag gctccaggca aggggctgga gtgggtggca | 1200 |
| gttatatcat atgatggaag caataaatac tacgcagact ccgtgaaggg ccgattcgcc | 1260 |
| atctccagag acaattccaa gaacacgctg tatctgcaaa tgaacagcct gagagctgag | 1320 |

-continued

```
gacacggctg tgtattactg tgcgagagcg ctgggggagct ggggggggttg ggaccactac    1380 atggacgtct ggggcaaagg gaccacggtc accgtctcct caggtggcgg cggatcaggt    1440
gggggtggat caggtggcgg tggctccggt ggcgggggat cagtggtgac tcagccaccc    1500
tcagcgtctg gaccccccgg gcagagggtc accatctctt gttctggaag cagctccaac    1560
atcggaagta atactgtaaa ctggtaccag cagctcccag gaacggcccc caaactcctc    1620
atctatagta ataatcagcg gccctcaggg gtccctgacc gattctctgg ctccaagtct    1680
ggcacctcag cctccctggc catcagtggg ctccagtctg aggatgaggc tgattattac    1740
tgtgcagcat gggatgacag cctgaatggt tgggtgttcg gcggagggac caagctgacc    1800
gtcctaggtc agcccggtgg cggtggctcc ggcggaggtg ggtccggtgg cggcggatca    1860 ggtggggggtg gatcaggcgg tggaggttcc ggtggcgggg gatcagacaa aactcacaca    1920
tgcccaccgt gcccagcacc ggaactactg ggcggaccgt cagtcttcct cttcccccca    1980
aaacccaagg acaccctcat gatctcccgg acccctgagg tcacatgcgt ggtggtggac    2040
gtgagccacg aagaccctga ggtcaagttc aactggtacg tggacggcgt ggaggtgcat    2100
aatgccaaga caaagccgcg ggaggagcag tacaacagca cgtaccgtgt ggtcagcgtc    2160
ctcaccgtcc tgcaccagga ctggctgaat ggcaaggagt acaagtgcaa ggtctccaac    2220
aaagccctcc cagcccccat cgagaaaacc atctccaaag ccaagggca gccccgagaa    2280 ccacaggtgt acaccctgcc cccatcccgg gatgagctga ccaagaacca ggtcagcctg    2340
acctgcctgg tcaaaggctt ctatcccagc gacatcgccg tggagtggga gagcaatggg    2400
cagccggaga acaactacaa gaccacgcct cccgtgttgg actccgacgg ctccttcttc    2460
ctctacagca agctcaccgt ggacaagagc aggtggcagc aggggaacgt cttctcatgc    2520
tccgtgatgc atgaggctct gcacaaccac tacacgcaga agagcctctc cctgtctccg    2580
ggtaaatga                                                            2589
```

```
<210> SEQ ID NO 835
<211> LENGTH: 862
<212> TYPE: PRT
<213> ORGANISM: Artificial Sequence
<220> FEATURE:
<223> OTHER INFORMATION: Fc-046
<220> FEATURE:
<221> NAME/KEY: SIGNAL
<222> LOCATION: (1)..(20)
<220> FEATURE:
<221> NAME/KEY: SITE
<222> LOCATION: (54)..(83)
<223> OTHER INFORMATION: LINKER
<220> FEATURE:
<221> NAME/KEY: SITE
<222> LOCATION: (311)..(314)
<223> OTHER INFORMATION: FURIN CLEAVAGE SITE
<220> FEATURE:
<221> NAME/KEY: SITE
<222> LOCATION: (346)..(351)
<223> OTHER INFORMATION: FURIN CLEAVAGE SITE
<220> FEATURE:
<221> NAME/KEY: SITE
<222> LOCATION: (606)..(635)
<223> OTHER INFORMATION: LINKER

<400> SEQUENCE: 835
```

```
Met Glu Thr Asp Thr Leu Leu Leu Trp Val Leu Leu Leu Trp Val Pro
1               5                   10                  15

Gly Ser Thr Gly Gly Pro Arg Ile Arg Thr Val Gly Pro Gly Ser Arg
            20                  25                  30
```

```
Ser Ala Ser Gly Lys Leu Thr Cys Leu Ala Ser Tyr Cys Trp Leu Phe
        35                  40                  45

Trp Thr Gly Ile Ala Gly Gly Gly Ser Gly Gly Gly Gly Ser Gly
    50                  55                  60

Gly Gly Gly Ser Gly Gly Gly Ser Gly Gly Gly Ser Gly Gly
65                  70                  75                  80

Gly Gly Ser Asp Lys Thr His Thr Cys Pro Pro Cys Pro Ala Pro Glu
            85                  90                  95

Leu Leu Gly Gly Pro Ser Val Phe Leu Phe Pro Pro Lys Pro Lys Asp
            100                 105                 110

Thr Leu Met Ile Ser Arg Thr Pro Glu Val Thr Cys Val Val Val Asp
            115                 120                 125

Val Ser His Glu Asp Pro Glu Val Lys Phe Asn Trp Tyr Val Asp Gly
        130                 135                 140

Val Glu Val His Asn Ala Lys Thr Lys Pro Arg Glu Glu Gln Tyr Asn
145                 150                 155                 160

Ser Thr Tyr Arg Val Val Ser Val Leu Thr Val Leu His Gln Asp Trp
                165                 170                 175

Leu Asn Gly Lys Glu Tyr Lys Cys Lys Val Ser Asn Lys Ala Leu Pro
            180                 185                 190

Ala Pro Ile Glu Lys Thr Ile Ser Lys Ala Lys Gly Gln Pro Arg Glu
        195                 200                 205

Pro Gln Val Tyr Thr Leu Pro Pro Ser Arg Asp Glu Leu Thr Lys Asn
        210                 215                 220

Gln Val Ser Leu Thr Cys Leu Val Lys Gly Phe Tyr Pro Ser Asp Ile
225                 230                 235                 240

Ala Val Glu Trp Glu Ser Asn Gly Gln Pro Glu Asn Asn Tyr Lys Thr
            245                 250                 255

Thr Pro Pro Val Leu Asp Ser Asp Gly Ser Phe Phe Leu Tyr Ser Lys
            260                 265                 270

Leu Thr Val Asp Lys Ser Arg Trp Gln Gln Gly Asn Val Phe Ser Cys
        275                 280                 285

Ser Val Met His Glu Ala Leu His Asn His Tyr Thr Gln Lys Ser Leu
        290                 295                 300

Ser Leu Ser Pro Gly Lys Arg Arg Arg Ser Gly Gly Gly Gly Ser
305                 310                 315                 320

Gly Gly Gly Gly Ser Gly Gly Gly Ser Gly Gly Gly Ser Gly
                325                 330                 335

Gly Gly Gly Ser Gly Gly Gly Gly Ser Arg Lys Arg Lys Arg Gln
            340                 345                 350

Val Lys Leu Leu Glu Ser Gly Gly Gly Val Val Gln Pro Gly Arg Ser
        355                 360                 365

Leu Arg Leu Ser Cys Ala Ala Ser Gly Phe Thr Phe Ser Ser Tyr Ala
        370                 375                 380

Met His Trp Val Arg Gln Ala Pro Gly Lys Gly Leu Glu Trp Val Ala
385                 390                 395                 400

Val Ile Ser Tyr Asp Gly Ser Asn Lys Tyr Tyr Ala Asp Ser Val Lys
            405                 410                 415

Gly Arg Phe Ala Ile Ser Arg Asp Asn Ser Lys Asn Thr Leu Tyr Leu
            420                 425                 430

Gln Met Asn Ser Leu Arg Ala Glu Asp Thr Ala Val Tyr Tyr Cys Ala
        435                 440                 445
```

-continued

Arg Ala Leu Gly Ser Trp Gly Gly Trp Asp His Tyr Met Asp Val Trp
450                 455                 460
Gly Lys Gly Thr Thr Val Thr Val Ser Ser Gly Gly Gly Gly Ser Gly
465                 470                 475                 480
Gly Gly Gly Ser Gly Gly Gly Ser Gly Gly Gly Ser Val Val
            485                 490                 495
Thr Gln Pro Pro Ser Ala Ser Gly Thr Pro Gly Gln Arg Val Thr Ile
            500                 505                 510
Ser Cys Ser Gly Ser Ser Ser Asn Ile Gly Ser Asn Thr Val Asn Trp
        515                 520                 525
Tyr Gln Gln Leu Pro Gly Thr Ala Pro Lys Leu Leu Ile Tyr Ser Asn
530                 535                 540
Asn Gln Arg Pro Ser Gly Val Pro Asp Arg Phe Ser Gly Ser Lys Ser
545                 550                 555                 560
Gly Thr Ser Ala Ser Leu Ala Ile Ser Gly Leu Gln Ser Glu Asp Glu
                565                 570                 575
Ala Asp Tyr Tyr Cys Ala Ala Trp Asp Asp Ser Leu Asn Gly Trp Val
            580                 585                 590
Phe Gly Gly Gly Thr Lys Leu Thr Val Leu Gly Gln Pro Gly Gly Gly
        595                 600                 605
Gly Ser Gly Gly Gly Gly Ser Gly Gly Gly Gly Ser Gly Gly Gly Gly
    610                 615                 620
Ser Gly Gly Gly Gly Ser Gly Gly Gly Gly Ser Asp Lys Thr His Thr
625                 630                 635                 640
Cys Pro Pro Cys Pro Ala Pro Glu Leu Leu Gly Gly Pro Ser Val Phe
                645                 650                 655
Leu Phe Pro Pro Lys Pro Lys Asp Thr Leu Met Ile Ser Arg Thr Pro
            660                 665                 670
Glu Val Thr Cys Val Val Val Asp Val Ser His Glu Asp Pro Glu Val
        675                 680                 685
Lys Phe Asn Trp Tyr Val Asp Gly Val Glu Val His Asn Ala Lys Thr
690                 695                 700
Lys Pro Arg Glu Glu Gln Tyr Asn Ser Thr Tyr Arg Val Val Ser Val
705                 710                 715                 720
Leu Thr Val Leu His Gln Asp Trp Leu Asn Gly Lys Glu Tyr Lys Cys
                725                 730                 735
Lys Val Ser Asn Lys Ala Leu Pro Ala Pro Ile Glu Lys Thr Ile Ser
            740                 745                 750
Lys Ala Lys Gly Gln Pro Arg Glu Pro Gln Val Tyr Thr Leu Pro Pro
        755                 760                 765
Ser Arg Asp Glu Leu Thr Lys Asn Gln Val Ser Leu Thr Cys Leu Val
    770                 775                 780
Lys Gly Phe Tyr Pro Ser Asp Ile Ala Val Glu Trp Glu Ser Asn Gly
785                 790                 795                 800
Gln Pro Glu Asn Asn Tyr Lys Thr Thr Pro Val Leu Asp Ser Asp
                805                 810                 815
Gly Ser Phe Phe Leu Tyr Ser Lys Leu Thr Val Asp Lys Ser Arg Trp
            820                 825                 830
Gln Gln Gly Asn Val Phe Ser Cys Ser Val Met His Glu Ala Leu His
        835                 840                 845
Asn His Tyr Thr Gln Lys Ser Leu Ser Leu Ser Pro Gly Lys
850                 855                 860

<210> SEQ ID NO 836
<211> LENGTH: 1737
<212> TYPE: DNA
<213> ORGANISM: Artificial Sequence
<220> FEATURE:
<223> OTHER INFORMATION: Fc-045

<400> SEQUENCE: 836

```
atggagacag acacactcct gctatgggta ctgctgctct ggttccagg ttccactggt      60
gacaaaactc acacatgccc accgtgccca gctccggaac tcctgggagg accgtcagtc    120
ttcctcttcc ccccaaaacc caaggacacc ctcatgatct cccggacccc tgaggtcaca    180
tgcgtggtgg tggacgtgag ccacgaagac cctgaggtca agttcaactg gtacgtggac    240
ggcgtggagg tgcataatgc aagacaaag ccgcgggagg agcagtacaa cagcacgtac    300
cgtgtggtca gcgtcctcac cgtcctgcac caggactggc tgaatggcaa ggagtacaag    360
tgcaaggtct ccaacaaagc cctcccagcc cccatcgaga aaaccatctc caaagccaaa    420
gggcagcccc gagaaccaca ggtgtacacc ctgcccccat cccgggatga gctgaccaag    480
aaccaggtca gcctgacctg cctggtcaaa ggcttctatc ccagcgacat cgccgtggag    540
tgggagagca atgggcagcc ggagaacaac tacaagacca cgcctcccgt gttggactcc    600
gacggctcct tcttcctcta cagcaagctc accgtcgaca agagcaggtg gcagcagggg    660
aacgtcttct catgctccgt gatgcatgag gctctgcaca accactacac gcagaagagc    720
ctctccctgt ctccgggtaa acggcgccgc cggagcggtg gcggcggatc aggtggggt    780
ggatcaggcg gtgaaggttc cggtggcggg ggatctggcg gtggaggttc cggtgggggt    840
ggatccagga agaggaggaa gagggcccc cggatccgga cagtgggccc cggcagccgg    900
agcgccagcg gcaagctgac ctgcctggcc agctactgct ggctgttctg gaccggcatc    960
gccggtggcg gtggatccgg cggaggtggg tccggtggcg gcggatcagg tggggtgga   1020
tcaggcggtg gaggttccgg tggcggggga tcagacaaaa ctcacacatg cccaccgtgc   1080
ccagcaccgg aactcctggg cggaccgtca gtcttcctct cccccaaa acccaaggac   1140
accctcatga tctcccggac ccctgaggtc acatgcgtgg tggtggacgt gagccacgaa   1200
gaccctgagg tcaagttcaa ctggtacgtg gacggcgtgg aggtgcataa tgccaagaca   1260
aagccgcggg aggagcagta caacagcacg taccgtgtgg tcagcgtcct caccgtcctg   1320
caccaggact ggctgaatgg caaggagtac aagtgcaagg tctccaacaa agccctccca   1380
gcccccatcg agaaaaccat ctccaaagcc aaagggcagc ccgagaacc acaggtgtac   1440
accctgcccc catcccggga tgagctgacc aagaaccagg tcagcctgac ctgcctggtc   1500
aaaggcttct atcccagcga catcgccgtg gagtgggaga gcaatgggca gccggagaac   1560
aactacaaga ccacgcctcc cgtgttggac tccgacggct ccttcttcct ctacagcaag   1620
ctcaccgtgg acaagagcag gtggcagcag gggaacgtct tctcatgctc cgtgatgcat   1680
gaggctctgc acaaccacta cacgcagaag agcctctccc tgtctccggg taaatga      1737
```

<210> SEQ ID NO 837
<211> LENGTH: 578
<212> TYPE: PRT
<213> ORGANISM: Artificial Sequence
<220> FEATURE:
<223> OTHER INFORMATION: Fc-045
<220> FEATURE:
<221> NAME/KEY: SIGNAL
<222> LOCATION: (1)..(20)
<220> FEATURE:
<221> NAME/KEY: SITE

```
<222> LOCATION: (248)..(351)
<223> OTHER INFORMATION: FURIN CLEAVAGE SITE
<220> FEATURE:
<221> NAME/KEY: SITE
<222> LOCATION: (283)..(288)
<223> OTHER INFORMATION: FURIN CLEAVAGE SITE
<220> FEATURE:
<221> NAME/KEY: SITE
<222> LOCATION: (322)..(351)
<223> OTHER INFORMATION: LINKER

<400> SEQUENCE: 837

Met Glu Thr Asp Thr Leu Leu Leu Trp Val Leu Leu Leu Trp Val Pro
1               5                   10                  15

Gly Ser Thr Gly Asp Lys Thr His Thr Cys Pro Pro Cys Pro Ala Pro
            20                  25                  30

Glu Leu Leu Gly Gly Pro Ser Val Phe Leu Phe Pro Pro Lys Pro Lys
        35                  40                  45

Asp Thr Leu Met Ile Ser Arg Thr Pro Glu Val Thr Cys Val Val Val
    50                  55                  60

Asp Val Ser His Glu Asp Pro Glu Val Lys Phe Asn Trp Tyr Val Asp
65                  70                  75                  80

Gly Val Glu Val His Asn Ala Lys Thr Lys Pro Arg Glu Glu Gln Tyr
                85                  90                  95

Asn Ser Thr Tyr Arg Val Val Ser Val Leu Thr Val Leu His Gln Asp
            100                 105                 110

Trp Leu Asn Gly Lys Glu Tyr Lys Cys Lys Val Ser Asn Lys Ala Leu
        115                 120                 125

Pro Ala Pro Ile Glu Lys Thr Ile Ser Lys Ala Lys Gly Gln Pro Arg
    130                 135                 140

Glu Pro Gln Val Tyr Thr Leu Pro Pro Ser Arg Asp Glu Leu Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
    210                 215                 220

Cys Ser Val Met His Glu Ala Leu His Asn His Tyr Thr Gln Lys Ser
225                 230                 235                 240

Leu Ser Leu Ser Pro Gly Lys Arg Arg Arg Ser Gly Gly Gly Gly
                245                 250                 255

Ser Gly Gly Gly Ser Gly Gly Gly Ser Gly Gly Gly Ser
        260                 265                 270

Gly Gly Gly Gly Ser Gly Gly Gly Ser Arg Lys Arg Lys Arg
        275                 280                 285

Gly Pro Arg Ile Arg Thr Val Gly Pro Gly Ser Arg Ser Ala Ser Gly
    290                 295                 300

Lys Leu Thr Cys Leu Ala Ser Tyr Cys Trp Leu Phe Trp Thr Gly Ile
305                 310                 315                 320

Ala Gly Gly Gly Gly Ser Gly Gly Gly Ser Gly Gly Gly Ser
                325                 330                 335

Gly Gly Gly Gly Ser Gly Gly Gly Ser Gly Gly Gly Ser Asp
        340                 345                 350
```

```
Lys Thr His Thr Cys Pro Cys Pro Ala Pro Glu Leu Leu Gly Gly
            355                 360                 365

Pro Ser Val Phe Leu Phe Pro Pro Lys Pro Lys Asp Thr Leu Met Ile
    370                 375                 380

Ser Arg Thr Pro Glu Val Thr Cys Val Val Val Asp Val Ser His Glu
385                 390                 395                 400

Asp Pro Glu Val Lys Phe Asn Trp Tyr Val Asp Gly Val Glu Val His
                405                 410                 415

Asn Ala Lys Thr Lys Pro Arg Glu Glu Gln Tyr Asn Ser Thr Tyr Arg
            420                 425                 430

Val Val Ser Val Leu Thr Val Leu His Gln Asp Trp Leu Asn Gly Lys
    435                 440                 445

Glu Tyr Lys Cys Lys Val Ser Asn Lys Ala Leu Pro Ala Pro Ile Glu
450                 455                 460

Lys Thr Ile Ser Lys Ala Lys Gly Gln Pro Arg Glu Pro Gln Val Tyr
                465                 470                 475                 480

Thr Leu Pro Pro Ser Arg Asp Glu Leu Thr Lys Asn Gln Val Ser Leu
            485                 490                 495

Thr Cys Leu Val Lys Gly Phe Tyr Pro Ser Asp Ile Ala Val Glu Trp
        500                 505                 510

Glu Ser Asn Gly Gln Pro Glu Asn Asn Tyr Lys Thr Thr Pro Pro Val
    515                 520                 525

Leu Asp Ser Asp Gly Ser Phe Phe Leu Tyr Ser Lys Leu Thr Val Asp
530                 535                 540

Lys Ser Arg Trp Gln Gln Gly Asn Val Phe Ser Cys Ser Val Met His
545                 550                 555                 560

Glu Ala Leu His Asn His Tyr Thr Gln Lys Ser Leu Ser Leu Ser Pro
                565                 570                 575

Gly Lys

<210> SEQ ID NO 838
<211> LENGTH: 2385
<212> TYPE: DNA
<213> ORGANISM: Artificial Sequence
<220> FEATURE:
<223> OTHER INFORMATION: CysFc-044

<400> SEQUENCE: 838
atggagacag acacactcct gctatgggta ctgctgctct gggttccagg ttccactggt    60
tgcccgccgt gcccggctcc ggaactcctg gaggaccgt cagtcttcct cttcccccca    120
aaacccaagg acaccctcat gatctcccgg acccctgagg tcacatgcgt ggtggtggac    180
gtgagccacg aagaccctga ggtcaagttc aactggtacg tggacggcgt ggaggtgcat    240
aatgccaaga caaagccgcg ggaggagcag tacaacagca cgtaccgtgt ggtcagcgtc    300
ctcaccgtcc tgcaccagga ctggctgaat ggcaaggagt acaagtgcaa ggtctccaac    360
aaagccctcc cagcccccat cgagaaaacc atctccaaag ccaagggcag ccccgagaa    420 ccacaggtgt acaccctgcc cccatcccgg gatgagctga ccaagaacca ggtcagcctg    480
acctgcctgg tcaaaggctt ctatcccagc gacatcgccg tggagtggga gagcaatggg    540
cagccggaga acaactacaa gaccacgcct cccgtgttgg actccgacgg ctccttcttc    600
ctctacagca agctcaccgt cgacaagagc aggtggcagc aggggaacgt cttctcatgc    660
tccgtgatgc atgaggctct gcacaaccac tacacgcaga gagcctctc cctgtctccg    720 ggtaaacggc gccgccggag cggtggcggc ggatcaggtg ggggtggatc aggcggtgga    780
```

```
ggttccggtg gcggggatc cggcggtgga ggttccggtg ggggtggatc aaggaagagg    840
aggaagaggc aggtgaaact gctcgagtct ggggaggcg tggtccagcc tgggaggtcc    900
ctgagactct cctgtgcagc ctctggattc accttcagta gctatgctat gcactgggtc   960
cgccaggctc caggcaaggg gctggagtgg gtggcagtta tatcatatga tggaagcaat  1020
aaatactacg cagactccgt gaagggccga ttcgccatct ccagagacaa ttccaagaac  1080
acgctgtatc tgcaaatgaa cagcctgaga gctgaggaca cggctgtgta ttactgtgcg  1140
agagcgctgg ggagctgggg gggttgggac cactacatgg acgtctgggg caaagggacc  1200
acggtcaccg tctcctcagg tggcggcgga tcaggtgggg gtggatcagg tggcggtggc  1260
tccggtggcg ggggatcagt ggtgactcag ccaccctcag cgtctgggac ccccgggcag  1320
agggtcacca tctcttgttc tggaagcagc tccaacatcg gaagtaatac tgtaaactgg  1380
taccagcagc tcccaggaac ggccccaaa ctcctcatct atagtaataa tcagcggccc  1440
tcaggggtcc ctgaccgatt ctctggctcc aagtctggca cctcagcctc cctggccatc  1500
agtgggctcc agtctgagga tgaggctgat tattactgtg cagcatggga tgacagcctg  1560
aatggttggg tgttcggcgg agggaccaag ctgaccgtcc taggtcagcc cggtggcggt  1620
ggctccggcg gaggtgggtc cggtggcggc ggatcaggtg ggggtggatc aggcggtgga  1680
ggttccggtg gcggggatc agacaaaact cacacatgcc caccgtgccc agcaccggaa  1740
ctactgggcg gaccgtcagt cttcctcttc cccccaaaac ccaaggacac cctcatgatc  1800
tcccggaccc ctgaggtcac atgcgtggtg gtggacgtga gccacgaaga ccctgaggtc  1860
aagttcaact ggtacgtgga cggcgtggag gtgcataatg ccaagacaaa gccgcgggag  1920
gagcagtaca acagcacgta ccgtgtggtc agcgtcctca ccgtcctgca ccaggactgg  1980
ctgaatggca aggagtacaa gtgcaaggtc tccaacaaag ccctcccagc ccccatcgag  2040
aaaaccatct ccaaagccaa agggcagccc cgagaaccac aggtgtacac cctgcccca   2100 tcccgggatg agctgaccaa gaaccaggtc agcctgacct gcctggtcaa aggcttctat  2160
cccagcgaca tcgccgtgga gtgggagagc aatgggcagc cggagaacaa ctacaagacc  2220
acgcctcccg tgttggactc cgacggctcc ttcttcctct acagcaagct caccgtggac  2280
aagagcaggt ggcagcaggg gaacgtcttc tcatgctccg tgatgcatga ggctctgcac  2340
aaccactaca cgcagaagag cctctccctg tctccgggta aatga                  2385

<210> SEQ ID NO 839
<211> LENGTH: 794
<212> TYPE: PRT
<213> ORGANISM: Artificial Sequence
<220> FEATURE:
<223> OTHER INFORMATION: CysFc-044
<220> FEATURE:
<221> NAME/KEY: SIGNAL
<222> LOCATION: (1)..(20)
<220> FEATURE:
<221> NAME/KEY: SITE
<222> LOCATION: (243)..(246)
<223> OTHER INFORMATION: FURIN CLEAVAGE SITE
<220> FEATURE:
<221> NAME/KEY: SITE
<222> LOCATION: (278)..(283)
<223> OTHER INFORMATION: FURIN CLEAVAGE SITE
<220> FEATURE:
<221> NAME/KEY: SITE
<222> LOCATION: (538)..(567)
<223> OTHER INFORMATION: LINKER

<400> SEQUENCE: 839
```

```
Met Glu Thr Asp Thr Leu Leu Leu Trp Val Leu Leu Leu Trp Val Pro
1               5                   10                  15

Gly Ser Thr Gly Cys Pro Cys Pro Ala Pro Glu Leu Leu Gly Gly
            20              25                  30

Pro Ser Val Phe Leu Phe Pro Pro Lys Pro Lys Asp Thr Leu Met Ile
        35              40                  45

Ser Arg Thr Pro Glu Val Thr Cys Val Val Asp Val Ser His Glu
    50              55                  60

Asp Pro Glu Val Lys Phe Asn Trp Tyr Val Asp Gly Val Glu Val His
65              70                  75                  80

Asn Ala Lys Thr Lys Pro Arg Glu Glu Gln Tyr Asn Ser Thr Tyr Arg
            85                  90                  95

Val Val Ser Val Leu Thr Val Leu His Gln Asp Trp Leu Asn Gly Lys
            100                 105                 110

Glu Tyr Lys Cys Lys Val Ser Asn Lys Ala Leu Pro Ala Pro Ile Glu
            115                 120                 125

Lys Thr Ile Ser Lys Ala Lys Gly Gln Pro Arg Glu Pro Gln Val Tyr
        130                 135                 140

Thr Leu Pro Pro Ser Arg Asp Glu Leu Thr Lys Asn Gln Val Ser Leu
145                 150                 155                 160

Thr Cys Leu Val Lys Gly Phe Tyr Pro Ser Asp Ile Ala Val Glu Trp
                165                 170                 175

Glu Ser Asn Gly Gln Pro Glu Asn Asn Tyr Lys Thr Thr Pro Pro Val
            180                 185                 190

Leu Asp Ser Asp Gly Ser Phe Phe Leu Tyr Ser Lys Leu Thr Val Asp
        195                 200                 205

Lys Ser Arg Trp Gln Gln Gly Asn Val Phe Ser Cys Ser Val Met His
    210                 215                 220

Glu Ala Leu His Asn His Tyr Thr Gln Lys Ser Leu Ser Leu Ser Pro
225                 230                 235                 240

Gly Lys Arg Arg Arg Arg Ser Gly Gly Gly Ser Gly Gly Gly Gly
                245                 250                 255

Ser Gly Gly Gly Ser Gly Gly Gly Gly Ser Gly Gly Gly Gly Ser
            260                 265                 270

Gly Gly Gly Gly Ser Arg Lys Arg Arg Lys Arg Gln Val Lys Leu Leu
        275                 280                 285

Glu Ser Gly Gly Gly Val Val Gln Pro Gly Arg Ser Leu Arg Leu Ser
    290                 295                 300

Cys Ala Ala Ser Gly Phe Thr Phe Ser Ser Tyr Ala Met His Trp Val
305                 310                 315                 320

Arg Gln Ala Pro Gly Lys Gly Leu Glu Trp Val Ala Val Ile Ser Tyr
                325                 330                 335

Asp Gly Ser Asn Lys Tyr Tyr Ala Asp Ser Val Lys Gly Arg Phe Ala
            340                 345                 350

Ile Ser Arg Asp Asn Ser Lys Asn Thr Leu Tyr Leu Gln Met Asn Ser
        355                 360                 365

Leu Arg Ala Glu Asp Thr Ala Val Tyr Tyr Cys Ala Arg Ala Leu Gly
    370                 375                 380

Ser Trp Gly Gly Trp Asp His Tyr Met Asp Val Trp Gly Lys Gly Thr
385                 390                 395                 400

Thr Val Thr Val Ser Ser Gly Gly Gly Ser Gly Gly Gly Gly Ser
                405                 410                 415
```

Gly Gly Gly Gly Ser Gly Gly Gly Ser Val Val Thr Gln Pro Pro
            420                 425                 430

Ser Ala Ser Gly Thr Pro Gly Gln Arg Val Thr Ile Ser Cys Ser Gly
        435                 440                 445

Ser Ser Ser Asn Ile Gly Ser Asn Thr Val Asn Trp Tyr Gln Gln Leu
    450                 455                 460

Pro Gly Thr Ala Pro Lys Leu Leu Ile Tyr Ser Asn Asn Gln Arg Pro
465                 470                 475                 480

Ser Gly Val Pro Asp Arg Phe Ser Gly Ser Lys Ser Gly Thr Ser Ala
                485                 490                 495

Ser Leu Ala Ile Ser Gly Leu Gln Ser Glu Asp Glu Ala Asp Tyr Tyr
            500                 505                 510

Cys Ala Ala Trp Asp Asp Ser Leu Asn Gly Trp Val Phe Gly Gly Gly
        515                 520                 525

Thr Lys Leu Thr Val Leu Gly Gln Pro Gly Gly Gly Ser Gly Gly
    530                 535                 540

Gly Gly Ser Gly Gly Gly Ser Gly Gly Gly Ser Gly Gly
545                 550                 555                 560

Gly Ser Gly Gly Gly Ser Asp Lys Thr His Thr Cys Pro Pro Cys
            565                 570                 575

Pro Ala Pro Glu Leu Leu Gly Gly Pro Ser Val Phe Leu Phe Pro Pro
        580                 585                 590

Lys Pro Lys Asp Thr Leu Met Ile Ser Arg Thr Pro Glu Val Thr Cys
    595                 600                 605

Val Val Val Asp Val Ser His Glu Asp Pro Glu Val Lys Phe Asn Trp
610                 615                 620

Tyr Val Asp Gly Val Glu Val His Asn Ala Lys Thr Lys Pro Arg Glu
625                 630                 635                 640

Glu Gln Tyr Asn Ser Thr Tyr Arg Val Val Ser Val Leu Thr Val Leu
            645                 650                 655

His Gln Asp Trp Leu Asn Gly Lys Glu Tyr Lys Cys Lys Val Ser Asn
        660                 665                 670

Lys Ala Leu Pro Ala Pro Ile Glu Lys Thr Ile Ser Lys Ala Lys Gly
    675                 680                 685

Gln Pro Arg Glu Pro Gln Val Tyr Thr Leu Pro Pro Ser Arg Asp Glu
690                 695                 700

Leu Thr Lys Asn Gln Val Ser Leu Thr Cys Leu Val Lys Gly Phe Tyr
705                 710                 715                 720

Pro Ser Asp Ile Ala Val Glu Trp Glu Ser Asn Gly Gln Pro Glu Asn
            725                 730                 735

Asn Tyr Lys Thr Thr Pro Pro Val Leu Asp Ser Asp Gly Ser Phe Phe
        740                 745                 750

Leu Tyr Ser Lys Leu Thr Val Asp Lys Ser Arg Trp Gln Gln Gly Asn
    755                 760                 765

Val Phe Ser Cys Ser Val Met His Glu Ala Leu His Asn His Tyr Thr
770                 775                 780

Gln Lys Ser Leu Ser Leu Ser Pro Gly Lys
785                 790

<210> SEQ ID NO 840
<211> LENGTH: 32
<212> TYPE: PRT
<213> ORGANISM: Artificial Sequence
<220> FEATURE:
<223> OTHER INFORMATION: Synthetic

<400> SEQUENCE: 840

Ser Lys Gln Gly Arg Pro Ile Ser Pro Asp Arg Arg Ala Ala Gly Lys
1               5                   10                  15

Leu Thr Cys Leu Ala Ser Tyr Cys Trp Leu Phe Trp Thr Gly Ile Ala
            20                  25                  30

<210> SEQ ID NO 841
<211> LENGTH: 32
<212> TYPE: PRT
<213> ORGANISM: Artificial Sequence
<220> FEATURE:
<223> OTHER INFORMATION: Synthetic

<400> SEQUENCE: 841

Arg Arg Ala Pro Gly Lys Leu Thr Cys Leu Ala Ser Tyr Cys Trp Leu
1               5                   10                  15

Phe Gly Ser Gly Ile Ser Leu Ser Arg Ala Pro Glu Ser Ala Ala Pro
            20                  25                  30

<210> SEQ ID NO 842
<211> LENGTH: 32
<212> TYPE: PRT
<213> ORGANISM: Artificial Sequence
<220> FEATURE:
<223> OTHER INFORMATION: Synthetic

<400> SEQUENCE: 842

Arg Arg Phe Val Gly Gly Ser Leu Ser Gln Arg Arg Ala Pro Gly Lys
1               5                   10                  15

Leu Thr Cys Leu Ala Ser Tyr Cys Trp Leu Phe Trp Thr Gly Ile Ala
            20                  25                  30

<210> SEQ ID NO 843
<211> LENGTH: 32
<212> TYPE: PRT
<213> ORGANISM: Artificial Sequence
<220> FEATURE:
<223> OTHER INFORMATION: Synthetic

<400> SEQUENCE: 843

Pro Gln Thr Arg Asp Pro Ser Ser Arg Asp Arg Arg Ala Pro Gly Lys
1               5                   10                  15

Leu Thr Cys Leu Ala Ser Tyr Cys Trp Leu Phe Trp Thr Gly Ile Ala
            20                  25                  30

<210> SEQ ID NO 844
<211> LENGTH: 9
<212> TYPE: PRT
<213> ORGANISM: Artificial Sequence
<220> FEATURE:
<223> OTHER INFORMATION: FXIa cleavage site

<400> SEQUENCE: 844

Thr Gln Ser Phe Asn Asp Phe Thr Arg
1               5

<210> SEQ ID NO 845
<211> LENGTH: 10
<212> TYPE: PRT
<213> ORGANISM: Artificial Sequence
<220> FEATURE:
<223> OTHER INFORMATION: FXIa cleavage site

<400> SEQUENCE: 845

Ser Val Ser Gln Thr Ser Lys Leu Thr Arg
1               5                   10

<210> SEQ ID NO 846
<211> LENGTH: 10
<212> TYPE: PRT
<213> ORGANISM: Artificial Sequence
<220> FEATURE:
<223> OTHER INFORMATION: Thrombin cleavage site

<400> SEQUENCE: 846

Asp Phe Leu Ala Glu Gly Gly Gly Val Arg
1               5                   10

<210> SEQ ID NO 847
<211> LENGTH: 11
<212> TYPE: PRT
<213> ORGANISM: Artificial Sequence
<220> FEATURE:
<223> OTHER INFORMATION: Thrombin cleavage site

<400> SEQUENCE: 847

Asp Phe Leu Ala Glu Glu Gly Gly Gly Val Arg
1               5                   10

<210> SEQ ID NO 848
<211> LENGTH: 7
<212> TYPE: PRT
<213> ORGANISM: Artificial Sequence
<220> FEATURE:
<223> OTHER INFORMATION: Thrombin cleavage site

<400> SEQUENCE: 848

Thr Thr Lys Ile Lys Pro Arg
1               5

<210> SEQ ID NO 849
<211> LENGTH: 5
<212> TYPE: PRT
<213> ORGANISM: Artificial Sequence
<220> FEATURE:
<223> OTHER INFORMATION: Thrombin cleavage site

<400> SEQUENCE: 849

Ala Leu Val Pro Arg
1               5

<210> SEQ ID NO 850
<211> LENGTH: 5
<212> TYPE: PRT
<213> ORGANISM: Artificial Sequence
<220> FEATURE:
<223> OTHER INFORMATION: Thrombin cleavage site

<400> SEQUENCE: 850

Ala Leu Arg Pro Arg
1               5

<210> SEQ ID NO 851
<211> LENGTH: 10
<212> TYPE: PRT
<213> ORGANISM: Artificial Sequence
<220> FEATURE:
<223> OTHER INFORMATION: Thrombin cleavage site

<400> SEQUENCE: 851

```
Ala Leu Arg Pro Arg Val Val Gly Gly Ala
1               5                   10
```

<210> SEQ ID NO 852
<211> LENGTH: 32
<212> TYPE: PRT
<213> ORGANISM: Artificial Sequence
<220> FEATURE:
<223> OTHER INFORMATION: CTP peptide

<400> SEQUENCE: 852

```
Asp Pro Arg Phe Gln Asp Ser Ser Ser Ser Lys Ala Pro Pro Pro Ser
1               5                   10                  15

Leu Pro Ser Pro Ser Arg Leu Pro Gly Pro Ser Asp Thr Pro Ile Leu
            20                  25                  30
```

<210> SEQ ID NO 853
<211> LENGTH: 28
<212> TYPE: PRT
<213> ORGANISM: Artificial Sequence
<220> FEATURE:
<223> OTHER INFORMATION: CTP peptide

<400> SEQUENCE: 853

```
Ser Ser Ser Ser Lys Ala Pro Pro Pro Ser Leu Pro Ser Pro Ser Arg
1               5                   10                  15

Leu Pro Gly Pro Ser Asp Thr Pro Ile Leu Pro Gln
            20                  25
```

<210> SEQ ID NO 854
<211> LENGTH: 20
<212> TYPE: PRT
<213> ORGANISM: Artificial Sequence
<220> FEATURE:
<223> OTHER INFORMATION: PAS sequence

<400> SEQUENCE: 854

```
Ala Ser Pro Ala Ala Pro Ala Pro Ala Ser Pro Ala Ala Pro Ala Pro
1               5                   10                  15

Ser Ala Pro Ala
            20
```

<210> SEQ ID NO 855
<211> LENGTH: 20
<212> TYPE: PRT
<213> ORGANISM: Artificial Sequence
<220> FEATURE:
<223> OTHER INFORMATION: PAS seqeunce

<400> SEQUENCE: 855

```
Ala Ala Pro Ala Ser Pro Ala Pro Ala Ala Pro Ser Ala Pro Ala Pro
1               5                   10                  15

Ala Ala Pro Ser
            20
```

<210> SEQ ID NO 856
<211> LENGTH: 20
<212> TYPE: PRT
<213> ORGANISM: Artificial Sequence
<220> FEATURE:
<223> OTHER INFORMATION: PAS sequence

<400> SEQUENCE: 856

```
Ala Pro Ser Ser Pro Ser Pro Ser Ala Pro Ser Ser Pro Ser Pro Ala
1               5                   10                  15
```

Ser Pro Ser Ser
            20

<210> SEQ ID NO 857
<211> LENGTH: 19
<212> TYPE: PRT
<213> ORGANISM: Artificial Sequence
<220> FEATURE:
<223> OTHER INFORMATION: PAS sequence

<400> SEQUENCE: 857

Ala Pro Ser Ser Pro Ser Pro Ser Ala Pro Ser Ser Pro Ser Pro Ala
1               5                   10                  15

Ser Pro Ser

<210> SEQ ID NO 858
<211> LENGTH: 20
<212> TYPE: PRT
<213> ORGANISM: Artificial Sequence
<220> FEATURE:
<223> OTHER INFORMATION: PAS sequence

<400> SEQUENCE: 858

Ser Ser Pro Ser Ala Pro Ser Pro Ser Ser Pro Ala Ser Pro Ser Pro
1               5                   10                  15

Ser Ser Pro Ala
            20

<210> SEQ ID NO 859
<211> LENGTH: 24
<212> TYPE: PRT
<213> ORGANISM: Artificial Sequence
<220> FEATURE:
<223> OTHER INFORMATION: PAS sequence

<400> SEQUENCE: 859

Ala Ala Ser Pro Ala Ala Pro Ser Ala Pro Pro Ala Ala Ala Ser Pro
1               5                   10                  15

Ala Ala Pro Ser Ala Pro Pro Ala
            20

<210> SEQ ID NO 860
<211> LENGTH: 20
<212> TYPE: PRT
<213> ORGANISM: Artificial Sequence
<220> FEATURE:
<223> OTHER INFORMATION: PAS sequence

<400> SEQUENCE: 860

Ala Ser Ala Ala Ala Pro Ala Ala Ser Ala Ala Ser Ala Pro
1               5                   10                  15

Ser Ala Ala Ala
            20

<210> SEQ ID NO 861
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (12)..(12)
<223> OTHER INFORMATION: PEG

<400> SEQUENCE: 861

Lys Leu Thr Cys Leu Ala Ser Tyr Cys Trp Leu Phe
1               5                   10

<210> SEQ ID NO 862
<211> LENGTH: 21
<212> TYPE: PRT
<213> ORGANISM: Artificial Sequence
<220> FEATURE:
<223> OTHER INFORMATION: Synthetic

<400> SEQUENCE: 862

Gly Trp Lys Pro Phe Leu Trp Asp Pro Arg Val Leu Leu Ser Ser Gly
1               5                   10                  15

Trp Tyr Gly Arg Gly
            20

<210> SEQ ID NO 863
<211> LENGTH: 24
<212> TYPE: PRT
<213> ORGANISM: Artificial Sequence
<220> FEATURE:
<223> OTHER INFORMATION: Synthetic

<400> SEQUENCE: 863

Pro Trp Arg Arg Phe Trp Ala Trp Asn Pro Arg Ser Leu Ala Leu Ser
1               5                   10                  15

Thr Trp Phe Gly Arg Gly Cys Asp
            20

<210> SEQ ID NO 864
<211> LENGTH: 45
<212> TYPE: PRT
<213> ORGANISM: Artificial Sequence
<220> FEATURE:
<223> OTHER INFORMATION: Synthetic

<400> SEQUENCE: 864

Gly Trp Lys Pro Phe Leu Trp Asp Pro Arg Val Leu Leu Ser Ser Gly
1               5                   10                  15

Trp Tyr Gly Arg Gly Gly Gly Gly Gly Trp Lys Pro Phe Leu Trp Asp
            20                  25                  30

Pro Arg Val Leu Leu Ser Ser Gly Trp Tyr Gly Arg Gly
            35                  40                  45

<210> SEQ ID NO 865
<211> LENGTH: 75
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (22)..(22)
<223> OTHER INFORMATION: (NNB)5
<220> FEATURE:
<221> NAME/KEY: misc_feature
<222> LOCATION: (58)..(58)
<223> OTHER INFORMATION: (NNB)5

<400> SEQUENCE: 865
atgggcccag ccggccatgg caaagctgac gtgtctggcc agttattgtt ggctgttcgc    60
ggccgcaggt agcta                                                      75

```
<210> SEQ ID NO 866
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Fmoc-Cys(Acm)
<220> FEATURE:
<221> NAME/KEY: MISC_FEATURE
<222> LOCATION: (6)..(7)
<223> OTHER INFORMATION: Dphe-Pip-Arg(Pbf)

<400> SEQUENCE: 866

Cys Gly Gly Gly Gly Phe Arg
1               5

<210> SEQ ID NO 867
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Fmoc-Cys(Acm)
<220> FEATURE:
<221> NAME/KEY: MISC_FEATURE
<222> LOCATION: (6)..(7)
<223> OTHER INFORMATION: Dphe-Pip-Arg(Pbf)-PABOH

<400> SEQUENCE: 867

Cys Gly Gly Gly Gly Phe Arg
1               5

<210> SEQ ID NO 868
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Fmoc-Cys(Acm)
<220> FEATURE:
<221> NAME/KEY: MISC_FEATURE
<222> LOCATION: (6)..(7)
<223> OTHER INFORMATION: Dphe-Pip-Arg(Pbf)-PABC-PNP

<400> SEQUENCE: 868

Cys Gly Gly Gly Gly Phe Arg
1               5

<210> SEQ ID NO 869
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(6)
<223> OTHER INFORMATION: rRAPGK(Alloc)
<220> FEATURE:
<221> NAME/KEY: MISC_FEATURE
<222> LOCATION: (1)..(1)
<223> OTHER INFORMATION: D-amino acid

<400> SEQUENCE: 869
```

Arg Arg Ala Pro Gly Lys Leu Thr Cys Leu Ala Ser Tyr Cys Trp Leu
1               5                   10                  15

Phe Trp Thr Gly Ile Ala
            20

<210> SEQ ID NO 870
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Fmoc-Cys(Acm)
<220> FEATURE:
<221> NAME/KEY: MISC_FEATURE
<222> LOCATION: (6)..(7)
<223> OTHER INFORMATION: Dphe-Pip-Arg(Pbf)-PABC
<220> FEATURE:
<221> NAME/KEY: MISC_FEATURE
<222> LOCATION: (8)..(13)
<223> OTHER INFORMATION: rRAPGK(Alloc)
<220> FEATURE:
<221> NAME/KEY: MISC_FEATURE
<222> LOCATION: (8)..(8)
<223> OTHER INFORMATION: D-amino acid

<400> SEQUENCE: 870

Cys Gly Gly Gly Gly Phe Arg Arg Arg Ala Pro Gly Lys Leu Thr Cys
1               5                   10                  15

Leu Ala Ser Tyr Cys Trp Leu Phe Trp Thr Gly Ile Ala
            20                  25

<210> SEQ ID NO 871
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Fmoc-Cys(Acm)
<220> FEATURE:
<221> NAME/KEY: MISC_FEATURE
<222> LOCATION: (6)..(7)
<223> OTHER INFORMATION: Dphe-Pip-Arg-PABC
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (8)..(13)
<223> OTHER INFORMATION: rRAPGK(Alloc)

<400> SEQUENCE: 871

Cys Gly Gly Gly Gly Phe Arg Arg Arg Ala Pro Gly Lys Leu Thr Cys
1               5                   10                  15

Leu Ala Ser Tyr Cys Trp Leu Phe Trp Thr Gly Ile Ala
            20                  25

<210> SEQ ID NO 872
<211> LENGTH: 29
<212> TYPE: PRT
<213> ORGANISM: Artificial Sequence
<220> FEATURE:
<223> OTHER INFORMATION: Synthetic
<220> FEATURE:

```
<221> NAME/KEY: MISC_FEATURE
<222> LOCATION: (1)..(1)
<223> OTHER INFORMATION: Fmoc-Cys(Acm)
<220> FEATURE:
<221> NAME/KEY: MISC_FEATURE
<222> LOCATION: (6)..(7)
<223> OTHER INFORMATION: Dphe-Pip-Arg-PABC
<220> FEATURE:
<221> NAME/KEY: MISC_FEATURE
<222> LOCATION: (8)..(8)
<223> OTHER INFORMATION: D-amino acid

<400> SEQUENCE: 872

Cys Gly Gly Gly Gly Phe Arg Arg Arg Ala Pro Gly Lys Leu Thr Cys
1               5                   10                  15

Leu Ala Ser Tyr Cys Trp Leu Phe Trp Thr Gly Ile Ala
            20                  25

<210> SEQ ID NO 873
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Cys(Acm)
<220> FEATURE:
<221> NAME/KEY: MISC_FEATURE
<222> LOCATION: (6)..(7)
<223> OTHER INFORMATION: Dphe-Pip-Arg-PABC
<220> FEATURE:
<221> NAME/KEY: MISC_FEATURE
<222> LOCATION: (8)..(8)
<223> OTHER INFORMATION: D-amino acid

<400> SEQUENCE: 873

Cys Gly Gly Gly Gly Phe Arg Arg Arg Ala Pro Gly Lys Leu Thr Cys
1               5                   10                  15

Leu Ala Ser Tyr Cys Trp Leu Phe Trp Thr Gly Ile Ala
            20                  25

<210> SEQ ID NO 874
<211> LENGTH: 32
<212> TYPE: PRT
<213> ORGANISM: Artificial Sequence
<220> FEATURE:
<223> OTHER INFORMATION: Synthetic

<400> SEQUENCE: 874

Pro Arg Ile Arg Thr Val Gly Pro Gly Ser Arg Ser Ala Ser Gly Lys
1               5                   10                  15

Leu Thr Cys Leu Ala Ser Tyr Cys Trp Leu Phe Trp Thr Gly Ile Ala
            20                  25                  30

<210> SEQ ID NO 875
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Fmoc-Cys(Acm)
<220> FEATURE:
<221> NAME/KEY: MISC_FEATURE
<222> LOCATION: (6)..(7)
<223> OTHER INFORMATION: Dphe-Pip-Arg(Pbf)
```

<400> SEQUENCE: 875

Cys Gly Gly Gly Gly Phe Arg
1               5

<210> SEQ ID NO 876
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Fmoc-Cys(Acm)
<220> FEATURE:
<221> NAME/KEY: MISC_FEATURE
<222> LOCATION: (6)..(7)
<223> OTHER INFORMATION: Dphe-Pip-Arg(Pbf)-PABOH

<400> SEQUENCE: 876

Cys Gly Gly Gly Gly Phe Arg
1               5

<210> SEQ ID NO 877
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Fmoc-Cys(Acm)
<220> FEATURE:
<221> NAME/KEY: MISC_FEATURE
<222> LOCATION: (6)..(7)
<223> OTHER INFORMATION: Dphe-Pip-Arg(Pbf)-PABC-PNP

<400> SEQUENCE: 877

Cys Gly Gly Gly Gly Phe Arg
1               5

<210> SEQ ID NO 878
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (6)..(6)
<223> OTHER INFORMATION: allyloxycarbonyl

<400> SEQUENCE: 878

Arg Arg Ala Pro Gly Lys Leu Thr Cys Leu Ala Ser Tyr Cys Trp Leu
1               5                   10                  15

Phe Trp Thr Gly Ile Ala
            20

<210> SEQ ID NO 879
<211> LENGTH: 29
<212> TYPE: PRT
<213> ORGANISM: Artificial Sequence
<220> FEATURE:
<223> OTHER INFORMATION: Synthetic

```
<220> FEATURE:
<221> NAME/KEY: MISC_FEATURE
<222> LOCATION: (1)..(1)
<223> OTHER INFORMATION: Fmoc-Cys(Acm)
<220> FEATURE:
<221> NAME/KEY: MISC_FEATURE
<222> LOCATION: (6)..(7)
<223> OTHER INFORMATION: Dphe-Pip-Arg(Pbf)-PABC
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (8)..(13)
<223> OTHER INFORMATION: rRAPGK(Alloc)

<400> SEQUENCE: 879

Cys Gly Gly Gly Gly Phe Arg Arg Arg Ala Pro Gly Lys Leu Thr Cys
1               5                   10                  15

Leu Ala Ser Tyr Cys Trp Leu Phe Trp Thr Gly Ile Ala
            20                  25

<210> SEQ ID NO 880
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Fmoc-Cys(Acm)
<220> FEATURE:
<221> NAME/KEY: MISC_FEATURE
<222> LOCATION: (6)..(7)
<223> OTHER INFORMATION: Dphe-Pip-Arg-PABC
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (8)..(13)
<223> OTHER INFORMATION: rRAPGK(Alloc)

<400> SEQUENCE: 880

Cys Gly Gly Gly Gly Phe Arg Arg Arg Ala Pro Gly Lys Leu Thr Cys
1               5                   10                  15

Leu Ala Ser Tyr Cys Trp Leu Phe Trp Thr Gly Ile Ala
            20                  25

<210> SEQ ID NO 881
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Fmoc-Cys(Acm)
<220> FEATURE:
<221> NAME/KEY: MISC_FEATURE
<222> LOCATION: (6)..(7)
<223> OTHER INFORMATION: Dphe-Pip-Arg-PABC
<220> FEATURE:
<221> NAME/KEY: MISC_FEATURE
<222> LOCATION: (8)..(8)
<223> OTHER INFORMATION: D-amino acid

<400> SEQUENCE: 881
```

```
Cys Gly Gly Gly Gly Phe Arg Arg Arg Ala Pro Gly Lys Leu Thr Cys
1               5                   10                  15

Leu Ala Ser Tyr Cys Trp Leu Phe Trp Thr Gly Ile Ala
            20                  25

<210> SEQ ID NO 882
<211> LENGTH: 5
<212> TYPE: PRT
<213> ORGANISM: Artificial Sequence
<220> FEATURE:
<223> OTHER INFORMATION: Gly/Ser linker
<220> FEATURE:
<221> NAME/KEY: MISC_FEATURE
<222> LOCATION: (1)..(5)
<223> OTHER INFORMATION: where the sequence can be repeated up to 10
      times

<400> SEQUENCE: 882

Gly Gly Gly Gly Ser
1               5

<210> SEQ ID NO 883
<211> LENGTH: 6
<212> TYPE: PRT
<213> ORGANISM: Artificial Sequence
<220> FEATURE:
<223> OTHER INFORMATION: Gly/Ser linker
<220> FEATURE:
<221> NAME/KEY: MISC_FEATURE
<222> LOCATION: (2)..(6)
<223> OTHER INFORMATION: where the sequence can be repeated up to 10
      times

<400> SEQUENCE: 883

Ser Gly Gly Gly Gly Ser
1               5

<210> SEQ ID NO 884
<211> LENGTH: 30
<212> TYPE: PRT
<213> ORGANISM: Artificial Sequence
<220> FEATURE:
<223> OTHER INFORMATION: Gly/Ser linker

<400> SEQUENCE: 884

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 885
<211> LENGTH: 31
<212> TYPE: PRT
<213> ORGANISM: Artificial Sequence
<220> FEATURE:
<223> OTHER INFORMATION: Gly/Ser linker

<400> SEQUENCE: 885

Ser Gly Gly Gly Gly Ser Gly Gly Gly Gly Ser Gly Gly Gly Ser
1               5                   10                  15

Gly Gly Gly Gly Ser Gly Gly Gly Gly Ser Gly Gly Gly Gly Ser
            20                  25                  30

<210> SEQ ID NO 886
<211> LENGTH: 20
<212> TYPE: PRT
<213> ORGANISM: Artificial Sequence
```

<220> FEATURE:
<223> OTHER INFORMATION: Gly/Ser linker

<400> SEQUENCE: 886

Gly Gly Gly Gly Ser Gly Gly Gly Gly Ser Gly Gly Gly Gly Ser Gly
1               5                   10                  15

Gly Gly Gly Ser
            20

<210> SEQ ID NO 887
<211> LENGTH: 21
<212> TYPE: PRT
<213> ORGANISM: Artificial Sequence
<220> FEATURE:
<223> OTHER INFORMATION: Gly/Ser linker

<400> SEQUENCE: 887

Ser Gly Gly Gly Gly Ser Gly Gly Gly Gly Ser Gly Gly Gly Gly Ser
1               5                   10                  15

Gly Gly Gly Gly Ser
            20

<210> SEQ ID NO 888
<211> LENGTH: 5
<212> TYPE: PRT
<213> ORGANISM: Artificial Sequence
<220> FEATURE:
<223> OTHER INFORMATION: Gly/Ser linker
<220> FEATURE:
<221> NAME/KEY: MISC_FEATURE
<222> LOCATION: (1)..(5)
<223> OTHER INFORMATION: where the sequence can be repeated up to 50
      times

<400> SEQUENCE: 888

Gly Gly Ser Gly Gly
1               5

<210> SEQ ID NO 889
<211> LENGTH: 3
<212> TYPE: PRT
<213> ORGANISM: Artificial Sequence
<220> FEATURE:
<223> OTHER INFORMATION: Gly/Ser linker
<220> FEATURE:
<221> NAME/KEY: MISC_FEATURE
<222> LOCATION: (1)..(3)
<223> OTHER INFORMATION: where the sequence can be repeated up to 50
      times

<400> SEQUENCE: 889

Gly Gly Ser
1

<210> SEQ ID NO 890
<211> LENGTH: 4
<212> TYPE: PRT
<213> ORGANISM: Artificial Sequence
<220> FEATURE:
<223> OTHER INFORMATION: Gly/Ser linker
<220> FEATURE:
<221> NAME/KEY: MISC_FEATURE
<222> LOCATION: (1)..(4)
<223> OTHER INFORMATION: where the sequence can be repeated up to 50
      times

```
<400> SEQUENCE: 890

Gly Gly Gly Ser
1

<210> SEQ ID NO 891
<211> LENGTH: 5
<212> TYPE: PRT
<213> ORGANISM: Artificial Sequence
<220> FEATURE:
<223> OTHER INFORMATION: Gly/Ser linker
<220> FEATURE:
<221> NAME/KEY: MISC_FEATURE
<222> LOCATION: (1)..(5)
<223> OTHER INFORMATION: where the sequence can be repeated up to 50
      times

<400> SEQUENCE: 891

Gly Gly Gly Gly Ser
1               5

<210> SEQ ID NO 892
<211> LENGTH: 7
<212> TYPE: PRT
<213> ORGANISM: Artificial Sequence
<220> FEATURE:
<223> OTHER INFORMATION: Inverso variant
<220> FEATURE:
<221> NAME/KEY: MISC_FEATURE
<222> LOCATION: (1)..(1)
<223> OTHER INFORMATION: D-amino acid

<400> SEQUENCE: 892

Lys Cys Leu Ala Ser Tyr Cys
1               5

<210> SEQ ID NO 893
<211> LENGTH: 200
<212> TYPE: PRT
<213> ORGANISM: Artificial Sequence
<220> FEATURE:
<223> OTHER INFORMATION: HAP sequence

<400> SEQUENCE: 893

Gly Gly Gly Gly Gly Gly Gly Gly Gly Gly Gly Gly Gly Gly Gly Gly
1               5                   10                  15

Gly Gly Gly Gly Gly Gly Gly Gly Gly Gly Gly Gly Gly Gly Gly Gly
            20                  25                  30

Gly Gly Gly Gly Gly Gly Gly Gly Gly Gly Gly Gly Gly Gly Gly Gly
        35                  40                  45

Gly Gly Gly Gly Gly Gly Gly Gly Gly Gly Gly Gly Gly Gly Gly Gly
    50                  55                  60

Gly Gly Gly Gly Gly Gly Gly Gly Gly Gly Gly Gly Gly Gly Gly Gly
65                  70                  75                  80

Gly Gly Gly Gly Gly Gly Gly Gly Gly Gly Gly Gly Gly Gly Gly Gly
                85                  90                  95

Gly Gly Gly Gly Gly Gly Gly Gly Gly Gly Gly Gly Gly Gly Gly Gly
            100                 105                 110

Gly Gly Gly Gly Gly Gly Gly Gly Gly Gly Gly Gly Gly Gly Gly Gly
        115                 120                 125

Gly Gly Gly Gly Gly Gly Gly Gly Gly Gly Gly Gly Gly Gly Gly Gly
    130                 135                 140
```

```
Gly Gly Gly Gly Gly Gly Gly Gly Gly Gly Gly Gly Gly Gly Gly Gly
145                 150                 155                 160

Gly Gly Gly Gly Gly Gly Gly Gly Gly Gly Gly Gly Gly Gly Gly
            165                 170                 175

Gly Gly Gly Gly Gly Gly Gly Gly Gly Gly Gly Gly Gly Gly Gly
            180                 185                 190

Gly Gly Gly Gly Gly Gly Gly Gly
        195                 200

<210> SEQ ID NO 894
<211> LENGTH: 7
<212> TYPE: PRT
<213> ORGANISM: Artificial Sequence
<220> FEATURE:
<223> OTHER INFORMATION: Retro-variant
<220> FEATURE:
<221> NAME/KEY: MISC_FEATURE
<222> LOCATION: (7)..(7)
<223> OTHER INFORMATION: D-amino acid

<400> SEQUENCE: 894

Cys Tyr Ser Ala Leu Cys Lys
1               5

<210> SEQ ID NO 895
<211> LENGTH: 12
<212> TYPE: PRT
<213> ORGANISM: Artificial Sequence
<220> FEATURE:
<223> OTHER INFORMATION: Synthetic

<400> SEQUENCE: 895

Lys Leu Thr Cys Leu Ala Ser Tyr Cys Trp Leu Phe
1               5                   10

<210> SEQ ID NO 896
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: REPEAT
<222> LOCATION: (1)..(12)
<220> FEATURE:
<221> NAME/KEY: MISC_FEATURE
<222> LOCATION: (12)..(12)
<223> OTHER INFORMATION: =N-O-(CH2)3-O-N=

<400> SEQUENCE: 896

Lys Leu Thr Cys Leu Ala Ser Tyr Cys Trp Leu Phe
1               5                   10

<210> SEQ ID NO 897
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: REPEAT
<222> LOCATION: (1)..(13)
<220> FEATURE:
<221> NAME/KEY: MISC_FEATURE
<222> LOCATION: (13)..(13)
<223> OTHER INFORMATION: =N-O-(CH2)3-O-N=
```

<400> SEQUENCE: 897

Lys Leu Thr Cys Leu Ala Ser Tyr Cys Trp Leu Phe Gly
1               5                   10

<210> SEQ ID NO 898
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: COCH2CH2CO
<220> FEATURE:
<221> NAME/KEY: REPEAT
<222> LOCATION: (1)..(12)
<220> FEATURE:
<221> NAME/KEY: MISC_FEATURE
<222> LOCATION: (12)..(12)
<223> OTHER INFORMATION: CONH2
<220> FEATURE:
<221> NAME/KEY: MISC_FEATURE
<222> LOCATION: (12)..(12)
<223> OTHER INFORMATION: =N-O-(CH2)3-O-N=

<400> SEQUENCE: 898

Lys Leu Thr Cys Leu Ala Ser Tyr Cys Trp Leu Phe
1               5                   10

<210> SEQ ID NO 899
<211> LENGTH: 19
<212> TYPE: DNA
<213> ORGANISM: Artificial Sequence
<220> FEATURE:
<223> OTHER INFORMATION: Synthetic

<400> SEQUENCE: 899
atgggcccag ccggccatg                                              19

<210> SEQ ID NO 900
<211> LENGTH: 4
<212> TYPE: PRT
<213> ORGANISM: Artificial Sequence
<220> FEATURE:
<223> OTHER INFORMATION: PCSK5 enzymatic cleavage site

<400> SEQUENCE: 900

Arg Arg Arg Arg
1

<210> SEQ ID NO 901
<211> LENGTH: 6
<212> TYPE: PRT
<213> ORGANISM: Artificial Sequence
<220> FEATURE:
<223> OTHER INFORMATION: PCSK5 enzymatic cleavage site

<400> SEQUENCE: 901

Arg Lys Arg Arg Lys Arg
1               5

<210> SEQ ID NO 902
<211> LENGTH: 17
<212> TYPE: DNA
<213> ORGANISM: Artificial Sequence
<220> FEATURE:
<223> OTHER INFORMATION: Synthetic

```
<400> SEQUENCE: 902
tagctacctg cggccgc                                                17

<210> SEQ ID NO 903
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = any amino acid having a side chain
<220> FEATURE:
<221> NAME/KEY: MISC_FEATURE
<222> LOCATION: (6)..(6)
<223> OTHER INFORMATION: Xaa = any amino acid having a side chain

<400> SEQUENCE: 903

Xaa Leu Ala Ser Tyr Xaa
1               5

<210> SEQ ID NO 904
<211> LENGTH: 32
<212> TYPE: PRT
<213> ORGANISM: Artificial Sequence
<220> FEATURE:
<223> OTHER INFORMATION: SYN4002
<220> FEATURE:
<221> NAME/KEY: MISC_FEATURE
<222> LOCATION: (1)..(1)
<223> OTHER INFORMATION: having a L-propargylglycine-PEG4 side chain
<220> FEATURE:
<221> NAME/KEY: MISC_FEATURE
<222> LOCATION: (32)..(32)
<223> OTHER INFORMATION: having an amine side chain

<400> SEQUENCE: 904

Pro Arg Ile Arg Thr Val Gly Pro Gly Ser Arg Ser Ala Ser Gly Lys
1               5                   10                  15

Leu Thr Cys Leu Ala Ser Tyr Cys Trp Leu Phe Trp Thr Gly Ile Ala
            20                  25                  30
```

PRO-COAGULANT COMPOUNDS AND METHODS OF USE THEREOF

CROSS-REFERENCE TO ELECTRONICALLY SUBMITTED SEQUENCE LISTING VIA EFS-WEB

The content of the electronically submitted substitute sequence listing (Name: 2159.1380007_SL_ST25.txt, Size: 434,176 bytes; and Date of Creation: Aug. 31, 2015) submitted herewith, is incorporated herein by reference in its entirety.

BACKGROUND OF THE INVENTION

1. Field of the Invention

The present invention relates to pro-coagulant compounds useful for the treatment of coagulation disorders, such as hemophilia A and B.

2. Background of the Invention

The blood coagulation pathway, in part, involves the formation of an enzymatic complex of Factor VIIIa. (FVIIIa) and Factor IXa (FIXa) (Xase complex) on the surface of platelets. FIXa is a serine protease with relatively weak catalytic activity without its cofactor FVIIIa. The Xase complex cleaves Factor X (FX) into Factor Xa (FXa), which in turn interacts with Factor Va (FVa) to cleave prothrombin and generate thrombin.

Hemophilia A is a bleeding disorder caused by mutations and/or deletions in the Factor VIII (FVIII) gene resulting in a deficiency of FVIII activity. In some cases, patients have reduced levels of FVIII due to the presence of FVIII inhibitors, such as anti-FVIII antibodies.

Hemophilia A is characterized by spontaneous hemorrhage and excessive bleeding after trauma. Over time, the repeated bleeding into muscles and joints, which often begins in early childhood, results in hemophilic arthropathy and irreversible joint damage. This damage is progressive and can lead to severely limited mobility of joints, muscle atrophy and chronic pain (Rodriguez-Merchan, E. C., *Semin. Thromb. Hemost.* 29:87-96 (2003), which is herein incorporated by reference in its entirety).

The disease can be treated by replacement therapy targeting restoration of FVIII activity to 1 to 5% of normal levels to prevent spontaneous bleeding (see, e.g., Mannucci, P. M., et al., *N. Engl. J. Med.* 344:1773-9 (2001), herein incorporated by reference in its entirety). There are plasma-derived and recombinant FVIII products available to treat bleeding episodes on-demand or to prevent bleeding episodes from occurring by treating prophylactically. Based on the half-life of these products (10-12 hr) (White G. C., et al., *Thromb. Haemost.* 77:660-7 (1997); Morfini, M., *Haemophilia* 9 (suppl 1):94-99; discussion 100 (2003)), treatment regimens require frequent intravenous administration, commonly two to three times weekly for prophylaxis and one to three times daily for on-demand treatment (Manco-Johnson, M. J., et al., *N. Engl. J. Med.* 357:535-544 (2007)), each of which is incorporated herein by reference in its entirety. Such frequent administration is painful and inconvenient.

Although on-demand treatment is frequently used, there is a trend toward prophylaxis and the prevention of joint damage (Blanchette P, et al., *Haemophilia* 2004: 10;679-683, Manco-Johnson, M J, et al., *N. Engl. J. Med.* 2007; 357:535-544). Current FVIII products are administered every two to three days for prophylaxis due to the relatively short half-life of 10-12 hr in order to maintain a FVIII:C above 1 in patients (Morfini, M, *Haemophilia* 2003; 9 (suppl 1):94-99; discussion 100, White G C, et al., *Thromb. Haemost.* 1997:77:660-7, Blanchette, P, et al., *J. Thromb. Haemost.* 2008 August;6(8):1319-26). Longer-acting FVIII therapies that provide prolonged protection from bleeding would represent an improvement in the quality of life for patients with hemophilia A.

Strategies to extend the half-life of clotting factors include pegylation (Rostin J, et al., *Biocoj. Chem.* 2000; 11:387-96), glycopegylation (Stennicke H R, et al., *Thromb. Haemost.* 2008; 100:920-8), formulation with pegylated liposomes (Spira J, et al., *Blood* 2006;108:3668-3673, Pan J, et al., *Blood* 2009;114:2802-2811) and conjugation with albumin (Schulte S., *Thromb. Res.* 2008; 122 Suppl 4:S14-9).

D K Liles et al. (1997) *Blood* Vol 90 No 10 Supplement 1 (463a, poster abstract) discloses a peptide from FVIII which can promote FIXa mediated activation of FX on a phospholipid surface. However, in the presence of the peptide inhibits FIXa mediated activation of FX. A peer-reviewed publication by these authors confirming the disclosed results was not available at time of this application.

Blostein et al (2000) *Biochemistry* 39:12000-12006 discloses that amphipathic alpha helices can interact with FIXa Gla domains and increases activation of FX in the absence of phospholipid.

Under normal conditions, activated platelets provide the lipid surface supporting coagulation. Since platelets are activated by thrombin, which is formed at sites of vascular injury, coagulation processes are restricted to the sites of injuries. However, it is undesirable to provide the body with peptides that are general substitutes for procoagulant lipids as this would cause systemic coagulation and ultimately lead to disseminated intravascular coagulation (DIC).

U.S. Pat. Nos. 7,109,170 and 6,624,289 disclose regions of the FIXa protease domain that interact with FVIIIa and that comprise the FVIIIa binding site of FIXa. The peptides inhibit binding of FIXa to FVIIIa. The disclosed peptides may be useful as anticoagulants for preventing or treating thrombosis.

US20010014456A1 discloses binding molecules for human FVIII and FVIII-like proteins. These polypeptides bind FVIII and/or FVIII-like polypeptides and are useful for the detection and purification of human FVIII and/or FVIII-like polypeptides from solutions such as blood or conditioned media.

In U.S. Pat. No. 7,033,590 FIX/FIXa activating antibodies and antibody derivatives are used for increasing the amidolytic activity of FIXa, and for treating blood coagulation disorders such as hemophilia A and hemorrhagic diathesis.

U.S. Pat. No. 7,084,109 discloses FVIIIa antagonists that are peptides and inhibit FVIIa activity. The peptides may be useful for the prevention of arterial thrombosis in combination with thrombolytic therapy.

Hemophilia B (also known as Christmas disease) is one of the most common inherited bleeding disorders in the world. It results in decreased in vivo and in vitro blood clotting activity and requires extensive medical monitoring throughout the life of the affected individual.

In the absence of intervention, the afflicted individual may suffer from spontaneous bleeding in the joints, which produces severe pain and debilitating immobility. Bleeding into muscles results in the accumulation of blood in those tissues. Spontaneous bleeding in the throat and neck may cause asphyxiation if not immediately treated. Bleeding into the urine, and severe bleeding following surgery, minor accidental injuries, or dental extractions also are prevalent.

Hemophilia B is caused by a deficiency in Factor IX that may result from either the decreased synthesis of the Factor IX protein or a defective molecule with reduced activity.

Human FIX, one member of the group of vitamin K-dependent polypeptides, is a single-chain glycoprotein with a molecular weight of 57 kDa, which is secreted by liver cells into the blood stream as an inactive zymogen of 415 amino acids. It contains 12 γ-carboxy-glutamic acid residues localized in the N-terminal Gla-domain of the polypeptide. The Gla residues require vitamin K for their biosynthesis. Following the Gla domain there are two epidermal growth factor domains, an activation peptide, and a trypsin-type serine protease domain. Further posttranslational modifications of FIX encompass hydroxylation (Asp 64), N-(Asn157 and Asn167) as well as O-type glycosylation (Ser53, Ser61, Thr159, Thr169, and Thr172), sulfation (Tyr155), and phosphorylation (Ser158). FIX is converted to its active form, Factor IXa, by proteolysis of the activation peptide at Arg145-Ala146 and Arg180-Val181 leading to the formation of two polypeptide chains, an N-terminal light chain (18 kDa) and a C-terminal heavy chain (28 kDa), which are held together by one disulfide bridge. Activation cleavage of Factor IX can be achieved in vitro e.g. by Factor XIa or Factor VIIa/TF. Factor IX is present in human plasma in a concentration of 5-10 µg/ml. Terminal plasma half-life of Factor IX in humans was found to be about 15 to 18 hours (White G C et al. 1997. Recombinant factor IX. *Thromb Haemost.* 78: 261-265; Ewenstein B M et al. 2002. Pharmacokinetic analysis of plasma-derived and recombinant F IX concentrates in previously treated patients with moderate or severe hemophilia B. *Transfusion* 42:190-197).

The treatment of hemophilia B occurs by replacement of the missing clotting factor by exogenous factor concentrates highly enriched in Factor IX. However, generating such a concentrate from blood is difficult. Purification of Factor IX from plasma (plasma derived Factor IX; pdFIX) almost exclusively yields active Factor IX. However, such purification of FIX from plasma is very difficult because FIX is only present in low concentration in plasma (Andersson, Thrombosis Research 7: 451 459 (1975). Further, purification from blood requires the removal or inactivation of infectious agents such as HIV and HCV. In addition, pdFIX has a short half-life and therefore requires frequent dosing. Recombinant FIX (rFIX) is also available, but suffers from the same short half-life and need for frequent dosing (e.g., 2-3 times per week for prophylaxis) as pdFIX.

A recombinant FVIIa product is marketed by Novo Nordisk (NovoSeven).

Reduced mortality, prevention of joint damage and improved quality of life have been important achievements due to the development of plasma-derived and recombinant clotting factors. Prolonged protection from bleeding would represent another key advancement in the treatment of hemophilia patients. However, to date, no products that allow for prolonged protection have been developed.

However, there remains a great need for improved pro-coagulant therapies for the treatment (e.g., prophylactic treatment) of hemophilia and other blood coagulation disorders that are more tolerable and more effective than current therapies. Small-molecule therapies, which can be administered by a non-intravenous route are particularly useful.

BRIEF SUMMARY OF THE INVENTION

The present invention provides low molecular weight compounds (e.g., peptides or peptide derivatives) with pro-coagulant activity useful for the treatment (e.g., intravenous or non-intravenous treatment) of bleeding diathesis (e.g., blood coagulation disorders/coagulopathies, such as hemophilia A and hemophilia B) or for the treatment of deficiencies in at least one of Factor V (FV), Factor FVII (FVII), Factor VIII (FVIII), Factor IX (FIX), Factor X (FX), Factor XI (FXI), Factor XII (FXII), Factor XIII (FXIII), and von Willebrand Factor (vWF). In one example, the current compounds exhibit greater in vivo stability than known treatments (e.g., FVIII, FIX, or FVIIa) and have the potential to significantly reduce the cost of treating coagulation disorders.

In various embodiments, the compounds of the present invention are capable of increasing the catalytic activity of a blood coagulation factor (e.g., FIXa or FVIIa). In other embodiments, the compounds of the invention exhibit biological activity in the presence of FVIII (i.e., possess additive activity with FVIII). In another example, the current compounds are useful for the treatment of impaired coagulation in FVIII inhibitor patients.

The present disclosure further provides conjugates containing a polypeptide selected from blood coagulation factors (e.g., FVIII, FIX, FVIIa), and platelet targeting moieties (e.g., PDG-13), wherein the polypeptide is linked to a compound of the present disclosure (e.g., a pro-coagulant peptide or a peptide derivative), optionally via a linker. The present disclosure further provides conjugates wherein a compound (e.g., a peptide or peptide derivative) has pro-coagulant activity.

The present invention provides a compound (e.g., a peptide or peptide derivative) comprising: (a) an amino acid sequence comprising Formula (I):

$C^1LASYC^2$ (SEQ ID NO: 903)    (I)

or (b) a retro-, an inverso- or a retro-inverso variant of the amino acid sequence of (a). A compound can be present as a pharmaceutically acceptable salt. In Formula (I), L is L-leucine; A is L-alanine; S is L-serine; Y is L-tyrosine, wherein one or two of L, A, S, and Y are optionally replaced with a replacement amino acid independently selected from D- and L-amino acids. Exemplary amino acids and replacement amino acids for L, A, S, and Y are described herein.

In some embodiments, a compound of the present invention includes at least 9 and not more than about 500 amino acid residues. In some embodiments, a compound of the present invention includes at least 12 and not more than about 100 amino acid residues. Other suitable ranges for the number of amino acids in the compounds of the present disclosure are described herein.

In Formula (I), $C^1$ and $C^2$ are independently selected from amino acids having a side chain, wherein the side chains of $C^1$ and $C^2$ are linked to form a loop. In one example, $C^1$ and $C^2$ are independently selected from amino acids having a side chain comprising a —S—H group, and wherein the side chains of $C^1$ and $C^2$ are reversibly linked via a disulfide bond. In another example, the side chains of $C^1$ and $C^2$ are covalently linked via an amide bond to form a lactam ring. In yet another example, the side chains of $C^1$ and $C^2$ are covalently linked via an optionally substituted triazole moiety.

The invention further provides a compound (e.g., a peptide or peptide derivative) containing an amino acid sequence having $C^1$ and $C^2$, wherein $C^1$ and $C^2$ are independently selected amino acids having a side chain, wherein the side chains of $C^1$ and $C^2$ are linked, and wherein $C^1$ and $C^2$ are separated by 4, 5 or 6 amino acids, wherein a compound includes at least 9 and not more than 500 amino acids. In one embodiment, $C^1$ and $C^2$ are separated by 4 amino acids.

In one example, compounds of the present disclosure have an $EC_{50}$ of about 5 μM or less in a Factor Xa (FXa) generation assay measuring conversion of Factor X (FX) to FXa (e.g., in the presence of FIXa). A suitable FXa generation assay is described in Example 2 of this application. In a particular example, a compound has an $EC_{50}$ of about 1 μM or less (e.g., 200 nM or less). Certain compounds of the present disclosure, at a concentration of 5 μM or less, increase the catalytic activity ($k_{cat}$) of at least one blood coagulation factor (e.g., FIXa or FVIIa). For example, compounds of the present disclosure, at a concentration of 5 μM or less, increase the catalytic activity ($k_{cat}$) of Factor IXa (FIXa) or FVIIa for conversion of FX to FXa in a FXa generation assay when compared to a reference catalytic activity of the FIXa or the FVIIa measured in the absence of the compound. In one example, a compound increases the catalytic activity ($k_{cat}$) of FIXa by at least 50 fold or at least 100 fold.

In another example, a compound increases the catalytic activity ($k_{cat}$) of FVIIa by at least 200 fold, at least 400 fold or at least 1000 fold.

The invention further provides polypeptide conjugates comprising (a) a polypeptide selected from FVIII, FIX, FVIIa, and platelet targeting moieties, and (b) a compound of the present disclosure, wherein the compound is linked to the polypeptide, optionally via a linker.

The compounds and conjugates of the present disclosure, upon administration to a human or other animal, may produce an augmented prophylactic or therapeutic effect, lower dosing and/or dosing frequency of coagulation factors, or increased specific activity and catalytic activity of the coagulation factors.

The invention further provides a pharmaceutical composition containing at least one compound or conjugate of the present disclosure and a pharmaceutically acceptable carrier. Suitable pharmaceutically acceptable carriers are described herein.

The invention further provides a method of increasing the catalytic activity ($k_{cat}$) of a blood coagulation factor (e.g., FIXa or FVIIa). The method includes contacting the blood coagulation factor (in vitro or in vivo) with a compound or conjugate of the present disclosure. In one example, a compound or conjugate interacts with the blood coagulation factor at a region corresponding to amino acid sequence: MFCAG (SEQ ID NO: 1). In a particular example, the blood coagulation factor that is contacted with a compound or conjugate of the present disclosure is FIXa or FVIIa.

The invention further provides a method for treating bleeding diathesis in a mammalian subject (e.g., a human subject). An exemplary method includes administering to the subject a therapeutically effective amount of a compound or conjugate of the present disclosure or a pharmaceutical composition of the present disclosure. In one example, the bleeding diathesis is caused by a blood coagulation disorder, such as hemophilia (e.g., hemophilia A) or von Willebrand disease (vWD).

The invention further provides methods for making the compounds and conjugates of the present disclosure. An exemplary method includes forming a peptide incorporating a desired amino sequence (or a retro-, inverso- or retro-inverso variant thereof) using solid-phase peptide synthesis. In one example, the method further includes covalently linking the peptide to a heterologous moiety that can extend the half-life of a compound, e.g., selected from a PEG moiety, Fc, IgG, FcRn binding ligand, albumin, albumin-binding ligand, transferrin, PAS, a half-life extension polypeptide (i.e., XTEN), or a hydroxyethyl starch

BRIEF DESCRIPTION OF THE FIGURES

In FIGS. 9 to 12, the processing can involve intracellular activation/processing, which may be accomplished, e.g., by co-transfection of processing enzymes such as PC5 and PACE.

Figure 1:
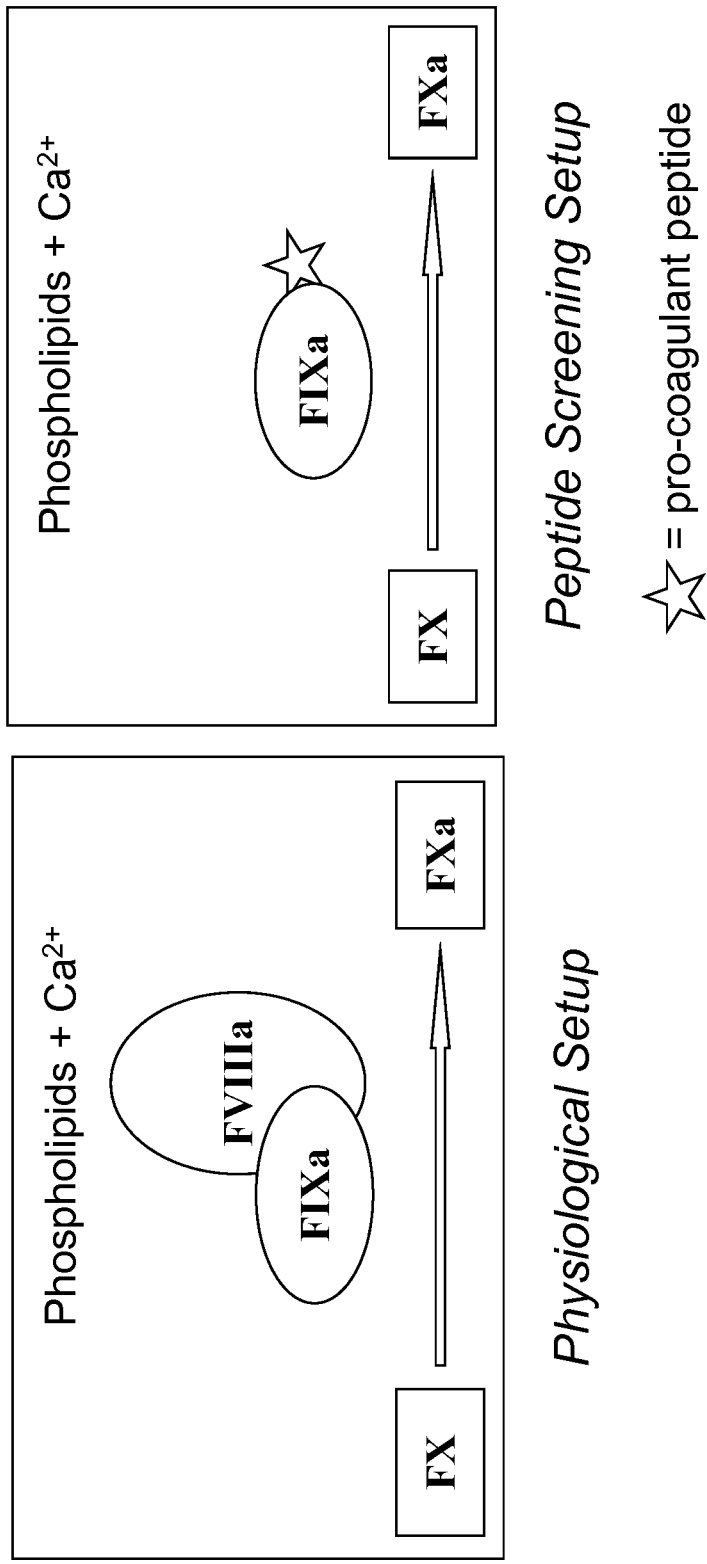
FIG. 1 is a scheme illustrating an exemplary FXa generation assay. In one example, the FXa generation assay is performed using human FIXa (hFIXa), e.g., at 10 nM, and human FX (hFX), e.g., at 100 nM. In another example, the FXa generation assay is performed using human FVIIa (hFVIIa) and human FX (hFX).

The present disclosure also provides a compound that includes:
(a) an amino acid sequence including Formula (I):

$C^1$LASY$C^2$ (SEQ ID NO: 903)     (I)

(b) a retro-, an inverso- or a retro-inverso variant of the amino acid sequence of (a). The present disclosure further provides pharmaceutically acceptable salts or solvates of the above compound.

In Formula (I), $C^1$ and $C^2$ are amino acids having a side chain, wherein the side chains of $C^1$ and $C^2$ are linked to form a loop. In one example, the side chains of $C^1$ and $C^2$ are covalently linked (e.g., via a disulfide bond or an amide bond).

In one example. In Formula (I), one, two or three additional amino acids can be inserted anywhere between $C^1$ and $C^2$. In one example according to any of the above embodiments, one or two additional amino acids are optionally inserted into Formula (I) anywhere between $C^1$ and $C^2$. In another example, one amino acid is optionally inserted into Formula (I) anywhere between $C^1$ and $C^2$. In another example, $C^1$ and $C^2$ are separated by exactly 4 amino acids.

In Formula (I), L is L-leucine, A is L-alanine, S is L-serine, and Y is L-tyrosine. In Formula (I), one, two or three of L, A, S, and Y are optionally replaced with an independently selected replacement amino acid. In one example, one or two of L, A, S, and Y are optionally replaced with an independently selected replacement amino acid. In another example, exactly one of L, A, S, and Y is optionally replaced with an independently selected replacement amino acid. In one example, the amino acid sequence of a compound includes the sequence CLASYC (SEQ ID NO: 782).

In one example, each replacement amino acid is independently selected from L- and D-amino acids. In another example, the replacement amino acid is a proteinogenic amino acid. In another example, the replacement amino acid is a non-proteinogenic amino acid. Exemplary non-proteinogenic amino acids are described herein and include, e.g., homo-analogs, such as homo-phenylalanine, and homo-cysteine. In yet another example, the replacement amino acid is a modified amino acid (including modified proteinogenic and modified non-proteinogenic amino acids). Examples of modified amino acids include, e.g., alpha-N-alkylated amino acids, tyrosine derivatives (e.g., those in which the hydroxyl group is converted to an ether or ester group), lysine derivatives (e.g., those in which the $NH_2$ group is converted to an amide group or sulfonamide group), and amino acids, in which a carboxylic acid group is derivatized, e.g., esterified, converted to an amide group, and the like. Other examples of suitable replacement amino acids are disclosed herein. In one example, L, A, S and Y are selected from amino acids other than those having a side chain comprising a —S—H group or a —Se—H group (e.g., other than cysteine).

In one example in Formula (I), $C^1$ and $C^2$ are independently selected from amino acids having a side chain comprising a —S—H group or a —Se—H group and the side chains of $C^1$ and $C^2$ are linked (e.g., reversibly linked) via a disulfide bond (—S—S—), a diselenide bond (—Se—Se—), a —Se—S— or a —S—Se— bond. In another example in Formula (I), $C^1$ and $C^2$ are independently selected from cysteine, homo-cysteine (HCy), seleno-cysteine (U), homo-seleno cysteine, and D-amino acids thereof. In another example in Formula (I), $C^1$ is selected from cysteine, homo-cysteine (HCy), seleno-cysteine (U), homo-seleno cysteine, and D-amino acids thereof. In another example in Formula (I), $C^2$ is selected from L-cysteine, L-homo-cysteine (HCy), L-seleno-cysteine (U), and L-homo-seleno cysteine. In yet another example, $C^1$ in Formula (I) is selected from cysteine, homo-cysteine (HCy), seleno-cysteine (U), homo-seleno cysteine, and D-amino acids thereof, and $C^2$ is selected from L-cysteine, L-homo-cysteine (HCy), L-seleno-cysteine (U), and L-homo-seleno cysteine.

In one example in Formula (I), $C^1$ and $C^2$ are independently selected from amino acids having a side chain comprising a —S—H group, wherein the side chains of $C^1$ and $C^2$ are linked (e.g., reversibly linked) via a disulfide bond. In another example, $C^1$ and $C^2$ are independently selected from cysteine and homo-cysteine. In yet another example, $C^1$ and $C^2$ are both cysteine. In yet another example in Formula (I), $C^1$ is selected from L-cysteine and D-cysteine. In yet another example in Formula (I), $C^2$ is L-cysteine. In another example in Formula (I), $C^1$ is selected from L-cysteine and D-cysteine, and $C^2$ is L-cysteine.

The covalent linkage between the side chains of $C^1$ and $C^2$ can be reversible. In one example according to the above embodiments in which $C^1$ and $C^2$ are selected from amino acids having a side chain incorporating a —SH or Se—H group, a certain percentage (e.g., less than 50%, less than about 40%, less than about 30%, less than about 20%, less than about 10%, less than about 8%, less than about 6%, less than about 4%, or less than about 2%) of a compound can exists in an open form (i.e., in which the side chains of $C^1$ and $C^2$ are not linked to form a loop). Thus, those linkages are referred to as being reversible. For example, when side chains of $C^1$ and $C^2$ comprise an —SH group (e.g., cysteine), then $C^1$ and $C^2$ can be reversibly linked by a disulfide bond, wherein some molecules exist in an open form, but wherein the majority will be covalently linked by a disulfide bond. Whether or not the side chains of $C^1$ and $C^2$ are covalently linked can depend on the chemical environment in which a compound exists. For example, in a reducing environment, a disulfide bond may be broken or may not be formed.

In one example according to any of the above embodiments, the side chains of $C^1$ and $C^2$ in are covalently linked via an amide bond to form a lactam ring. In one embodiment according to this example, one of $C^1$ and $C^2$ is selected from amino acids having a side chain with a primary or secondary amino group (e.g., —$NH_2$ group), and the other of $C^1$ and $C^2$ is selected from an amino acid with a side chain having a carboxylic acid group (e.g., —COOH group), wherein the amino group and the carboxylic acid group form an amide bond. Methods for the formation of amide bonds between the side chains of $C^1$ and $C^2$ are described herein (see, e.g., Example 1). For example, the carboxylic acid group can first be activated prior to reaction with the amino group.

In another example according to any of the above embodiments, one of $C^1$ and $C^2$ is selected from amino acids having a straight or branched aminoalkyl, e.g., $(C_1\text{-}C_{10})$aminoalkyl, side chain, and the other of $C^1$ and $C^2$ is selected from amino acids having a straight or branched carboxyalkyl, e.g., $(C_1\text{-}C_{10})$carboxyalkyl, side chain, wherein an amino group of the aminoalkyl side chain and a carboxylic acid group of the carboxyalkyl side chain are linked to form an amide bond. In yet another example, one of $C^1$ and $C^2$ is selected from lysine (2,6-diamino-hexanoic acid), 2,5-diamino-pentanoic acid (ornithine; Orn), 2,4-diamino-butyric acid (Dab), 2,3-diamino-propionic acid (Dpr), 2,7-diamino-heptanoic acid, and 2,8-diamino-octanoic acid, and the other of $C^1$ and $C^2$ is selected from aspartic acid, glutamic acid (2-aminopentanedioic acid), 2-amino-hexanedioic acid, 2-aminoheptanedioic acid, and 2-amino-octanedioic acid.

In yet another example according to any of the above embodiments, one of $C^1$ and $C^2$ is selected from lysine (K), 2,4-diaminobutyric acid (Dab), 2,3-diaminoproprionic acid (Dpr), and ornithine (Orn), and the other of $C^1$ and $C^2$ is selected from aspartic acid and glutamic acid. In another example, one of $C^1$ and $C^2$ is lysine and the other of $C^1$ and $C^2$ is selected from aspartic acid and glutamic acid.

In a further example, the side chains of $C^1$ and $C^2$ are covalently linked via a triazole moiety. The triazole moiety can optionally be substituted, e.g., with alkyl, e.g., $(C_1-C_4)$ alkyl, or $OR^9$, wherein $R^9$ is selected from H and $(C_1-C_4)$ alkyl. Methods to form a triazole moiety are known to those of skill in the art (see e.g., Holland-Nell, K, and Meldal, M; *Angew. Chem Int. Ed.* 2011, 50: 5204-5206 and references cited therein, all of which are incorporated herein by reference in their entirety). In one example the triazole moiety is formed between an azide group of one of the side chains of $C^1$ and $C^2$, and an alkyne moiety of the side chain of the other of $C^1$ and $C^2$ (e.g., Huisgen cycloaddition). In one example, one of $C^1$ and $C^2$ is selected from amino acids having a straight or branched azidoalkyl, e.g., $(C_1-C_{10})$ azidoalkyl, side chain and the other of $C^1$ and $C^2$ is selected from amino acids having a straight or branched alkynyl, e.g., $(C_1-C_{10})$alkynyl, side chain, wherein an azide moiety of the azidoalkyl group and an alkyne moiety of the alkynyl group are linked to form a triazole moiety (e.g., a 1,4-triazole moiety or a 1,5-triazole moiety). In one example, the alkyno-functionalized amino acid is propargylglycine (Pra). In another example, the alkyno-functionalized amino acid is selected from 2-amino-4-azide-butyric acid (2Abu(γN₃) and 5-azido-norvaline (NVA(δN₃)). Formation of the triazole ring can be accomplished using a suitable catalyst, such as a copper, e.g., Cu(I) catalyst (e.g., CuSO₄/tris(carboxyethyl) phosphine), or a suitable ruthenium-based catalyst.

In one example according to any of the above embodiments, S in Formula (I) is selected from serine and replacement amino acids having a side chain comprising a hydroxyl group. In another example, S in Formula (I) is serine. In another example, S in Formula (I) is L-serine.

In one example in Formula (I), each replacement amino acid for L, A, S, and Y, when present, is selected from L-amino acids. In a further example in Formula (I), S is L-serine or a replacement amino acid, L is L-leucine or a replacement amino acid, A is L-alanine or a replacement amino acid, and Y is L-tyrosine or a replacement amino acid, wherein each replacement amino acid for L, A, S and Y is independently selected from L-amino acids.

In another example in Formula (I), S is serine, L, is L-leucine or a replacement amino acid, A is L-alanine or a replacement amino acid, and Y is L-tyrosine or a replacement amino acid, wherein each replacement amino acid for L, A and Y is independently selected from L-amino acids.

In another example in Formula (I), S is L-serine, L is L-leucine or a replacement amino acid, A is L-alanine or a replacement amino acid, and Y is L-tyrosine or a replacement amino acid, wherein each replacement amino acid for L, A, and Y is independently selected from L-amino acids.

In one example according to any of the above embodiments, replacement of one or two of L, A, S, and Y in Formula (I) with a replacement amino acid, or insertion of an additional amino acid, results in a neutral net-charge between $C^1$ and $C^2$. In another example according to any of the above embodiments, S is serine and replacement of one or two of L, A, and Y in Formula (I) with a replacement amino acid, or insertion of an additional amino acid, results in a neutral net-charge between $C^1$ and $C^2$. A non-neutral net-charge between $C^1$ and $C^2$ results, e.g., when one of L, A, S and Y in Formula (I) is chosen from an amino acid having a side chain incorporating an acidic, e.g., carboxylic acid group (i.e., —COO⁻) or a basic, e.g., amino group (i.e., —NH₃⁺) while the remaining of L, A, S and Y are chosen from amino acids with a hydrophobic or polar uncharged side chain. Hence, in one example according to any of the above embodiments, each replacement amino acid for L, A, S and Y in Formula (I), when present, is independently selected from amino acids having a hydrophobic or a polar uncharged side chain; e.g., are independently selected from G, A, V, I, L, M, F, W, Y, S, T, N, Q, and P (e.g., G, A, V, I, L, M, F, W, Y, S, T, N, and Q).

In a further example, S is L-serine or a replacement amino acid, L is L-leucine or a replacement amino acid, A is L-alanine or a replacement amino acid, and Y is L-tyrosine or a replacement amino acid, wherein each replacement amino acid for L, A, S and Y is independently selected from amino acids having a hydrophobic or a polar uncharged side chain.

In a further example, S is L-serine or a replacement amino acid, L is L-leucine or a replacement amino acid, A is L-alanine or a replacement amino acid, and Y is L-tyrosine or a replacement amino acid, wherein each replacement amino acid for L, A, S and Y is independently selected from G, A, V, I, L, M, F, W, Y, S, T, N, Q and P (e.g., G, A, V, I, L, M, F, W, Y, S, T, N, and Q). In a further example, S is serine, L is L-leucine or a replacement amino acid, A is L-alanine or a replacement amino acid, and Y is L-tyrosine or a replacement amino acid, wherein each replacement amino acid for L, A, and Y, when present, is independently selected from G, A, V, I, L, M, F, W, Y, S, T, N, Q, and P (e.g., G, A, V, I, L, M, F, W, Y, S, T, N, and Q). In a further example, S is L-serine, L is L-leucine or a replacement amino acid, A is L-alanine or a replacement amino acid, and Y is L-tyrosine or a replacement amino acid, wherein each replacement amino acid for L, A, and Y is independently selected from G, A, V, I, L, F, W, Y, S, N, and P (e.g., G, A, V, I, L, M, F, W, Y, S, T, N, and Q).

In another example according to any of the above embodiments, at least one of L, A, S and Y in Formula (I) is replaced with a replacement amino acid. In another example, exactly one of L, A, S and Y is replaced with a replacement amino acid. In another example, exactly one of L, A, S and Y is replaced with a replacement amino acid, wherein the replacement amino acid is selected from L-amino acids. In another example, at least one of L, A, S and Y is replaced with a replacement amino acid, wherein the replacement amino acid is selected from G, A, V, I, L, M, F, W, Y, S, T, N, Q, and P (e.g., G, A, V, I, L, M, F, W, Y, S, T, N, and Q). In another example, exactly one of L, A, S and Y is replaced with a replacement amino acid, wherein the replacement amino acid is selected from G, A, V, I, L, M, F, W, Y, S, T, N, Q, and P (e.g., G, A, V, I, L, M, F, W, Y, S, T, N, and Q).

In another example, S is serine and at least one of L, A, and Y in Formula (I) is replaced with a replacement amino acid. In another example, S is serine and exactly one of L, A, and Y is replaced with a replacement amino acid. In another example, S is serine and at least one of L, A, and Y is replaced with a replacement amino acid, wherein the replacement amino acid is selected from L-amino acids. In another example, S is serine and exactly one of L, A, and Y is replaced with a replacement amino acid, wherein the replacement amino acid is selected from L-amino acids. In another example, S is serine and at least one of L, A, and Y is replaced with a replacement amino acid, wherein the replacement amino acid is selected from G, A, V, I, L, M, F, W, Y, S, T, N, Q, and P (e.g., G, A, V, I, L, M, F, W, Y, S, T, N, and Q). In another example, S is serine and exactly one of L, A, and Y is replaced with a replacement amino acid, wherein the replacement amino acid is selected from G, A, V, I, L, M, F, W, Y, S, T, N, Q and P (e.g., G, A, V, I, L, M, F, W, Y, S, T, N, and Q).

In one example, S is L-serine, and at least one of L, A, and Y in Formula (I) is replaced with a replacement amino acid. In another example, S is L-serine, and exactly one of L, A, and Y is replaced with a replacement amino acid. In another example, S is L-serine, and at least one of L, A, and Y is replaced with a replacement amino acid, wherein the replacement amino acid is selected from L-amino acids. In another example, S is L-serine, and exactly one of L, A, and Y is replaced with a replacement amino acid, wherein the replacement amino acid is selected from L-amino acids. In another example, S is L-serine, and at least one of L, A, and Y is replaced with a replacement amino acid, wherein the replacement amino acid is selected from G, A, V, I, L, M, F, W, Y, S, T, N, Q, and P (e.g., G, A, V, I, L, M, F, W, Y, S, T, N, and Q). In another example, S is L-serine, and exactly one of L, A, and Y is replaced with a replacement amino acid, wherein the replacement amino acid is selected from G, A, V, I, L, M, F, W, Y, S, T, N, Q, and P (e.g., G, A, V, I, L, M, F, W, Y, S, T, N, and Q). In a further example in Formula (I), S is L-serine, L is L-leucine, A is L-alanine, and Y is L-tyrosine, and none of L, A, S and Y is replaced with a replacement amino acid.

In another example, exactly two of L, A, S and Y are replaced with a replacement amino acid. In another example, exactly two of L, A, S and Y are replaced with a replacement amino acid, wherein each replacement amino acid is independently selected from L-amino acids. In another example, S is serine and exactly two of L, A, and Y are replaced with a replacement amino acid. In another example, S is serine and exactly two of L, A, and Y are replaced with a replacement amino acid, wherein each replacement amino acid is independently selected from L-amino acids. In another example, S is serine and exactly two of L, A, and Y are replaced with a replacement amino acid, wherein each replacement amino acid for L, A and Y is independently selected from G, A, V, I, L, M, F, W, Y, S, T, N, Q, and P (e.g., G, A, V, I, L, M, F, W, Y, S, T, N, and Q). In another example, S is L-serine and exactly two of L, A, and Y are replaced with a replacement amino acid, wherein each replacement amino acid for L, A and Y is independently selected from G, A, V, I, L, M, F, W, Y, S, T, N, Q, and P (e.g., G, A, V, I, L, M, F, W, Y, S, T, N, and Q).

The present disclosure further provides a compound that contains a peptide of Formula (II):

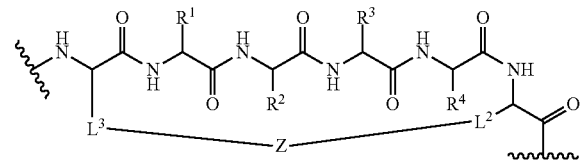

(II)

or a retro-, an inverso- or a retro-inverso variant thereof.

In Formula (II), $R^1$, $R^2$, $R^3$ and $R^4$ are members independently selected from amino acid side chains. In Formula (II), $L^2$ and $L^3$ are linker groups independently selected from straight or branched alkylene, and straight or branched heteroalkylene. In one example, $L^2$ and $L^3$ are independently selected from straight or branched ($C_1$-$C_{20}$)alkylene. In another example, $L^2$ and $L^3$ are independently selected from straight or branched ($C_1$-$C_{10}$)alkylene. In yet another example, $L^2$ and $L^3$ are independently selected from straight or branched ($C_1$-$C_6$)alkylene. In yet another example, $L^2$ and $L^3$ are independently selected from straight or branched ($C_1$-$C_4$)alkylene. In a further example, $L^2$ and $L^3$ are independently selected from heteroalkylene, e.g., ($C_1$-$C_{10}$)heteroalkylene. In one example, the heteroalkylene includes from 1 to 10 heteroatoms (e.g., from 1 to 7, from 1 to 5 heteroatoms, or from 1 to 3 heteroatoms) selected from O, S and N. In another example, at least one of $L^2$ and $L^3$ incorporate a water-soluble polymeric moiety, such as a polyethylene glycol (PEG) or polypropylene glycol (PPG) moiety (e.g., with a molecular weight from about 1000 Da to about 60,000 Da. Other PEG or PPG moieties are described herein.

In Formula (II), Z is a linking moiety. In one example, Z is selected from an amino group, an amide group, a disulfide group, a diselenide group, a —S—Se— group, alkylene, e.g., ($C_2$-$C_4$)alkylene, alkenyl, e.g., ($C_2$-$C_4$)alkenyl, alkynyl, e.g., ($C_2$-$C_4$)alkynyl, cycloalkyl (e.g., ($C_3$-$C_8$)cycloalkyl containing from 1 to 4 double bonds), heterocycloalkyl (e.g., 3- to 8-membered heterocyclic ring comprising from 1 to 6 heteroatoms selected from O, S and N), aryl (e.g., ($C_3$-$C_7$) aryl), and heteroaryl (e.g., 3- to 8-membered heteroaryl comprising from 1 to 6 heteroatoms selected from O, S and N). In another example, Z in Formula (II) is selected from —$NR^5$—, —$NR^5C(O)$—, —S—S—, —S—Se—, —Se—Se—, —$CR^6$=$CR^7$—, —$CR^{6a}R^6$—$CR^{7a}R^7$—, and triazolenyl (e.g., 1,4-triazolenyl, or 1,5-triazolenyl), wherein $R^5$, $R^6$, $R^{6a}$, $R^7$, and $R^{7a}$ are independently selected from H, ($C_1$-$C_4$)alkyl, ($C_1$-$C_4$)heteroalkyl comprising from 1 to 3 heteroatoms selected from O, S and N. In one example, $R^6$ and $R^7$ are combined to form a 4- to 7-membered carbocyclic ring optionally comprising from 1 to 3 double bonds, a 3- to 7-membered heterocyclic ring comprising from 1 to 5 heteroatoms selected from O, S and N, a ($C_5$-$C_7$)aromatic ring, or a 5- to 7-membered heteroaromatic ring comprising from 1 to 5 heteroatoms selected from O, S and N. In another example, $R^6$ and $R^7$ are combined to form a 4- to 6-membered carbocyclic ring. In another example, $R^6$ and $R^7$ are combined to form a 4-membered carbocyclic ring. In another example, $R^6$ and $R^7$ are combined to form a 4- to 7-membered heterocyclic ring comprising from 1 to 3 heteroatome selected from O, S and N, wherein the heterocyclic ring optionally comprises 1 or 2 double bonds. The carbocyclic or heterocyclic ring is optionally substituted with from 1 to 6 (e.g., 1 to 3) substituents selected from straight or branched ($C_1$-$C_4$)alkyl, straight or branched ($C_1$-$C_4$) heteroalkyl comprising from 1 to 3 heteroatoms selected from O, S and N, halogen (e.g., F, Cl, Br), and $OR^{10}$, wherein $R^{10}$ is selected from H, straight or branched ($C_1$-$C_4$)alkyl, straight or branched ($C_1$-$C_4$)heteroalkyl comprising from 1 to 3 heteroatoms selected from O, S and N. In yet another example, Z in Formula (II) is selected from —$NR^5$—, —$NR^5C(O)$—, —S—S—, and a triazole moiety, wherein $R^5$ is defined as above. In one example, the triazole moiety is a 1,4-triazole. In another example, the triazole moiety is a 1,5-triazole.

In another example, a compound of the present disclosure contains a peptide of Formula (IIa), Formula (IIb), Formula (IIc), Formula (IId), Formula (IIe), Formula (IIf), or Formula (IIg):

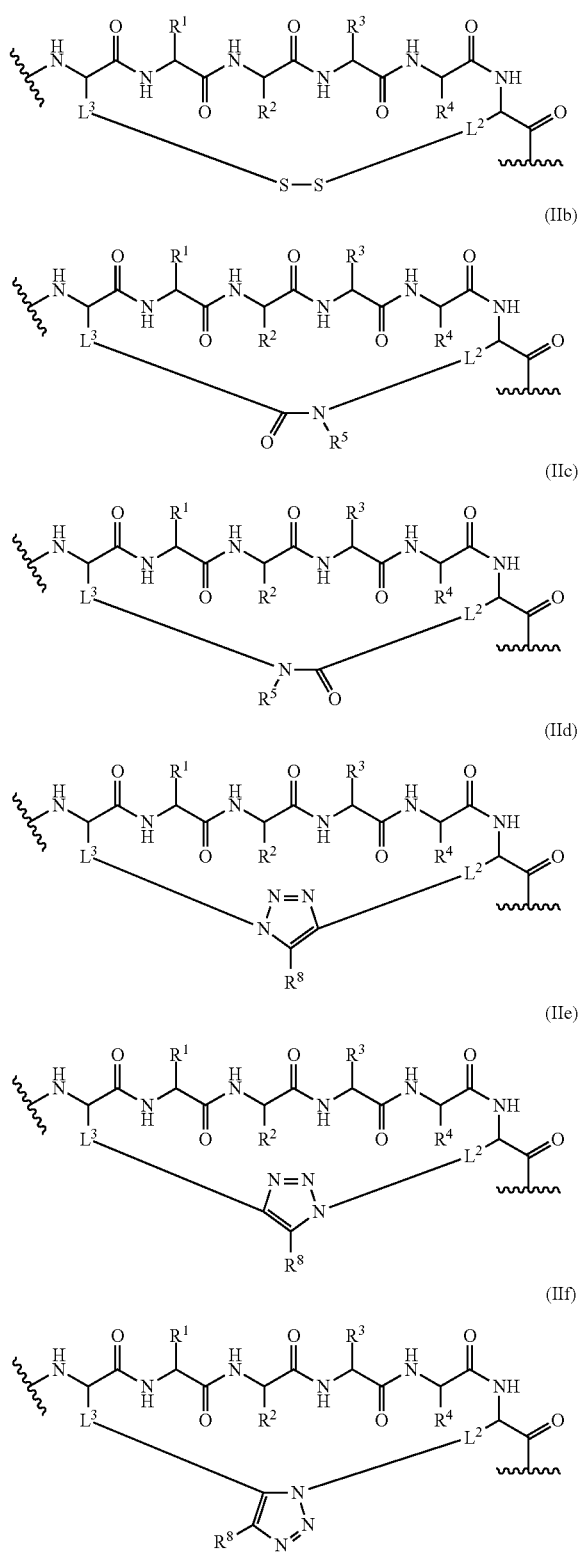

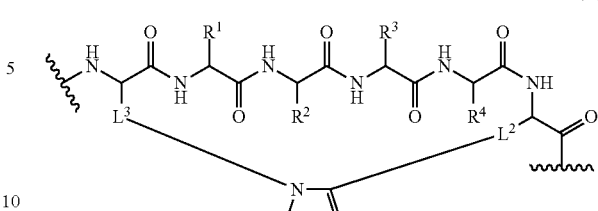

or a retro-, an inverso- or a retro-inverso variant thereof, wherein $R^1$, $R^2$, $R^3$, $R^4$, $R^5$, $R^8$, $L^2$, and $L^3$ are defined as for Formula (II) above. In one example in the above formulae, $R^5$ and $R^8$ are each selected from H and alkyl, e.g., $(C_1-C_4)$ alkyl.

In another example, in Formula (II), (IIa), (IIb), (IIc), (IId), (IIe), (IIf), and (IIg), $R^1$, $R^2$, $R^3$ and $R^4$ are members independently selected from H, straight or branched alkyl, e.g., $(C_1-C_6)$alkyl, straight or branched heteroalkyl, e.g., $(C_1-C_6)$heteroalkyl comprising from 1 to 5 heteroatoms selected from O, S and N, and straight or branched aralkyl, e.g., $(C_1-C_6)$aralkyl. In one example, the aryl group in the aralkyl moiety is selected from aromatic and heteroaromatic rings disclosed herein. In one example, the aryl moiety of the aralkyl group is selected from phenyl, hydroxyphenyl, indolyl, and naphthyl. In another example, the aryl group in the aralkyl moiety is selected from phenyl, 4-hydroxyphenyl, and indolyl. In another example, $R^1$, $R^2$, $R^3$ and $R^4$ are independently selected from hydrophobic and polar uncharged side chains. In another example, $R^1$, $R^2$, $R^3$ and $R^4$ are independently selected from the side chains of G, A, V, I, L, M, F, W, Y, S, T, N, and Q. In another example, $R^1$ is 2-methyl-propyl, $R^2$ is methyl, $R^3$ is hydroxymethyl, and $R^4$ is (4-hydroxy-phenyl)methyl.

In another example according to any of the above embodiments, $L^2$ and $L^3$ in Formula (II), (IIa), (IIb), (IIc), (IId), (IIe), (IIf), and (IIg) are independently selected from straight or branched $(C_1-C_6)$alkylene.

In various embodiments, a compound of the present disclosure comprises at least one of the following amino acid sequences: KGASYE (SEQ ID NO: 560), KLGSYE (SEQ ID NO: 561), KLASGE (SEQ ID NO: 562), kGASYE (SEQ ID NO: 563), kLGSYE (SEQ ID NO: 564), kLASGE (SEQ ID NO: 565), KAASYE (SEQ ID NO: 566), KLASAE (SEQ ID NO: 567), kAASYE (SEQ ID NO: 568), kLASAE (SEQ ID NO: 569), KVASYE (SEQ ID NO: 570), KLVSYE (SEQ ID NO: 571), KLASVE (SEQ ID NO: 572), kVASYE (SEQ ID NO: 573), kLVSYE (SEQ ID NO: 574), kLASVE (SEQ ID NO: 575), KIASYE (SEQ ID NO: 576), KLISYE (SEQ ID NO: 577), KLASIE (SEQ ID NO: 578), kIASYE (SEQ ID NO: 579), kLISYE (SEQ ID NO: 580), kLASIE (SEQ ID NO: 581), KLASYE (SEQ ID NO: 582), KLLSYE (SEQ ID NO: 583), KLASLE (SEQ ID NO: 584), kLASYE (SEQ ID NO: 585), kLLSYE (SEQ ID NO: 586), kLASLE (SEQ ID NO: 587), KFASYE (SEQ ID NO: 588), KLFSYE (SEQ ID NO: 589), KLASFE (SEQ ID NO: 590), kFASYE (SEQ ID NO: 591), kLFSYE (SEQ ID NO: 592), kLASFE (SEQ ID NO: 593), KWASYE (SEQ ID NO: 594), KLWSYE (SEQ ID NO: 595), KLASWE (SEQ ID NO: 596), kWASYE (SEQ ID NO: 597), kLWSYE (SEQ ID NO: 598), kLASWE (SEQ ID NO: 599), KYASYE (SEQ ID NO: 600), KLYSYE (SEQ ID NO: 601), kYASYE (SEQ ID NO: 602), kLYSYE (SEQ ID NO: 603), KQASYE (SEQ ID NO: 604), KLQSYE (SEQ ID NO: 605), KLASQE (SEQ ID NO:

606), kQASYE (SEQ ID NO: 607), kLQSYE (SEQ ID NO: 608), kLASQE (SEQ ID NO: 609), EGASYK (SEQ ID NO: 610), ELGSYK (SEQ ID NO: 611), ELASGK (SEQ ID NO: 612), eGASYK (SEQ ID NO: 613), eLGSYK (SEQ ID NO: 614), eLASGK (SEQ ID NO: 615), EAASYK (SEQ ID NO: 616), ELASAK (SEQ ID NO: 617), eAASYK (SEQ ID NO: 618), eLASAK (SEQ ID NO: 619), EVASYK (SEQ ID NO: 620), ELYSYK (SEQ ID NO: 621), ELASVK (SEQ ID NO: 622), eVASYK (SEQ ID NO: 623), eLVSYK (SEQ ID NO: 624), eLASVK (SEQ ID NO: 625), EIASYK (SEQ ID NO: 626), ELISYK (SEQ ID NO: 627), ELASIK (SEQ ID NO: 628), eIASYK (SEQ ID NO: 629), eLISYK (SEQ ID NO: 630), eLASIK (SEQ ID NO: 631), ELASYK (SEQ ID NO: 632), ELLSYK (SEQ ID NO: 633), ELASLK (SEQ ID NO: 634), eLASYK (SEQ ID NO: 635), eLLSYK (SEQ ID NO: 636), eLASLK (SEQ ID NO: 637), EFASYK (SEQ ID NO: 638), ELFSYK (SEQ ID NO: 639), ELASFK (SEQ ID NO: 640), eFASYK (SEQ ID NO: 641), eLFSYK (SEQ ID NO: 642), eLASFK (SEQ ID NO: 643), EWASYK (SEQ ID NO: 644), ELWSYK (SEQ ID NO: 645), ELASWK (SEQ ID NO: 646), eWASYK (SEQ ID NO: 647), eLWSYK (SEQ ID NO: 648), eLASWK (SEQ ID NO: 649), EYASYK (SEQ ID NO: 650), ELYSYK (SEQ ID NO: 651), eYASYK (SEQ ID NO: 652), eLYSYK (SEQ ID NO: 653), EQASYK (SEQ ID NO: 654), ELQSYK (SEQ ID NO: 655), ELASQK (SEQ ID NO: 656), eQASYK (SEQ ID NO: 657) eLQSYK (SEQ ID NO: 658), or eLASQK (SEQ ID NO: 659), or a retro-, an inverso- or a retro-inverse variant thereof.

In one example in the above sequences, each K (L-lysine) is optionally replaced with a replacement L-amino acid having a side chain comprising an amino group (e.g., —NH$_2$ group), each k (D-lysine) is optionally replaced with a replacement D-amino acid having a side chain comprising an amino group. Exemplary replacement amino acids for lysine (K) in the above sequences include ornithine (Orn), 2,4-diaminobutyric acid (Dab), and 2,3-diaminopropionic acid (Dap, also referred to as Dpr). In one example, a compound of the present disclosure comprises an amino acid sequence selected from Orn-LASYE (SEQ ID NO: 660), ELASY-Orn (SEQ ID NO: 661), Dab-LASYE (SEQ ID NO: 662), Dap-LASYE (SEQ ID NO: 663), and ELASY-Dap (SEQ ID NO: 664).

In another example in the above sequences, each E (L-glutamic acid) is optionally and independently replaced with L-aspartic acid (D) or another replacement L-amino acid having a side chain comprising a carboxylic acid (i.e., —COOH) group, and each e (D-glutamic acid) is optionally and independently replaced with D-aspartic acid (d) or another replacement D-amino acid having a side chain comprising a carboxylic acid group. In certain embodiments, a compound of the present disclosure comprises a sequence selected from: DLASYK (SEQ ID NO: 665), DLASY-Orn (SEQ ID NO: 666), DLASY-Dpr (SEQ ID NO: 667), and Dab-LASYD (SEQ ID NO: 668).

In certain embodiments, a compound of the present disclosure comprises a sequence selected from: DLASYK (SEQ ID NO: 665) and DLASY-Orn (SEQ ID NO: 666).

In the above peptides, the amino acid side chains of K or k (or a replacement amino acid of K or k) and E or e (or a replacement amino acid of E or e) are covalently linked via a peptide bond formed between the amino group and the carboxylic acid group to form a lactam ring.

In other embodiments, a compound of the present disclosure comprises at least one of the following amino acid sequences: CGASYC (SEQ ID NO: 760), CLGSYC (SEQ ID NO: 761), CLASGC (SEQ ID NO: 762), cGASYC (SEQ ID NO: 763), cLGSYC (SEQ ID NO: 764), cLASGC (SEQ ID NO: 765), CAASYC (SEQ ID NO: 766), CLASAC (SEQ ID NO: 767), cAASYC (SEQ ID NO: 768), cLASAC (SEQ ID NO: 769), CVASYC (SEQ ID NO: 770), CLVSYC (SEQ ID NO: 771), CLASVC (SEQ ID NO: 772), cVASYC (SEQ ID NO: 773), cLYSYC (SEQ ID NO: 774), cLASVC (SEQ ID NO: 775), CIASYC (SEQ ID NO: 776), CLISYC (SEQ ID NO: 777), CLASIC (SEQ ID NO: 778), cIASYC (SEQ ID NO: 779), cLISYC (SEQ ID NO: 780), cLASIC (SEQ ID NO: 781), CLASYC (SEQ ID NO: 782), CLLSYC (SEQ ID NO: 783), CLASLC (SEQ ID NO: 784), cLASYC (SEQ ID NO: 785), cLLSYC (SEQ ID NO: 786), cLASLC (SEQ ID NO: 787), FASYC (SEQ ID NO: 788), CLFSYC (SEQ ID NO: 789), CLASFC (SEQ ID NO: 790), cFASYC (SEQ ID NO: 791), cLFSYC (SEQ ID NO: 792), cLASFC (SEQ ID NO: 793), CWASYC (SEQ ID NO: 794), CLWSYC (SEQ ID NO: 795), CLASWC (SEQ ID NO: 796), cWASYC (SEQ ID NO: 797), cLWSYC (SEQ ID NO: 798), cLASWC (SEQ ID NO: 799), CYASYC (SEQ ID NO: 800), CLYSYC (SEQ ID NO: 801), cYASYC (SEQ ID NO: 802), cLYSYC (SEQ ID NO: 803), CQASYC (SEQ ID NO: 804), CLQSYC (SEQ ID NO: 805), CLASQC (SEQ ID NO: 806), cQASYC (SEQ ID NO: 807), cLQSYC (SEQ ID NO: 808), and cLASQC (SEQ ID NO: 809), CLASSC (SEQ ID NO: 810), CLAsYC (SEQ ID NO: 811), CLASyC (SEQ ID NO: 812), or a retro-, an inverso- or a retro-inverso variant thereof.

In one example, a compound of the present disclosure comprises the sequence CLASYC (SEQ ID NO: 782).

In one example in the above sequences, each C (L-cysteine) is optionally and independently replaced with L-homo-cysteine (HCy), L-seleno-cysteine (U), or L-homo-seleno cysteine, and each c (D-cysteine) is optionally and independently replaced with D-homo-cysteine, D-seleno-cysteine (u), or D-homo-seleno cysteine.

In one example, the invention provides a compound comprising:
(a) an amino acid sequence comprising Formula (I):

$$C^1LASYC^2 \text{ (SEQ ID NO: 903)} \qquad (I)$$

or (b) a retro-, an inverso- or a retro-inverso variant of the amino acid sequence of (a), wherein S is L-serine, L is L-leucine, A is L-alanine, Y is L-tyrosine, wherein one or two of L, A and Y are optionally and individually replaced with a replacement L-amino acid. $C^1$ and $C^2$ are independently selected from amino acids having a side chain comprising a —S—H group, wherein the side chains of $C^1$ and $C^2$ are reversibly linked to form a disulfide bond. In one example, $C^2$ is L-cysteine and $C^1$ is selected from L-cysteine, D-cysteine, penicillamine, L-homocysteine, and D-homocysteine. In another example, $C^1$ and $C^2$ are both C. An additional L-amino acid is optionally inserted between Y (or a replacement amino acid thereof) and $C^2$.

In another example, the invention provides a compound comprising:
(a) an amino acid sequence comprising Formula (I):

$$C^1LASYC^2 \text{ (SEQ ID NO: 903)} \qquad (I)$$

or (b) a retro-, an inverso- or a retro-inverso variant of the amino acid sequence of (a), wherein S is L-serine, L is L-leucine, A is L-alanine, Y is L-tyrosine, wherein one of L, A and Y is optionally and individually replaced with a replacement L-amino acid. $C^1$ and $C^2$ are independently selected from cysteine and homo-cysteine. In one example, $C^1$ is selected. from L-cysteine, D-cysteine, L-homocysteine, and D-homocysteine, and $C^2$ is selected from L-cysteine and L-homocysteine. In another example, $C^1$ and $C^2$ are both C.

In yet another example, the invention provides a compound comprising:
(a) an amino acid sequence comprising Formula (I):

C$^1$LASYC$^2$ (SEQ ID NO: 903)  (I)

or (b) a retro-, an inverso- or a retro-inverso variant of the amino acid sequence of (a), wherein S is L-serine; L is L-leucine; A is L-alanine; and Y is L-tyrosine. C$^1$ and C$^2$ are independently selected from amino acids having a side chain comprising a —S—H group. In one example, C$^2$ is selected from L-amino acids having a side chain comprising a —S—H group. In another example, C$^1$ and C$^2$ are independently selected from cysteine and homocysteine. In yet another example, C$^1$ is selected from L-cysteine, D-cysteine, L-homocysteine, and D-homocysteine, and C$^2$ is selected from L-cysteine and L-homocysteine. In another example, C$^1$ and C$^2$ are both C.

In yet another example, the invention provides a compound comprising:
(a) an amino acid sequence comprising Formula (I):

C$^1$LASYC$^2$ (SEQ ID NO: 903)  (I)

or (b) a retro-, an inverso- or a retro-inverso variant of the amino acid sequence of (a), wherein S is L-serine; L is L-leucine; A is L-alanine; and Y is L-tyrosine. C$^1$ and C$^2$ are selected from one of C$^1$ and C$^2$ is selected from amino acids having a side chain with a primary or secondary amino group (e.g., —NH$_2$ group), and the other of C$^1$ and C$^2$ is selected from an amino acid with a side chain having a carboxylic acid group (e.g., —COOH group), wherein the amino group and the carboxylic acid group form an amide bond. In one example, C1 is selected from K, ornithine (Orn), 2,4-diaminobutyric acid (Dab), and 2,3-diaminopropionic acid (Dap, also referred to as Dpr), and C$^2$ is selected from glutamic acid (E) and aspartic acid (D). In another example, C$^2$ is selected from K, ornithine (Orn), 2,4-diaminobutyric acid (Dab), and 2,3-diaminopropionic acid (Dap, also referred to as Dpr), and C$^1$ is selected from glutamic acid (E) and aspartic acid (D).

In yet another example, the invention provides a compound comprising:
(a) an amino acid sequence comprising Formula (III):

C$^1$X$^1$X$^2$SX$^3$C$^2$  (III)

or (b) a retro-, an inverso- or a retro-inverso variant of the amino acid sequence of (a).

In Formula (III), S, C$^1$ and C$^2$ are defined as for Formula (I) according to any of the above embodiments. In one example, S in Formula (III) is L-serine. In another example in Formula (III), C$^1$ and C$^2$ are independently selected from amino acids having a side chain comprising a —S—H group or a —Se—H group. In another example in Formula (III), C$^1$ is selected from amino acids having a side chain comprising a —S—H group or —Se—H group, and C$^2$ is selected from L-amino acids having a side chain comprising a —S—H group or a —Se—H group. In another example, C$^1$ and C$^2$ are independently selected from cysteine and homo-cysteine. In another example, C$^1$ and C$^2$ are independently selected from cysteine and homo-cysteine.

In Formula (III), X$^1$, X$^2$ and X$^3$ are independently selected from amino acids (e.g., L-amino acids) having a hydrophobic or a polar uncharged side chain. In one example, in Formula (III), X$^1$, X$^2$ and X$^3$ are independently selected from G, A, V, I, L, M, F, W, Y, S, T, N, Q, and derivatives thereof.

In another example according to any of the above embodiments, X$^1$ is selected from A, L, M, V, and Q. In another example, X$^1$ is L. In another example according to any of the above embodiments, X$^2$ is selected from G, A, alpha-aminobutyric acid (Abu), V, L, I and S. In yet another example, X$^2$ is selected from G, A, alpha-aminobutyric acid (Abu), V, L, and I. In another example, X$^2$ is A. In another example according to any of the above embodiments, X$^3$ is selected from A, V, Y, Q, F. In another example, X$^3$ is Y.

In another example, a compound of the present disclosure includes:
(a) an amino acid sequence comprising Formula (IV):

X$^4$X$^5$X$^6$C$^1$LASYC$^2$X$^7$X$^8$X$^9$  (IV)

or (b) a retro-, an inverso- or a retro-inverso variant of the amino acid sequence of (a).

In Formula (IV), L, A, S, Y, C$^1$ and C$^2$ are defined as for Formula (I) or any embodiment thereof.

In Formula (IV), X$^4$, X$^5$, X$^7$, X$^8$ and X$^9$ are either absent or pressent, an when present are independently selected from amino acids. In one example, all of X$^4$, X$^5$, X$^7$, X$^8$ and X$^9$ in Formula (IV) are present.

In one example in Formula (IV), X$^4$ is either absent or present and, when present, is N, Q, an amino acid having a side chain comprising a basic moiety, or a modified (e.g., alpha-N-alkylated) amino acid thereof. In one example, X$^4$ in Formula (IV) is an amino acid having a side chain comprising a basic moiety. In one example, X$^4$ in Formula (IV) is selected from lysine (K), arginine (R), histidine (H), 2,4-diaminobutyric acid (Dab), 2,3-diaminoproprionic acid (Dpr), ornithine (Orn), 2,7-diamino-heptanoic acid, 2,8-diamino-octanoic acid, and modified (e.g., alpha-N-alkylated) amino acids thereof. In another example X$^4$ in Formula (IV) is lysine or N-methyl lysine. In another example, X$^4$ in Formula (IV) is L-lysine (K).

In one example in Formula (IV), X$^5$ is either absent or present and, when present, is an amino acid having a hydrophobic or a polar uncharged side chain, or an alpha-N-alkylated amino acid thereof. In one example X$^5$ is selected from L, V, M, P, and modified (e.g., alpha-N-alkylated) amino acids thereof. In one example, X$^5$ in Formula (IV) is leucine or alpha-N-alkylated leucine. In another example, X$^5$ is L-leucine (L). In yet another example, X$^5$ is other than E and R.

In Formula (IV), X$^6$ is an amino acid. In one example, X$^6$ is a modified (e.g., alpha-N-alkylated) amino acid. In another example, X$^6$ in Formula (IV) is selected from L-threonine, D-threonine, A, S, Q, R, and K. In one example, X$^6$ is selected from L-threonine and D-threonin, A, and K. In another example, X$^6$ is selected from L-threonine and D-threonin. In another example X$^6$ is T. In yet another example, X$^6$ is other than an amino acid with an acidic side chain (e.g., other than E).

In another example in Formula (IV), X$^7$, X$^8$ and X$^9$ are independently either absent or present and, when present, are independently selected from amino acids (e.g., L-amino acids). In another example in Formula (IV), X$^7$, X$^8$ and X$^9$, when present, are independently selected from amino acids having a hydrophobic side chain and amino acids having a polar uncharged side chain. In another example in Formula (IV), X$^7$, X$^8$ and X$^9$, when present, are independently selected from L-amino acids having a hydrophobic side chain and amino acids having a polar uncharged side chain. In yet another example in Formula (IV), X$^7$, X$^8$ and X$^9$ are independently either absent or present and when present are independently selected from L, norleucine (Nle), I, V, M, F, W, Y, S, T, N, and Q.

In one example, according to any of the above embodiments, X$^7$ is selected from G, L, Q and amino acids having a side chain containing an aromatic moiety. In another example, $X^7$ is selected from G, L, Q, W, F, Y, and 1-aryl-alanine (e.g., 1-naphthyl-alanine). In another example, $X^7$ is F. In another example, $X^7$ is L-tryptophan, D-tryptophan, F, L, or 1-naphthyl-alanine (e.g., L-1-naphthyl-alanine). In another example, $X^7$ is not an NMe amino acid. In another example, $X^7$ is 1-naphthyl-alanine. In yet another example, $X^7$ is L-tryptophan or D-tryptophan. In another example, $X^7$ is W. In another example, $X^7$ is Y. In a further example, $X^7$ is modified tyrosine as defined herein.

In one example $X^8$ in Formula (IV) is selected from from amino acids having a hydrophobic side chain and amino acids having a polar uncharged side chain. In one example, $X^8$ is selected from L, I, not-leucine (Nle), V, Y, Q, and M. In another example, $X^8$ is selected from hydrophobic L-amino acids. In one example, $X^8$ is selected from L, Y, I and L-norleucine. In another example, $X^8$ is L.

In one example, $X^9$ in Formula (IV) is selected from F, V, and L. n another example, $X^9$ in Formula (IV) is V. In another example, $X^9$ in Formula (IV) is selected from F and L. In another example, $X^9$ in Formula (IV) is F. I In one example, a compound of the present disclosure comprises:

(a) an amino acid sequence comprising Formula (V):

$$C^1X_mLX_nAX_oSX_pYX_qC^2 \quad (V)$$

or (b) a retro-, an inverso- or a retro-inverso variant of the amino acid sequence of (a). In Formula (V), L is L-leucine; A is L-alanine; S is L-serine; Y is L-tyrosine, wherein one or two of L, A, S, and Y are optionally replaced with an independently selected replacement amino acid. In Formula (V), each X is independently selected from amino acids. In one example, each X is independently selected from amino acids having a hydrophobic or a polar uncharged side chain. In Formula (V), m, n, o, p, and q are integers independently selected from 1 and 0. In one example, m, n, o, p, and q are all zero. In another example, one of m, n, o, p, and q is 1 and the remaining of m, n, o, p, and q are zero. In Formula (V), $C^1$ and $C^2$ are independently selected from amino acids having a side chain comprising a —S—H group or a —Se—H group. In one example in Formula (V), both of $C^1$ and $C^2$ are C.

In another example according to the above embodiment, a compound of the present disclosure comprises an amino acid sequence comprising Formula (Va), Formula (Vb), Formula (Vc), Formula (Vd), or Formula (Ve):

$$C^1XLASYC^2 \quad (Va)$$

$$C^1LXASYC^2 \quad (Vb)$$

$$C^1LAXSYC^2 \quad (Vc)$$

$$C^1LASXYC^2 \quad (Vd)$$

$$C^1LASYXC^2 \quad (Ve)$$

wherein X represents an amino acid. In one example in the above formulae, X is selected from amino acids having a hydrophobic or a polar uncharged side chain.

In one example according to any of the above embodiments, the amino acid sequence is (b) the retro-inverso variant of the amino acid sequence of (a).

In one example, a compound of the present disclosure comprises:

(a) an amino acid sequence comprising Formula (VI):

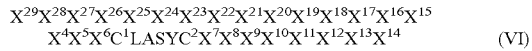
$$X^{29}X^{28}X^{27}X^{26}X^{25}X^{24}X^{23}X^{22}X^{21}X^{20}X^{19}X^{18}X^{17}X^{16}X^{15}X^4X^5X^6C^1LASYC^2X^7X^8X^9X^{10}X^{11}X^{12}X^{13}X^{14} \quad (VI)$$

(b) a retro-, an inverso- or a retro-inverso variant of the amino acid sequence of (a). In Formula (VI), L, A, S, an Y are defined as for Formula (I). In one example, in Formula (VI), L is L-leucine; A is L-alanine; S is L-serine; Y is selected from A, F, L-tyrosine, D-tyrosine, L-tyrosine (OMe), and D-tyrosine (OMe). In one example, in Formula (VI), L is L-leucine; A is L-alanine; S is L-serine; and Y is L-tyrosine.

$X^{29}$ (position 1) is either absent or present and when present is an amino acid. In one example $X^{29}$ is S or P.

$X^{28}$ (position 2) is either absent or present and when present is an amino acid. In one example $X^{28}$ is selected from a basic amino acid (e.g., R) and S.

$X^{27}$ (a position 3) is either absent or present and when present is an amino acid. In one example $X^{27}$ is S or I.

$X^{26}$ (at position 4) is either absent or present and when present is an amino acid. In one example $X^{26}$ is selected from basic amino acids (e.g., L- or D-arginine).

$X^{25}$ (position 5) is either absent or present and when present is an amino acid. In one example $X^{25}$ is T or S.

$X^{24}$ (position 6) is either absent or present and when present is an amino acid. In one example $X^{24}$ is V or S.

$X^{23}$ (position 7) is either absent or present and when present is an amino acid. In one example $X^{23}$ is G or S.

$X^{22}$ (position 8) is either absent or present and when present is an amino acid. In one example $X^{22}$ is S or P.

$X^{21}$ (position 9) is either absent or present and when present is an amino acid. In one example $X^{21}$ is G or S.

$X^{20}$ (position 10) is either absent or present and when present is an amino acid. In one example $X^{20}$ is S.

$X^{19}$ (position 11) is an amino acid. In one example $X^{19}$ is a basic amino acid (e.g., L-arginine, D-arginine, or K).

$X^{18}$ (position 12) is an amino acid. In one example $X^{18}$ is L-arginine, D-arginine or S.

$X^{17}$ (position 13) is an amino acid. In one example $X^{17}$ is a hydrophobic amino acid. In another example, $X^{17}$ is A or NMe-alanine.

$X^{16}$ (position 14) is an amino acid. In one example $X^{16}$ is S, P or A. In another example $X^{16}$ is not K or a D-amino acid (e.g., not D-proline).

$X^{15}$ (position 15) is an amino acid. In one example $X^{15}$ is G, sarcosine, or A. In another example $X^{15}$ is not K. In another example, $X^{15}$ is selected from G and sarcosine.

$X^4$ (position 16) is L-lysine or D-lysine, L-ornithine, D-ornithine, L-2,4-diaminobutyric acid, D-2,4-diaminobutyric acid, L-2,3-diaminopropionic acid, or D-2,3-diaminopropionic acid. In one example $X^4$ is selected from L-lysine and D-lysine.

$X^5$ (position 17) is selected from hydrophobic amino acids. In one example, $X^5$ is selected from A, L-leucine, D-leucine, and S. In one example, $X^5$ is L.

$X^6$ (position 18) is selected from L-threonine, D-threonine, A, Q, and K. In one example, $X^6$ is selected from T, A, Q, and K. In another example, $X^6$ is selected from L-threonine and D-threonin. In another example $X^6$ is T.

$C^1$ (position 19) is selected from L-cysteine, D-cysteine, penicillamine, L-homocysteine, and D-homocysteine. In one example, $C^1$ is C.

$C^2$ (position 24) is selected from L-cysteine, D-cysteine, penicillatnine, L-homocysteine, and D-homocysteine. In one example, $C^2$ is C.

In one example, in Formula (VI) both of $C^1$ and $C^2$ are C.

$X^7$ (position 25) is selected from L-tryptophan, D-tryptophan, F, L or 1-naphthyl-alanine (e.g., L-1-naphthyl-alanine). In another example, $X^7$ is not an NMe amino acid. In another example, $X^7$ is W.

X$^8$ (position 26) is selected from hydrophobic L-amino acids. In one example, X$^8$ is selected from L, Y, I and L-norleucine. In another example, X$^8$ is L.

X$^9$ (position 27) is selected from F and L. In one example, X$^9$ is F.

X$^{10}$ (position 28) is either absent or present and when present is selected from W, A, S, F and L. In one example, X$^{10}$ is W.

X$^{11}$ (position 29) is either absent or present, and when present is an amino acid. In one example, X$^{11}$ is selected from L-threonine, D-threonine, and S.

X$^{12}$ (position 30) is either absent or present, and when present is an amino acid. In one example, X$^{12}$ is selected from G, A, sarcosine, L, F and S. In one example, X$^{12}$ is selected from G, A, and sarcosine. In one example, X$^{12}$ is selected from G and sarcosine. In another example, X$^{12}$ is G.

X$^{13}$ (position 31) is either absent or present, and when present is an amino acid. In one example, X$^{13}$ is selected from I, L, F, L-norleucine, L-1-naphthyl-alanine, 3-cyclohexyl-L-alanine, and L-tert-leucine. In another example, X$^{13}$ is selected from I, L, F, L-norleucine, and L-1-naphthyl-alanine. In one example, X$^{13}$ is I.

X$^{14}$ (position 32) is either absent or present, and when present is an amino acid. In one example, X$^{14}$ is A.

In one example, all of X$^{10}$ to X$^{14}$ are present. In another example, all of X$^{20}$ to X$^{29}$ are present.

In one example, the amino acid sequence of a compound of the present disclosure includes at least one of the following sequences:

```
                                         (SEQ ID NO: 200)
KLTCLASYCWLF (SEQ ID NO: 232)
k-MeLeu-TCLASYCWLF (SEQ ID NO: 4)
RRAPGKLQCLASYCWLFWTGIA (SEQ ID NO: 29)
RRAPGKLTCLASYCWLFWTGIA (SEQ ID NO: 67)
rRAPGKLTCLASYCWLFWTGIA (SEQ ID NO: 421)
rRAPGKSTCLASYCWLFWTGIA (SEQ ID NO: 874)
PRIRTVGPGSRSASGKLTCLASYCWLFWTGIA (SEQ ID NO: 426)
PRIrTVGPGSrSASGKLTCLASYCWLFWTGIA (SEQ ID NO: 441)
PRIRTVGPGSRSASGKSTCLASYCWLFWTGIA (SEQ ID NO: 445)
SRIRTVGPGSRSASGKSTCLASYCWLFWTGIA (SEQ ID NO: 446)
PRIRTVSPGSRSASGKSTCLASYCWLFWTGIA (SEQ ID NO: 447)
SRIRTVSPGSRSASGKSTCLASYCWLFWTGIA (SEQ ID NO: 448)
PRSRTVGPGSRSASGKSTCLASYCWLFWTGIA (SEQ ID NO: 449)
SRSRTVSPGSRSASGKSTCLASYCWLFWTGIA (SEQ ID NO: 442)
PRIrTVGPGSrSASGKSTCLASYCWLFWTGIA (SEQ ID NO: 840)
SKQGRPISPDRRAAGKLTCLASYCWLFWTGIA (SEQ ID NO: 471)
SKQGRPISPDrRAAGKLTCLASYCWLFWTGIA (SEQ ID NO: 841)
RRAPGKLTCLASYCWLFGSGISLSRAPESAAP (SEQ ID NO: 842)
RRFVGGSLSQRRAPGKLTCLASYCWLFWTGIA (SEQ ID NO: 843)
PQTRDPSSRDRRAPGKLTCLASYCWLFWTGIA.
```

Additional amino acid residues may be added to the N- or C-terminus of the above sequences to form a compound of the present disclosure.

In various embodiments, a compound of the present disclosure includes an amino acid sequence incorporating a particular number of amino acid residues. The number of amino acids is defined by a lower and an upper limit. The lenghth of the amino acid sequence can be defined by any combination of the lower and upper limits given below:

Lower Limit

In one example according to any of the above embodiments, the amino acid sequence of a compound comprises at least 7, at least 8, at least 9, or at least 10 amino acids. In another example according to any of the above embodiments, the amino acid sequence of a compound comprises at least 11, at least 12, at least 13, at least 14, at least 15, at least 16, at least 17, at least 18, at least 19, or at least 20 amino acids. In another example according to any of the above embodiments, the amino acid sequence of a compound comprises at least 21, at least 22, at least 23, at least 24, at least 25, at least 26, at least 27, at least 28, at least 29, at least 30 amino acids, at least 31 amino acids, or at least 32 amino acids.

Upper Limit

In one example according to any of the above embodiments, the amino acid sequence of a compound comprises not more than 500, not more than 400, not more than 300, not more than 200, or not more than 100 amino acids. In another example according to any of the above embodiments, the amino acid sequence of a compound comprises not more than 90, not more than 80, not more than 70, not more than 60, not more than 50, or not more than 40 amino acids.

Exemplary Ranges

In yet another example, the amino acid sequence of a compound comprises at least 9 and not more than 500 amino acids. In yet another example, the amino acid sequence of a compound comprises at least 10 and not more than 500 amino acids. In yet another example, the amino acid sequence of a compound comprises at least 11 and not more than 500 amino acids. In yet another example, the amino acid sequence of a compound comprises at least 12 and not more than 500 amino acids. In yet another example, the amino acid sequence of a compound comprises at least 13 and not more than 500 amino acids. In yet another example, the amino acid sequence of a compound comprises at least 14 and not more than 500 amino acids. In yet another example, the amino acid sequence of a compound comprises at least 15 and not more than 500 amino acids. In yet another example, the amino acid sequence of a compound comprises at least 16 and not more than 500 amino acids. In yet another example, the amino acid sequence of a compound comprises at least 17 and not more than 500 amino acids. In yet another example, the amino acid sequence of a compound comprises at least 18 and not more than 500 amino acids. In yet another example, the amino acid sequence of a compound comprises at least 19 and not more than 500 amino acids. In yet another example, the amino acid sequence of a compound comprises at least 20 and not more than 500 amino acids.

In yet another example, the amino acid sequence of a compound comprises at least 9 and not more than 300 amino acids. In yet another example, the amino acid sequence of a compound comprises at least 10 and not more than 300 amino acids. In yet another example, the amino acid sequence of a compound comprises at least 11 and not more than 300 amino acids. In yet another example, the amino acid sequence of a compound comprises at least 12 and not more than 300 amino acids. In yet another example, the amino acid sequence of a compound comprises at least 13 and not more than 300 amino acids. In yet another example, the amino acid sequence of a compound comprises at least 14 and not more than 300 amino acids. In yet another example, the amino acid sequence of a compound comprises at least 15 and not more than 300 amino acids. In yet another example, the amino acid sequence of a compound comprises at least 16 and not more than 300 amino acids. In yet another example, the amino acid sequence of a compound comprises at least 17 and not more than 300 amino acids. In yet another example, the amino acid sequence of a compound comprises at least 18 and not more than 300 amino acids. In yet another example, the amino acid sequence of a compound comprises at least 19 and not more than 300 amino acids. In yet another example, the amino acid sequence of a compound comprises at least 20 and not more than 300 amino acids.

In yet another example, the amino acid sequence of a compound comprises at least 9 and not more than 100 amino acids. In yet another example, the amino acid sequence of a compound comprises at least 10 and not more than 100 amino acids. In yet another example, the amino acid sequence of a compound comprises at least 11 and not more than 100 amino acids. In yet another example, the amino acid sequence of a compound comprises at least 12 and not more than 100 amino acids. In yet another example, the amino acid sequence of a compound comprises at least 13 and not more than 100 amino acids. In yet another example, the amino acid sequence of a compound comprises at least 14 and not more than 100 amino acids. In yet another example, the amino acid sequence of a compound comprises at least 15 and not more than 100 amino acids. In yet another example, the amino acid sequence of a compound comprises at least 16 and not more than 100 amino acids. In yet another example, the amino acid sequence of a compound comprises at least 17 and not more than 100 amino acids. In yet another example, the amino acid sequence of a compound comprises at least 18 and not more than 100 amino acids. In yet another example, the amino acid sequence of a compound comprises at least 19 and not more than 100 amino acids. In yet another example, the amino acid sequence of a compound comprises at least 20 and not more than 100 amino acids. In yet another example, the amino acid sequence of a compound comprises at least 21 and not more than 100 amino acids. In yet another example, the amino acid sequence of a compound comprises at least 22 and not more than 100 amino acids. In yet another example, the amino acid sequence of a compound comprises at least 23 and not more than 100 amino acids. In yet another example, the amino acid sequence of a compound comprises at least 24 and not more than 100 amino acids. In yet another example, the amino acid sequence of a compound comprises at least 25 and not more than 100 amino acids. In yet another example, the amino acid sequence of a compound comprises at least 26 and not more than 100 amino acids. In yet another example, the amino acid sequence of a compound comprises at least 27 and not more than 100 amino acids. In yet another example, the amino acid sequence of a compound comprises at least 28 and not more than 100 amino acids. In yet another example, the amino acid sequence of a compound comprises at least 29 and not more than 100 amino acids. In yet another example, the amino acid sequence of a compound comprises at least 30 and not more than 100 amino acids In one example according to any of the above embodiments, a compound of the present disclosure contains not more than 500, not more than 400, not more than 300, not more than 200, or not more than 100 amino acids. In another example according to any of the above embodiments, a compound comprises not more than 90, not more than 80, not more than 70, not more than 60, or not more than 50 amino acids. In one example according to any of the above embodiments, a compound comprises not more than 500, not more than 400, not more than 300, not more than 200, or not more than 100 consecutive amino acids.

In yet another example, a compound comprises at least 9 and not more than 500 amino acids. In yet another example, a compound comprises at least 10 and not more than 500 amino acids. In yet another example, a compound comprises at least 11 and not more than 500 amino acids. In yet another example, a compound comprises at least 12 and not more than 500 amino acids. In yet another example, a compound comprises at least 13 and not more than 500 amino acids. In yet another example, a compound comprises at least 14 and not more than 500 amino acids. In yet another example, a compound comprises at least 15 and not more than 500 amino acids. In yet another example, a compound comprises at least 16 and not more than 500 amino acids. In yet another example, a compound comprises at least 17 and not more than 500 amino acids. In yet another example, a compound comprises at least 18 and not more than 500 amino acids. In yet another example, a compound comprises at least 19 and not more than 500 amino acids. In yet another example, a compound comprises at least 20 and not more than 500 amino acids.

In yet another example, a compound comprises at least 9 and not more than 300 amino acids. In yet another example, a compound comprises at least 10 and not more than 300 amino acids. In yet another example, a compound comprises at least 11 and not more than 300 amino acids. In yet another example, a compound comprises at least 12 and not more than 300 amino acids. In yet another example, a compound comprises at least 13 and not more than 300 amino acids. In yet another example, a compound comprises at least 14 and not more than 300 amino acids. In yet another example, a compound comprises at least 15 and not more than 300 amino acids. In yet another example, a compound comprises at least 16 and not more than 300 amino acids. In yet another example, a compound comprises at least 17 and not more than 300 amino acids. In yet another example, a compound comprises at least 18 and not more than 300 amino acids. In yet another example, a compound comprises at least 19 and not more than 300 amino acids. In yet another example, a compound comprises at least 20 and not more than 300 amino acids.

In yet another example, a compound comprises at least 9 and not more than 100 amino acids. In yet another example, a compound comprises at least 10 and not more than 100 amino acids. In yet another example, a compound comprises at least 11 and not more than 100 amino acids. In yet another example, a compound comprises at least 12 and not more than 100 amino acids. In yet another example, a compound comprises at least 13 and not more than 100 amino acids. In yet another example, a compound comprises at least 14 and not more than 100 amino acids. In yet another example, a compound comprises at least 15 and not more than 100 amino acids. In yet another example, a compound comprises at least 16 and not more than 100 amino acids. In yet another example, a compound comprises at least 17 and not more than 100 amino acids. In yet another example, a compound comprises at least 18 and not more than 100 amino acids. In yet another example, a compound comprises at least 19 and not more than 100 amino acids. In yet another example, a compound comprises at least 20 and not more than 100 amino acids. In yet another example, a compound comprises at least 21 and not more than 100 amino acids. In yet another example, a compound comprises at least 22 and not more than 100 amino acids. In yet another example, a compound comprises at least 23 and not more than 100 amino acids. In yet another example, a compound comprises at least 24 and not more than 100 amino acids. In yet another example, a compound comprises at least 25 and not more than 100 amino acids. In yet another example, a compound comprises at least 26 and not more than 100 amino acids. In yet another example, a compound comprises at least 27 and not more than 100 amino acids. In yet another example, a compound comprises at least 28 and not more than 100 amino acids. In yet another example, a compound comprises at least 29 and not more than 100 amino acids. In yet another example, a compound comprises at least 30 and not more than 100 amino acids In one example, a compound of the present disclosure is a peptide or peptide derivative containing at least 21 amino acids, wherein amino acid 21 (counted from the N-terminus towards the C-terminus) is an amino acid with a hydrophobic side chain (e.g., G, A, L, I). In another example, a compound is a peptide or peptide derivative containing at least 21 amino acids, wherein the peptide has a positively charged N-terminal amino acid (i.e., basic amino acid, such as K or R). In another example a compound of the present disclosure is a peptide or peptide derivative having a neutral C-terminus. For example, the final 6, final 5, final 4, final 3, final 2 or the final C-terminal amino acids are selected from amino acids having a hydrophobic or a polar uncharged side chain. In one example, the C-terminal amino acid is A. In another example, the C-terminal 3 amino acids are -GIA. In another example, the C-terminal 4 amino acids are -TGIA. In another example, the C-terminal 5 amino acids are -WTGIA. In another example, the C-terminal 6 amino acids are -FWTGIA. In another example, at least one of the N-terminal 3 amino acids is a D-amino acid. In one example, a compound of the present disclosure is a peptide or peptide derivative, wherein the N-terminal amino acid is D-arginine (r). In another example, the N-terminal two amino acids of the peptide are Rr- or rR-.

In one example according to any of the above embodiments, the amino acid sequence of a compound is acylated, e.g., acetylated at the N-terminus (i.e., —NHCOCH₃ or -NHAc). In another example according to any of the above embodiments, the amino acid sequence of a compound is amidated (i.e., —CONHCH₃ or —CONH₂) at the C-terminus. In yet another example according to any of the above embodiments, the amino acid sequence of a compound is acylated, acetylated at the N-terminus and amidated (i.e., —CONHCH₃ or —CONH₂) at the C-terminus. In a further example according to any of the above embodiments, the amino acid sequence of a compound has a free amino terminus (—NH₂ or a salt form thereof) and is amidated (i.e., —CONH₂) at the C-terminus.

In one example according to any of the above embodiments, a compound of the present disclosure is a peptide or a peptide derivative. In another example, a compound is a peptide derivative, in which the N-terminal amino acid is acylated, acetylated (i.e., —NHCOCH₃). In another example, a compound is a peptide derivative, in which the C-terminal amino acid is amidated (i.e., —CONHCH₃ or —CONH₂). In one example, a compound is a peptide derivative, which is acylated, e.g., acetylated at the N-terminus and amidated (i.e., —CONHCH₃ or —CONH₂) at the C-terminus. In one example, a compound is a peptide derivative, which has a free N-terminus (—NH₂ or a salt form thereof) and is amidated (i.e., —CONH₂) at the C-terminus.

In one example, a compound of the present disclosure contains an amino acid sequence selected from or is a peptide selected from those listed in Table 1, hereinbelow, or a retro-, an inverso- or a retro-inverso variant thereof. In one example in those peptides, the N-terminus is acetylated. In another example in those peptides, the N-terminus is free (—NH₂). In another example in those peptides, the C-terminus is amidated. In another example in those peptides, the N-terminus is free and the C-terminus is amidated.

Conjugates
Compounds Linked to a Heterologous Moiety

In certain embodiments, the compound of the present disclosure is linked to a heterologous moiety. For example, the pro-coagulant peptide of the present disclosure is covalenly linked to a heterologous moiety, optionally via a linker (L₁) thereby forming a conjugate. Linker (L₁) is different than the linking moiety Z defined herein above.

The heterologous moiety is useful to increase the bioavailability or the in vivo stability/half-life of the compound. Exemplary heterologous moieties include, e.g., known half-life extending moieties, e.g., water-soluble polymers, such as polyethylene glycol (PEG) and polypropylene glycol (PPG), Fc, PAS, HES, XTEN, and albumin. In one example, the heterologous moiety is a polymer, e.g., a water-soluble polymer, such as polyethylene glycol (PEG). In another example, the heterologous moiety is a half-life prolonging protein, such as albumin. In another example, the heterologous moiety is an Fc moiety. In another example, the heterologous moiety is a XTEN moiety. In another example, the heterologous moiety is a HES moiety. In another example, the heterologous moiety is a PAS moiety. Other useful heterologous moieties are known in the art and others are further described herein.

In one embodiment the conjugate formed between the compound and the heterologous moiety has a structure according to Formula (A1) or Formula (A2):

Het-(L₁)ₘ-Pep (A1)

Pep-(L₁)ₘ-Het (A2)

wherein
Het is a heterologous moiety as described herein;
m is an integer selected from 0 and 1;
L₁ is either absent (m=0) or present (m=1), and when present is a linker as described herein; and
Pep is a compound (e.g., pro-coagulant peptide or peptide derivative) of the present disclosure.

Polypeptide Conjugates

In other embodiments, the compound of the present disclosure is covalently linked to a polypeptide. In one example, the polypeptide is selected from a blood coagulation factor and platelet targeting moieties. In other embodiments, the blood coagulation factor is selected from FVIIa, FVIII, and FIX. In one example, the compound is linked to an internal amimo acid residue of the polypeptide (e.g., FVIIa or FIX).

The present disclosure further provides polypeptide conjugates comprising a polypeptide selected from FVIII, FIX, FVIIa, and platelet targeting moieties, and a compound of the present disclosure (e.g., a pro-coagulant peptide or peptide derivative), wherein the compound is linked, e.g., covalently linked, to the polypeptide, optionally via a linker.

In another embodiments, the present disclosure provides conjugates comprising a polypeptide selected from FVIII, FIX, FVIIa, and platelet targeting moieties, a compound of the present disclosure (e.g., a pro-coagulant peptide or peptide derivative), and at least one linker, which links the compound to the polypeptide.

In another example, the present disclosure provides polypeptide conjugates comprising a polypeptide, a heterologous moiety, a compound of the present disclosure (e.g., a pro-coagulant peptide or peptide derivative), and at least one linker, which covalently links the compound to the polypeptide and the heterologous moiety. In one example according to this embodiment, the compound (e.g., peptide or peptide derivative) is interposed between the polypeptide and the heterologous moiety. In another example according to this embodiment, the heterologous moiety is linked to the polypeptide, and the compound (e.g., peptide or peptide derivative) is linked to either the polypeptide or the heterologous moiety.

In one example, the polypeptide is activatable, e.g., by an enzyme, which, e.g., cleaves a number of amino acids from the polypeptide sequence. In one example, the polypeptide is activatable by an enzyme of the blood coagulation cascade, e.g., thrombin. In one example, the polypeptide is a thrombin activatable FVII or FVIIa polypeptide. Exemplary thrombin-activatable FVII polypeptides are disclosed in WO2012/006635, incorporated herein by reference in its entirety.

FVIII Conjugates

In various embodiments, the compound of the present disclosure (e.g., peptide or peptide derivative) is covalently linked to FVIII or a FVIII-heterologous moiety construct.

In one example, the conjugate of the present disclosure includes a FVIII-heterologous moiety construct (e.g., FVIII-Fc, FVIII-albumin, FVIII-PEG) and the compound (e.g., peptide or peptide derivative) is covalently linked to the FVIII-portion of the construct. In another example, the conjugate of the present disclosure includes a FVIII-heterologous moiety construct (e.g., FVIII-Fc, FVIII-albumin, FVIII-PEG) and the compound (e.g., peptide or peptide derivative) is covalently linked to the heterologous moiety portion of the construct.

In one example according to the above embodiments, the heterologous moiety is Fc. Accordingly, the present disclosure provides a conjugate comprising a FVIII-Fc construct (FVIII-Fc) and a compound of the present disclosure (e.g., a pro-coagulant peptide or peptide derivative), and a linker, which covalently links the compound (e.g., peptide or peptide derivative) to the FVIII-Fc. In one example according to this embodiment, the compound (e.g., peptide or peptide derivative) is covalently linked to the FVIII portion of the FVIII-Fc (e.g., via a linker). In another example, the compound (e.g., peptide or peptide derivative) is covalently linked to the Fc portion of the FVIII-Fc (e.g., via a linker).

In one example according to any of above embodiments, the FVIII is B-domain deleted FVIII.

In one example, the compound of the present disclosure (e.g., the pro-coagulant peptide or peptide derivative) is covalently linked to the N-terminus of the FVIII heavy chain (HC). In another example, the compound is covalently linked to the C-terminus of the FVIII HC. In yet another example, the compound (e.g., the pro-coagulant peptide or peptide derivative) is covalently linked to the N-terminus of the FVIII light chain (LC). In yet another example, the compound (e.g., the pro-coagulant peptide or peptide derivative) is covalently linked to the C-terminus of the FVIII LC.

In a further example according to any of the above embodiments, the compound (e.g., the pro-coagulant peptide or peptide derivative) is covalently linked to an internal amino acid residue of the FVIII molecule (internal conjugation), e.g., via a cysteine residue. In one example, the cysteine residue is engineered into the FVIII amino acid sequence. In one example, the site of internal conjugation is selected from those described in Mei, B. et. al. Rational design of a fully active, long-acting PEGylated FVIII for hemophilia A treatment. *Blood* (2010) 116:270-279; and U.S. Patent Application US2006/0115876 to Pan C. et al. (Site-directed modification of FVIII), each of which is incorporated herein by reference in its entirety.

Figure 20:
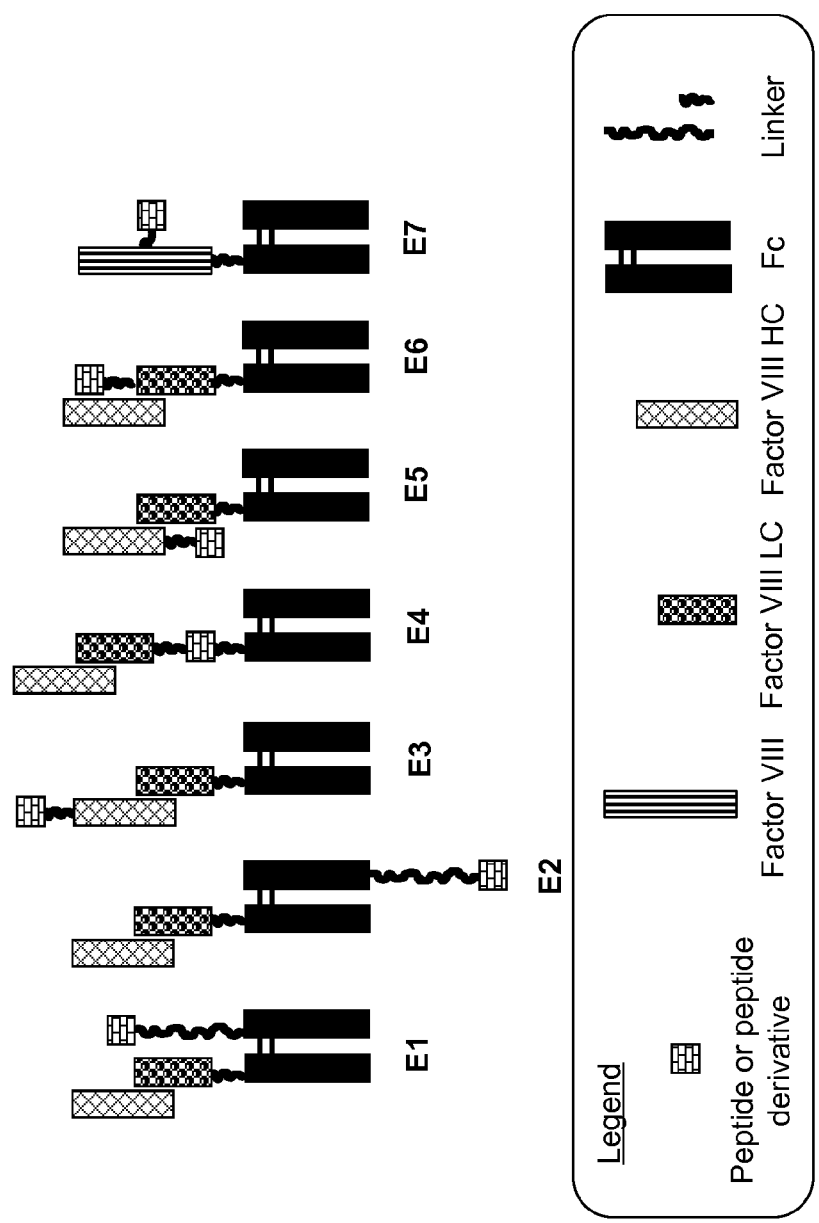
Figure 21:
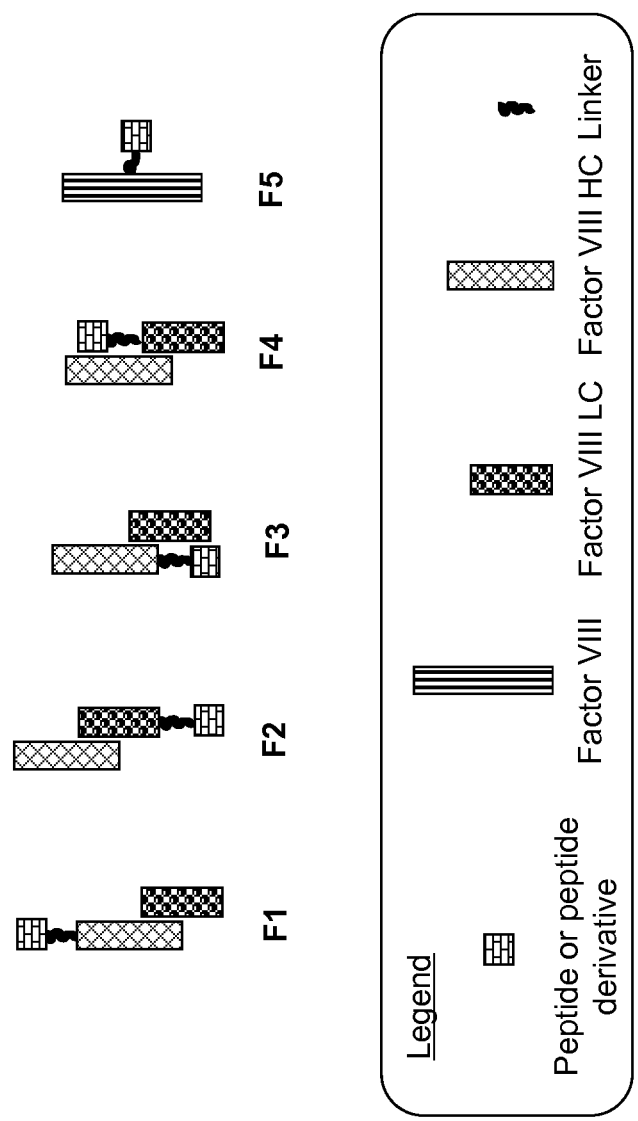

Exemplary FVIII conjugates are illustrated in FIGS. 20 and 21.

Figure 23:
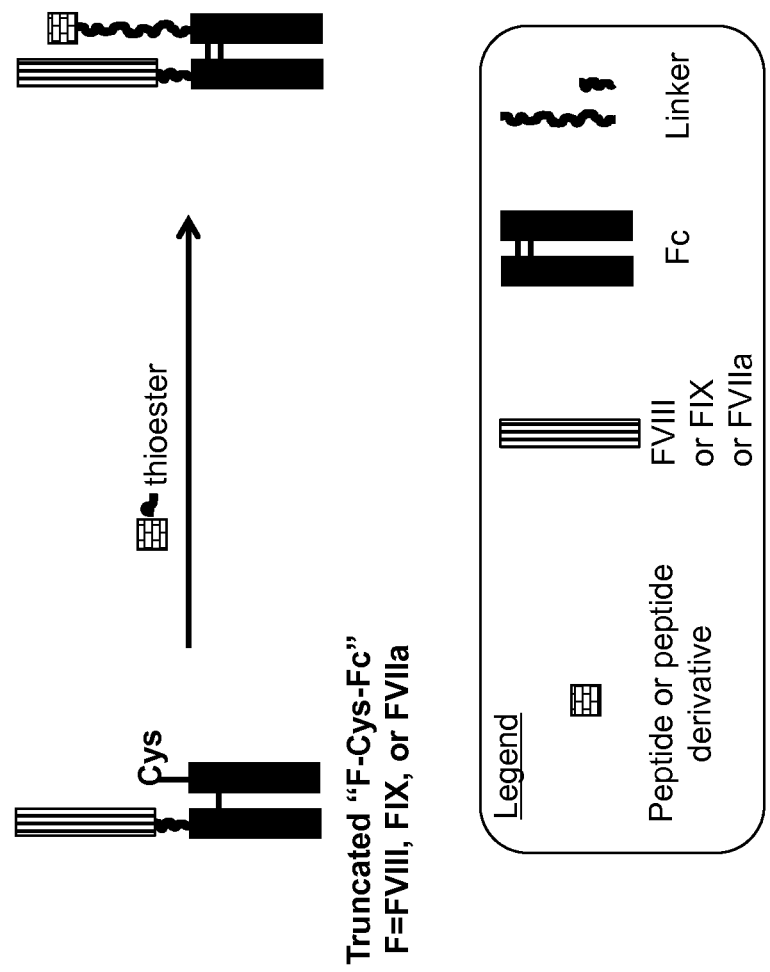
Figure 24:
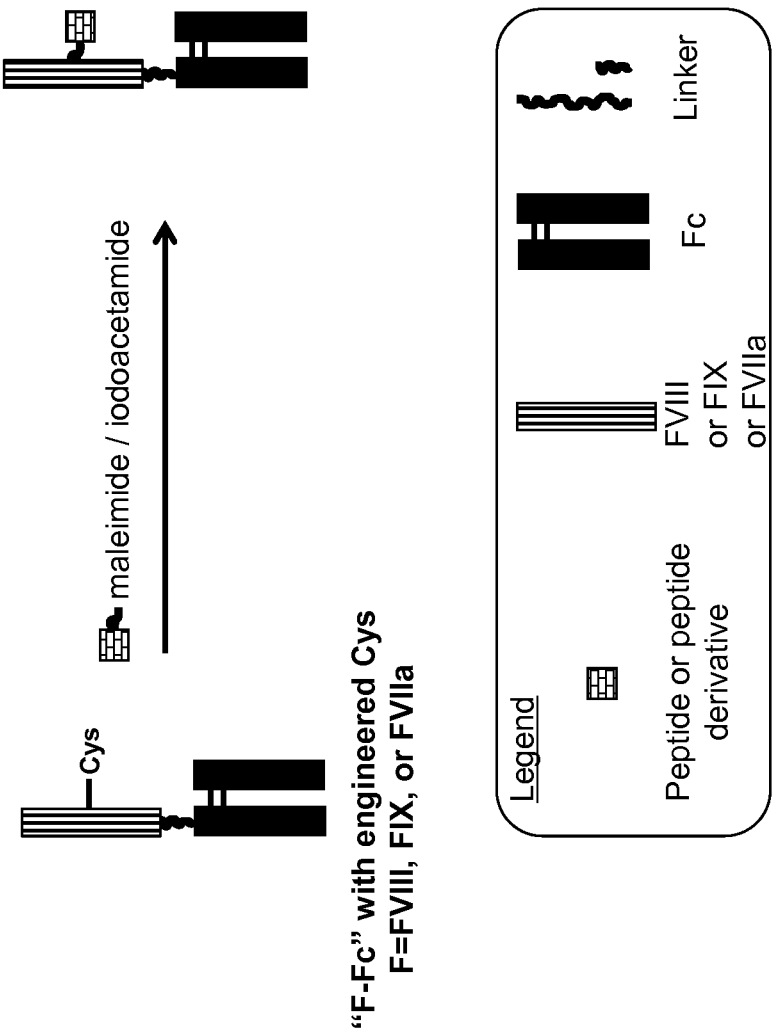

FIG. 20 illustrates various conjugates of the present disclosure, in which a compound (indicated as a peptide or peptide derivative) is covalently linked to a FVIII-heterologous moiety construct, wherein the heterologous moiety is represented in this figure as an Fc, optionally via a linker, wherein the peptide can be linked to the FVIII portion of the FVIII-fusion (e.g., constructs E3, E5-E7), to the heterologous moiety portion of the FVIII-fusion (constructs E1 and E2), or can be interposed between the FVIII and the heterologous moiety of the FVIII-fusion (E4). In constructs E1 and E2, in which the heterologous moiety is shown as an Fc, FVIII is linked to one chain of the Fc and the peptide or peptide derivative is linked to the other (free) Fc chain. In other constructs similar to E2, compound can be placed on either or both of the Fc chains. In constructs E3-E6, the compound is linked to the N- or C-terminal amino acid of the FVIII heavy chain (HC) or light chain (LC), respectively. In construct E7, the peptide or peptide derivative is covalently linked to an internal amino acid residue of the FVIII molecule (e.g., cysteine). It is understood that in other conjugates, the heterologous moiety (represented in this figure as Fc) can be e.g., PEG, PPG, albumin, XTEN, etc. In one example, constructs E1-E6 of FIG. 20 can be made recombinantly. In another example, constructs E1 and E7 of FIG. 20 can be made semi-recombinantly e.g., as illustrated in FIGS. 23 and 24.

FIG. 21 illustrates various conjugates of the present disclosure, in which a compound (indicated as a peptide or peptide derivative) is covalently linked to a FVIII protein. In constructs F1-F4 the pro-coagulant peptide is linked to the N- or C-terminal amino acid of the FVIII heavy chain (HC) or light chain (LC), respectively. In construct F5, the peptide or peptide derivative is covalently linked to an internal amino acid residue of the FVIII. In one example, constructs F1-F4 of FIG. 21 can be made recombinantly. In another example, construct F5 can be made semi-recombinantly as illustrated in FIGS. 23 and 24.

FVIIa Conjugates

In various embodiments, the compound of the present disclosure (e.g., peptide or peptide derivative) is covalently linked to FVIIa or a FVIIa-heterologous moiety construct.

In one example, the conjugate of the present disclosure includes a FVIIa-heterologous moiety construct (e.g., FVIIa-Fc, FVIIa-albumin, FVIIa-PEG, FVIIa-XTEN) and the compound (e.g., peptide or peptide derivative) is covalently linked to the FVIIa-portion of the construct. In another example, the conjugate of the present disclosure includes a FVIIa-heterologous moiety construct (e.g., FVIIa-Fc, FVIIa-albumin, FVIIa-PEG, FVIIa-XTEN) and the compound (e.g., peptide or peptide derivative) is covalently linked to the heterologous moiety portion of the construct.

In one example according to the above embodiments, the heterologous moiety is Fc. Accordingly, the present disclosure provides a conjugate comprising a FVIIa-Fc construct (FVIIa-Fc) and a compound of the present disclosure (e.g., a pro-coagulant peptide or peptide derivative), and a linker, which covalently links the compound to the FVIIa-Fc. In one example according to this embodiment, the compound is covalently linked to the FVIIa portion of the FVIIa-Fc (e.g., via a linker). In another example according to this embodiment, the compound is covalently linked to the Fc portion of the FVIIa-Fc (e.g., via a linker). These optional linkers can be cleavable linkers as described herein elsewhere.

In one example according to any of the above embodiments, the compound is covalently linked to the C-terminus of the FVIIa HC (e.g., the compound is interposed between the heterologous moiety and the FVIIa HC). In yet another example according to any of the above embodiments, the compound is covalently linked to the C-terminus of the FVIIa LC. In another example according to any of the above embodiments, the compound is covalently linked to the N-terminus of the FVIIa heavy chain (HC) with a cleavable linker to allow for conversion to an active protease. In a further example according to any of the above embodiments, the compound (e.g., the pro-coagulant peptide or peptide derivative) is covalently linked to an internal amino acid residue of the FVIIa molecule (internal conjugation), e.g., via a cysteine residue. In one example, the cysteine residue is engineered into the FVIIa amino acid sequence, e.g., according to the procedures described in Mei, B. et. al. Rational design of a fully active, long-acting PEGylated FVIIa for hemophilia A treatment. *Blood* (2010) 116:270-279; and U.S. Patent Application US2006/0115876 to Pan C. et al. (Site-directed modification of FVIIa), each of which is incorporated herein by reference in its entirety.

Figure 18:
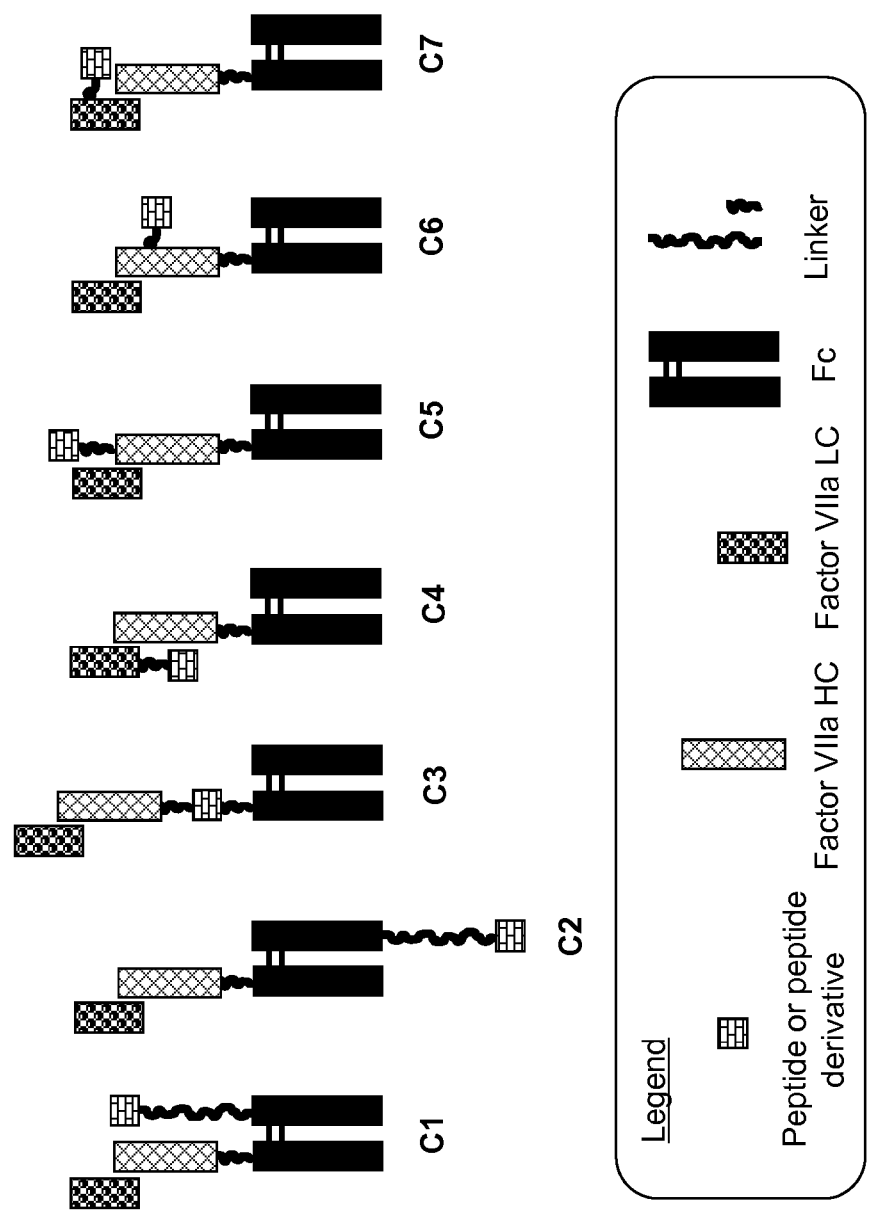
Figure 19:
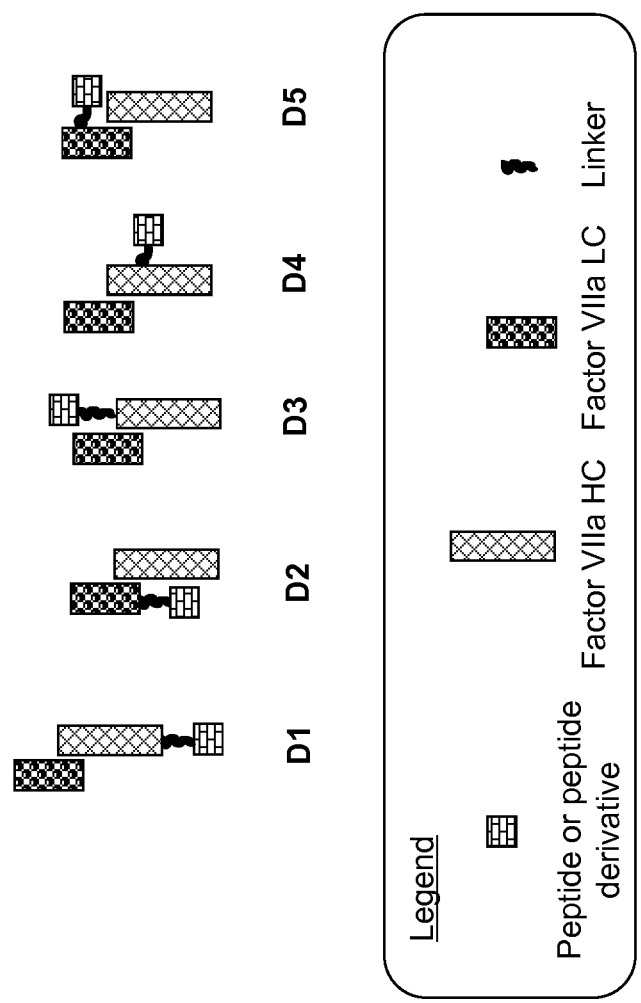

Exemplary FVIIa conjugates are illustrated in FIGS. 18 and 19.

FIG. 18 illustrates various conjugates of the present disclosure, in which a compound (shown as a peptide or peptide derivative) is covalently linked to a FVIIa heterologous moiety construct, wherein the heterologous moiety is represented in this figure as an Fc, optionally via a linker, wherein the peptide can be linked to the FVIIa portion of the FVIIa-fusion (e.g., constructs C4-C7), to the heterologous moiety portion of the FVIIa-fusion (constructs C1 and C2), or can be interposed between the FVIIa and the heterologous moiety of the FVIIa-fusion (C3). In constructs C1 and C2, in which the heterologous moiety is shown as an Fc, FVIIa is linked to one chain of the Fc and the peptide or peptide derivative is linked to the other (free) Fc chain. In other constructs similar to E2, compound can be placed on either or both of the Fc chains. In constructs C3 and C4, the peptide or peptide derivative is linked to the C-terminal amino acid of the FVIIa heavy chain (HC) or light chain (LC), respectively; for C3, the peptide or peptide derivative is also linked to the N-terminus of the heterologous moiety. In construct C5, the peptide or peptide derivative is linked to the N-terminus of the HC; in this case in particular, the linker could be cleavable by proteases activated during the clotting cascade (such as disclosed in International Patent Application No. PCT/US2011/043599 filed Jul. 11, 2011), in order to generate the free N-terminus of the HC required for protease activity. In constructs C6 and C7, the peptide or peptide derivative is covalently linked to an internal amino acid residue (e.g., cysteine) of the FVIIa molecule HC or LC, respectively. It is understood that in other conjugates, the heterologous moiety (represented in this figure as Fc) can be e.g., PEG, PPG, albumin, XTEN, etc. In one example, constructs C1-C5 can be made recombinantly. In another example, constructs C1, C6 and C7 can be made semi-recombinantly e.g., as illustrated in FIGS. 23 and 24.

FIG. 19 illustrates various conjugates of the present disclosure, in which a peptide or peptide derivative (e.g., a pro-coagulant peptide or peptide derivative, such as those disclosed herein) is covalently linked to a FVIIa protein. In constructs D1-D2, the peptide or peptide derivative is linked to the C-terminal amino acid of the FVIIa heavy chain (HC) or light chain (LC), respectively. In construct D3, the peptide or peptide derivative is linked to the N-terminus of the HC; in this case in particular, the linker could be cleavable by proteases activated during the clotting cascade (such as disclosed in International Patent Application No. PCT/US2011/043599 filed Jul. 11, 2011), in order to generate the free N-terminus of the HC required for protease activity. In constructs D4 and D5, the peptide or peptide derivative is covalently linked to an internal amino acid residue of the FVIIa HC or LC, respectively. In one example, constructs D1-D3 can be made recombinantly. In another example, constructs D4 and D5 can be made semi-recombinantly as illustrated in FIGS. 23 and 24.

FIX Conjugates

In various embodiments, the compound of the present disclosure (e.g., peptide or peptide derivative) is covalently linked to FIX or a FIXa-heterologous moiety construct.

In one example, the conjugate of the present disclosure includes a FIX-heterologous moiety construct (e.g., FIX-Fc, FIX-albumin, FIX-PEG) and the compound (e.g., peptide or peptide derivative) is covalently linked to the FIX-portion of the construct. In another example, the conjugate of the present disclosure includes a FIX-heterologous moiety construct (e.g., FIX-Fc, FIX-albumin, FIX-PEG) and the compound (e.g., peptide or peptide derivative) is covalently linked to the heterologous moiety portion of the construct, optionally via a linker.

In one example, the linker of the FIX conjugate is sufficiently long for the compound (e.g., the pro-coagulant peptide or peptide derivative) to bind to the FIX (e.g., once it is converted to FIXa) at an amino acid sequence around Tyr177 (FIXa numbering) as described herein. Such binding of the compound (e.g., peptide or peptide derivative) to the FIX can increase the catalytic activity of the FIXa or its inactivated form FIX. In another example, the linker is sufficiently long for the compound (e.g., peptide or peptide derivative) to be capable of binding to the amino acid sequence: MFCAG (SEQ ID NO: 1) of FIX or FIXa. In another example, the linker is sufficiently long to be capable of interacting with the amino acid sequence: YNNMFCAGFHE (SEQ ID NO: 2) of FIX or FIXa. In another example, the linker is sufficiently long to be capable of interacting with the amino acid sequence: RSTKFTIYNNMFCAGFHEGGRDSCQG (SEQ ID NO: 3) of FIX or FIXa.

In one example according to the above embodiments, the heterologous moiety is Fc. Accordingly, the present disclosure provides a conjugate comprising a FIX-Fc construct (FIX-Fc) and a compound of the present disclosure (e.g., a pro-coagulant peptide or peptide derivative), and a linker, which covalently links the compound (e.g., peptide or peptide derivative) to the FIX-Fc. In one example according to this embodiment, the compound (e.g., peptide or peptide derivative) is covalently linked to the FIX portion of the FIX-Fc (e.g., via a linker). In another example according to this embodiment, the compound (e.g., peptide or peptide derivative) is covalently linked to the Fc portion of the FIX-Fc (e.g., via a linker).

In another example, the peptide or peptide derivative is interposed between the FIX and the Fc. In another example, the compound (e.g., peptide or peptide derivative) is inserted between the FIX heavy chain (HC) and the FIX light chain (LC), replacing all, part, or none of the FIX activation peptide, while maintaining a protease cleavage site at the N-terminus of the HC to enable the generation of an active protease.

In one example, the compound is covalently linked to the C-terminus of the FIX heavy chain (HC). In another example, the compound is covalently linked to the C-terminus of the FIX HC and is interposed between the FIX HC and a heterologous moiety (e.g., Fc). In yet another example according to any of the above embodiments, the compound (e.g., the pro-coagulant peptide or peptide derivative) is inserted between the FIX LC and the FIX HC, replacing all, part, or none of the FIX activation peptide, while maintaining a FXIa/FVIIa-TF cleavage site at the N-terminus of the HC to enable the generation of an active protease. Alternatively, the compound linked to the N-terminus of the FIX HC can be inserted with a linker that is cleavable by proteases activated during the clotting cascade in order to generate the free N-terminus of the HC required for protease activity (such as disclosed in International Patent Application No. PCT/US2011/043599 filed Jul. 11, 2011). In a further example, the FIX LC and FIX HC could be separated with one or both chains covalently linked at the C-terminus to the N-terminus of a heterologous moiety (e.g. Fc), with the compound linked to the HC as described above to enable generation of an active protease after cleavage. In a further example according to any of the above embodiments, the compound (e.g., the pro-coagulant peptide or peptide derivative) is covalently linked to an internal amino acid residue of the FIX molecule (internal conjugation), e.g., via a cysteine residue. In one example, the cysteine residue is engineered into the FIX amino acid sequence, e.g., according to the procedures described in Mei, B. et. al. US2006/0115876 to Pan C. et al.

Figure 16:
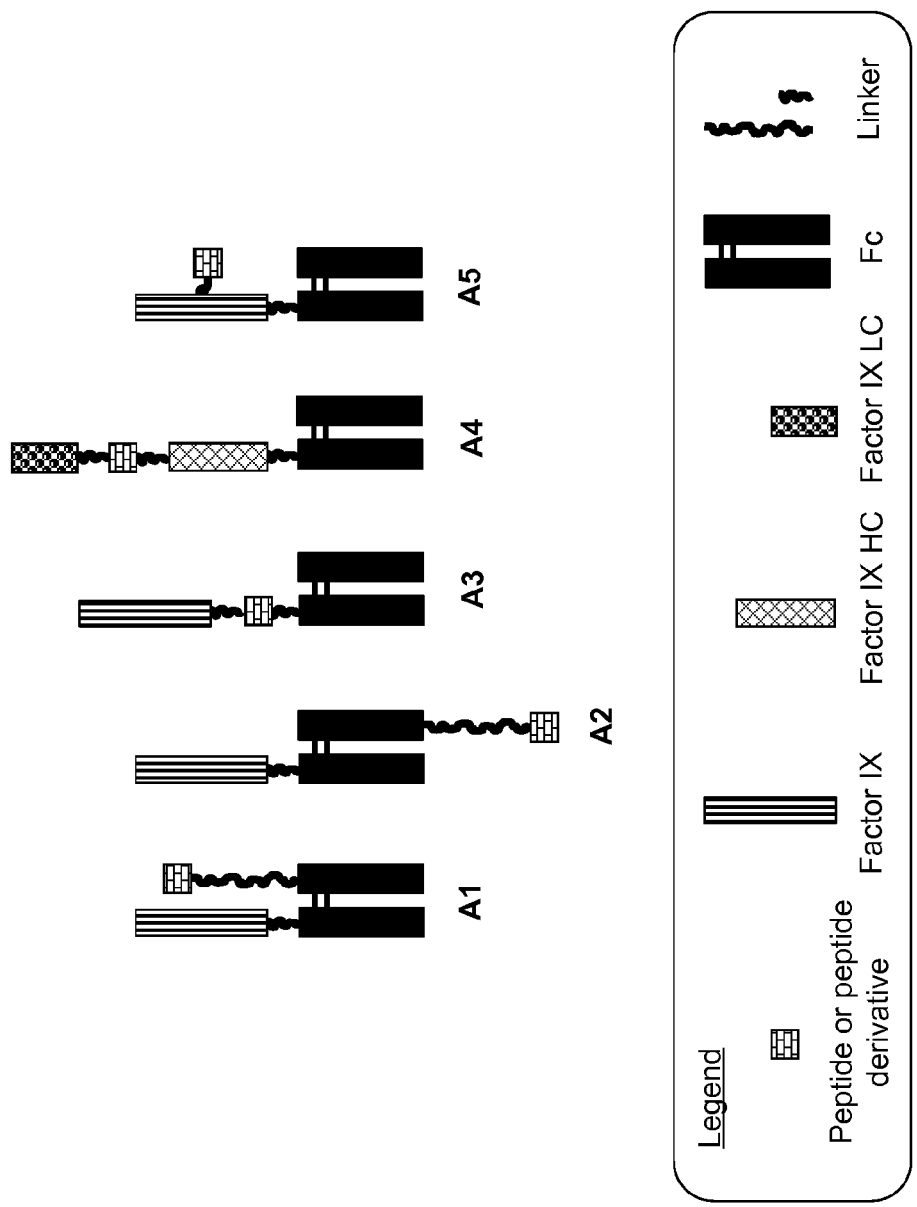
Figure 17:
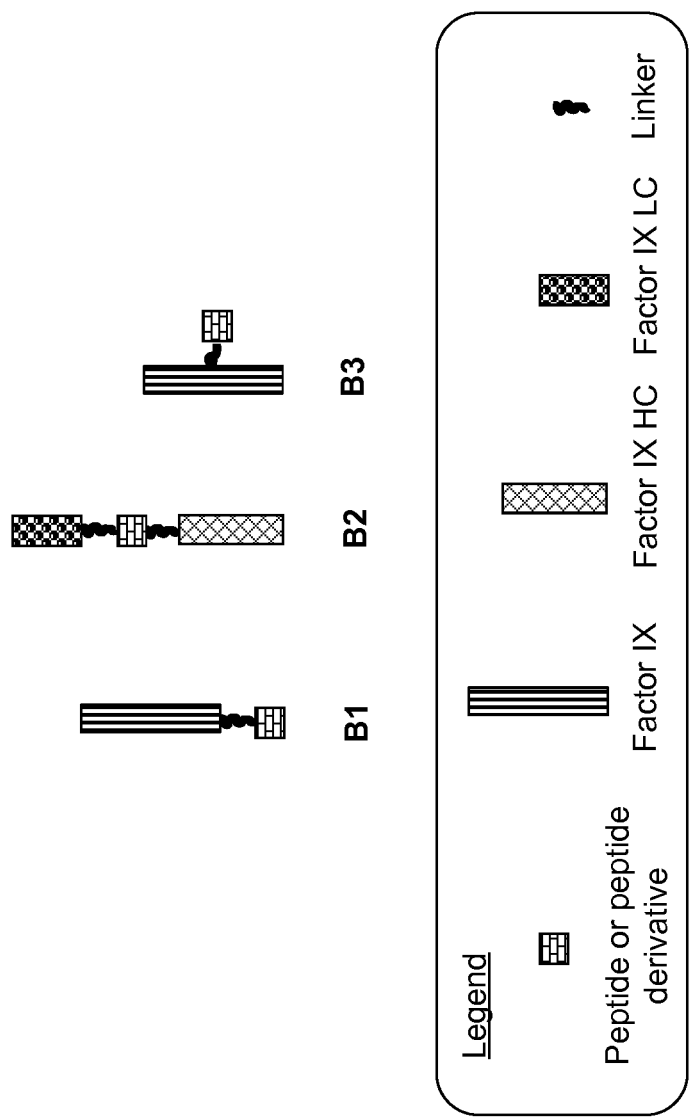

Exemplary FIX conjugates are illustrated in FIGS. 16 and 17.

FIG. 16 illustrates various conjugates of the present disclosure, in which a compound (shown as a peptide or peptide derivative) is covalently linked to an FIX heterologous moiety construct, wherein the heterologous moiety is represented in this figure as an Fc and wherein the peptide can be linked to the FIX portion of the FIX-Fc (e.g., constructs A4 and A5), to the Fc portion of the FIX-Fc (constructs A1 and A2), or can be interposed between the FIX and the Fc of the FIX-Fc (A3). In constructs A1 and A2, FIX is linked to one chain of the Fc and the peptide or peptide derivative is linked to the other (free) Fc chain. In other constructs similar to E2, compound can be placed on either or both of the Fc chains. In construct A3, the peptide or peptide derivative is interposed between the FIX HC and the Fc. In construct A4, the peptide or peptide derivative is inserted between the FIX LC and the FLX HC, and replacing all, part, or none of the FIX activation peptide, while maintaining a FXIa/FVIIa-TF cleavage site at the N-terminus of the HC to enable the generation of an active protease. Alternatively, the compound linked to the N-terminus of the FIX HC can be inserted with a linker that is cleavable by proteases activated during the clotting cascade in order to generate the free N-terminus of the HC required for protease activity (such as disclosed in International Patent Application No. PCT/US2011/043599 filed Jul. 11, 2011). In construct A5, the peptide or peptide derivative is covalently linked to an internal amino acid residue of the FIX molecule (e.g., cysteine). In one example, constructs A1-A4 can be made recombinantly. In another example, constructs A1 and A5 can be made semi-recombinantly e.g., as illustrated in FIGS. 23 and 24. It is understood that in other conjugates, the heterologous moiety (represented in this figure as Fc) can be e.g., PEG, PPG, albumin, XTEN, etc.

FIG. 17 illustrates various conjugates of the present disclosure, in which a compound (shown as a peptide or peptide derivative) is covalently linked to a FIX protein. In construct B1, the peptide or peptide derivative is linked to the C-terminal amino acid of the FIX heavy chain (HC). In construct B2, the peptide or peptide derivative is inserted between the FIX LC and the FIX HC, and replacing all, part, or none of the FIX activation peptide, while maintaining a FXIa/FVIIa-TF cleavage site at the N-terminus of the HC to enable the generation of an active protease. Alternatively, the compound linked to the N-terminus of the FIX HC can be inserted with a linker that is cleavable by proteases activated during the clotting cascade in order to generate the free N-tertninus of the HC required for protease activity (such as disclosed in International Patent Application No. PCT/US2011/043599 filed Jul. 11, 2011). In construct B3, the peptide or peptide derivative is covalently linked to an internal amino acid residue of the FIX. In one example, constructs B1 and B2 of FIG. 17 can be made recombinantly. In another example, construct B3 can be made semi-recombinantly, e.g., as illustrated in FIGS. 23 and 24.

Platelet-Targeting Moiety (PTM) Conjugates

In various embodiments, the compound of the present disclosure (e.g., peptide or peptide derivative) is covalently linked to a PTM (e.g., PDG-13) or a PTM-heterologous moiety construct. In various embodiments the compound of the present disclosure is covalenly linked to a platelet targeting moiety Linking the compound of the present disclosure (e.g., a pro-coagulant peptide or peptide derivative) to a platelet targeting moiety can be useful for targeting the compound (e.g., the pro-coagulant peptide or peptide derivative) to the surface of platelets (e.g., in vivo). In one example, the compound is targeted to platelets in order to enhance its efficacy by localizing the compound to the site of coagulation using a "targeting moiety" which binds to a molecule expressed on platelets. In addition to increasing the local concentration through the PTM, the concomitant interaction of the peptide or peptide derivative with FIXa may stabilize FIX association with the Xase complex on platelet surfaces, similar to the mechanism of action of FVIIIa. Preferably the targeted molecules are not expressed on cells or tissues other than platelets, i.e., the targeting moieties specifically bind to platelets. Linking the peptide or peptide derivative to the targeting moiety may enhance its biological activity. This strategy may reduce the compound dose necessary to obtain a desired pharmaceutical effect, and thus can reduce potential side effects that the compound may have. Accordingly, in one example, the conjugates of the present disclosure bind (e.g., specifically) to platelets.

In one example, the targeting moiety binds to receptors/conformations found on resting platelets. By doing so, sites for coagulation could be primed for enhanced efficacy. Targeting such molecule may also extend half life of the compound (e.g., peptide or peptide derivative) and/or prevent clearance. Exemplary platelet targeting moieties according to this embodiment include GpIb (e.g., GpIbalpha) of the GpIb/V/IX complex, GpVI, and nonactive forms of GPIIb/IIIa.

In another example, the platelet targeting moiety binds to receptors/conformations only found on activated platelets in order to localize the compound (e.g., peptide or peptide derivative) to a site of active coagulation. Exemplary such molecules include the active form of GpIIb/IIIa as well as CD62P.

In another embodiment the platelet targeting moiety selectively binds to a target selected from the group consistingof: P selectin, GMP-33, LAMP-1, LAMP-2, CD40L, and LOX-1.

The platelet targeting moiety can be, e.g. MB9, SCE5, scFv, AP3, or peptides (e.g., "RGD" peptides) targeting GPIIbIIIa, a fatty acid or small molecule capable of inserting into plasma membranes, OS1, OS2, and PS4 targeting GP1b. In one embodiment, the platelet targeting moiety is OS1, OS2 and PS4 targeting GP1b.

In another embodiment, the platelet targeting moiety is a moiety that binds to GPIIbIIIa (e.g., PDG-13).

In one example, the conjugate of the present disclosure includes a platelet targeting moiety-heterologous moiety construct (e.g., PTM-Fc, PTM-albumin, PTM-PEG) and the compound (e.g., peptide or peptide derivative) is covalently linked to the platelet targeting moiety-portion of the construct. In another example, the conjugate of the present disclosure includes a platelet targeting moiety-heterologous moiety construct (e.g., PTM-Fc, PTM-albumin, PTM-PEG) and the compound (e.g., peptide or peptide derivative) is covalently linked to the heterologous moiety portion of the construct.

In one example according to the above embodiments, the heterologous moiety is Fc. Accordingly, the present disclosure provides a conjugate comprising a PTM-Fc construct (PTM-Fc) and a compound of the present disclosure (e.g., a pro-coagulant peptide or peptide derivative), and a linker, which covalently links the compound (e.g., peptide or peptide derivative) to the PTM-Fc. In one example according to this embodiment, the compound (e.g., peptide or peptide derivative) is covalently linked to the PTM portion of the PTM-Fc (e.g., via a linker). In another example according to this embodiment, the compound (e.g., peptide or peptide derivative) is covalently linked to the Fc portion of the PTM-Fc (e.g., via a linker).

In one example according to any of the above embodiments, the compound (e.g., the pro-coagulant peptide or peptide derivative) is covalently linked to the N-terminus of the platelet targeting moiety. In another example according to any of the above embodiments, the compound (e.g., the pro-coagulant peptide or peptide derivative) is covalently linked to the C-terminus of the platelet targeting moiety. In a further example according to any of the above embodiments, the compound (e.g., the pro-coagulant peptide or peptide derivative) is covalently linked to an internal amino acid residue of the platelet targeting moiety molecule (internal conjugation), e.g., via a cysteine residue. In one example, the cysteine residue is engineered into the platelet targeting moiety amino acid sequence, e.g., according to the procedures described in Mei, B. et. al. and US2006/0115876 to Pan C. et al.

The conjugates of the present disclosure can comprise one or more targeting moiety. Additionally, two or more targeting moieties may be linked to each other (e.g., via a polypeptide linker) in series. When two or more targeting moieties are present in a conjugate of the present disclosure, the moieties may be the same or different.

Figure 22:
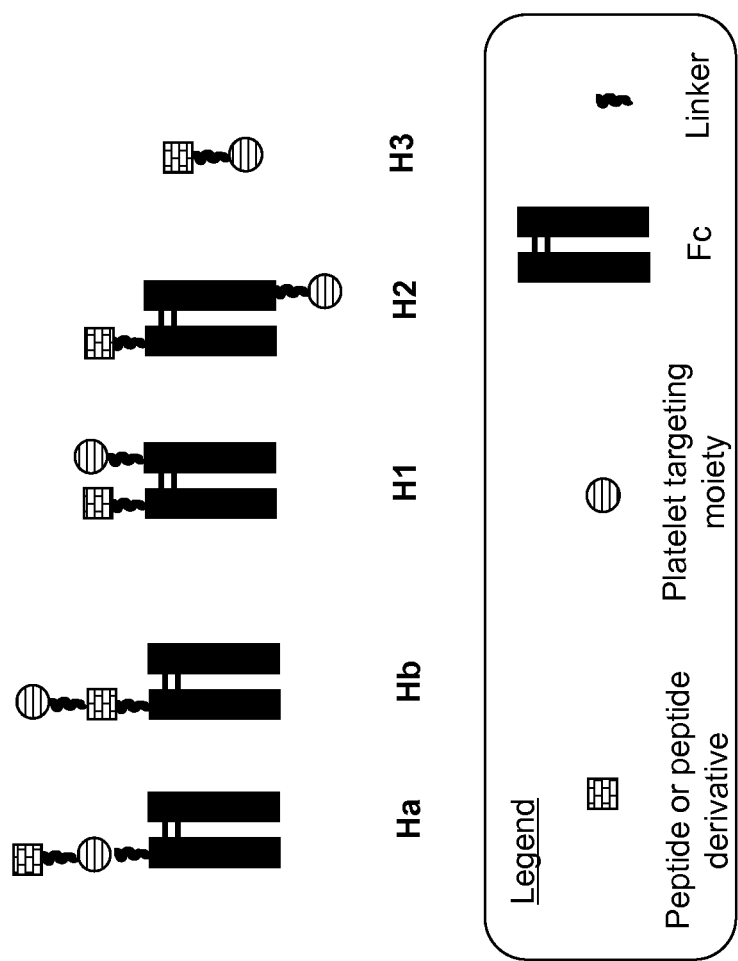

Exemplary platelet targeting moiety conjugates are illustrated in FIG. 22.

FIG. 22 illustrates various conjugates of the present disclosure, in which a compound of the present disclosure (e.g., a pro-coagulant peptide or peptide derivative) is covalently linked to a platelet targeting moiety (construct H3) or a platelet targeting moiety-heterologous moiety construct (H1, H2, Ha, Hb) optionally via a linker. The peptide or peptide derivative can be linked to the platelet targeting moiety portion of the construct (Ha), to the heterologous moiety (e.g., Fc) portion of the construct (H1, H2), or can be interposed between the platelet targeting moiety and the heterologous moiety (e.g., Fc) of the platelet targeting moiety-fusion construct (Hb). In FIG. 22, the heterologous moiety is represented as an Fc, which can be replaced with other heterologous moietys described herein. In constructs H1 and H2, in which the heterologous moiety is shown as an Fc, the platelet targeting moiety is linked to one chain of the Fc and the peptide or peptide derivative is linked to the other (free) Fc chain. In constructs H3, the peptide or peptide derivative is linked to the N- or C-terminal amino acid of the platelet targeting moiety. In other constructs, the peptide or peptide derivative is covalently linked to an internal amino acid residue of the platelet targeting moiety (e.g., cysteine). It is understood that in other conjugates, the heterologous moiety (represented in FIG. 22 as Fc) can be any other heterologous moiety, e.g., PEG, PPG, albumin, XTEN, etc.

Figure 25:
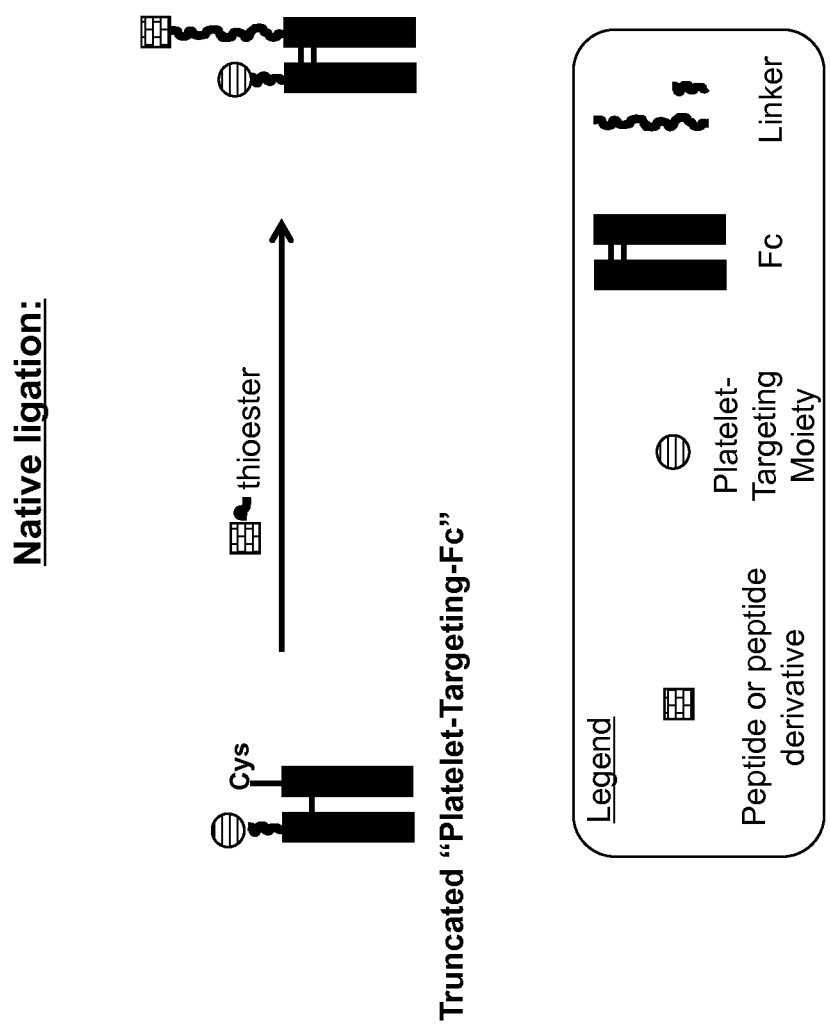
Figure 26:
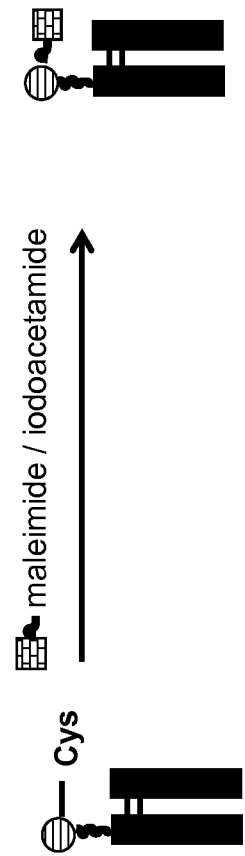
Figure 26:
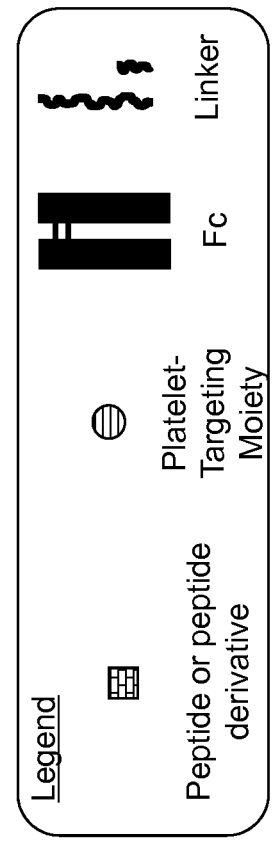

In one example, the conjugates of FIG. 22 can be made recombinantly. In another example, the conjugates of FIG. 22 (e.g., H1, H3) can be made semi-recombinantly e.g., as illustrated in FIGS. 25 and 26.

Heterologous moieties useful in any of the above embodiments are described herein. Exemplary heterologous moietys according to any of the above embodiments include, e.g., any half-life extending molecule known in the art, e.g., polyethylene glycol (PEG), polypropylene glycol (PPG), PAS, HES, XTEN, albumin, as well as antibodies and antibody fragments (e.g., Fc).

Exemplary Conjugates

In one example, the polypeptide conjugate of the present disclosure has a structure comprising a polypeptide (e.g., FVIII, FIX, FVIIa, or a platelet targeting moiety), a compound of the present disclosure (e.g., a pro-coagulant peptide or peptide derivative), optionally at least one linker, and optionally at least one heterologous moiety. Examples of such structures include, e.g., those according to one of Formula (B1) to Formula (G2) below:

$$U_1\text{-}(L_1)_m\text{-Pep} \quad (B1)$$

$$\text{Pep-}(L_1)_m\text{-}U_1 \quad (B2)$$

$$\text{Het-}(L_1)_m\text{-}U_1\text{-}(L_1)_m\text{-Pep} \quad (C1)$$

$$\text{Pep-}(L_1)_m\text{-}U_1\text{-}(L_1)_m\text{-Het} \quad (C2)$$

$$U_1\text{-}(L_1)_m\text{-Het-}(L_1)_m\text{-Pep} \quad (D1)$$

$$\text{Pep-}(L_1)_m\text{-Het-}(L_1)_m\text{-}U_1 \quad (D2)$$

$$U_1\text{-}(L_1)_m\text{-Pep-}(L_1)_m\text{-Het} \quad (E1)$$

$$\text{Het-}(L_1)_m\text{-Pep-}(L_1)_m\text{-}U_1 \quad (E2)$$

In Formula (B1), (B2), (C1), (C2), (D1), (D2), (E1), and (E2), $U_1$ is a polypeptide selected from a blood coagulation factor and a platelet targeting moiety, wherein the blood coagulation factor is selected from FVIIa, FVIII, and FIX. In one example, FVIII is B-domain deleted FVIII. In Formulas (F1) an (F2), FIX(HC) is the heavy chain of FIX, and FIX(LC) is the light chain of FIX. In Formulas (FG) an (G2), FVIIa(HC) is the heavy chain of FVIIa, and FVIIa(LC) is the light chain of FVIIa.

In Formulas (B1) through (E2), m is an integer selected from 0 and 1.

Het is a heterologous moiety as defined herein. In one example, Het is a half-life extending moiety, selected from, e.g., PEG, PPG, HES, PAS, XTEN, albumin, and Fc.

In Formulas (B1) through (E2), Pep is a compound of the present disclosure. In one example, the compound is a pro-coagulant peptide or peptide derivative of the present disclosure.

In Formulas (B1) through (G2), each $L_1$ is either absent (m=0) or present (m=1), and when present is a linker as described herein. The linker covalently links the compound (e.g., the peptide or peptide derivative), directly or indirectly (e.g., via a heterologous moiety Het), to the polypeptide (e.g., FVIII, FIX, FVIIa, or a platelet targeting moiety). Exemplary linkers are described herein.

In one embodiment, the present invention is directed to a conjugate comprising the compound disclosed herein and a heterologous moiety which are linked to each other via an optional linker. The conjugate can be represented by a structure comprising formula Het1-$(L_1)_m$-Pep or Pep-$(L_1)_m$-Het1, wherein Het1 is a heterologous moiety; m is an integer selected from 0 and 1; $L_1$ is either absent (m=0) or present (m=1), and when present is a linker; Pep is a compound according to claim 1; and (—) is a covalent bond. In another embodiment, the heterologous moiety comprises a half-life extending molecule, e.g., an immunoglobulin constant region or a portion thereof, albumin, an XTEN sequence, transferrin, an albumin binding moiety, a PAS sequence, a HES sequence, the β subunit of the C-terminal peptide (CTP) of human chorionic gonadotropin, polyethylene glycol (PEG), hydroxyethyl starch (HES), albumin-binding small molecules, or any combinations thereof. In a specific embodiment, the immunoglobulin constant region or a portion thereof is an Fc moiety or an FcRn binding partner.

In certain embodiments, the conjugate of the invention further comprises a second heterologous moiety (Het2), wherein the second heterologous moiety is linked to or associated with the heterologous moiety (Het or Het1). The conjugate can be represented as Het2:Het1-(L1)-Pep or Pep-(L1)-Het1:Het2, wherein L1 is an optional linker, Pep is the compound of the invention, Het1 is a first heterologous moiety, and Het2 is a second heterologous moiety. In still other embodiment, the conjugate comprises two polypeptide chains, a first chain comprising the compound of the invention linked to a first heterologous moiety by a first linker and a second chain comprising a second heterologous moiety. In yet other embodiments, the second heterologous moiety is a half-life extending molecule. The second heterologous moiety can comprise an immunoglobulin constant region or a portion thereof, albumin, transferrin, an albumin binding moiety, a PAS sequence, a HES sequence, the β subunit of the C-terminal peptide (CTP) of human chorionic gonadotropin, polyethylene glycol (PEG), hydroxyethyl starch (HES), albumin-binding small molecules, or any combinations thereof. In a particular embodiment, the immunoglobulin constant region or a portion thereof is an Fc moiety or an FcRn binding partner. In yet other embodiments, the heterologous moiety and the second heterologous moiety are associated by a covalent bond, e.g., a peptide bond, a disulfide bond, a metal bond, a hydrogen bond, a disulfide bond, a sigma bond, a pi bond, a delta bond, a glycosidic bond, an agnostic bond, a bent bond, a dipolar bond, a Pi backbond, a double bond, a triple bond, a quadruple bond, a quintuple bond, a sextuple bond, conjugation, hyperconjugation, aromaticity, hapticity, or antibonding. In another embodiment, the heterologous moiety and the second heterologous moiety are associated by a non-covalent interaction, e.g., an ionic interaction, a hydrophobic interaction, a hydrophilic interaction, a Van der Waals interaction, or a hydrogen bond. In some embodiments, the association between the heterologous moiety and the second heterologous moiety is a covalent bond or a non-covalent bond. In a particular embodiment, the association is a disulfide bond.

In still other embodiments, the conjugate comprises further comprises a scFc linker (X), which is linked to the second heterologous moiety and the compound. Therefore, the conjugate can be represented as Het2-X-Pep-L1-Het1 or Het1-L1-Pep-X-Het2, wherein the scFv linker comprises at least one intracellular processing site and a linker (Lx). In one embodiment, a first intracellular processing site (P1) interposed between the second heterologous moiety and the linker (Lx). In another embodiment, a second intracellular processing site (P2) interposed between the linker (Lx) and the compound. The intracellular processing site inserted therein can be processed (cleaved) by an intracellular processing enzyme upon expression in a host cell, thereby allowing formation of a zymogen-like heterodimer. Examples of the intracellular processing enzymes include furin, a yeast Kex2, PCSK1 (also known as PC1/Pc3), PCSK2 (also known as PC2), PCSK3 (also known as furin or PACE), PCSK4 (also known as PC4), PCSK5 (also known as PC5 or PC6), PCSK6 (also known as PACE4), or PCSK7 (also known as PC7/LPC, PC8, or SPC7). Other processing sites are known in the art.

The conjugate comprising two polypeptide chains as shown above can further comprise FVIII, FIX, FVIIa, or a platelet targeting moiety, wherein the polypeptide is linked to the compound or to the second heterologous moiety via a second optional linker. In one embodiment, the polypeptide (either a heavy chain or a light chain) is linked to the second heterologous moiety via the second optional linker. Therefore, the conjugate can comprises two polypeptide chains, a first chain comprising the compound, the heterologous moiety, and the linker, and a second chain comprising the polypeptide, the second heterologous moiety, and the second optional linker, wherein the first polypeptide chain and the second polypeptide chain are associated with each other.

In other embodiments, the conjugate comprises two polypeptide chains selected from the group consisting of:
(a) the first polypeptide chain comprising the compound linked to the N-terminus of the first heterologous moiety by the first linker and the second polypeptide chain comprising the polypeptide linked to the N terminus of the second heterologous moiety by the second linker,
(i) wherein the polypeptide is FIX or a platelet targeting moiety, and
(ii) wherein the first polypeptide chain and the second polypeptide chain are chemically or physically associated with each other; (FIG. 16 A1 and FIG. 22 H1) and
(b) the first polypeptide chain comprising the compound linked to the C-terminus of the first heterologous moiety by the first linker and the second polypeptide chain comprising the polypeptide linked to the N terminus of the second heterologous moiety by the second linker,
(i) wherein the polypeptide is FIX or a platelet targeting moiety, and
(ii) wherein the first polypeptide chain and the second polypeptide chain are chemically or physically associated with each other; (FIG. 16 A2 and FIG. 22 H2).

In yet other embodiments, the conjugate comprises three polypeptide chains selected from the group consisting of:
(a) the first polypeptide chain comprising the compound linked to the N-terminus of the first heterologous moiety by the first linker, the second polypeptide chain comprising the heavy chain of the polypeptide linked to the N-terminus of the second heterologous moiety by the second linker, and the third polypeptide chain comprising the light chain of the polypeptide,
(i) wherein the polypeptide is FVIII or FVIIa, and
(ii) wherein the second polypeptide chain is chemically or physically associated with the first polypeptide chain and the third polypeptide chain; and (FIG. 18 C1 and FIG. 20 E1), and
(b) the first polypeptide chain comprising the compound linked to the C-terminus of the first heterologous moiety by the first linker, the second polypeptide chain comprising the heavy chain of the polypeptide linked to the N-terminus of the second heterologous moiety by the second linker, and the third polypeptide chain comprising the light chain of the polypeptide
(i) Wherein the polypeptide is FVIII or FVIIa, and
(ii) wherein the second polypeptide chain is chemically or physically associated with the first polypeptide chain and the third polypeptide chain. (FIG. 18 C2 and FIG. 20 E2).

In still yet other embodiments, the conjugate can be represented by formula:

Pep-(L$_1$)$_m$-Het1

U$_1$-(L$_2$)$_m$-Het2;

wherein Het1 is the first heterologous moiety;
L1 is either absent (m=0) or present (m=1), and when present is a linker;
m is an integer selected from 0 and 1;
Pep is the compound of any one of originally filed claims 1 to 82 of PCT Application No. PCT/US2012/041777,
Het2 is the second heterologous moiety;
L2 is either absent (m=0) or present (m=1), and when present is a linker;
U1 is the polypeptide comprising FIX, FVIII, FVIIa, or the platelet targeting moiety;
(—) is a peptide bond; and
wherein Het1 and Het2 associate chemically or physically with each other. The chemical or physical association can be a covalent bond, e.g., a disulfide bond, or a non-covalent bond. Left represents N-terminus, and right represents C-terminus.

In another example the conjugate comprises:

Het1-(L$_1$)$_m$-Pep and Het2-(L$_2$)$_m$-U$_1$;

or

Het1-(L$_1$)$_m$-Pep and U$_1$-(L$_2$)$_m$-Het2;

or

Pep-(L$_1$)$_m$-Het1 and Het2-(L$_2$)$_m$-U$_1$;

or

Pep-(L$_1$)$_m$-Het1 and U$_1$-(L$_2$)$_m$-Het2,

U$_1$-(L$_2$)$_m$-Het2 and Het1-(L$_1$)$_m$-Pep, or

U$_1$-(L$_2$)$_m$-Het2 and Pep-(L$_1$)$_m$-Het1, or wherein
Het1 is the first heterologous moiety;
L$_1$ is either absent (m=0) or present (m=1), and when present is a linker;
m is an integer selected from 0 and 1;
Pep is the compound of any one of originally filed claims 1 to 82 of PCT Application No. PCT/US2012/041777,
Het2 is the second heterologous moiety;
L$_2$ is either absent (m=0) or present (m=1), and when present is a linker;
U$_1$ is the polypeptide comprising FIX, FVIII, FVIIa, or the platelet targeting moiety;
(—) is a covalent bond,
wherein Het1 and Het2 associate chemically or physically with each other.

In some embodiments, the conjugate comprising two polypeptide chains or three polypeptide chains as shown above can further comprise a scFc linker. In one embodiment, the scFc linker is linked to the second heterologous moiety and the compound. In another embodiment, the scFc linker comprises a linker (Lx) and a first intracellular processing site (P1) interposed between the second heterologous moiety and the linker (Lx). The scFc linker can further comprise a second intracellular processing site (P2) interposed between the linker (Lx) and the compound. In a further embodiment, the scFc linker comprises two intracellular processing sites which are recognized by the same or by different intracellular processing enzymes. The intracellular processing site can be recognized by a intracellular processing enzyme selected from the group consisting of a yeast Kex2, PCSK1, PCSK2, PCSK3, PCSK4, PCSK5, PCSK6, and PCSK7. In a specific embodiment, the at least one intracellular processing site is processed by PCSK5. In other embodiments, each of the two intracellular processing sites is processed by PCSK5. In one embodiment, the two intracellular processing sites are the same. In other embodiments, the two intracellular processing sites are different. Examples of the intracellular processing site processed by the intracellular processing enzyme comprises the amino sequence R-X-[R/K]-R, wherein X can be any amino acid, and [R/K] indicated that the amino acid can be R or K. Each of the PCSK5 enzymatic cleavage sites independently comprises the sequence RRRR (SEQ ID NO: 900) or (RKR)$_n$ (SEQ ID NO: 901), where n is 2. The PCSK5 enzymatic cleavage site at the C-terminal end of the scFc linker comprises the sequence RRRR (SEQ ID NO: 900) and the PCSK5 enzymatic cleavage site at the N-terminal end of the cscFc linker comprises the sequence (RKR)$_2$ (SEQ ID NO: 901). In one embodiment, the scFc linker has a length of about 10 to about 50 amino acids and about 20 to about 30 amino acids. In another embodiment, the scFc linker comprises a gly/ser peptide. In some embodiment, the gly/ser peptide comprises an amino acid sequence of formula (Gly$_4$Ser)$_n$ (SEQ ID NO: 882) or Ser(Gly$_4$Ser)$_n$ (SEQ ID NO: 883), wherein n is a positive integer selected from the group consisting of 1, 2, 3, 4, 5, 6, 7, 8, 9 and 10. Examples of the linker include the (Gly$_4$ Ser)$_n$ peptide, e.g., an amino acid sequence selected from the group consisting of (Gly$_4$Ser)$_6$ (SEQ ID NO: 884), Ser(Gly$_4$Ser)6 (SEQ ID NO: 885), (Gly$_4$Ser)$_4$ (SEQ ID NO: 886) and Ser(Gly$_4$Ser)$_4$ (SEQ ID NO: 887).

In certain embodiments, FVIII and FVIIa can be heterodimers comprising a heavy chain and a light chain, wherein the heavy chain and the light chain are associated with each other by a metal bond.

In one aspect, a conjugate comprises (a) a polypeptide selected from a heavy chain of FVIII (FVIII HC), a light chain of FVIII (FVIII LC), a heavy chain of FIX (FIX HC), a light chain of FIX (FIX LC), a heavy chain of activatable or activated FVII (FVIIa HC), a light chain of activatable or activated FVII (FVIIa LC), and a platelet targeting moiety, and (b) a compound of any one of originally filed claims 1 to 82 of PCT Application No. PCT/US2012/041777, wherein the compound is linked to the polypeptide, optionally via a linker. The N-terminus, C-terminus, or an internal amino acid residue of the compound of the invention is linked to the N-terminus, C-terminus, or an internal amino acid residue of the polypeptide via the linker. See FIG. 17 B3, FIG. 19 D4 and D5, and FIG. 21 F5. One embodiment of the invention includes a conjugate comprising the compound of the invention linked to (1) the C-terminus of FIX HC via a linker, (2) the C-terminus of FIX LC via a linker, (3) the C-terminus of FIX LC via a first linker and the N-terminus of FIX HC via a second linker, or (4) an internal amino acid residue of FIX HC or FIX LC via a linker. See FIG. 17 B1, B2, and B3. Another embodiment of the invention includes the compound of the invention linked to the N-terminus or the C-terminus of FVIIa HC (FIG. 19 D1 and D3), the C-terminus of FVIIa LC (FIG. 19 D2), or an internal amino acid residue of FVIIa HC or FVIIa LC (FIG. 19 D4 and D5). In some embodiments, FVIIa HC or FVIIa LC forms a heterodimer with FVIIa LC or FVIIa HC, respectively. In other embodiments, the compound is linked to the N-terminal of activatable FVII HC via a linker, wherein said linker comprises a protease-cleavable substrate.

In one embodiment, the conjugate comprises the compound of the invention linked to the N terminus or the C terminus of FVIII HC (FIG. 21 F1 and F3), the N-terminus or the C-terminus of FVIII LC (FIG. 21 F2 and F4), or an internal amino acid residue of FVIII HC or FVIII LC. (FIG. 21 F5). In this construct, FVIII HC or FVIII LC can form a heterodimer with FVIII LC or FVIII HC, respectively.

In another embodiment, the compound of the invention can be linked to the N-terminus or the C-terminus of the platelet targeting moiety. (See FIG. 22, Ha, Hb, H3). In one embodiment, the compound or the Factor IX HC is further linked to a heterologous moiety (Het or Het1) by an optional linker. (See FIG. 16, A3, A4, and A5). In another embodiment, the compound or FVIIa HC is further linked to a heterologous moiety (Het or Het1) by an optional linker. (See FIG. 18, C3, C4, C5, and C6). In some embodiments, the compound or FVIII LC is further linked to a heterologous moiety (Het or Het1) by an optional linker. (FIG. 20, E3, E4, E5, E6, and E7). In other embodiments, the compound or the targeting moiety is further linked to a heterologous moiety (Het or Het1) by an optional linker. (See FIG. 22, Ha, Hb).

The heterologous moiety (Het or Het1) as used herein can comprise an immunoglobulin constant region or a portion thereof, albumin, transferrin, an albumin binding moiety, a PAS sequence, a HES sequence, an XTEN sequence, the β subunit of the C-terminal peptide (CTP) of human chorionic gonadotropin, polyethylene glycol (PEG), hydroxyethyl starch (HES), albumin-binding small molecules, or any combinations thereof. In one embodiment, the heterologous moiety is an Fc moiety or an FcRn binding partner. In another embodiment, the conjugate further comprises a second heterologous moiety (Het2). Examples of the second heterologous moiety (Het2) comprises an immunoglobulin constant region or a portion thereof, albumin, transferrin, an albumin binding moiety, an XTEN sequence, a PAS sequence, a HES sequence, the β subunit of the C-terminal peptide (CTP) of human chorionic gonadotropin, polyethylene glycol (PEG), hydroxyethyl starch (HES), albumin-binding small molecules, or any combinations thereof. In a specific embodiment, the immunoglobulin constant region or a portion thereof of the second heterologous moiety is an Fc moiety or an FcRn binding partner.

In further embodiments, the conjugate is polysialylated, pegylated, glycosylated, hesylated, garnma-carboyxlated, or any combinations thereof.

Linker ($L_1$)

The linker is used to covalently link the compound of the present disclosure (e.g., the pro-coagulant peptide) to the heterologous moiety or a polypeptide (e.g., a platelet targeting moiety, or a blood coagulation factor selected from FVIIa, FVIII, and FIX), or or polypeptide construct (e.g., FVIIa-Fc). In other embodiments, a linker is interposed between the polypeptide and a heterologous moiety. Each conjugate can contain multiple linkers.

When the compound (e.g., the peptide or peptide derivative) is interposed between the polypeptide (e.g., FVIII, FIX, FVIIa, or the platelet targeting moiety) and a heterologous moiety (e.g., Fc), then the compound (e.g., the peptide or peptide derivative) is divalent and the conjugate of the present disclosure can include more than one (e.g., 2 linkers), which are independently selected.

In some embodiments, the linker is a hydrophilic linker, e.g., a peptide linker, such as those comprised of Gly and Ser (e.g., $(GGSGG)_n$ (SEQ ID NO: 888) where n=1-50) or Gly and Val. In other embodiments, the linker is a water-soluble polymer, such as polyethylene glycol (PEG) or polypropylene glycol (PPG). In one example, the linker is a PEG moiety. In other embodiments, the linker is a hydroxyethyl starch (HES) moiety.

The compound can be coupled with the heterologous moiety or the polypeptide chemically or using recombinant techniques, e.g., by recombinant expression of a fusion protein.

Chemical linkage can be achieved by linking together chemical moieties present on the compound and on the heterologous moiety or the polypeptide, e.g., using moieties such as amino, carboxyl, sulfydryl, hydroxyl groups, and carbohydrate groups. A variety of homo- and hetero-bifunctional linker molecules can be used that have groups that are activated, or can be activated to link these moieties. Some useful reactive groups on linker molecules include maleimides, N-hydroxy-succinimide esters and hydrazides. Many different spacers of different chemical composition and length can be used for separating these reactive groups including, for example, polyethylene glycol (PEG), aliphatic groups, alkylene groups, cycloalkylene groups, fused or linked aryl groups, peptides and/or peptidyl mimetics, e.g., peptides having from one to 20 amino acids or amino acid analogs.

In one embodiment, the linker is a non-cleavable linker. In one example according to this embodiment, the linker is a "gly-ser polypeptide linker", e.g., includes the amino acid sequence (GGS)n (SEQ ID NO: 889), (GGGS)n (SEQ ID NO: 890), or (GGGGS)n (SEQ ID NO: 891) where n is 1-50 (e.g., n is 6).

In another example, the linker is cleavable (e.g., cleavable in vivo). In one example, the compound is linked to the heterologous moiety or the polypeptide in such a way that the compound is released from the heterologous moiety or the polypeptide in vivo (e.g., near the site of biological activity of the compound in the body). In one example, the cleavage of such linker liberates the compound from a potential activity-compromising steric hindrance that may be caused by the heterologous moiety (e.g., PEG moiety).

In other embodiments, the compound is linked to the polypeptide in such a way that in vivo a functional form of the polypeptide (e.g., the coagulation factor) is released (e.g., near the site of biological activity of the coagulation factor in the body). The cleavage of such linkers liberates the polypeptide from a potential activity-compromising steric hindrance that may be caused by the linked compound (e.g., peptide or peptide derivative), and thereby allows the generation of polypeptide conjugates which retain a high molar specific activity of the polypeptide.

In some embodiments, the linker is a peptide linker that is proteolytically cleavable. In other embodiments, the linker is cleavable by an enzyme from the coagulation cascade.

In some embodiments, the release of the polypeptide (e.g., a coagulation factor) from the conjugate form can be achieved by linking the compound (e.g., the peptide or peptide derivative) to a site on the polypeptide that is removed in vivo. For example, the release of a coagulation factor from the conjugate form can be achieved by linking the compound (e.g., the peptide or peptide derivative) to a site on the coagulation factor that is removed during the activation process.

"Proteolytic cleavage in a coagulation-related mode," as used herein, means any proteolytic cleavage that occurs as a consequence of the activation of at least one coagulation factor or coagulation cofactor. The phrase "activated coagulation factor after the linker is proteolytically cleaved in a coagulation-related mode," as used herein means that the coagulation factor is either activated almost in parallel to the proteolytic cleavage of the linker, or that the coagulation factor was already activated before the proteolytic cleavage of the linker. Activation may occur, for example, by proteolytic cleavage of the coagulation factor or by binding to a cofactor.

The release of the compound from the conjugate form can be achieved using a linker that degrades in a controlled manner, e.g., by one or more proteolytic enzymes (e.g., in the blood). For example, sugar polymers or peptides can be used that are susceptible to general blood proteases or hydrolases. A variety of such technologies are known in the art and have been used to generate pro-drugs.

The linker could be further engineered to be cleaved specifically at sites where pro-coagulant compounds are most needed, such as sites of inflammation or blood coagulation sites triggered through trauma. For example, the linker may be susceptible to specific proteases produced only at the desired site of action, such as proteases released by the inflammation process or generated by the blood coagulation cascade. This selective release of the compound and/or the polypeptide (e.g., the coagulation factor) may lower the potential for side effects and increase the efficiency of the compound and/or the polypeptide at its site of action.

In one embodiment, the linker is cleavable by an enzyme from the coagulation cascade. In one example the linker includes a thrombin cleavable site (thrombin cleavable substrate moiety) or a FXIa cleavable site (FXIa cleavable substrate moiety). Exemplary FXIa cleavage sites include: TQSFNDFTR (SEQ ID NO:844) and SVSQTSKLTR (SEQ ID NO:845). Exemplary thrombin cleavage sites include: DFLAEGGGVR (SEQ ID NO:846), DFLAEEGGGVR (SEQ ID NO:847), TTKIKPR (SEQ ID NO:848), ALVPR (SEQ ID NO:849), ALRPR (SEQ ID NO:850) and ALRPRVVGGA (SEQ ID NO:851). In one embodiment, the thrombin cleavable site includes (D-Phe)-Pro-Arg. In one embodiment, the thrombin cleavable site includes (D-Phe)-Pip-Arg, wherein Pip is pipecolic acid.

The cleavable peptide linker may comprise a sequence derived from
a) the coagulation factor itself if it contains proteolytic cleavage sites that are proteolytically cleaved during activation of the coagulatioan factor,
b) a substrate polypeptide of this coagulation factor, or
c) a substrate polypeptide cleaved by a protease which is activated or formed by the direct or indirect involvement of the coagulation factor.

Some embodiments of the invention are coagulation factors wherein the peptide linker is cleavable by the protease that normally activates the coagulation factor in vivo, thereby ensuring that the cleavage of the linker is linked to the activation of the coagulation factor at a site at which coagulation occurs.

Other exemplary conjugates according to the invention are those wherein the linker is cleavable by the coagulation factor which is part of the conjugate once it is activated, thus also ensuring that cleavage of the conjugate is connected with a coagulatory event.

Other exemplary therapeutic conjugates according to the invention are those wherein the linker is cleavable by a protease, which itself is activated directly or indirectly by the activity of the coagulation factor which is part of the conjugate, thus also ensuring that cleavage of the fusion protein is connected with a coagulatory event.

In another example, the linker includes a thrombin-cleavable chimeric protein, such as those disclosed in U.S. Pat. No. 7,589,178 to Le Bonniec, which is herein incorporated by reference in its entirety.

In another embodiment, the compound of the present disclosure is covalently linked to the linker without further linkage of the linker to a heterologous moiety or protein. Such conjugate between a compound and a linker can be useful as a "pro-drug". For example, the linker is cleavable by a protease, which is activated directly or indirectly by the activity of the compound, thus ensuring that cleavage of the linker is connected with a coagulatory event.

Linkers Containing a Self-Immolative Moiety

In one embodiment the linker includes a self-immolative moiety, e.g., interposed between the compound and a cleavable substrate moiety. For example, such self-immolating moiety has the advantage that the cleavability of the substrate moiety is not negatively impacted by the terminal amino acid residue of the compound (e.g., the pro-coagulant peptide).

In one embodiment, the self-immolative moiety is derived from para-aminobenzylalkohol (PAB), e.g., connected to the compound via a carbamate, a carbonate or an ether bond. In one example, the self-immolative moiety is p-aminobenzyl carbamate (PABC). In another example, the self-immolative moiety is a heteroaromatic analog of PABC. Examplary self-immolative moieties are disclosed, e.g., in U.S. Pat. Nos. 7,375,078 and 7,754,681, each of which are incorporated herein by reference in its entirety.

In various embodiments, the conjugate includes a linker containing a self-immolative moiety ($B_X$). In one example according to this embodiments, the conjugate formed between the compound and the heterologous moiety, or between the compound and the polypeptide has a structure according to Formula (K1), (K2), (L1), or (L2):

  (K1)

  (K2)

  (L1)

  (L2)

wherein
k is an integer selected from 0 and 1;
Het is either absent (k=0) or present (k=1), and when present is a heterologous moiety (e.g., a half-life extending molecule);
$U_1$ is either absent (k=0) or present (k=1), and when present is a polypeptide selected from blood coagulation factor (e.g., FVIIa, FVIII, and FIXa) and a platelet targeting moiety, wherein U₁ is optionally further linked to a heterologous moiety;

n is an integer selected from 0 and 1;

Sp is a spacer moiety, which is either absent (n=0) or present (n=1);

$Z_Y$ is a cleavable substrate moiety (e.g., a protease-cleavable substrate moiety, e.g., a thrombin-cleavable substrate moiety, or a FXIa-cleavable substrate moiety);

$B_X$ is a self-immolative moiety (e.g., a PABC moiety); and

Pep is a compound (e.g., pro-coagulant peptide or peptide derivative) of the present disclosure.

In one example, the conjugate has a structure according to Formula (M), (N), (O), or (P):

(Het)$_k$-(Sp)$_n$-DPhe-Pip-Arg-PABC-Pep (M)

(Het)$_k$-(Sp)$_n$-DPhe-Pro-Arg-PABC-Pep (N)

(U₁)$_k$-(Sp)$_n$-DPhe-Pip-Arg-PABC-Pep (O)

(U₁)$_k$-(Sp)$_n$-DPhe-Pro-Arg-PABC-Pep (P)

wherein k, Het, U₁, Sp, and Pep are defined as for Formulae K1-L2.

Compounds Linked to a Cleavable Substrate Moiety

In certain embodiments, the compound of the present disclosure is linked to a cleavable substrate moiety. The cleavable substrate moiety can be cleaved by a proteolytic enzyme as described herein (e.g., by an enzyme of the coagulation cascade).

In one example, the cleavable substrate moiety is linked to the compound via a self-immolative moiety ($B_X$). For example, the pro-coagulant compound of the present disclosure is covalently linked to a heterologous moiety, optionally via a linker (L₁) thereby forming a conjugate. The Linker (L₁) is different than the linking moiety Z previously defined.

In another example, two or more compounds are linked to each other via a cleavable linker (e.g., a cleavable linker having a self-immolative moiety).

In one example according to the various embodiments above, the conjugate can have a structure selected from the following formulae:

$Z_Y$-Pep

Pep-$Z_Y$ $Z_Y$-$B_X$-Pep

Pep-$B_X$-$Z_Y$ ($Z_Y$-$B_X$-Pep)$_p$ wherein Pep, $Z_Y$, and $B_X$ are defined as above, and the integer p is selected from 1-50.

Heterologous Moiety

In some embodiments, the conjugate of the invention includes one heterologous moiety. For example, the compound of the present disclosure is linked to one heterologous moiety. In other embodiments, the conjugate includes two heterologous moieties, which may be the same or different. For example, a compound of the present disclosure is linked to two heterologous moieties (i.e., a first heterologous moiety, "Het 1", and a second heterologous moiety "Het2"). In yet other embodiments, the conjugate of the present disclosure includes more than two heterologous moieties, e.g., three, four, five, or more than five heterologous moieties. In some embodiments, all the heterologous moieties are identical. In some embodiments, at least one heterologous moiety is different from the other heterologous moieties. In some embodiments, the two, three or more than three heterologous moieties are linked in tandem. In other embodiments, the conjugate of the invention can comprise two, three, or more than three heterologous moieties wherein at least an additional moiety (e.g., a spacer moiety, a protease-cleavable substrate, a self-immolative moiety, or combinations thereof) is interposed between two heterologous moieties.

A heterologous moiety can comprise a heterologous polypeptide moiety, or a heterologous non-polypeptide moiety, or both. In some aspects, the heterologous moiety comprises a combination of a heterologous polypeptide and a heterologous non-polypeptide moiety.

In certain embodiments, the first heterologous moiety (e.g., a first Fc region) and the second heterologous moiety (e.g., a second Fc region) are associated with each other to form a dimer. In one embodiment, the second heterologous moiety is a second Fc region, wherein the second Fc region is linked to or associated with the first heterologous moiety, e.g., the first Fc region. For example, the second heterologous moiety (e.g., the second Fc region) can be linked to the first heterologous moiety (e.g., the first Fc region) by a linker or associated with the first heterologous moiety by a covalent or non-covalent bond In some embodiments, the heterologous moiety is a peptide or polypeptide with either unstructured or structured characteristics that are associated with the prolongation of in vivo half-life when incorporated in a procoagulant compound of the invention. Non-limiting examples include albumin, albumin fragments, Fc fragments of immunoglobulins, the β subunit of the C-terminal peptide (CTP) of human chorionic gonadotropin, a HAP sequence, XTEN, a transferrin or a fragment thereof, a PAS polypeptide, polyglycine linkers, polyserine linkers, albumin-binding moieties, or any fragments, derivatives, variants, or combinations of these polypeptides. In other related aspects a heterologous moiety can include an attachment site (e.g., a. cysteine amino acid) for a non-polypeptide moiety such as polyethylene glycol (PEG), hydroxyethyl starch (HES), polysialic acid, or any derivatives, variants, or combinations of these elements. In some aspects, a heterologous moiety consisting of a cysteine amino acid that function as an attachment site for a non-polypeptide moiety such as polyethylene glycol (PEG), hydroxyethyl starch (HES), polysialic acid, or any derivatives, variants, or combinations of these elements.

In some embodiments, the heterologous moiety is a polypeptide comprising, consisting essentially of, or consisting of at least about 10, 100, 200, 300, 400, 500, 600, 700, 800, 900, 1000, 1100, 1200, 1300, 1400, 1500, 1600, 1700, 1800, 1900, 2000, 2500, 3000, or 4000 amino acids. In other embodiments, the heterologous moiety is a polypeptide comprising, consisting essentially of, or consisting of about 100 to about 200 amino acids, about 200 to about 300 amino acids, about 300 to about 400 amino acids, about 400 to about 500 amino acids, about 500 to about 600 amino acids, about 600 to about 700 amino acids, about 700 to about 800 amino acids, about 800 to about 900 amino acids, or about 900 to about 1000 amino acids.

In certain embodiments, a heterologous moiety improves one or more pharmacokinetic properties of the compound or conjugate without significantly affecting its biological activity.

In certain embodiments, a heterologous moiety increases the in vivo and/or in vitro half-life of the procoagulant compound or conjugate of the invention. In other embodiments, a heterologous moiety facilitates visualization or localization of the compound or conjugate of the invention. Visualization and/or location of the procoagulant compound of the invention or a fragment thereof can be in vivo, in vitro, ex vivo, or combinations thereof.

In other embodiments, a heterologous moiety increases stability of the procoagulant compound or conjugate of the invention. As used herein, the term "stability" refers to an art-recognized measure of the maintenance of one or more physical properties of the procoagulant compound in response to an environmental condition (e.g., an elevated or lowered temperature). In certain aspects, the physical property can be the maintenance of the covalent structure of the procoagulant compound (e.g., the absence of proteolytic cleavage, unwanted oxidation or deamidation). In other aspects, the physical property can also be the presence of the procoagulant compound in a properly folded state (e.g., the absence of soluble or insoluble aggregates or precipitates). In one aspect, the stability of the procoagulant compound is measured by assaying a biophysical property of the procoagulant compound, for example thermal stability, pH unfolding profile, stable removal of glycosylation, solubility, biochemical function (e.g., ability to bind to a protein, receptor or ligand), etc., and/or combinations thereof. In another aspect, biochemical function is demonstrated by the binding affinity of the interaction. In one aspect, a measure of protein stability is thermal stability, i.e., resistance to thermal challenge. Stability can be measured using methods known in the art, such as, HPLC (high performance liquid chromatography), SEC (size exclusion chromatography), DLS (dynamic light scattering), etc. Methods to measure thermal stability include, but are not limited to differential scanning calorimetry (DSC), differential scanning fluorimetry (DSF), circular dichroism (CD), and thermal challenge assay.

Half-Life Extender Heterologous Moieties

In certain aspects, the heterologous moiety is a half-like extender, i.e., a heterologous moiety which increases the in vivo half-life of the compound or conjugate with respect to the in vivo half-life of the corresponding procoagulant compound or conjugate lacking such heterologous moiety. The in vivo half-life can be determined by any method known to those of skill in the art, e.g., activity assays (chromogenic assay or one stage clotting aPTT assay), ELISA, etc.

In some embodiments, the presence of one or more half-life extenders results in the half-life of the procoagulant compound or conjugate to be increased compared to the half life of the corresponding compound or conjugate lacking such one or more half-life extenders. The half-life of the procoagulant conjugate comprising a half-life extender is at least about 1.5 times, at least about 2 times, at least about 2.5 times, at least about 3 times, at least about 4 times, at least about 5 times, at least about 6 times, at least about 7 times, at least about 8 times, at least about 9 times, at least about 10 times, at least about 11 times, or at least about 12 times longer than the in vivo half-life of the corresponding procoagulant compound lacking such half-life extender.

In one embodiment, the half-life of the compound or conjugate linked to a half-life extender is about 1.5-fold to about 20-fold, about 1.5 fold to about 15 fold, or about 1.5 fold to about 10 fold longer than the in vivo half-life of the corresponding compound or conjugate not linked to such half-life extender. In another embodiment, the half-life of the compound or conjugate linked to a half-life extender is extended about 2-fold to about 10-fold, about 2-fold to about 9-fold, about 2-fold to about 8-fold, about 2-fold to about 7-fold, about 2-fold to about 6-fold, about 2-fold to about 5-fold, about 2-fold to about 4-fold, about 2-fold to about 3-fold, about 2.5-fold to about 10-fold, about 2.5-fold to about 9-fold, about 2.5-fold to about 8-fold, about 2.5-fold to about 7-fold, about 2.5-fold to about 6-fold, about 2.5-fold to about 5-fold, about 2.5-fold to about 4-fold, about 2.5-fold to about 3-fold, about 3-fold to about 10-fold, about 3-fold to about 9-fold, about 3-fold to about 8-fold, about 3-fold to about 7-fold, about 3-fold to about 6-fold, about 3-fold to about 5-fold, about 3-fold to about 4-fold, about 4-fold to about 6 fold, about 5-fold to about 7-fold, or about 6-fold to about 8 fold as compared to the in vivo half-life of the corresponding compound or conjugate not linked to such half-life extender.

In other embodiments, the half-life of the compound or conjugate linked to a half-life extender is at least about 10 hours, at least about 17 hours, at least about 18 hours, at least about 19 hours, at least about 20 hours, at least about 21 hours, at least about 22 hours, at least about 23 hours, at least about 24 hours, at least about 25 hours, at least about 26 hours, at least about 27 hours, at least about 28 hours, at least about 29 hours, at least about 30 hours, at least about 31 hours, at least about 32 hours, at least about 33 hours, at least about 34 hours, at least about 35 hours, at least about 36 hours, at least about 48 hours, at least about 60 hours, at least about 72 hours, at least about 84 hours, at least about 96 hours, or at least about 108 hours.

In still other embodiments, the half-life of the compound or conjugate linked to a half-life extender is about 15 hours to about two weeks, about 16 hours to about one week, about 17 hours to about one week, about 18 hours to about one week, about 19 hours to about one week, about 20 hours to about one week, about 21 hours to about one week, about 22 hours to about one week, about 23 hours to about one week, about 24 hours to about one week, about 36 hours to about one week, about 48 hours to about one week, about 60 hours to about one week, about 24 hours to about six days, about 24 hours to about five days, about 24 hours to about four days, about 24 hours to about three days, or about 24 hours to about two days.

In some embodiments, the average half-life per subject of the compound or conjugate linked to a half-life extender is about 15 hours, about 16 hours, about 17 hours, about 18 hours, about 19 hours, about 20 hours, about 21 hours, about 22 hours, about 23 hours, about 24 hours (1 day), about 25 hours, about 26 hours, about 27 hours, about 28 hours, about 29 hours, about 30 hours, about 31 hours, about 32 hours, about 33 hours, about 34 hours, about 35 hours, about 36 hours, about 40 hours, about 44 hours, about 48 hours (2 days), about 54 hours, about 60 hours, about 72 hours (3 days), about 84 hours, about 96 hours (4 days), about 108 hours, about 120 hours (5 days), about six days, about seven days (one week), about eight days, about nine days, about 10 days, about 11 days, about 12 days, about 13 days, or about 14 days.

(a) Low Complexity Polypeptides

In certain aspects, the compound or conjugate of the disclosure is linked to a heterologous moiety comprising a polypeptide with low compositional and/or structural complexity (e.g., a disordered polypeptide with no secondary or tertiary structure in solution under physiologic conditions).

(b) CTP

In certain aspects, the compound or conjugate of the disclosure is linked to a heterologous moiety comprising one β subunit of the C-terminal peptide (CTP) of human chorionic gonadotropin or fragment, variant, or derivative thereof. One or more CTP peptides inserted into a recombinant protein is known to increase the in vivo half-life of that protein. See, e.g., U.S. Pat. No. 5,712,122, incorporated by reference herein in its entirety. Exemplary CTP peptides include DRPRFQDSSSSKAPPPSLPSPSRLPGPSDTPIL (SEQ ID NO: 852) or SSSSKAPPPSLPSPSRLPGPSDTPILPQ (SEQ ID NO: 853). See, e.g., U.S. Patent Application Publication No. US 2009/0087411 A1, incorporated herein by reference in its entirety.

(c) Immunoglobulin_Constant Region (Fc) or Portion Thereof

In certain aspects, the compound or the conjugate of the invention is linked to at least one Fc region. The term "Fc" or "Fc region" as used herein, means a functional neonatal Fc receptor (FcRn) binding partner comprising an Fc domain, variant, or fragment thereof which maintains the desirable properties of an Fc region in a chimeric protein, e.g., an increase in in vivo half-life, Myriad mutants, fragments, variants, and derivatives are described, e.g., in PCT Publication Nos. WO 2011/069164 A2, WO 2012/006623 A2, WO 2012/006635 A2 or WO 2012/006633 A2, all of which are incorporated herein by reference in their entireties. An Fc region is comprised of domains denoted CH (constant heavy) domains (CH1, CH2, etc.). Depending on the isotype (i.e. IgG, IgM, IgA IgD, or IgE), the Fc region can be comprised of three or four CH domains. Some isotypes (e.g. IgG) Fc regions also contain a hinge region. See Janeway et al. 2001, *Immunobiology*, Garland Publishing, N.Y., N.Y.

An Fc region or a portion thereof for producing the procoagulant conjugate of the present invention can be obtained from a number of different sources. In some embodiments, an Fc region or a portion thereof is derived from a human immunoglobulin. It is understood, however, that the Fc region or a portion thereof can be derived from an immunoglobulin of another mammalian species, including for example, a rodent (e.g. a mouse, rat, rabbit, guinea pig) or non-human primate (e.g. chimpanzee, macaque) species. Moreover, the Fc region or a portion thereof can be derived from any immunoglobulin class, including IgM, IgG, IgD, IgA and IgE, and any immunoglobulin isotype, including IgG1, IgG2, IgG3 and IgG4. In one embodiment, the human isotype IgG1 is used.

Conjugates comprising an Fc region of an immunoglobulin bestow several desirable properties on a chimeric protein including increased stability, increased serum half-life (see Capon et al., 1989, *Nature* 337:525) as well as binding to Fc receptors such as the neonatal Fc receptor (FcRn) (U.S. Pat. Nos. 6,086,875, 6,485,726, 6,030,613; WO 03/077834; US2003-0235536A1), which are incorporated herein by reference in their entireties.

In certain embodiments, the compound or conjugate is linked to one or more truncated Fc regions that are nonetheless sufficient to confer Fc receptor (FcR) binding properties to the Fc region. For example, the portion of an Fc region that binds to FcRn (i.e., the FcRn binding portion) comprises from about amino acids 282-438 of IgG1, EU numbering (with the primary contact sites being amino acids 248, 250-257, 272, 285, 288, 290-291, 308-311, and 314 of the CH2 domain and amino acid residues 385-387, 428, and 433-436 of the CH3 domain. Thus, an Fc region in a procoagulant compound of the invention may comprise or consist of an FcRn binding portion. FcRn binding portions may be derived from heavy chains of any isotype, including IgG1, IgG2, IgG3 and IgG4. In one embodiment, an FcRn binding portion from an antibody of the human isotype IgG1 is used. In another embodiment, an FcRn binding portion from an antibody of the human isotype IgG4 is used.

In certain embodiments, an Fc region comprises at least one of: a hinge (e.g., upper, middle, and/or lower hinge region) domain (about amino acids 216-230 of an antibody Fc region according to EU numbering), a CH2 domain (about amino acids 231-340 of an antibody Fc region according to EU numbering), a CH3 domain (about amino acids 341-438 of an antibody Fc region according to EU numbering), a CH4 domain, or a variant, portion, or fragment thereof. In other embodiments, an Fc region comprises a complete Fc domain (i.e., a hinge domain, a CH2 domain, and a CH3 domain). In some embodiments, an Fc region comprises, consists essentially of, or consists of a hinge domain (or a portion thereof) fused to a CH3 domain (or a portion thereof), a hinge domain (or a portion thereof) fused to a CH2 domain (or a portion thereof), a CH2 domain (or a portion thereof) fused to a CH3 domain (or a portion thereof), a CH2 domain (or a portion thereof) fused to both a hinge domain (or a portion thereof) and a CH3 domain (or a portion thereof). In still other embodiments, an Fc region lacks at least a portion of a CH2 domain (e.g., all or part of a CH2 domain). In a particular embodiment, an Fc region comprises or consists of amino acids corresponding to EU numbers 221 to 447.

An Fc in a procoagulant compound of the invention can include, for example, a change (e.g., a substitution) at one or more of the amino acid positions disclosed in Int'l. PCT Publs. WO88/07089A1, WO96/14339A1, WO98/05787A1, WO98/23289A1, WO99/51642A1, WO99/58572A1, WO00/09560A2, WO00/32767A1, WO00/42072A2, WO02/44215A2, WO02/060919A2, WO03/074569A2, WO04/016750A2, WO04/029207A2, WO04/035752A2, WO04/063351A2, WO04/074455A2, WO04/099249A2, WO05/040217A2, WO04/044859, WO05/070963A1, WO05/077981A2, WO05/092925A2, WO05/123780A2, WO06/019447A1, WO06/047350A2, and WO06/085967A2; U.S. Pat. Publ. Nos, US 2007/0231329, US2007/0231329, US2007/0237765, US2007/0237766, US2007/0237767, US2007/0243188, US2007/0248603, US2007/0286859, US2008/0057056; or U.S. Pat. Nos. 5,648,260; 5,739,277; 5,834,250; 5,869,046; 6,096,871; 6,121,022; 6,194,551; 6,242,195; 6,277,375; 6,528,624; 6,538,124; 6,737,056; 6,821,505; 6,998,253; 7,083,784; 7,404,956, and 7,317,091, each of which is incorporated by reference herein in its entirety. In one embodiment, the specific change (e.g., the specific substitution of one or more amino acids disclosed in the art) may be made at one or more of the disclosed amino acid positions. In another embodiment, a different change at one or more of the disclosed amino acid positions (e.g., the different substitution of one or more amino acid position disclosed in the art) may be made.

An Fc region used in the invention may also comprise an art recognized amino acid substitution which alters its glycosylation. For example, the Fc has a mutation leading to reduced glycosylation (e.g., N- or O-linked glycosylation) or may comprise an altered glycoform of the wild-type Fc moiety (e.g., a low fucose or fucose-free glycan).

(d) Albumin or Fragment, or Variant Thereof

In certain embodiments, the compound or conjugate of the invention is linked to a heterologous moiety comprising albumin or a functional fragment thereof. Human serum albumin (HSA, or HA), a protein of 609 amino acids in its full-length form, is responsible for a significant proportion of the osmotic pressure of serum and also functions as a carrier of endogenous and exogenous ligands. The term "albumin" as used herein includes full-length albumin or a functional fragment, variant, derivative, or analog thereof. Examples of albumin or the fragments or variants thereof are disclosed in US Pat. Publ. Nos. 2008/0194481A1, 2008/0004206 A1, 2008/0161243 A1, 2008/0261877 A1, or 2008/0153751 A1 or PCT Appl. Publ. Nos. 2008/033413 A2, 2009/058322 A1, or 2007/021494 A2, which are incorporated herein by reference in their entireties.

In one embodiment, the heterologous moiety is albumin, a fragment, or a variant thereof which is further linked to a heterologous moiety selected from the group consisting of an immunoglobulin constant region or portion thereof (e.g., an Fc region), a PAS sequence, HES, and PEG.

(e) Albumin Binding Moiety

In certain embodiments, the heterologous moiety is an albumin binding moiety, which comprises an albumin binding peptide, a bacterial albumin binding domain, an albumin-binding antibody fragment, or any combinations thereof.

For example, the albumin binding protein can be a bacterial albumin binding protein, an antibody or an antibody fragment including domain antibodies (see U.S. Pat. No. 6,696,245). An albumin binding protein, for example, can be a bacterial albumin binding domain, such as the one of streptococcal protein G (Konig, T. and Skerra, A. (1998) *J. Immunol. Methods* 218, 73-83). Other examples of albumin binding peptides that can be used as conjugation partner are, for instance, those having a Cys-Xaa$_1$-Xaa$_2$-Xaa$_3$-Xaa$_4$-Cys consensus sequence, wherein Xaa$_1$ is Asp, Asn, Ser, Thr, or Trp; Xaa$_2$ is Asn, Gln, H is, Ile, Leu, or Lys; Xaa$_3$ is Ala, Asp, Phe, Trp, or Tyr; and Xaa$_4$ is Asp, Gly, Leu, Phe, Ser, or Thr as described in US patent application 2003/0069395 or Dennis et al. (Dennis et al. (2002) *J. Biol. Chem.* 277, 35035-35043).

Domain 3 from streptococcal protein G, as disclosed by Kraulis et al., FEBS Lett. 378:190-194 (1996) and Linhult et al., Protein Sci. 11:206-213 (2002) is an example of a bacterial albumin-binding domain. Examples of albumin-binding peptides include a series of peptides having the core sequence DICLPRWGCLW (SEQ ID NO:45). See, e.g., Dennis et al., J. Biol. Chem. 2002, 277: 35035-35043 (2002). Examples of albumin-binding antibody fragments are disclosed in Muller and Kontermann, Curr. Opin. Mol. Ther. 9:319-326 (2007); Rooverset al., Cancer Immunol. Immunother. 56:303-317 (2007), and Holt et al., Prot. Eng. Design Sci., 21:283-288 (2008), which are incorporated herein by reference in their entireties. An example of such albumin binding moiety is 2-(3-maleimidopropanamido)-6-(4-(4-iodophenyl)butanamido) hexanoate ("Albu" tag) as disclosed by Trusselet al., Bioconjugate Chem. 20:2286-2292 (2009).

(f) PAS Sequence

In other embodiments, the heterologous moiety is a PAS sequence. A PAS sequence, as used herein, means an amino acid sequence comprising mainly alanine and serine residues or comprising mainly alanine, serine, and proline residues, the amino acid sequence forming random coil conformation under physiological conditions. Accordingly, the PAS sequence is a building block, an amino acid polymer, or a sequence cassette comprising, consisting essentially of, or consisting of alanine, serine, and proline which can be used as a part of the heterologous moiety in the procoagulant compound. Yet, the skilled person is aware that an amino acid polymer also may form random coil conformation when residues other than alanine, serine, and proline are added as a minor constituent in the PAS sequence. The term "minor constituent" as used herein means that amino acids other than alanine, serine, and proline may be added in the PAS sequence to a certain degree, e.g., up to about 12%, i.e., about 12 of 100 amino acids of the PAS sequence, up to about 10%, i.e. about 10 of 100 amino acids of the PAS sequence, up to about 9%, about 9 of 100 amino acids, up to about 8%, i.e., about 8 of 100 amino acids, about 6%, i.e., about 6 of 100 amino acids, about 5%, i.e., about 5 of 100 amino acids, about 4%, i.e., about 4 of 100 amino acids, about 3%, i.e., about 3 of 100 amino acids, about 2%, i.e., about 2 of 100 amino acids, about 1%, i.e., about 1 of 100 of the amino acids. The amino acids different from alanine, serine and proline may be selected from the group consisting of Arg, Asn, Asp, Cys, Gln, Glu, Gly, His, Ile, Leu, Lys, Met, Phe, Thr, Trp, Tyr, and Val.

Under physiological conditions, the PAS sequence stretch forms a random coil conformation and thereby can mediate an increased in vivo and/or in vitro stability to procoagulant compound. Since the random coil domain does not adopt a stable structure or function by itself, the biological activity mediated by the Pep1 and/or Pep2 polypeptides in the procoagulant compound is essentially preserved. In other embodiments, the PAS sequences that form random coil domain are biologically inert, especially with respect to proteolysis in blood plasma, immunogenicity, isoelectric point/electrostatic behaviour, binding to cell surface receptors or internalisation, but are still biodegradable, which provides clear advantages over synthetic polymers such as PEG.

Non-limiting examples of the PAS sequences forming random coil conformation comprise an amino acid sequence selected from the group consisting of ASPAAPAPASPAA-PAPSAPA (SEQ ID NO: 854), AAPASPAPAAPSAPA-PAAPS (SEQ ID NO: 855), APSSPSPSAPSSPSPASPSS (SEQ ID NO: 856), APSSPSPSAPSSPSPASPS (SEQ NO: 857), SSPSAPSPSSPASPSPSSPA (SEQ ID NO: 858), AASPAAPSAPPAAASPAAPSAPPA (SEQ ID NO: 859), and ASAAAPAAASAAASAPSAAA (SEQ ID NO: 860), or any combinations thereof. Additional examples of PAS sequences are known from, e.g., US Pat. Publ. No. 2010/0292130 A1 and PCT Appl. Publ. No. WO 2008/155134 A1.

(g) HAP Sequence

In certain embodiments, the heterologous moiety is a glycine-rich homo-amino-acid polymer (HAP). The HAP sequence can comprise a repetitive sequence of glycine, which has at least 50 amino acids, at least 100 amino acids, 120 amino acids, 140 amino acids, 160 amino acids, 180 amino acids, 200 amino acids, 250 amino acids, 300 amino acids, 350 amino acids, 400 amino acids, 450 amino acids, or 500 amino acids in length. In one embodiment, the HAP sequence is capable of extending half-life of a moiety fused to or linked to the HAP sequence. Non-limiting examples of the HAP sequence includes, but are not limited to (Gly)$_n$ (SEQ ID NO: 893), (Gly$_4$Ser)$_n$ (SEQ ID NO: 882) or S(Gly$_4$Ser)$_n$ (SEQ ID NO: 883), wherein n is 1, 2, 3, 4, 5, 6, 7, 8, 9, 10, 11, 12, 13, 14, 15, 16, 17, 18, 19, or 20. In one embodiment, n is 20, 21, 22, 23, 24, 25, 26, 26, 28, 29, 30, 31, 32, 33, 34, 35, 36, 37, 38, 39, or 40. In another embodiment, n is 50, 60, 70, 80, 90, 100, 110, 120, 130, 140, 150, 160, 170, 180, 190, or 200.

(h) Transferrin or Fragements Thereof

In certain embodiments, the heterologous moiety is transferrin or a fragment thereof. Any transferrin may be used to make the conjugates of the invention. As an example, wild-type human Tf (Tf) is a 679 amino acid protein, of approximately 75 KDa (not accounting for glycosylation), with two main domains, N (about 330 amino acids) and C (about 340 amino acids), which appear to originate from a gene duplication. See GenBank accession numbers NM001063, XM002793, M12530, XM039845, XM 039847 and S95936 (www.ncbi.nlm.nih.gov/), all of which are herein incorporated by reference in their entirety. Transferrin comprises two domains, N domain and C domain. N domain comprises two subdomains, N1 domain and N2 domain, and C domain comprises two subdomains, C1 domain and C2 domain.

In one embodiment, the transferrin heterologous moiety includes a transferrin splice variant. In one example, a transferrin splice variant can be a splice variant of human transferrin, e.g., Genbank Accession AAA61140. In another embodiment, the transferrin portion of the chimeric protein includes one or more domains of the transferrin sequence, e.g., N domain, C domain, N1 domain, N2 domain, C1 domain, C2 domain or any combinations thereof.

(i) Polymer, e.g., Polyethylene Glycol (PEG)

In other embodiments, the heterologous moiety is a soluble polymer known in the art, including, but not limited to, polyethylene glycol, ethylene glycol/propylene glycol copolymers, carboxymethylcellulose, dextran, or polyvinyl alcohol. Also provided by the invention are procoagulant compounds of the invention comprising heterologous moieties which may provide additional advantages such as increased solubility, stability and circulating time of the polypeptide, or decreased immunogenicity (see U.S. Pat. No. 4,179,337). Such heterologous moieties for modification can be selected from the group consisting of water soluble polymers including, but not limited to, polyethylene glycol, ethylene glycol/propylene glycol copolymers, carboxymethylcellulose, dextran, and polyvinyl alcohol, poly (alkylene oxide), poly(vinyl pyrrolidone), polyoxazoline, or poly(acryloylmorpholine).

The polymer can be of any molecular weight, and can be branched or unbranched. For polyethylene glycol, in one embodiment, the molecular weight is between about 1 kDa and about 100 kDa, for ease in handling and manufacturing. Other sizes may be used, depending on the desired profile (e.g., the duration of sustained release desired, the effects, if any on biological activity, the ease in handling, the degree or lack of antigenicity and other known effects of the polyethylene glycol to a protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 45,000, 50,000, 55,000, 60,000, 65,000, 70,000, 75,000, 80,000, 85,000, 90,000, 95,000, or 100,000 kDa.

In some embodiments, the polyethylene glycol may have a branched structure. Branched polyethylene glycols are described, for example, in U.S. Pat. No. 5,643,575; Morpurgo et al., *Appl. Biochem. Biotechnol.* 56:59-72 (1996); Vorobjev et al., *Nucleosides Nucleotides* 18:2745-2750 (1999); and Caliceti et al., *Bioconjug. Chem.* 10:638-646 (1999), each of which is incorporated herein by reference in its entirety.

The number of polyethylene glycol moieties attached to each compound or conjugate of the invention (i.e., the degree of substitution) may also vary. For example, the PEGylated compound or conjugate may be linked, on average, to 1, 2, 3, 4, 5, 6, 7, 8, 9, 10, 12, 15, 17, 20, or more polyethylene glycol molecules. Similarly, the average degree of substitution within ranges such as 1-3, 2-4, 3-5, 4-6, 5-7, 6-8, 7-9, 8-10, 9-11, 10-12, 11-13, 12-14, 13-15, 14-16, 15-17, 16-18, 17-19, or 18-20 polyethylene glycol moieties per protein molecule. Methods for determining the degree of substitution are discussed, for example, in Delgado et al., *Crit. Rev. Thera. Drug Carrier Sys.* 9:249-304 (1992).

In one example, the heterologous moiety is a water-soluble polymer, e.g., a straight or branched polyethylene glycol (PEG) moieties, straight or branched polypropylene glycol (PPG) moiety, a hydroxyethyl starch (HES) moiety, or a half-life extension polypeptide (e.g., XTEN; see, e.g. Schellenberger V. et al., *Nat Biotechnol.* 2009 December; 27(12):11.86-90, US20100189682, PCT/US07/05952, U.S. Ser. No. 12/228,859, U.S. Ser. No. 12/646,566, PCT/US08/09787, U.S. Ser. No. 12/699,761, and PCT/US2010/23106, each of which is incorporated herein by reference in its entirety). The polymer can be attached to the N-terminus, the C-terminus of the peptide sequence or an internal amino acid of the compound or the polypeptide. In one example, the polymer is attached to the N-terminal amino acid, e.g. via an amide bond. In another example, the polymer is attached to the C-terminal amino acid via an amide bond. In yet another example, the polymer is attached to the peptide sequence through derivatization of an amino acid side chain located at an internal position of the amino acid sequence. For example, the polymer is attached to the peptide sequence via derivatization of a tyrosine side chain, a lysine side chain or a aspartic acid or glutamic acid side chain.

Suitable methods of PEGylation are disclosed, e.g., in U.S. Pat. Nos. 5,122,614 to Zalipsky et al., and 5,539,063 to Hakimi et al., all of which PEGylation methods are incorporated herein by reference. Various molecular weights of PEG may be used, suitably from 1000 Da to 80,000 Da (or from 5000 Da to 60,000 DA). In one example, the PEG is monodisperse, meaning that there is little variation in molecular weight between PEG molecules. PEGylation may improve the solubility and plasma half-life of a peptide.

In one example according to this embodiment, the compound of the present disclosure contains an amino acid sequence selected from or is a peptide selected from:

```
                                         (SEQ ID NO: 861)
KLTCLASYCWLF-(PEG)

(SEQ ID NO: 292)
(PEG)27-KLTCLASYCWLF, (SEQ ID NO: 293)
(PEG)27(PEG)27-KLTCLASYCWLF, (SEQ ID NO: 91)
PEG4-RRAPGKLTCLASYCWLFWTGIA,
and (SEQ ID NO: 112)
RRAPGKLTCLASYCWLFWTGIA-PEG4
``` or a retro-, an inverso- or a retro-inverso variant thereof. In one example in the above peptides, the N-terminal amino acid is acetylated, and the C-terminal amino acid is amidated. In another example in the above peptides, the N-terminus is free (—NH$_2$ or a salt form thereof), and the C-terminal amino acid is amidated.

(j) XTEN Moieties

In certain aspects, a compound of the invention is covalently linked to at least one heterologous moiety that is or comprises an XTEN polypeptide or fragment, variant, or derivative thereof. As used here "XTEN polypeptide" refers to extended length polypeptides with non-naturally occurring, substantially non-repetitive sequences that are composed mainly of small hydrophilic amino acids, with the sequence having a low degree or no secondary or tertiary structure under physiologic conditions. As a heterologous moiety, XTENs can serve as a half-life extension moiety. In addition, XTEN can provide desirable properties including but are not limited to enhanced pharmacokinetic parameters and solubility characteristics.

The incorporation of a heterologous moiety comprising an XTEN sequence into a conjugate of the invention can confer one or more of the following advantageous properties to the resulting conjugate: conformational flexibility, enhanced aqueous solubility, high degree of protease resistance, low immunogenicity, low binding to mammalian receptors, or increased hydrodynamic (or Stokes) radii.

In certain aspects, an XTEN moiety can increase pharmacokinetic properties such as longer in vivo half-life or increased area under the curve (AUC), so that a compound or conjugate of the invention stays in vivo and has procoagulant activity for an increased period of time compared to a compound or conjugate with the same but without the XTEN heterologous moiety.

Examples of XTEN moieties that can be used as heterologous moieties in procoagulant conjugates of the invention are disclosed, e.g., in U.S. Patent Publication Nos. 2010/0239554 A1, 2010/0323956 A1, 2011/0046060 A1, 2011/0046061 A1, 2011/0077199 A1, or 2011/0172146 A1, or International Patent Publication Nos. WO 2010091122 A1, WO 2010144502 A2, WO 2010144508 A1, WO 2011028228 A1, WO 2011028229 A1, or WO 2011028344 A2, each of which is incorporated by reference herein in its entirety.

(k) Hydroxyethyl Starch (HES)

In certain embodiments, the heterologous moiety is hydroxyethyl starch (HES) or a derivative thereof. Hydroxyethyl starch (HES) is a derivative of naturally occurring amylopectin and is degraded by alpha-amylase in the body. HES is a substituted derivative of the carbohydrate polymer amylopectin, which is present in corn starch at a concentration of up to 95% by weight HES exhibits advantageous biological properties and is used as a blood volume replacement agent and in hemodilution therapy in the clinics (Sommermeyer et al., *Krankenhauspharmazie,* 8(8), 271-278 (1987); and Weidler et al., *Arzneim.-Forschung/Drug Res.,* 41, 494-498 (1991)).

Amylopectin contains glucose moieties, wherein in the main chain alpha-1,4-glycosidic bonds are present and at the branching sites alpha-1,6-glycosidic bonds are found. The physical-chemical properties of this molecule are mainly determined by the type of glycosidic bonds. Due to the nicked alpha-1,4-glycosidic bond, helical structures with about six glucose-monomers per turn are produced. The physico-chemical as well as the biochemical properties of the polymer can be modified via substitution. The introduction of a hydroxyethyl group can be achieved via alkaline hydroxyethylation. By adapting the reaction conditions it is possible to exploit the different reactivity of the respective hydroxy group in the unsubstituted glucose monomer with respect to a hydroxyethylation. Owing to this fact, the skilled person is able to influence the substitution pattern to a limited extent.

HES is mainly characterized by the molecular weight distribution and the degree of substitution. The degree of substitution, denoted as DS, relates to the molar substitution, is known to the skilled people. See Sommermeyer et al., *Krankenhauspharmazie,* 8(8), 271-278 (1987), as cited above, in particular p. 273.

In one embodiment, hydroxyethyl starch has a mean molecular weight (weight mean) of from 1 to 300 kD, from 2 to 200 kD, from 3 to 100 kD, or from 4 to 70 kD. hydroxyethyl starch can further exhibit a molar degree of substitution of from 0.1 to 3, preferably 0.1 to 2, more preferred, 0.1 to 0.9, preferably 0.1 to 0.8, and a ratio between C2:C6 substitution in the range of from 2 to 20 with respect to the hydroxyethyl groups. A non-limiting example of HES having a mean molecular weight of about 130 kD is a HES with a degree of substitution of 0.2 to 0.8 such as 0.2, 0.3, 0.4, 0.5, 0.6, 0.7, or 0.8, preferably of 0.4 to 0.7 such as 0.4, 0.5, 0.6, or 0.7. In a specific embodiment, HES with a mean molecular weight of about 130 kD is VOLUVEN® from Fresenius. VOLUVEN® is an artificial colloid, employed, e.g., for volume replacement used in the therapeutic indication for therapy and prophylaxis of hypovolemia. The characteristics of VOLUVEN® are a mean molecular weight of 130,000+/−20,000 D, a molar substitution of 0.4 and a C2:C6 ratio of about 9:1. In other embodiments, ranges of the mean molecular weight of hydroxyethyl starch are, e.g., 4 to 70 kD or 10 to 70 kD or 12 to 70 kD or 18 to 70 kD or 50 to 70 kD or 4 to 50 kD or 10 to 50 kD or 12 to 50 kD or 18 to 50 kD or 4 to 18 kD or 10 to 18 kD or 12 to 18 kD or 4 to 12 kD or 10 to 12 kD or 4 to 10 kD. In still other embodiments, the mean molecular weight of hydroxyethyl starch employed is in the range of from more than 4 kD and below 70 kD, such as about 10 kD, or in the range of from 9 to 10 kD or from 10 to 11 kD or from 9 to 11 kD, or about 12 kD, or in the range of from 11 to 12 kD) or from 12 to 13 kD or from 11 to 13 kD, or about 18 kD, or in the range of from 17 to 18 kD or from 18 to 19 kD or from 17 to 19 kD, or about 30 kD, or in the range of from 29 to 30, or from 30 to 31 kD, or about 50 kD, or in the range of from 49 to 50 kD or from 50 to 51 kD or from 49 to 51 kD.

In certain embodiments, the heterologous moiety can be a mixture of hydroxyethyl starches having different mean molecular weights and/or different degrees of substitution and/or different ratios of C2:C6 substitution. Therefore, mixtures of hydroxyethyl starches may be employed having different mean molecular weights and different degrees of substitution and different ratios of C2:C6 substitution, or having different mean molecular weights and different degrees of substitution and the same or about the same ratio of C2:C6 substitution, or having different mean molecular weights and the same or about the same degree of substitution and different ratios of C2:C6 substitution, or having the same or about the same mean molecular weight and different degrees of substitution and different ratios of C2:C6 substitution, or having different mean molecular weights and the same or about the same degree of substitution and the same or about the same ratio of C2:C6 substitution, or having the same or about the same mean molecular weights and different degrees of substitution and the same or about the same ratio of C2:C6 substitution, or having the same or about the same mean molecular weight and the same or about the same degree of substitution and different ratios of C2:C6 substitution, or having about the same mean molecular weight and about the same degree of substitution and about the same ratio of C2:C6 substitution.

(l) Polysialic Acids (PSA)

In certain embodiments, the heterologous moiety is a polysialic acids (PSAs) or a derivative thereof. Polysialic acids (PSAs) are naturally occurring unbranched polymers of sialic acid produced by certain bacterial strains and in mammals in certain cells Roth J., et al. (1993) in *Polysialic Acid: From Microbes to Man,* eds Roth J., Rutishauser U., Troy F. A. (Birkhäuser Verlag, Basel, Switzerland), pp 335-348. They can be produced in various degrees of polymerisation from n=about 80 or more sialic acid residues down to n=2 by limited acid hydrolysis or by digestion with neuraminidases, or by fractionation of the natural, bacterially derived forms of the polymer. The composition of different polysialic acids also varies such that there are homopolymeric forms i.e. the alpha-2,8-linked polysialic acid comprising the capsular polysaccharide of *E. coli* strain K1 and the group-B meningococci, which is also found on the embryonic form of the neuronal cell adhesion molecule (N-CAM). Heteropolymeric forms also exist—such as the alternating alpha-2,8 alpha-2,9 polysialic acid of *E. coli* strain K92 and group C polysaccharides of *N. meningitidis*. Sialic acid may also be found in alternating copolymers with monomers other than sialic acid such as group W135 or group Y of *N. meningitidis*. Polysialic acids have important biological functions including the evasion of the immune and complement systems by pathogenic bacteria and the regulation of glial adhesiveness of immature neurons during foetal development (wherein the polymer has an anti-adhesive function) Cho and Troy, *P.N.A.S., USA*, 91 (1994) 11427-11431, although there are no known receptors for polysialic acids in mammals. The alpha-2,8-linked polysialic acid of *E. coli* strain K1 is also known as 'colominic acid' and is used (in various lengths) to exemplify the present invention. Various methods of attaching or conjugating polysialic acids to a polypeptide have been described (for example, see U.S. Pat. No. 5,846,951; WO-A-0187922, and US 2007/0191597 A1, which are incorporated herein by reference in their entireties.

(m) Clearance Receptors

In some embodiments the heterologous moiety comprising a clearance receptor, fragment, variant, or derivative thereof. For example, soluble forms of clearance receptors, such as the low density lipoprotein-related protein receptor LRP1, or fragments thereof, can block binding of a polypeptide (e.g., FVIII or FIX) to clearance receptors and thereby extend its in vivo half-life.

LRP1 is a 600 kDa integral membrane protein that is implicated in the receptor-mediate clearance of a variety of proteins. See, e.g., Lenting et al., Haemophilia 16:6-16 (2010). LRP1 also mediates clearance of Factor IX (see, e.g., Strickland & Medved. J. Thromb. Haemostat. 4:1481-1486 (2006).

Other suitable clearance receptors are, e.g., LDLR (low-density lipoprotein receptor), VLDLR (very low-density lipoprotein receptor), and megalin (LRP-2), or fragments thereof. See, e.g., Bovenschen et al., Blood 106:906-912 (2005); Bovenschen, Blood 116:5439-5410 (2010); Martinelli et al., Blood 116:5688-5697 (2010).

Visualization and Location

In certain embodiments, the heterologous moiety facilitates visualization or localization of the compounds or conjugate of the invention. Peptides and other moieties for insertion or conjugation into a compound which facilitate visualization or localization are known in the art. Such moieties can be used to facilitate visualization or localization in vitro, in vivo, ex vivo or any combination thereof.

Since thrombin plays a central role in the coagulation cascade, detection of imaging of its activity in vivo is highly desired. Accordingly, various heterologous moieties facilitate visualization or localization of the compounds or conjugates of the invention (e.g., fluorescent dyes) and can be engineered into the conjugates of the invention. In some embodiments, fluorescent dyes can be engineered to be non-fluorescent until their amines are regenerated upon thrombin cleavage.

Non-limiting examples of peptides or polypeptides which enable visualization or localization include biotin acceptor peptides which can facilitate conjugation of avidin- and streptavidin-based reagents, lipoic acid acceptor peptides which can facilitate conjugation of thiol-reactive probes to bound lipoic acid or direct ligation of fluorescent lipoic acid analogs, fluorescent proteins, e.g., green fluorescent protein (GFP) and variants thereof (e.g., EGFP, YFP such as EYFP, mVenus, YPet or Citrine, or CFP such as Cerulean or ECFP) or red fluorescent protein (RFP), cysteine-containing peptides for ligation of biarsenical dyes such as 4',5'-bis(1,3,2-dithioarsolan-2-yl)fluorescein (FlAsH), or for conjugating metastable technetium, peptides for conjugating europium clathrates for fluorescence resonance energy transfer (FRET)-based proximity assays, any variants, thereof, and any combination thereof.

Procoagulant compounds of the present disclosure labeled by these techniques can be used, for example, for 3-D imaging of pathological thrombus formation and dissolution, tumor imaging in procoagulant malignancies, flow cytometric quantitation and characterization of procoagulant microparticles in blood and plasma, monitoring of thrombus formation by intravital microscopy.

Polypeptides
FVIII

The term "FVIII" or "Factor VIII", as used herein, means functional FVIII protein in its normal role in coagulation, unless otherwise specified (i.e., refers to any FVIII moiety which exhibits biological activity that is associated with native FVIII). Thus, the term FVIII includes FVIII variant proteins that are functional. Preferred FVIII proteins are primate (e.g., chimpanzee), human, porcine, canine, and murine FVIII proteins. The full length polypeptide and polynucleotide sequences of FVIII are known, as are many functional fragments, mutants and modified versions. Exemplary FVIII sequences are disclosed, e.g., in WO2011/069164. FVIII polypeptides include, e.g., full-length FVIII, full-length FVIII minus Met at the N-terminus, mature FVIII (minus the signal sequence), mature FVIII with an additional Met at the N-terminus, and/or FVIII with a full or partial deletion of the B domain. In one example, the FVIII is a variant in which the B domain is deleted, either partially or fully. An exemplary sequence of FVIII can be found as NCBI Accession Number NP000123 or UniProtKB/Swiss-Prot entry P00451.

A number of functional FVIII molecules, including B-domain deletions, are disclosed in the following patents: U.S. Pat. No. 6,316,226 and U.S. Pat. No. 6,346,513, both assigned to Baxter; U.S. Pat. No. 7,041,635 assigned to In2Gen; U.S. Pat. No. 5,789,203, U.S. Pat. No. 6,060,447, U.S. Pat. No. 5,595,886, and U.S. Pat. No. 6,228,620 assigned to Chiron; U.S. Pat. No. 5,972,885 and U.S. Pat. No. 6,048,720 assigned to Biovitrum, U.S. Pat. No. 5,543, 502 and U.S. Pat. No. 5,610,278 assigned to Novo Nordisk; U.S. Pat. No. 5,171,844 assigned to Immuno Ag; U.S. Pat. No. 5,112,950 assigned to Transgene S.A.; U.S. Pat. No. 4,868,112 assigned to Genetics Institute, each of which is incorporated herein by reference in its entirety.

As used herein, "plasma-derived FVIII" includes all forms of the protein found in blood obtained from a mammal having the property of activating the coagulation pathway.

"B domain" of FVIII, as used herein, is the same as the B domain known in the art that is defined by internal amino acid sequence identity and sites of proteolytic cleavage by thrombin, e.g., residues Ser741-Arg1648 of full length human FVIII. The other human FVIII domains are defined by the following amino acid residues: A1, residues Ala1-Arg372; A2, residues Ser373-Arg740; A3, residues Ser1690-Ile2032; C1, residues Arg2033-Asn2172; C2, residues Ser2173-Tyr2332. The A3-C1-C2 sequence includes residues Ser1690-Tyr2332. The remaining sequence, residues Glu1649-Arg1689, is usually referred to as the FVIII light chain activation peptide. The locations of the boundaries for all of the domains, including the B domains, for porcine, mouse and canine FVIII are also known in the art. Preferably, the B domain of FVIII is deleted ("B domain deleted FVIII" or "BDD FVIII"). An example of a BDD FVIII is REFACTO (recombinant BDD FVIII).

Figure 2:
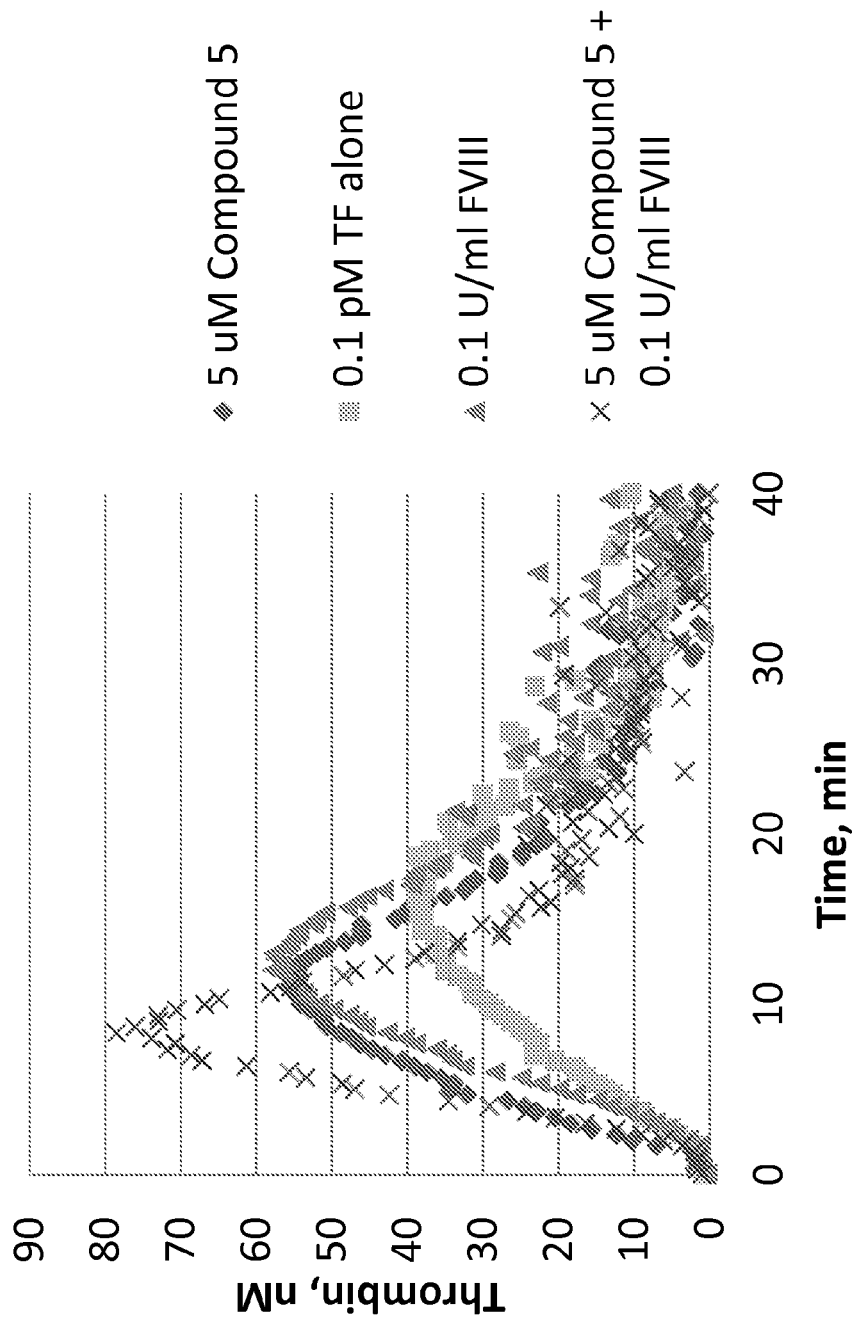
FIG. 2 is a graph illustrating the additive effect between FVIII and compound 5 of the present invention in a thrombin generation assay (TGA) utilizing 0.1 pM of lipidated tissue factor (TF) as the clotting cascade activator. Results indicate that compound 5 does not compete with FVIII, but shows additive thrombin generation activity with FVIII. Compound 5 increases the thrombin peak in the presence of low amounts of rFVIII.
Figure 3:
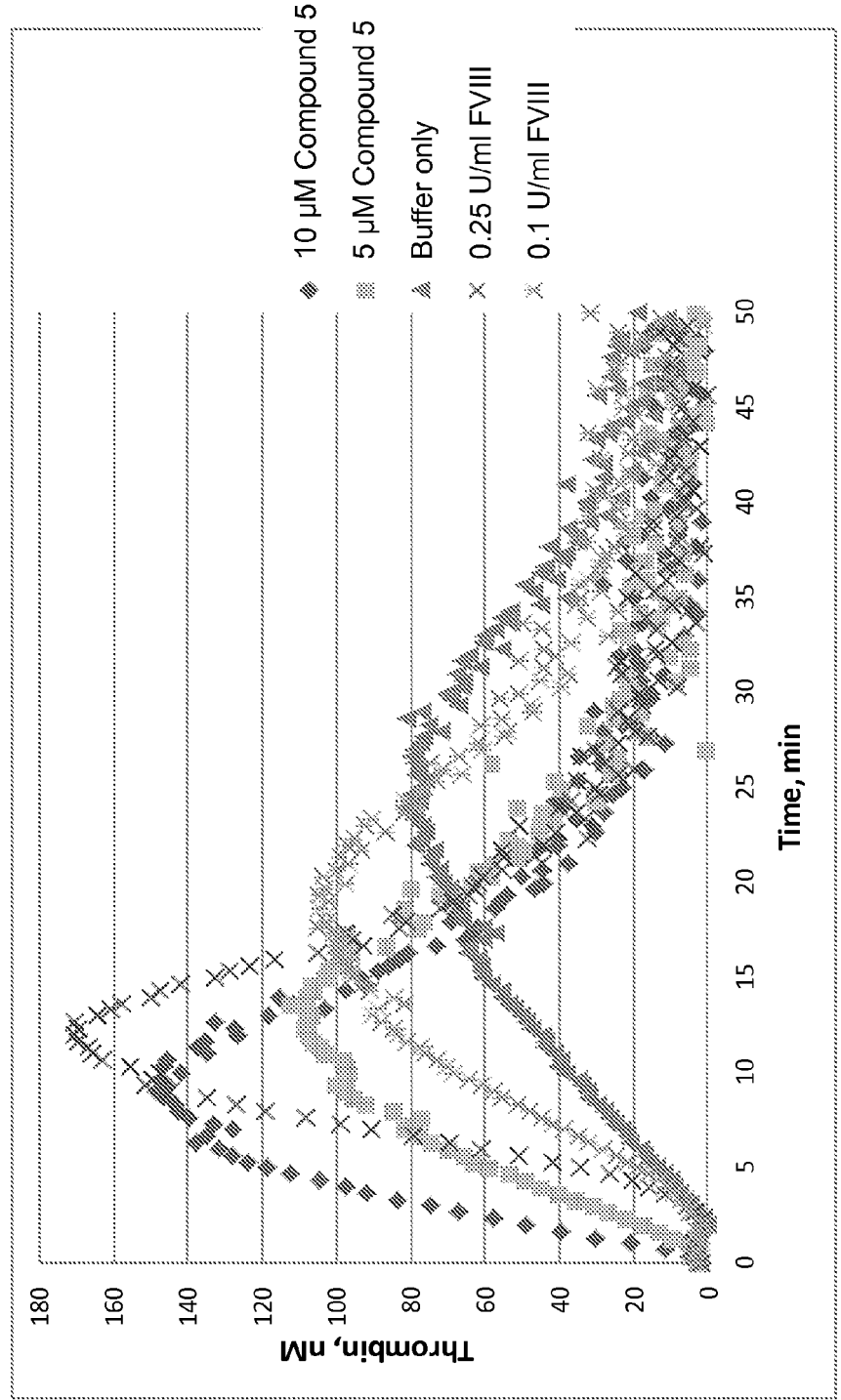
FIG. 3 is a graph illustrating that compound 5 enhances thrombin generation in human FVIII-deficient plasma. Thrombin generation was measured for compound 5 at 10 μM and 5 μM in a thrombin generation assay (TGA) using 0.1 pM lipTF as an activator. In this experiment, compound 5 has a shorter lag time than 0.1 or 0.25 U/mL of FVIII. The amount of thrombin generated by 5 or 10 μM compound 5 is larger than the amount generated by 0.1 U/mL of FVIII. Compound 5 at 10 μM generates similar amounts of thrombin than about 0.2 IU/mL of rFVIII.

A "B domain deleted FVIII" may have the full or partial deletions disclosed in U.S. Pat. Nos. 6,316,226, 6,346,513, 7,011,635, 5,789,203, 6,060,147, 5,595,886, 6,228,620, 5,972,885, 6,048,720, 5,543,502, 5,610,278, 5,171,844, 5,112,950, 4,868,112, and 6,458,563, each of which is incorporated herein by reference in its entirety. In some embodiments, a B domain deleted FVUIII sequence of the present invention comprises any one of the deletions disclosed at col. 4, line 4 to col. 5, line 28 and examples 1-5 of U.S. Pat. No. 6,316,226 (also in U.S. Pat. No. 6,346,513). In some embodiments, a B domain deleted FVIII of the present invention has a deletion disclosed at col. 2, lines 26-51 and examples 5-8 of U.S. Pat. No. 5,789,203 (also U.S. Pat. No. 6,060,447, U.S. Pat. No. 5,595,886, and U.S. Pat. No. 6,228,620). In some embodiments, a B domain deleted FVIII has a deletion described in col. 1, lines 25 to col. 2, line 40 of U.S. Pat. No. 5,972,885; col. 6, lines 1-22 and example 1 of U.S. Pat. No. 6,048,720; col. 2, lines 17-46 of U.S. Pat. No. 5,543,502; col. 4, line 22 to col. 5, line 36 of U.S. Pat. No. 5,171,844; col. 2, lines 55-68, FIG. 2, and example 1 of U.S. Pat. No. 5,112,950; col. 2, line 2 to col. 19, line 21 and table 2 of U.S. Pat. No. 4,868,112; col. 2, line 1 to col. 3, line 19, col. 3, line 40 to col. 4, line 67, col. 7, line 43 to col. 8, line 26, and col. 11, line 5 to col. 13, line 39 of U.S. Pat. No. 7,041,635; or col. 4, lines 25-53, of U.S. Pat. No. 6,458,563. In some embodiments, a B domain deleted FVIII has a deletion of most of the B domain, but still contains amino-terminal sequences of the B domain that are essential for in vivo proteolytic processing of the primary translation product into two polypeptide chain, as disclosed in WO 91/09122, which is incorporated herein by reference in its entirety. In some embodiments, a B domain deleted FVIII is constructed with a deletion of amino acids 747-1638, i.e., virtually a complete deletion of the B domain. Hoeben R. C., et al. *J. Biol. Chem,* 265 (13): 7318-7323 (1990), incorporated herein by reference in its entirety. A B domain deleted FVIII may also contain a deletion of amino acids 771-1666 or amino acids 868-1562 of FVIII. Meulien P., et al. *Protein Eng.* 2(4): 301-6 (1988), incorporated herein by reference in its entirety. Additional B domain deletions that are part of the invention include, e.g.,: deletion of amino acids 982 through 1562 or 760 through 1639 (Toole et al., Proc. Natl. Acad. Sci. U.S.A. (1986) 83, 5939-5942)), 797 through 1562 (Eaton, et al. Biochemistry (1986) 25:8343-8347)), 741 through 1646 (Kaufman (PCT published application No. WO 87/04187)), 747-1560 (Sarver, et al., DNA (1987) 6:553-564)), 741 through 1648 (Pasek (PCT application No.88/00831)), 816 through 1598 or 741 through 1689 (Lagner (Behring Inst. Mitt. (1988) No 82:16-25, EP 295597)), each of which is incorporated herein by reference in its entirety. Each of the foregoing deletions may be made in any FVIII sequence.

In one example, the FVIII polypeptide is a single-chain FVIII.

In some embodiments, the FVIII has an increased half-life (t½) due to linkage to a heterologous moiety that is a half-life extending moiety. Examples include, e.g., FVIII fused to Fc (including, e.g., FVIII constructs in the form of a hybrid such as a FVIIIFc monomer dimer hybrid; see e.g., U.S. Pat. Nos. 7,404,956 and 7,348,004), FVIII fused to albumin, FVIII fused to XTEN, FVIII fused to PAS, FVIII fused to HES, and FVIII fused to a water-soluble polymer, such as PEG.

The half-life is increased compared to a "reference FVIII" not fused to the half-life extending moiety (e.g., the FVIII without the Fc portion, or without the albumin portion). Likewise, the reference FVIII in the case of a modified FVIII is the same FVIII without the modification, e.g., a FVIII without the pegylation.)

In one example, the FVIII is fused to one or more albumin polypeptides (FVIII-albumin construct), e.g., human albumin. FVIII can be fused to either the N-terminal end of the albumin or to the C-terminal end of the albumin, provided the FVIII component of the FVIII-albumin fusion protein can be processed by an enzymaticaliy-active proprotein convertase to yield a processed FVIII-containing polypeptide. Examples of albumin, e.g., fragments thereof, that may be used in the present invention are known. e.g., U.S. Pat. No. 7,592,010; U.S. Pat. No. 6,686,179; and Schulte, Thrombosis Res. 124 Suppl. 2:S6-S8 (2009), each of which is incorporated herein by reference in its entirety.

Functional FVIII variants are known, as is discussed herein. In addition, hundreds of nonfunctional mutations in FVIII have been identified in hemophilia patients, and it has been determined that the effect of these mutations on FVIII function is due more to where they lie within the 3-dimensional structure of FVIII than on the nature of the substitution (Cutler et al., Hum. Mutat. 19:274-8 (2002)), incorporated herein by reference in its entirety. In addition, comparisons between FVIII from humans and other species have identified conserved residues that are likely to be required for function (Cameron et al., Thromb. Haemost. 79:317-22 (1998); U.S. Pat. No. 6,251,632), incorporated herein by reference in its entirety.

The human FVIII gene was isolated and expressed in mammalian cells (Toole, J. J., et al., Nature 312:342-347 (1984); Gitschier, J., et al., Nature 312:326-330 (1984); Wood, W. I., et al., Nature 312:330-337 (1984); Vehar, G. A., et al., Nature 312:337-342 (1984); WO 87/04187; WO 88/08035; WO 88/03558; U.S. Pat. No. 4,757,006), each of which is incorporated herein by reference in its entirety, and the amino acid sequence was deduced from cDNA. Capon et al., U.S. Pat. No. 4,965,199, incorporated herein by reference in its entirety, disclose a recombinant DNA method for producing FVIII in mammalian host cells and purification of human FVIII. Human FVIII expression in CHO (Chinese hamster ovary) cells and BHKC (baby hamster kidney cells) has been reported. Human FVIII has been modified to delete part or all of the B domain (U.S. Pat. Nos. 4,994,371 and 4,868,112, each of which is incorporated herein by reference in its entirety), and replacement of the human FVIII B domain with the human factor V B domain has been performed (U.S. Pat. No. 5,004,803, incorporated herein by reference in its entirety). The cDNA sequence encoding human FVIII and predicted amino acid sequence are shown in SEQ ID NOs: 1 and 2, respectively, of US Application Publ. No. 2005/0100990, incorporated herein by reference in its entirety.

U.S. Pat. No. 5,859,204, Lollar, J. S., incorporated herein by reference in its entirety, reports functional mutants of FVIII having reduced antigenicity and reduced immunoreactivity. U.S. Pat. No. 6,376,463, Lollar, J. S., incorporated herein by reference in its entirety, also reports mutants of FVIII having reduced immunoreactivity. US Application Publ. No. 2005/0100990, Saenko et al., incorporated herein by reference in its entirety, reports functional mutations in the A2 domain of FVIII.

The porcine FVIII sequence is published, (Toole, J. J., et al., Proc. Natl. Acad. Sci. USA 83:5939-5942 (1986)), incorporated herein by reference in its entirety, and the complete porcine cDNA sequence obtained from PCR amplification of FVIII sequences from a pig spleen cDNA library has been reported (Healey, J. F., et al., Blood 88:4209-4214 (1996), incorporated herein by reference in its entirety). Hybrid human/porcine FVIII having substitutions of all domains, all subunits, and specific amino acid sequences were disclosed in U.S. Pat. No. 5,364,771 by Lollar and Runge, and in WO 93/20093, incorporated herein by reference in its entirety. More recently, the nucleotide and corresponding amino acid sequences of the A1 and A2 domains of porcine FVIII and a chimeric FVIII with porcine A1 and/or A2 domains substituted for the corresponding human domains were reported in WO 94/11503, incorporated herein by reference in its entirety. U.S. Pat. No. 5,859,204, Lollar, J. S., also discloses the porcine cDNA and deduced amino acid sequences. U.S. Pat. No. 6,458,563, incorporated herein by reference in its entirety assigned to Emory discloses a B-domain deleted porcine FVIII.

In one example, the FVIII is linked to Fc. Such constructs are known in the art. Exemplary FVIII and FVIII-Fc polypeptides include, e.g., SEQ ID NOs: 700-711 or a portion thereof.

The FVIII may be at least 85%, 90%, 95%, 96%, 97%, 98% or 99% identical to a portion of the FVIII amino acid sequence of SEQ ID NOs:701, 705, 707, 709, or 711 without a signal sequence (e.g., amino acids 20 to 1457 of SEQ NO:701; amino acids 20 to 2351 of SEQ ID NO:705; amino acids 20 to 759 of SEQ ID NO:707; amino acids 20 to 764 of SEQ ID NO:709; or amino acids 20 to 703 of SEQ ID NO:711).

The FVIII (or FVIII portion of a conjugate) may be identical to a portion of the FVIII amino acid sequence of SEQ ID NOs:701, 705, 707, 709, or 711 without a signal sequence (e.g., amino acids 20 to 1457 of SEQ ID NO:701; amino acids 20 to 2351 of SEQ ID NO:705; amino acids 20 to 759 of SEQ ID NO:707; amino acids 20 to 764 of SEQ ID NO:709; or amino acids 20 to 703 of SEQ ID NO:711).

The FVIII (or FVIII portion of a conjugate) may be at least 85%, 90%, 95%, 96%, 97%, 98% or 99% identical to a portion of the FVIII amino acid sequence of SEQ ID NOs:701, 705, 707, 709, or 711, with a signal sequence (e.g., amino acids 1 to 1457 of SEQ ID NO:701; amino acids 1 to 2351 of SEQ ID NO:705; amino acids 1 to 759 of SEQ ID NO:707; amino acids 1 to 764 of SEQ ID NO:709; or amino acids 1 to 703 of SEQ ID NO:711).

The FVIII (or FVIII portion of a chimeric polypeptide) may be identical to a FVIII amino acid sequence of SEQ ID NOs:701, 705, 707, 709, or 711, with a signal sequence (e.g., amino acids 1 to 1457 of SEQ ID NO:701; amino acids 1 to 2351 of SEQ ID NO:705; amino acids 1 to 759 of SEQ ID NO:707; amino acids 1 to 764 of SEQ ID NO:709; or amino acids 1 to 703 of SEQ ID NO:711).

In one example, the FVIII is linked to Fc. Such constructs are known in the art. The FVIII-Fc may comprise a sequence at least 90% or 95% identical to the FVIII-Fc amino acid sequences of SEQ ID NOs:701, 705, 707, 709, or 711 without a signal sequence (e.g., amino acids 20 to 1684 of SEQ ID NO:701) or at least 90% or 95% identical to the FVIII and Fc amino acid sequence of SEQ ID NOs:701, 705, 707, 709, or 711 with a signal sequence (e.g., amino acids 1 to 1684 of SEQ ID NO:701).

The FVIII-Fc may comprise a sequence identical to the FVIII and Fc amino acid sequence of SEQ ID NOs:701, 705, 707, 709, or 711 without a signal sequence (e.g., amino acids 20 to 1684 of SEQ ID NO:701) or identical to the FVIII and Fc amino acid sequence of SEQ ID NOs:701, 705, 707, 709, or 711 with a signal sequence (e.g., amino acids 1 to 1684 of SEQ ID NO:701).

The polynucleotide variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5-10, 1-5, or 1-2 amino acids are substituted, deleted, or added in any combination are also preferred. Polynucleotide variants can be produced for a variety of reasons, e.g., to optimize codon expression for a particular host (change codons in the human mRNA to those preferred by a bacterial host such as E. coli).

In some embodiments, FVIII is modified, e.g., pegylated, at any convenient location. In some embodiments, FVIII is pegylated at a surface exposed amino acid of FVIII, preferably a surface exposed cysteine, which may be an engineered cysteine. Mei et al. (2010). In some embodiments, modified FVIII, e.g., pegylated FVIII, is a long-acting FVIII.

In one example, the FVIII of the present disclosure is a polypeptide having FVIII-like activity, but does not have the amino acid sequence of FVIII. For example, the polypeptide having FVIII-like activity increases the catalytic activity of FIXa. In one example, the polypeptide having FVIII-like activity is an antibody (e.g., FIX/FIXa activating antibodies and antibody derivatives). Exemplary polypeptides having FVIII-like activity are disclosed in U.S. Pat. No. 7,033,590, which is incorporated herein by reference in its entirety.

Methods for the preparation of recombinant FVIII or FVIII-Fc constructs are disclosed, e.g., in WO2011/069164, which is incorporated herein by reference in its entirety.

FIX

"Factor IX" or "FIX," as used herein, means functional Factor IX polypeptide in its normal role in coagulation, unless otherwise specified. Thus, the term Factor IX includes FIX variant polypeptides that are functional and the polynucleotides that encode such functional variant polypeptides. Preferred Factor IX polypeptides are the human, bovine, porcine, canine, feline, and murine Factor IX polypeptides. The full length polypeptide and polynucleotide sequences of Factor IX are known, as are many functional variants, e.g., fragments, mutants and modified versions. Factor IX polypeptides include full-length Factor IX, full-length Factor IX minus Met at the N-terminus, mature Factor IX (minus the signal sequence), and mature Factor IX with an additional Met at the N-terminus.

The FIX may be at least 85%, 90%, 95%, 96%, 97%, 98% or 99% identical to a FIX amino acid sequence without a signal sequence (e.g., amino acids 47 to 461 of SEQ ID NO:713). The FIX may be identical to a FIX amino acid sequence without a signal sequence (e.g., amino acids 47 to 461 of SEQ ID NO:713).

The FIX may be at least 85%, 90%, 95%, 96%, 97%, 98% or 99% identical to a FIX amino acid sequence with a signal sequence (e.g., amino acids 1 to 461 of SEQ ID NO:713). The FIX may be identical to a FIX amino acid sequence with a signal sequence (e.g., amino acids 1 to 461 of SEQ ID NO:713).

In one example, FIX is linked to Fc. Exemplary FIX-Fc amino acid and DNA sequences include SEQ ID NOs:712 and 713, with or without its signal sequence.

The FIX-Fc polypeptide may comprise a sequence at least 85%, 90%, 95%, 96%, 97%, 98% or 99% identical to the FIX and Fc amino acid sequences without a signal sequence (amino acids 47 to 688 of SEQ ID NO:713) or at least 85%, 90%, 95%, 96%, 97%, 98% or 99% identical to the Factor IX and Fc amino acid sequence with a signal sequence (amino acids 1 to 688 of SEQ ID NO:713).

The FIX-Fc polypeptide may comprise a sequence identical to the Factor IX and Fc amino acid sequence without a signal sequence (amino acids 47 to 688 of SEQ ID NO:713) or identical to the Factor IX and Fc amino acid sequence with a signal sequence (amino acids 1 to 688 of SEQ ID NO:713).

A great many functional FIX variants are known. International publication number WO 02/040544 A3, which is herein incorporated by reference in its entirety, discloses mutants that exhibit increased resistance to inhibition by heparin at page 4, lines 9-30 and page 15, lines 6-31. International publication number WO 03/020764 A2, which is herein incorporated by reference in its entirety, discloses Factor IX mutants with reduced T cell immunogenicity in Tables 2 and 3 (on pages 14-24), and at page 12, lines 1-27. International publication number WO 2007/149406 A2, which is herein incorporated by reference in its entirety, discloses functional mutant Factor IX molecules that exhibit increased protein stability, increased in vivo and in vitro half life, and increased resistance to proteases at page 4, line 1 to page 19, line 11. WO 2007/149406 A2 also discloses chimeric and other variant Factor IX molecules at page 19, line 12 to page 20, line 9. International publication number WO 08/118507 A2, which is herein incorporated by reference in its entirety, discloses Factor IX mutants that exhibit increased clotting activity at page 5, line 14 to page 6, line 5. International publication number WO 09/051717 A2, which is herein incorporated by reference in its entirety, discloses Factor IX mutants having an increased number of N-linked and/or O-linked glycosylation sites, which results in an increased half life and/or recovery at page 9, line 11 to page 20, line 2. International publication number WO 09/137254 A2, which is herein incorporated by reference in its entirety, also discloses Factor IX mutants with increased numbers of glycosylation sites at page 2, paragraph [006] to page 5, paragraph [011] and page 16, paragraph [044] to page 24, paragraph [057]. International publication number WO 09/130198 A2, which is herein incorporated by reference in its entirety, discloses functional mutant Factor IX molecules that have an increased number of glycosylation sites, which result in an increased half life, at page 4, line 26 to page 12, line 6. International publication number WO 09/140015 A2, which is herein incorporated by reference in its entirety, discloses functional Factor IX mutants that an increased number of Cys residues, which may be used for polymer (e.g., PEG) conjugation, at page 11, paragraph [0043] to page 13, paragraph [0053].

In addition, hundreds of non-functional mutations in Factor IX have been identified in hemophilia patients, many of which are disclosed in Table 1, at pages 11-14 of International publication number WO 09/137254 A2, which is herein incorporated by reference in its entirety. Such non-functional mutations are not included in the invention, but provide additional guidance for which mutations are more or less likely to result in a functional Factor IX polypeptide.

In various embodiments FIX is fused to one or more XTEN polypeptides. Schellenburger et al., Nat. Biotech. 27:1186-90 (2009), which is incorporated herein by reference in its entirety. FIX can be fused to either the N-terminal end of the XTEN polypeptide or to the C-terminal end of the XTEN polypeptide, provided the FIX component of the FIX-XTEN construct can be processed by a protease to yield a processed FIX containing polypeptide. A protease site may be included between the XTEN portion and the FIX portion to allow such processing. XTEN polypeptides include, e.g., those disclosed in WO 2009/023270, WO 2010/091122, WO 2007/103515, US 2010/0189682, and US 2009/0092582, each of which is incorporated herein by reference in its entirety.

Variant FIX polynucleotides may comprise, or alternatively consist of, a nucleotide sequence which is at least 85%, 90%, 95%, 96%, 97%, 98% or 99% identical to, for example, the nucleotide coding sequence in SEQ ID NO:712 (the Factor IX portion, the Fc portion, individually or together) or the complementary strand thereto, the nucleotide coding sequence of known mutant and recombinant Factor IX or Fc such as those disclosed in the publications and patents cited herein or the complementary strand thereto, a nucleotide sequence encoding the polypeptide of SEQ ID NO:713 or SEQ ID NO:703 (the Factor IX portion, the Fc portion, individually or together), and/or polynucleotide fragments of any of these nucleic acid molecules (e.g., those fragments described herein). Polynucleotides which hybridize to these nucleic acid molecules under stringent hybridization conditions or lower stringency conditions are also included as variants, as are polypeptides encoded by these polynucleotides as long as they are functional.

Variant FIX polypeptides may comprise, or alternatively consist of, an amino acid sequence which is at least 85%, 90%, 95%, 96%, 97%, 98%, 99% identical to, for example, the polypeptide sequence shown in SEQ ID NO:713 or 703 (the Factor IX portion, the Fc portion, individually or together), and/or polypeptide fragments of any of these polypeptides (e.g., those fragments described herein).

FVIIa

The term "Factor VII" or "FVII", includes "Factor VIIa", or "FVIIa", and herein, means functional FVII protein or functional FVIIa protein in its normal role in coagulation, unless otherwise specified (i.e., refers to any FVII moiety which exhibits biological activity that is associated with native FVII). Thus, the term FVII includes variant proteins that are functional. Preferred FVII proteins are primate (e.g., chimpanzee), human, porcine, canine, and murine FVII proteins. The full length polypeptide and polynucleotide sequences of FVII are known, as are many functional fragments, mutants and modified versions. Exemplary chimeric and hybrid FVII sequences are disclosed, e.g., in US 2009/0291890 A1, US2009/0041744 A1, and US 2008/0318276 A1. Factor VII polypeptides include, e.g., full-length FVII, full-length FVII minus Met at the N-terminus, mature FVII (minus the signal sequence), and mature FVII with an additional Met at the N-terminus. An exemplary sequence of FVII can be found as NCBI Accession Number NP000122.

As used herein, "plasma-derived FVII" includes all forms of the protein found in blood obtained from a mammal having the property of activating the coagulation pathway.

The term Factor VII includes variant polypeptides that are functional. Preferred factor VII proteins are the human, porcine, canine, and murine factor VII proteins. As described in the Background Art section, the full length polypeptide and polynucleotide sequences are known, as are many functional fragments, mutants and modified versions. The one chain zymogen Factor VII is a polypeptide comprising 406 amino acid residues, 10 of which are γ-carboxylated glutamic acid residues, N-glycosylated asparagines residues (no 145 and no 322), and O-glycosylated serine residues in position 52 and 60. The variant forms of FVII encompasses i.a. molecules wherein one or more amino acid residues have been substituted, added or deleted, molecules with different number of GLA residues, molecules with a modified or uncornplete glycosylation pattern. Non-limiting examples of modifications of amino acid residues are amidation, alkylation, acylation and PEGylation.

Examples of human FVII amino acid and DNA sequences are shown as subsequences in SEQ ID NO:714 and SEQ ID NO:715. FVII poly peptides include, e.g., full-length FVII, full-length FVII minus Met at the N-terminus, mature FVII (minus the signal sequence), and/or mature FVII with an additional Met at the N-terminus.

The term "activated Factor VII" or "FVIIa" refers to the enzymatically active two-chain form of circulating FVII generated as well as variants thereof in case coagulation activity (e.g. thrombin generation) is needed. The two-chain Factor VIIa is a polypeptide produced from FVII by hydrolysis of the Arg152-Ile153 peptide bond of FVII. FVIIa also comprises 406 amino acid residues, 10 of which are γ-carboxylated glutamic acid residues, N-glycosylated asparagines residues (no 145 and no 322), and O-glycosylated serine residues in position 52 and 60. The variant forms of FVIIa encompasses i.a. molecules wherein one or more amino acid residues have been substituted, added or deleted, molecules with different number of GLA residues, molecules with a modified or uncomplete glycosylation pattern. The terms "FVII" and "activated FVII" include naturally occurring FVII and activated FVII but also encompass function conservative variants and modified forms thereof.

The term "Factor FVIIa" or "FVIIa" includes activatable FVII.

Exemplary FVII sequences are disclosed herein. For example, the FVII may be at least 90% or 95% identical to a FVII amino acid sequence without a signal sequence (e.g., amino acids 61 to 466 of SEQ ID NO:715). The FVII may be identical to a Factor VII amino acid sequence without a signal sequence (e.g., amino acids 61 to 466 of SEQ ID NO:715).

The Factor VII may be at least 90% or 95% identical to a Factor VII amino acid sequence with a signal sequence (e.g., amino acids 1 to 466 of SEQ ID NO:715). The Factor VII may be identical to a FVII amino acid sequence with a signal sequence (e.g., amino acids 1 to 466 of SEQ ID NO:715).

In one example FVII is linked to Fc. Exemplary FVII-Fc amino acid and DNA sequences are represented by SEQ ID NO:714 and 715. The FVII-Fc may comprise a sequence at least 90% or 95% identical to the FVII and Fc amino acid sequence without a signal sequence (e.g., amino acids 61 to 693 of SEQ ID NO:715) or at least 90% or 95% identical to the FVII and Fc amino acid sequence with a signal sequence (e.g., amino acids 1 to 693 of SEQ ID NO:715).

The FVII-Fc may comprise a sequence identical to the FVII and Fc amino acid sequence without a signal sequence (e.g., amino acids 61 to 693 of SEQ ID NO:715) or identical to the FVII and Fc amino acid sequence with a signal sequence (e.g., amino acids 1 to 693 of SEQ ID NO:715).

FYII polynucleotides include, e.g., those of SEQ ID NO:714 and fragments thereof, e.g., those that encode the FVII fragment.

The term "Factor VIIa derivative" or "FVIIa derivative" as used herein, is intended to designate a FVIIa polypeptide exhibiting substantially the same or improved biological activity relative to wild-type Factor VIIa, in which one or more of the amino acids of the parent peptide have been genetically and/or chemically and/or enzymatically modified, e.g. by alkylation, glycosylation, deglycosylation, PEGylation, acylation, ester formation or amide formation or the like. This includes but is not limited to PEGylated Factor VIIa, cysteine-PEGylated human Factor VIIa and variants thereof.

The term "PEGylated Factor VIIa" (and the like) means a Factor VIIa polypeptide conjugated with a PEG molecule. It is to be understood, that the PEG molecule may be attached to any part of the Factor VIIa polypeptide including any amino acid residue or carbohydrate moiety of the Factor VIIa polypeptide. The term "cysteine-PEGylated Factor VIIa" means Factor VIIa polypeptide having a PEG molecule conjugated to a sulfhydryl group of a non-native cysteine of the Factor VIIa polypeptide.

Non-limiting examples of Factor VIIa derivatives includes GlycoPegylated FVIIa derivatives as disclosed in WO 03/31464 and US Patent applications US 20040043446, US 20040063911, US 20040142856, US 20040137557, and US 20040132640 (Neose Technologies, Inc.); FVIIa conjugates as disclosed in WO 01/04287, US patent application 20030165996, WO 01/58935, WO 03/93465 (Maxygen ApS) and WO 02/02764, US patent application 20030211094 (University of Minnesota).

The term "improved biological activity" refers to FVIIa polypeptides with i) substantially the same or increased proteolytic activity compared to recombinant wild type human Factor VIIa or ii) to FVIIa polypeptides with substantially the same or increased TF binding activity compared to recombinant wild type human Factor VIIa or iii) to FVIIa polypeptides with substantially the same or increased half life in blood plasma compared to recombinant wild type human Factor VIIa.

The term "PEGylated human Factor VIIa" means human Factor VIIa, having a PEG molecule conjugated to a human Factor VIIa polypeptide. It is to be understood, that the PEG molecule may be attached to any part of the Factor VIIa polypeptide including any amino acid residue or carbohydrate moiety of the Factor VIIa polypeptide.

Non-limiting examples of FVIIa variants having increased biological activity compared to wild-type FVIIa include FVIIa variants as disclosed in WO 01/83725, WO 02/22776, WO 02/077218, PCT/DK02/00635 (corresponding to WO 03/027147), Danish patent application PA 2002 01423 (corresponding to WO 04/029090), Danish patent application PA 2001 01627 (corresponding to WO 03/027147); WO 02/38162 (Scripps Research Institute); and FVIIa variants with enhanced activity as disclosed in IP 2001061479 (Chemo-Sero-Therapeutic Res Inst.).

Variant polynucleotides may comprise, or alternatively consist of, a nucleotide sequence which is at least 85%, 90%, 95%, 96%, 97%, 98% or 99% identical to, for example, the nucleotide coding sequence in SEQ ID NO:15 (the factor VII portion, the Fc portion, individually or together) or the complementary strand thereto, the nucleotide coding sequence of known mutant and recombinant factor VII or Fc such as those disclosed in the publications and patents cited herein or the complementary strand thereto, a nucleotide sequence encoding the polypeptide of SEQ ID NO:16 or 4

(the factor VII portion, the Fc portion, individually or together), and/or polynucleotide fragments of any of these nucleic acid molecules (e.g., those fragments described herein). Polynucleotides which hybridize to these nucleic acid molecules under stringent hybridization conditions or lower stringency conditions are also included as variants, as are polypeptides encoded by these polynucleotides as long as they are functional.

Variant polypeptides may comprise, or alternatively consist of, an amino acid sequence which is at least 85%, 90%, 95%, 96%, 97%, 98%, 99% identical to, for example, the polypeptide sequence shown in SEQ ID NO:715 or 703 (the FVII portion, the Fc portion, individually or together), and/or polypeptide fragments of any of these polypeptides (e.g., those fragments described herein).

Using known methods of protein engineering and recombinant DNA technology, variants may be generated to improve or alter the characteristics of the polypeptides. For instance, one or more amino acids can be deleted from the N-terminus or C-terminus of the secreted protein without substantial loss of biological function. The authors of Ron et al., J. Biol. Chem. 268: 2981-2988 (1993), incorporated herein by reference in its entirety, reported variant KGF proteins having heparin binding activity even after deleting 3, 8, or 27 amino-terminal amino acid residues. Similarly, Interferon gamma exhibited up to ten times higher activity after deleting 8-10 amino acid residues from the carboxy terminus of this protein. (Dobeli et al., J. Biotechnology 7:199-216 (1988), incorporated herein by reference in its entirety.)

As stated above, polypeptide variants include, e.g., modified polypeptides. Modifications include, e.g., acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation (Mei et al., Blood 116:270-79 (2010), which is incorporated herein by reference in its entirety), proteolytic processing, phosphorylation, prenylation, racemization, selenoylation, sulfation, transfer-RNA mediated addition of amino acids to proteins such as arginylation, and ubiquitination. In some embodiments, FVII is modified, e.g., pegylated, at any convenient location. In some embodiments, FVII is pegylated at a surface exposed amino acid of Factor VII, preferably a surface exposed.

In one embodiment, an enhanced clotting factor of the invention is manufactured in an activated form. For example, FVII, is generally produced recombinantly as a zymogen, and requires activation during manufacturing to produce the active form for administration. In one embodiment, an enhanced clotting factor of the invention is secreted from the cell in which it is expressed in active form to improve manufacturability. Such clotting factors can be produced by expressing the light chain of a clotting factor and the heavy chain of a clotting factor separately. In one embodiment, such a polypeptide comprises an intracellular processing site upstream of the heavy chain. Activation of such a construct is delayed until late in the secretory pathway, e.g., when the protein colocalizes with active processing enzymes in the trans-Golgi apparatus. In one embodiment, such a construct comprises an Fc scaffold moiety, for example an scFc scaffold in which the scFc linker comprises one or more intracellular processing sites.

In another embodiment, an enhanced clotting factor of the invention is made in activatable form. For use in bypass therapy exogenous clotting factors are only efficacious when given in the activated form. However, such activated clotting factors are rapidly inactivated by endogenous pathways (e.g. antithrombin III, TFPI), leading to clearance of the active form and a short effective half life. Giving higher doses does not solve this problem as it can result in thrombogenic effects. Thus, in one embodiment, the invention pertains to an "activatable" enhanced clotting factor constructs which circulate as zymogens. These molecules have a longer half life, but can readily be activated at the site of clotting by cleavage by an enzyme. In one embodiment, such an enzyme is one produced during the clotting cascade. For example, in one embodiment, the cleavage site of an activatable construct comprises a Factor XIa, Xa, or thrombin cleavage site. Exemplary FXIa cleavage sites include: TQSFNDFTR (SEQ ID NO: 844) and SVSQTSKLTR (SEQ ID NO: 845). Exemplary Thrombin cleavage sites include: DFLAEGGGVR (SEQ ID NO: 846), TTKIKPR (SEQ ID NO: 848), and ALRPRVVGGA (SEQ ID NO: 851).

As discussed above, exemplary polypeptides include FVII fused to one or more XTEN polypeptides. Schellenburger et al., Nat. Biotech. 27:1186-90 (2009), which is incorporated herein by reference in its entirety. FVII can be fused to either the N-terminal end of the XTEN polypeptide or to the C-terminal end of the XTEN polypeptide, provided the Factor VII component of the Factor VII-XTEN fusion protein can be processed by a protease to yield a processed Factor VII containing polypeptide. A protease site may be included between the XTEN portion and the Factor VII portion to allow such processing. XTEN polypeptides include, e.g., those disclosed in WO 2009/023270, WO 2010/091122, WO 2007/103515, US 2010/0189682, and US 2009/0092582, each of which is incorporated herein by reference in its entirety.

Exemplary polypeptides also include FVII fused to one or more albumin polypeptides. Preferably the albumin is human albumin. Factor VII can be fused to either the N-terminal end of the albumin or to the C-terminal end of the albumin, provided the Factor VII component of the Factor VII-albumin fusion protein can be processed by an enzymatically-active proprotein convertase to yield a processed Factor VII-containing polypeptide. Examples of albumin, e.g., fragments thereof, that may be used in the present invention are known. e.g., U.S. Pat. No. 7,592,010; U.S. Pat. No. 6,686,179; and Schulte, Thrombosis Res. 124 Suppl. 2:S6-S8 (2009), each of which is incorporated herein by reference in its entirety.

In some embodiments, a chimeric polypeptide comprising a Factor VII portion has an increased half-life (t½) over a polypeptide consisting of the same Factor VII portion without the non Factor VII portion. A chimeric Factor VII polypeptide with an increased t½ may be referred to herein as a long-acting Factor VII. Long-acting chimeric Factor VII polypeptides include, e.g., Factor VII fused to Fc (including, e.g., chimeric Factor VII polypeptides in the form of a hybrid such as a FVIIFc monomer dimer hybrid; see Table 1), Factor VII fused to XTEN, and Factor VII fused to albumin.

Platelet Targeting Moiety

In one embodiment, the platelet targeting moiety comprises at least one of an antigen binding site (e.g., an antigen binding site of an antibody, antibody variant, or antibody fragment), a polypeptide, a receptor binding portion of ligand, or a ligand binding portion of a receptor which specifically binds to platelets, e.g., resting or activated platelets. Exemplary targeting moieties include scFv molecules or peptides which bind to molecules to be targeted. In one embodiment, the targeting moiety binds to resting platelets. In one embodiment, the targeting moiety selectively binds to activated platelets.

In one embodiment, the targeting moiety selectively binds to a target selected from the group consisting of: GPIba, GPVI, and the nonactive form of GPIIb/III.a. In another embodiment, the targeting moiety selectively binds to a target selected from the group consisting of: GPIIb/IIa, P selectin, GMP-33, LAMP-1, LAMP-2, CD40L, and LOX-1. Examples of platelet targeting moieties are described below.

Antigen Binding Sites

In certain embodiments, the platelet targeting moiety is an antigen binding portion (e.g., binding site) of an antibody. In one embodiment, the antigen binding portion targets the composition to platelets In other embodiments, a binding site of a polypeptide of the invention may comprise an antigen binding fragment. The term "antigen-binding portion" refers to a polypeptide fragment of an immunoglobulin, antibody, or antibody variant which binds antigen or competes with intact antibody (i.e., with the intact antibody from which they were derived) for antigen binding (i.e., specific binding). For example, said antigen binding fragments can be derived from any of the antibodies or antibody variants described supra. Antigen binding portions can be produced by recombinant or biochemical methods that are well known in the art. Exemplary antigen-binding fragments include Fv, Fab, Fab', and (Fab')$_2$ as well as scFv molecules.

In other embodiments, the targeting moiety is a binding site from a single chain binding molecule (e.g., a single chain variable region or scFv). Techniques described for the production of single chain antibodies (U.S. Pat. No. 4,694,778; Bird, *Science* 242:423-442 (1988); Huston et al., *Proc. Natl. Acad. Sci. USA* 85:5879-5883 (1988), and Ward et al., *Nature* 334:544-554 (1989)) can be adapted to produce single chain binding molecules. Single chain antibodies are formed by linking the heavy and light chain fragments of the Fv region via an amino acid bridge, resulting in a single chain antibody. Techniques for the assembly of functional Fv fragments in *E coli* may also be used (Skerra et al., *Science* 242:1038-1041 (1988)).

In certain embodiments, the platelet targeting moiety includes one or more binding sites or regions comprising or consisting of a single chain variable region sequence (scFv). Single chain variable region sequences comprise a single polypeptide having one or more antigen binding sites, e.g., a $V_L$ domain linked by a flexible linker to a $V_H$ domain. The VL and/or VH domains may be derived from any of the antibodies or antibody variants described supra. ScFv molecules can be constructed in a $V_H$-linker-$V_L$ orientation or $V_L$-linker-$V_H$ orientation. The flexible linker that links the $V_L$ and $V_H$ domains that make up the antigen binding site preferably comprises from about 10 to about 50 amino acid residues. In one embodiment, the polypeptide linker is a gly-ser polypeptide linker. An exemplary gly/ser polypeptide linker is of the formula (Gly4Ser)n (SEQ ID NO: 882), wherein n is a positive integer (e.g., 1, 2, 3, 4, 5, or 6). Other polypeptide linkers are known in the art. Antibodies having single chain variable region sequences (e.g. single chain Fv antibodies) and methods of making said single chain antibodies are well-known in the art (see e.g., Ho et al. 1989. Gene 77:51; Bird et al. 1988 Science 242:423; Pantoliano et al. 1991. Biochemistry 30:10117; Milenic et al. 1991. Cancer Research 51:6363; Takkinen et al. 1991. Protein Engineering 4:837).

In certain embodiments, a scFv molecule is a stabilized scFv molecule. In one embodiment, the stabilized cFv molecule may comprise a scFv linker interposed between a $V_H$ domain and a $V_L$ domain, wherein the $V_H$ and $V_L$ domains are linked by a disulfide bond between an amino acid in the $V_H$ and an amino acid in the $V_L$ domain. In other embodiments, the stabilized scFv molecule may comprise a scFv linker having an optimized length or composition. In yet other embodiments, the stabilized scFv molecule may comprise a $V_H$ or $V_L$ domain having at least one stabilizing amino acid substitution(s). In yet another embodiment, a stabilized scFv molecule may have at least two of the above listed stabilizing features.

Stabilized scFv molecules have improved protein stability or impart improved protein stability to the polypeptide to which it is operably linked. Preferred scFv linkers of the invention improve the thermal stability of a polypeptide of the invention by at least about 2° C. or 3° C. as compared to a conventional polypeptide Comparisons can be made, for example, between the scFv molecules of the invention. In certain preferred embodiments, the stabilized scFv molecule comprises a (Gly$_4$Ser)$_4$ (SEQ ID NO: 886)scFv linker and a disulfide bond which links $V_H$ amino acid 44 and $V_L$ amino acid 100. Other exemplary stabilized scFv molecules which may be employed in the polypeptides of the invention are described in U.S. patent application Ser. No. 11/725,970, filed on Mar. 19, 2007, incorporated herein by reference in its entirety.

In one example, the platelet targeting moiety includes a variable region or portion thereof (e.g. a VL and/or VH domain) derived from an antibody using art recognized protocols. For example, the variable domain may be derived from antibody produced in a non-human mammal, e.g., murine, guinea pig, primate, rabbit or rat, by immunizing the mammal with the antigen or a fragment thereof. See Harlow & Lane, supra, incorporated by reference for all purposes. The immunoglobulin may be generated by multiple subcutaneous or intraperitoneal injections of the relevant antigen (e.g., purified tumor associated antigens or cells or cellular extracts comprising such antigens) and an adjuvant. This immunization typically elicits an immune response that comprises production of antigen-reactive antibodies from activated splenocytes or lymphocytes.

Optionally, antibodies may be screened for binding to platelets of a specific activation state or to a specific region or desired fragment of the antigen without binding to other nonoverlapping fragments of the antigen. The latter screening can be accomplished by determining binding of an antibody to a collection of deletion mutants of the antigen and determining which deletion mutants bind to the antibody. Binding can be assessed, for example, by Western blot or ELISA. The smallest fragment to show specific binding to the antibody defines the epitope of the antibody. Alternatively, epitope specificity can be determined by a competition assay is which a test and reference antibody compete for binding to the antigen. If the test and reference antibodies compete, then they bind to the same epitope or epitopes sufficiently proximal such that binding of one antibody interferes with binding of the other.

In other embodiments, the binding site is derived from a fully human antibody. Human or substantially human antibodies may be generated in transgenic animals (e.g., mice) that are incapable of endogenous immunoglobulin production (see e.g., U.S. Pat. Nos. 6,075,181, 5,939,598, 5,591, 669 and 5,589,369, each of which is incorporated herein by reference). Another means of generating human antibodies using SCID mice is disclosed in U.S. Pat. No. 5,811,524 which is incorporated herein by reference. It will be appreciated that the genetic material associated with these human antibodies may also be isolated and manipulated as described herein.

Yet another highly efficient means for generating recombinant antibodies is disclosed by Newman, *Biotechnology*, 10: 1455-1460 (1992). Specifically, this technique results in the generation of primatized antibodies that contain monkey variable domains and human constant sequences. This reference is incorporated by reference in its entirety herein. Moreover, this technique is also described in commonly assigned U.S. Pat. Nos. 5,658,570, 5,693,780 and 5,756,096 each of which is incorporated herein by reference.

In another embodiment, a variable region domain of an altered antibody of the invention consists of a $V_H$ domain, e.g., derived from camelids, which is stable in the absence of a $V_L$ chain (Hamers-Casterman et al. (1993). *Nature*, 363:446; Desmyter et al. (1996). *Nat. Struct. Biol.* 3: 803; Decanniere et al. (1999). *Structure*, 7:361; Davies et al. (1996). *Protein Eng.*, 9:531; Kortt et al. (1995). *Protein Chem.*, 14:167). p Further, the platelet targeting moiety may comprise a variable domain or CDR derived from a fully murine, fully human, chimeric, humanized, non-human primate or primatized antibody. Non-human antibodies, or fragments or domains thereof, can be altered to reduce their immunogenicity using art recognized techniques.

In one embodiment, the variable domains are altered by at least partial replacement of one or more CDRs. In another embodiment, variable domains can optionally be altered, e.g., by partial framework region replacement and sequence changing. In making a humanized variable region the CDRs may be derived from an antibody of the same class or even subclass as the antibody from which the framework regions are derived, however, it is envisaged that the CDRs will be derived from an antibody of different class and preferably from an antibody from a different species. It may not be necessary to replace all of the CDRs with the complete CDRs from the donor variable region to transfer the antigen binding capacity of one variable domain to another. Rather, it may only be necessary to transfer those residues that are necessary to maintain the activity of the binding domain. Given the explanations set forth in U.S. Pat. Nos. 5,585,089, 5,693,761 and 5,693,762, it will be well within the competence of those skilled in the art, either by carrying out routine experimentation or by trial and error testing to obtain a functional antigen binding site with reduced immunogenicity.

In other aspects, the polypeptides of the invention may comprise antigen binding sites, or portions thereof, derived from modified forms of antibodies. Exemplary such forms include, e.g., minibodies, diabodies, triabodies, nanobodies, camelids, Dabs, tetravalent antibodies, intradiabodies (e.g., Jendreyko et al. 2003. J. Biol. Chem. 278:47813), fusion proteins (e.g., antibody cytokine fusion proteins, proteins fused to at least a portion of an Fc receptor), and bispecific antibodies. Other modified antibodies are described, for example in U.S. Pat. No. 4,745,055; EP 256,654; Faulkner et al., Nature 298:286 (1982); EP 120,694; EP 125,023; Morrison, J. Immun. 123:793 (1979); Kohler et al., Proc. Natl. Acad. Sci. USA 77:2197 (1980); Raso et al., Cancer Res. 41:2073 (1981); Morrison et al., Ann. Rev. Immunol. 2:239 (1984); Morrison, Science 229:1202 (1985); Morrison et al., Proc. Natl. Acad. Sci. USA 81:6851 (1984); EP 255,694; EP 266,663; and WO 88/03559. Reassorted immunoglobulin chains also are known. See, for example, U.S. Pat. No. 4,444,878; WO 88/03565; and EP 68,763 and references cited therein.

In another embodiment, the platelet targeting moiety includes an antigen binding site or region which is a diabody or an antigen binding site derived therefrom. Diabodies are dimeric, tetravalent molecules each having a polypeptide similar to scFv molecules, but usually having a short (e.g., less than 10 and preferably 1-5) amino acid residue linker connecting both variable domains, such that the $V_L$ and $V_H$ domains on the same polypeptide chain cannot interact. Instead, the $V_L$ and $V_H$ domain of one polypeptide chain interact with the $V_H$ and $V_L$ domain (respectively) on a second polypeptide chain (see, for example, WO 02/02781). In one embodiment, an immature polypeptide of the invention comprises a diabody which is operably linked to the N-terminus and/or C-terminus of at least one genetically-fused Fc region (i.e., scFc region).

Exemplary single-domain antibodies employed in the binding molecules of the invention include, for example, the Camelid heavy chain variable domain (about 118 to 136 amino acid residues) as described in Hamers-Casterman, et al., Nature 363:446-448 (1993), and Dumoulin, et al., Protein Science 11:500-515 (2002). Other exemplary single domain antibodies include single VH or VL domains, also known as Dabs® (Domantis Ltd., Cambridge, UK). Yet other single domain antibodies include shark antibodies (e.g., shark Ig-NARs). Shark Ig-NARs comprise a homodimer of one variable domain (V-NAR) and five C-like constant domains (C-NAR), wherein diversity is concentrated in an elongated CDR3 region varying from 5 to 23 residues in length. In camelid species (e.g., llamas), the heavy chain variable region, referred to as VHH, forms the entire antigen-binding domain. Methods for making single domain binding molecules are described in U.S. Pat. Nos. 6,005,079 and 6,765,087, both of which are incorporated herein by reference. Exemplary single domain antibodies comprising VHH domains include Nanobodies® (Ablynx Nev., Ghent, Belgium).

Exemplary antibodies from which binding sites can be derived for use in the binding molecules of the invention are known in the art. Antibodies known to bind to platelets can be used to derive binding sites, for example, the MB9 antibody described in US 2007/0218067 or the variable region or an scFv molecule comprising the variable region can be used as a targeting moiety in a construct of the invention.

Non-Immuoglobulin Platelet Binding Molecules

In certain other embodiments, the targeting moiety comprise one or more binding sites derived from a non-immunoglobulin binding molecule. As used herein, the term "non-immunoglobulin binding molecules" are binding molecules whose binding sites comprise a portion (e.g., a scaffold or framework) which is derived from a polypeptide other than an immunoglobulin, but which may be engineered (e.g., mutagenized) to confer a desired binding specificity.

Other examples of binding molecules comprising binding sites not derived from antibody molecules include receptor binding sites and ligand binding sites which bind to platelets.

Non-immunoglobulin binding molecules may be identified by selection or isolation of a target-binding variant from a library of binding molecules having artificially diversified binding sites. Diversified libraries can be generated using completely random approaches (e.g., error-prone PCR, exon shuffling, or directed evolution) or aided by art-recognized design strategies. For example, amino acid positions that are usually involved when the binding site interacts with its cognate target molecule can be randomized by insertion of degenerate codons, trinucleotides, random peptides, or entire loops at corresponding positions within the nucleic acid which encodes the binding site (see e.g., U.S. Pub. No. 20040132028). The location of the amino acid positions can be identified by investigation of the crystal structure of the binding site in complex with the target molecule. Candidate positions for randomization include loops, flat surfaces, helices, and binding cavities of the binding site. In certain embodiments, amino acids within the binding site that are likely candidates for diversification can be identified using techniques known in the art. Following randomization, the diversified library may then be subjected to a selection or screening procedure to obtain binding molecules with the desired binding characteristics, e.g. specific binding platelets using methods known in the art. Selection can be achieved by art-recognized methods such as phage display, yeast display, or ribosome display. In one embodiment, molecules known in the art to bind to platelets may be employed in the constructs of the invention. For example, peptides which bind to GPIba as described in the art (e.g., PS4, 0S1, or 0S2) may be used (Benard et al. 2008. *Biochemistry* 47:4674-4682).

In one example, the targeting moieties is linked to an Fc moiety.

Biological Activity

In various embodiments, the compounds and conjugates of the present disclosure have pro-coagulant activity. It will be appreciated that different assays are available to measure pro-coagulant activity. In one example, the conjugate has pro-coagulant activity when it shows activity in at least one of: a Fxa generation assay, a thrombin generation assay (TGA), and a rotational thromboelastometry (ROTEM) assay, which are described herein, e.g., in Examples 2, 3, and 4, respectively.

A compound or conjugate of the present disclosure may promote coagulation in plasma depleted of FV, FVII, FVIII, FIX, FX, FXI, or vWF. In one example, the compound or conjugate of the present disclosure promotes thrombin generation and/or fibrin deposition in plasma in which FVIII is depleted or absent. This type of activity is referred to as coagulation FVIII activity. Where the plasma is from an individual lacking FVIII or having reduced levels of FVIII, the activity is typically referred to as FVIII equivalent activity. Where the plasma contains inhibitors against FVIII, the activity is typically referred to as FVIII inhibitor bypassing equivalent activity. Other pro-coagulant activities include FV activity, FVII activity, FX activity and FXI activity.

Individual compounds and conjugates can vary in their relative efficacy between different types of assay. Therefore, even if a compound or conjugate appears to have a low efficacy in a particular assay, it may nevertheless possess a suitably high level of pro-coagulant activity in another assay.

Other suitable assays useful to determine pro-coagulant activity include those disclosed, e.g., in Patent Application Publication U.S. 2010/0022445 to Scheiflinger and Dockal, which is incorporated herein by reference in its entirety.

In one example according to any of the above embodiments, the compound of the present disclosure has an $EC_{50}$ of about 20 µM or less, e.g., of about 10 µM or less, or about 5 µM or less in a Factor Xa (FXa) generation assay measuring conversion of Factor X (FX) to FXa. In one example, the compound has an $EC_{50}$ in the FXa generation assay of about 4 µM or less, of about 3 µM or less, about 2 µM or less, or about 1 µM or less. In another example, the compound has an $EC_{50}$ in the FXa generation assay of about 900 nM or less, about 800 nM or less, about 700 nM or less, about 600 nM or less, about 500 nM or less, about 400 nM or less, about 300 nM or less, or of about 200 nM or less. An exemplary FXa generation assay useful to determine the $EC_{50}$ of a compound of the present disclosure is described in Example 2 of this application.

In another example, the compound of the present disclosure increases the catalytic activity (e.g., increases the $k_{cat}$) of a blood coagulation factor, such as FIXa or FVIIa, e.g., when compared to a reference catalytic activity measured in the absence of the compound, e.g., by at least 2-fold. In one example according to any of the above embodiments, the compound of the present disclosure increases the catalytic activity (e.g., increases the $k_{cat}$) of a blood coagulation factor (e.g., FIXa or FIVIIa) in vitro (e.g., in a suitable in vitro assay system, such as a FXa generation assay), e.g., by at least 2-fold. In another example, the compound of the present disclosure increases the catalytic activity (e.g., increases the $k_{cat}$) of a blood coagulation factor (e.g., FIXa or FVIIa) in vivo, e.g., by at least 2-fold.

In various embodiments, compounds of the present disclosure lower the $K_M$ and increase the $k_{cat}$ of hFIXa or hFVIIa. In one example according to any of the above embodiments, the compound of the present disclosure increases the catalytic activity of FIXa or FVIIa by at least 2-fold at a compound concentration from about 1 nM to about 1 mM, from about 10 nM to about 500 µM, from about 50 nM to about 100 µM, from about 100 nM to about 50 µM, from about 200 nM to about 40 µM, from about 300 nM to about 30 µM, or from about 400 nM to about 20 µM. In another example, the compound of the present disclosure increases the catalytic activity of the FIXa or FVIIa by at least 2-fold at a concentration from about 500 nM to about 20 µM, or from about 1 µM to about 20 µM, or from about 2 µM to about 20 µM, or from about 4 µM to about 20 µM, or from about 5 µM to about 10 µM. In another example, the compound of the present disclosure increases the catalytic activity of the FIXa or FVIIa by at least 2-fold at a concentration of 100 µM or less, e.g., 50 µM or less, 40 µM or less, 30 µM or less, 20 µM or less, 15 µM or less, 10 µM or less, or 5 µM or less.

In one example according to any of the above embodiments, the compound is used in vitro and is present in the assay mixture at a concentration of from about 0.1 µM to about 100 µM, from about 1 µM to about 100 µM, from about 1 µM to about 50 µM, from about 1 µM to about 20 µM, from 1 µM to about 10 µM, from 5 µM to about 20 µM, or from about 5 µM to about 10 µM.

In one example according to any of the above embodiments, the compound of the present disclosure increases the catalytic activity (e.g., increases the $k_{cat}$) of FIXa (e.g., at a concentration of about 5 µM or less, or at a concentration of about 1 µM or less) measured for the conversion of FX to FXa (e.g., in a suitable FXa generation assay) when compared to a reference catalytic activity (e.g., reference $k_{cat}$) of the FIXa measured in the absence of the compound.

In another example according to any of the above embodiments, the compound of the present disclosure increases the catalytic activity (e.g., increases the $k_{cat}$) of FVIIa (e.g., at a concentration of about 5 µM or less, or at a concentration of about 1 µM or less) measured for the conversion of FX to FXa (e.g., in a suitable FXa generation assay) when compared to a reference catalytic activity (e.g., reference $k_{cat}$) of the FVIIa measured in the absence of the compound.

In other embodiments, the compound of the present disclosure increases the catalytic activity (e.g., increases the $k_{cat}$) of a blood coagulation factor selected from FXa (e.g., for the conversion of pro-thrombin to thrombin), and thrombin (e.g., for a conversion selected from: FVIII to fibrinogen to fibrin, FV to FVa, protein C to active protein C, FXI to FXIa, and FXIII to FXIIIa).

In another example, the compound of the present disclosure increases the catalytic activity of at least one blood coagulation factor selected from FIXa, FXa, FVIIa and thrombin. In another example, the compound of the present disclosure increases the catalytic activity of at least one blood coagulation factor selected from FIXa and FVIIa. In yet another example according to any of the above embodiments, the compound of the present disclosure increases the catalytic activity of at least two different blood coagulation factors selected from FIXa, FXa, FVIIa, and thrombin. In yet another example according to any of the above embodiments, the compound of the present disclosure increases the catalytic activity of FIXa as well as FVIIa.

In other embodiments, the compound of the present disclosure increases the catalytic activity of FIXa and/or FVIIa, e.g., as measured using a FXa generation assay, but does not substantially increase the catalytic activity of FXa (e.g., as measured using a thrombin generation assay). For example, the inventors have discovered that compound 5 does not significantly affect the activity of FXa (e.g., towards a chromogenic or macromolecular substrate when using a thrombin generation assay, e.g., a TGA with purified components, e.g., as described in Example 3). The inventors have further discovered that compound 5 does not significantly increase the activity of the prothrombinase complex (FXa/FVa) when using a thrombin generation assay, e.g., a TGA with purified components, e.g., as described in Example 3b).

In other embodiments, the compound of the present disclosure increases the catalytic activity of FIXa and/or FVIIa, e.g., as measured using a FXa generation assay, but does not substantially increase the catalytic activities of FXa (e.g., as measured using a thrombin generation assay), and does not significantly increase the catalytic activity of thrombin (e.g., as measured using a fibrinogen cleavage assay). For example, the inventors have discovered that compound 5 does not substantially affect the amidolyfic activity of alpha-thrombin (see, e.g., Example 12).

In other examples according to any of the above embodiments, the compound of the present disclosure increases the catalytic activity ($k_{cat}$) of a blood coagulation factor (e.g., FIXa or FVIIa) by at least about 5 fold, at least about 10 fold, at least about 20 fold, at least about 30 fold, at least about 40 fold, at least about 50 fold, at least about 60 fold, at least about 70 fold, at least about 80 fold, at least about 90 fold, or at least about 100 fold. In another example, the compound increases the catalytic activity ($k_{cat}$) of the blood coagulation factor (e.g., FIXa or FVIIa) by at least about 120 fold, at least about 140 fold, at least about 160 fold, at least about 180 fold, or at least about 200 fold. In another example, compound increases the catalytic activity ($k_{cat}$) of the blood coagulation factor (e.g., FIXa or FVIIa) by at least about 250 fold, at least about 300 fold, at least about 350 fold, at least about 400 fold, at least about 450 fold, or at least about 500 fold.

In one example according to any of the above embodiments, the compound is present at a concentration sufficient to cause the specified increase in catalytic activity. In one example according to any of the above embodiments, the compound is present at a concentration of from about 0.1 µM to about 100 µM, from about 1 µM to about 100 µM, from about 1 µM to about 50 µM, from about 1 µM to about 20 µM, from 1 µM to about 10 µM, from 5 µM to about 20 µM, or from about 5 µM to about 10 µM to cause any of the above specified increase in catalytic activity. In another example according to any of the above embodiments, the compound is present at a concentration below about 100 nM to to cause any of the above specified increase in catalytic activity.

Exemplary FXa generation assays useful to measure the catalytic activities of either FIXa or FVIIa in the presence or absence of a compound of the present disclosure are described in Example 2 of this application.

In another example according to any of the above embodiments, the compound of the present disclosure is capable of reducing clotting time in a suitable coagulation assay, e.g., as measured in an activated partial thromboplastin time (aPTT) assay, a modified activated partial thromboplastin time (aPTT*) assay or a rotational thromboelastometry (ROTEM) assay when compared to a reference clotting time measured in the absence of the compound.

In one example according to any of the above embodiments, the compound is present at a concentration sufficient to reduce the clotting time (e.g., by at least 10% when compared to the reference clotting time). In one example according to any of the above embodiments, the compound reduces clotting time by at least 10% at a concentration of from about 0.1 µM to about 100 µM, from about 1 µM to about 100 µM , from about 1 µM to about 50 µM , from about 1 µM to about 20 µM, from 1 µM to about 10 µM, from 5 µM to about 20 µM, or from about 5 µM to about 10 µM. In another example according to any of the above embodiments, the compound of the present disclosure reduces clotting time by at least 10% at a concentration from about 1 nM to about 1 mM, from about 10 nM to about 500 µM, from about 50 nM to about 100 µM, from about 100 nM to about 50 µM, from about 200 nM to about 40 µM, from about 300 nM to about 30 µM, or from about 400 nM to about 20 µM. In another example, the compound of the present disclosure reduces the clotting time by at least 10% at a concentration from about 500 nM to about 20 µM, or from about 1 µM to about 20 µM, or from about 2 µM to about 20 µM, or from about 4 µM to about 20 µM, or from about 5 µM to about 10 µM. In another example, the compound of the present disclosure reduces clotting time by at least 10% at a concentration of 100 µM or less, e.g., 50 µM or less, 40 µM or less, 30 µM or less, 20 µM or less, 15 µM or less, 10 µM or less, or 5 µM or less. In one example according to any of the above embodiments, the compound is tested in vitro and is present in the assay mixture at a concentration of from about 0.1 µM to about 100 µM, from about 1 µM to about 100 µM, from about 1 µM to about 50 µM, from about 1 µM to about 20 µM, from 1 µM to about 10 µM, from 5 µM to about 20 µM, or from about 5 µM to about 10 µM.

For example, in a suitable assay, a 10% reduction of a 10-minute reference clotting time (measured in the absence of the compound), means that clotting occurs after 9 minutes in the presence of the compound. Exemplary assays useful to measure clotting time are known in the art. Suitable assays are described in Example 9 (aPPT assay) and Example 4 (ROTEM assay).

In one example according to any of the above embodiments, the compound reduces the clotting time by more than 10%, e.g., by at least about 20%, at least about 30%, at least about 40%, at least about 50%, at least about 60%, at least about 70%, at least about 80%, or at least about 90% compared to a reference clotting time measured in the absence of the compound.

In one embodiment the clotting time measured for a compound of the present disclosure (e.g., in a ROTEM assay) is calcium-dependent. This calcium-dependency of the clotting time is comparable to the calcium-dependency measured for FVIII. The procoagulant activities of compounds of the present disclosure were examined for calcium dependence using a Rotem assay, e.g., as described in Example 4. For example, compound 5 at 2.5 and 5 µM and 0.1 IU/mL of FVIII were tested at 7 different calcium concentrations ranging from 0 to about 16 mM calcium. Similar to the FVIII control, the procoagulant effect observed for compound 5 was sensitive to the calcium concentration (i.e., the clotting time measured for a particular compound concentration was higher at elevated calcium concentrations).

In another example according to any of the above embodiments, the compound of the present disclosure reduces clotting time or increases the α-angle (e.g., in a dose-dependent manner) in a ROTEM assay using blood coagulation factor-deficient plasma (e.g., human or canine coagulation factor-deficient plasma) when compared to a reference clotting time or a reference α-angle measured in the absence of the compound.

In one example, the compound of the present disclosure reduces clotting time (e.g., in a dose-dependent manner) in a ROTEM assay involving FVIII-deficient plasma (e.g., human or canine FVIII deficient plasma). An exemplary ROTEM assay useful to measure the clotting time and the α-angle is described in Example 4 of this application.

In another example, the compound of the present disclosure reduces the clotting time (e.g., in a dose-dependent manner) or increases the α-angle in a ROTEM assay involving FIX-deficient plasma (e.g., human or canine FIX-deficient plasma). The inventors have discovered that the compounds of the present disclosure reduce clotting time in FIX-deficient plasma even in the presence of anti-FIX antibodies (e.g., anti-FIX pAb). The addition of anti-FIX antibodies to FIX-deficient plasma removes residual FIX activity from the plasma sample. These results indicate that the compounds of the present disclosure can reduce clotting time or increase the α-angle employing a mechanism other than by increasing the catalytic activity of FIXa (e.g., via activation of the extrinsic pathway of the blood coagulation cascade).

In one example, the compounds of the present disclosure reduce clotting time or increase α-angle by increasing the catalytic activity of FVIIa. For example, the inventors have discovered that the clotting time measured in the presence of a current compound in a ROTEM assay employing FVIII-deficient plasma is significantly increased (i.e., clot formation is significantly reduced) in the presence of an anti-FVII antibody (e.g., anti-FVII pAb). Likewise the α-angle measured in the presence of a current compound is significantly reduced when anti-FVII antibody is added to the assay mixture. These results indicate that the current compounds can induce clotting by modulating FVIIa catalytic activity (e.g., in addition to increasing the catalytic activity of FIXa).

Additive Effect with FVIII

In another example according to any of the above embodiments, the compound of the present disclosure does not compete with FVIII, but instead shows at least additive (or even synergistic) activity with FVIII in at least one suitable assay. Exemplary assays are selected from thrombin generation assays (e.g., those described herein) and ROTEM assays (e.g., those described herein). In one example, the compound shows additive activity with FVIII (i.e., the compound's activity is not inhibited or reduced by the presence of FVIII; or the activity of FVIII is not inhibited by the presence of the compound) when the FVIII is present at a low concentration (e.g., at physiological concentration). In one example, the FVIII is present at a concentration from about 0.005 U/mL to about 1.0 U/mL, or from about 0.01 U/mL to about 0.5 U/mL, or from about 0.01 U/mL to about 0.3 U/mL, or from about 0.01 U/mL to about 0.2 U/mL or from about 0.04 U/mL to about 0.2 U/mL).

In one example, the compound shows additive activity with FVIII in a thrombin generation assay when FVIII is present at a concentration of about 0.01 U/mL to about 0.5 U/mL, or from about 0.05 U/mL to about 0.2 U/mL. In another example, the compound shows additive activity with FVIII in a ROTEM assay when FVIII is present at a concentration of about 0.01 U/mL to about 0.5 U/mL, or from about 0.05 U/mL to about 0.1 U/mL.

In one example according to any of the above embodiments, the compound is present at a concentration sufficient to have additive activity with FVIII.

In another example according to any of the above embodiments, the compound of the present disclosure is present (e.g., in the assay mixture used to measure the additive effect with FVIII) at a concentration from about 1 nM to about 1 mM, from about 10 nM to about 500 µM, from about 50 nM to about 100 µM, from about 100 nM to about 50 µM, from about 200 nM to about 40 µM, from about 300 nM to about 30 µM, or from about 400 nM to about 20 µM. In another example, the compound of the present disclosure is present at a concentration from about 500 nM to about 20 µM, or from about 1 µM to about 20 µM, or from about 2 µM to about 20 µM, or from about 4 µM to about 20 µM, or from about 2 µM to about 10 µM. In another example, the compound of the present disclosure is present at a concentration of 100 µM or less, e.g., 50 µM or less, 40 µM or less, 30 µM or less, 20 µM or less, 15 µM or less, 10 µM or less, or 5 µM or less. In one example according to any of the above embodiments, the compound is tested in vitro and is present in the assay mixture at a concentration of from about 0.1 µM to about 100 µM, from about 1 µM to about 100 µM, from about 1 µM to about 50 µM, from about 1 µM to about 20 µM, from 1 µM to about 10 µM, from 5 µM to about 20 µM, or from about 5 µM to about 10 µM.

An exemplary thrombin generation assay or ROTE41 assay useful to measure the additive (or synergistic) activity between the compound and FVIII, are described in Examples 3 and 4, respectively of this application.

Additive Effect with FIX

In other embodiments, the compound of the present disclosure does not compete with FIX, but instead shows at least additive activity with FIX or FVIIa in at least one suitable assay. Exemplary assays are selected from thrombin generation assays and ROTEM assays (e.g., those described herein in Examples 3 and 4).

In one example, the compound shows additive activity with FIX (i.e., the compound's activity is not inhibited or reduced by the presence of FIX; or the activity of FIX is not inhibited by the presence of the compound) when the FIX is present at a low concentration (e.g., at physiological concentration). In one example, the FIX is present at a concentration from about 0.05 U/ml to about 2.0 U/mL, or from about 0.1 U/mL to about 1.0 U/mL, or from about 0.1 U/mL to about 0.3 U/mL, or about 0.25 U/mL. In one example, the FIX is FIX-Fc.

In one example, the compound shows additive activity with FIX (e.g., FIX-Fc) in a thrombin generation assay, e.g., when the FIX is present at a concentration of about 0.1 U/mL to about 0.3 U/mL, or about 0.25 U/mL. In another example, the compound shows additive activity with FIX in a ROTEM assay (e.g., using FIX-deficient plasma), e.g. when FIX is present at a concentration of about 0.1 U/mL to about 0.3 U/mL, or about 0.25 U/mL (see, e.g., Example 12).

Additive Effect with FVIIa

In other embodiments, the compound of the present disclosure does not compete with FVIIa, but instead shows at least additive activity with FVIIa in at least one suitable assay. Exemplary assays are selected from thrombin generation assays and ROTEM assays (e.g., those described herein in Examples 3 and 4).

In one example, the compound shows additive activity with FVIIa (i.e., the compound's activity is not inhibited or reduced by the presence of FIX; or the activity of FVIIa is not inhibited by the presence of the compound), e.g., when the FVIIa is present at a low concentration (e.g., at physiological concentration). In one example, the FVIIa is present in the assay mixture at a concentration from about 1 U/mL to about 50 U/mL, or from about 1 U/mL to about 30 U/mL, or from about 5 U/mL to about 25 U/mL, or from about 10 U/mL to about 22 U/mL. In one example, the FVIIa is linked to Fc.

In one example, the compound shows additive activity with FVIIa (e.g., FVIIa-Fc) in a thrombin generation assay, e.g., when the FVIIa is present at a concentration of about 10 U/mL to about 20 U/mL. In another example, the compound shows additive activity with FVIIa in a ROTEM assay (e.g., using FVIII-deficient plasma), e.g. when FVIIa is present at a concentration of about 10 U/mL to about 20 U/mL (see, e.g., Example 12).

In another example according to any of the above embodiments, the compound of the present disclosure is present (e.g., in the assay mixture used to measure the additive effect with FIX or FVIIa) at a concentration from about 1 nM to about 1 mM, from about 10 nM to about 500 µM, from about 50 nM to about 100 µM, from about 100 nM to about 50 µM, from about 200 nM to about 40 µM, from about 300 nM to about 30 µM, or from about 400 nM to about 20 µM. In another example, the compound of the present disclosure is present at a concentration from about 500 nM to about 20 µM, or from about 1 µM to about 20 µM, or from about 2 µM to about 20 µM, or from about 4 µM to about 20 µM, or from about 2 µM to about 10 µM. In another example, the compound of the present disclosure is present at a concentration of 100 µM or less, e.g., 50 µM or less, 40 µM or less, 30 µM or less, 20 µM or less, 15 µM or less, 10 µM or less, or 5 µM or less. In one example according to any of the above embodiments, the compound is tested in vitro and is present in the assay mixture at a concentration of from about 0.1 µM to about 100 µM, from about 1 µM to about 100 µM, from about 1 µM to about 50 µM, from about 1 µM to about 20 µM, from about 1 µM to about 10 µM, from about 1 µM to about 5 µM, from about 1 µM to about 3 µM, or about 2.5 µM. In one example according to any of the above embodiments, the compound is present at a concentration sufficient to have additive activity with FIX. In one example according to any of the above embodiments, the compound is present at a concentration sufficient to have additive activity with FVIIa.

Because the compounds of the present disclosure do not compete with FVIII, FIX and FVII, e.g., with respect to their ability to reduce clotting time or enhance the formation of thrombin, they are suitable to be used in co-therapy with either of these clotting factors. In one example, the compound is used in a co-therapy with FVIII. In another example, the compound is used in a co-therapy with FIX (e.g., FIX-Fc). In yet another example, the compound is used in co-therapy with FVIIa (e.g., FVIIa-Fc).

Replacement of FVIII

In various embodiments, the compound of the present disclosure induces the formation of thrombin, e.g., in a suitable thrombin generation assay in the absence (or the presence of very low levels) of FVIII. In one example, the compound of the present disclosure induces the formation of thrombin in a thrombin generation assay utilizing FVIII-deficient plasma. In another example, the compound of the present disclosure induces the formation of thrombin in a thrombin generation assay (e.g., utilizing FVIII-deficient plasma) with a thrombin-generation activity comparable to a recombinant FVIII (rFVIII) standard. In one example, the compound of the present disclosure at an assay concentration of about 20 µM exhibits at least as much thrombin-generation activity as about 0.1 U/mL of rFVIII. In another example, the compound of the present disclosure at an assay concentration of about 20 µM exhibits at least as much thrombin-generation activity as about 0.25 U/mL of rFVIII. In yet another example, the compound of the present disclosure at an assay concentration of about 20 µM exhibits at least as much thrombin-generation activity as about 0.5 U/mL of rFVIII. In a further example, the compound of the present disclosure at an assay concentration of about 20 µM exhibits as much thrombin-generation activity as about 0.5 U/mL of rFVIII. In another example, the compound of the present disclosure at an assay concentration of about 20 µM exhibits at least as much thrombin-generation activity as about 0.5 U/mL of rFVIII. A suitable thrombin-generation assay (TGA) to measure the above activities is described in Example 3.

Because the compounds of the present disclosure enhance thrombin formation in the absence of FVIII, they are suitable to be used instead of a FVIII therapy or in conjunction with FVIII therapy.

FIXa and FVIIa Binding

The compounds of the present disclosure can bind to soluble FIXa or FVIIa, e.g., with a dissociation constant ($K_D$) of about 300 nM or less, e.g., from about 80 nM to about 300 nM, or from about 100 nM to about 250 nM (see, e.g., Example 8).

Unexpectedly, the inventors have found that certain compounds of the present disclosure activate FIXa by interacting with a region of the polypeptide sequence near $Tyr_{177}$ (which can also be referred to as the 170 loop) ($Tyr_{177}$: FIXa chymotrypsin numbering; corresponds to $Tyr_{345}$ when using FIX numbering). Since this region of FIXa is known to interact with FVIIIa, the compounds of the present disclosure may activate FIXa similarly to FVIIII by moving the loop. In one example according to any of the above embodiments, the compound of the present disclosure is capable of interacting with (e.g., binding to) a peptide, which includes the amino acid sequence:

MFCAG (SEQ ID NO: 1).

In another example, the compound of the present disclosure is capable of interacting with (e.g., binding to) a peptide, which includes the amino acid sequence:

YNNMFCAGFHE (SEQ ID NO: 2).

In another example, the compound of the present disclosure is capable of interacting with (e.g., binding to) a peptide, which includes the amino acid sequence:

RSTKFTIYNNMFCAGFHEGGRDSCQG (SEQ ID NO: 3), or an amino acid sequence having at least 20/26, at least 21/26, at least 22/26, at least 23/26, at least 24/26, or at least 25/26 homology with SEQ ID NO: 3 (e.g., at least 20, at least 21, at least 22, at least 23, at least 24, or at least 25 of the 26 amino acids are those as shown in SEQ ID NO: 3; or not more than 6, not more than 5, not more than 4, not more than 3, not more than 2, or not more than 1 of the 26 amino acids of SEQ ID NO: 3 are replaced by another amino acid).

In another example, the compound of the present disclosure is capable of interacting with a FIXa protein at a region corresponding to amino acid sequence:

MFCAG. (SEQ ID NO: 1)

In another example, the compound of the present disclosure is capable of interacting with a FIXa protein at a region corresponding to amino acid sequence:

YNNMFCAGFHE. (SEQ ID NO: 2)

In another example, the compound of the present disclosure is capable of interacting with a FIXa protein at a region corresponding to amino acid sequence:

RSTKFTIYNNMFCAGFHEGGRDSCQG, (SEQ ID NO: 3)

or an amino acid sequence having at least 20/26, at least 21/26, at least 22/26, at least 23/26, at least 24/26, or at least 25/26 homology with SEQ ID NO: 3 (e.g., at least 20, at least 21, at least 22, at least 23, at least 24, or at least 25 of the 26 amino acids are those as shown in SEQ ID NO: 3; or not more than 6, not more than 5, not more than 4, not more than 3, not more than 2, or not more than 1 of the 26 amino acids of SEQ ID NO: 3 are replaced by another amino acid).

There is a strong homology between proteases in the coagulation cascade, e.g., FIX, FX, prothrombin, FVII, and protein C. One amino acid region that showed changes in HDX levels (amino acids FCAG) in FIXa is conserved across these peptides indicating that the compound of the invention can potentially interact with at least one of these blood coagulation factors other than FIXa. For example, the compounds of the present disclosure can potentially increase the catalytic activity of e.g. FVIIa, FXa or thrombin in addition to FIXa. For example, given the structural similarities between FIXa and FVIIa, the pro-coagulant compounds of the present disclosure may employ a similar mechanism for increasing the catalytic activities of FVIIa.

In one example, the compound of the present disclosure has pro-coagulant activity. It will be appreciated that different assays are available to determine pro-coagulant activity. In one example, the compound of the present disclosure has pro-coagulant activity when it shows activity in at least one of: an activated partial thromboplastin time (aPTT) assay, a modified activated partial thromboplastin time (aPTT*) assay, a thrombin generation assay (TGA), and a rotational thromboelastometry (ROTEM) assay, which are described herein, e.g., in Examples 9, 3, and 4, respectively.

A compound of the present disclosure may promote coagulation in plasma depleted of FV, FVII, FVIII, FX, FXI, or vWF. In one example, a compound of the present disclosure promotes thrombin generation and/or fibrin deposition in plasma in which FVIII is depleted or absent. This type of activity is referred to as coagulation FVIII activity. Where the plasma is from an individual lacking FVIII or having reduced levels of FVIII, the activity is typically referred to as FVIII equivalent activity. Where the plasma contains inhibitors against FVIII, the activity is typically referred to as FVIII inhibitor bypassing equivalent activity. Other procoagulant activities include FV activity, FVII activity, FX activity and FXI activity.

Individual compounds can vary in their relative efficacy between different types of assay. Therefore, even if a compound appears to have a low efficacy in a particular assay, it may nevertheless possess a suitably high level of procoagulant activity in another assay.

Other suitable assays useful to determine pro-coagulant activity include those disclosed, e.g., in Patent Application Publication U.S. 2010/0022445 to Scheiflinger and Dockal, which is incorporated herein by reference in its entirety.

In one example according to any of the above embodiments, certain compounds of the present disclosure (e.g., a compound listed in Table 1) inhibit heparin catalyzed (heparin accelerated) FIXa-AT complex formation when compared to FIXa-AT complex formation in the absence of the compound.

"FIXa-AT" is a covalent and equimolar complex formed between FIXa and antithrombin (AT). Antithrombin belongs to the serpin family of inhibitors and is a known physiological inhibitor of coagulation proteases, e.g. FIXa. On the surface of intact endothelium, AT interacts with heparin sulfate and its rate of protease inhibition accelerates. (see, e.g., Johnson, D. J. D. et al, *PNAS* 2010, 107, 645-650; Yang L. et al, *Journal of Biological Chemistry*, 2002, 277, 50756-50760).

FIXa-AT complex formation can be measured, e.g., as described herein in Example 11. In one embodiment FIXa-AT complex formation is measured in the presence of heparin at a concentration of from about 10 nM to about 200 nM. In another embodiment FIXa-AT complex formation is measured in the presence of heparin at a concentration of from about 50 nM to about 150 nM. In one embodiment FIXa-AT complex formation is measured in the presence of about 10 nM heparin. In another embodiment FIXa-AT complex formation is measured in the presence of about 50 nM heparin. In another embodiment FIXa-AT complex formation is measured in the presence of about 100 nM heparin. In yet another embodiment FIXa-AT complex formation is measured in the presence of about 150 nM heparin.

In another embodiment, FIXa-AT complex formation is measured at a compound concentration of from about 0.1 µM to about 100 µM. In another embodiment. FIXa-AT complex formation is measured at a compound concentration of from about 0.5 µM to about 50 µM. In another embodiment, FIXa-AT complex formation is measured at a compound concentration of from about 1 µM to about 20 µM. In another embodiment, FIXa-AT complex formation is measured at a compound concentration of from about 1 µM to about 10 µM. In another embodiment, FIXa-AT complex formation is measured at a compound concentration of about 0.1 µM, about 0.5 µM, about 1 µM, about 2 µM, about 3 µM, about 4 µM, about 5 µM, about 6 µM, about 7 µM, about 8 µM, about 9 µM, about 10 µM, about 12 µM, about 14 µM, about 16 µM, about 18 µM, or about 20 µM.

In another embodiment FIXa-AT complex formation is measured in the presence of heparin at a concentration of from about 10 nM to about 200 nM and at a compound concentration of from about 0.1 µM to about 100 µM. In another embodiment FIXa-AT complex formation is measured in the presence of heparin at a concentration of from about 50 nM to about 150 nM and at a compound concentration of from about 0.5 µM to about 50 µM. In another embodiment FIXa-AT complex formation is measured in the presence of heparin at a concentration of from about 50 nM to about 150 nM and at a compound concentration of from about 1 µM to about 20 µM.

In another embodiment FIXa-AT complex formation is measured in the presence of heparin at a concentration of about 100 nM and at a compound concentration of about 1 µM. In another embodiment FIXa-AT complex formation is measured in the presence of about 100 nM heparin and at a compound concentration of about 2 µM. In another embodiment FIXa-AT complex formation is measured in the presence of about 100 nM heparin and at a compound concentration of about 3 µM. In another embodiment FIXa-AT complex formation is measured in the presence of about 100 nM heparin and at a compound concentration of about 4 µM. In another embodiment FIXa-AT complex formation is measured in the presence of about 100 nM heparin and at a compound concentration of about 5 µM. In another embodiment FIXa-AT complex formation is measured in the presence of about 100 nM heparin and at a compound concentration of about 6 µM. In another embodiment FIXa-AT complex formation is measured in the presence of about 100 nM heparin and at a compound concentration of about 7 µM. In another embodiment FIXa-AT complex formation is measured in the presence of about 100 nM heparin and at a compound concentration of about 8 µM. In another embodiment FIXa-AT complex formation is measured in the presence of about 100 nM heparin and at a compound concentration of about 9 µM. In another embodiment FIXa-AT complex formation is measured in the presence of about 100 nM heparin and at a compound concentration of about 10 µM.

In one example according to any one of the above embodiments, the FIXa-AT complex formation measured for a compound of the present disclosure is inhibited by between about 5% and about 90% compared to the complex formation in the absence of the compound. In one example according to any one of the above embodiments, the FIXa-AT complex formation measured for a compound of the present disclosure is inhibited by between about 10% and about 80% compared to the complex formation in the absence of the compound. In one example according to any one of the above embodiments, the FIXa-AT complex formation measured for a compound of the present disclosure is inhibited by between about 20% and about 80% compared to the complex formation in the absence of the compound.

In another example according to any one of the above embodiments, the FIXa-AT complex formation measured for a compound of the present disclosure is inhibited by at least about 5% when compared to the complex formation in the absence of the compound. In another example according to any one of the above embodiments, the FIXa-AT complex formation is inhibited by at least about 10%. In another example according to any one of the above embodiments, the FIXa-AT complex formation is inhibited by at least about 20%. In yet another example according to any one of the above embodiments, the FIXa-AT complex formation is inhibited by at least about 30%. In another example according to any one of the above embodiments, the FIXa-AT complex formation is inhibited by at least about 40%. In another example according to any one of the above embodiments, the FIXa-AT complex formation is inhibited by at least about 50%. In another example according to any one of the above embodiments, the FIXa-AT complex formation is inhibited by at least about 60%. In another example according to any one of the above embodiments, the FIXa-AT complex formation is inhibited by at least about 70%. In another example according to any one of the above embodiments, the FIXa-AT complex formation is inhibited by at least about 80%.

In one embodiment, the compounds of the present disclosure can compete with heparin forr binding to FIXa, and can thus be viewed as heparin antagonists.

In one embodiment the compounds of the present disclosure antagonize the delay in plasma clotting caused by heparin (e.g., low molecular weight heparin). In another example, the compounds of the present disclosure can be used as antidotes for hemorrhagic complications associated with heparin therapy. In another example, the compounds of the present disclosure can be used as antidotes for hemorrhagic complications associated with antithrombotic therapies (e.g., SH and LMWH antithrombotic therapies).

In one example, the invention provides a method of providing an antidote to heparin (e.g., low molecular weight heparin) overdose in a subject in need thereof, the method comprising administering to the subject an effective amount of a compound of the present disclosure, or an acceptable salt or solvate thereof, or a pharmaceutical composition comprising a compound of the present disclosure.

Assays for determining the heparin-neutralizing activity of a polymer or oligomer are either described herein or are well known to those of skill in the art. See, e.g., Kandrotas, R. J., *Clin. Pharmacokinet.* 22:359-374 (1992)), Diness, V. O., and Østergaard, P. B., *Thromb. Haemost.* 56:318-322 (1986)), and references cited therein, Wong, P. C., et al., *J. Pharm. Exp. Therap.* 292:351-357 (2000), Ryn-McKenna, J. V., et al., *Thromb. Haemost.* 63:271-274 (1990), and Wakefield, T. W., et al., *J. Surg. Res.* 63:280-286 (1996).

Effect on Platelets

In one embodiment, the compounds of the present disclosure do not impact platelet function and do not induce platelet aggregation as shown, e.g., in Example 13.

Animal Model

In one example, a compound of the present disclosure can at least partially compensate for the absence of biologically active FVIII when administered in an animal model of severe human hemophilia A. For example, a compound can be active in controlling bleeding in FVIII deficient mice or dogs.

A exemplary assay to test the ability of a compound or conjugate to control bleeding is the tail clip assay (see, e.g., Pan J, et al., *Blood* 2009;114:2802-2811). Compounds or conjugates are administered to mice in a suitable vehicle, typically i.v., i.p. or s.c. Different doses of each peptide or peptide derivative may be administered to different groups of mice to determine dose-dependency. In one example, mice administered the compound or conjugate have a blood loss in the tail clip assay at 62 minutes from tail clip of no more than 70% of the blood loss of mice administered the vehicle alone, more preferably no more than 60%, and most preferably no more than 50% of the blood loss of mice administered the vehicle alone.

In another example, survival of mice administered the compound or conjugate in the above assay is at least 40%, more preferably at least 60% and most preferably at least 80% at 2 hours after tail clip. Preferably, survival of mice administered the compound or conjugate in the tail clip assay is at least 20%, more preferably at least 30% and most preferably at least 40% at 24 hours after tail clip.

Exemplary compounds of the present disclosure and their in vitro biological activities measured using a FXa generation assay are described in Example 2.

Exemplary compounds of the present disclosure and their in vitro biological activities measured using a thrombin generation assay are described in Example 3.

In one example, the compound of the present disclosure (e.g., compound 5 or 6) has improved chemical stability in human plasma (e.g., in the presence of FIXa). For example, the compound of the present disclosure, after incubation of 30 minutes, 60 minutes, or 120 minutes in human plasma, is at least 50%, at least 70%, at least 80%, at least 90%, at least 95%, at least 98% or at least 99% stable. A stability of 100% indicates that no detectable degradation of the compound has occurred during the specified incubation time in human plasma. In one example, the compound is chemically stable (e.g., at least about 90% stable, or 100% stable) for at least about 60 min when incubated in human plasma. In another example, the compound is stable for at least about 80 min when incubated in human plasma. In yet another example, the compound is stable for at least about 100 min when incubated in human plasma. In a further example, the compound is stable for at least about 120 min. A suitable assay to determine stability in human plasma is described in Example 6.

In another example, the compound of the present disclosure has an aqueous solubility in phosphate buffered saline at pH 7.4 and 25° C. of at least about 25 µM, preferably at least about 60 µM, and most preferably at least about 100 µM.

Methods of Making the Compounds

The compounds of the present disclosure (e.g., peptides or peptide derivatives) can be produced by chemical synthesis, recombinant DNA technology, biochemical or enzymatic fragmentation of larger molecules, combinations of the foregoing or by any other method.

In one example, the method comprises forming the amino acid sequence of the compound, or a retro-, inverso- or retro-inverso variant thereof using solid-phase peptide synthesis. Exemplary methods of making the compounds of the invention are described herein in Example 1. Other methods to form peptides are known to those of skill in the art.

For example, the compounds of the present disclosure can be synthesised using solid-phase peptide synthesis as described in "*Fmoc Solid Phase Peptide Synthesis—A Practical Approach*", edited by W. C. Chan, P. D. White, Oxford University Press, New York 2000 and references therein. Temporary N-amino group protection is afforded, e.g., by a 9-fluorenylmethyloxycarbonyl (Fmoc) group. Repetitive cleavage of this highly base-labile protecting group is effected, e.g., using 20% piperidine in N,N-dimethylformamide. Side-chain functionalities may be protected as their butyl ethers (in the case of serine, threonine and tyrosine), butyl esters (in the case of glutamic acid and aspartic acid), butyloxycarbonyl derivative (in the case of lysine and histidine), trityl derivative (in the case of cysteine, asparagine and glutamine) and 4-methoxy-2,3,6-trimethylbenzenesulphonyl derivative (in the case of arginine). The solid-phase support can be based on a polydimethyl-acrylamide polymer constituted from the three monomers dimethylacrylamide (backbone-monomer), bisacryloylethylene diamine (cross linker) and acryloylsarcosine methyl ester (functionalising agent), or can be based on polyethylene glycol (PEG), such as Rink Amide resin (e.g., NovaPEG Rink Amide). The peptide-to-resin cleavable linked agent can be the acid-labile 4-hydroxymethyl-phenoxyacetic acid derivative, or in case of C-terminal amides, the Rink-amide linker. All amino acid derivatives can be added as their preformed symmetrical anhydride derivatives with the exception of asparagine and glutamine, which are added using a reversed N,N-dicyclohexyl-carbodiimide/1-hydroxybenzotriazole mediated coupling procedure. Alternatively, other peptide coupling reagents, such as O-benzotriazole-N,N,N',N'-tetramethyl-uronium-hexafluoro-phosphate (HBTU) or 2-(6-chloro-1-H-benzotriazole-1-yl)-1,1,3,3-tetramethylaminium haxafluorophosphate (HCTU) can be used (e.g., in situ). Coupling and deprotection reactions can be monitored using ninhydrin, trinitrobenzene sulphonic acid or isotin test procedures. Upon completion of synthesis, peptides are cleaved from the resin support with concomitant removal of side-chain protecting groups, e.g., by treatment with 95% trifluoroacetic acid containing about 5-50% scavenger. Scavengers commonly used are TIPS (triisopropylsilane), ethanedithiol, phenol, anisole water, and mixtures thereof. The exact choice depends on the constituent amino acids of the peptide being synthesised. For methionine containing peptides one can use, e.g., a mixture of TIPS (e.g., 2-5%) and ethanedithiol (e.g., 2-5%).

Trifluoroacetic acid can subsequently be removed by evaporation in vacuo, with subsequent trituration with diethyl ether affording the crude peptide. Any scavengers present can be removed by a simple extraction procedure which on lyophilisation of the aqueous phase affords the crude peptide free of scavengers.

Reagents for peptide synthesis are generally available, e.g., from Calbiochem-Novabiochem (UK), or EMD4Biosciences (U.S.).

Purification of the peptides may be effected by any one, or a combination of, techniques such as size exclusion chromatography, ion-exchange chromatography, affinity chromatography, differential solubility, and reverse-phase high performance liquid chromatography. Analysis of peptides may be carried out using thin layer chromatography, reverse-phase high performance liquid chromatography, mass spectroscopy (e.g., LC-MS), amino-acid analysis after acid hydrolysis and by fast atom bombardment (FAB) mass spectrometry.

SPOT-synthesis, which allows the positional addressable, chemical synthesis of peptides on continuous cellulose membranes may be also used (see, e.g., R. Frank, *Tetrahedron* (1992) 48, 9217).

The compounds of the present disclosure may also be produced by recombinant protein expression or in vitro translation systems (see, e.g., Sambrook et al., "*Molecular cloning: A laboratory manual*", 2001, 3rd edition, Cold Spring Harbor Laboratory Press, Cold Spring Harbor, N.Y.). Recombinant methods are generally preferred when the peptide is particularly large, e.g., larger than 50 amino acids, or larger than 100 amino acids.

Methods of Making the Polypeptide Conjugates

The conjugates of the present disclosure can be made recombinantly, see, e.g., procedures for FVIII-Fc expression and purification described in WO2011/069164, which is incorporated herein by reference in its entirety.

For example, the suitable expression vector or vectors are transfected or co-transfected into a suitable target cell, which will express the polypeptides. Transfection techniques known in the art include, but are not limited to, calcium phosphate precipitation (Wigler et al. (1978) *Cell* 14:725), electroporation (Neumann et al. (1982) *EMBO J* 1:841), and liposome-based reagents. A variety of host-expression vector systems may be utilized to express the proteins described herein including both prokaryotic and eukaryotic cells. These include, but are not limited to, microorganisms such as bacteria (e.g., *E. coli*) transformed with recombinant bacteriophage DNA or plasmid DNA expression vectors containing an appropriate coding sequence; yeast or filamentous fungi transformed with recombinant yeast or fungi expression vectors containing an appropriate coding sequence; insect cell systems infected with recombinant virus expression vectors (e.g., baculovirus) containing an appropriate coding sequence; plant cell systems infected with recombinant virus expression vectors (e.g., cauliflower mosaic virus or tobacco mosaic virus) or transformed with recombinant plasmid expression vectors (e.g., Ti plasmid) containing an appropriate coding sequence; or animal cell systems, including mammalian cells (e.g., HEK 293, CHO, Cos, HeLa, HKB11, and BHK cells).

In one embodiment, the host cell is a eukaryotic cell. As used herein, a eukaryotic cell refers to any animal or plant cell having a definitive nucleus. Eukaryotic cells of animals include cells of vertebrates, e.g., mammals, and cells of invertebrates, e.g., insects. Eukaryotic cells of plants specifically can include, without limitation, yeast cells. A eukaryotic cell is distinct from a prokaryotic cell, e.g., bacteria.

In certain embodiments, the eukaryotic cell is a mammalian cell. A mammalian cell is any cell derived from a mammal. Mammalian cells specifically include, but are not limited to, mammalian cell lines. In one embodiment, the mammalian cell is a human cell. In another embodiment, the mammalian cell is a HEK 293 cell, which is a human embryonic kidney cell line. HEK 293 cells are available as CRL-1533 from American Type Culture Collection, Manassas, Va., and as 293-H cells, Catalog No. 11631-017 or 293-F cells, Catalog No. 11625-019 from Invitrogen (Carlsbad, Calif.). In some embodiments, the mammalian cell is a PER.C6® cell, which is a human cell line derived from retina. PER.C6® cells are available from Crucell (Leiden, The Netherlands). In other embodiments, the mammalian cell is a Chinese hamster ovary (CHO) cell. CHO cells are available from American Type Culture Collection, Manassas, Va. (e.g., CHO-K1; CCL-61). In still other embodiments, the mammalian cell is a baby hamster kidney (BHK) cell. BHK cells are available from American Type Culture Collection, Manassas, Va. (e.g., CRL-1632). In some embodiments, the mammalian cell is a HKB11 cell, which is a hybrid cell line of a HEK293 cell and a human B cell line. Mei et al., *Mol. Biotechnol.* 34(2): 165-78 (2006).

In another example, the conjugates of the present disclosure can be made semi-recombinantly e.g., as illustrated in FIGS. 23-26 (see, e.g., U.S. Pat. No. 7,381,408 to Mezo, A. R. and Peters, R. P.; Dawson, P. E., Kent, S. B. *Ann. Rev. Biochem*, (2000) 69:923-9600; Mei, B. et. al., *Blood* (2010) 116:270-279; and U.S. Patent Application Publication US2006/0115876 to Pan, C. et. al., each of which is incorporated herein in its entirety). In one example, the polypeptide or the polypeptide construct containing a suitable amino acid moiety is made recombinantly. The pro-coagulant compound is then attached to the polypeptide or polypeptide construct via chemical ligation as decribed herein.

FIG. 23 illustrates a general method for covalently linking a peptide or peptide derivative to a FVIII-Fc, a FIX-Fc, or a FVIIa-Fc construct using a native ligation strategy (see, e.g., Mezo, A. R.; Peters, R. P., Methods for Chemically Synthesizing Immunoglobulin Chimeric Proteins. U.S. Pat. No. 7,381,408; and Dawson, P. E., Kent, S. B. Synthesis of native proteins by chemical ligation. *Ann. Rev. Biochem.* (2000) 69: 923-9600). An exemplary method includes contacting a FVIII-Fc construct (e.g., a truncated FVIII-Fc construct) having a free sulthydryl group located at the Fc portion of the construct (e.g., having an N-terminal cysteine) with a peptide or peptide derivative having a reactive group selected from a thioester moiety, a maleimide moiety and a iodoacetamide moiety, under reaction conditions sufficient to form a covalent bond between the peptide or peptide derivative and the FVIII-Fc construct. FVIII in the FVIII-Fc construct can be replaced by FIX or FVIIa, and the resulting construct can be ligated to a peptide or peptide derivative in the same way.

FIG. 24 illustrates a general method for covalently linking a peptide or peptide derivative to a FVIII-Fc construct, a FIX-Fc construct, or a FVIIa-Fc construct using a site-directed ligation strategy (see, e.g., Mei, B. et. al. Rational design of a fully active, long-acting PEGylated FVIII for hemophilia A treatment. *Blood* (2010) 116:270-279; and Pan, C. et. al. Site-directed modification of FVIII. U.S. Patent Application Publication US2006/0115876). This linking strategy is also useful for the preparation of FVIII conjugates, in which the peptide or peptide derivative is linked to FVIII instead of a FVIII-Fc construct. An exemplary method includes contacting FVIII having a free sulfhydryl group (e.g., an internal cysteine), or a FVIII-Fc construct having a free sulfhydryl group located at the FVIII portion of the construct (e.g., an internal cysteine) with a peptide or peptide derivative having a reactive group (e.g., a maleimide or iodoacetamide moiety), under reaction conditions sufficient to form a covalent bond between the peptide or peptide derivative and the FVIII or the FVIII-Fc construct. This linking strategy is also useful for the preparation of FIX or FVIIa conjugates by the same method described above for FVIII. Other reagents useful to form a covalent bond between a sulfhydryl group and another moiety are known to those of skill in the art.

FIG. 25 illustrates a general method for covalently linking a peptide or peptide derivative to a platelet targeting moiety-Fc construct using a native ligation strategy (see, e.g., Mezo, A. R.; Peters, R. P., Methods for Chemically Synthesizing Immunoglobulin Chimeric Proteins. U.S. Pat. No. 7,381, 408; and Dawson, P. E., Kent, S. B. Synthesis of native proteins by chemical ligation. *Ann. Rev. Biochem.* (2000) 69: 923-9600). An exemplary method includes contacting a platelet targeting moiety-Fc construct (e.g., a truncated platelet targeting moiety-Fc construct) having a free sulfhydryl group located at the Fc portion of the construct (e.g., having an N-terminal cysteine) with a peptide or peptide derivative having a reactive group selected from a thioester moiety, a maleimide moiety and a iodoacetamide moiety, under reaction conditions sufficient to form a covalent bond between the peptide or peptide derivative and the platelet targeting moiety-Fc construct.

FIG. 26 illustrates a general method for covalently linking a peptide or peptide derivative to a platelet targeting moiety-Fc construct using a site-directed ligation strategy (see, e.g., Mei, B. et. al. Rational design of a fully active, long-acting PEGylated FVIII for hemophilia A treatment. *Blood* (2010) 116:270-279; and Pan, C. et. al. Site-directed modification of FVIII. U.S. Patent Application Publication US2006/ 0115876). This linking strategy is also useful for the preparation of platelet targeting moiety conjugates, in which the peptide or peptide derivative is linked to the platelet targeting moiety instead of a platelet targeting moiety-Fc construct. An exemplary method includes contacting the platelet targeting moiety having a free sulfhydryl group (e.g., an internal cysteine), or a platelet targeting moiety-Fc construct having a free sulfhydryl group located at the platelet targeting moiety portion of the construct (e.g., an internal cysteine) with a peptide or peptide derivative having a reactive group (e.g., a maleimide or iodoacetamide moiety), under reaction conditions sufficient to form a covalent bond between the peptide or peptide derivative and the platelet targeting moiety or the platelet targeting moiety-Fc construct. Other reagents useful to form a covalent bond between a sulfhydryl group and another moiety are known to those of skill in the art (see, e.g., U.S. Pat. No. 7,381,408).
Pharmaceutical Formulations The invention also provides a pharmaceutical composition (also referred to as pharmaceutical formulation) containing at least one compound of the present disclosure according to any of the above embodiments and a pharmaceutically acceptable carrier.

The invention further provides a pharmaceutical composition containing at least one conjugate of the present disclosure according to any of the above embodiments and a pharmaceutically acceptable carrier.

The term "pharmaceutically acceptable carrier" means all pharmaceutically acceptable ingredients known to those of skill in the art, which are typically considered non-active ingredients. The term "pharmaceutically acceptable carrier" includes, e.g., solvents, solid or liquid diluents, additives, vehicles, adjuvants, excipients, glidants, binders, granulating agents, dispersing agents, suspending agents, wetting agents, lubricating agents, disintegrants, solubilizers, stabilizers, preservatives, emulsifiers, fillers, preservatives (e.g., anti-oxidants), flavoring agents, sweetening agents, thickening agents, buffering agents, coloring agents and the like, as well as any mixtures thereof. Exemplary carriers (i.e., excipients) are described in, e.g., Handbook of Pharmaceutical Manufacturing Formulations, Volumes 1-6, Niazi, Sarfaraz K., Taylor & Francis Group 2005, which is incorporated herein by reference in its entirety. Pharmaceutical compositions may additionally comprise, for example, one or more of water, buffers (e.g., neutral buffered saline or phosphate buffered saline), ethanol, mineral oil, vegetable oil, dimethylsulfoxide, carbohydrates (e.g., glucose, mannose, sucrose or dextrans), mannitol, proteins, adjuvants, polypeptides or amino acids such as glycine, antioxidants, chelating agents such as EDTA or glutathione and/or preservatives.

Pharmaceutical compositions may be formulated for any appropriate manner of administration, including, for example, topical (e.g., transdermal or ocular), oral, buccal, nasal, vaginal, rectal or parenteral administration. In some embodiments, the compound or conjugate of the present disclosure is administered parenterally, e.g., intraveneously or subcutaneously.

The term parenteral as used herein includes subcutaneous, intradermal, intravascular (e.g., intravenous), intramuscular, spinal, intracranial, intrathecal, intraocular, periocular, intraorbital, intrasynovial and intraperitoneal injection, as well as any similar injection or infusion technique. It is preferred that subcutaneous, intraperitoneal, buccal, intravenous and other parenteral formulations are sterile and endotoxin free.

Compounds or conjugates of the present disclosure may be administered parenterally in a sterile medium. The compound or conjugate, depending on the vehicle and concentration used, can either be suspended or dissolved in the vehicle. In one embodiment, adjuvants such as local anesthetics, preservatives and buffering agents can be dissolved in the vehicle.

In one example, the compounds of the present disclosure are administered to the subject using a non-intravenous route, e.g., by subcutaneous, nasal, buccal, oral or pulmonary delivery.

Forms suitable for oral use include, for example, tablets, troches, lozenges, aqueous or oily suspensions, dispersible powders or granules, emulsion, hard or soft capsules, or syrups or elixirs. Compositions provided herein may be formulated as a lyophilizate.

Compositions intended for oral use may be prepared according to any method known for the manufacture of pharmaceutical compositions. Such compositions may contain one or more agents chosen from the group consisting of sweetening agents, flavoring agents, coloring agents and preservative agents in order to provide pharmaceutically elegant and palatable preparations. Tablets can contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques. In some cases such coatings may be prepared by known techniques to delay disintegration and absorption in the gastrointestinal tract and thereby provide a sustained action over a longer period (i.e., tablets can be enterically coated). For example, a time delay material such as glyceryl monosterate or glyceryl distearate may be employed.

Formulations for oral use may also be presented as hard gelatin capsules, wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil. In another example, the active ingredient is formulated in capsules containing optionally coated microtablets or micropellets. Formulations for oral use may also be presented as lozenges. The composition can be also for example a suspension, emulsion, sustained release formulation, cream, gel or powder. The composition can be formulated as a suppository, with traditional binders and carriers such as triglycerides.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide palatable oral preparations. These compositions may be preserved by the addition of an antioxidant such as ascorbic acid.

In one example, the pharmaceutical formulation is a liquid formulation, e.g., a buffered, isotonic, aqueous solution. In one example, the pharmaceutical composition has a pH that is physiologic, or close to physiologic. In another example, the aqueous formulation has a physiologic or close to physiologic osmolarity and salinity. It can contain sodium chloride and/or sodium acetate.

Aqueous suspensions contain the active ingredient(s) in admixture with excipients suitable for the manufacture of aqueous suspensions. Such excipients include suspending agents (e.g., sodium carboxymethylcellulose, methylcellulose, hydropropylmethylcellulose, sodium alginate, polyvinyl-pyrrolidone, gum tragacanth and gum acacia); and dispersing or wetting agents (e.g., naturally-occurring phosphatides such as lecithin, condensation products of an alkylene oxide with fatty acids such as polyoxyethylene stearate, condensation products of ethylene oxide with long chain aliphatic alcohols such as heptadecaethyleneoxycetanol, condensation products of ethylene oxide with partial esters derived from fatty acids and a hexitol such as polyoxyethylene sorbitol monooleate, or condensation products of ethylene oxide with partial esters derived from fatty acids and hexitol anhydrides such as polyethylene sorbitan monooleate). Aqueous suspensions may also comprise one or more preservatives, for example ethyl, or n-propyl p-hydroxybenzoate, one or more coloring agents, one or more flavoring agents, and one or more sweetening agents, such as sucrose or saccharin.

Dispersible powders and granules suitable for preparation of an aqueous suspension by the addition of water can provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, may also be present.

Pharmaceutical compositions of the present disclosure may also be in the form of oil-in-water emulsions. The oily phase may be a vegetable oil or a mineral oil or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol, glucose or sucrose. Such formulations may also contain a demulcent, a preservative, a flavoring agent or a coloring agent. The pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be a sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present disclosure may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

Compounds of the present disclosure can be formulated for local or topical administration, such as for topical application to the skin, wounds or mucous membranes, such as in the eye. Formulations for topical administration typically comprise a topical vehicle combined with active agent(s), with or without additional optional components. Suitable topical vehicles and additional components are well known in the art, and it will be apparent that the choice of a vehicle will depend on the particular physical form and mode of delivery. Topical vehicles include water; organic solvents such as alcohols (e.g., ethanol or isopropyl alcohol) or glycerin; glycols (e.g., butylene, isoprene or propylene glycol); aliphatic alcohols (e.g., lanolin); mixtures of water and organic solvents and mixtures of organic solvents such as alcohol and glycerin; lipid-based materials such as fatty acids, acylglycerols (including oils, such as mineral oil, and fats of natural or synthetic origin), phosphoglycerides, sphingolipids and waxes; protein-based materials such as collagen and gelatin; silicone-based materials (both non-volatile and volatile); and hydrocarbon-based materials such as microsponges and polymer matrices. A composition may further include one or more components adapted to improve the stability or effectiveness of the applied formulation, such as stabilizing agents, suspending agents, emulsifying agents, viscosity adjusters, gelling agents, preservatives, antioxidants, skin penetration enhancers, moisturizers and sustained release materials. Examples of such components are described in Martindale—The Extra Pharmacopoeia (Pharmaceutical Press, London 1993) and Martin (ed.), Remington's Pharmaceutical Sciences. Formulations may comprise microcapsules, such as hydroxy-methylcellulose or gelatin-microcapsules, liposomes, albumin microspheres, micro-emulsions, nanoparticles or nanocapsules.

For disorders of the eye or other external tissues, e.g., mouth and skin, the formulations are applied, for example, as a topical gel, spray, ointment or cream, or as a scleral suppository, containing the active ingredients in a total amount of, for example, 0.075 to 30% w/w, 0.2 to 20% w/w or such as 0.4 to 15% w/w. When formulated in an ointment, the active ingredients may be employed with either paraffinic or a water-miscible ointment base.

Formulations suitable for topical administration to the eye also include eye drops wherein the active ingredients are dissolved or suspended in suitable carrier, especially an aqueous solvent for the active ingredients. The anti-inflammatory active ingredients may, for example, be present in such formulations in a concentration of 0.5 to 20%, such as 0.5 to 10%, for example about 1.5% w/w. For therapeutic purposes, the active compounds of the present disclosure are ordinarily combined with one or more adjuvants appropriate to the indicated route of administration. The compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound, which enhances absorption or penetration of the active ingredient through the skin or other affected areas. Examples of such dermal penetration enhancers include dimethylsulfoxide and related analogs. The compounds of this present disclosure can also be administered by a transdermal device. In one embodiment, topical administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane. The transdermal patch may include the compound in a suitable solvent system with an adhesive system, such as an acrylic emulsion, and a polyester patch. The oily phase of the emulsions of this present disclosure may be constituted from known ingredients in a known manner. While the phase may comprise merely an emulsifier, it may comprise a mixture of at least one emulsifier with a fat or oil or with both a fat and an oil. In one embodiment, a hydrophilic emulsifier is included together with a lipophilic emulsifier, which acts as a stabilizer. The phase may, for example, include both an oil and a fat. Together, the emulsifier(s) with or without stabilizer(s) make-up the so-called emulsifying wax, and the wax together with the oil and fat make up the so-called emulsifying ointment base, which forms the oily, dispersed phase of the cream formulations. Emulsifiers and emulsion stabilizers suitable for use in the formulation of the present disclosure include Tween 60, Span 80, cetostearyl alcohol, myristyl alcohol, glyceryl monostearate, and sodium lauryl sulfate, among others. The choice of suitable oils or fats for the formulation is based on achieving the desired cosmetic properties, since the solubility of the active compound in most oils likely to be used in pharmaceutical emulsion formulations is very low. Thus, the cream may, for example, be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

A pharmaceutical composition may be formulated as inhaled formulations, including sprays, mists, or aerosols. For inhalation formulations, the compounds provided herein may be delivered via any inhalation methods known to those skilled in the art. Such inhalation methods and devices include, but are not limited to, metered dose inhalers with propellants such as CFC or HFA or propellants that are physiologically and environmentally acceptable. Other suitable devices are breath operated inhalers, multidose dry powder inhalers and aerosol nebulizers. Aerosol formulations for use in the subject method typically include propellants, surfactants and co-solvents and may be filled into conventional aerosol containers that are closed by a suitable metering valve.

Formulations suitable for inhalation or insufflation include solutions and suspensions in pharmaceutically acceptable aqueous or organic solvents, or mixtures thereof, and powders. The liquid or solid compositions may contain suitable pharmaceutically acceptable excipients as describe above. The compositions may be administered by oral or nasal respiratory route for local or systemic effect. Compositions may be nebulized by use of inert gases or vaporized, and breathed directly from the nebulizing/vaporizing device or the nebulizing device may be attached to a facemask tent or intermittent positive pressure-breathing machine.

Inhalant compositions may comprise liquid or powdered compositions containing the active ingredient that are suitable for nebulization and intrabronchial use, or aerosol compositions administered via an aerosol unit dispensing metered doses. Suitable liquid compositions comprise the active ingredient in an aqueous, pharmaceutically acceptable inhalant solvent, e.g., isotonic saline or bacteriostatic water. The solutions are administered by means of a pump or squeeze-actuated nebulized spray dispenser, or by any other conventional means for causing or enabling the requisite dosage amount of the liquid composition to be inhaled into the patient's lungs. Suitable formulations, wherein the carrier is a liquid, for administration, as for example, a nasal spray or as nasal drops, include aqueous or oily solutions of the active ingredient Formulations or compositions suitable for nasal administration, wherein the carrier is a solid, include a coarse powder having a particle size, for example, in the range of 20 to 500 microns which is administered in the manner in which snuff is administered (i.e., by rapid inhalation through the nasal passage from a container of the powder held close up to the nose). Suitable powder compositions include, by way of illustration, powdered preparations of the active ingredient thoroughly intermixed with lactose or other inert powders acceptable for intrabronchial administration. The powder compositions can be administered via an aerosol dispenser or encased in a breakable capsule which may be inserted by the patient into a device that punctures the capsule and blows the powder out in a steady stream suitable for inhalation.

Pharmaceutical compositions may be formulated as sustained release formulations (i.e., a formulation such as a capsule that effects a slow release of modulator following administration). Such formulations may generally be prepared using well known technology and administered by, for example, oral, rectal or subcutaneous implantation, or by implantation at the desired target site. Carriers for use within such formulations are biocompatible, and may also be biodegradable; preferably the formulation provides a relatively constant level of modulator release. The amount of modulator contained within a sustained release formulation depends upon, for example, the site of implantation, the rate and expected duration of release and the nature of the condition to be treated or prevented.

In one example, the pharmaceutical formulations provided herein can include one or more additional active agent (i.e., other biologically active ingredient). In one example, the additional active agent is selected from known drugs approved for the treatment of a coagulation disorder, such as hemophilia A. For example, the pharmaceutical formulation can further include a blood coagulation factor.

In another example, the pharmaceutical formulation further contains a blood coagulation factor selected from FVIII and FIX. In another example, the pharmaceutical formulation further includes FVIII. In another example, the pharmaceutical formulation further includes FIX. In another example, the pharmaceutical formulation includes desmopressin (DDVAP).

Pharmaceutical compositions may be formulated with an agent to improve bioavailability, such an as organic solvent. For example, Cremophor EL.RTM. (Product No. 00647/1/63; BASF Aktiengesellschaft, Germany) is a polyethoxylated castor oil which is prepared by reacting 35 moles of ethylene oxide with each mole of castor oil. It may be used to stabilize emulsions of non-polar materials in aqueous systems. Alternatively, peptide, peptide derivative or dual peptide may be incorporated within or bound to a proteinaceous micro or nano-particle for improved bioavailability. Suitable micro- and nano-particles are described in U.S. Pat. No. 5,439,686 (Desai et al; Vivorx Pharmaceuticals, Inc., CA) and U.S. Pat. No. 5,498,421 (Grinstaff et al; Vivorx Pharmaceuticals, Inc., CA). Suitably, the proteinaceous nano-particle comprises human serum albumin, particularly human serum albumin or a recombinant form thereof WO 2007/077561 (Gabbai; Do-Coop Technologies Ltd., Israel) describe another suitable carrier comprising nanostructures and a liquid, referred to therein as Neowater.TM.

For veterinary use, a compound of the present disclosure is administered as a suitably acceptable formulation in accordance with normal veterinary practice and the veterinary surgeon will determine the dosing regimen and route of administration which will be most appropriate for a particular animal. For administration to non-human animals, the composition may be added to the animal feed or drinking water. It may be convenient to formulate the animal feed and drinking water compositions so that the animal takes in a therapeutically appropriate quantity of the composition along with its diet. It may also be convenient to present the composition as a premix for addition to the feed or drinking water.

Methods

The invention further provides a method (e.g., an in vitro or an in vivo method) of increasing/enhancing the catalytic activity (kcat) of a blood coagulation factor (i.e., activating the blood coagulation factor). An exemplary method includes contacting the blood coagulation factor (e.g., FIXa or FVIIa) with a compound of the present disclosure according to any of the above embodiments. In one example, the blood coagulation factor useful in this method includes the amino acid sequence: MFCAG (SEQ ID NO: 1) (e.g., FIXa, FXa, FVIIa and thrombin). In one example, the blood coagulation factor being activated is FXa. In another example, the blood coagulation factor being activated is thrombin.

The invention further provides a method of increasing/enhancing the catalytic activity (kcat) of FIXa (e.g., in vitro or in vivo), the method includes contacting the FIXa with a compound of the present disclosure according to any of the above embodiments.

The invention further provides a method of increasing/enhancing the catalytic activity (kcat) of FVIIa (e.g., in vitro or in vivo), the method includes contacting the FVIIa with a compound of the present disclosure according to any of the above embodiments.

In one example according to the above method, the compound interacts with the blood coagulation factor (e.g., binds to the blood coagulation factor) at a region corresponding to amino acid sequence: MFCAG (SEQ ID NO: 1).

In a further example, the blood coagulation factor being activated is FIXa (e.g., human or canine FIXa). In one example according to this embodiment, the compound of the present disclosure interacts with the FIXa at a region corresponding to amino acid sequence: YNNMFCAGFHE (SEQ ID NO: 2). In yet another example, the compound of the present disclosure interacts with the FIXa at a region corresponding to amino acid sequence: RSTKFTIYNNMFCAGFHFGGRDSCQG (SEQ ID NO: 3).

In another example according to any of the above embodiments, the method is an in vitro method involving measuring conversion of FX to FXa. Such method is also generally referred to as a "FXa generation assay". An exemplary FXa generation assay is described in Example 2.

In one embodiment the compound is used in an in vitro assay system useful for the identification of other candidate compounds with pro-coagulant activity (e.g., a competition assay). In one example, the compound of the present disclosure is used as a reference compound in such assay system. In another example, the compound is used in a binding competition experiment as a probe. In one example, the compound of the present disclosure is used as a probe to measure binding of a candidate compound to a polypeptide (e.g., FIXa, FVIIa, or peptide including amino acid sequence of SEQ ID NO: 1, 2, or 3). For this purpose, the compound of the present disclosure can be linked to a detection molecule, such as an antibody (e.g., ELISA assay), biotin, a fluorescent molecule, a phage particle (e.g., phage display competition assay), and the like.

The invention further provides a method (e.g., an in vitro or an in vivo method) for identifying a candidate compound (e.g., a candidate compound with pro-coagulant activity) (e.g., within a screening procedure for the identification of compounds with pro-coagulant activity), the method comprising contacting a peptide or polypeptide comprising the amino acid sequence of SEQ ID NO: 1, 2, or 3 with a compound of the present disclosure according to any of the above embodiments.

Pharmaceutical Methods

The present invention further provides methods for treating bleeding diathesis in a mammalian subject (e.g., a human patient) using the compounds or conjugates or the present disclosure.

Pharmaceutical Method 1

In some embodiments, the present disclosure provides a method for treating bleeding diathesis in a mammalian subject (e.g., a human patient), comprising: administering to the subject in need thereof a therapeutically effective amount of a compound of the present disclosure or a pharmaceutical composition comprising a compound of the present disclosure.

In some embodiments of pharmaceutical method 1, the compound or the pharmaceutical composition containing the compound is administered to the subject orally. In other embodiments, the compound or the pharmaceutical composition containing the compound is administered to the subject parenterally, e.g., intravenously or subcutaneously.

Pharmaceutical Method 2

In some embodiments, the present disclosure provides a method for treating bleeding diathesis in a mammalian subject (e.g., a human patient), comprising: administering to the subject in need thereof a therapeutically effective amount of a conjugate of the present disclosure or a pharmaceutical composition comprising a conjugate of the present disclosure.

In some embodiments of pharmaceutical method 2, the conjugate or the pharmaceutical composition comprising the conjugate is administered to the subject orally. In other embodiments, the conjugate or the pharmaceutical composition containing the conjugate is administered to the subject parenterally, e.g., intravenously or subcutaneously.

In one example according to any of the above embodiments of pharmaceutical methods 1 and 2, the bleeding diathesis is caused by or associated with a blood coagulation disorder. A blood coagulation disorder can also be referred to as a coagulopathy. In a particular example, the blood coagulation disorder, which can be treated with a compound or conjugate of the current disclosure, is hemophilia or von Willebrand disease (vWD). In a particular example, the blood coagulation disorder, which can be treated is hemophilia. In another example, the hemophilia is hemophilia A. In yet another example, the hemophilia is hemophilia B.

In another example, the type of bleeding associated with the bleeding diathesis is selected from hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, and bleeding in the illiopsoas sheath.

In another example, the subject suffering from bleeding diathesis is in need of treatment for surgery, including, e.g., surgical prophylaxis or peri-operative management. In one example, the surgery is selected from minor surgery and major surgery. Exemplary surgical procedures include tooth extraction, tonsillectomy, inguinal herniotomy, synovectomy, craniotomy, osteosynthesis, trauma surgery, intracranial surgery, intra-abdominal surgery, intrathoracic surgery, joint replacement surgery (e.g., total knee replacement, hip replacement, and the like), heart surgery, and caesarean section.

In some embodiments, the coagulation disorder is caused by a deficiency in at least one blood coagulation factor (e.g., FVIII). The current disclosure provides methods of treating a mammalian subject (e.g., a human subject) having a deficiency in at least one blood coagulation factor selected from von Willebrand Factor (vWF), FV, FVII, FVIII, FIX, FX, FXI, and activated forms thereof (e.g., for both the prophylaxis and for the treatment of acute bleeds).

Pharmaceutical Method 3

In some embodiments, the present disclosure provides a method for treating a coagulation disorder in a mammalian subject (e.g., a human patient) having a deficiency in at least one blood coagulation factor selected from von Willebrand Factor (vWF), FV, FVII, FVIII, FIX, FX, FXI, and activated forms thereof (e.g., for both the prophylaxis and for the treatment of acute bleeds), the method comprising: administering to the subject in need thereof a therapeutically effective amount of a compound of the present disclosure or a pharmaceutical composition comprising a compound of the present disclosure.

Pharmaceutical Method 4

In some embodiments, the present disclosure provides a method for treating a coagulation disorder in a mammalian subject (e.g., a human patient) having a deficiency in at least one blood coagulation factor selected from von Willebrand Factor (vWF), FV, FVII, FVIII, FIX, FX, FXI, and activated forms thereof (e.g., for both the prophylaxis and for the treatment of acute bleeds), the method comprising: administering to the subject in need thereof a therapeutically effective amount of a conjugate of the present disclosure or a pharmaceutical composition comprising a conjugate of the present disclosure.

In one example according to any of the above embodiments of pharmaceutical methods 1, 2, 3, and 4, the subject has a deficiency in FVIII. In another example, the subject responds to FVIII treatment.

Pharmaceutical Method 5

In some embodiments, the current disclosure provides a method of treating a mammalian subject (e.g., a human subject) having a deficiency in FVIII, the method includes administering to the subject a therapeutically effective amount of a compound of the current disclosure or a pharmaceutical composition containing a compound of the current disclosure.

Pharmaceutical Method 6

In some embodiments, the current disclosure provides a method of treating a mammalian subject (e.g., a human subject) having a deficiency in FVIII, the method includes administering to the subject a therapeutically effective amount of a conjugate of the current disclosure or a pharmaceutical composition containing a conjugate of the current disclosure.

Patients with a FVIII deficiency (i.e., hemophilia A) can develop inhibitor antibodies to FVIII. The biological activity of certain compounds or conjugates of the present disclosure is essentially not influenced by the presence of FVIII inhibitors, such as antibodies against FVIII. Hence, in one example according to any of the above embodiments of pharmaceutical methods 1-6, the mammalian subject (e.g., a human patient) suffering from a FVIII deficiency is a FVIII inhibitor patient (e.g., produces antibodies against FVIII). The magnitude of the antibody response to FVIII can be quantified using a functional inhibitor assay, such as that described in Kasper C K et al. (1975) Proceedings: A more uniform measurement of factor VIII inhibitors. *Thromb. Diath. Haemorrh.* 34(2):612. FXI inhibitors could be quantified by an aPTT assay as described by Kasper C K et al.. Inhibitors of FV, FVII and FX could be quantified by a PT based assay following the procedure of Kasper C K et al.

Inhibitor development (to FIX) is also known in FIX deficiency (i.e., hemophilia B). The biological activity (e.g., FXa generation assay activity) of certain compounds of the present disclosure is essentially not influenced by the presence of FIX inhibitors, such as antibodies against FIX. Since FV, FVII, FXI and FX deficiencies are very rare congenital disorders little is known about inhibitor development, although it is feasible that patients having such disorders might develop inhibitors. Treatment of inhibitor patients is contemplated by the current invention. Such inhibitor patients may have either a high titer response of greater than 5 BU or a low titer response of between 0.5 and 5 BU. Typically, the inhibitors are directed against FVIII and the patients have hemophilia A.

In one example according to any of the above embodiments, the mammalian subject is a human subject (i.e., a human patient). In another example according to any of the above embodiments, the mammalian subject (e.g, human patient) is concomitantly treated with at least one additional active agent, e.g., a drug approved for the treatment of coagulation disorders. In one example, the additional active agent is selected from a coagulation factor (e.g., FVIII or FIX) and desmopressin (DDVAP). In a particular example, the mammalian subject (e.g, human patient) is concomitantly treated with FVIII. In one example, the additional active agent is administered to the subject at the same time that the compound or conjugate of the present disclosure is administered to the subject. For example, the at least one additional active agent is contained in a pharmaceutical composition that also contains the compound or conjugate of the present disclosure. In another example, the additional active agent is administered to the subject at a different time but within the treatment period for the compound or conjugate of the present disclosure. For example, the additional active agent is administered alternatingly with the compound or conjugate of the present disclosure.

In another example, the mammalian subject (e.g, human patient) is concomitantly treated with FIX. Because the compounds or conjugates of the invention are capable of activating FIXa, they could be used to pre-activate the FIXa polypeptide before administration of the FIXa to the subject.

In yet another example, the mammalian subject (e.g, human subject) is concomitantly treated with desmopressin (DDVAP).

The methods of the invention may be practiced on a subject in need of prophylactic treatment or on-demand treatment.

In various embodiments, the compounds of the present disclosure can be used as a replacement therapy (e.g., replacing FVIII treatment) in subjects in need of treatment for hemophilia A. In other embodiments, the compounds of the present disclosure can be used in conjunction with other therapies (e.g., FVIII or FIX therapy) in subjects in need of treatment for hemophilia A or B. In other embodiments, the compounds of the present disclosure are useful as a bypass therapy in subjects in need of treatment for hemophilia A (e.g., hemophilia A patients with inhibitors).

Administration of Compounds

For oral and parenteral administration of compounds to patients, including human patients, the daily dosage level of the compound (e.g., peptide or peptide derivative) of the current disclosure will usually be from 2 to 2000 mg per adult (i.e. from about 0.03 to 30 mg/kg), administered in single or divided doses.

A unit dosage form (for example tablet or capsule) can contain from 2 mg to 2000 mg of active compound. The unit dosage form can be administered once, twice or more times per day as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention.

Administration of Polypeptide Conjugates

The calculation of the required dosage for the polypeptide conjugates of the present disclosure is based upon the empirical finding that, on average, 1 IU of FVIII per kg body weight raises the plasma FVIII activity by approximately 2 IU/dL. The required dosage is determined using the following formula:

Required units=body weight (kg)×desired FVIII rise (IU/dL or % of normal)×0.5(IU/kg per IU/dL).

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Dosage levels of the order of from about 0.005 mg to about 80 mg per kilogram of body weight per day are useful in the treatment of the diseases and conditions described herein (e.g., about 0.35 mg to about 5.6 g per human patient per day, based on an average adult person weight of 70 kg). The amount of active ingredient that may be combined with the carrier materials to produce a single dosage form will vary depending upon the host treated and the particular mode of administration. Dosage unit forms will generally contain between from about 1 mg to about 500 mg of an active ingredient. The daily dose can be administered in one to four doses per day. In the case of skin conditions, it may, for example, be applied as a topical preparation of compounds of this present disclosure on the affected area one to four times a day.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Definitions

The definitions and explanations below are for the terms as used throughout this entire document including both the specification and the claims. Throughout the specification and the appended claims, a given formula or name shall encompass all isomers thereof, such as stereoisomers, geometrical isomers, optical isomers, tautomers, and mixtures thereof where such isomers exist, as well as pharmaceutically acceptable salts and solvates thereof, such as hydrates.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

"Therapeutic dose," as used herein, means a dose that achieves a therapeutic goal, as described herein.

The phrase "therapeutically effective amount" as used herein means that amount of a compound, material, or composition of the present disclosure, which is effective for producing a desired therapeutic effect, at a reasonable benefit/risk ratio applicable to any medical treatment. For example, a "therapeutically effective amount" is an amount effective to reduce or lessen at least one symptom of the disease or condition being treated or to reduce or delay onset of one or more clinical markers or symptoms associated with the disease or condition, or to modify or reverse the disease process.

As used herein, the term "pharmaceutically acceptable" means approved by a regulatory agency of US or EU or other government or listed in the U.S. Pharmacopeia or other generally recognized pharmacopeia for use in humans. Hence, the term "pharmaceutically acceptable" refers to those properties and/or substances that are acceptable to a patient (e.g., human patient) from a toxicological and/or safety point of view.

The terms "treatment" or "treating" when referring to a disease or condition, means producing a desired therapeutic effect. Exemplary therapeutic effects include delaying onset or reducing at least one symptom associated with the disease, positively affecting (e.g., reducing or delaying onset) a clinical marker associated with the disease and slowing or reversing disease progression.

Where substituent groups are specified by their conventional chemical formulae, written from left to right, they equally encompass the chemically identical substituents, which would result from writing the structure from right to left. For example, "—CH$_2$O—" is intended to also recite "—OCH$_2$—".

The term "alkyl," by itself or as part of another substituent, mean, unless otherwise stated, a straight or branched chain hydrocarbon radical having the number of carbon atoms designated (e.g., C$_1$-C$_{10}$ means one to ten carbon atoms). Typically, an alkyl group will have from 1 to 24 carbon atoms, for example having from 1 to 10 carbon atoms, from 1 to 8 carbon atoms or from 1 to 6 carbon atoms. A "lower alkyl" group is an alkyl group having from 1 to 4 carbon atoms. The term "alkyl" includes di- and multivalent radicals. For example, the term "alkyl" includes "alkylene" wherever appropriate, e.g., when the formula indicates that the alkyl group is divalent or when substituents are joined to form a ring. Examples of alkyl radicals include, but are not limited to, methyl, ethyl, n-propyl, iso-propyl, n-butyl, tert-butyl, iso-butyl, sec-butyl, as well as homologs and isomers of, for example, n-pentyl, n-hexyl, n-heptyl and n-octyl.

The term "alkylene" by itself or as part of another substituent means a divalent (diradical) alkyl group, wherein alkyl is defined herein, "Alkylene" is exemplified, but not limited, by —$CH_2CH_2CH_2CH_2$—. Typically, an "alkylene" group will have from 1 to 24 carbon atoms, for example, having 10 or fewer carbon atoms (e.g., 1 to 8 or 1 to 6 carbon atoms). A "lower alkylene" group is an alkylene group having from 1 to 4 carbon atoms.

The term "alkenyl" by itself or as part of another substituent refers to a straight or branched chain hydrocarbon radical having from 2 to 24 carbon atoms and at least one double bond. A typical alkenyl group has from 2 to 10 carbon atoms and at least one double bond. In one embodiment, alkenyl groups have from 2 to 8 carbon atoms or from 2 to 6 carbon atoms and from 1 to 3 double bonds. Exemplary alkenyl groups include vinyl, 2-propenyl, 1-but-3-enyl, crotyl, 2-(butadienyl), 2,4-pentadienyl, 3-(1,4-pentadienyl), 2-isopentenyl, 1-pent-3-enyl, 1-hex-5-enyl and the like.

The term "alkynyl" by itself or as part of another substituent refers to a straight or branched chain, unsaturated or polyunsaturated hydrocarbon radical having from 2 to 24 carbon atoms and at least one triple bond. A typical "alkynyl" group has from 2 to 10 carbon atoms and at least one triple bond. In one aspect of the disclosure, alkynyl groups have from 2 to 6 carbon atoms and at least one triple bond. Exemplary alkynyl groups include prop-1-ynyl, prop-2-ynyl (i.e., propargyl), ethynyl and 3-butynyl.

The terms "alkoxy," "alkylamino" and "alkylthio" (or thioalkoxy) are used in their conventional sense, and refer to alkyl groups that are attached to the remainder of the molecule via an oxygen atom, an amino group, or a sulfur atom, respectively.

The term "heteroalkyl," by itself or in combination with another term, means a stable, straight or branched chain hydrocarbon radical consisting of the stated number of carbon atoms (e.g., $C_2$-$C_{10}$, or $C_2$-$C_8$) and at least one heteroatom chosen, e.g., from N, O, S, Si, B and P (in one embodiment, N, O and S), wherein the nitrogen, sulfur and phosphorus atoms are optionally oxidized, and the nitrogen atom(s) are optionally quaternized. The heteroatom(s) is/are placed at any interior position of the heteroalkyl group. Examples of heteroalkyl groups include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH=CH—O—$CH_3$, —$CH_2$—Si($CH_3$)$_3$, —$CH_2$—CH=N—$OCH_3$, and —CH=CH—N($CH_3$)—$CH_3$. Up to two heteroatoms can be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. Typically, a heteroalkyl group will have from 3 to 24 atoms (carbon and heteroatoms, excluding hydrogen) (3- to 24-membered heteroalkyl). In another example, the heteroalkyl group has a total of 3 to 10 atoms (3- to 10-membered heteroalkyl) or from 3 to 8 atoms (3- to 8-membered heteroalkyl). The term "heteroalkyl" includes "heteroalkylene" wherever appropriate, e.g., when the formula indicates that the heteroalkyl group is divalent or when substituents are joined to form a ring.

The term "cycloalkyl" by itself or in combination with other terms, represents a saturated or unsaturated, non-aromatic carbocyclic radical having from 3 to 24 carbon atoms, for example, having from 3 to 12 carbon atoms (e.g., $C_3$-$C_8$ cycloalkyl or $C_3$-$C_6$ cycloalkyl). Examples of cycloalkyl include, but are not limited to, cyclopropyl, cyclobutyl, cyclopentyl, cyclohexyl, cycloheptyl, 1-cyclohexenyl, 3-cyclohexenyl, cycloheptyl and the like. The term "cycloalkyl" also includes bridged, polycyclic (e.g., bicyclic) structures, such as norbornyl, adamantyl and bicyclo[2.2.1]heptyl. The "cycloalkyl" group can be fused to at least one (e.g., 1 to 3) other ring selected from aryl (e.g., phenyl), heteroaryl (e.g., pyridyl) and non-aromatic (e.g., carbocyclic or heterocyclic) rings. When the "cycloalkyl" group includes a fused aryl, heteroaryl or heterocyclic ring, then the "cycloalkyl" group is attached to the remainder of the molecule via the carbocyclic ring.

The term "heterocycloalkyl," "heterocyclic," "heterocycle," or "heterocyclyl," by itself or in combination with other terms, represents a carbocyclic, non-aromatic ring (e.g., 3- to 8-membered ring and for example, 4-, 5-, 6- or 7-membered ring) containing at least one and up to 5 heteroatoms selected from, e.g., N, O, S, Si, B and P (for example, N, O and S), wherein the nitrogen, sulfur and phosphorus atoms are optionally oxidized, and the nitrogen atom(s) are optionally quaternized (e.g., from 1 to 4 heteroatoms selected from nitrogen, oxygen and sulfur), or a fused ring system of 4- to 8-membered rings, containing at least one and up to 10 heteroatoms (e.g., from 1 to 5 heteroatoms selected from N, O and S) in stable combinations known to those of skill in the art. Exemplary heterocycloalkyl groups include a fused phenyl ring. When the "heterocyclic" group includes a fused aryl, heteroaryl or cycloalkyl ring, then the "heterocyclic" group is attached to the remainder of the molecule via a heterocycle. A heteroatom can occupy the position at which the heterocycle is attached to the remainder of the molecule. Exemplary heterocycloalkyl or heterocyclic groups of the present disclosure include morpholinyl, thiomorpholinyl, thiomorpholinyl S-oxide, thiomorpholinyl S,S-dioxide, piperazinyl, homopiperazinyl, pyrrolidinyl, pyrrolinyl, imidazolidinyl, tetrahydropyranyl, piperidinyl, tetrahydrofuranyl, tetrahydrothienyl, piperidinyl, homopiperidinyl, homomorpholinyl, homothiomorpholinyl, homothiomorpholinyl S,S-dioxide, oxazolidinonyl, dihydropyrazolyl, dihydropyrrolyl, dihydropyrazolyl, dihydropyridyl, dihydropyrimidinyl, dihydrofuryl, dihydropyranyl, tetrahydrothienyl, S-oxide, tetrahydrothienyl S,S-dioxide, homothiomorpholinyl S-oxide, 1-(1, 2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

By "aryl" is meant a 5-, 6- or 7-membered, aromatic carbocyclic group having a single ring (e.g., phenyl) or being fused to other aromatic or non-aromatic rings (e.g., from 1 to 3 other rings). When the "aryl" group includes a non-aromatic ring (such as in 1,2,3,4-tetrahydronaphthyl) or heteroaryl group then the "aryl" group is bonded to the remainder of the molecule via an aryl ring (e.g., a phenyl ring). The aryl group is optionally substituted (e.g., with 1 to 5 substituents described herein). In one example, the aryl group has from 6 to 10 carbon atoms. Non-limiting examples of aryl groups include phenyl, 1-naphthyl, 2-naphthyl, quinoline, indanyl, indenyl, dihydronaphthyl, fluorenyl, tetralinyl, benzo[d][1,3]dioxolyl or 6,7,8,9-tetrahydro-5H-benzo[a]cycloheptenyl. In one embodiment, the aryl group is selected from phenyl, benzo[d][1,3]dioxolyl and naphthyl. The aryl group, in yet another embodiment, is phenyl.

The term "arylalkyl" or "aralkyl" is meant to include those radicals in which an aryl group or heteroaryl group is attached to an alkyl group to create the radicals -alkyl-aryl and -alkyl-heteroaryl, wherein alkyl, aryl and heteroaryl are defined herein. Exemplary "arylalkyl" or "aralkyl" groups include benzyl, phenethyl, pyridylmethyl and the like.

By "aryloxy" is meant the group —O-aryl, where aryl is as defined herein. In one example, the aryl portion of the aryloxy group is phenyl or naphthyl. The aryl portion of the aryloxy group, in one embodiment, is phenyl.

The term "heteroaryl" or "heteroaromatic" refers to a polyunsaturated, 5-, 6- or 7-membered aromatic moiety containing at least one heteroatom (e.g., 1 to 5 heteroatoms, such as 1-3 heteroatoms) selected from N, O, S, Si and B (for example, N, O and S), wherein the nitrogen and sulfur atoms are optionally oxidized, and the nitrogen atom(s) are optionally quaternized. The "heteroaryl" group can be a single ring or be fused to other aryl, heteroaryl, cycloalkyl or heterocycloalkyl rings (e.g., from 1 to 3 other rings). When the "heteroaryl" group includes a fused aryl, cycloalkyl or heterocycloalkyl ring, then the "heteroaryl" group is attached to the remainder of the molecule via the heteroaryl ring. A heteroaryl group can be attached to the remainder of the molecule through a carbon- or heteroatom. In one example, the heteroaryl group has from 4 to 10 carbon atoms and from 1 to 5 heteroatoms selected from O, S and N. Non-limiting examples of heteroaryl groups include pyridyl, pyrimidinyl, quinolinyl, benzothienyl, indolyl, indolinyl, pyridazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, triazolyl, tetrazolyl, isothiazolyl, naphthyridinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridyl, benzotetrahydrofuranyl, benzotetrahydrothienyl, purinyl, benzodioxolyl, triazinyl, pteridinyl, benzothiazolyl, imidazopyridyl, imidazothiazolyl, dihydrobenzisoxazinyl, benzisoxazinyl, benzoxazinyl, dihydrobenzisothiazinyl, benzopyranyl, benzothiopyranyl, chromonyl, chromanonyl, pyridyl-N-oxide, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl-N-oxide, oxadiazolyl N-oxide, thiadiazolyl N-oxide, triazolyl-N-oxide, tetrazolyl N-oxide, benzothiopyranyl S-oxide, benzothiopyranyl S,S-dioxide. Exemplary heteroaryl groups include imidazolyl, pyrazolyl, thiadiazolyl, triazolyl, isoxazolyl, isothiazolyl, imidazolyl, thiazolyl, oxadiazolyl, and pyridyl. Other exemplary heteroaryl groups include 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, pyridin-4-yl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable aryl group substituents described below.

For brevity, the term "aryl" when used in combination with other terms (e.g., aryloxy, arylthioxy, arylalkyl) includes both aryl and heteroaryl rings as defined above.

Each of the above terms (e.g., "alkyl," "cycloalkyl," "heteroalkyl," heterocycloalkyl," "aryl" and "heteroaryl") are meant to include both substituted and unsubstituted forms of the indicated radical. The term "substituted" for each type of radical is explained below. When a compound of the present disclosure includes more than one substituent, then each of the substituents is independently chosen.

The term "substituted" in connection with alkyl, alkenyl, alkenyl, cycloalkyl, heteroalkyl and heterocycloalkyl radicals (including those groups referred to as alkylene, heteroalkylene, heteroalkenyl, cycloalkenyl, heterocycloalkenyl, and the like) refers to one or more substituents, wherein each substituent is independently selected from, but not limited to, 3- to 10-membered heteroalkyl, $C_3$-$C_{10}$ cycloalkyl, 3- to 10-membered heterocycloalkyl, aryl, heteroaryl, —$OR^a$, —$SR^a$, =O, =$NR^a$, =N—$OR^a$, —$NR^aR^b$, -halogen, —$SiR^aR^bR^c$, —$OC(O)R^a$, —$C(O)R^e$, —$C(O)OR^a$, —$C(O)NR^aR^b$, —$OC(O)NR^aR^b$, —$NR^cC(O)R^e$, —$NR^cC(O)NR^aR^b$, —$NR^cC(S)NR^aR^b$, —$NR^cC(O)OR^a$, —$N^cC(NR^aR^b)$=$NR^d$, —$S(O)R^e$, —$S(O)_2R^e$, —$S(O)_2NR^aR^b$, -$NR^cS(O)_2R^a$, —CN and —$NO_2$. $R^a$, $R^b$, $R^c$, $R^d$ and $R^e$ each independently refer to hydrogen, $C_1$-$C_{24}$ alkyl (e.g., $C_1$-$C_{10}$ alkyl or $C_1$-$C_6$ alkyl), $C_3$-$C_{10}$ cycloalkyl, $C_1$-$C_{24}$ heteroalkyl (e.g., $C_1$-$C_{10}$ heteroalkyl or $C_1$-$C_6$ heteroalkyl), $C_3$-$C_{10}$ heterocycloalkyl, aryl, heteroaryl, arylalkyl and heteroarylalkyl, wherein, in one embodiment, $R^e$ is not hydrogen. When two of the above R groups (e.g., $R^a$ and $R^b$) are attached to the same nitrogen atom, they can be combined with the nitrogen atom to form a 5-, 6-, or 7-membered ring. For example, —$NR^aR^b$ is meant to include pyrrolidinyl, N-alkyl-piperidinyl and morpholinyl.

The term "substituted" in connection with aryl and heteroaryl groups, refers to one or more substituents, wherein each substituent is independently selected from, but not limited to, alkyl (e.g., $C_1$-$C_{24}$ alkyl, $C_1$-$C_{10}$ alkyl or $C_1$-$C_6$ alkyl), cycloalkyl (e.g., $C_3$-$C_{10}$ cycloalkyl, or $C_3$-$C_8$ cycloalkyl), alkenyl (e.g., $C_1$-$C_{10}$ alkenyl or $C_1$-$C_6$ alkenyl), alkynyl (e.g., $C_1$-$C_{10}$ alkynyl or $C_1$-$C_6$ alkynyl), heteroalkyl (e.g., 3- to 10-membered heteroalkyl), heterocycloalkyl (e.g., $C_3$-$C_8$ heterocycloalkyl), aryl, heteroaryl, —$R^a$, —$OR^a$, —$SR^a$, =O, =$NR^a$, =N—$OR^a$, —$NR^aR^b$, -halogen, —$SiR^aR^bR^c$, —$OC(O)R^a$, —$C(O)R^e$, —$C(O)OR^a$, —$C(O)NR^aR^b$, —$OC(O)NR^aR^b$, —$NR^cC(O)R^e$, —$NR^cC(O)NR^aR^b$, —$NR^cC(S)NR^aR^b$, —$NR^cC(O)OR^a$, —$NR^cC(NR^aR^b)$=$NR^d$, —$S(O)R^e$, —$S(O)_2R^e$, —$S(O)_2NR^aR^b$, —$NR^eS(O)_2R^a$, —CN, —$NO_2$, —$CH(Ph)_2$, fluoro($C_1$-$C_4$) alkoxy, and fluoro($C_1$-$C_4$)alkyl, in a number ranging from zero to the total number of open valences on the aromatic ring system, wherein $R^a$, $R^b$, $R^c$, $R^d$ and $R^e$ each independently refer to hydrogen, $C_1$-$C_{24}$ alkyl (e.g., $C_1$-$C_{10}$ alkyl or $C_1$-$C_6$ alkyl), $C_3$-$C_{10}$ cycloalkyl, $C_1$-$C_{24}$ heteroalkyl (e.g., $C_1$-$C_{10}$ heteroalkyl or $C_1$-$C_6$ heteroalkyl), $C_3$-$C_{10}$ heterocycloalkyl, aryl, heteroaryl, arylalkyl and heteroarylalkyl, wherein, in one embodiment, $R^e$ is not hydrogen. When two R groups (e.g., $R^a$ and $R^b$) are attached to the same nitrogen atom, they can be combined with the nitrogen atom to form a 5-, 6-, or 7-membered ring. For example, —$NR^aR^b$ is meant to include pyrrolidinyl, N-alkyl-piperidinyl and morpholinyl.

The term "substituted" in connection with aryl and heteroaryl groups also refers to one or more fused ring(s), in which two hydrogen atoms on adjacent atoms of the aryl or heteroaryl ring are optionally replaced with a substituent of the formula —T—C(O)—(CRR')$_q$—U—, wherein T and U are independently —NR—, —O—, —CRR'— or a single bond, and q is an integer from 0 to 3. Alternatively, two of the hydrogen atoms on adjacent atoms of the aryl or heteroaryl ring can optionally be replaced with a substituent of the formula —A—(CH$_2$)$_r$—B—, wherein A and B are independently —CRR'—, —O—, —NR—, —S—, —S(O)—, —S(O)$_2$—, —S(O)$_2$NR'— or a single bond, and r is an integer from 1 to 4. One of the single bonds of the ring so formed can optionally be replaced with a double bond. Alternatively, two of the hydrogen atoms on adjacent atoms of the aryl or heteroaryl ring can optionally be replaced with a substituent of the formula —(CRR')$_s$—X—(CR"R'")$_d$—, where s and d are independently integers from 0 to 3, and X is —O—, —NR'—, —S—, —S(O)—, —S(O)$_2$—, or —S(O)$_2$NR'—, wherein the substituents R, R', R" and R'" in each of the formulas above are independently selected from hydrogen and (C$_1$-C$_6$)alkyl.

The terms "halo" or "halogen," by themselves or as part er substituent, mean at least one of fluorine, chlorine, bromine and iodine.

By "haloalkyl" is meant an alkyl radical, wherein alkyl is as defined above and wherein at least one hydrogen atom is replaced by a halogen atom. The term "haloalkyl," is meant to include monohaloalkyl and polyhaloalkyl. For example, the term "halo(C$_1$-C$_4$)alkyl" or "(C$_1$-C$_4$)haloalkyl" is mean to include, but not limited to, chloromethyl, 1-bromoethyl, fluoromethyl, difluoromethyl, trifluoromethyl, 1,1,1-trifluoroethyl and 4-chlorobutyl, 3-bromopropyl.

As used herein, the term "acyl" describes the group —C(O)R$^e$, wherein R$^e$ is selected from hydrogen, C$_1$-C$_{24}$ alkyl (e.g., C$_1$-C$_{10}$ alkyl or C$_1$-C$_6$ alkyl), C$_1$-C$_{24}$ alkenyl (e.g., C$_1$-C$_{10}$ alkenyl or C$_1$-C$_6$ alkenyl), C$_1$-C$_{24}$ alkynyl (e.g., C$_1$-C$_{10}$ alkenyl or C$_1$-C$_6$ alkynyl), C$_3$-C$_{10}$ cycloalkyl, C$_1$-C$_{24}$ heteroalkyl (e.g., C$_1$-C$_{10}$ heteroalkyl or C$_1$-C$_6$ heteroalkyl), C$_3$-C$_{10}$ heterocycloalkyl, aryl, heteroaryl, arylalkyl and heteroarylalkyl. In one embodiment, R$^e$ is not hydrogen.

By "alkanoyl" is meant an acyl radical —C(O)—Alk-, wherein Alk is an alkyl radical as defined herein. Examples of alkanoyl include acetyl, propionyl, butyryl, isobutyryl, valeryl, isovaleryl, 2-methyl-butyryl, 2,2-dimethylpropionyl hexanoyl, heptanoyl, octanoyl and the like.

As used herein, the term "heteroatom" includes oxygen (O), nitrogen (N), sulfur (S), silicon (Si), boron (B) and phosphorus (P). In one embodiment, heteroatoms are O, S and N.

By "oxo" is meant the group =O.

By "sulfonamide" is meant a group having the formula —S(O)$_2$NRR, where each of the R variables are independently selected from the variables listed below for R.

The symbol "R" is a general abbreviation that represents a substituent group as described herein. Exemplary substituent groups include alkyl, alkenyl, alkynyl, cycloalkyl, heteroalkyl, aryl, heteroaryl and heterocycloalkyl groups, each as defined herein.

As used herein, the terms "aromatic ring" and "non-aromatic ring" are consistent with the definitions commonly used in the art. For example, aromatic rings include phenyl and pyridyl. Non-aromatic rings include cyclohexanes.

As used herein, the term "fused ring system" means at least two rings, wherein each ring has at least 2 atoms in common with another ring. "Fused ring systems can include aromatic as well as non-aromatic rings. Examples of "fused ring systems" are naphthalenes, indoles, quinolines, chromenes and the like. Likewise, the term "fused ring" refers to a ring that has at least two atoms in common with the ring to which it is fused.

The term compound and molecule are urged interchangeably. Other forms contemplated by the invention when the word "molecule" or "compound" is employed are salts, prodrugs, solvates, tautomers, stereoisomers and mixtures of stereoisomers. The compounds of this invention can be in the form of a pharmaceutically acceptable salt.

The term "pharmaceutically acceptable salt" means a salt of the compounds of the present disclosure, which may be prepared with relatively nontoxic acids or bases, depending on the particular substituents found on the compounds described herein. When compounds of the present disclosure contain relatively acidic functionalities (e.g., —COOH group), base addition salts can be obtained by contacting the compound (e.g., neutral form of such compound) with a sufficient amount of the desired base, either neat or in a suitable inert solvent. Examples of pharmaceutically acceptable base addition salts include lithium, sodium, potassium, calcium, ammonium, organic amino, magnesium and aluminum salts and the like. When compounds of the present disclosure contain relatively basic functionalities (e.g., amines), acid addition salts can be obtained, e.g., by contacting the compound (e.g., neutral form of such compound) with a sufficient amount of the desired acid, either neat or in a suitable inert solvent. Examples of pharmaceutically acceptable acid addition salts include those derived from inorganic acids like hydrochloric, trifluoroacetic, hydrobromic, nitric, carbonic, monohydrogencarbonic, phosphoric, diphosphoric, monohydrogenphosphoric, dihydrogenphosphoric, sulfuric, monohydrogensulfuric, hydriodic and the like, as well as the salts derived from relatively nontoxic organic acids like formic, acetic, propionic, isobutyric, malic, maleic, malonic, benzoic, succinic, suberic, fumaric, lactic, mandelic, phthalic, benzenesulfonic, p-tolylsulfonic, citric, tartaric, methanesulfonic, 2-hydroxyethylsulfonic, salicylic, stearic and the like. Also included are salts of amino acids such as arginate and the like, and salts of organic acids like glucuronic or galactunoric acids and the like (see, for example, Berge et al., *Journal of Pharmaceutical Science*, 1977, 66: 1-19). Certain specific compounds of the present disclosure contain both, basic and acidic, functionalities that allow the compounds to be converted into either base or acid addition salts.

The neutral forms of the compounds can be regenerated, for example, by contacting the salt with a base or acid and isolating the parent compound in the conventional manner. The parent form of the compound can differ from the various salt forms in certain physical properties, such as solubility in polar solvents, but otherwise the salts are equivalent to the parent form of the compound for the purposes of the present disclosure.

When a substituent includes a negatively charged oxygen atom "O$^-$", e.g., in "—COO$^-$", then the formula is meant to optionally include a proton (i.e., H+) or an organic or inorganic cationic counterion (e.g., Na+). In one example, the resulting salt form of the compound is pharmaceutically acceptable. Further, when a compound of the present disclosure includes an acidic group, such as a carboxylic acid group, e.g., written as the substituent "—COOH", "—CO₂H" or "—C(O)₂H", then the formula is meant to optionally include the corresponding "de-protonated" form of that acidic group, e.g., "—COO⁻", "—CO₂⁻" or "—C(O)₂⁻", respectively.

In addition to salt forms, the present disclosure provides compounds, which are in a prodrug form. Prodrugs of the compounds described herein are those compounds that readily undergo chemical changes under physiological conditions to provide the compounds of the present disclosure. Non-limiting examples of "pharmaceutically acceptable derivative" or "prodrug" include pharmaceutically acceptable esters, phosphate esters or sulfonate esters thereof as well as other derivatives of a compound of this present disclosure which, upon administration to a recipient, is capable of providing, either directly or indirectly, a compound of this present disclosure. In one embodiment, derivatives or prodrugs are those that increase the bioavailability of the compounds of this present disclosure when such compounds are administered to a mammal (e.g., by allowing an orally administered compound to be more readily absorbed into the blood stream) or which enhance delivery of the parent compound to a biological compartment (e.g., the brain or lymphatic system) relative to the parent species.

Prodrugs include a variety of esters (i.e., carboxylic acid ester). Ester groups, which are suitable as prodrug groups are generally known in the art and include benzyloxy, di($C_1$-$C_6$)alkylaminoethyloxy, acetoxymethyl, pivaloyloxymethyl, phthalidoyl, ethoxycarbonyloxyethyl, 5-methyl-2-oxo-1,3-dioxol-4-yl methyl, and ($C_1$-$C_6$)alkoxy esters, optionally substituted by N-morpholino and amide-forming groups such as di($C_1$-$C_6$)alkylamino. For example, ester prodrug groups include $C_1$-$C_6$ alkoxy esters. Those skilled in the art will recognize various synthetic methodologies that may be employed to form pharmaceutically acceptable prodrugs of the compounds of the present disclosure (e.g., via esterification of a carboxylic acid group).

In an exemplary embodiment, the prodrug is suitable for treatment/prevention of those diseases and conditions that require the drug molecule to cross the blood brain barrier. In one embodiment, the prodrug enters the brain, where it is converted into the active form of the drug molecule. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir together with a suitable enzyme or other chemical reagent.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure can exist in multiple crystalline or amorphous forms ("polymorphs"). In general, all physical forms are of use in the methods contemplated by the present disclosure and are intended to be within the scope of the present disclosure. "Compound or a pharmaceutically acceptable salt, hydrate, polymorph or solvate of a compound" intends the inclusive meaning of "and/or", in that materials meeting more than one of the stated criteria are included, e.g., a material that is both a salt and a solvate is encompassed.

The term "solvate" is intended to refer to a complex formed by combination of solute molecules or ions with solvent molecules. The solvent can be an organic compound, an inorganic compound, or a mixture of both. Exemplary solvents for the formation of solvates include, but are not limited to, methanol, N,N-dimethylformamide (DMF), tetrahydrofuran, dimethylsulfoxide, toluene, and water. In one embodiment, solvents having a higher boiling point, such as for example, DMF, DMA, and the like.

The compounds of the present disclosure can contain unnatural proportions of atomic isotopes at one or more of the atoms that constitute such compounds. For example, the compounds can be radiolabeled with radioactive isotopes, such as for example tritium ($^3$H), iodine-125 ($^{125}$I) or carbon-14 ($^{14}$C). All isotopic variations of the compounds of the present disclosure, whether radioactive or not, are intended to be encompassed within the scope of the present disclosure. Compounds described herein, in which one or more of the hydrogen atoms are replaced with another stable isotope of hydrogen (i.e., deuterium) or a radioactive isotope (i.e., tritium), are part of this disclosure.

The term "tautomer" is intended to refer to alternate forms of a compound that differ in the position of a proton, such as enol keto and imine enamine tautomers, or the tautomeric forms of heteroaryl groups containing a ring atom attached to both a ring NH moiety and a ring =N moiety such as pyrazoles, imidazoles, benzimidazoles, triazoles, and tetrazoles.

The term "amino acid" within the scope of the present invention means alpha-amino acid unless otherwise specified. The term "amino acid" includes naturally occurring, and non-naturally occurring (i.e., non-proteinogenic) amino acids. The one and three letter abbreviations for naturally occurring amino acids are used herein (see, e.g., Lehninger, Biochemistry, 2nd ed., Worth Publishers, New York, 1995: 71-92). The term "amino acid" also includes stereoisomers (for example D-amino acids) and modifications of naturally occurring amino acids (e.g., alpha-N-alkylated amino acids; modified phenylalanine or tyrosine derivatives, and the like).

Conventionally, L-amino acids are designated using upper case letters (e.g., the upper case letter "C" refers to L-cysteine), and D-amino acids are designated in lower case (e.g., the lower case letter "c" refers to D-cysteine). Where no indication of the isomer is given, both isomers are intended. For example, when the amino acid is referred to with its name, both L- and D-amino acids are included (e.g., the term "cysteine" includes both, L-cysteine and D-cysteine).

The term "modified amino acid" refers to amino acids, which are altered with respect to their original structure, e.g., by substitution. Examples of modified amino acids include, e.g., alpha-N-alkylated amino acids, tyrosine derivatives (e.g., those in which the hydroxyl group is converted to an ether or ester group, or those in which the phenyl ring is substituted, e.g., with a halogen atom), phenylalanine derivatives (e.g., those in which the phenyl ring is substituted, e.g., with a halogen atom), lysine derivatives (e.g., those in which the NH₂ group is converted to an amide group or sulfonamide group), and amino acids, in which a carboxylic acid group is derivatized, e.g., esterified, converted to an amide group, and the like. In one example, the modified amino acid is a tyrosine residue modified at the hydroxyl group and having the formula Y—OR″, wherein R″ is selected from straight or branched alkyl, e.g., ($C_1$-$C_{10}$)alkyl, straight or branched heteroalkyl, e.g., ($C_1$-$C_{10}$)heteroalkyl comprising from 1 to 5 heteroatoms selected from O, S and N, and a water-soluble polymer (e.g., a PEG moiety). In another example, the modified tyrosine is methoxy-tyrosine (Y—OMe).

Introduction of at least one non-natural amino acid, or modification of at least one amino acid can improve the stability or solubility of a peptide. It can further increase the resistance to protease degradation or alter the biological (e.g., in vitro biological) activity of the peptide.

Other modified and non-proteinogenic amino acids useful in the present invention are described, e.g., in Grant, Synthetic Peptides: A Users Guide, Oxford University Press, 1992, which is incorporated herein by reference in its entirety.

Non-proteinogenic amino acids may include but are not limited to norvaline (Nva), norleucine (Nle), 4-aminobutyric acid (gamma-Abu), 2-aminoisobutyric acid (Aib), 6-aminohexanoic acid (gamma-Ahx), ornithine (Orn), hydroxyproline (Hyp), sarcosine, citrulline, cysteic acid (Coh), cyclohexylalanine, methioninesulfoxide (Meo), methioninesulfone (Moo), homoserinemethylester propargylglycine (Eag), 5-fluorotryptophan (5Fw), 6-fluorotryptophan (6Fw), 3',4'-dimethoxtphenyl-alanine (Ear), 3',4'-difluorophenylalanine (Dff), 4'-fluorophenyl-alanine (Pff), 1-naphthyl-alanine (1-Nal), 1-naphthyl-alanine, 1-methyltryptophan (1Mw), penicillamine (Pen), homoserine (HSe). Further, such amino acids may include but are not limited to, alpha-amino isobutyric acid, t-butylglycine, t-butylalanine, phenylglycine (Phg), benzothienylalanine (Bta), L-homocysteine (L-Hcys), N--methyl-phenylalanine (NMF), 2-thienylalanine (Thi), 3,3-diphenylalanine (Ebw), homophenylalanine (Hfe), s-benzyl-L-cysteine (Ece) or cyclohexylalanine (Cha). These and other non-proteinogenic amino acids may exist as D- or L-isomers.

The term "hydrophobic amino acids" or "amino acids having a hydrophobic side chain" means any amino acid with an alkyl side chains (e.g., A, L, I, V, and P), any amino acid with an aromatic side chains (e.g., F, W, and Y), and other amino acids having a non-polar side chain, e.g., those containing an ether or thioether group (i.e., M), or having a side chain, which is not ionized under physiological conditions. The term "hydrophobic amino acid" includes glycine and amino acids having a cycloalkyl side chain, such as P.

The term "polar uncharged amino acid," or "amino acid having a polar uncharged side chain," means any amino acid having a side chain incorporating a functional group (e.g., —OH or —SH group, amide —C(O)NH$_2$ group, etc.), wherein the functional group is not ionized under physiological conditions.

The term "hydrophobic or polar uncharged amino acid", or "amino acid having a hydrophobic or polar uncharged side chain", means any amino acid, which is not ionized under physiological conditions (i.e., other than basic and acidic amino acids). Exemplary "amino acids having a hydrophobic or polar uncharged side chain" include G, A, V, I, L, M, F, W, Y, S, T, N, Q and P (e.g., G, A, V, I, L, M, F, W, Y, S, T, N, and Q).

The term "acidic amino acid," or "amino acid having an acidic side chain," or any variation thereof, means any amino acid having a side chain with an ionizable (negatively charged) group, such as a carboxylic acid group. Examples of "acidic amino acids" include D and E.

The term "basic amino acid," or "amino acid having a basic side chain," or any variation thereof, means any amino acid having a side chain with an ionizable (positively charged) group, such as a primary or secondary amino group. Examples of "basic amino acids" include K, R, and H.

The term "peptide" or "peptide sequence" includes molecules in which amino acids are joined by peptide (—CO—NH—) linkages (also referred to as amide bonds).

"Polypeptide" and "protein" are used interchangeably herein and refer to a polymeric compound comprised of covalently linked amino acid residues. In one example, the protein or polypeptide incorporates at least 500 amino acids. The term "polypeptide" as used herein further refers to a blood coagulation factor or a platelet targeting moiety as described herein.

The term "inverso-variant" of a peptide as used in this application means an enantiomer or mirror-image of a peptide. An "inverso-variant" is a peptide having the same amino acid sequence as its corresponding native peptide, but includes the corresponding D-amino acid for each L-amino acid in the native peptide, and the corresponding L-amino acid for each D-amino acid present in the native peptide (i.e., the chirality for each amino acid is inverted). For example, the inverso variant of the native peptide kCLASYC(SEQ ID NO: 892) is Kclasyc.

The term "retro-variant" of a peptide, means a peptide having the same amino acid sequence but in which the amino acids are assembled in opposite direction (reverse order) to the native peptide. For example, the retro-variant of the native peptide kCLASYC (SEQ ID NO: 892) is CYSALCk (SEQ ID NO: 894).

The term "retro-inverso variant" as used in this application means a retro-peptide as described herein, which is also reversed in its amino acid sequence as in a retro-variant described herein. Thus, a "retro-inverso variant" of a peptide refers to a peptide is made up of amino acid residues which are assembled in the opposite direction and which have inverted chirality with respect to the native peptide to which it is retro-inverso modified. For example, the retro-inverso variant of the peptide kCLASYC (SEQ ID NO: 892) is cysalcK (SEQ ID NO: 894).

A retro-inverso variant can maintain the topology of the side chains as in the native peptide sequence. For example, Guichard et al. (1994) Proc. Arad. Acad. Sci. USA 91:9765-9769 described that a retro-inverso peptide mimicked the structure and antigenic activity of the natural L-peptide IRGERA, but not of the D- and retro peptides. Such retro-inverso peptidomimetics may be made using methods known in the art, for example such as those described in Meziere et al. (1997) J. Immunol. 159, 3230-3237, incorporated herein by reference in its entirety. Partial retro-inverso peptide analogues are polypeptides in which only part of the sequence is reversed and replaced with enantiomeric amino acid residues. Processes for making such analogues are described, e.g., in European Patent EP0097994 to Pessi et al., which is incorporated by reference herein in its entirety.

Conventionally, where the amino acids are joined by peptide bonds, a peptide is represented such that the amino group at the N-terminus appears to the left and the carboxyl group at the C-terminus to the right. Peptides and peptide derivatives according to the present invention are represented in this manner.

A "peptide derivative" contains a modification of one or more amino acid residues or a linker group or other covalently linked group. Examples of amino acid derivatives include N-acyl derivatives of the amino terminal or of another free amino group, esters of the carboxyl terminal or of another free carboxyl or hydroxy group, amides of the carboxyl terminal or of another free carboxyl group produced by reaction with ammonia or with a suitable amine, glycosylated derivatives, hydroxylated derivatives, nucleotidylated derivatives, ADP-ribosylated derivatives, pegylated derivatives, phosphorylated derivatives, biotinylated derivatives, derivatives conjugated to an antibody or antibody fragment, albumin, transferrin, HES, and the like. Also included among the chemical derivatives are those obtained by modification of the peptide bond —CO—NH—, for example by reduction to —CH₂—NH— or alkylation to —CO—N(alkyl)-. Other derivativs include amide bond bioisosteres, ketomethylene and hydroxyethylene derivatives, as well as thioesters, thioamides and the like.

Other modifications include, e.g., acetylation, acylation, ADP-ribosylation, amidation, covalent attachment of flavin, covalent attachment of a home moiety, covalent attachment of a nucleotide or nucleotide derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, halogenation (e.g., iodination), methylation, myristoylation, oxidation, pegylation (Mei et al. *Blood* 116:270-79 (2010), which is incorporated herein by reference in its entirety), proteolytic processing, phosphorylation, prenylation, racemization, selenoylation, sulfation, transfer-RNA mediated addition of amino acids to proteins such as arginylation, and ubiquitination.

In one example, derivatisation is C-terminal amidation. C-terminal amidation of a peptide removes the negative charge of the C-terminal carboxyl group. Peptide derivatives having a C-terminal amide can be represented with "NH₂" at the C-terminus, for example KLTCLASYCWLFE—NH₂ (SEQ TD NO: 895). Another derivatisation is N-terminal acetylation. This removes the positive charge at the N-terminus. Blocking of the C- or N-terminus, such as by C-terminal amidation or N-terminal acetylation, may improve proteolytic stability due to reduced susceptibility to exoproteolytic digestion.

"Administering," as used herein, means to give a pro-coagulant compound of the present disclosure, or pharmaceutical composition containing a pro-coagulant compound of the present disclosure, to a subject (e.g., human subject) in need thereof via a pharmaceutically acceptable route of administration. In some embodiments, the route of administration is parenteral. In one embodiment, the pro-coagulant compound of the present disclosure is administered subcutaneously. In some embodiments, the route of administration is intravenous, e.g., intravenous injection or intravenous infusion. In other embodiments, the route of administration is selected from subcutaneous, intramuscular, oral, nasal, and pulmonary administration. In other embodiments, the route of administration is selected from subcutaneous and intravenous. The pro-coagulant compounds of the invention can be administered as part of a pharmaceutical composition comprising at least one pharmaceutically acceptable carrier.

"Area under the plasma concentration versus time curve (AUC)," as used herein, is the same as the term of art in pharmacology, and is based upon the rate and extent of absorption of the compound following administration. AUC is determined over a specified time period, such as 12, 18, 24, 36, 48, or 72 hours, or for infinity using extrapolation based on the slope of the curve. Unless otherwise specified herein, AUC is determined for infinity. The determination of AUC may be carried out in a single subject, or in a population of subjects for which the average is calculated.

"Equivalent amount," as used herein, means the same amount of FVIII activity as expressed in International Units, which is independent of molecular weight of the polypeptide in question. One International Unit (IU) of FVIII activity corresponds approximately to the quantity of FVIII in one milliliter of normal human plasma. Several assays are available for measuring FVIII activity, including the European Pharmacopoeia chromogenic substrate assay and a one stage clotting assay.

"Dosing interval," as used herein, means the amount of time that elapses between multiple doses being administered to a subject. The comparison of dosing interval may be carried out in a single subject or in a population of subjects and then the average obtained in the population may be calculated.

"On-demand treatment," as used herein, means treatment that is intended to take place over a short course of time and is in response to an existing condition, such as a bleeding episode, or a perceived need such as planned surgery. Conditions that may require on-demand treatment include, e.g., a bleeding episode, hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, or bleeding in the illiopsoas sheath. The subject may be in need of surgical prophylaxis, peri-operative management, or treatment for surgery. Such surgeries include, e.g., minor surgery, major surgery, tooth extraction, tonsillectomy, inguinal herniotomy, synovectomy, total knee replacement, craniotomy, osteosynthesis, trauma surgery, intracranial surgery, intra-abdominal surgery, intrathoracic surgery, or joint replacement surgery.

Preferably, on-demand treatment resolves greater than 80% (greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98%, greater than 99%, or 100%) or 80-100%, 80-90%, 85-90%, 90-100%, 90-95%, or 95-100% of bleeds (e.g., spontaneous bleeds) in a single dose. Preferably, greater than 80% (greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98%, or 100%) or 80-100%, 80-90%, 85-90%, 90-100%, 90-95%, or 95-100% of bleeding episodes are rated excellent or good by physicians after on-demand treatment. Preferably, greater than 5%, (greater than 6%, greater than 7%, greater than 8%, greater than 9%, greater than 10%, greater than 11%, greater than 12%, greater than 13%, greater than 14%, greater than 15%, greater than 16%, greater than 17%, greater than 18%, greater than 19%, greater than 20%), or 5-20%, 5-15%, 5-10%, 10-20%, or 10-15% of bleeding episodes are rated as fair by physicians after on-demand treatment.

"Prophylactic treatment," as used herein, means administering a pro-coagulant compound of the present disclosure to a subject over a course of time to increase the level of activity in a subject's plasma. Preferably, the increased level is sufficient to decrease the incidence of spontaneous bleeding or to prevent bleeding, e.g., in the event of an unforeseen injury. Preferably, during prophylactic treatment, the plasma protein level in the subject does not fall below the baseline level for that subject, or below the level that characterizes severe hemophilia.

Preferably, the prophylaxis regimen is "tailored" to the individual patient, preferably by determining PK data for each patient and administering the pro-coagulant compound of the present disclosure at a dosing interval that maintains a trough level equivalent to 1-3% FVIII activity. Adjustments may be made when a subject experiences unacceptable bleeding episodes defined as ≥2 spontaneous bleeding episodes over a rolling two-month period. In this case, adjustment will target trough levels of 3-5%. Preferably, prophylactic treatment results in prevention and control of bleeding, sustained control of bleeding, sustained protection from bleeding, and/or sustained benefit. Preferably, prophylaxis results in no spontaneous bleeding episodes within about 24, 36, 48, 72, or 96 hours (e.g., 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, or 96 hours, preferably within 72 hours), after treatment (e.g., the last injection). Preferably, prophylaxis results in greater than 30% (e.g., greater than 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90%, preferably greater than 50%), mean reduction in annualized bleeding episodes (e.g., with once weekly dosing).

"Subject," as used herein means a human or a non-human mammal. Non-human mammals include, e.g., mice, dogs, primates, monkeys, cats, horses, cows, pigs, and other domestic animals and small animals. In one embodiment, the "subject" is a human patient.

"Therapeutic dose," as used herein, means a dose that achieves a therapeutic goal, as described herein. The therapeutic doses that may be used in the methods of the invention are about 10-100 mg/kg, more specifically, 10-20, 20-30, 30-40, 40-50, 50-60, 60-70, 70-80, 80-90, or 90-100 mg/kg, and more specifically, 10, 15, 20, 25, 30, 35, 40, 45, 50, 55, 60, 65, 70, 75, 80, 85, 90, 95, or 100 mg/kg.

Additional therapeutic doses that may be used in the methods of the invention are about 10 to about 150 mg/kg, more specifically, about 100-110, 110-120, 120-130, 130-140, 140-150 mg/kg, and more specifically, about 110, 115, 120, 125, 130, 135, 140, 145, or 150 mg/kg.

"About," as used herein for a range, modifies both ends of the range. Thus, "about 10-20" means "about 10 to about 20."

By "procoagulant activity" is meant the ability to promote thrombin generation and/or fibrin deposition in a suitable test system. Exemplary assays useful to measure the procoagulant activity of a compound or conjugate of the present are described herein and include, e.g., FXa generation assays (see, e.g., Example 2), thrombin generation assays (see, e.g., Example 3), and ROTEM assays (see, e.g., Example 4).

The term "antibody variant" or "modified antibody" includes an antibody which does not occur in nature and which has an amino acid sequence or amino acid side chain chemistry which differs from that of a naturally-derived antibody by at least one amino acid or amino acid modification as described herein. As used herein, the term "antibody variant" includes synthetic forms of antibodies which are altered such that they are not naturally occurring, e.g., antibodies that comprise at least two heavy chain portions but not two complete heavy chains (such as, domain deleted antibodies or minibodies); multispecific forms of antibodies (e.g., bispecific, trispecific, etc.) altered to bind to two or more different antigens or to different epitopes on a single antigen); heavy chain molecules joined to scFv molecules; single-chain antibodies; diabodies; triabodies; and antibodies with altered effector function and the like.

As used herein the term "scFv molecule" includes binding molecules which consist of one light chain variable domain (VL) or portion thereof, and one heavy chain variable domain (VH) or portion thereof, wherein each variable domain (or portion thereof) is derived from the same or different antibodies. scFv molecules preferably comprise an scFv linker interposed between the VH domain and the VL domain. ScFv molecules are known in the art and are described, e.g., in U.S. Pat. No. 5,892,019, Ho et al. 1989. Gene 77:51; Bird et al. 1988 Science 242:423; Pantoliano et al. 1991. Biochemistry 30:10117; Milenic et al. 1991. Cancer Research 51:6363: Takkinen et al. 1991. Protein Engineering 4:837.

A "scFv linker" as used herein refers to a moiety interposed between the VL and VH domains of the scFv. scFv linkers preferably maintain the scFv molecule in a antigen binding conformation. In one embodiment, a scFv linker comprises or consists of an scFv linker peptide. In certain embodiments, a scFv linker peptide comprises or consists of a gly-ser polypeptide linker. In other embodiments, a scFv linker comprises a disulfide bond.

As used herein, the term "gly-ser polypeptide linker" refers to a peptide that consists of glycine and serine residues. An exemplary gly/ser polypeptide linker comprises the amino acid sequence (Gly4 Ser)n. In one embodiment, n=1. In one embodiment, n=2. In another embodiment, n=3, (Gly4 Ser)3. In another embodiment, n=4, i.e., (Gly4 Ser)4. In another embodiment, n=5. In yet another embodiment, n=6. In another embodiment, n=7. In yet another embodiment, n=8. In another embodiment, n=9. In yet another embodiment, n=10. Another exemplary gly/ser polypeptide linker comprises the amino acid sequence Ser(Gly4Ser)n (SEQ ID NO: 883). In one embodiment, n=1. In one embodiment, n=2. In a preferred embodiment, n=3. In another embodiment, n=4. In another embodiment, n=5. In yet another embodiment, n=6.

The term "glycosylation" refers to the covalent linking of one or more carbohydrates to a polypeptide. Typically, glycosylation is a posttranslational event which can occur within the intracellular milieu of a cell or extract therefrom. The term glycosylation includes, for example, N-linked glycosylation (where one or more sugars are linked to an asparagine residue) and/or O-linked glycosylation (where one or more sugars are linked to an amino acid residue having a hydroxyl group (e.g., serine or threonine). In one embodiment, a molecule of the invention is glycosylated. In another embodiment, a molecule of the invention is aglycosylated. In yet another embodiment, a molecule of the invention has reduced glycosylation as compared to that in a wild type Fc region.

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the CH1 and CL regions are linked by native disulfide bonds and the two heavy chains are linked by two native disulfide bonds at positions corresponding to 239 and 242 using the Kabat numbering system (position 226 or 229, EU numbering system).

The term "vector" or "expression vector" is used herein to mean vectors used in accordance with the present invention as a vehicle for introducing into and expressing a desired polynucleotide in a cell. As known to those skilled in the art, such vectors may easily be selected from the group consisting of plasmids, phages, viruses and retroviruses. In general, vectors compatible with the instant invention will comprise a selection marker, appropriate restriction sites to facilitate cloning of the desired gene and the ability to enter and/or replicate in eukaryotic or prokaryotic cells.

Numerous expression vector systems may be employed to produce the conjugates of the invention. For example, one class of vector utilizes DNA elements which are derived from animal viruses such as bovine papilloma virus, polyoma virus, adenovirus, vaccinia virus, baculovirus, retroviruses (RSV, MMTV or MOMLV) or SV40 virus. Additionally, cells which have integrated the DNA into their chromosomes may be selected by introducing one or more markers which allow selection of transfected host cells. The marker may provide for prototrophy to an auxotrophic host, biocide resistance (e.g., antibiotics) or resistance to heavy metals such as copper. The selectable marker gene can either be directly linked to the DNA sequences to be expressed, or introduced into the same cell by cotransformation. In one embodiment, an inducible expression system can be employed. Additional elements may also be needed for optimal synthesis of mRNA. These elements may include signal sequences, splice signals, as well as transcriptional promoters, enhancers, and termination signals. In one embodiment, a secretion signal, e.g., any one of several well characterized bacterial leader peptides (e.g., pelB, phoA, or ompA), can be fused in-frame to the N terminus of a polypeptide of the invention to obtain optimal secretion of the polypeptide. (Lei et al. (1988), Nature, 331:543; Better et al. (1988) Science, 240:1041; Mullinax et al., (1990). PNAS, 87:8095).

The term "host cell" refers to a cell that has been transformed with a vector constructed using recombinant DNA techniques and encoding at least one heterologous gene. In descriptions of processes for isolation of proteins from recombinant hosts, the terms "cell" and "cell culture" are used interchangeably to denote the source of protein unless it is clearly specified otherwise. In other words, recovery of protein from the "cells" may mean either from spun down whole cells, or from the cell culture containing both the medium and the suspended cells. The host cell line used for protein expression is most preferably of mammalian origin; those skilled in the art are credited with ability to preferentially determine particular host cell lines which are best suited for the desired gene product to be expressed therein. Exemplary host cell lines include, but are not limited to, DG44 and DUXB11 (Chinese Hamster Ovary lines, DHFR minus), HELA (human cervical carcinoma), CVI (monkey kidney line), COS (a derivative of CVI with SV40 T antigen), R1610 (Chinese hamster fibroblast) BALBC/3T3 (mouse fibroblast), HAK (hamster kidney line), SP2/O (mouse myeloma), P3x63-Ag3.653 (mouse myeloma), BFA-1c1BPT (bovine endothelial cells), RAJI (human lymphocyte) and 293 (human kidney). CHO cells are particularly preferred. Host cell lines are typically available from commercial services, the American Tissue Culture Collection or from published literature. The conjugates of the invention can also be expressed in non-mammalian cells such as bacteria or yeast or plant cells. In this regard it will be appreciated that various unicellular non-mammalian microorganisms such as bacteria can also be transformed; i.e. those capable of being grown in cultures or fermentation. Bacteria, which are susceptible to transformation, include members of the enterobacteriaceae, such as strains of *Escherichia coli* or *Salmonella*; Bacillaceae, such as *Bacillus subtilis*; Pneumococcus; Streptococcus, and Haemophilus influenzae. It will further be appreciated that, when expressed in bacteria, the polypeptides typically become part of inclusion bodies. The polypeptide conjugates must be isolated, purified and then assembled into functional molecules.

In addition to prokaryotes, eukaryotic microbes may also be used. *Saccharomyces cerevisiae*, or common baker's yeast, is the most commonly used among eukaryotic microorganisms although a number of other strains are commonly available including *Pichia pastoris*. For expression in *Saccharomyces*, the plasmid YRp7, for example, (Stinchcomb et al., (1979), Nature, 282:39; Kingsman et al., (1979), Gene, 7:141; Tschemper et al., (1980), Gene, 10:157) is commonly used. This plasmid already contains the TRP1 gene which provides a selection marker for a mutant strain of yeast lacking the ability to grow in tryptophan, for example ATCC No. 44076 or PEP4-1 (Jones, (1977), Genetics, 85:12). The presence of the trp1 lesion as a characteristic of the yeast host cell genome then provides an effective environment for detecting transformation by growth in the absence of tryptophan.

As used herein, the term "cleavage site" refers to a site recognized by an enzyme. In one embodiment, such an enzyme is one that is activated during the clotting cascade, such that cleavage of such sites occurs at the site of clot formation. Exemplary such sites include those recognized by thrombin, Factor XIa or Factor Xa In constructs that include more than one processing or cleavage site, it will be understood that such sites may be the same or different.

"Blood coagulation factor" or "coagulation factor" as used herein means FVIIa, FVIII, or FIX.

"Culture," "to culture" and "culturing," as used herein, means to incubate cells under in vitro conditions that allow for cell growth or division or to maintain cells in a "Polynucleotide" and "nucleic acid" are used interchangeably and refer to a polymeric compound comprised of covalently linked nucleotide residues. Polynucleotides may be DNA, cDNA, RNA, single stranded, or double stranded, vectors, plasmids, phage, or viruses.

"Variant," as used herein, refers to a polynucleotide or polypeptide differing from the original polynucleotide or polypeptide, but retaining essential properties thereof, e.g., FVIII coagulant activity or Fc (FcRn binding) activity. Generally, variants are overall closely similar, and, in many regions, identical to the original polynucleotide or polypeptide. Variants include, e.g., polypeptide and polynucleotide fragments, deletions, insertions, and modified versions of original polypeptides.

Naturally occurring variants are called "allelic variants," and refer to one of several alternate forms of a gene occupying a given locus on a chromosome of an organism (Genes II, Lewin, B., ed., John Wiley Sons, New York (1985)). These allelic variants can vary at either the polynucleotide and/or polypeptide level and are included in the present invention. Alternatively, non-naturally occurring variants may be produced by mutagenesis techniques or by direct synthesis.

Using known methods of protein engineering and recombinant DNA technology, variants may be generated to improve or alter the characteristics of the polypeptides. For instance, one or more amino acids can be deleted from the N-terminus or C-terminus of the secreted protein without substantial loss of biological function. The authors of Ron et al., *J. Biol. Chem.* 268: 2984-2988 (1993), incorporated herein by reference in its entirety, reported variant KGF proteins having heparin binding activity even after deleting 3, 8, or 27 amino-terminal amino acid residues. Similarly, Interferon gamma exhibited up to ten times higher activity after deleting 8-10 amino acid residues from the carboxy terminus of this protein. (Dobeli et al., J. Biotechnology 7:199-216 (1988), incorporated herein by reference in its entirety.)

Moreover, ample evidence demonstrates that variants often retain a biological activity similar to that of the naturally occurring protein. For example, Gayle and coworkers (J. Biol. Chem 268:22105-22111 (1993), incorporated herein by reference in its entirety) conducted extensive mutational analysis of human cytokine IL-1a. They used random mutagenesis to generate over 3,500 individual IL-1a mutants that averaged 2.5 amino acid changes per variant over the entire length of the molecule. Multiple mutations were examined at every possible amino acid position. The investigators found that "most of the molecule could be altered with little effect on either binding or biological activity." In fact, only 23 unique amino acid sequences, out of more than 3,500 nucleotide sequences examined, produced a protein that significantly differed in activity from wild-type.

As stated above, polypeptide variants include, e.g., modified polypeptides. Modifications include, e.g., acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation (Mei et al., Blood 116:270-79 (2010), which is incorporated herein by reference in its entirety), proteolytic processing, phosphorylation, prenylation, racemization, selenoylation, sulfation, transfer-RNA mediated addition of amino acids to proteins such as arginylation, and ubiquitination.

By a nucleic acid having a nucleotide sequence at least, for example, 95% "identical" to a reference nucleotide sequence, it is intended that the nucleotide sequence of the nucleic acid is identical to the reference sequence except that the nucleotide sequence may include up to five point mutations per each 100 nucleotides of the reference nucleotide sequence. In other words, to obtain a nucleic acid having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, (indels) or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular nucleic acid molecule or polypeptide is at least 85%, 90%, 95%, 96%, 97%, 98% or 99% identical to a nucleotide sequence or polypeptide of the present invention can be determined conventionally using known computer programs. A preferred method for determining the best overall match between a query sequence (reference or original sequence) and a subject sequence, also referred to as a global sequence alignment, can be determined using the FASTDB computer program based on the algorithm of Brutlag et al. (Comp. App. Biosci. (1990) 6:237-245), which is herein incorporated by reference in its entirety. In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Scor=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are made for the purposes of the present invention.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are to made for the purposes of the present invention.

Having now described the present invention in detail, the same will be more clearly understood by reference to the following examples, which are included herewith for purposes of illustration only and are not intended to be limiting of the invention. All patents and publications referred to herein are expressly incorporated by reference.

EXAMPLE 1

Preparation of Compounds

Compounds of the present disclosure (i.e., peptides) were synthesized by solid phase peptide synthesis using 9-fluorenylmethoxycarbonyl/tertiary-butyl (Fmoc/tBu) chemistry. Heating was accomplished using a microwave oven or other means. In most cases, the peptides were synthesized in 0.1 mmol scale using NovaPEG Rink Amide resin (35 mL reaction vessel). Standard methods for resin load, amino acid coupling, Fmoc deprotection and washing steps were performed on a CEM Liberty peptide synthesizer, whereas the trifluoroacetic acid (TEA) cleavage of the peptide was performed manually. Briefly, 5 eq. Fmoc protected amino acids dissolved in N,N-dimethylformamide (DMF) were linked subsequently to the resin in the presence of 5 eq. 2(6-chloro-1H-benzotriazole-1-yl)-1,1,3,3-tetramethylaminium hexafluorophosphate (HCTU) and 10 eq. (diisopropylethylamine) DIPEA. The microwave method for the coupling step was single coupling at 75° C. (20 W for 300 sec), except for cysteine and histidine at 50° C. (0 W for 120 sec, 20 W for 240 sec), and arginine was double coupled at 75° C. (0 W for 1500 sec, 20 W for 300 sec). The Fmoc deprotection was performed with 5% piperazine, 0.1 M 1-hydroxybenzotriazole (HOBt) in DMF at 75° C. (45 W for 30 sec, 45 W for 180 sec). Most amino acids and coupling reagents were purchased from Novabiochem EMD.

Following the automated peptide synthesis, the peptides were cleaved from the resin with 95% TFA and 5% triisopropylsilane (TIPS) for 4 hrs. Peptides containing methionine were cleaved from the resin with a mixture of 95% TFA, 2.5% TIPS and 2.5% ethanedithiol (EDT). Next, the peptides were filtered into round bottom reaction flasks, and in case of the methionine containing peptides 2.5% bromotrimethylsilane (TMSBr) was added. The solvents were removed in vacuo, and the concentrates containing the peptides were precipitated and further triturated with ice cold diethyl ether ($Et_2O$). The synthesized peptides were confirmed by mass spectral analysis.

Some of the peptides required modifications prior to cleavage from the resin, e.g. the peptides containing lactam loops. Here the orthogonal protection groups allyloxycarbonyl (Alloc) and Allyl or methyltrityl (Mtt) and 2-phenylisopropyl (2-PhiPr) were removed by $Pd[P(Ph)_3]_4$ or 1% TFA treatment, respectively. The subsequent lactam formation between the carboxylic acid and amine side chains occured in the presence of 10 eq. benzotriazol-1-yl-oxytripyrrolidinophosphonium hexafluorophosphate (PyBOP) and 10 eq. DIPEA in DMF.

Peptide Purification

The synthesized peptides were purified by preparative reverse phase high performance liquid chromatography (RP-HPLC) using Waters 600 controller and pump system with 2489 UV detector and fraction collector III. The purifications were typically performed on a Phenomenex Jupiter C18 10 micron 250×21.20 mm column with a flow rate of 20 mL/min. The acetonitrile/water (0.1% TFA) gradient was modified for each specific peptide based on hydrophobicity. The peptides were detected at two wavelengths 228 and 280 nm, and the fractions were further analyzed by liquid chromatography mass spectrometry (LC-MS). Fractions containing peptide of adequate purity were pooled, flash frozen and lyophilized.

Peptide Characterization

The peptides were characterized by LC-MS (A.gilent LC-MS TOF 6220 with 1200 series pump, auto handler and UV detection system). The LC separation was performed on a Phenomenex Jupiter C18 5 micron 250×2.00 mm column using a mobile phase of A (water+0.08% formic acid+0.02% trifluoroacetic acid) and B (acetonitrile+0.08% formic acid+0.02% trifluoroacetic acid). The general LC method had a gradient from 0-70% B over 12 min. Mass determination was achieved by electrospray ionization in positive mode. The purity of the peptides was determined by measuring the absorbance of UV light at 228 nm over the chromatogram.

EXAMPLE 2

FXa Generation Assay

Primary Screening Assay

FXa generation was utilized to assess the capability of the compounds of the present disclosure to enhance the catalytic activities of FIXa and/or FVIIa.

To measure the catalytic activity of FIXa, FIXa was mixed with FX and phospholipids in the presence of calcium chloride. Under these conditions FIXa cleaves the zymogen FX into the active form FXa.

The generation of FXa is monitored by the change in absorbance of the reaction at 405 nm due to the presence of a cleavable FXa chromogenic substrate (S-2765; Z-D-Arg-Gly-Arg-pNA; cleavage of p-nitroaniline). The assay components were obtained from the Coatest SP FVIII FXa generation kit (Chromogenix) utilized in the industry to assess the activity of FVIII. The kit contains all the FXa generation components, however, FIXa and FX obtained from this kit are from a bovine origin and were replaced with purified human FIXa or human FVIIa and human FX (Haematologic Technologies).

The assay was also modified to enhance the screening throughput. Instead of the sequential addition, all the assay components were mixed and added simultaneously to the purified compound to be assayed. A 125 µl reaction mix of the assay components was prepared in the buffer supplied by the manufacturer (50 mM Tris 7.3, and 1% BSA). The reaction mix contained hFIXa (12 nM), hFX (120 nM), S-2765 substrate (720 uM), calcium chloride (5 mM) and phospholipids (8.3 ul of the mixture of highly purified phospholipid stock supplied) based on the kit recommendations. The reaction mix (125 ul) was then added to 25 ul of compound diluted in water in a Costar-3651 flat bottom 96-well plate. This resulted in a final reaction concentration of 10 nM hFIXa, 100 nM hFX, 600 uM FXa substrate S-2765, and 4.17 mM calcium chloride. The absorbance was monitored over a period of 1 hour at 405 nm using a plate reader (Synergy 2, Biotek).

The 405 nm absorbance data were then analyzed to obtain the slope of the first derivative which reflects the rate of change in absorbance. The first derivative slope data for each compound concentration were plotted against the compound concentration and fitted to a four-parameter equation to obtain the EC50 and Vmax values for each compound tested.

Similarly, in order to measure the catalytic activity of FVIIa, a FXa generation assay measuring the ability of the compounds of the present disclosure to enhance the catalytic activity of FVIIa was established. The difference between the two assays was that the final concentration of 10 nM hFIXa was replaced with 10 nM hFVIIa. The remaining reagents and assay procedures described above were unchanged.

$Km/K_{cat}$

To determine the Km and Kcat of FIXa or FVIIa for the substrate FX, the FXa generation assay described above was used with the following modifications. A single peptide concentration was tested (typically one that gave the maximal rate of FXa generation) and the concentration of all assay components was similar to that described above with the exception of FX. Reactions were set up with varying concentrations of FX ranging between 400 and 0.8 nM and the rates of FXa generation were determined for each peptide at the different FX concentrations tested as described above. For each peptide assayed, the data were fitted to the following equation that gives the Michaelis-Menten constant (Km) and the Vmax for FIXa or FVIIa: v=Vmax [FX]/Km+[FX], wherein v is the rate of FXa generation determined as described above. The catalytic constant (Kcat) was calculated by normalizing the Vmax to the enzyme concentration.

Exemplary compounds of the present disclosure and their in vitro biological activities measured using the FXa generation assay as described above (using human FIXa) are summarized in Table 1, below. In Table 1, peptides are amidated (—$CONH_2$) at the C-terminus and have a free N-terminus, unless otherwise indicated.

TABLE 1

Exemplary Compounds of the Present Disclosure and their Activities in the FXa Generation Assay

| Sequence | $EC_{50}$ [µM] | Vmax | |
|---|---|---|---|
| RRAPGKLQCLASYCWLFWTGIA (compound 25) | (+++) | (+++) | SEQ ID NO: 4 |
| PLKWTASGCRWLGCIQLARFAY (compound B) | (+) | (++) | SEQ ID NO: 5 |
| LYTAWIKCQFARLPGCALSGRW (compound C) | >25 | >0.6 | SEQ ID NO: 6 |
| Biotin-$PEG_2$-LYTAWIKCQFARLPGCALSGRW | >10 | >1.5 | SEQ ID NO: 7 |
| RRAPG-k-NMeLeu-TCLASYCWLFWTGIA | (++) | (++++) | SEQ ID NO: 9 |
| k-NMeLeu-TCLASYCWLFWTGIA (compound 10) | (+++) | (++) | SEQ ID NO: 10 |
| RRAPGKLQCLASYCWLFWTGAA | (+) | (++++) | SEQ ID NO: 11 |
| RRAPGKLQCLASYCWLFWTAIA | (+++) | (+++) | SEQ ID NO: 12 |
| RRAPGKLQCLASYCWLFWAGIA | (++) | (++++) | SEQ ID NO: 13 |
| RRAPGKLQCLASYCWLFATAIA | (+++) | (++++) | SEQ ID NO: 14 |
| RRAPAKLQCLASYCWLFWTGIA | (+++) | (+++) | SEQ ID NO: 15 |
| RRAAGKLQCLASYCWLFWTGIA | (+++) | (+++) | SEQ ID NO: 16 |
| RAAPGKLQCLASYCWLFWTGIA | (+++) | (+++) | SEQ ID NO: 17 |
| ARAPGKLQCLASYCWLFWTGIA | (+++) | (+++) | SEQ ID NO: 18 |

TABLE 1-continued

Exemplary Compounds of the Present Disclosure
and their Activities in the FXa Generation Assay

| Sequence | EC$_{50}$ [μM] | Vmax | |
|---|---|---|---|
| rRAAGKLTCLASYCWLFATGIA | (+++) | (++) | SEQ ID NO: 414 |
| rRAAGKATCLASYCWLFATGIA | (++) | (++) | SEQ ID NO: 415 |
| rRAAGKLTCLASACWLFATGIA | (+) | (++) | SEQ ID NO: 416 |
| rRAAGKLTCLASYCWLAATGIA | >10 | >0.8 | SEQ ID NO: 417 |
| rRAAGKATCLASACWLAATGIA | >10 | >3 | SEQ ID NO: 418 |
| rRASGKLTCLASYCWLFWTGIA | (+++) | (++) | SEQ ID NO: 419 |
| rRAPGKLTCLASYCWLFSTGIA | (+++) | (++) | SEQ ID NO: 420 |
| rRAPGKSTCLASYCWLFWTGIA | (+++) | (++) | SEQ ID NO: 421 |
| rRAPGKLTCLASSCWLFWTGIA | (++) | (++) | SEQ ID NO: 422 |
| rRAPGKLTCLASYCWLSWTGIA | >5 | >1.8 | SEQ ID NO: 423 |
| RRAPGKLQCLASYCWLFWTGI | (++) | (+++) | SEQ ID NO: 19 |
| RRAPGKLQCLASYCWLFWTG | (+) | (+++) | SEQ ID NO: 20 |
| RRAPGKLQCLASYCWLFWT | (+) | (+++) | SEQ ID NO: 21 |
| RRAPGKLQCLASYCWLFW | (+) | (+++) | SEQ ID NO: 22 |
| RRAPGKLQCLASYCWLF | >5 | >1.1 | SEQ ID NO: 23 |
| RAPGKLQCLASYCWLFWTGIA | (+++) | (++) | SEQ ID NO: 24 |
| APGKLQCLASYCWLFWTGIA | (+++) | (++) | SEQ ID NO: 25 |
| PGKLQCLASYCWLFWTGIA | (+++) | (+++) | SEQ ID NO: 26 |
| GKLQCLASYCWLFWTGIA | (+++) | (+++) | SEQ ID NO: 27 |
| KLQCLASYCWLFWTGIA | (++) | (+++) | SEQ ID NO: 28 |
| RRAPGKLTCLASYCWLFWTGIA (compound 4) | (+++) | (+++) | SEQ ID NO: 29 |
| RRAPGKLQCLASYCWLFWTGLA | (+++) | (+++) | SEQ ID NO: 30 |
| RRAPGKLQCLASYCWLFWTG-Nle-A | (+++) | (+++) | SEQ ID NO: 31 |
| RRAPGKLQCLASYCWLFWTG-Tle-A | (+++) | (+++) | SEQ ID NO: 32 |
| RRAPGKLQCLASYCWLFWTGFA | (+++) | (+++) | SEQ ID NO: 33 |
| RRAPGKLQCLASYCWLFWTG-Cha-A | (++) | (++++) | SEQ ID NO: 34 |
| RRAPGKLQCLASYCWLFWTG-(1-Nal)-A | (+++) | (+++) | SEQ ID NO: 35 |
| RRAPGKLQCLASYCWLFWT-Aib-IA | (+) | (++) | SEQ ID NO: 36 |
| RRAPGKLQCLASYCWLFWTGIAAAAGAP | (++) | (++) | SEQ ID NO: 37 |
| RRAPGKLQCLASYCWLFWTGIK | (+) | (++) | SEQ ID NO: 38 |
| RRAPGKLQCLASYCWLFWTGKA | >5 | >1 | SEQ ID NO: 39 |
| RRAPGKLQCLASYCWLFWTKIA | (+) | (++) | SEQ ID NO: 40 |
| RRAPGKLQCLASYCWLFWKGIA | >5 | >1 | SEQ ID NO: 41 |
| RRAPGKLQCLASYCWLFKTGIA | >10 | >0.2 | SEQ ID NO: 42 |
| RRAPKKLQCLASYCWLFWTGIA | (+) | (++) | SEQ ID NO: 43 |
| RRAKGKLQCLASYCWLFWTGIA | (+) | (++) | SEQ ID NO: 44 |
| RRKPGKLQCLASYCWLFWTGIA | (+) | (+++) | SEQ ID NO: 45 |

TABLE 1-continued

Exemplary Compounds of the Present Disclosure
and their Activities in the FXa Generation Assay

| Sequence | EC$_{50}$ [µM] | Vmax | |
|---|---|---|---|
| RKAPGKLQCLASYCWLFWTGIA | (+) | (+++) | SEQ ID NO: 46 |
| KRAPGKLQCLASYCWLFWTGIA | (+++) | (+++) | SEQ ID NO: 47 |
| MeArg-RAPGKLTCLASYCWLFWTGIA | (+) | (+) | SEQ ID NO: 48 |
| R-MeArg-APGKLTCLASYCWLFWTGIA | (+++) | (++) | SEQ ID NO: 49 |
| RR-MeAla-PGKLTCLASYCWLFWTGIA | (+++) | (++++) | SEQ ID NO: 50 |
| RRAP-Sar-KLTCLASYCWLFWTGIA | (+++) | (+++) | SEQ ID NO: 51 |
| RRAPG-MeLys-LTCLASYCWLFWTGIA | (++) | (++) | SEQ ID NO: 52 |
| RRAPGK-MeLeu-TCLASYCWLFWTGIA | (+) | (++) | SEQ ID NO: 53 |
| RRAPGKL-MeThr-CLASYCWLFWTGIA | (+) | (+) | SEQ ID NO: 54 |
| RRAPGKLTC-MeLeu-ASYCWLFWTGIA | (+) | (++) | SEQ ID NO: 55 |
| RRAPGKLTCL-MeAla-SYCWLFWTGIA | (++) | (++) | SEQ ID NO: 56 |
| RRAPGKLTCLA-MeSer-YCWLFWTGIA | (+++) | (++) | SEQ ID NO: 57 |
| RRAPGKLTCLAS-MeTyr-CWLFWTGIA | (+) | (++) | SEQ ID NO: 58 |
| RRAPGKLTCLASYC-MeTrp-LFWTGIA | >10 | >1.1 | SEQ ID NO: 59 |
| RRAPGKLTCLASYCW-MeLeu-FWTGIA | >10 | | SEQ ID NO: 60 |
| RRAPGKLTCLASYCWL-MePhe-WTGIA | (+) | (+++) | SEQ ID NO: 61 |
| RRAPGKLTCLASYCWLF-MeTrp-TGIA | (++) | (+) | SEQ ID NO: 62 |
| RRAPGKLTCLASYCWLFW-MeThr-GIA | (++) | (+) | SEQ ID NO: 63 |
| RRAPGKLTCLASYCWLFWT-Sar-IA | (+++) | (++++) | SEQ ID NO: 64 |
| RRAPGKLTCLASYCWLFWTG-MeIle-A | >4 | >2.3 | SEQ ID NO: 65 |
| RRAPGKLTCLASYCWLFWTGI-MeAla | (+) | (++) | SEQ ID NO: 66 |
| rRAPGKLTCLASYCWLFWTGIA (compound 5) | (+++) | (+++) | SEQ ID NO: 67 |
| RrAPGKLTCLASYCWLFWTGIA (compound 6) | (+++) | (+++) | SEQ ID NO: 68 |
| RRaPGKLTCLASYCWLFWTGIA | (+) | (++) | SEQ ID NO: 69 |
| RRApGKLTCLASYCWLFWTGIA | (+++) | (++) | SEQ ID NO: 70 |
| RRAPGkLTCLASYCWLFWTGIA | (+++) | (+++) | SEQ ID NO: 71 |
| RRAPGKlTCLASYCWLFWTGIA | (+++) | (+++) | SEQ ID NO: 72 |
| RRAPGKLtCLASYCWLFWTGIA | (+) | (++) | SEQ ID NO: 73 |
| RRAPGKLTcLASYCWLFWTGIA | (++) | (++) | SEQ ID NO: 74 |
| RRAPGKLTClASYCWLFWTGIA | (+) | (++) | SEQ ID NO: 75 |
| RRAPGKLTCLaSYCWLFWTGIA | (+) | (+) | SEQ ID NO: 76 |
| RRAPGKLTCLAsYCWLFWTGIA | (+++) | (++) | SEQ ID NO: 77 |
| RRAPGKLTCLASyCWLFWTGIA | (+++) | (+++) | SEQ ID NO: 78 |
| RRAPGKLTCLASYcWLFWTGIA | (+) | (++) | SEQ ID NO: 79 |
| RRAPGKLTCLASYCwLFWTGIA | (++) | (+++) | SEQ ID NO: 80 |
| RRAPGKLTCLASYCWlFWTGIA | (+) | (++) | SEQ ID NO: 81 |

TABLE 1-continued

Exemplary Compounds of the Present Disclosure
and their Activities in the FXa Generation Assay

| Sequence | EC$_{50}$ [µM] | Vmax | |
|---|---|---|---|
| RRAPGKLTCLASYCWLfWTGIA | (+++) | (++) | SEQ ID NO: 82 |
| RRAPGKLTCLASYCWLFwTGIA | (++) | (++) | SEQ ID NO: 83 |
| RRAPGKLTCLASYCWLFWtGIA | (+++) | (++) | SEQ ID NO: 84 |
| RRAPGKLTCLASYCWLFWTGiA | (++) | (++) | SEQ ID NO: 85 |
| RRAPGKLTCLASYCWLFWTGIa | (+) | (++) | SEQ ID NO: 86 |
| CRRAPGKLQCLASYCWLFWTGIAC | (+) | (+++) | SEQ ID NO: 87 |
| CGGSGGRRAPGKLQCLASYCWLFWTGIAC | (+) | (++) | SEQ ID NO: 88 |
| CRRAPGKLQCLASYCWLFWTGIAGGSGGC | (+) | (+++) | SEQ ID NO: 89 |
| CGGSGGRRAPGKLQCLASYCWLFWTGIAGGSGGC | (+) | (++) | SEQ ID NO: 90 |
| PEG4-RRAPGKLTCLASYCWLFWTGIA | (+++) | (++++) | SEQ ID NO: 91 |
| Glu(Biotinyl-PEG)-RAPGKLTCLASYCWLFWTGIA | >4 | >0.8 | SEQ ID NO: 92 |
| RK(PEG2-Biotin)APGKLTCLASYCWLFWTGIA | (+++) | (++) | SEQ ID NO: 93 |
| RRK(PEG2-Biotin)PGKLTCLASYCWLFWTGIA | (+++) | (++) | SEQ ID NO: 94 |
| RRAK(PEG2-Biotin)GKLTCLASYCWLFWTGIA | (+) | (++) | SEQ ID NO: 95 |
| RRAPK(PEG2-Biotin)KLTCLASYCWLFWTGIA (compound 20) | (+++) | (+++) | SEQ ID NO: 96 |
| RRAPGK(PEG2-Biotin)LTCLASYCWLFWTGIA | (+++) | (++) | SEQ ID NO: 97 |
| RRAPGKK(PEG2-Biotin)TCLASYCWLFWTGIA | >5 | >2 | SEQ ID NO: 98 |
| RRAPGKLK(PEG2-Biotin)CLASYCWLFWTGIA | (++) | (++) | SEQ ID NO: 99 |
| RRAPGKLTCK(PEG2-Biotin)ASYCWLFWTGIA | (+++) | (++) | SEQ ID NO: 100 |
| RRAPGKLTCLK(PEG2-Biotin)SYCWLFWTGIA | (+++) | (++) | SEQ ID NO: 101 |
| RRAPGKLTCLAK(PEG2-Biotin)YCWLFWTGIA (compound 18) | (+++) | (+++) | SEQ ID NO: 102 |
| RRAPGKLTCLASK(PEG2-Biotin)CWLFWTGIA | (+++) | (++) | SEQ ID NO: 103 |
| RRAPGKLTCLASYCK(PEG2-Biotin)LFWTGIA | (+++) | (++) | SEQ ID NO: 104 |
| RRAPGKLTCLASYCWK(PEG2-Biotin)FWTGIA | (+) | (++++) | SEQ ID NO: 105 |
| RRAPGKLTCLASYCWLK(PEG2-Biotin)WTGIA | (+) | (+++) | SEQ ID NO: 106 |
| RRAPGKLTCLASYCWLFK(PEG2-Biotin)TGIA (compound 19) | (+++) | (+++) | SEQ ID NO: 107 |
| RRAPGKLTCLASYCWLFWK(PEG2-Biotin)GIA | (+++) | (++) | SEQ ID NO: 108 |
| RRAPGKLTCLASYCWLFWTK(PEG2-Biotin)IA | (++) | (+++) | SEQ ID NO: 109 |
| RRAPGKLTCLASYCWLFWTGK(PEG2-Biotin)A | (+++) | (++) | SEQ ID NO: 110 |
| RRAPGKLTCLASYCWLFWTGIK(PEG2-Biotin) | (+++) | (++) | SEQ ID NO: 111 |
| RRAPGKLTCLASYCWLFWTGIA-PEG4 | (+++) | (+++) | SEQ ID NO: 112 |
| QWQIAGQVLK RRAPA KLTCLASYCWLFWTGIA | (+++) | (+++) | SEQ ID NO: 113 |
| LQLSYGEQRQ SRAPG KLTCLASYCWLFWTGIA | (+++) | (++) | SEQ ID NO: 114 |
| WMSAEGIVGV RRATG KLTCLASYCWLFWTGIA | | | SEQ ID NO: 115 |
| TSGPFGFGGS SRAQG KLTCLASYCWLFWTGIA | (+) | (++) | SEQ ID NO: 116 |
| HLFGADWLGA RTAPG KLTCLASYCWLFWTGIA | (+) | (++) | SEQ ID NO: 117 |

TABLE 1-continued

Exemplary Compounds of the Present Disclosure
and their Activities in the FXa Generation Assay

| Sequence | EC$_{50}$ [μM] | Vmax | |
|---|---|---|---|
| QRAGRVARLH RRAPN KLTCLASYCWLFWTGIA | (+) | (+++) | SEQ ID NO: 118 |
| WRAGLDESQR DRAPG KLTCLASYCWLFWTGIA | (+++) | (++) | SEQ ID NO: 119 |
| PSGWAGWAPG RREPG KLTCLASYCWLFWTGIA | (+) | (+++) | SEQ ID NO: 120 |
| AVDSLPLYGA RSAPS KLTCLASYCWLFWTGIA | (+++) | (++) | SEQ ID NO: 121 |
| ASVWGALALV RRASG KLTCLASYCWLFWTGIA | | | SEQ ID NO: 122 |
| GYRVPVGGLV RRAHG KLTCLASYCWLFWTGIA | (+) | (+++) | SEQ ID NO: 123 |
| TQWAQVGPRG RRAQG KLTCLASYCWLFWTGIA | (+++) | (++++) | SEQ ID NO: 124 |
| VGSGDERALP SRASG KLTCLASYCWLFWTGIA | (+++) | (+++) | SEQ ID NO: 125 |
| TLWPWGGQGG RNAPG KLTCLASYCWLFWTGIA | (+) | (+++) | SEQ ID NO: 126 |
| TGLLQGRRDE RARPP KLTCLASYCWLFWTGIA | (+++) | (++++) | SEQ ID NO: 127 |
| RGGFFVWFLS RIAPG KLTCLASYCWLFWTGIA | | | SEQ ID NO: 128 |
| RRAPGKLTCLASYCWLF STGVA THANTTATAQ | (+) | (++++) | SEQ ID NO: 129 |
| RRAPGKLTCLASYCWLF WAGFA ASTLAPAHHQ | (++) | (+++) | SEQ ID NO: 130 |
| RRAPGKLTCLASYCWLF WSGFA SLGGLLWPVA | | | SEQ ID NO: 131 |
| RRAPGKLTCLASYCWLF WTGYA SGKPSRVYVI | (+) | (++++) | SEQ ID NO: 132 |
| RRAPGKLTCLASYCWLF WTGLS RYQWQAQEDV | (+) | (+++) | SEQ ID NO: 133 |
| RRAPGKLTCLASYCWLF GSGIS LSRAPESAAP | (++) | (++++) | SEQ ID NO: 134 |
| RRAPGKLTCLASYCWLF WTGWA VLARVPVGWT | (+++) | (+++) | SEQ ID NO: 135 |
| RRAPGKLTCLASYCWLF WTGLA PGRGQGGVAG | (++) | (++++) | SEQ ID NO: 136 |
| RRAPGKLTCLASYCWLF WTGIA DRLVWGVIST | | | SEQ ID NO: 137 |
| RRAPGKLTCLASYCWLF WTGFA FRVGLASSLY | (+++) | (++++) | SEQ ID NO: 138 |
| RRAPGKLTCLASYCWLF WTGLA STLYKTYTRE | (+) | (++) | SEQ ID NO: 139 |
| RRAPGKLTCLASYCWLF RTQIA TPESEYRQQA | (++) | (++++) | SEQ ID NO: 140 |
| RRAPGKLTCLASYCWLF WAGYP SLRGSLLVGV | (++) | (++++) | SEQ ID NO: 141 |
| RRAPGKLTCLASYCWLF QTGWA YWGYRQHPGS | (+++) | (+++) | SEQ ID NO: 142 |
| RRAPGKLTCLASYCWLF WTGWC RDTASHACDS | (+) | (++) | SEQ ID NO: 143 |
| RRAPGKLTCLASYCWLF WTGWS RDTASHASDS | (++) | (+++) | SEQ ID NO: 144 |
| RRAPGKLTCLASYCWLF WRGFA ERASEDTNQG | (+) | (+++) | SEQ ID NO: 145 |
| RRAPGKLTCLASYCWLF EPGIA QPYAKSPTRN | (+) | (+++) | SEQ ID NO: 146 |
| RRAPGKLTCLASYCWLF STPVA RKSLRRHQPT | >10 | (++++) | SEQ ID NO: 147 |
| PRIRTVGPGS RSASG KLTCLASYCWLFWTGIA (compound 21) | (+++) | (++++) | SEQ ID NO: 148 |
| TVGPGSRSASGKLTCLASYCWLFWTGIA | | | SEQ ID NO: 424 |
| PRIrTVGPGSRSASGKLTCLASYCWLFWTGIA | | | SEQ ID NO: 425 |
| PRIrTVGPGSrSASGKLTCLASYCWLFWTGIA (compound 23) | (+++) | (++++) | SEQ ID NO: 426 |
| PRIRTVGPGSRSASGKLTCLASYCWLFWTGIA-PEG4 | | | SEQ ID NO: 427 |
| PEG4-PRIRTVGPGSRSASGKLTCLASYCWLFWTGIA | | | SEQ ID NO: 428 |

TABLE 1-continued

Exemplary Compounds of the Present Disclosure
and their Activities in the FXa Generation Assay

| Sequence | EC$_{50}$ [µM] | Vmax | |
|---|---|---|---|
| PRIRTVGPGSRSASGKLTCLASYCWLFWTGIA-PEG4-Pra | | | SEQ ID NO: 429 |
| Pra-PEG4-PRIRTVGPGSRSASGKLTCLASYCWLFWTGIA | | | SEQ ID NO: 430 |
| Ac-PRIRTVGPGSRSASGKLTCLASYCWLFWTGIA | | | SEQ ID NO: 431 |
| SRIRTVGPGSRSASGKLTCLASYCWLFWTGIA | (+++) | (++++) | SEQ ID NO: 432 |
| PSIRTVGPGSRSASGKLTCLASYCWLFWTGIA | (+++) | (++++) | SEQ ID NO: 433 |
| PRSRTVGPGSRSASGKLTCLASYCWLFWTGIA | (+++) | (++++) | SEQ ID NO: 434 |
| PRISTVGPGSRSASGKLTCLASYCWLFWTGIA | (+++) | (++++) | SEQ ID NO: 435 |
| PRIRSVGPGSRSASGKLTCLASYCWLFWTGIA | (+++) | (++++) | SEQ ID NO: 436 |
| PRIRTSGPGSRSASGKLTCLASYCWLFWTGIA | (+++) | (++++) | SEQ ID NO: 437 |
| PRIRTVSPGSRSASGKLTCLASYCWLFWTGIA | (+++) | (++++) | SEQ ID NO: 438 |
| PRIRTVGSRSASGKLTCLASYCWLFWTGIA | (+++) | (++++) | SEQ ID NO: 439 |
| PRIRTVGPSSRSASGKLTCLASYCWLFWTGIA | (+++) | (++++) | SEQ ID NO: 440 |
| PRIRTVGPGSRSASGKSTCLASYCWLFWTGIA | (+++) | (++++) | SEQ ID NO: 441 |
| PRIrTVGPGSrSASGKSTCLASYCWLFWTGIA | | | SEQ ID NO: 442 |
| PRIrTVGPGSrSASGKSTCLASYCWLFWTGIA-PEG4-Pra | (+++) | (++++) | SEQ ID NO: 443 |
| Pra-PEG4-PRIrTVGPGSrSASGKSTCLASYCWLFWTGIA | (+) | (++) | SEQ ID NO: 444 |
| SRIRTVGPGSRSASGKSTCLASYCWLFWTGIA | (+++) | (++++) | SEQ ID NO: 445 |
| PRIRTVSPGSRSASGKSTCLASYCWLFWTGIA | (+++) | (++++) | SEQ ID NO: 446 |
| SRIRTVSPGSRSASGKSTCLASYCWLFWTGIA | (+++) | (++++) | SEQ ID NO: 447 |
| PRSRTVGPGSRSASGKSTCLASYCWLFWTGIA | (+++) | (++++) | SEQ ID NO: 448 |
| SRSRTVSPGSRSASGKSTCLASYCWLFWTGIA | (+++) | (++++) | SEQ ID NO: 449 |
| K(PEG2-biotin)-PEG4-PRIRTVGPGSRSASGKLTCLASYCWLFWTGIA | | | SEQ ID NO: 450 |
| PRIRTVGPGSRSASGKLTCLASYCWLAWTGIA | (+) | (++++) | SEQ ID NO: 451 |
| PRIRTVGPGSRSASGKLTCLASYCWLLWTGIA | (+++) | (++++) | SEQ ID NO: 452 |
| PRIRTVGPGSRSASGKLTCLASYCWLFATGIA | (+++) | (++++) | SEQ ID NO: 453 |
| PRIRTVGPGSRSASGKLTCLASYCWLFFTGIA | (+++) | (++++) | SEQ ID NO: 454 |
| PRIRTVGPGSRSASGKLTCLASYCWLFLTGIA | (+++) | (++++) | SEQ ID NO: 455 |
| PRIRTVGPGSRSASGKLTCLASYCWLFWSGIA | (+++) | (++++) | SEQ ID NO: 456 |
| PRIRTVGPGSRSASGKLTCLASYCWLFWTLIA | (+++) | (++++) | SEQ ID NO: 457 |
| PRIRTVGPGSRSASGKLTCLASYCWLFWTFIA | (+++) | (+++) | SEQ ID NO: 458 |
| PRIRTVGPGSRSASGKLTCLASYCWLFWTSIA | (+++) | (++++) | SEQ ID NO: 459 |
| PRIRTVGPGSRSASGKLTCLASYCWLFWTGI | (+++) | (++++) | SEQ ID NO: 460 |
| SRIrTVSPGSrSASGKSTCLASYCWLFWTGIA | (+) | (++++) | SEQ ID NO: 461 |
| PRIRTVGPGSRRASGKLTCLASYCWLFWTGIA | (+++) | (++++) | SEQ ID NO: 462 |
| PRIRTVGPGSRSASGKLSCLASYCWLFWTGIA | (+++) | (++++) | SEQ ID NO: 463 |
| PRIRTVGPGSRSASGKLTCAASYCWLFWTGIA | (+) | (+++) | SEQ ID NO: 464 |

TABLE 1-continued

Exemplary Compounds of the Present Disclosure
and their Activities in the FXa Generation Assay

| Sequence | EC$_{50}$ [µM] | Vmax | |
|---|---|---|---|
| PRIRTVGPGSRSASGKLTCSASYCWLFWTGIA | (+) | (++) | SEQ ID NO: 465 |
| PRIRTVGPGSRSASGKLTCIASYCWLFWTGIA | (++) | (+++) | SEQ ID NO: 466 |
| PRIRTVGPGSRSASGKLTCVASYCWLFWTGIA | (+) | (+++) | SEQ ID NO: 467 |
| PRIRTVGPGSRSASGKLTCFASYCWLFWTGIA | (+) | (+++) | SEQ ID NO: 468 |
| PRIRTVGPGSRSASGKLTCLASFCWLFWTGIA | | | SEQ ID NO: 469 |
| PRIRTVGPGSRSASGKLTCLASACWLFWTGIA | (+) | (++) | SEQ ID NO: 470 |
| PTDTGPVISG LRAPG KLTCLASYCWLFWTGIA | (+++) | (++) | SEQ ID NO: 149 |
| GSVRRALFVA ARAPA KLTCLASYCWLFWTGIA | (+++) | (+++) | SEQ ID NO: 150 |
| RRFVGGSLSQ RRAPG KLTCLASYCWLFWTGIA | (+++) | (++++) | SEQ ID NO: 151 |
| SKQGRPISPD RRAAG KLTCLASYCWLFWTGIA (compound 22) | (++) | (++++) | SEQ ID NO: 152 |
| SKQGRPISPDrRAAGKLTCLASYCWLFWTGIA (compound 24) | (+++) | (++++) | SEQ ID NO: 471 |
| SKQGRPISPDRRAAGKLTCLASYCWLFWTGIA-PEG2-K(PEG2-Biotin) | (+) | (++) | SEQ ID NO: 472 |
| SKQGRPISPDrRAAGKLTCLASYCWLFWTGI | (+++) | (++++) | SEQ ID NO: 473 |
| SKQGRPISPDrRAAGKLTCLASYCWLFWTG | (+++) | (+++) | SEQ ID NO: 474 |
| SKQGRPISPDrRAAGKLTCLASYCWLFWT | (+++) | (+++) | SEQ ID NO: 475 |
| SKQGRPISPDrRAAGKLTCLASYCWLFW | (+++) | (++++) | SEQ ID NO: 476 |
| SKQGRPISPDrRAAGKLTCLASYCWLF | (++) | (++++) | SEQ ID NO: 477 |
| AKQGRPISPDrRAAGKLTCLASYCWLFWTGIA | (+++) | (++++) | SEQ ID NO: 478 |
| SAQGRPISPDrRAAGKLTCLASYCWLFWTGIA | (+++) | (+++) | SEQ ID NO: 479 |
| SKAGRPISPDrRAAGKLTCLASYCWLFWTGIA | (+++) | (+++) | SEQ ID NO: 480 |
| SKQARPISPDrRAAGKLTCLASYCWLFWTGIA | (+) | (++++) | SEQ ID NO: 481 |
| SKQGAPISPDrRAAGKLTCLASYCWLFWTGIA | (+++) | (++++) | SEQ ID NO: 482 |
| SKQGRAISPDrRAAGKLTCLASYCWLFWTGIA | (+) | (++++) | SEQ ID NO: 483 |
| SKQGRPASPDrRAAGKLTCLASYCWLFWTGIA | (++) | (+++) | SEQ ID NO: 484 |
| SKQGRPIAPDrRAAGKLTCLASYCWLFWTGIA | (+++) | (++++) | SEQ ID NO: 485 |
| SKQGRPISADrRAAGKLTCLASYCWLFWTGIA | (+++) | (++++) | SEQ ID NO: 486 |
| SKQGRPISPArRAAGKLTCLASYCWLFWTGIA | (+++) | (++++) | SEQ ID NO: 487 |
| SKQGRPISPDrRAAGKLTCLaSYCWLFWTGIA | >10 | >0.5 | SEQ ID NO: 488 |
| SKQGRPISPDrRAAGKLTCLASYCWIFWTGIA | >10 | >2.4 | SEQ ID NO: 489 |
| SKQGRPISPDrRAAGKLTCLAS-NMeTyr-CWLFWTGIA | >10 | >0.3 | SEQ ID NO: 490 |
| SKQGRPISPDrRAAGKLTCLASYCW-NMeLeu-FWTGIA | >10 | >1.9 | SEQ ID NO: 491 |
| SKQGRPISSDrRAAGKLTCLASYCWLFWTGIA | (+++) | (++++) | SEQ ID NO: 492 |
| SKQGRPISSDrRAAGKSTCLASYCWLFWTGIA | (+++) | (++++) | SEQ ID NO: 493 |
| SKQGRPISSDrRASGKLTCLASYCWLFWTGIA | (+++) | (++++) | SEQ ID NO: 494 |
| SKQGRPISSDrRASGKSTCLASYCWLFWTGIA | (+++) | (++++) | SEQ ID NO: 495 |
| RPRSSAHDRP RRAAG KLTCLASYCWLFWTGIA | (+) | (++++) | SEQ ID NO: 153 |

TABLE 1-continued

Exemplary Compounds of the Present Disclosure
and their Activities in the FXa Generation Assay

| Sequence | EC$_{50}$ [μM] | Vmax | |
|---|---|---|---|
| TALSRGLVTM RTAPD KLTCLASYCWLFWTGIA | (+++) | (++) | SEQ ID NO: 154 |
| PARGKERELM RRAPG KLTCLASYCWLFWTGIA | (+) | (++++) | SEQ ID NO: 155 |
| GRAMAAEPWP RQAPG KLTCLASYCWLFWTGIA | (+++) | (+++) | SEQ ID NO: 156 |
| LYPRLYTPGS RRAYG KLTCLASYCWLFWTGIA | (++) | (+++) | SEQ ID NO: 157 |
| AQWVGRGQWA IRAPG KLTCLASYCWLFWTGIA | (+) | (+++) | SEQ ID NO: 158 |
| MQIRQAHQPR RSAPQ KLTCLASYCWLFWTGIA | (++) | (+++) | SEQ ID NO: 159 |
| PRTTANRRSS RRAPA KLTCLASYCWLFWTGIA | (+++) | (++++) | SEQ ID NO: 160 |
| PNLLRVRTSE VRNPG KLTCLASYCWLFWTGIA | (+++) | (++) | SEQ ID NO: 161 |
| SLISMTNPSG RRVPG KLTCLASYCWLFWTGIA | (+++) | (+++) | SEQ ID NO: 162 |
| NGALGFRSVV PRAAG KLTCLASYCWLFWTGIA | (+++) | (+++) | SEQ ID NO: 163 |
| RSHSLDRMAG RRAPG KLTCLASYCWLFWTGIA | (++) | (++++) | SEQ ID NO: 164 |
| AVVRGQEPTH RRTPG KLTCLASYCWLFWTGIA | (++) | (++++) | SEQ ID NO: 165 |
| PQTRDPSSRD RRAPG KLTCLASYCWLFWTGIA | (+++) | (++++) | SEQ ID NO: 166 |
| RRAPGKLTCLASYCWLF LGGIA PEGASTRTAN | (++) | (++++) | SEQ ID NO: 167 |
| RRAPGKLTCLASYCWLF VTGTA HAPRVAPAPA | (+) | (++++) | SEQ ID NO: 168 |
| RRAPGKLTCLASYCWLF WTAVG GQPYMLLAWR | (+++) | (++) | SEQ ID NO: 169 |
| RRAPGKLTCLASYCWLF WAGIA PHRPLKERVR | (+) | (+++) | SEQ ID NO: 170 |
| RRAPGKLTCLASYCWLF WAVIA PPKVKGTRQS | (+) | (+++) | SEQ ID NO: 171 |
| RRAPGKLTCLASYCWLF ATGVT FPQIWAIPSP | (+) | (++++) | SEQ ID NO: 172 |
| RRAPGKLTCLASYCWLF YTGIA HGHPMEHRKS | (+) | (++++) | SEQ ID NO: 173 |
| RRAPGKLTCLASYCWLF LTGWA RVPLPPRPHP | (+) | (++) | SEQ ID NO: 174 |
| RRAPGKLTCLASYCWLF WTGIA RWPSHRSGPS | (+) | (++) | SEQ ID NO: 175 |
| RRAPGKLTCLASYCWLF WTTYA SYATKPADTT | (+++) | (+++) | SEQ ID NO: 176 |
| RRAPGKLTCLASYCWLF FTGVA RSTTATTNTQ | (++) | (+++) | SEQ ID NO: 177 |
| RRAPGKLTCLASYCWLF WSGIA PQPPNMRPSV | (+++) | (++++) | SEQ ID NO: 178 |
| RRAPGKLTCLASYCWLF WTTFA WVFVVAVYGS | | | SEQ ID NO: 179 |
| RRAPGKLTCLASYCWLF WTALA TLSVSMRSPF | | | SEQ ID NO: 180 |
| RRAPGKLTCLASYCWLF WTTWT TAPTTPPLTT | (+++) | (+++) | SEQ ID NO: 181 |
| RRAPGKLTCLASYCWLF WTGLL DYPTPQSHEP | (+++) | (+++) | SEQ ID NO: 182 |
| RRAPGKLTCLASYCWLF WTGIA LGHPPRPAPK | | | SEQ ID NO: 183 |
| SKQGRPISPDRRAAGKLTCLASYCWLFGSGISLSRAPE-SAAP | >10 | (+) | SEQ ID NO: 496 |
| RRAPGKLCALASYCWLFWTGIA-COOH | (+) | (+++) | SEQ ID NO: 184 |
| RRAPGKCTALASYCWLFWTGIA-COOH | (+) | (++) | SEQ ID NO: 185 |
| RRAPGCLTALASYCWLFWTGIA-COOH | (+) | (+++) | SEQ ID NO: 186 |
| RRAPGKLTCLASYACLFWTGIA-COOH | (++) | (+++) | SEQ ID NO: 187 |
| RRAPGKLTCLASYAWCFWTGIA-COOH | (+) | (+++) | SEQ ID NO: 188 |
| RRAPGKLTCLASYAWLCWTGIA-COOH | >10 | >0.5 | SEQ ID NO: 189 |

TABLE 1-continued

Exemplary Compounds of the Present Disclosure
and their Activities in the FXa Generation Assay

| Sequence | EC$_{50}$ [µM] | Vmax | |
|---|---|---|---|
| RRAPGKLCALASYACLFWTGIA-COOH | >10 | >0.3 | SEQ ID NO: 190 |
| RRAPGKCTALASYAWCFWTGIA-COOH | (+) | (+++) | SEQ ID NO: 191 |
| RRAPGCLTALASYAWLCWTGIA-COOH | >20 | >0.1 | SEQ ID NO: 192 |
| RRAPGKLCALASYCWLFWTGIA-CONH$_2$ | (+) | (+++) | SEQ ID NO: 497 |
| RRAPGKCTALASYCWLFWTGIA-CONH$_2$ | (+) | (+++) | SEQ ID NO: 498 |
| RRAPGCLTALASYCWLFWTGIA-CONH$_2$ | (+) | (++) | SEQ ID NO: 499 |
| RRAPGKLTCLASYACLFWTGIA-CONH$_2$ | (+) | (++++) | SEQ ID NO: 500 |
| RRAPGKLTCLASYAWCFWTGIA-CONH$_2$ | >20 | (+) | SEQ ID NO: 501 |
| RRAPGKLTCLASYAWLCWTGIA-CONH$_2$ | >10 | (+) | SEQ ID NO: 502 |
| RRAPGKLCALASYACLFWTGIA-CONH$_2$ | >10 | (+) | SEQ ID NO: 503 |
| RRAPGKCTALASYAWCFWTGIA-CONH$_2$ | (+) | (++) | SEQ ID NO: 504 |
| RRAPGCLTALASYAWLCWTGIA-CONH$_2$ | (+) | (++) | SEQ ID NO: 505 |
| RRAPGKLT-Lys-LASY-Asp-WLFWTGIA-COOH | >10 | >0.5 | SEQ ID NO: 193 |
| RRAPGKLT-Asp-LASY-Lys-WLFWTGIA-COOH | (+++) | (++) | SEQ ID NO: 194 |
| RRAPGKLT-Orn-LASY-Asp-WLFWTGIA-COOH | (+) | (+++) | SEQ ID NO: 195 |
| RRAPGKLT-Asp-LASY-Orn-WLFWTGIA-COOH | (+++) | (++) | SEQ ID NO: 196 |
| RRAPGKLT-Dab-LASY-Asp-WLFWTGIA-COOH | (++) | (++) | SEQ ID NO: 506 |
| RRAPGKLT-Asp-LASY-Dab-WLFWTGIA-COOH | >10 | >1.0 | SEQ ID NO: 197 |
| RRAPGKLT-Dap-LASY-Asp-WLFWTGIA-COOH | >10 | >0.8 | SEQ ID NO: 198 |
| RRAPGKLT-Asp-LASY-Dap-WLFWTGIA-COOH | (+) | (++) | SEQ ID NO: 199 |
| RRAPGKLT-Lys-LASY-Glu-WLFWTGIA-COOH | (+++) | (++) | SEQ ID NO: 507 |
| RRAPGKLT-Lys-LASY-Asp-WLFWTGIA-CONH$_2$ | (+) | (++) | SEQ ID NO: 508 |
| RRAPGKLT-Asp-LASY-Lys-WLFWTGIA-CONH$_2$ | (+++) | (+++) | SEQ ID NO: 509 |
| RRAPGKLT-Orn-LASY-Asp-WLFWTGIA-CONH$_2$ | >10 | (+) | SEQ ID NO: 510 |
| RRAPGKLT-Asp-LASY-Orn-WLFWTGIA-CONH$_2$ | (+++) | (+++) | SEQ ID NO: 511 |
| RRAPGKLT-Dab-LASY-Asp-WLFWTGIA-CONH$_2$ | (+) | (+++) | SEQ ID NO: 512 |
| RRAPGKLT-Dap-LASY-Asp-WLFWTGIA-CONH$_2$ | >10 | (+) | SEQ ID NO: 513 |
| RRAPGKLT-Asp-LASY-Dap-WLFWTGIA-CONH$_2$ | (+) | (+++) | SEQ ID NO: 514 |
| RRAPGKLT-Lys-LASY-Glu-WLFWTGIA-CONH$_2$ | (+) | (++) | SEQ ID NO: 515 |
| RRAPGKLT-Asp-LASY-Dab-WLFWTGIA-CONH$_2$ | >10 | (++) | SEQ ID NO: 516 |
| SKQGRPISPDRRAAGKLT-Asp-LASY-Orn-WLFWTGIA | (+++) | (++++) | SEQ ID NO: 517 |
| RRAPGKLT-Asp-LASY-Orn-WLFGSGISLSRAPESAAP | | | SEQ ID NO: 518 |
| PRIRTVGPGSRSASGKLT-Asp-LASY-Orn-WLFWTGIA | | | SEQ ID NO: 519 |
| RRFVGGSLSQRRAPGKLT-Asp-LASY-Orn-WLFWTGIA | | | SEQ ID NO: 520 |
| PQTRDPSSRDRRAPGKLT-Asp-LASY-Orn-WLFWTGIA | | | SEQ ID NO: 521 |
| C(PEG5k)GGG-RRAPGKLT-Asp-LASY-Lys-WLFWTGIA | (+) | (++) | SEQ ID NO: 522 |
| CGGG-RRAPGKLT-Asp-LASY-Lys-WLFWTGIA | (+++) | (+++) | SEQ ID NO: 523 |

TABLE 1-continued

Exemplary Compounds of the Present Disclosure
and their Activities in the FXa Generation Assay

| Sequence | EC$_{50}$ [μM] | Vmax | |
|---|---|---|---|
| CGGGLVPRGGG-RRAPGKLT-Asp-LASY-Lys-WLFWTGIA | (+++) | (+++) | SEQ ID NO: 524 |
| C(PEG5K)GGGLVPRGGG-RRAPGKLT-Asp-LASY-Lys-WLFWTGIA | (++) | (++) | SEQ ID NO: 525 |
| C(N-ethylmaleimide)-PEG4-LVPR-PEG4-rRAPGKLTCLASYCWLFWTGIA | (+) | (++) | SEQ ID NO: 526 |
| rRAPGKLTCLASYCWLFWTGIA-PEG4-C(N-PEG5k maleimide) | (+) | (+++) | SEQ ID NO: 527 |
| C(N-PEG5kmaleimide)-PEG4-LVPR-PEG4-rRAPGKLTCLASYCWLFWTGIA | (+) | (++) | SEQ ID NO: 528 |
| C(N-PEG5kmaleimide)-PEG4-SKQGRPISPDrRAAGKLTCLASYCWLFWTGIA | (+) | (+) | SEQ ID NO: 529 |
| SKQGRPISPDrRAAGKLTCLASYCWLFWTGIA-PEG4-C(N-PEG5k maleimide) | >5 | >0.5 | SEQ ID NO: 530 |
| C(Acm)GGGGfpipR-PEG5-rRAPGKLTCLASYCWLFWTGIA | (+) | (++++) | SEQ ID NO: 531 |
| CKTYFWKpGNIMVTFC-PEG12-Lys(PEG2-Biotin)-PEG12-rRAPGKLTCLASYCWLFWTGIA | >20 | | SEQ ID NO: 532 |
| rrapgkltclasycwlfwtgia (inverso) | (+++) | (+++) | SEQ ID NO: 533 |
| AIGTWFLWCYSALCTLKGPARR (retro) | (+) | (++) | SEQ ID NO: 534 |
| aigtwflwcysalctlkgparr (retro-inverso) | (+) | (+++) | SEQ ID NO: 535 |
| RRAPGKLTCLASYCWLFWTGIA-COOH | (++) | (+++) | SEQ ID NO: 536 |
| rRAPGKLTCLASYCWLFWTGIA-COOH | (++) | (+++) | SEQ ID NO: 537 |
| KLTCLASYCWLF (compound 1) | (+++) | (+++) | SEQ ID NO: 200 |
| RRRKLTCLASYCWLFRRR | (+) | (++) | SEQ ID NO: 201 |
| RRRRKLTCLASYCWLFRRRRR | (++) | (+++) | SEQ ID NO: 202 |
| KKKKLTCLASYCWLFKKK | >5 | | SEQ ID NO: 203 |
| KLTCLASYCWLFK | (++) | (++++) | SEQ ID NO: 204 |
| KKLTCLASYCWLF | (+++) | (++++) | SEQ ID NO: 205 |
| ALTCLASYCWLF | (+) | (++) | SEQ ID NO: 206 |
| KATCLASYCWLF | (+++) | (+++) | SEQ ID NO: 207 |
| KLACLASYCWLF | (+++) | (+++) | SEQ ID NO: 208 |
| KLTALASYCWLF | (+) | (++) | SEQ ID NO: 209 |
| KLTCAASYCWLF | (+++) | (++) | SEQ ID NO: 210 |
| KLTCLAAYCWLF | (++) | (++) | SEQ ID NO: 211 |
| KLTCLASACWLF | (+++) | (+++) | SEQ ID NO: 212 |
| KLTCLASYAWLF | (+) | (++) | SEQ ID NO: 213 |
| KLTCLASYCALF | (+) | (++++) | SEQ ID NO: 214 |
| KLTCLASYCWAF | (++) | (+++) | SEQ ID NO: 215 |
| KLTCLASYCWLA | (+++) | (++++) | SEQ ID NO: 216 |
| ALTCLAAYCALF | (+) | (++) | SEQ ID NO: 217 |

TABLE 1-continued

Exemplary Compounds of the Present Disclosure
and their Activities in the FXa Generation Assay

| Sequence | EC$_{50}$ [μM] | Vmax | |
|---|---|---|---|
| KAACLASACWLA | >20 | | SEQ ID NO: 218 |
| kLTCLASYCWLF | (+++) | (+++) | SEQ ID NO: 219 |
| KITCLASYCWLF | (+++) | (+++) | SEQ ID NO: 220 |
| KLtCLASYCWLF | (++) | (+++) | SEQ ID NO: 221 |
| KLTcLASYCWLF | (++) | (+++) | SEQ ID NO: 222 |
| KLTCIASYCWLF | >5 | | SEQ ID NO: 223 |
| KLTCLaSYCWLF | >5 | | SEQ ID NO: 224 |
| KLTCLAsYCWLF | (+) | (+++) | SEQ ID NO: 225 |
| KLTCLASyCWLF | >5 | | SEQ ID NO: 226 |
| KLTCLASYcWLF | (+) | (++++) | SEQ ID NO: 227 |
| KLTCLASYCwLF | (++) | (++++) | SEQ ID NO: 228 |
| KLTCLASYCWlF | (+) | (++++) | SEQ ID NO: 229 |
| KLTCLASYCWLf | (+) | (++++) | SEQ ID NO: 230 |
| MeLys-LTCLASYCWLF | (+++) | (++) | SEQ ID NO: 231 |
| K-MeLeu-TCLASYCWLF | (+++) | (+++) | SEQ ID NO: 232 |
| KL-MeThr-CLASYCWLF | (+++) | (++) | SEQ ID NO: 233 |
| KLTC-MeLeu-ASYCWLF | >20 | (+) | SEQ ID NO: 234 |
| KLTCL-MeAla-SYCWLF | >20 | (+) | SEQ ID NO: 235 |
| KLTCLA-MeSer-YCWLF | >20 | (+) | SEQ ID NO: 236 |
| KLTCLAS-MeTyr-CWLF | >20 | (+) | SEQ ID NO: 237 |
| KLTCLASYC-MeTrp-LF | >20 | (+) | SEQ ID NO: 238 |
| KLTCLASYCW-MeLeu-F | (+) | (+++) | SEQ ID NO: 239 |
| KLTCLASYCWL-MePhe | (+) | (++) | SEQ ID NO: 240 |
| k-MeLeu-TCLASYCWLF (compound 2) | (+++) | (++++) | SEQ ID NO: 241 |
| KLTCLASYCWL | (++) | (++++) | SEQ ID NO: 242 |
| KLTCLASYCW | >10 | (+) | SEQ ID NO: 243 |
| KLTCLASYC | (+) | (++++) | SEQ ID NO: 244 |
| LTCLASYCWLF | (++) | (++) | SEQ ID NO: 245 |
| TCLASYCWLF | (+++) | (+) | SEQ ID NO: 246 |
| CLASYCWLF | >20 | (+) | SEQ ID NO: 247 |
| WSLCFKLTCAYL (compound A) | >100 | (+) | SEQ ID NO: 248 |
| KLTALASYAWLF | >5.8 | (+++) | SEQ ID NO: 249 |
| KLTSLASYSWLF | >15 | (+) | SEQ ID NO: 250 |
| KLT-Pen-LASYCWLF | >20 | (+) | SEQ ID NO: 251 |
| KLTCLASY-Pen-WLF | >20 | (+) | SEQ ID NO: 252 |
| KLT-HCy-LASYCWLF | (++) | (+++) | SEQ ID NO: 253 |

TABLE 1-continued

Exemplary Compounds of the Present Disclosure
and their Activities in the FXa Generation Assay

| Sequence | EC$_{50}$ [µM] | Vmax | |
|---|---|---|---|
| KLTCLASY-HCy-WLF | (++) | (++++) | SEQ ID NO: 254 |
| KLT-Lys-LASY-Glu-WLF | (+++) | (++) | SEQ ID NO: 255 |
| KLT-Glu-LASY-Lys-WLF | (++) | (++) | SEQ ID NO: 256 |
| KLT-Glu-LASY-Orn-WLF | (+++) | (++) | SEQ ID NO: 257 |
| KLT-Orn-LASY-Glu-WLF-COOH | (+++) | (+) | SEQ ID NO: 258 |
| KLT-Orn-LASY-Glu-WLF-CONH$_2$ | (+++) | (++) | SEQ ID NO: 538 |
| KLT-Glu-LASY-Dab-WLF | (+) | (++) | SEQ ID NO: 539 |
| KLT-Dab-LASY-Glu-WLF | (++) | (++) | SEQ ID NO: 540 |
| KLT-Glu-LASY-Dap-WLF | (+++) | (++) | SEQ ID NO: 541 |
| KLT-Dap-LASY-Glu-WLF | (+++) | (++) | SEQ ID NO: 542 |
| KKTCLASYCWLF | >50 | (++) | SEQ ID NO: 259 |
| KLKCLASYCWLF | (++) | (++++) | SEQ ID NO: 260 |
| KLTCKASYCWLF | (+) | (++++) | SEQ ID NO: 261 |
| KLTCLKSYCWLF | (+) | (++) | SEQ ID NO: 262 |
| KLTCLASKCWLF | >100 | (+) | SEQ ID NO: 263 |
| KLTCLASYCWLK | >100 | (+) | SEQ ID NO: 264 |
| RLTCLASYCWLF | (++) | (+++) | SEQ ID NO: 265 |
| Dpr-LTCLASYCWLF | (+) | (+++) | SEQ ID NO: 266 |
| Dab-LTCLASYCWLF | (++) | (++) | SEQ ID NO: 267 |
| QLTCLASYCWLF | >20 | (+) | SEQ ID NO: 268 |
| Orn-LTCLASYCWLF | (+++) | (++) | SEQ ID NO: 269 |
| Lys(Me)-LTCLASYCWLF | (++) | (++) | SEQ ID NO: 270 |
| Lys(Me)2-LTCLASYCWLF | (+) | (+) | SEQ ID NO: 271 |
| Lys(Me3CI)-LTCLASYCWLF | (+) | (+) | SEQ ID NO: 272 |
| KLTCLSSYCWLF | (+) | (+++) | SEQ ID NO: 273 |
| KLTCLVSYCWLF | (++) | (+++) | SEQ ID NO: 274 |
| KLTCL-Dpr-SYCWLF | (+) | (++) | SEQ ID NO: 275 |
| KLTCL-Abu-SYCWLF | (+) | (+++) | SEQ ID NO: 276 |
| KLTCLGSYCWLF | (+) | (+++) | SEQ ID NO: 277 |
| KLTCL-Aib-SYCWLF | >20 | (+) | SEQ ID NO: 278 |
| KLTCLA-HSe-YCWLF | (+) | (++) | SEQ ID NO: 279 |
| KLTCLA-Dpr-YCWLF | >20 | (+) | SEQ ID NO: 280 |
| KLTCLATYCWLF | (+) | (++) | SEQ ID NO: 281 |
| KLTCLASYC-Nal-LF | (+++) | (++++) | SEQ ID NO: 282 |
| KLTCLASYCFLF | (++) | (++++) | SEQ ID NO: 283 |
| KLTCLASYCLLF | (++) | (+++) | SEQ ID NO: 284 |
| KLTCLASYCW-Nle-F | (+++) | (+++) | SEQ ID NO: 285 |

TABLE 1-continued

Exemplary Compounds of the Present Disclosure
and their Activities in the FXa Generation Assay

| Sequence | EC$_{50}$ [µM] | Vmax | |
|---|---|---|---|
| KLTCLASYCWYF | (+++) | (+++) | SEQ ID NO: 286 |
| KLTCLASYCWIF | (++) | (+++) | SEQ ID NO: 287 |
| TGS-KLTCLASYCWLF-APG | (++) | (+++) | SEQ ID NO: 288 |
| KLTCLASYCWLF-COOH | (+) | (++) | SEQ ID NO: 289 |
| Ac-KLTCLASYCWLF | (+) | (++) | SEQ ID NO: 290 |
| KLTCLASYCWLF-(PEG)4-CONH$_2$ | (+) | (++) | SEQ ID NO: 291 |
| (PEG)27-KLTCLASYCWLF | (+) | (+++) | SEQ ID NO: 292 |
| (PEG)27(PEG)27-KLTCLASYCWLF | (+) | (+) | SEQ ID NO: 293 |
| KLTCQASYCWLF | (+) | (++) | SEQ ID NO: 294 |
| KLTCLASQCWLF | (+++) | (+++) | SEQ ID NO: 295 |
| KLTCLASYCQLF | (++) | (++++) | SEQ ID NO: 296 |
| QQTCQASQCQLF | >20 | (+) | SEQ ID NO: 297 |
| NPTCQASYCQLF | >20 | (+) | SEQ ID NO: 298 |
| QLTCLASECGLS | >20 | (+) | SEQ ID NO: 299 |
| AQTRVARCCQLF | >20 | (+) | SEQ ID NO: 300 |
| KKTCVASFCQMI | >5 | >4 | SEQ ID NO: 301 |
| NLTGRASYGWLP | >20 | (+) | SEQ ID NO: 302 |
| KGRCLTSHCWLF | >20 | (+) | SEQ ID NO: 303 |
| TLTCRASYCQLF | (+) | (+) | SEQ ID NO: 304 |
| KLTCRASYCQLF | (+) | (+++) | SEQ ID NO: 305 |
| KLSCQAGQCWVF | (+) | (+++) | SEQ ID NO: 306 |
| KLTCLASYCQLV | (+++) | (+++) | SEQ ID NO: 307 |
| KLKCLSSECQLL | >20 | (+) | SEQ ID NO: 308 |
| QLTCLASYCGGV | >20 | (+) | SEQ ID NO: 309 |
| EQTCLASYCWLF | >20 | (+) | SEQ ID NO: 310 |
| QLPCLASYCGLF | >20 | (+) | SEQ ID NO: 311 |
| MLTCIASYCQLG | >20 | (+) | SEQ ID NO: 312 |
| SLADTQLTWLARQYWLSVSEGS | >20 | (+) | SEQ ID NO: 313 |
| RRCPGKLQALASYCWLFWTGIA | (+) | (+++) | SEQ ID NO: 314 |
| RRAPGKLQCLASYCWLFWTGIA (compound 3) | (+++) | (++++) | SEQ ID NO: 315 |
| DSRSAKRKCLASYCWLFGIGQA | >20 | (+) | SEQ ID NO: 316 |
| GASSDKLTCRTRHCSMFQPLSV | >20 | (+) | SEQ ID NO: 317 |
| GCSSDKLTARTRHCSMFQPLSV | >20 | (+) | SEQ ID NO: 318 |
| GSCRDQLTCLSSDRWQFFRRVS | >20 | (+) | SEQ ID NO: 319 |
| KEGFAQLPCLVCQGGLFSPRAI | >20 | (+) | SEQ ID NO: 320 |
| LRTQPKVTGLASCSGLVNCSRD | >20 | (+) | SEQ ID NO: 321 |
| RCAQSRLPWLVSYCWLFSPYGM | >5 | >1.5 | SEQ ID NO: 322 |

TABLE 1-continued

Exemplary Compounds of the Present Disclosure
and their Activities in the FXa Generation Assay

| Sequence | EC$_{50}$ [µM] | Vmax | |
|---|---|---|---|
| LQELTKLTCLARSGWLVCNPGY | >20 | (+) | SEQ ID NO: 323 |
| WVPQWKVTCLASCSRLFHGFDA | >5 | >1.5 | SEQ ID NO: 324 |
| SCVKHELKCLSSDSRLFSAVQR | >20 | (+) | SEQ ID NO: 325 |
| VAHYGKVTCLASYCQPLPSVGA | >20 | (+) | SEQ ID NO: 326 |
| MEGTRQPTCLASYCSPFQYVAP | >20 | (+) | SEQ ID NO: 327 |
| RPGGGKVTCQASYCWPFLARAG | >20 | (+) | SEQ ID NO: 328 |
| ERYRLDMTCMASQCWQFPPAAG | (+++) | (++) | SEQ ID NO: 329 |
| VGEHRKISCVASNCQLLRSGLA | >20 | (+) | SEQ ID NO: 330 |
| SISGQQLTCRASHCWLNLPWHS | >20 | (+) | SEQ ID NO: 331 |
| TLDSKNLQCLGSSCWLFSSGLS | >20 | (+) | SEQ ID NO: 332 |
| VQRSTQLTCLYGGCRLFGWNYH | >20 | (+) | SEQ ID NO: 333 |
| VSGTGRLTCVASYCWMFQLGSF | (+++) | (++) | SEQ ID NO: 334 |
| MAGMLKLTCFASYCGLFPLVSS | (+++) | (++) | SEQ ID NO: 335 |
| GAQLDKETCLASYCQLFSTVRR | >20 | (+) | SEQ ID NO: 336 |
| HMQWGKLPCLASYCWLFWYGIG | (+) | (+++) | SEQ ID NO: 337 |
| LRQRLAKTCVASYCWLFSLVAS | >10 | >1.5 | SEQ ID NO: 338 |
| WHERQQLTCLASYCGLFVGQVA | (+++) | (+) | SEQ ID NO: 339 |
| RYQRARLTCLASYCGLLFSMSA | >15 | >0.5 | SEQ ID NO: 340 |
| AVAINKVPCVASYCQLFESKIH | >20 | (+) | SEQ ID NO: 341 |
| AWPYHKPTCLASQCWQFLAQGS | >20 | (+) | SEQ ID NO: 342 |
| SYGRTKLTCLASSCWLFGQVHG | >10 | (+) | SEQ ID NO: 343 |
| GVEDRQLTCLASSCWVFSRHSV | (+) | (++) | SEQ ID NO: 344 |
| RSFTSELTCLASSCRRFHHVPP | >20 | (+) | SEQ ID NO: 345 |
| AQLRRKLTCLASYCWLFGFFSP | (+) | (++) | SEQ ID NO: 346 |
| HMQWGKLPCLASYCWLFWYGIG | (+) | (+++) | SEQ ID NO: 347 |
| QQRQIKMSCLASYCWLFGSIPW | (++) | (++) | SEQ ID NO: 348 |
| GGALQQLTCPASYCWLFPMEHS | >10 | (+) | SEQ ID NO: 349 |
| HYARVQLRCLDGYCWLLTKSRM | >10 | >2.5 | SEQ ID NO: 350 |
| YARDSTLTCQARTCQLVDYLGP | >50 | (+) | SEQ ID NO: 351 |
| QGQARKLACLASYCWLFPSSAG | >50 | (+) | SEQ ID NO: 352 |
| APPGGKRMCLVSGCQLFPWSAS | >50 | (+) | SEQ ID NO: 353 |
| QDGDGKLTCRASYCRRFLVGVH | >50 | (+) | SEQ ID NO: 354 |
| GIQGSEVACRASFCRLFEQGHV | >50 | (+) | SEQ ID NO: 355 |
| RFQTTQLTCLGSASCLFNLSVR | (+) | (+) | SEQ ID NO: 356 |
| AWPYHKPTCLASQCWQFLAQGS | >50 | (+) | SEQ ID NO: 357 |
| GFGSRKLTSLASYGWLIQDRLP | >50 | (+) | SEQ ID NO: 358 |
| SGRGGKLTCQASFCQLFGNGLS | (+++) | (++) | SEQ ID NO: 359 |

TABLE 1-continued

Exemplary Compounds of the Present Disclosure
and their Activities in the FXa Generation Assay

| Sequence | EC$_{50}$ [μM] | Vmax | |
|---|---|---|---|
| RSQGRKLTCLASYCWLFLVVHR | (++) | (++) | SEQ ID NO: 360 |
| EGRRDKLTCLASYCWLVGHGQH | >25 | >0.3 | SEQ ID NO: 361 |
| RGRSAKLRCLASYCWLFFGVIL | (+++) | (+++) | SEQ ID NO: 362 |
| LLQIPNLTCLGSYCWLDNGVYA | >50 | (+) | SEQ ID NO: 363 |
| FGQPSRLTCLASYCWLFGNLVT | (++) | (++) | SEQ ID NO: 364 |
| GEGGGKLSCVAIQCGLFKGLGR | >50 | (+) | SEQ ID NO: 365 |
| VDKGHQLRCQAGYCWLLGYNRE | >50 | (+) | SEQ ID NO: 366 |
| SGFGMKLTCLASYCGLFQGEIG | (+++) | (+) | SEQ ID NO: 367 |
| LLHAQKLSCLASYCWVFDAEWD | (+++) | (+) | SEQ ID NO: 368 |
| SGGSGKLTCLASYCWPFGSQVR | >50 | (+) | SEQ ID NO: 369 |
| QDGVEKLTCLASYCWRFGDHGA | >50 | (+) | SEQ ID NO: 370 |
| DAGPNKLRCLASYCQLFGGGHA | >50 | (+) | SEQ ID NO: 371 |
| TLLYQNRTCLASYCWLFDKRSV | >50 | (+) | SEQ ID NO: 372 |
| LTWREKLACLASYCWLFLWGAP | (++) | (++) | SEQ ID NO: 373 |
| RQLWNKLTCLASYCALIGLSGT | (+) | (++) | SEQ ID NO: 374 |
| KGAYQKLTCLASYCLLFLLTAQ | (+++) | (++) | SEQ ID NO: 375 |
| QEQPAKLTCRGSYCWLFKRGDQ | >50 | (+) | SEQ ID NO: 376 |
| HDSLDQLTCLASVCQLASMGAR | (+) | (+) | SEQ ID NO: 377 |
| SRQSDKPTCLAISCSLLTSNVR | >50 | (+) | SEQ ID NO: 378 |
| HGLADRLTCLSSDCWLQPFGTS | >50 | (+) | SEQ ID NO: 379 |
| VARASKVECLASYCQLFVGGEV | (+) | (+) | SEQ ID NO: 380 |
| GASGRRRTCVASYCLLFQSGLP | >25 | >0.1 | SEQ ID NO: 381 |
| FPIQHKLTCLSSDCWLFPSHSY | >50 | (+) | SEQ ID NO: 382 |
| QAKMLKLTCLASYCWLFWVTRS | (+++) | (+++) | SEQ ID NO: 383 |
| RGRSAKLRCLASYCWLFFGVIL | (+++) | (+++) | SEQ ID NO: 384 |
| RGRSAKLTCLASYCWLFFGVIL | (+++) | (+++) | SEQ ID NO: 385 |
| RGRSAKLRCLASYCWLFFTVIL | (+++) | (+++) | SEQ ID NO: 386 |
| VSGTGRLTCVASYCWMFQLGSF | (+++) | (++) | SEQ ID NO: 387 |
| VSGTGRLTCVASYCWMFQLGIF | (+++) | (++) | SEQ ID NO: 388 |
| VSGTGKLTCLASYCWLFQLGSF | (+++) | (++) | SEQ ID NO: 389 |
| HQQRRKLTCLAGYCWLFVLGPS | (+) | (+++) | SEQ ID NO: 390 |
| GDSGRKLSCLGSYCWLSVQFMA | (+++) | (++) | SEQ ID NO: 391 |
| RSTVSQMRCLASYCWLFPALVS | (+++) | (++) | SEQ ID NO: 392 |
| NGGMQKPACLASQCWLFANPLP | (+) | (++) | SEQ ID NO: 393 |
| RHSNHNLTCQASYCWLLPAGLQ | (+) | (+) | SEQ ID NO: 394 |
| HLGSPKLTCGASQCWLLNHEVS | >50 | (+) | SEQ ID NO: 395 |
| DAKVAKLRCLGSQCWLLQYAPG | (+++) | (++) | SEQ ID NO: 396 |

TABLE 1-continued

Exemplary Compounds of the Present Disclosure
and their Activities in the FXa Generation Assay

| Sequence | EC$_{50}$ [μM] | Vmax | |
|---|---|---|---|
| SKWEHQRGCLANNCWLFTLAPG | >50 | (+) | SEQ ID NO: 397 |
| RGSVHQPTCLGGYCGRLHSSWV | >50 | (+) | SEQ ID NO: 398 |
| KRYVYRQMCLVSACWLLQLGYA | (+++) | (++) | SEQ ID NO: 399 |
| k-MeLeu-TCLASYCWLF | (+++) | (++++) | SEQ ID NO: 400 |
| K-k-MeLeu-TCLASYCWLF | (+) | (++++) | SEQ ID NO: 401 |
| Ac-K-k-MeLeu-TCLASYCWLF | (+++) | (+++) | SEQ ID NO: 402 |
| KK-k-MeLeu-TCLASYCWLF | >10 | | SEQ ID NO: 403 |
| KKK-k-MeLeu-TCLASYCWLF | >20 | | SEQ ID NO: 404 |
| k-k-MeLeu-TCLASYCWLF | >2.5 | | SEQ ID NO: 405 |
| R-k-MeLeu-TCLASYCWLF | (+) | (++++) | SEQ ID NO: 406 |
| k-MeLeu-TCLASFCWLF | (++) | (+++) | SEQ ID NO: 407 |
| k-MeLeu-TCLAS-(Y—OMe)-CWLF | (+++) | (++++) | SEQ ID NO: 408 |
| k-MeLeu-TCLASYCQLF | (+) | (++++) | SEQ ID NO: 409 |
| k-MeLeu-TCLASYCWLA | (+) | (+++) | SEQ ID NO: 410 |
| (KLTCLASYCWLF)$_2$=N—O—(CH$_2$)$_3$—O—N= | (++) | (++++) | SEQ ID NO: 411 |
| (KLTCLASYCWLFG)$_2$=N—O—(CH$_2$)$_3$—O—N= | (+++) | (++++) | SEQ ID NO: 412 |
| "=N—O—(CH$_2$)$_3$—O—N=(COCH$_2$CH$_2$CO-KLTCLASYCWLF)$_2$" | (++) | (++++) | SEQ ID NO: 413 |
| KLLKLLLKLLLKLLK-k-MeLeu-TCLASYCWLF | (+++) | (+++) | SEQ ID NO: 543 |
| FAM-GGSGG-k-MeLeu-TCLASYCWLF | | | SEQ ID NO: 544 |
| Palmitoyl-(PEG)27-KLTCLASYCWLF | (+) | (+) | SEQ ID NO: 545 |
| Palmitoyl-(PEG)27(PEG)27-KLTCLASYCWLF | >20 | >0.3 | SEQ ID NO: 546 |
| H3N-KLTCLASYCWLFG=N—O—CH2—CO-PEG27-CNPRGD-(Y—OEt)-RC | >50 | | SEQ ID NO: 547 |
| (CNPRGD-(Y—OEt)-RC)-PEG27-CO—CH2—O—N=CH2NHCOCH2CH2CO—KLTCLASYCWLF | | | SEQ ID NO: 548 |
| 5-FAM-CNPRGD(Y—OEt)RC | | | SEQ ID NO: 549 |
| rRAPGKLTCLASYCWLFWTGIA-PEG16-Lys(PEG2-Biotin)-PEG16-Lys(palmitoyl) | (+) | (++++) | SEQ ID NO: 550 |
| Lys(palmitoyl)-PEG16-Lys(PEG2-Biotin)-PEG16-rRAPGKLTCLASYCWLFWTGIA | (++) | (++++) | SEQ ID NO: 551 |
| rRAPGKLTCLASYCWLFWTGIA-PEG16-Lys(PEG2-Biotin)-PEG16 | (+++) | (++++) | SEQ ID NO: 552 |
| rRAPGKLTCLASYCWLFWTGIA-PEG16-Lys(PEG2-Biotin)-PEG16-CNPRGD-Tyr(OEt)-RC | (++) | (++++) | SEQ ID NO: 553 |
| PEG16-Lys(PEG2-Biotin)-PEG16-rRAPGKLTCLASYCWLFWTGIA | (+) | (++++) | SEQ ID NO: 554 |
| CNPRGD-Tyr(OEt)-RC-PEG16-Lys(PEG2-Biotin)-PEG16-rRAPGKLTCLASYCWLFWTGIA | (++) | (++++) | SEQ ID NO: 555 |

In Table 1, above, the following indicators were used:

EC$_{50}$:

(+)>1
(++) 0.5-1.0
(+++)≤0.5

Vmax:

(+)<1
(++) 1-2
(+++)>2
(++++)>3

In Table 1, "(H$_3$N-KLTCLASYCWLF)$_2$=N—O—(CH$_2$)$_3$—O—N=" (SEQ ID NO: 896) has the structure:

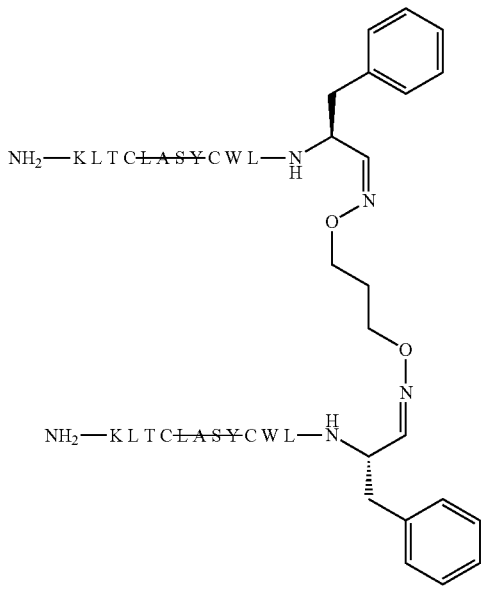

In Table 1, "(H$_3$N-KLTCLASYCWLFG)$_2$=N—O—(CH$_2$)$_3$—O—N=" (SEQ ID NO: 897) has the structure:

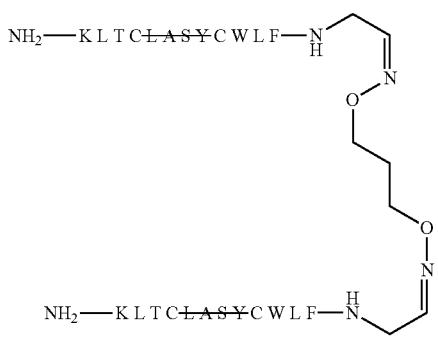

In Table 1, "=N—O—(CH2)3—O—N= (COCH$_2$CH$_2$CO—KLTCLASYCWLF—CONH$_2$)$_2$" (SEQ ID NO: 898) has the structure:

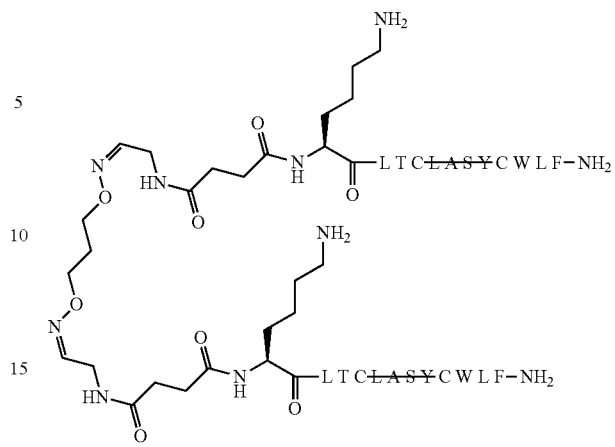

Activity of Compound 1 and its Derivatives

Alanine mutants, D-amino acid mutants, and alpha-N-methyl derivatives of compound 1, and D-amino acid mutants, and alpha-N-methyl derivatives of compound 4 were prepared and tested according to the procedure of Example 2. Results indicate that the critical amino acid residues of the compounds of the present disclosure (e.g., compound 1 and compound 4) are located within the cysteine loop (between C$^1$ and C$^2$) and towards the C-terminus of the amino acid sequence of compound 1.

Catalytic Activities of FIXa in the Absence and Presence of Various Compounds

The catalytic constants k$_{cat}$ and K$_M$ for human FIXa (10 nM) measured in the absence and presence of various compounds of the present disclosure in the above described FXa generation assay are summarized below. Compound C (scrambled peptide; see Table 1) was used as a control at 10 µM. Compound 1 was used at 3 µM, compounds 3, 4, and 5 were used at 1 µM, and compound 10 was used at 0.3 µM. FIXa was used at 10 nM, and FX was used at 10-1000 nM. The assay was performed in the presence of phospholipids (PL) and calcium chloride. Certain compounds of the present disclosure lower the K$_M$ and increase the k$_{cat}$ of hFIXa. In this experiment, compounds of the present disclosure increased the catalytic activity of FIXa (i.e., increased the k$_{cat}$ of hFIXa) by at least 160-fold. As a comparison, known FIXa mutants increase k$_{cat}$ up to 20-fold (see, e.g., J Thromb Haemost, 2009, 7, 1656-1662), and known FIXa enhancing antibodies increase the k$_{cat}$ about 10-fold (see, e.g., Thromb Haemost, 2008, 6, 315-322).

|  | k$_{cat}$ (min$^{-1}$) | Δ k$_{cat}$ | K$_M$ (nM) | Δ K$_M$ Km$_{compound}$/Km$_{buffer}$ |
|---|---|---|---|---|
| Buffer | 0.00009 | 1.0 | 78 ± 30 | 1.0 |
| Compound 1 | 0.0144 | 160 | 24 ± 4.8 | 0.31 |
| Compound 3 | 0.0177 | 197 | 16 ± 3.5 | 0.21 |
| Compound 4 | 0.0171 | 190 | 11 ± 2.7 | 0.14 |
| Compound 5 | 0.0179 | 199 | 11 ± 2.3 | 0.14 |
| Compound C | 0.00044 | 6 | 99 ± 76 | ~1 |

Comparison of the catalytic activities of FIXa and FVIIa in the absence and presence of compound 5

The the catalytic activities (k$_{cat}$) and K$_M$ values for FIXa and FVIIIa were measured in the absence and presence of compound 5 using the above described modified FXa generation assay. The results are summarized below:

| Δ $k_{cat}$ | | Δ $k_M$ | |
|---|---|---|---|
| FVIIa | FIXa | FVIIa | FIXa |
| 2419 | 199 | 0.3 | 0.14 |

$k_{cat}/K_M$

The $k_{cat}/K_M$ for FIXa was measured using various concentrations of FIXa (4, 2, 1, 0.5, and 0.25 µM) and a FIXa substrate in the absence and presence of compound 1 at 10 µM (~25 fold $EC_{50}$) and the positive control ethylene glycol (EG) 33%. The results for the chromogenic FIXa substrate, $CH_3SO_2$—(D)-CHG-Gly-Arg-pNA (AcOH, BIOPHEN CS-51; $[S]_0$=50 nM constant; $[S]_0$<<Km) are summarized below.

| Sample | $(k_{cat}/K_M)_{app}$ ($M^{-1}s^{-1}$) | Rel $k_{cat}/K_M$ |
|---|---|---|
| FIXa only | 1,591 | — |
| FIXa + compound 1 | 1,358 | 0.85 |
| FIXa + EG | 29,730 | 18.7 |

Similar results were obtained for a fluorogenic FIXa substrate (Pefafluor FIXa 3688). The above results indicate that the compounds of the present disclosure do not increase the amidolytic activity of FIXa directly (similarly to FVIIIa).

Mouse Versus Human FIXa

The $EC_{50}$ values for compound 1 in a FXa generation assay using either mouse FIXa (mFIXa) or human FIXa (hFIXa) were measured. The $EC_{50}$ values of compound 1 measured for mouse and human FIXa are similar (0.44 µM and 0.30 µM, respectively), however, the Vmax is greatly reduced with mFIXa compared to hFIXa. The data confirms that the peptide was selected for binding to hFIXa.

Compounds of the present disclosure are not a substrate for FIXa

Compound 3 (100 µM) was incubated in FXa generation assay buffer containing various concentrations of FIXa (0, 10 nM, 1 µM) in the absence or presence of bovine serum albumin (BSA) for 3 hours. The mixtures were then analyzed by LC-MS. No significant differences were seen in the chromatograms or the mass spectra for compound 3 in the above samples. The results indicate that compound 3 is not a substrate for FIXa.

EXAMPLE 3

(a) Thrombin Generation Assay (TGA)

A thrombogram was generated for selected compounds of the present disclosure in order to assess the thrombin potential in a physiological plasma environment. The TGA assay was carried out using a Calibrated Automated Thrombogram (CAT) test. Briefly, lyophilized and citrated FVIII deficient human plasma (Siemens) was reconstituted with 1 ml of distilled water, allowed to stand for 20 min at RT and mixed well before use. Alternatively, frozen FVIII-deficient plasma from Precision Biologics or HRF was used. FVIII deficient plasma was in some cases spiked with lyophilized platelets (Helena Laboratories, final concentration 0.66×10$^8$ cells/mL). Dilutions of peptide or controls such as FVIII were prepared in PBS (—Ca, —Mg) or in deficient plasma. In a 96-well round bottom plate, 20 µl of activator solution (PRP reagent [final 0.1 pM rTF], Thrombinoscope bv) was added to each sample well and 20 µl of Thrombin calibrator (Thrombinoscope bv) was added to calibrator well. Whenever plasma samples were used without platelets, PPP Low reagent [final 1 pM rTF, 4 µM phospholipids], Thrombinoscope bv was used as activator instead of the PRP reagent. Subsequently, 80 µl of blank plasma was added to the calibrator well and 80 µl of plasma containing compounds of the present disclosure, controls such as FVIII or blank was added to sample wells. All samples were prepared in duplicates and the plate was incubated at 37° C. for 10 minutes. After the incubation, 20 µl of Fluca solution ($Ca^{2+}$+fluorogenic substrate, Diagnostica Stago) was added to each well and fluorescence was measured in a microtiter plate fluorometer (Fluroskan Ascent, Thermo Scientific, Thrombinoscope software) for 1 hr. Similarly. TGA experiments were performed in FIX-deficient plasma.

Exemplary compounds of the present disclosure and their in vitro biological activities measured using the thrombin generation assay are summarized in Table 2, below. In Table 2, peptides are amidated (—$CONH_2$) at the C-terminus and have a free N-terminus, unless otherwise indicated. In Table 2, compound activities are based on thrombin peak height (nM thrombin). TGA experiments were performed in FVIII-deficient plasma from two different sources exhibiting different baseline values: HRF FVIII-deficient plasma (1) and Precision Biologics FVIII-deficient plasma (2).

TABLE 2

Exemplary Compounds of the Present Disclosure and their Activities in the TGA

| Compound | Concentration (µM) | Thrombin Above Baseline (nM)[a] |
|---|---|---|
| Baseline (1) | 0 | — |
| FVIII | 0.1 IU/mL | + |
| FVIII | 0.25 IU/mL | ++ |
| FVIII | 0.5 IU/mL | +++ |
| FVIII | 0.75 IU/mL | ++++ |
| FVIII | 1 IU/mL | ++++ |
| KLTCLASYCWLF (SEQ ID NO: 200) | 2.5 uM | — |
|  | 5 | — |
|  | 10 | — |
|  | 20 | — |
| k-MeLeu-TCLASYCWLF (SEQ ID NO: 232) | 2.5 | + |
|  | 5 | — |
|  | 10 | — |
|  | 20 | + |
| rRAPGKLTCLASYCWLFWTGIA (SEQ ID NO: 67) | 2.5 | + |
|  | 5 | + |
|  | 10 | ++ |
|  | 20 | ++ |
| PRIRTVGPGSRSASGKLTCLASYCWLF WTGIA (SEQ ID NO: 874) | 2.5 | + |
|  | 5 | ++ |
|  | 10 | +++ |
|  | 20 | +++ |
| PRIrTVGPGSrSASGKLTCLASYCWLF WTGIA (SEQ ID NO: 425) | 2.5 | ++ |
|  | 5 | +++ |
|  | 10 | +++ |

TABLE 2-continued

Exemplary Compounds of the Present Disclosure and their Activities in the TGA

| Compound | Concentration (μM) | Thrombin Above Baseline (nM)[a] |
|---|---|---|
| Baseline (2) | | |
| SRIRTVGPGSRSASGKLTCLASYCWLFWTGIA (SEQ ID NO: 432) | 2.5<br>5<br>10 | ++<br>+++<br>++++ |
| PSIRTVGPGSRSASGKLTCLASYCWLFWTGIA (SEQ ID NO: 433) | 2.5<br>5<br>10 | +<br>+<br>+ |
| PRSRTVGPGSRSASGKLTCLASYCWLFWTGIA (SEQ ID NO: 434) | 2.5<br>5<br>10 | ++<br>+++<br>+++ |
| PRISTVGPGSRSASGKLTCLASYCWLFWTGIA (SEQ ID NO: 435) | 2.5<br>5<br>10 | +<br>+<br>+ |
| PRIRSVGPGSRSASGKLTCLASYCWLFWTGIA (SEQ ID NO: 436) | 2.5<br>5<br>10 | ++<br>+++<br>+++ |
| PRIRTSGPGSRSASGKLTCLASYCWLFWTGIA (SEQ ID NO: 437) | 2.5<br>5<br>10 | +<br>++<br>++ |
| PRIRTVSPGSRSASGKLTCLASYCWLFWTGIA (SEQ ID NO: 438) | 2.5<br>5<br>10 | ++<br>+++<br>++++ |
| PRIRTVGSGSRSASGKLTCLASYCWLFWTGIA (SEQ ID NO: 439) | 2.5<br>5<br>10 | +<br>+<br>+ |
| PRIRTVGPSSRSASGKLTCLASYCWLFWTGIA (SEQ ID NO: 440) | 2.5<br>5<br>10 | +<br>++<br>++ |
| PRIRTVGPGSRSASGKSTCLASYCWLFWTGIA (SEQ ID NO: 441) | 2.5<br>5<br>10 | +<br>++<br>+++ |
| PRIRTVGPGSRSASGKLTCLASYCWLFWTGIA (SEQ ID NO: 874) | 2.5<br>5<br>10 | ++<br>+++<br>+++ |
| Baseline (2) | | |
| PRIRTVGPGSRSASGKSTCLASYCWLFWTGIA (SEQ ID NO: 441) | 2.5<br>5<br>10<br>20 | +<br>+++<br>++++<br>++++ |
| SRIRTVGPGSRSASGKSTCLASYCWLFWTGIA (SEQ ID NO: 445) | 2.5<br>5<br>10 | +++<br>++++<br>++++ |
| PRIRTVSPGSRSASGKSTCLASYCWLFWTGIA (SEQ ID NO: 446) | 2.5<br>5<br>10<br>20 | ++<br>+++<br>++++<br>++++ |
| SRIRTVSPGSRSASGKSTCLASYCWLFWTGIA (SEQ ID NO: 447) | 2.5<br>5<br>10<br>20 | +++<br>+++<br>++++<br>++++ |
| PRSRTVGPGSRSASGKSTCLASYCWLFWTGIA (SEQ ID NO: 448) | 2.5<br>5<br>10<br>20 | ++<br>+++<br>++++<br>++++ |
| SRSRTVSPGSRSASGKSTCLASYCWLFWTGIA (SEQ ID NO: 449) | 2.5<br>5<br>10 | +++<br>++++<br>++++ |

In Table 2, above, the following indicators were used:
Thrombin Above Baseline
1-10 nM (1) or 1-29 nM (2) (+)
11-20 nM (1) or 30-59 nM (2) (++)
21-30 nM (1) or 60-90 nM (2) (+++)
>30 nM (1) or >90 nM (2) (++++)
At or about baseline (−)

The TGA activities of compound 7 (GWKPFLWDPRV-LLSSGWYGRG) (SEQ ID NO: 862), compound 8 (PWR-RFWAWNPRSLALSTWFGRGCD) SEQ ID NO: 863), and compound 9 (GWKPFLWDPRVLLSSGWYGRGGGGG-WKPFLWDPRVLLSSGWYGRG) SEQ ID NO: 864), which are less potent and structurally unrelated to the compounds of the present disclosure, were measured in the presence of FVIII. Compound 7 was used at at 100, 50, 25, 12.5 and 6.3 uM in the presence of 0.1 U/mL of FVIII; compound 8 was used at at 50, 25, 12.5, 6.3 and 3.1 uM in the presence of 0.1 U/mL of FVIII; and compound 9 was used at 50, 25, 12.5, 6.3 and 3.1 uM in the presence of 0.1 U/mL of FVIII. Under these conditions, each compound competes with FVIII in the TGA. The opposite phenomena was observed for the compounds of the present disclosure.

(b) Thrombin Generation Assay Using Purified Hemostatic Components

A purified thrombin generation assay was used to measure the selectivity of the compounds of the present disclosure. The assay was modified from the procedures described in Aljamali M N et al., Epub 2009 Jul. 29, Thrombin generation and platelet activation induced by rFVIIa (NovoSeven) and NN1731 in a reconstituted cell-based model mimicking haemophilia conditions, *Haemophilia* 2009, 15(6):1318-26; and Christiansen M L et al., Functional characteristics of N8, a new recombinant FVIII, *Haemophilia* 2010, 16(6):878-87.

Figure 5:
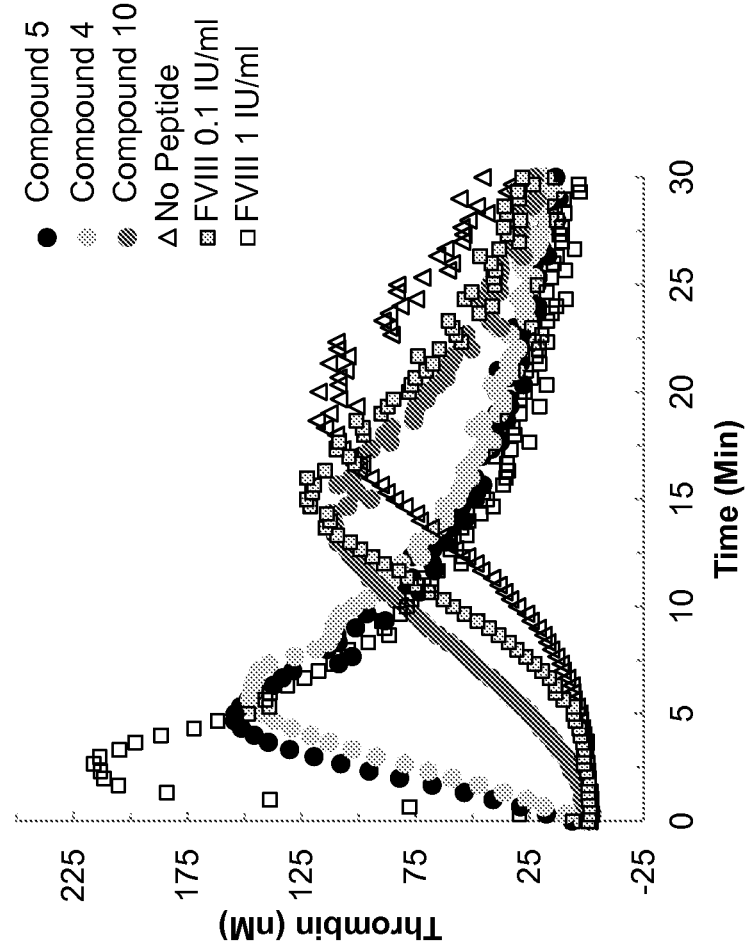
FIG. 5 is graph illustrating the activity of various compounds of the present disclosure in a thrombin generation assay using purified hemostatic components as described in Example 3.

The thrombin generation assay mixture was composed of FXI (3.1 ug/mL), FIX (3.1 ug/mL), FVII (6.3 nM), FVIIa (6.3 pM), tissue factor (10 fM), FV (4.4 ug/mL), FX (5 ug/mL), FII (54 ug/mL), antithrombin III (ATIII) (75 ug/mL), tissue factor pathway inhibitor (TFPI) (0.06 ug/mL) and lyophilized platelets (6E+07/mL). Purified recombinant human coagulation factors V, XI, II, X, IX, VII, VIIa, recombinant tissue factor and antithrombin III (ATIII) were obtained from Haematologic Technologies (Essex Junction, Vt., USA). Lyophilized platelets were from Helena Laboratorires (Beaumont, Tex.); TFPI was from American Diagnostica. Compound 5 (1 uM), compound 4 (1 μM), compound 10 (1 μM), FVIII at 10% (0.1 IU/mL) or 100% (1 IU/mL) or buffer was added to the assay mixture together with the thrombin substrate (Fuca-kit, Thrombinoscope BV, The Netherlands) and the thrombin generation was measured with a Thrombinoscope Instrument (Thrombinoscope BV, The Netherlands). Both, FVIII and the pro-coagulant compounds of the present disclosure induce thrombin generation in this assay (i.e., in the presence of purified hemostatic components). The thrombin generation activities of compound 5, 4, and 10 are illustrated in FIG. 5.

Figure 6:
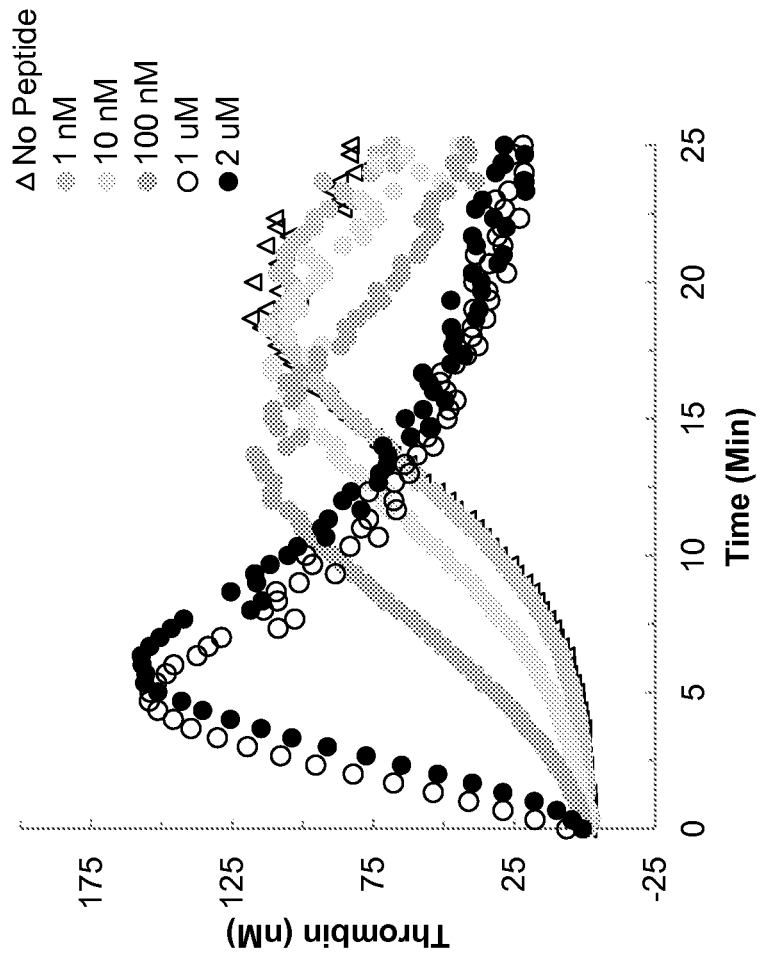
FIG. 6 is a graph illustrating that compound 5 enhances thrombin generation in a dose-dependent manner when measured in a thrombin generation assay using purified hemostatic components as described in Example 3.

In a second experiment, compound 5 was tested at various concentrations (1 nM, 10 nM, 100 nM, 1 µM, and 2 µM). The results of this experiment are illustrated in FIG. 6, which shows that compound 5 enhances thrombin generation in a dose-dependent manner.

Figure 7:
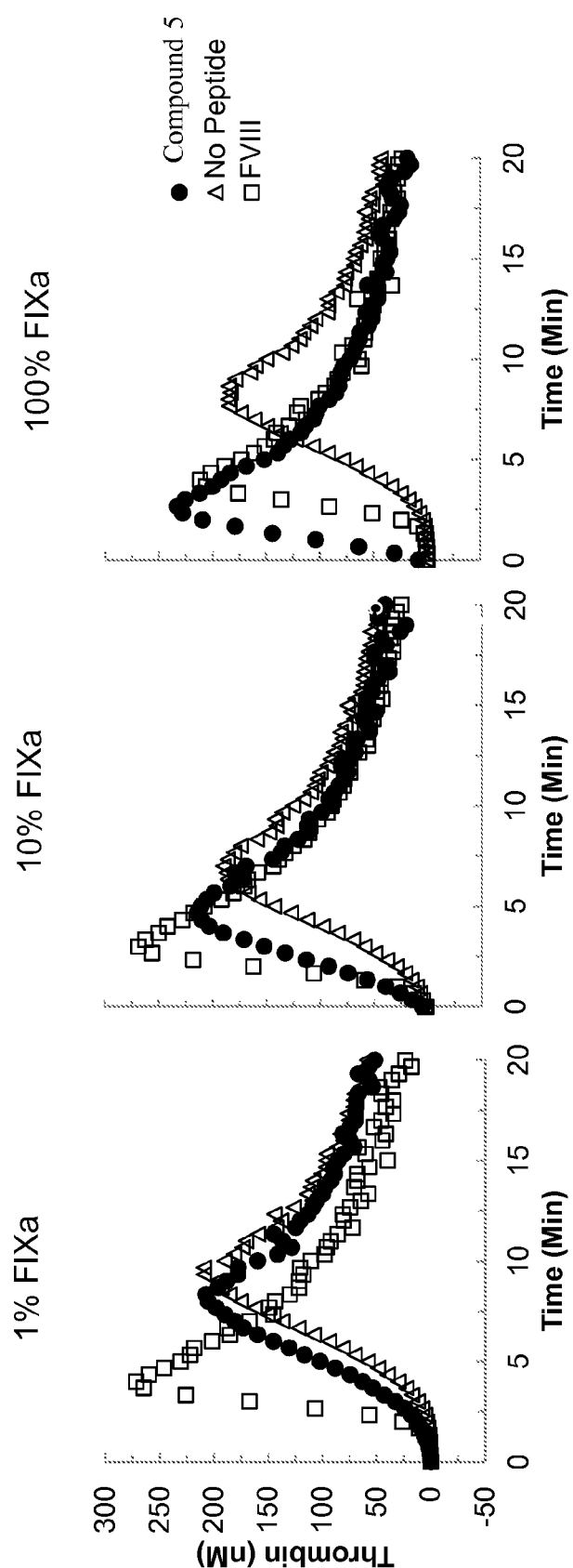
FIG. 7 contains three graphs illustrating that the thrombin generation activity of compound 5 is FIXa-dependent when measured in a thrombin generation assay using purified hemostatic components as described in Example 3.

In a third experiment it was investigated whether thrombin formation induced by FVIII or compound 5 is dependent on FIXa. The components of the thrombin generation assay were combined to generate the following final concentranons: FV (4.4 ug/mL), FX (5 ug/mL), FII (54 ug/mL), ATIII (75 ug/mL), and lyophilized platelets (6E+07/ml) in the presence of either 1%, 10% or 100% (3.1 µg/mL) of physiological FIXa. FVIII (0.01 U/mL) or compound 5 (1 µM) were added together with the thrombin substrate (Fluca-kit) and the plate was read using a thrombinoscope. Results show that the thrombin generation induced by compound 5 is dependent on the FIXa concentration present in the assay mixture. The results of this experiment are illustrated in FIG. 7.

Figure 8:
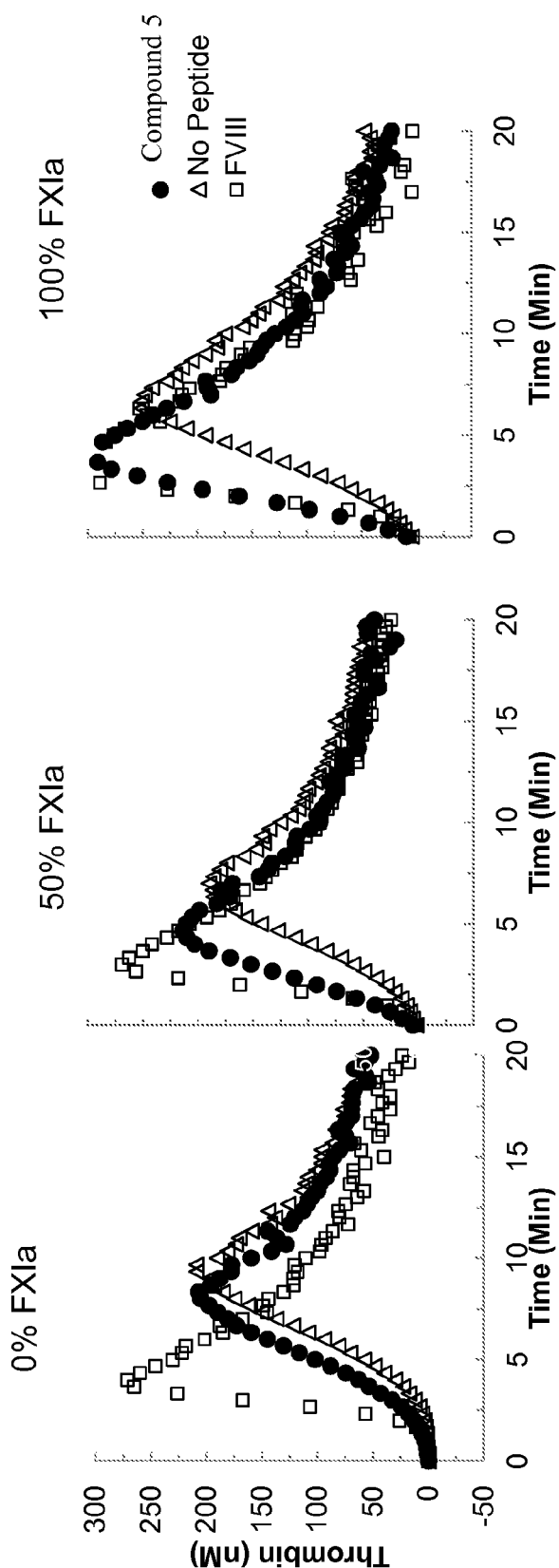
FIG. 8 contains three graphs illustrating that the thrombin generation activity of compound 5 is FXIa-dependent when measured in a thrombin generation assay using purified hemostatic components as described in Example 3.

In a fourth experiment it was investigated whether thrombin formation induced by FVIII or compound 5 is dependent on FXIa. The components of the thrombin generation assay were combined to generate the following final concentrations: FIX (3.1 ug/mL), FV (4.4 ug/mL), FX (5 ug/mL), FII (54 ug/mL), ATIII (75 ug/mL), and lyophilized platelets (6E+07/ml) in the absence or presence of either 50%, or 100% FXIa. (100% FXIa corresponds to the physiological concentration of 3.1 µg/mL). FVIII (0.01 U/mL) or compound 5 (1 µM) were added together with the thrombin substrate (Fluca-kit) and the plate was read using a thrombinoscope. Results show that the thrombin generation induced by compound 5 is dependent on the FXIa concentration present in the assay mixture. The results of this experiment are illustrated in FIG. 8.

In another experiment compound 5 in the above assay system enhanced thrombin generation in the absence of FIX/FIXa indicating that compounds of the present disclosure, in addition to increasing the intrinsic pathway, can enhance thrombin formation through the extrinsic pathway (e.g., via increasing the catalytic activity of FVIIa). In this experiment, the thrombin generation assay mixture contained the following components: FVII (6.3 nM), FVIIa (6.3 pM), tissue factor (10 fM), FV (4.4 ug/mL), FX (5 ug/mL), FII (54 ug/mL), ATIII (75 ug/mL), TFPI (0.06 ug/mL) and lyophilized platelets (6E+07/mL). Compound 5 (1 µM) or buffer was added to the assay mixture together with the thrombin substrate (Fluca-kit) and the kinetics were read using a thrombinoscope.

Compounds of the Present Disclosure Do Not Directly Increase FXa Activity

In another experiment it was determined whether or not the compounds of the present disclosure directly enhance the activity of FXa or the prothrombinase complex. In this experiment, compound 5 (1 µM), compound 4 (1 µM) or buffer was added to a thrombin generation assay mixture containing the following components at the indicated final concentrations: FII (54 ug/mL), FXa (0.05 ug/mL), ATIII (75 ug/mL), TFPI (0.06 ug/mL) and lyophilized platelets (6E+07/mL) with or without FV (4.4 ug/mL).

A thrombin substrate (Fluca-kit) was added and the thrombin generation was measured using a thrombinoscope. Under these conditions, compound 5 and compound 4 did not substantially increase the catalytic activity of FXa or the prothrombinase complex.

Compounds of the Present Disclosure Do Not Directly Increase Thrombin Activity

In another experiment it was investigated whether or not the compounds of the present disclosure increase the thrombin activity directly. The thrombin activity was measured in the absence or presence of compound 5 using a fibrin generation assay with the following assay components having the indicated final concentrations in the assay mixture: fibrinogen (0.45 g/L), calcium (16.5 mM), platelets (6E+07/mL), α-thrombin (0 or 0.1 IU/mL). The generation of fibrin was determined by measuring the absorbance at OD405 with the Biotek Synergy 2 multi-detection microplate reader.

In this experiment, compound 5 (1 uM) did not substantially increase the catalytic activity of thrombin directly (i.e., did not directly increase the amidolytic activity of alpha-thrombin).

EXAMPLE 4

Rotational Thromboelastometry (ROTEM®) Assay

Compounds of the present disclosure were tested by rotational thromboelastometry to evaluate coagulation parameters such as clotting time (CT), α-angle, clot formation time (CFT), maximum clot firmness (MCF). Briefly, lyophilized and citrated FVIII deficient human plasma (Siemens) was reconstituted with 1 mL of distilled water, allowed to stand for 20 min at RT and mixed well before use. Alternatively, an aliquot of citrated (non-lyophilized) FVIII deficient human plasma (HRF, George King, Precision Biologics, or real-time donors) was thawed for 10 min in a 37° C. water bath and when needed centrifuged at 2800 g for 5 min at 25° C. FVIII deficient plasma was spiked with lyophilized platelets (Helena Laboratories, final concentration $0.5 \times 10^8$ cells/ml) and compounds, FVIII, or both compound and FVIII. Dilutions of compounds of the present disclosure and controls, such as FVIII, were prepared in PBS (—Ca, —Mg). Next, 300 µl of the spiked plasma was transferred to a ROTEM cup already containing 20 µl of StarTEM (concentrated calcium chloride solution) and 20 µl of lipidated TF (American Diagnostica, final concentration 10 fM) or Kaolin (Sigma-Aldrich, final concentration 0.4 µg/ml) and recording was initiated. The cups were maintained at 37° C. during the testing. All tests were run for 1.5 to 2 hrs.

Clotting times and α-angles for FVIII and compound 3 measured in a ROTEM assay using FVIII-deficient human plasma containing lyophilized platelets and 10 fM lipTF were compared. Clotting times and α-angles measured in the presence of FVIII and compound 3 at various concentrations are summarized below. In this experiment, compound 3 (at 5 µM) has a faster clotting time than about 100% FVIII (100% FVIII corresponding to 1 IU/mL). In this experiment, compound 3 (at 10 µM) has an α-angle corresponding to about 20% FVIII. Results are summarized in Tables 3 and 4, below.

TABLE 3

| | Compound 3 in human HemA plasma | | | | | |
|---|---|---|---|---|---|---|
| Conc., μM | 0 | 0.625 | 1.25 | 2.5 | 5 | 10 |
| Clotting time, sec (avg.) | 989 | 792 | 588 | 452 | 329 | 205 |
| α-angle, degrees (avg.) | 18 | 29 | 29 | 33 | 38 | 51 |

TABLE 4

| | rFVIII in human HemA plasma | | | | | |
|---|---|---|---|---|---|---|
| Conc., IU/mL | 0.01 | 0.05 | 0.10 | 0.25 | 0.50 | 1 |
| Clotting time, sec (avg.) | 852 | 761 | 610 | 521 | 458 | 363 |
| α-angle, degrees (avg.) | 26 | 35 | 48 | 60 | 63 | 71 |

The clotting times and α-angles for compound 3 in FVIII-deficient plasma in the absence and presence of neutralizing antibodies (polyclonal sheep IgG against human FVIII, 18.4 mg/mL at 1:100 dilution) were also measured. In this experiment, the clotting time for compound 3 at 10 uM is independent of residual FVIII, and the presence of a neutralizing anti-FVIII antibody. The α-angle measured for compound 3 at 10 uM is independent of residual FVIII and the presence of a neutralizing anti-FVIII antibody. Results are summarized in Table 5, below.

TABLE 5

| | Compound 5 in human HemA plasma | | | | | |
|---|---|---|---|---|---|---|
| Conc., μM | 0 | 0 | 5 | 5 | 10 | 10 |
| Anti-FVIII pab | − | + | − | + | − | + |
| Clotting time, sec | 777; 775 | 1,063; 1,202 | 154; 164 | 197; 194 | 101; 105 | 108; 110 |
| α-angle, degrees | 42; 41 | 10; 11 | 51; 58 | 48; 53 | 70; 68 | 67; 69 |

Similarly, clotting times and α-angles for FVIII and compound 23 at various concentrations were measured in a ROTEM assay using FVIII-deficient human plasma (HRF) were compared. Results are summarized in Tables 6 and 7, below.

TABLE 6

| | Compound 23 in human HemA plasma (HRF) | | | | |
|---|---|---|---|---|---|
| Conc., μM | 0 | 2.5 | 5 | 10 | 20 |
| Clotting time, sec (avg.) | 2,208 | 983 | 673 | 486 | 472 |
| α-angle, degrees (avg.) | 9 | 13 | 22 | 32 | 39 |

TABLE 7

| | rFVIII in human HemA plasma (HRF) | | | | |
|---|---|---|---|---|---|
| Conc., IU/mL | 0 | 0.10 | 0.25 | 0.50 | 0.75 | 1 |
| Clotting time, sec (avg.) | 1,823.5 | 1,062 | 821 | 783 | 654.5 | 608 |
| α-angle, degrees (avg.) | 18 | 21.5 | 25 | 32 | 38.5 | 35 |

Clotting times of compound 5 at 5 μM and 10 μM were measured using FIX-deficient human plasma containing lyophilized platelets and 10 fM TF. In this assay, compound 5 significantly reduces clotting time in FIX-deficient plasma. Results are summarized in Table 8, below.

TABLE 8

| | Compound 5 in human HemB plasma | | | rFIX in HemB plasma |
|---|---|---|---|---|
| Conc. (μM) | 0 | 5 | 10 | 1 IU/mL |
| Clotting time (sec) | 1,188; 1,288 | 836; 810 | 804; 773 | 468; 468 |
| α-angle (degrees) | 19; 18 | 24; 20 | 22; 21 | 54; 51 |

The clotting time (CT) in a ROTEM assay using either FVIII-deficient human plasma (containing platelets) or FIX-deficient plasma (containing platelets) was measured in the absence and presence of compound 5. The results, summarized in Table 9, below, indicate that compound 5 significantly reduced clotting time in both FVIII- and FIX-deficient plasma. The effect is more pronounced in FVIII-deficient human plasma.

TABLE 9

| | FVIII-deficient plasma | | FIX-deficient plasma | |
|---|---|---|---|---|
| Compound 5, μM | 0 | 10 | 0 | 10 |
| Clotting time, sec | 1,563; 1,666 | 277; 298 | 1,617; 1,628 | 1,311; 1,328 |
| α-angle, degrees | 14; 17 | 34; 27 | 20; 15 | 15; 19 |

The clotting time α-angle for compound 5 in FIX-deficient plasma in the absence and presence of neutralizing anti-FIX antibodies (polyclonal sheep IgG against human FIX, 3.96 mg/mL at 1:50 dilution) was measured. In these experiments, compound 5 reduces clotting time and increases α-angle in FIX-inhibited FIX-deficient plasma indicating that compound 5 is capable of enhancing the catalytic activity of other proteins, e.g., other blood clotting factors, in addition to FIXa. Results are summarized in Table 10, below.

TABLE 10

| | Compound 5 in human HemB plasma | | | | | |
|---|---|---|---|---|---|---|
| Conc., µM | 0 | 0 | 5 | 5 | 10 | 10 |
| Anti-FIX pab | − | + | − | + | − | + |
| Clotting time, sec | 3,450; 3,267 | 5,138; 5,131 | 1,420; 1,556 | 1,660; 1,661 | 1,182; 1,194 | 1,125; 989 |
| α-angle, degrees | 8; 6 | — | 11; 12 | 9 | 12; 12 | 13; 10 |

The clotting time in the absence and presence of compound 5 at various concentrations in a ROTEM assay using canine FVIII-deficient plasma containing lyophilized human platelets and 10 fM lipTF was measured. Results are summarized in Table 11, below.

TABLE 11

| | Compound 5 in canine HemA plasma | | | | | | Compound C in canine HemA plasma | Normal canine plasma |
|---|---|---|---|---|---|---|---|---|
| Conc. (µM) | 0 | 0.625 | 1.25 | 2.5 | 5 | 10 | 10 | 0 |
| Clotting time (sec) | 1,062; 1,029 | 687; 539 | 404 | 346; 356 | 295; 369 | 286; 294 | 1,136; 1,491 | 364; 390 |
| α-angle (degrees) | 9; 14 | 12 | 14 | 15; 15 | 29; 28 | 58; 57 | 7 | 55; 44 |

The clotting time α-angle for compound 21 in whole blood was measured. The only difference from the above described plasma Rotem is that the experiment is done in human HemA (severe) whole blood. No platelets were added as they are already present the in whole blood. Rotem activity was measured after 30 min pre-incubation of compound 21 in whole blood. Results are summarized in Table 12, below:

TABLE 12

| | Compound 21 in human HemA (severe) whole blood | | | | | | rFVIII in HemA WB |
|---|---|---|---|---|---|---|---|
| Conc. (µM) | 0 | 1.25 | 2.5 | 5 | 10 | 20 | 1 IU/mL |
| Clotting time (sec) | 2,360; 2,910 | 1,140; 1,137 | 1,057; 1,090 | 930 | 748; 703 | 952; 625 | 702; 618 |
| α-angle (degrees) | 15 | 22; 24 | 32 | 32 | 44; 52 | 42; 43 | 42; 46 |

EXAMPLE 5

Hydrogen Deuterium Exchange (HDX)

Hydrogen/deuterium exchange mass spectrometry (H/DX-MS) was utilized to study the higher-order structural analysis of recombinant human factor IXa (hFIXa) in combination with and without compound 4. The general method can be found in the following references: Engen and Smith (2001) *Anal. Chem.* 73, 256A-265A.; Wales and Engen (2006) *Mass Spectrum. Rev.* 25, 158-170.

Experimental Conditions:

Samples and Buffers:

Samples contained human FIXa (1 µM, Hematologic Technologies) in 50 mM Tris, pH 7.4; 100 mM NaCl; 2 mM $CaCl_2$ (98.8% $D_2O$) with our without the presence of compound 4 (12 µM).

H/DX-MS Analysis:

FIXa samples were equilibrated at ambient temperature (20±1° C.) for 1 hour before labeling with deuterated buffer (reaction buffers described above). The samples were then diluted 1:15 with deuterated buffer and incubated, allowing hydrogen exchange to occur for various amounts of time (10 seconds, 1, 10, 60, and 240 minutes), before the reaction was quenched with a 1:1 dilution of 200 mM citrate, 8 M guanidinium HCl, and 0.5 M TCEP, pH 2.33. Quenched samples were then incubated for 20 seconds before being further diluted 1:1 with 0.1% formic acid and immediately injected into the LC-MS system for analysis.

Approximately 7 µg of exchanged/quenched FIXa was injected onto an immobilized pepsin column where the digestion and peptide trapping were performed for 3 minutes with a flow rate of 0.1 mL/min in 0.1% formic acid at 10° C. (Houde D. et al., 2010 Post-Translational Modifications Differentially Affect IgG1 conformation and receptor binding. *Mol. Cell. Proteomics*, 9 (8): p1716). The peptic peptides were trapped on an ACQUITY BEH C18 1.7 µm peptide pre-column trap (Waters Corp. Milford, Mass.) maintained at 0° C. Flow was diverted by a switching valve and the trapped peptides flushed from the trap onto an ACQUITY BEH C18 1.7 µm, 1 mm×100 mm column (Waters Corp, Milford, Mass.) to separate the peptides at 0° C. using a 9 minute linear acetonitrile gradient (2-55%) with 0.1% formic acid at a flow rate of 40 µL/min (Wales T E, Fadgen K E, Gerhardt G C, Engen J R. 2008. High-speed and high-resolution UPLC separation at zero degrees Celsius. *Anal. Chem.* 80(17): p6815). Eluate from the C18 column was directed into a Waters Synapt HD mass spectrometer with electrospray ionization and lock-mass correction (using Glu-fibrinogen peptide). Mass spectra were acquired and peptic peptides were identified using a combination of exact mass and MS, aided by Waters Identity software (Silva J C et al., 2006. Absolute quantification of proteins by LCMSE: a virtue of parallel MS acquisition. Mol Cell Proteomics, 5(1): p144). All data was averaged from duplicate injections. The amount of deuterium in each peptide was determined by subtracting the mass of the undeuterated peptide from the mass of the deuterated peptide, incubated at various HDX time points (which were uncorrected for any back exchange). The mass data was then plotted as a function of deuterium exposure time.

Results:

69 peptides were identified, representing approximately 75% of the hFIXa amino acid sequence, which corresponded to 37% coverage of the light chain and 99% coverage of the heavy chain. The resulting data produced 69 deuterium incorporation (HDX) graphs for both the FIXa control and FIXa with compound 4.

The difference in deuterium exchange between FIXa and FIXa with compound 4 was determined by subtracting the mass of each FIXa peptide from the mass of the corresponding FIXa with compound 4. This subtraction was done for each H/D exchange time point (0.17, 1, 10, 60, and 240 minutes). The sum of these differences, across all time points, was calculated. The values for the mass differences and the sum can be either positive or negative. Positive values indicate that FIXa exchanges more rapidly than FIXa with compound 4, which may indicate that FIXa has a more open, flexible, or weakly H-bonded structure. Negative values mean the reverse. For a sample to be considered not comparable, the following criteria must be achieved: (1) At least one time point must fall outside of the ±0.5 Da threshold; and (2) the corresponding difference sum value, for a peptide containing a difference value that exceeded the ±0.5 Da threshold (criteria 1), must also exceed the ±1.1 Da threshold. These criteria represent a rigorous measure for assessing comparability and are based on pure statistical experimental uncertainties associated with the H/DX-MS method. The rigor of how large a difference needs to be before establishing non-comparability between two nearly identical biopharmaceuticals is a variable that depends on the nature of the biopharmaceutical and where in the biopharmaceutical a difference is observed.

Figure 4:
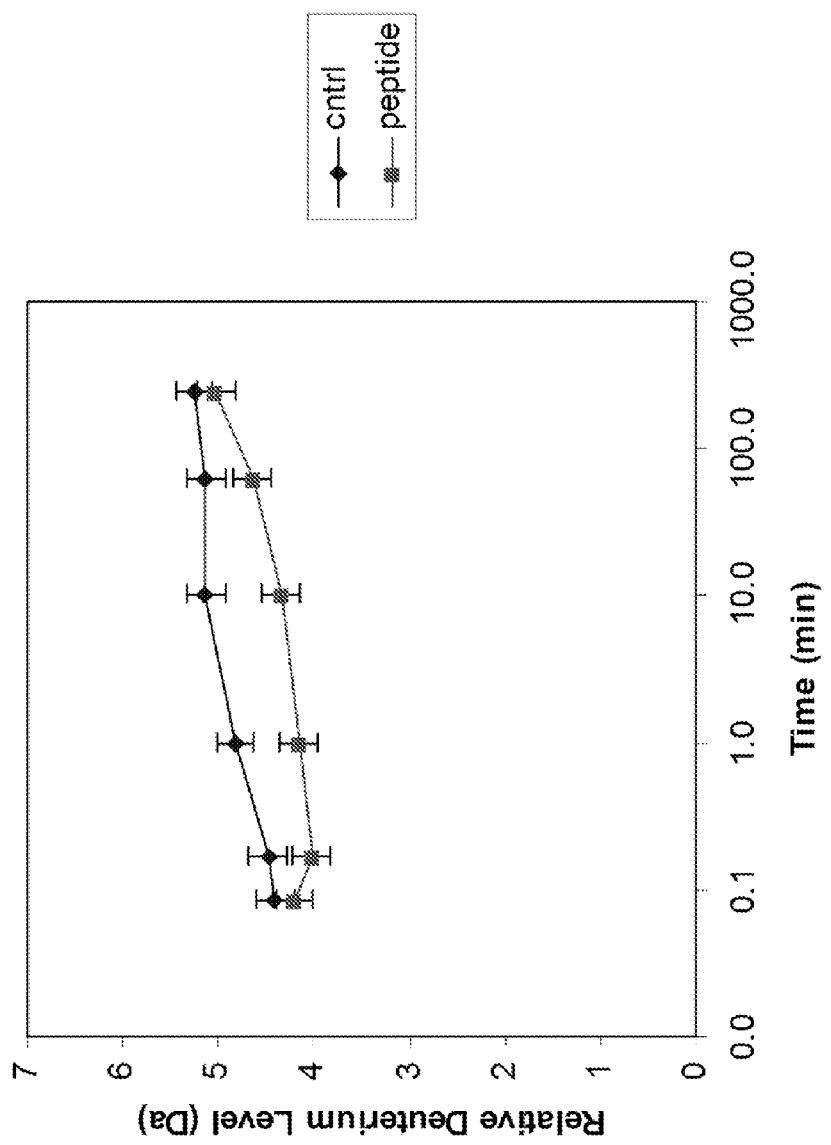
FIG. 4 is a graph illustrating hydrogen-deuteriutn exchange (HDX) for amino acids 177-185 of hFIXa in the absence and presence of compound 4.

In order to further assess the presence of non-comparability in H/DX-MS experiments two quantitative difference indices, DI(1) and DI(2) were developed and reported as whole numbers. The DI(1) value is determined by summing up all the absolute values for the difference sum that exceed the threshold (1.1) and meet the criteria above. If a difference sum value is negative, the number is assigned a value of zero. In expressing DI values, a final value >0 indicates that the samples are not comparable. The DI(2) value is determined similarly, but for each individual time point. The value for DI(1) and DI(2) for these experiments are 2 and 0, respectively. There were two peptides that showed statistically significant differences in H/D exchange When comparing FIXa to FIXa with compound 4: light chain peptide 85-97 (peptide number 4) and most importantly heavy chain peptide 177-185 (peptide number 57). The region of difference within the heavy chain peptide 177-185 could be further resolved from overlapping peptides. Heavy chain peptide 169-180 was found and the H/D exchange was shown to be similar between FIXa and FIXa with compound 4. Results are illustrated in FIG. 4.

As a result, the difference observed in heavy chain peptide 177-185 could be localized to residues 180-185. The difference detected within the FIXa light chain is very small but appears significant at the later H/D exchange time points (60 and 240 minutes). The difference seen within the FIXa heavy chain is significant and is visible across nearly all time points. These residues are within close proximity to those regions on FIXa which are reported to interact with factor VIIIa (Bajaj S P et al. 2001. Factor IXa:factorVIIIa interaction: helix 330-338 of factor IXa interacts with residues 558-565 and spacially adjacent regions of the A2 subunit of factor VIIIa. J. Biol. Chem. 276(19): p16302).

Amino acid sequence alignments of human, canine and mouse FIXa suggest that the measured selectivity of the compounds of the present invention for human and canine FIXa as compared to mouse FIXa can be due to F184Y and H185R.

EXAMPLE 6

In Vitro Stability of The Compounds

Plasma Stability

Certain compounds of the present disclosure have limited chemical stability in plasma. For example, compound 1 shows significant degradation after 0.5 hours of incubation in mouse plasma at 37° C. However, compound 2 is stable in mouse plasma for at least 3 h.

The stability, e.g., in vitro plasma stability of the compounds of the present disclosure can be increased by including D-amino acids or N-methylated amino acid residues into the peptide sequence. For example, the stability of a compound can be increased by replacing arginine (R) with D-arginine (r).

The in vitro plasma stabilities for the compounds of the present disclosure were determined using a LC-MS method. Selected compounds were spiked into 120 μL of human FVIII deficient plasma (Siemens) to give a final concentration of 50 μg/mL. An aliquot of 20 μL was taken from the sample at time 0 as control. The remaining sample was incubated at 37° C. for 2 hrs. Additional aliquots of 20 μL were taken at time points 30 min, 1 hr, 2 hrs. All samples (20 μL aliquots) were treated immediately with 100 μL of cold 100% acetonitrile, vortexed for 10 min and centrifuged at 13000 rpm for 8 min. The 100 μL of supernant was transferred to a new vial and dried by speedvac and reconstituted with 100 μL of 20% acetonitrile and 0.1% formic acid. 90 μL of reconstituted sample was injected for LC-UV-MS/MS analysis. The MS was set at triple play with full scan, zoom scan and MS/MS scans with top five ions using dynamic exclusions. 5 μL of 10 μg/mL neat peptide in water was injected as a standard control. HPLC conditions: A. 0.1% FA in water; B. 0.1% formic acid in acetonitrile, column temperature 50° C.; flow rate 0.4 mL/min; 8 min run time with fast gradient. Samples were analyzed by LC-MS, and the data was reviewed to identify any breakdown products.

The chemical stability of various compounds of the present disclosure in human plasma was measured according to the above procedure. After two hours of incubation at 37° C., compounds 5 and 6 showed no detectable degradation, while compound 3 showed about 85% degradation after 2 hours. The results indicate that compounds of the present disclosure, which incorporate a D-amino acid at the N-terminus or close to the N-terminus (i.e., D-arginine), such as compounds 5 and 6, are more stable in plasma (e.g., human plasma) than a corresponding compound, which does not incorporate such D-amino acid (e.g., compound 3). The results are summarized in Table 13, below:

TABLE 13

| Compound | Time (min) | Degradation (%) |
|---|---|---|
| 3 | 0 | 0.00 |
| 3 | 30 | 64.72 |
| 3 | 60 | 75.71 |
| 3 | 120 | 85.26 |
| 5 | 0 | 0.00 |
| 5 | 30 | 0.00 |
| 5 | 60 | 0.00 |
| 5 | 120 | 0.00 |
| 6 | 0 | 0.00 |
| 6 | 30 | 0.00 |
| 6 | 60 | 0.00 |
| 6 | 120 | 0.00 |

In a similar fashion, the plasma stability of compound 23 was improved when compared to compound 21, and the chemical stability of compound 24 was improved compared to the stability of compound 22, while maintaining biological activity in each case.

Degradation Products in Mouse Plasma

The stabilities of compound 1 and 2 were tested in mouse plasma Compound 1 showed significant degradation after 0.5 h of incubation. Two degradation products were found for compound 1, which were identified using mass spectroscopy:
1. TCLASYCWLF (SEQ ID NO: 246) (m/z theoretical: 1204.50; found 1204.44)
2. LTCLASYCWLF (SEQ ID NO: 245) (m/z theoretical: 1317.50; found 1317.60).

Contrarily, no degradation products were detectable for compound 2, even after incubation at 37° C. for 3 hours in mouse plasma.

Whole Blood Stability

Compound 5 was also stable in whole blood for at least 120 min.

EXAMPLE 7

Screening of Phage Libraries for FIXa Binders

Selected Peptides capable of binding to FIXa were identified by screening filamentous phage display libraries licensed from Dyax Corp. (Cambridge, Mass.). More specifically, the following seven libraries were used in combination; TN6.VII, TN7.IV, TN8.IX, TN-9-IV, TN10-X, TN-11-I and TN-12-I were used in the screen. The total number of individual viable phage contained in each library was reflected by the number of transformants established for each library when the libraries were expressed in *E. coli* and plated at a clonal dilution as described by the Dyax protocol. The number of transformants for TN6.VII, TN7.IV, TN8.IX, TN-9-IV, TN10-X, TN-11-I and TN-12-I was $1.2 \times 10^9$, $2.3 \times 10^9$, $5.0 \times 10^9$, $3.2 \times 10^9$, $2 \times 10^9$, $2.7 \times 10^9$ and $1.4 \times 10^9$, respectively. Another way to refer to the absolute number of viable phage in a given volume is by stating the plaque forming units (pfu) per unit volume.

Reagents

The following reagents were used for the screening of FIXa-binding peptides:

1. Ampicillin: 100 g ampicillin in 1 L MQ water; filter sterilized (0.22 μm).
2. NZCYM medium: 10 g Casein Hydrolysate Enzymatic, 5 g NaCl (sodium chloride), 5 g Bacto Yeast Extract, 1 g Bacto Casamino Acids (Casein Digest), 1 g $MgSO_4$ anhydrous powder (magnesium sulfate). Ingredients were dissolved in 800 mL MQ water and pH adjusted to 7.5 with 1 N NaOH (sodium hydroxide), then brought up to a total volume of 1 L with MQ water and autoclaved at 120° C. for 20 min.
3. NZCYM-A50 plates: NZCYM medium containing 15 g Bacto Agar/1 L and 100 μg ampicillin/mL.
4. NZCYM-T12.5 medium: NZCYM medium containing tetracycline at 12.5 μg/mL NZCYM-T12.5 plates: NZCYM medium containing 15 g Bacto Agar/L and tetracycline at 12.5 μg/mL.
5. PBS: 150 mM NaCl (sodium chloride), 8 mM $Na_2HPO_4$ anhydrous powder (sodium phosphate, dibasic), 1.5 mM $KH_2PO_4$ anhydrous powder (potassium phosphate, monobasic). Adjust pH to 7.4-7.6.
6. PEG/NaCl: 20% polyethylene glycol 6000 (PEG), 2.5 M NaCl (sodium chloride). The buffer was filter sterilized (0.22 μm). To make this solution, a 40% PEG solution stock was made in MQ water. An equal volume of 5 M NaCl was added while stirring to make the 20% PEG/2.5 M NaCl stock solution.
7. TBS: 10 mM Tris-HCl (pH 7.5), 150 mM NaCl (sodium chloride)
8. TEA, 100 mM: 100 mM triethylamine (TEA). Buffer was freshly prepared (pH).
9. Tetracycline: 12.5 g tetracycline in 1 L ethanol. Buffer was stored in dark at −20° C.
10. Tris-HCl, pH 7.4: 1 M Tris Base in MQ water. Adjust pH with HCl to pH=7.4. The buffer was filter sterilized (0.22 μm).

Screening Protocol: Round 1

Nunc plates were coated with 5, 50 and 500 μg/mL human Factor IXa (hFIXa, Hematologic Technologies) in TBS/5 mM $CaCl_2$/pH 7.4 overnight at 4° C. The solution was removed and the plate was blocked with 2% milk in TBS/5 mM $CaCl_2$/pH 7.4 for 1-2 hours at room temperature.

Aliquots (10 μL for each condition) of the 7 Tn libraries (Tn6~Tn12) were pooled and mixed with an equal volume of PBS/2% Milk for 1-2 hours at room temperature. From this solution, 100 μL was added to each target well. The phages were allowed to bind to hFIXa for 1 hour at room temperature. Subsequently, the solution was removed and the wells were washed 13 times with 2% milk in TBS/5 mM $CaCl_2$/pH 7.4. Next, phage were eluted with 100 μL of the TEA solution per well, the solution was removed after 2-5 minutes and neutralized with 50 μL per well of 1 M Tris-HCl pH 7.4. The eluted phages were used to transfect competent *E. coli* XL1-Blue MRF' (Stratagene) and amplified overnight at 37° C. as described below.

Phage Infection

A single colony of *E. Coli* XL1-Blue MRF' from a NZCYM-T12.5 plate was inoculated into 25 mL of NZCYM-T12.5 broth (tetracycline at 12.5 μg/mL). The culture was grown overnight at 37° C. at 250 rpm. The following day, the XL1 blue MRF' *E. coli* cells were diluted 1:100 into 25 mL NZCYM-T12.5 and grown for about 2 hours until the culture reached an optical density of 0.5 at 600 nm. At this stage, 10 mL of the XL1 blue MRF' culture was infected with phage at 37° C. for 15 mins.

Phage Titer

A 2.0 μL aliquot of the above phage-infected XL1 blue MRF' culture was diluted with NZCYM broth in a serial manner ($10^4$, $10^5$ and $10^6$). Each dilution was spread onto NZCYM-A50 plates which prior had been dried in a 37° C. incubator for 1 hour. The plates were incubated in an inverted position overnight at 37° C. The titer was calculated the following day from a plate containing 30 to 300 plaques. The phage titer was derived from the equation: Phage titer=number of plaque×1/dilution×1/fraction plated.

Phage Amplification

The infected cells were concentrated by centrifuging them at 3000 rpm, followed by resuspension in 10 mL of NZCYM overnight at 37° C. without shaking. Next, the suspension was centrifuged at 10K at 4° C. for 10 min and the supernatant was precipitated with 0.5 mL 30% PEG on ice for 1 hour. The precipitated phage was isolated by centrifugation and the supernatant was discarded. The phage pellet was resuspended in 100 μL per well of PBS/2% Milk.

Round 2 and 3

The amplified phage library was used for a similar panning as described above. Screening Protocol; Round 1. At the completion of Round 3, the phages in the eluent were titered and assayed for FIXa binding using phage enzyme linked immunosorbent assay (ELISA).

Phage ELISA

The following steps were carried out to identify phages encoding peptides that were able to bind hFIXa. Individual agar plugs containing phage plaques were picked with autoclaved Pasteur pipets. Phage Titer. Plugs were deposited in 96-well sterile deep well plates (Nunc), to which 400 μL per well of NZCYM media was added per well. Phage were grown overnight at 37° C. In addition, 100 μL of 1 μg/mL of hFIXa in TBS/Ca was coated on Nunc plates overnight at 4° C. The hFIXa solution was removed the following day and the plate was washed one time with TBS/Ca/tween. Subsequently, the wells were blocked with TBS/Ca/2% milk for 1-2 hours at room temperature. The wells were again washed with TBS/Ca/tween before 100 μL of phage were added. Phage were allowed to bind to hFIXa for 1-2 hours at room temperature. Next, the wells were washed three times with TBS/Ca/tween before adding 100 μL anti-M13 HRP antibody (diluted 1:5000 in TBS/Ca/2% milk) for 1 hour. Again, the wells were washed three times with TBS/Ca/tween, and the ELISA signal was detected by adding 100 μL TMB, and scanning the plate at 650 nm. About 5% of the peptides identified as binding to FIXa from the phage ELISA possessed activity in the FXa generation assay.

Sequencing

An aliquot (50 μL) of the supernatant from positive phage clones (ELISA target signal/milk background signal>2.0) was collected and sequenced using Dyax's designed primer (3seq-80: 5'gataaaccgatacaattaaaggctcc 3'). Among them the sequence of compound 1 was discovered.

Isolation of Compound 3

A secondary phage library was built based on the compound 1 primary sequence. The library contained the compound 1 sequence engineered with a 30% chance of an amino acid change within the compound 1 sequence, as well as an additional five randomized amino acid residues flanking both ends of the core sequence.

DNA fragments coding for the peptides within the 22 amino acid secondary library were generated in the following manner: A 105-base oligonucleotide was synthesized to contain the sequence $(NNB)_5$ compound 1 sequence $(NNB)_5$, where N=A, C, T or G and B=C, G or T. This oligonucleotide was used as the template (0.5 nM, 1 μL) in PCR amplification along with two shorter oligonucleotide primers (10 μM, 1 μL), both of which complement the 5' and the 3' end of the oligo (oligos A and B, respectively). The resulting PCR product was purified and concentrated with QIAquick spin columns (Qiagen), then digested with NcoI and NotI. The pSYNPHE phagemid (Syntonix) was also digested with NcoI and NotI, followed by phosphatase treatment. The digested DNAs were resolved using a 1% agarose gel, excised and purified by QIAEX II treatment (Qiagen). The vector and insert were ligated overnight at 15° C. The ligation product was purified using QIAquick spin columns and electroporation was performed in an electroporation cuvette (0.1 mm gap; 0.5 ml volume) containing 12.5 μg of DNA and 500 μg of TG1 electrocompetent cells (Stratagene). Immediately after the pulse, 12.5 mL of pre-warmed (37° C.) 2YT medium containing 2% glucose was added and the transformants were grown at 37° C. for 1 hour. Cell transformants were pooled, the volume measured and an aliquot was plated onto 2YT containing 100 μg/ml amp plates to determine the total number of transformants.

Cells were grown to 0.5 ($A_{600}$) in 2YT-amp/2% glucose at 30° C. at 250 rpm (shaker). M13K07 helper phage (Biolab) was then added (moi=10), and the cells were incubated for 1 hr at the conditions described above. Cells were pelleted at 2500× g for 10 min and the supernatant discarded. The cell pellet was re-suspended in the initial culture volume of media, containing 100 mg/mL amp and 50 mg/mL kanamycin and grown overnight at 30° C. at 250 rpm. The cells were then pelleted at 2500× g for 10 min and the supernatant was transferred to another container and precipitated by adjusting the solution to 4% PEG, 500 mM NaCl, and chilled at 4° C. for 1 hr before centrifugation at 10,000 g for 10 min. The pellet was re-suspended in TBS (1:100 of the initial culture volume). The phage was titered by infecting TG1 cells.

(SEQ ID NO: 865)
5'ATGGGCCCAGCCGGCCATGGCA(NNB)$_5$AAGCTGACGTGTCTGGCC
AGTTATTGTTGGCTGTTC(NNB)$_5$GCGGCCGCAGGTAGCTA3'

(SEQ ID NO: 899)
oligo A: 5'ATGGGCCCAGCCGGCCATG 3'

(SEQ ID NO: 902)
oligo B: 5'TAGCTACCTGCGGCCGC 3'

PCR conditions: 95° C. 5 min
95° C. 30 sec
65° C. 30 sec 7-11x
72° C. 30 sec
72° C. 5 min
4° C. ∞

Panning and the subsequent ELISA were performed as described above.

EXAMPLE 8 hFIXa or hFVIIa Binding Across Captured Biotinylated Compounds of the Disclosure via Immobilized Streptavidin Probes The affinity of soluble human FIXa or soluble FVIIa to captured biotinylated peptides of the disclosure were measured using Streptavidin (SA) probes. Bio-Layer Interferometry (BLI) based measurements were obtained at 25° C. with a ForteBio Octet 384 instrument using HBS-P buffer (10 mM, HEPES, pH 7.4, 150 mM NaCl, 5 mM CaCl and 0.05% surfactant P20). Briefly, a layer of molecules attached to the tip of an optical fiber creates an interference pattern upon incident white light. The combination of the optical fiber and biocompatible surface creates the physical conditions needed for BLI, allowing the detection of changes in mass accumulation on the tip of the probe. This is measured by alterations in the spectral shift (nm). These changes are recorded as a binding profile, a continuous, real-time monitoring of the association and dissociation of interacting molecules.

All biotinylated peptides (20 µg/mL) were diluted in 4 M guanidinium chloride and loaded across streptavidin (SA) biosensors for 120 sec, yielding approximately 0.5-1.0 nm binding on the reaction probes. Control SA probes were loaded with 4 M guanidinium chloride in the absence of biotinylated peptide for reference subtraction. After loading, probes were incubated in HBS-P for 300 sec to establish a new baseline. Subsequently, biosensor probes were incubated in solutions of human FIXa or FVIIa (at 0, 2, 6, 20, 60, 200, 600, 2000 nM) for 1 hour at room temperature to establish an equilibrium state known as the association phase. The probes were then incubated in HBS-P buffer, permitting human FIXa or FVIIa to dissociate from the probe. This is described as the dissociation phase. The equilibrium KD was derived from the non-linear regression analysis of the subtracted data (Reaction probe minus Reference probe) using a 1:1 binding model with ForteBio software (Version 7.0).

hFIXa binding to immobilized compound 19 (compound 4 biotinylated at K18), RRAPGKLTCLASYCWLFK(PEG$_2$-Biotin)TGIA (SEQ ID NO: 107), was measured (steady state analysis). Association and dissociation time curves using various hFIXa concentrations were also recorded. In this experiment, the $R_{max}$ for the binding of compound 19 to human FIXa was found to be 1.65±0.116, and the dissociation constant ($K_D$) was found to be 120 nM±33 nM.

In a similar fashion, binding to human FVIIa (hFVIIa) was assessed. For example, hFVIIa binding to compound 25 was measured, and the $K_D$ was found to be 250 nM±36 nM.

EXAMPLE 9

Activated Partial Thromboplastin Time (aPTT) Assay

For the activated Partial Thromboplastin Time (aPTT) assay peptides to be tested were first diluted in 10% FVIII-deficient human plasma. For the aPTT* the peptides were diluted in 10% FVIII-deficient human plasma that contained traces of hFIXa (anywhere between 0 and 8.8 nM hFIXa depending on the assay) in Tris/NaCl/BSA buffer. The peptides were incubated for 10 minutes at room temperature and then assayed for clotting on a Sysmex instrument that recorded the clotting time observed for each sample. The times were compared to those of a standard curve derived from standards with known FVIII activity (U/mL) in order to determine the clotting outcome.

Clotting times for compound 1, compound 2, and compound A (scrambled control) were measured using the above described modified activated partial thromboplastin time (aPTT*) assay. Compounds were tested at 5, 10, and 20 µM. Results summarized in the Table 14, below, indicate that the decrease of clotting time observed for compounds of the present disclosure is FIXa dependent.

TABLE 14

|  | Compound 1 | | | Compound 2 | | | Compound A | | Blank + FIXa |
|---|---|---|---|---|---|---|---|---|---|
| Conc. (µM) | 20 | 10 | 5 | 20 | 10 | 5 | 20 | 10 | — |
| Clotting time, (sec) | 43.5; 43.8 | 44.2; 43.3 | 47.3; 47.9 | 42.4; 42.3 | 42.9; 42.2 | 51.1; 50.3 | 122.0; 123.2 | 120.6; 123.2 | 120.2; 120.2 |

Clotting times for compound 1 and compound 2 were further measured in the presence of various FIXa concentrations, and activities were compared to a blank sample (containing no peptide). The resuls are summarized in Table 15, below:

TABLE 15

| FIXa | Compound 1 | | | | Compound 2 | | | | Blank | | | |
|---|---|---|---|---|---|---|---|---|---|---|---|---|
| (nM) | 1 | 2 | 4 | 8 | 1 | 2 | 4 | 8 | 1 | 2 | 4 | 8 |
| Clotting time (sec) | 105.8; 107.4 | 84.4; 82.8 | 50.9; 50.6 | 40.1; 40.6 | 86.8; 91.4 | 51.3; 49.6 | 46.0; 42.7 | 34.4; 37.1 | 119.8; 120.6 | 119; 120.4 | 114.6; 115.4 | 107.8; 108.4 |

Clotting times were measured in a modified activated partial thromboplastin time (aPTT*) assay for D-amino acid mutants of compound 1 and were compared to $EC_{50}$ values obtained using a FXa generation assay (compare Table 1). Results summarized in Table 16 below indicate a strong correlation between the FXa generation activity and the clotting time values measured for the compound 1 family of D-amino acid mutants. These results further confirm that D-amino acid replacement of the loop amino acids (positions 5 to 9), and certain C-terminal amino acids within compound 1 results in reduced biological activity compared to the native peptide.

TABLE 16

| D-amino acid scan | D-amino acid Mutations of Compound 1, per position | | | | | | | | | | | | | |
|---|---|---|---|---|---|---|---|---|---|---|---|---|---|---|
| | 1 | 2 | 3 | 4 | 5 | 6 | 7 | 8 | 9 | 10 | 11 | 12 | WT | Blank |
| EC50, µM | (+++) | (+++) | (++) | (++) | >5 | >5 | (+) | >5 | (+) | (++) | (+) | (+) | (+++) | — |
| Clotting time, sec | 60.6; 61.8 | 69.2; 69.8 | 79.4; 80.6 | 60.8; 61.8 | 115.6; 115.4 | 117.2; 117.8 | 117; 118 | 113.8; 115 | 115; 113.8 | 63.1; 68.8 | 96; 98.4 | 87.6; 87.8 | 47.9; 47.8 | 116; 117 |

Clotting times were measured for compound 3 in a modified activated partial thromboplastin time (aPTT*) assay in the absence and presence of various concentrations of exogenous hFIXa as indicated. In this assay, compound 3 reduces clotting time in a FIXa-dependent manner. The results are summarized in the table 17, below:

TABLE 17

| | Compound 3 | | | Blank | | |
|---|---|---|---|---|---|---|
| FIXa, nM | 0.5 | 2.2 | 8.8 | 0.5 | 2.2 | 8.8 |
| Clotting time, sec | 115.6; 115.2 | 90.8; 89 | 45.4; 41.9 | 122.6; 124 | 119.8; 119.8 | 106.8; 106.8 |

EXAMPLE 10

Phospholipid Dependency (a) $EC_{50}$ and $V_{max}$ values were measured for various compounds of the present disclosure in a FXa generation assay (Example 2) in the absence and presence of phospholipids (PL). The results indicate limited phospholipid dependence for the $EC_{50}$ and $V_{max}$ values. Results are shown in Table 18, below:

TABLE 18

| Compound | PL | $EC_{50}$ (µM) | Vmax (mOD/min min) |
|---|---|---|---|
| 1 | Yes | 0.49 | 3.98 |
| 1 | No | 0.40 | 2.60 |
| 2 | Yes | 0.23 | 4.22 |
| 2 | No | 0.20 | 3.05 |
| 3 | Yes | 0.125 | 3.90 |
| 3 | no | 0.115 | 2.77 |

(b) In another experiment, the impact of phospholipids on hFIXa in the presence of FVIIIa in the FXa generation assay was tested. Assay components of the control were FVIIIa, FIXa, PL, FX, and FXa substrate. FIXa (100 nM) was pre-incubated with anti-FIX antibodies (1000 nM) specific for the Gla domain of FIX or IgG control for 20 minutes on ice. Following this incubation the activity of FIXa was assayed using a FXa generation assay in the presence of FVIIIa.

(b.1.) FVIII (4 nM) was activated with thrombin (0.5 nM) for 5 minutes at RT. Hirudin (5 nM) was then added to the reaction to inhibit thrombin activity. FVIIIa (2 nM) and FIXa or FIXa pre-treated with antibodies (4 nM) were then incubated at RT for 10 minutes in the absence or presence of 200 µM phospholipid (PL) vesicles to form the Xase complex. Following this 50 µl of the reaction was mixed with FX (100 nM) and a FXa-specific chromogenic substrate (0.5 mM) and the absorbance was monitored at 405 nm. The FXa generation rates (nM/min) were measured. The results relative to the control (100%) are summarized in Table 19, below:

TABLE 19

| Experiment | Percentage of control |
|---|---|
| Control | 100 |
| No FIXa | 0.0 |
| No PL | 0.01 |
| Anti-FIX IgG (Gla) | 12.5 |
| control IgG | 98.6 |

In this experiment, FXa generation depends on the presence of phospholipids. Removal of the phospholipid vesicles reduces the FXa generation rate by 10,000 fold. FXa generation further depends on FIXa. In the presence of anti-FIXa antibodies, FXa generation rate is reduced by 8-fold.

(b.2.) In another experiment the impact of phospholipids on hFIXa in the presence of compound 3 in the FXa generation assay was measured.

For the assay involving a compound of the invention, FIXa (100 nM) was pre-incubated with anti-FIX antibodies (1000 nM) specific for the Gla domain of FIX. Following this incubation FIXa (10 nM) was mixed with compound 3 (1 µM) in the presence of FX (100 nM), calcium and phospholipids from the Coatest SP FVIIII chromogenic assay kit. Formation of FXa was monitored using a chromogenic substrate as described in the FXa generation assay directly above (see b.1.). The results relative to the control (presence of PL, 100%) are summarized in Table 20, below:

TABLE 20

| Experiment | | Percentage of control |
|---|---|---|
| compound 3 | +PL | 100 |
| compound 3 | −PL | 90 |
| compound 3 | +PL +anti-FIX IgG (Gla) | 58.0 |
| water | +PL | 0.62 |
| water | −PL | 1.85 |
| water | +PL +anti-FIX IgG (Gla) | 1.48 |

In this experiment, FXa generation does not depend on the presence of phospholipids and is significantly less dependent on a functional Gla domain of FIXa than in the FVIIIa experiment above (The Gla domain of FIXa is responsible for phospholipid binding). Treatment with anti-FIX Gla antibody reduces the FXa generation rate by less than 2-fold. In this experiment, water was used as the control, which did essentially not generate any FXa.

The above results indicate that compound 3 increases the catalytic activity of FIXa with limited phospholipid dependency (i.e., the absence of phospholipids in the above assay system does not substantially decrease the enhancement of FIXa activity by compounds of the present disclosure (e.g., compound 3).

In similar experiments the impact of phospholipids on hFVIIa in the FXa generation assay was tested in the absence and presence of compound 5. Results indicate that while the increase of FIXa catalytic activity by compound 5 is marginally phospholipid dependent (about 80% of control in the absence of PL), the increase of FVIIa activity by compound 5 is significantly phospholipid dependent; i.e., significantly reduced in the absence of PL (about 10% of control). These results indicate that compounds of the present disclosure (e.g., compound 5) enhance FVIIa activity in a phospholipid dependent manner.

EXAMPLE 11

A Shared FIXa Binding Site for the Pro-Coagulant Compounds and Heparin

Procoagulant peptides enhance the activity of hFIXa by interacting near the FVIIIa binding site on the protease domain.

The interaction between certain pro-coagulant peptides and FIXa was studied by hydrogen/deuterium exchange mass spectrometry (H/DX-MS). The data revealed that the pro-coagulant peptides interact near the 330 loop (FIX numbering) on FIXa which is close to the postulated FVIIIa binding site, as well as the heparin binding site.

Heparin is believed to have two functions in the FIXa inactivation: Heparin catalyzed inhibition of FIXa by antithrombin (heparin causes a conformational change of antithrombin), and heparin mediated bridging of FIXa and antithrombin (PNAS 2010, 107, 645-650; J. Biol. Chem. 2002, 277, 50756-50760; J. Biol. Chem. 2003, 278, 35767-35774; J. Biol. Chem. 1998, 273, 120).

Heparin Accelerated FIXa-AT Complex Formation Assay

Competition studies between the pro-coagulant peptides and heparin: compounds of the present disclosure were tested in a heparin competition assay in an effort to further map the peptide's binding site on FIXa. FIXa inactivation by antithrombin (AT) was assessed by gel electrophoresis in the presence of heparin and varying procoagulant peptide concentrations. The rate of FIXa-AT complex formation was quantified over a 15 minute time course. Test samples contained 2 µM human FIXa (Haemotologic Technologies Inc.); 20 µM antithrombin (Haemotologic Technologies Inc.); 0, 1, 10, or 100 nM heparin (Heparin Sodium Injection USP APPP Pharmaceuticals LLC) and 0, 0.1, 1 or 10 µM of compound 5 in 50 mM Tris pH 7.4, 0.1 M NaCl, 10 mM $CaCl_2$ buffer. The samples were incubated at 37° C. in a water bath and 12.5 µL aliquots were removed at each time point (0.5, 2, 5, 10, 15 min) and immediately mixed with 12.5 µL SDS 2× non-reducing sample buffer. The samples were heated at 90° C. for 3 min and loaded onto a 4-20% BioRad gel (20 µL/lane). The gel was run at 300V for 25 min, and the bands were quantified using Quantity One software from BioRad.

The rate of heparin-catalyzed FIXa-antithrombin (AT) complex formation in the absence or presence of compound 5 was measured. In the absence of heparin, the inactivation of FIXa by AT was unaffected by compound 5. At heparin concentrations that significantly accelerated the AT inactivation of FIXa (e.g., about 100 nM), certain compounds of the present disclosure (e.g., compound 5) inhibited the heparin-catalyzed FIXa-AT complex formation (e.g., in a concentration-dependent manner). The results show that in the absence of heparin, the inactivation of FIXa by AT was unaffected by the presence of compound 5. However, at heparin concentrations (100 nM) that significantly accelerated the AT inactivation of FIXa, compound 5 inhibited the FIXa-AT complex formation in a concentration-dependent manner. Results suggest a shared FIXa binding site for compounds of the present disclosure (e.g., compound 5) and heparin. Results are summarized in Table 21, below:

TABLE 21

| Compound 5 | % FIXa-AT complex formation in the presence of Compound 5 | | | |
|---|---|---|---|---|
| | 0 µM | 0.1 µM | 1 µM | 10 µM |
| 0 min | 0% | 0% | 0% | 0% |
| 0.5 min | 52% | 57% | 30% | 18% |
| 2 min | 71% | 72% | 45% | 28% |
| 5 min | 79% | 82% | 55% | 41% |
| 10 min | 81% | 82% | 70% | 54% |
| 15 min | 83% | 83% | 74% | 62% |

EXAMPLE 12

Additive Effect Between Compounds of the Present Disclosure and FIX-Fc or FVIIa-Fc The additive effect between the compounds of the present disclosure and FVIIa-Fc or FIX-Fc was assessed by a rotational thromboelastometry (ROTEM®) assay as described in Example 4 using either FIX-deficient plasma or FVIII-deficient plasma.

Additive Effect Between Compound 5 and FVIIa-Fc

The effect of 5, 10 and 20 IU/mL of FVIIa-Fc was tested in the absence or presence of 2.5 or 5 µM of compound 5 in FVIII-deficient plasma.

In the absence of compound 5, FVIIa-Fc (10 or 20 IU/mL) reduced the clotting time to 1058 and 581 seconds and improved the alpha-angle to 12 and 21 degrees, respectively. The baseline clotting time was 2439 seconds and α-angle 9 degrees with trigger alone. In the presence of compound 5 (2.5 µM), the clotting time was further reduced to 303.5 and 115 seconds and the α-angle was further increased to 38.5 and 63 degrees, respectively. Similar trends were observed for 5 IU/mL of FVIIa-Fc and 5 µM, of compound 5.

Additive Effect Between Compound 5 and FIX-Fc

The additive effect between FIX-Fc and compound 5 was also evaluated in FIX-deficient plasma. FIX-Fc at 0.25 IU/mL reduced the clotting time to 1173 seconds and the α-angle to 26 degrees compared to the baseline clotting time of 3204 seconds and α-angle of 10 degrees with trigger alone. In the presence of 2.5 µM compound 5, the clotting time was further reduced to 876.5 seconds and the α-angle was further ernhanced to 39.5 degrees. All values listed in this example are averages of duplicates.

The above results show that compounds of the present disclosure enhance the procoagulant effect of FVIIa-Fc and FIX-Fc in FVIII- and FIX-deficient plasma, respectively.

Because a combination of FVIIa-Fc and a compound of the present disclosure reduces clotting time and increases α-angle further than either component alone, FVIIa-Fc and compounds of the present disclosure are suitable to be used in conjunction (i.e., in a combination therapy, e.g. to treat hemophilia, such as hemophilia A).

Likewise, because a combination of FIX-Fc and a compound of the present disclosure reduces clotting time and increases α-angle further than either component alone, FIX-Fc and compounds of the present disclosure are suitable to be used in conjunction (i.e., in a combination therapy, e.g. to treat hemophilia, such as hemophilia A).

The above results also indicate that conjugates between FVIIa, FVIIa-Fc, FIX, or FIX-Fc with compounds of the present disclosure (e.g., cleavable conjugates) are useful in the therapy of hemophilia (e.g., hemophilia A). Exemplary conjugates are disclosed herein.

EXAMPLE 13

Compounds of the Present Disclosure Have No Effect on Platelet Aggregation

In order to determine whether the compounds of the present disclosure cause platelet aggregation directly, compound 5 and compound 22 were tested using an aggregometer (Platelet Aggregation Profiler PAPS v.2.0 from BIO/DATA Corporation). ADP was used as a positive control for platelet aggregation.

For example, compound 5 did not exhibit a significant effect on adenosine 5'-diphosphate-activated (ADP-activated) platelets when used at a concentration of up to 10 µM, and did exhibit only a moderate effect on ADP-activated platelets when used at a very high concentration of 30 µM. Furthermore, compound 5 did not induce platelet aggregation even at a high concentration of about 30 µM. Compound 22 did also not induce platelet aggregation at 10 µM and 30 µM.

EXAMPLE 14

Preparation of FVIIa Conjugates

Cloning was performed using Rapid DNA Ligation Kit from Roche Diagnosticas (cat # 11635379001) following manufacturer's guidelines. Briefly, 10-50 ng of vector or fragment DNA were added to a final volume of 10 ul ligation mixture containing 1× Rapid DNA Ligation buffer and 1 ul Rapid DNA Ligase. Reaction was allowed to proceed for 5-30 min at room temperature and placed on ice. 2 ul of ligation reaction were transformed in 50 ul Mach 1 *E. coli* competent cells from Invitrogen (cat # C869601) and plated on an appropriate antibiotic for selection.

The 3.1 kb DNA fragment comprising the region from HindIII to EcoRI of pSYN-FVII-171 was synthesized and subcloned into the HindIII/EcoRI sites of pcDNA4 vector (Invitrogen) to generate pSYN-FVII-171.

For expression of FVII-171, HEK-293-F cells were grown in suspension in Freestyle media (Invitrogen) supplemented with vitamin K3 (Sigma Aldrich, St. Louis, Mo.) to 2 µg/liter (growth media) as suspension cells at 37° C./10% CO2. Cells we subcultured every three to four days by seeding at cell density of $5 \times 10^5$ cells/ml.

Figure 9:
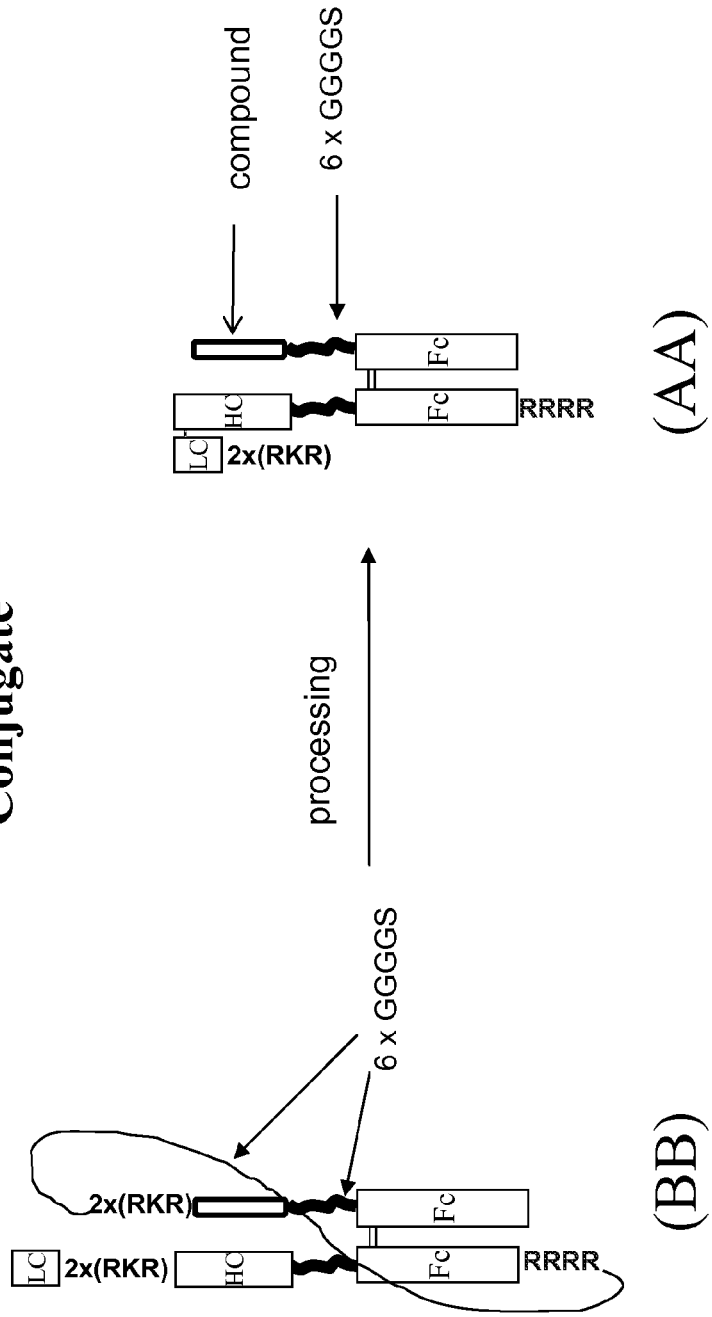
FIG. 9 is a scheme of a conjugate including FVIIa (AA), a heterologous moiety (represented by Fc) and a compound of the present disclosure. An exemplary conjugate according to FIG. 9 is described in Example 14. In one example the FVIIa conjugate is formed from a precursor (BB) via further processing. Processing involves, e.g., cleavage of a cleavable linker, e.g., through intracellular activation/processing (e.g., by co-transfection of processing enzymes such as PC5 and PACE). In one example, in FIG. 9, the compound is compound 21.
Figure 10:
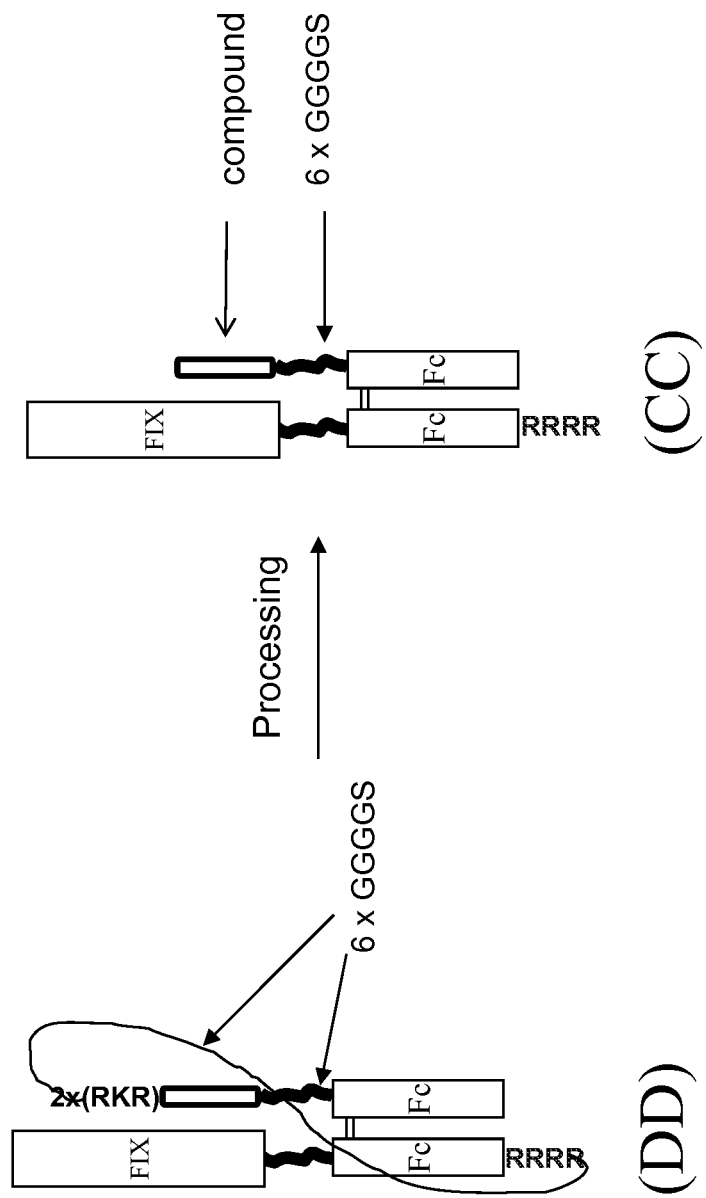
FIG. 10 is a scheme of a conjugate including FIX (CC), a heterologous moiety (represented by Fc) and a compound of the current disclosure. An exemplary conjugate according to FIG. 10 is described in Example 15. In one example the FIX conjugate is formed from a precursor (DD) via further processing. Processing involves, e.g., cleavage of a cleavable linker, e.g., through intracellular activation/processing (e.g., by co-transfection of processing enzymes such as PC5 and PACE). In one example, in FIG. 10, the compound is compound 21.
Figure 11:
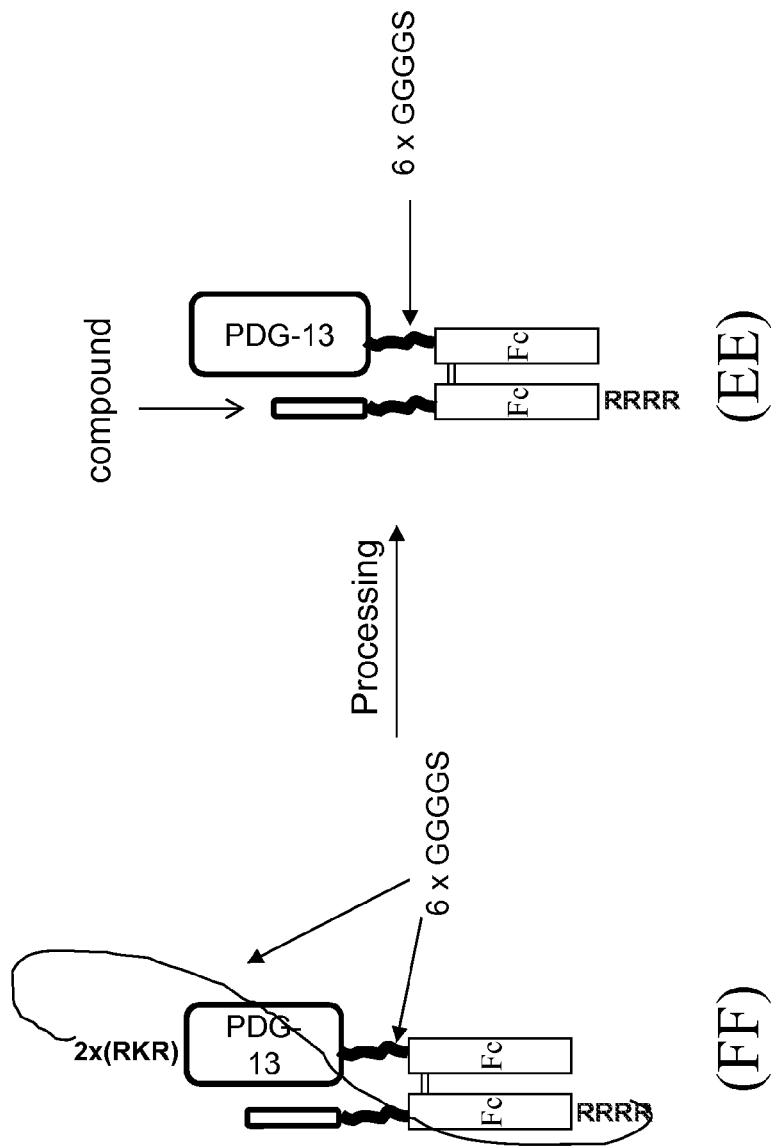
FIG. 11 is a scheme of a platelet targeting moiety conjugate (EE) including a platelet targeting moiety (represented by PDG-13), a heterologous moiety (represented by Fc) and a compound of the present disclosure. An exemplary conjugate according to FIG. 11 is described in Example 16. In one example the conjugate (EE) is formed from a precursor (FF) via further processing. Processing involves, e.g., cleavage of a cleavable linker, e.g. through intracellular activation/processing (e.g., by co-transfection of processing enzymes such as PC5 and PAGE). In one example, in FIG. 11, the compound is compound 21.
Figure 12:
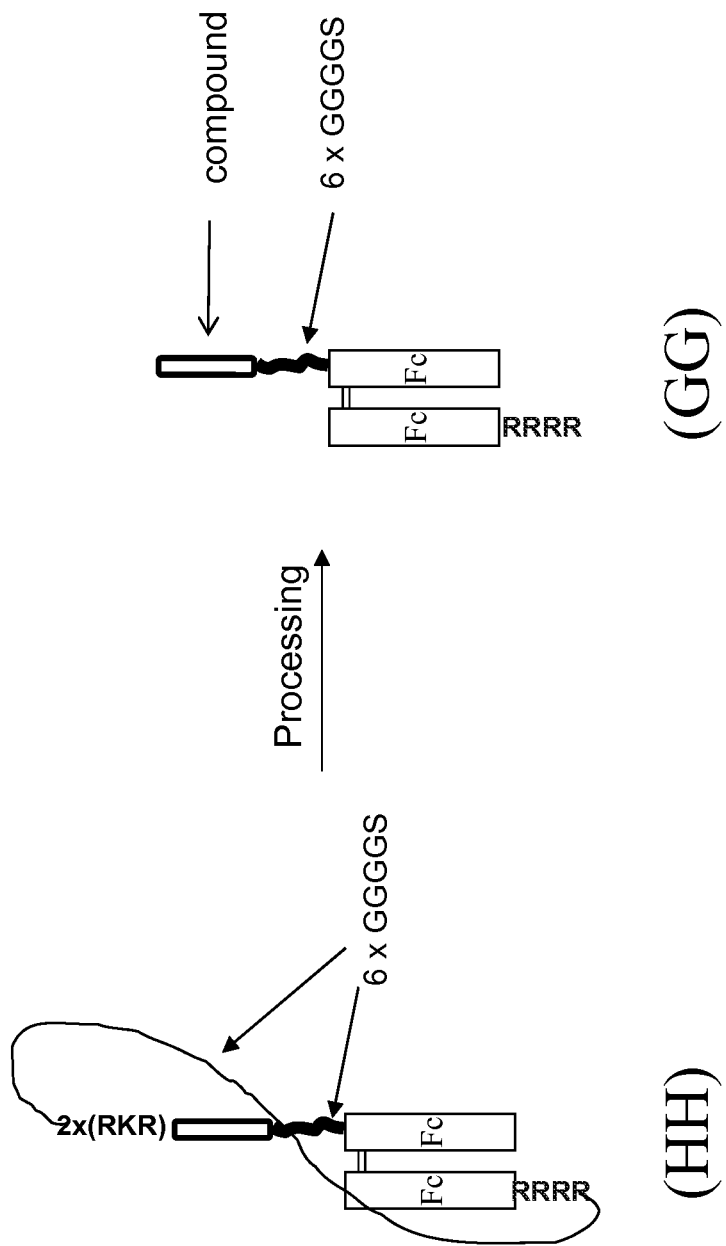
FIG. 12 is a scheme of a conjugate (GG) including a heterologous moiety (represented by Fc) and a compound of the present disclosure. An exemplary conjugate according to FIG. 12 is described in Example 17. In one example the conjugate (GG) is formed from a precursor (HH) via further processing. Processing involves, e.g., cleavage of a cleavable linker, e.g., through intracellular activation/processing (e.g., by co-transfection of processing enzymes such as PC5 and PACE). In one example, in FIG. 12, the compound is compound 21.
Figure 13:
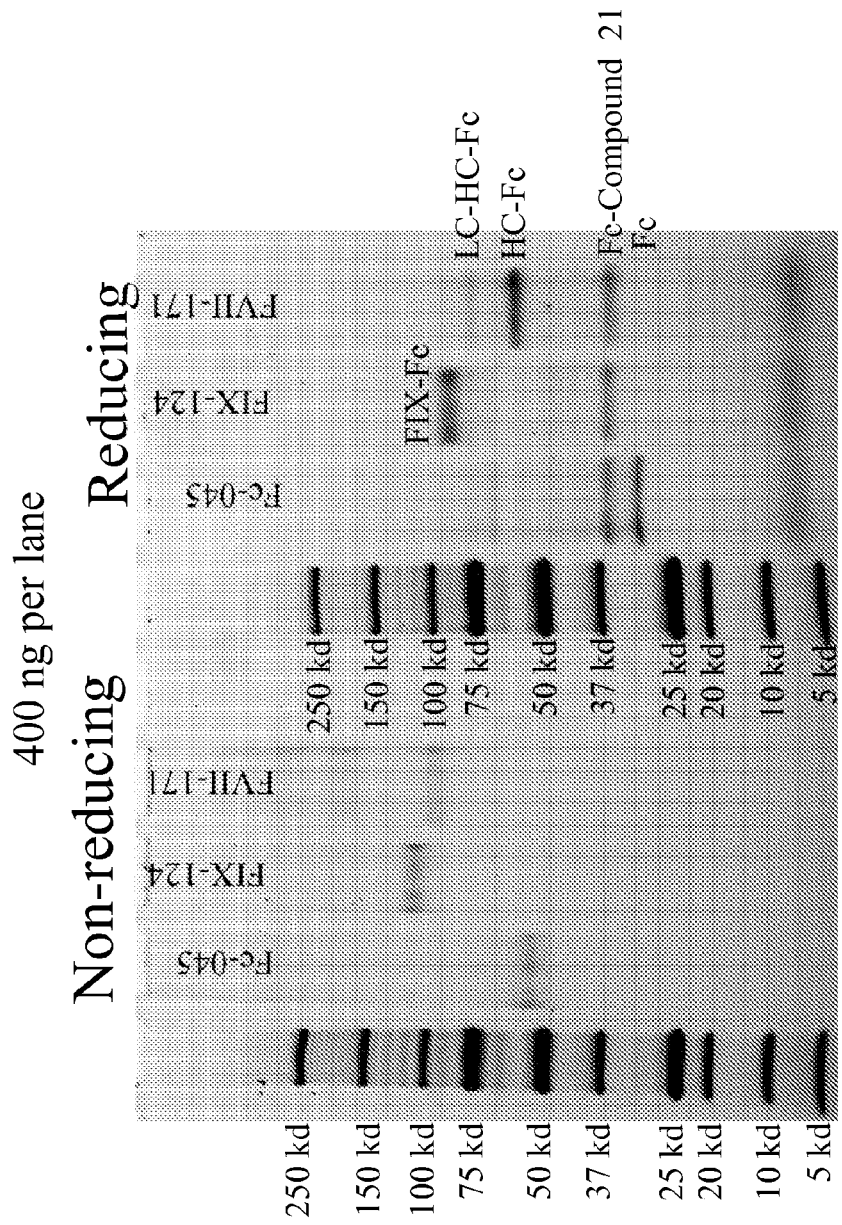
FIG. 13 is a gel showing the presence of various conjugates of the present disclosure (as prepared according to the procedures of Examples 14-17) after shFcRn-conjugated bead pulldown from conditioned media.
Figure 14:
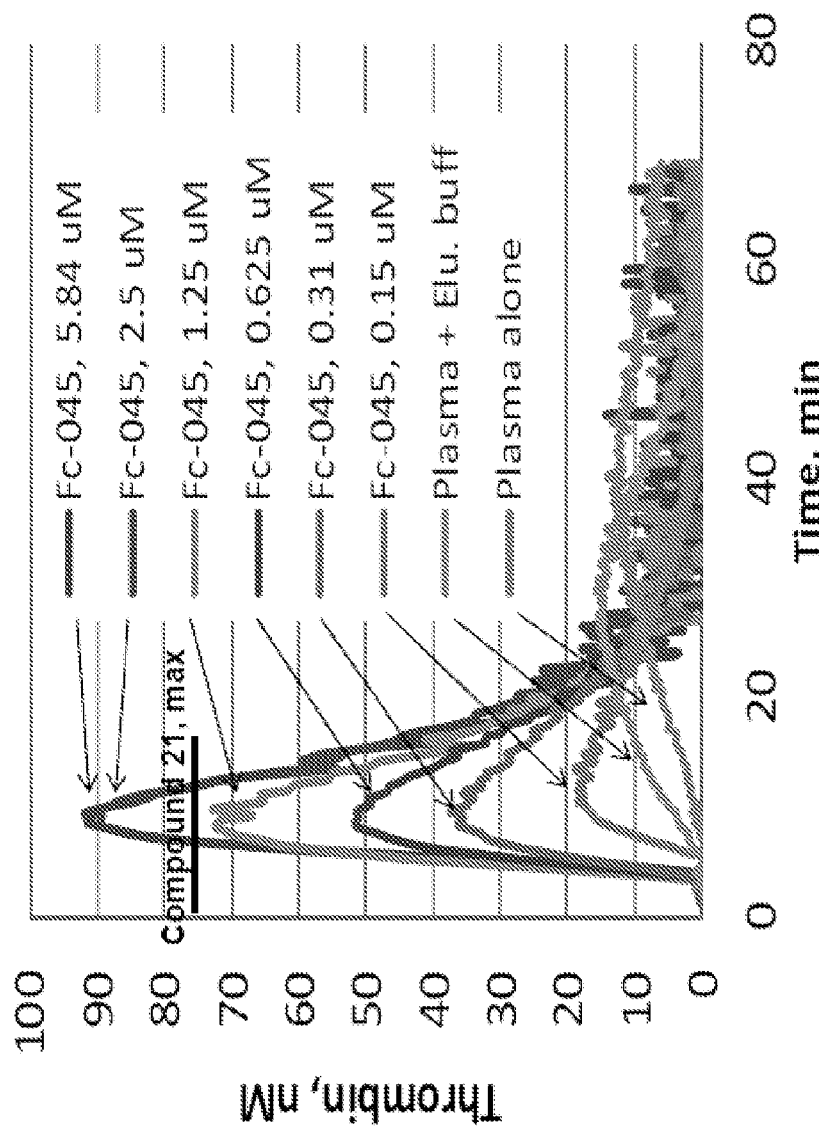
FIG. 14 is a graph illustrating the TGA activity of an Fc-compound 21 conjugate as described in FIG. 12 and In one example according to any of the above embodiments, a compound that includes the amino acid sequence incorporating $C^1$ and $C^2$ contains at least 9 and not more than 500 amino acids. In another example, a compound comprises at least 12 and not more than 100 amino acids. In a further example, a compound comprises at least 20 and not more than 100 or 50 amino acids. Further suitable ranges for the number of amino acids in a compound of the present disclosure are described herein.
Figure 15:
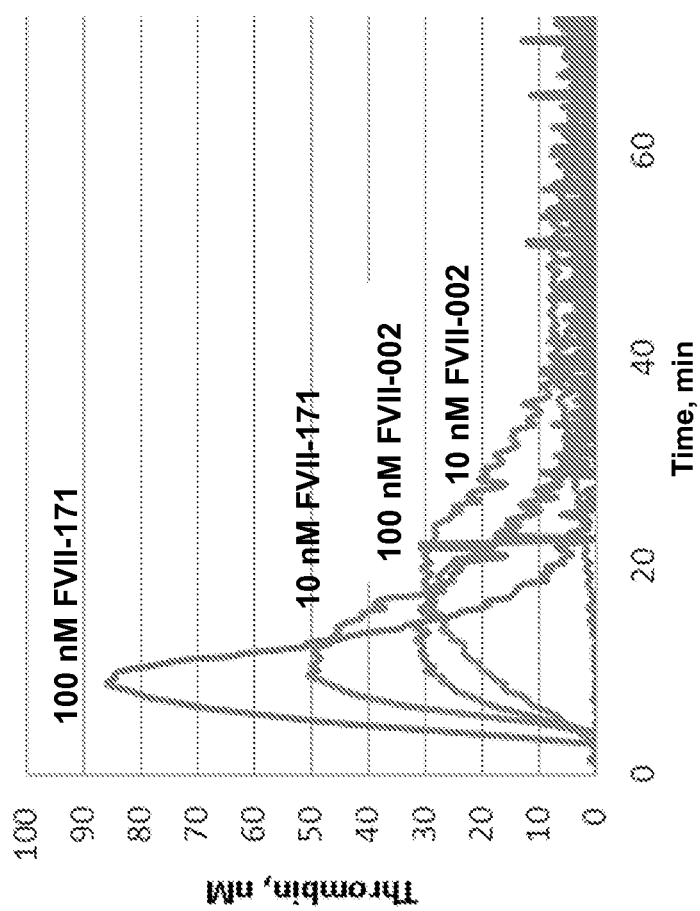

Twenty-four hours prior to transfection cells were seeded at a density of $7 \times 10^5$ cells/ml in growth media. On the day of transfection, a transfection solution was made with a volume equal to 5% of the total volume of the cell culture to be transfected. In the transfection solution DNA was added (final concentration 20 mg/L) to a freshly made solution of PEI (60 mg/L) in growth media. The solution was swirled for 30 seconds and incubated for five minutes at room temperature before adding directly to the cell culture. Four hours later a volume equal to the cell culture volume of OptiCHO (Invitrogen) supplemented with vitamin K3 and 200 mM L-glutamine was added to the cells. The cell culture was allowed to grow as shown above and daily media samples were taken to assess protein expression. On the day of harvest, the cells were spun down and the media filtered in preparation for protein purification or protein analysis by protein A pulldown. For expression of FVII-171, a plasmid encoding FVII-171 was contransfected with a plasmid encoding the propeptide endopeptidase PC5 or PACE to ensure cleavage of the propeptide endopeptidase sites in the linker connecting the Fc to compound and between the HC and LC of FVII (FIG. 9).

FVII-171 DNA sequence (SEQ ID NO: 830):

```
  1 ATGGTCTCCC AGGCCCTCAG GCTCCTCTGC CTTCTGCTTG GGCTTCAGGG CTGCCTGGCT

61 GCAGTCTTCG TAACCCAGGA GGAAGCCCAC GGCGTCCTGC ACCGGCGCCG GCGCGCCAAC

121 GCGTTCCTGG AGGAGCTGCG GCCGGGCTCC CTGGAGAGGG AGTGCAAGGA GGAGCAGTGC

181 TCCTTCGAGG AGGCCCGGGA GATCTTCAAG GACGCGGAGA GGACGAAGCT GTTCTGGATT

241 TCTTACAGTG ATGGGGACCA GTGTGCCTCA AGTCCATGCC AGAATGGGGG CTCCTGCAAG

301 GACCAGCTCC AGTCCTATAT CTGCTTCTGC CTCCCTGCCT TCGAGGGCCG GAACTGTGAG

361 ACGCACAAGG ATGACCAGCT GATCTGTGTG AACGAGAACG GCGGCTGTGA GCAGTACTGC

421 AGTGACCACA CGGGCACCAA GCGCTCCTGT CGGTGCCACG AGGGGTACTC TCTGCTGGCA

481 GACGGGGTGT CCTGCACACC CACAGTTGAA TATCCATGTG GAAAAATACC TATTCTAGAA

541 AAAAGAAATG CCAGCAAACC CCAAGGCCGA AGGAAGAGGA GGAAGAGGAT TGTGGGGGGC

601 AAGGTGTGCC CCAAAGGGGA GTGTCCATGG CAGGTCCTGT TGTTGGTGAA TGGAGCTCAG

661 TTGTGTGGGG GGACCCTGAT CAACACCATC TGGGTGGTCT CCGCGGCCCA CTGTTTCGAC
```

| FVII-171 DNA sequence (SEQ ID NO: 830): |
| --- |
| 721 AAAATCAAGA ACTGGAGGAA CCTGATCGCG GTGCTGGGCG AGCACGACCT CAGCGAGCAC |
| 781 GACGGGGATG AGCAGAGCCG GCGGGTGGCG CAGGTCATCA TCCCCAGCAC GTACGTCCCG |
| 841 GGCACCACCA ACCACGACAT CGCGCTGCTC CGCCTGCACC AGCCCGTGGT CCTCACTGAC |
| 901 CATGTGGTGC CCCTCTGCCT GCCCGAACGG ACGTTCTCTG AGAGGACGCT GGCCTTCGTG |
| 961 CGCTTCTCAT TGGTCAGCGG CTGGGGCCAG CTGCTGGACC GTGGCGCCAC GGCCCTGGAG |
| 1021 CTCATGGTCC TCAACGTGCC CCGGCTGATG ACCCAGGACT GCCTGCAGCA GTCACGGAAG |
| 1081 GTGGGAGACT CCCCAAATAT CACGGAGTAC ATGTTCTGTG CCGGCTACTC GGATGGCAGC |
| 1141 AAGGACTCCT GCAAGGGGGA CAGTGGAGGC CCACATGCCA CCCACTACCG GGGCACGTGG |
| 1201 TACCTGACGG GCATCGTCAG CTGGGGCCAG GGCTGCGCAA CCGTGGGCCA CTTTGGGGTG |
| 1261 TACACCAGGG TCTCCCAGTA CATCGAGTGG CTGCAAAAGC TCATGCGCTC AGAGCCACGC |
| 1321 CCAGGAGTCC TCCTGCGAGC CCCATTTCCC GGTGGCGGTG GCTCCGGCGG AGGTGGGTCC |
| 1381 GGTGGCGGCG GATCAGGTGG GGGTGGATCA GGCGGTGGAG GTTCCGGTGG CGGGGGCTCC |
| 1441 GACAAAACTC ACACATGCCC ACCGTGCCCA GCTCCGGAAC TCCTGGGAGG ACCGTCAGTC |
| 1501 TTCCTCTTCC CCCCAAAACC CAAGGACACC CTCATGATCT CCCGGACCCC TGAGGTCACA |
| 1561 TGCGTGGTGG TGGACGTGAG CCACGAAGAC CCTGAGGTCA AGTTCAACTG GTACGTGGAC |
| 1621 GGCGTGGAGG TGCATAATGC CAAGACAAAG CCGCGGGAGG AGCAGTACAA CAGCACGTAC |
| 1681 CGTGTGGTCA GCGTCCTCAC CGTCCTGCAC CAGGACTGGC TGAATGGCAA GGAGTACAAG |
| 1741 TGCAAGGTCT CCAACAAAGC CCTCCCAGCC CCCATCGAGA AAACCATCTC CAAAGCCAAA |
| 1801 GGGCAGCCCC GAGAACCACA GGTGTACACC CTGCCCCCAT CCCGGGATGA GCTGACCAAG |
| 1861 AACCAGGTCA GCCTGACCTG CCTGGTCAAA GGCTTCTATC CCAGCGACAT CGCCGTGGAG |
| 1921 TGGGAGAGCA ATGGGCAGCC GGAGAACAAC TACAAGACCA CGCCTCCCGT GTTGGACTCC |
| 1981 GACGGCTCCT TCTTCCTCTA CAGCAAGCTC ACCGTCGACA AGAGCAGGTG GCAGCAGGGG |
| 2041 AACGTCTTCT CATGCTCCGT GATGCATGAG GCTCTGCACA ACCACTACAC GCAGAAGAGC |
| 2101 CTCTCCCTGT CTCCGGGTAA ACGGCGCCGC CGGAGCGGTG GCGGCGGATC AGGTGGGGGT |
| 2161 GGATCAGGCG GTGGAGGTTC CGGTGGCGGG GGATCTGGCG GTGGAGGTTC CGGTGGGGGT |
| 2221 GGATCCAGGA GAGGAGGAA GAGGGGCCCC GGATCCGGA CAGTGGGCCC CGGCAGCCGG |
| 2281 AGCGCCAGCG GCAAGCTGAC CTGCCTGGCC AGCTACTGCT GGCTGTTCTG GACCGGCATC |
| 2341 GCCGGTGGCG GTGGATCCGG CGGAGGTGGG TCCGGTGGCG GCGGATCAGG TGGGGGTGGA |
| 2401 TCAGGCGGTG GAGGTTCCGG TGGCGGGGGA TCAGACAAAA CTCACACATG CCCACCGTGC |
| 2461 CCAGCACCGG AACTCCTGGG CGGACCGTCA GTCTTCCTCT TCCCCCCAAA ACCCAAGGAC |
| 2521 ACCCTCATGA TCTCCCGGAC CCCTGAGGTC ACATGCGTGG TGGTGGACGT GAGCCACGAA |
| 2581 GACCCTGAGG TCAAGTTCAA CTGGTACGTG GACGGCGTGG AGGTGCATAA TGCCAAGACA |
| 2641 AAGCCGCGGG AGGAGCAGTA CAACAGCACG TACCGTGTGG TCAGCGTCCT CACCGTCCTG |
| 2701 CACCAGGACT GGCTGAATGG CAAGGAGTAC AAGTGCAAGG TCTCCAACAA AGCCCTCCCA |
| 2761 GCCCCCATCG AGAAAACCAT CTCCAAAGCC AAAGGGCAGC CCCGAGAACC ACAGGTGTAC |
| 2821 ACCCTGCCCC CATCCCGGGA TGAGCTGACC AAGAACCAGG TCAGCCTGAC CTGCCTGGTC |
| 2881 AAAGGCTTCT ATCCCAGCGA CATCGCCGTG GAGTGGGAGA GCAATGGGCA GCCGGAGAAC |
| 2941 AACTACAAGA CCACGCCTCC CGTGTTGGAC TCCGACGGCT CCTTCTTCCT CTACAGCAAG |

-continued

FVII-171 DNA sequence (SEQ ID NO: 830):

3001 CTCACCGTGG ACAAGAGCAG GTGGCAGCAG GGGAACGTCT TCTCATGCTC CGTGATGCAT

3061 GAGGCTCTGC ACAACCACTA CACGCAGAAG AGCCTCTCCC TGTCTCCGGG TAAATGA

---

FVII-171 amino acid sequence (SEQ ID NO: 831)
Signal sequence is underlined, propeptide is double underlined, furin cleavage site separating light chain and heavy chain is in dotted underline, linker region connecting heavy chain to Fc region is in dashed underline, furin cleavage site separating Fc and linker is in thick underline, furin cleavage site separating linker and compound 21 is in wave underline and linker region separating compound 21 and Fc is in dot-dot-dash underline.

```
   1 MVSQALRLLC LLLGLQGCLA AVFVTQEEAH GVLHRRRRAN AFLEELRPGS LERECKEEQC
  61 SFEEAREIFK DAERTKLFWI SYSDGDQCAS SPCQNGGSCK DQLQSYICFC LPAFEGRNCE
 121 THKDDQLICV NENGGCEQYC SDHTGTKRSC RCHEGYSLLA DGVSCTPTVE YPCGKIPILE
 181 KRNASKPQGR RKRRKRIVGG KVCPKGECPW QVLLLVNGAQ LCGGTLINTI WVVSAAHCFD
 241 KIKNWRNLIA VLGEHDLSEH DGDEQSRRVA QVIIPSTYVP GTTNHDIALL RLHQPVVLTD
 301 HVVPLCLPER TFSERTLAFV RFSLVSGWGQ LLDRGATALE LMVLNVPRLM TQDCLQQSRK
 361 VGDSPNITEY MFCAGYSDGS KDSCKGDSGG PHATHYRGTW YLTGIVSWGQ GCATVGHFGV
 421 YTRVSQYIEW LQKLMRSEPR PGVLLRAPFP GGGGSGGGGS GGGGSGGGGS GGGGSGGGGS
 481 DKTHTCPPCP APELLGGPSV FLFPPKPKDT LMISRTPEVT CVVVDVSHED PEVKFNWYVD
 541 GVEVHNAKTK PREEQYNSTY RVVSVLTVLH QDWLNGKEYK CKVSNKALPA PIEKTISKAK
 601 GQPREPQVYT LPPSRDELTK NQVSLTCLVK GFYPSDIAVE WESNGQPENN YKTTPPVLDS
 661 DGSFFLYSKL TVDKSRWQQG NVFSCSVMHE ALHNHYTQKS LSLSPGKRRR RSGGGGSGGG
 721 GSGGGGSGGG GSGGGGSGGG GSRKRRKRGP RIRTVGPGSR SASGKLTCLA SYCWLFWTGI
 781 AGGGGSGGGG SGGGGSGGGG SGGGGSGGGG SDKTHTCPPC PAPELLGGPS VFLFPPKPKD
 841 TLMISRTPEV TCVVVDVSHE DPEVKFNWYV DGVEVHNAKT KPREEQYNST YRVVSVLTVL
 901 HQDWLNGKEY KCKVSNKALP APIEKTISKA KGQPREPQVY TLPPSRDELT KNQVSLTCLV
 961 KGFYPSDIAV EWESNGQPEN NYKTTPPVLD SDGSFFLYSK LTVDKSRWQQ GNVFSCSVMH
1021 EALHNHYTQK SLSLSPGK
```

EXAMPLE 15

Preparation of FIX Conjugates

FIX-124 Construction

Cloning and expression was performed as described in Example 14.

The 3.4 kb DNA fragment comprising the region from HindIII to EcoRI of pSYN-FIX-124 was synthesized and subcloned into the HindIII/EcoRI sites of pcDNA4 vector (Invitrogen) to generate pSYN-FIX-124 (FIX-Fc-compound 21 conjugate).

FIX-124 DNA sequence (SEQ ID NO: 832)

```
  1 ATGCAGCGCG TGAACATGAT CATGGCAGAA TCACCAGGCC TCATCACCAT CTGCCTTTTA
 61 GGATATCTAC TCAGTGCTGA ATGTACAGTT TTTCTTGATC ATGAAAACGC CAACAAAATT
121 CTGAATCGGC CAAAGAGGTA TAATTCAGGT AAATTGGAAG AGTTTGTTCA AGGGAATCTA
181 GAGAGAGAAT GTATGGAAGA AAAGTGTAGT TTTGAAGAAG CACGAGAAGT TTTTGAAAAC
241 ACTGAAAGAA CAACTGAATT TTGGAAGCAG TATGTTGATG GAGATCAGTG TGAGTCCAAT
```

| FIX-124 DNA sequence (SEQ ID NO: 832) |
| --- |
|  301 CCATGTTTAA ATGGCGGCAG TTGCAAGGAT GACATTAATT CCTATGAATG TTGGTGTCCC |
|  361 TTTGGATTTG AAGGAAAGAA CTGTGAATTA GATGTAACAT GTAACATTAA GAATGGCAGA |
|  421 TGCGAGCAGT TTTGTAAAAA TAGTGCTGAT AACAAGGTGG TTTGCTCCTG TACTGAGGGA |
|  481 TATCGACTTG CAGAAAACCA GAAGTCCTGT GAACCAGCAG TGCCATTTCC ATGTGGAAGA |
|  541 GTTTCTGTTT CACAAACTTC TAAGCTCACC CGTGCTGAGA CTGTTTTTCC TGATGTGGAC |
|  601 TATGTAAATT CTACTGAAGC TGAAACCATT TTGGATAACA TCACTCAAAG CACCCAATCA |
|  661 TTTAATGACT TCACTCGGGT TGTTGGTGGA GAAGATGCCA AACCAGGTCA ATTCCCTTGG |
|  721 CAGGTTGTTT TGAATGGTAA AGTTGATGCA TTCTGTGGAG GCTCTATCGT TAATGAAAAA |
|  781 TGGATTGTAA CTGCTGCCCA CTGTGTTGAA ACTGGTGTTA AAATTACAGT TGTCGCAGGT |
|  841 GAACATAATA TTGAGGAGAC AGAACATACA GAGCAAAAGC GAAATGTGAT TCGAATTATT |
|  901 CCTCACCACA ACTACAATGC AGCTATTAAT AAGTACAACC ATGACATTGC CCTTCTGGAA |
|  961 CTGGACGAAC CCTTAGTGCT AAACAGCTAC GTTACACCTA TTTGCATTGC TGACAAGGAA |
| 1021 TACACGAACA TCTTCCTCAA ATTTGGATCT GGCTATGTAA GTGGCTGGGG AAGAGTCTTC |
| 1081 CACAAAGGGA GATCAGCTTT AGTTCTTCAG TACCTTAGAG TTCCACTTGT TGACCGAGCC |
| 1141 ACATGTCTTC GATCTACAAA GTTCACCATC TATAACAACA TGTTCTGTGC TGGCTTCCAT |
| 1201 GAAGGAGGTA GAGATTCATG TCAAGGAGAT AGTGGGGGAC CCATGTTAC TGAAGTGGAA |
| 1261 GGGACCAGTT TCTTAACTGG AATTATTAGC TGGGGTGAAG AGTGTGCAAT GAAAGGCAAA |
| 1321 TATGGAATAT ATACCAAGGT GTCCCGGTAT GTCAACTGGA TTAAGGAAAA AACAAAGCTC |
| 1381 ACTGACAAAA CTCACACATG CCCACCGTGC CCAGCTCCGG AACTCCTGGG AGGACCGTCA |
| 1441 GTCTTCCTCT TCCCCCCAAA ACCCAAGGAC ACCCTCATGA TCTCCCGGAC CCCTGAGGTC |
| 1501 ACATGCGTGG TGGTGGACGT GAGCCACGAA GACCCTGAGG TCAAGTTCAA CTGGTACGTG |
| 1561 GACGGCGTGG AGGTGCATAA TGCCAAGACA AAGCCGCGGG AGGAGCAGTA CAACAGCACG |
| 1621 TACCGTGTGG TCAGCGTCCT CACCGTCCTG CACCAGGACT GGCTGAATGG CAAGGAGTAC |
| 1681 AAGTGCAAGG TCTCCAACAA AGCCCTCCCA GCCCCCATCG AGAAAACCAT CTCCAAAGCC |
| 1741 AAAGGGCAGC CCCGAGAACC ACAGGTGTAC ACCCTGCCCC CATCCCGGGA TGAGCTGACC |
| 1801 AAGAACCAGG TCAGCCTGAC CTGCCTGGTC AAAGGCTTCT ATCCCAGCGA CATCGCCGTG |
| 1861 GAGTGGGAGA GCAATGGGCA GCCGGAGAAC AACTACAAGA CCACGCCTCC CGTGTTGGAC |
| 1921 TCCGACGGCT CCTTCTTCCT CTACAGCAAG CTCACCGTCG ACAAGAGCAG GTGGCAGCAG |
| 1981 GGGAACGTCT TCTCATGCTC CGTGATGCAT GAGGCTCTGC ACAACCACTA CACGCAGAAG |
| 2041 AGCCTCTCCC TGTCTCCGGG TAAACGGCGC CGCCGGAGCG GTGGCGGCGG ATCAGGTGGG |
| 2101 GGTGGATCAG GCGGTGGAGG TTCCGGTGGC GGGGGATCTG GCGGTGGAGG TTCCGGTGGG |
| 2161 GGTGGATCCA GGAAGAGGAG GAAGAGGGGC CCCGGATCC GGACAGTGGG CCCCGGCAGC |
| 2221 CGGAGCGCCA GCGGCAAGCT GACCTGCCTG GCCAGCTACT GCTGGCTGTT CTGGACCGGC |
| 2281 ATCGCCGGTG GCGGTGGATC CGGCGGAGGT GGGTCCGGTG GCGGCGGATC AGGTGGGGGT |
| 2341 GGATCAGGCG GTGGAGGTTC CGGTGGCGGG GGATCAGACA AAACTCACAC ATGCCCACCG |
| 2401 TGCCCAGCAC CGGAACTCCT GGGCGGACCG TCAGTCTTCC TCTTCCCCCC AAAACCCAAG |
| 2461 GACACCCTCA TGATCTCCCG GACCCCTGAG GTCACATGCG TGGTGGTGGA CGTGAGCCAC |

| FIX-124 DNA sequence (SEQ ID NO: 832) |
| --- |

```
2521 GAAGACCCTG AGGTCAAGTT CAACTGGTAC GTGGACGGCG TGGAGGTGCA TAATGCCAAG

2581 ACAAAGCCGC GGGAGGAGCA GTACAACAGC ACGTACCGTG TGGTCAGCGT CCTCACCGTC

2641 CTGCACCAGG ACTGGCTGAA TGGCAAGGAG TACAAGTGCA AGGTCTCCAA CAAAGCCCTC

2701 CCAGCCCCCA TCGAGAAAAC CATCTCCAAA GCCAAAGGGC AGCCCCGAGA ACCACAGGTG

2761 TACACCCTGC CCCCATCCCG GGATGAGCTG ACCAAGAACC AGGTCAGCCT GACCTGCCTG

2821 GTCAAAGGCT TCTATCCCAG CGACATCGCC GTGGAGTGGG AGAGCAATGG GCAGCCGGAG

2881 AACAACTACA AGACCACGCC TCCCGTGTTG GACTCCGACG GCTCCTTCTT CCTCTACAGC

2941 AAGCTCACCG TGGACAAGAG CAGGTGGCAG CAGGGGAACG TCTTCTCATG CTCCGTGATG

3001 CATGAGGCTC TGCACAACCA CTACACGCAG AAGAGCCTCT CCCTGTCTCC GGGTAAATGA
```

| FIX-124 amino acid sequence (SEQ ID NO: 833) |
| --- |
| Signal sequence is underlined, propeptide is double underlined, Fc separating Factor IX and furin cleavage site is in dotted underline, linker separating 2 furin cleavage sites is in wave underline, compound 21 separating furin cleavage sites is in wave underline, compound 21 separating furin cleavage site and linker is in dased underline, Fc is in dot-dot-dash underline. |

```
  1 MQRVNMIMAE SPGLITICLL GYLLSAECTV FLDHENANKI LNRPKRYNSG KLEEFVQGNL

61 ERECMEEKCS FEEAREVFEN TERTTEFWKQ YVDGDQCESN PCLNGGSCKD DINSYECWCP

121 FGFEGKNCEL DVTCNIKNGR CEQFCKNSAD NKVVCSCTEG YRLAENQKSC EPAVPFPCGR

181 VSVSQTSKLT RAETVFPDVD YVNSTEAETI LDNITQSTQS FNDFTRVVGG EDAKPGQFPW

241 QVVLNGKVDA FCGGSIVNEK WIVTAAHCVE TGVKITVVAG EHNIEETEHT EQKRNVIRII

301 PHHNYNAAIN KYNHDIALLE LDEPLVLNSY VTPICIADKE YTNIFLKFGS GYVSGWGRVF

361 HKGRSALVLQ YLRVPLVDRA TCLRSTKFTI YNNMFCAGFH EGGRDSCQGD SGGPHVTEVE

421 GTSFLTGIIS WGEECAMKGK YGIYTKVSRY VNWIKEKTKL TDKTHTCPPC PAPELLGGPS

481 VFLFPPKPKD TLMISRTPEV TCVVVDVSHE DPEVKFNWYV DGVEVHNAKT KPREEQYNST

541 YRVVSVLTVL HQDWLNGKEY KCKVSNKALP APIEKTISKA KGQPREPQVY TLPPSRDELT

601 KNQVSLTCLV KGFYPSDIAV EWESNGQPEN NYKTTPPVLD SDGSFFLYSK LTVDKSRWQQ

661 GNVFSCSVMH EALHNHYTQK SLSLSPGKRR RRSGGGGSGG GGSGGGGSGG GGSGGGGSGG

721 GGSRKRRKRG PRIRTVGPGS RSASGKLTCL ASYCWLFWTG IAGGGGSGGG GSGGGGSGGG

781 GSGGGGSGGG GSDKTHTCPP CPAPELLGGP SVFLFPPKPK DTLMISRTPE VTCVVVDVSH

841 EDPEVKFNWY VDGVEVHNAK TKPREEQYNS TYRVVSVLTV LHQDWLNGKE YKCKVSNKAL

901 PAPIEKTISK AKGQPREPQV YTLPPSRDEL TKNQVSLTCL VKGFYPSDIA VEWESNGQPE

961 NNYKTTPPVL DSDGSFFLYS KLTVDKSRWQ QGNVFSCSVM HEALHNHYTQ KSLSLSPGK
```

The TGA activity of FIX-124 was compared to FIX-Fc (without peptide).

TGA activity of FIX-124 was measured in pooled FIX-deficient HRF plasma with the results summarized in Table 22, below:

TABLE 22

| | TGA activity of FIX-124 and FIXFc in FIX-deficient plasma | | | | |
| --- | --- | --- | --- | --- | --- |
| Conc. (nM) | 0 | 6.7 | 33.5 | 67 | 134 |
| FIX-124, nM thrombin peak height | 32.48; 29.88 | 97.98; 96.48 | 111.59; 102.01 | 106.71; 106.15 | 103.19; 101.87 |

TABLE 22-continued

| | TGA activity of FIX-124 and FIXFc in FIX-deficient plasma | | | | |
|---|---|---|---|---|---|
| Conc. (nM) | 0 | 6.7 | 33.5 | 67 | 134 |
| FIXFc, nM thrombin peak height | | 35.11; 35.42 | 40.42; 40.93 | 46.45; 48.00 | 75.08; 80.78 |

TGA activity of FIX-124 was measured in FVIII-deficient Precision Biologics plasma with the results summarized in Table 23, below:

TABLE 23

| | TGA activity of FIX-124 and FIXFc in FVIII-deficient plasma | | | |
|---|---|---|---|---|
| Conc. ( nM) | 0 | 6.7 | 33.5 | 134 |
| FIX-124, nM thrombin peak height | 18.24; 14.64 | 32.09; 29.17 | 39.72; 38.02 | 40.79; 36.89 |

TABLE 23-continued

| | TGA activity of FIX-124 and FIXFc in FVIII-deficient plasma | | | |
|---|---|---|---|---|
| Conc. ( nM) | 0 | 6.7 | 33.5 | 134 |
| FIXFc, nM thrombin peak height | | 21.06; 20.56 | 18.54; 18.4 | 22.23; 21.83 |

EXAMPLE 16

Preparation of Platelet-Targeting Moiety Conjugates pSYN-Fc-046 Construction

Cloning and expression was performed as described in Example 14.

The 2.6 kb DNA fragment comprising the region from HindIII to EcoRI of pSYN-Fc-046 was synthesized and subcloned into the HindIII/EcoRI sites of pcDNA4 vector (Invitrogen) to generate pSYN-Fc-046 (PDG13-Fc-compound 21 conjugate).

```
                     Fc-046 DNA sequence (SEQ ID NO: 834)

1 ATGGAGACAG ACACACTCCT GCTATGGGTA CTGCTGCTCT GGGTTCCAGG TTCCACTGGT

61 GGCCCCCGGA TTCGGACAGT GGGCCCCGGC AGCCGGAGCG CCAGCGGCAA GCTGACCTGC

121 CTGGCCAGCT ACTGCTGGCT GTTCTGGACC GGCATCGCCG GTGGCGGTGG ATCCGGCGGA

181 GGTGGGTCCG GTGGCGGCGG ATCAGGTGGG GGTGGATCAG GCGGTGGAGG TTCCGGTGGC

241 GGGGGATCAG ACAAAACTCA CACATGCCCA CCGTGCCCAG CTCCGGAACT CCTGGGAGGA

301 CCGTCAGTCT TCCTCTTCCC CCCAAAACCC AAGGACACCC TCATGATCTC CCGGACCCCT

361 GAGGTCACAT GCGTGGTGGT GGACGTGAGC CACGAAGACC CTGAGGTCAA GTTCAACTGG

421 TACGTGGACG GCGTGGAGGT GCATAATGCC AAGACAAAGC CGCGGGAGGA GCAGTACAAC

481 AGCACGTACC GTGTGGTCAG CGTCCTCACC GTCCTGCACC AGGACTGGCT GAATGGCAAG

541 GAGTACAAGT GCAAGGTCTC CAACAAAGCC CTCCCAGCCC CCATCGAGAA AACCATCTCC

601 AAAGCCAAAG GGCAGCCCCG AGAACCACAG GTGTACACCC TGCCCCCATC CCGGGATGAG

661 CTGACCAAGA ACCAGGTCAG CCTGACCTGC CTGGTCAAAG GCTTCTATCC CAGCGACATC

721 GCCGTGGAGT GGGAGAGCAA TGGGCAGCCG GAGAACAACT ACAAGACCAC GCCTCCCGTG

781 TTGGACTCCG ACGGCTCCTT CTTCCTCTAC AGCAAGCTCA CCGTCGACAA GAGCAGGTGG

841 CAGCAGGGGA ACGTCTTCTC ATGCTCCGTG ATGCATGAGG CTCTGCACAA CCACTACACG

901 CAGAAGAGCC TCTCCCTGTC TCCGGGTAAA CGGCGCCGCC GGAGCGGTGG CGGCGGATCA

961 GGTGGGGGTG GATCAGGCGG TGGAGGTTCC GGTGGCGGGG GATCCGGCGG TGGAGGTTCC

1021 GGTGGGGGTG GATCAAGGAA GAGGAGGAAG AGGCAGGTGA AACTGCTCGA GTCTGGGGGA

1081 GGCGTGGTCC AGCCTGGGAG GTCCCTGAGA CTCTCCTGTG CAGCCTCTGG ATTCACCTTC

1141 AGTAGCTATG CTATGCACTG GGTCCGCCAG GCTCCAGGCA AGGGGCTGGA GTGGGTGGCA

1201 GTTATATCAT ATGATGGAAG CAATAAATAC TACGCAGACT CCGTGAAGGG CCGATTCGCC

1261 ATCTCCAGAG ACAATTCCAA GAACACGCTG TATCTGCAAA TGAACAGCCT GAGAGCTGAG

1321 GACACGGCTG TGTATTACTG TGCGAGAGCG CTGGGGAGCT GGGGGGGTTG GGACCACTAC

1381 ATGGACGTCT GGGGCAAAGG GACCACGGTC ACCGTCTCCT CAGGTGGCGG CGGATCAGGT

1441 GGGGGTGGAT CAGGTGGCGG TGGCTCCGGT GGCGGGGGAT CAGTGGTGAC TCAGCCACCC
```

| Fc-046 DNA sequence (SEQ ID NO: 834) |
| --- |
| 1501 TCAGCGTCTG GGACCCCGG GCAGAGGGTC ACCATCTCTT GTTCTGGAAG CAGCTCCAAC |
| 1561 ATCGGAAGTA ATACTGTAAA CTGGTACCAG CAGCTCCCAG GAACGGCCCC CAAACTCCTC |
| 1621 ATCTATAGTA ATAATCAGCG GCCCTCAGGG GTCCCTGACC GATTCTCTGG CTCCAAGTCT |
| 1681 GGCACCTCAG CCTCCCTGGC CATCAGTGGG CTCCAGTCTG AGGATGAGGC TGATTATTAC |
| 1741 TGTGCAGCAT GGGATGACAG CCTGAATGGT TGGGTGTTCG GCGGAGGGAC CAAGCTGACC |
| 1801 GTCCTAGGTC AGCCCGGTGG CGGTGGCTCC GGCGGAGGTG GTCCGGTGG CGGCGGATCA |
| 1861 GGTGGGGGTG GATCAGGCGG TGGAGGTTCC GGTGGCGGGG GATCAGACAA AACTCACACA |
| 1921 TGCCCACCGT GCCCAGCACC GGAACTACTG GCGGACCGT CAGTCTTCCT CTTCCCCCCA |
| 1981 AAACCCAAGG ACACCCTCAT GATCTCCCGG ACCCCTGAGG TCACATGCGT GGTGGTGGAC |
| 2041 GTGAGCCACG AAGACCCTGA GGTCAAGTTC AACTGGTACG TGGACGGCGT GGAGGTGCAT |
| 2101 AATGCCAAGA CAAAGCCGCG GGAGGAGCAG TACAACAGCA CGTACCGTGT GGTCAGCGTC |
| 2161 CTCACCGTCC TGCACCAGGA CTGGCTGAAT GGCAAGGAGT ACAAGTGCAA GGTCTCCAAC |
| 2221 AAAGCCCTCC CAGCCCCCAT CGAGAAAACC ATCTCCAAAG CCAAAGGGCA GCCCCGAGAA |
| 2281 CCACAGGTGT ACACCCTGCC CCCATCCCGG GATGAGCTGA CCAAGAACCA GGTCAGCCTG |
| 2341 ACCTGCCTGG TCAAAGGCTT CTATCCCAGC GACATCGCCG TGGAGTGGGA GAGCAATGGG |
| 2401 CAGCCGGAGA ACAACTACAA GACCACGCCT CCCGTGTTGG ACTCCGACGG CTCCTTCTTC |
| 2461 CTCTACAGCA AGCTCACCGT GGACAAGAGC AGGTGGCAGC AGGGGAACGT CTTCTCATGC |
| 2521 TCCGTGATGC ATGAGGCTCT GCACAACCAC TACACGCAGA AGAGCCTCTC CCTGTCTCCG |
| 2581 GGTAAATGA |

Fc-046 amino acid sequence (SEQ ID NO: 835):
Signal sequence is underlined, linker connecting compound 21 to Fc is in dotted underline, furin cleavage site separating Fc and the linker region is in thick underline, furin cleavage site separating the linker region and PDG13 scFv is in wave underline, and the linker connecting PDG13 and Fc is in dashed underline.

```
  1 METDTLLLWV LLLWVPGSTG GPRIRTVGPG SRSASGKLTC LASYCWLFWT GIAGGGGSGG
 61 GGSGGGGSGG GGSGGGGSGG GGSDKTHTCP PCPAPELLGG PSVFLFPPKP KDTLMISRTP
121 EVTCVVVDVS HEDPEVKFNW YVDGVEVHNA KTKPREEQYN STYRVVSVLT VLHQDWLNGK
181 EYKCKVSNKA LPAPIEKTIS KAKGQPREPQ VYTLPPSRDE LTKNQVSLTC LVKGFYPSDI
241 AVEWESNGQP ENNYKTTPPV LDSDGSFFLY SKLTVDKSRW QQGNVFSCSV MHEALHNHYT
301 QKSLSLSPGK RRRRSGGGGS GGGGSGGGGS GGGGSGGGGS GGGGSRKRRK RQVKLLESGG
361 GVVQPGRSLR LSCAASGFTF SSYAMHWVRQ APGKGLEWVA VISYDGSNKY ADSVKGRFA
421 ISRDNSKNTL YLQMNSLRAE DTAVYYCARA LGSWGGWDHY MDVWGKGTTV TVSSGGGGSG
481 GGGSGGGGSG GGGSVVTQPP SASGTPGQRV TISCSGSSSN IGSNTVNWYQ QLPGTAPKLL
541 IYSNNQRPSG VPDRFSGSKS GTSASLAISG LQSEDEADYY CAAWDDSLNG WVFGGGTKLT
601 VLGQPGGGGS GGGSGGGGS GGGGSGGGGS GGGGSDKTHT CPPCPAPELL GGPSVFLFPP
661 KPKDTLMISR TPEVTCVVVD VSHEDPEVKF NWYVDGVEVH NAKTKPREEQ YNSTYRVVSV
721 LTVLHQDWLN GKEYKCKVSN KALPAPIEKT ISKAKGQPRE PQVYTLPPSR DELTKNQVSL
```

```
781 TCLVKGFYPS DIAVEWESNG QPENNYKTTP PVLDSDGSFF LYSKLTVDKS RWQQGNVFSC
841 SVMHEALHNH YTQKSLSLSP GK
```

EXAMPLE 17

Preparation of Fc Conjugates pSYN-Fc-045 Construction

Cloning and expression was performed as described in Example 14.

The 1.8 kb DNA fragment comprising the region from HindIII to EcoRI of pSYN-Fc-045 was synthesized and subcloned into the HindIII/EcoRI sites of pcDNA4 vector (Invitrogen) to generate pSYN-Fc-045 (Fc-compound 21 conjugate).

Fc-045 DNA sequence (SEQ ID NO: 836)

```
   1 ATGGAGACAG ACACACTCCT GCTATGGGTA CTGCTGCTCT GGGTTCCAGG TTCCACTGGT
  61 GACAAAACTC ACACATGCCC ACCGTGCCCA GCTCCGGAAC TCCTGGGAGG ACCGTCAGTC
 121 TTCCTCTTCC CCCCAAAACC CAAGGACACC CTCATGATCT CCCGGACCCC TGAGGTCACA
 181 TGCGTGGTGG TGGACGTGAG CCACGAAGAC CCTGAGGTCA AGTTCAACTG GTACGTGGAC
 241 GGCGTGGAGG TGCATAATGC CAAGACAAAG CCGCGGGAGG AGCAGTACAA CAGCACGTAC
 301 CGTGTGGTCA GCGTCCTCAC CGTCCTGCAC CAGGACTGGC TGAATGGCAA GGAGTACAAG
 361 TGCAAGGTCT CCAACAAAGC CCTCCCAGCC CCCATCGAGA AAACCATCTC CAAAGCCAAA
 421 GGGCAGCCCC GAGAACCACA GGTGTACACC CTGCCCCCAT CCCGGGATGA GCTGACCAAG
 481 AACCAGGTCA GCCTGACCTG CCTGGTCAAA GGCTTCTATC CAGCGACAT CGCCGTGGAG
 541 TGGGAGAGCA ATGGGCAGCC GGAGAACAAC TACAAGACCA CGCCTCCCGT GTTGGACTCC
 601 GACGGCTCCT TCTTCCTCTA CAGCAAGCTC ACCGTCGACA AGAGCAGGTG GCAGCAGGGG
 661 AACGTCTTCT CATGCTCCGT GATGCATGAG GCTCTGCACA ACCACTACAC GCAGAAGAGC
 721 CTCTCCCTGT CTCCGGGTAA ACGGCGCCGC CGGAGCGGTG GCGGCGGATC AGGTGGGGGT
 781 GGATCAGGCG GTGGAGGTTC CGGTGGCGGG GGATCTGGCG GTGGAGGTTC CGGTGGGGGT
 841 GGATCCAGGA AGAGGAGGAA GAGGGGCCCC CGGATCCGGA CAGTGGGCCC CGGCAGCCGG
 901 AGCGCCAGCG GCAAGCTGAC CTGCCTGGCC AGCTACTGCT GGCTGTTCTG GACCGGCATC
 961 GCCGGTGGCG GTGGATCCGG CGGAGGTGGG TCCGGTGGCG GCGGATCAGG TGGGGGTGGA
1021 TCAGGCGGTG GAGGTTCCGG TGGCGGGGGA TCAGACAAAA CTCACACATG CCCACCGTGC
1081 CCAGCACCGG AACTCCTGGG CGGACCGTCA GTCTTCCTCT TCCCCCCAAA ACCCAAGGAC
1141 ACCCTCATGA TCTCCCGGAC CCCTGAGGTC ACATGCGTGG TGGTGGACGT GAGCCACGAA
1201 GACCCTGAGG TCAAGTTCAA CTGGTACGTG GACGGCGTGG AGGTGCATAA TGCCAAGACA
1261 AAGCCGCGGG AGGAGCAGTA CAACAGCACG TACCGTGTGG TCAGCGTCCT CACCGTCCTG
1321 CACCAGGACT GGCTGAATGG CAAGGAGTAC AAGTGCAAGG TCTCCAACAA AGCCCTCCCA
1381 GCCCCCATCG AGAAAACCAT CTCCAAAGCC AAAGGGCAGC CCCGAGAACC ACAGGTGTAC
1441 ACCCTGCCCC CATCCCGGGA TGAGCTGACC AAGAACCAGG TCAGCCTGAC CTGCCTGGTC
1501 AAAGGCTTCT ATCCCAGCGA CATCGCCGTG GAGTGGGAGA GCAATGGGCA GCCGGAGAAC
1561 AACTACAAGA CCACGCCTCC CGTGTTGGAC TCCGACGGCT CCTTCTTCCT CTACAGCAAG
1621 CTCACCGTGG ACAAGAGCAG GTGGCAGCAG GGGAACGTCT TCTCATGCTC CGTGATGCAT
1681 GAGGCTCTGC ACAACCACTA CACGCAGAAG AGCCTCTCCC TGTCTCCGGG TAAATGA
```

| Fc-045 amino acid sequence (SEQ ID NO: 837) Signal sequence is underlined, furin cleavage site separating Fc and linker is in dotted underline, furin cleavage site separating linker and compound 21 is in thick underline, linker region connecting compound 21 to the Fc region is in wave underline. |
|---|
| 1 METDTLLLWV LLLWVPGSTG DKTHTCPPCP APELLGGPSV FLFPPKPKDT LMISRTPEVT |
| 61 CVVVDVSHED PEVKFNWYVD GVEVHNAKTK PREEQYNSTY RVVSVLTVLH QDWLNGKEYK |
| 121 CKVSNKALPA PIEKTISKAK GQPREPQVYT LPPSRDELTK NQVSLTCLVK GFYPSDIAVE |
| 181 WESNGQPENN YKTTPPVLDS DGSFFLYSKL TVDKSRWQQG NVFSCSVMHE ALHNHYTQKS |
| 241 LSLSPGKRRR RSGGGGSGGG GSGGGGSGGG GSGGGGSGGG GSRKRRKRGP RIRTVGPGSR |
| 301 SASGKLTCLA SYCWLFWTGI AGGGGSGGGG SGGGGSGGGG SGGGGSGGGG SDKTHTCPPC |
| 361 PAPELLGGPS VFLFPPKPKD TLMISRTPEV TCVVVDVSHE DPEVKFNWYV DGVEVHNAKT |
| 421 KPREEQYNST YRVVSVLTVL HQDWLNGKEY KCKVSNKALP APIEKTISKA KGQPREPQVY |
| 481 TLPPSRDELT KNQVSLTCLV KGFYPSDIAV EWESNGQPEN NYKTTPPVLD SDGSFFLYSK |
| 541 LTVDKSRWQQ GNVFSCSVMH EALHNHYTQK SLSLSPGK |

EXAMPLE 18

Preparation of Conjugates Useful for Subsequent Chemical Ligation To Compounds pSYN-CysFc-044 Construction Cloning was performed as described in Example 14.

The 3.2 kb DNA fragment comprising the region from HindIII to EcoRI of pSYN-CysFc-044 was synthesized and subcloned into the HindIII/EcoRI sites of pcDNA4 vector (Invitrogen) to generate pSYN-CysFc-044 (PDG13-CysFc).

| CysFc-044 DNA sequence (SEQ ID NO: 838) |
|---|
| 1 ATGGAGACAG ACACACTCCT GCTATGGGTA CTGCTGCTCT GGGTTCCAGG TTCCACTGGT |
| 61 TGCCCGCCGT GCCCGGCTCC GGAACTCCTG GGAGGACCGT CAGTCTTCCT CTTCCCCCCA |
| 121 AAACCCAAGG ACACCCTCAT GATCTCCCGG ACCCCTGAGG TCACATGCGT GGTGGTGGAC |
| 181 GTGAGCCACG AAGACCCTGA GGTCAAGTTC AACTGGTACG TGGACGGCGT GGAGGTGCAT |
| 241 AATGCCAAGA CAAAGCCGCG GGAGGAGCAG TACAACAGCA CGTACCGTGT GGTCAGCGTC |
| 301 CTCACCGTCC TGCACCAGGA CTGGCTGAAT GGCAAGGAGT ACAAGTGCAA GGTCTCCAAC |
| 361 AAAGCCCTCC CAGCCCCCAT CGAGAAAACC ATCTCCAAAG CCAAAGGGCA GCCCCGAGAA |
| 421 CCACAGGTGT ACACCCTGCC CCCATCCCGG GATGAGCTGA CCAAGAACCA GGTCAGCCTG |
| 481 ACCTGCCTGG TCAAAGGCTT CTATCCCAGC GACATCGCCG TGGAGTGGGA GAGCAATGGG |
| 541 CAGCCGGAGA ACAACTACAA GACCACGCCT CCCGTGTTGG ACTCCGACGG CTCCTTCTTC |
| 601 CTCTACAGCA AGCTCACCGT CGACAAGAGC AGGTGGCAGC AGGGGAACGT CTTCTCATGC |
| 661 TCCGTGATGC ATGAGGCTCT GCACAACCAC TACACGCAGA AGAGCCTCTC CCTGTCTCCG |
| 721 GGTAAACGGC GCCGCCGGAG CGGTGGCGGC GGATCAGGTG GGGGTGGATC AGGCGGTGGA |
| 781 GGTTCCGGTG GCGGGGGATC CGGCGGTGGA GGTTCCGGTG GGGGTGGATC AAGGAAGAGG |
| 841 AGGAAGAGGC AGGTGAAACT GCTCGAGTCT GGGGGAGGCG TGGTCCAGCC TGGGAGGTCC |
| 901 CTGAGACTCT CCTGTGCAGC CTCTGGATTC ACCTTCAGTA GCTATGCTAT GCACTGGGTC |
| 961 CGCCAGGCTC CAGGCAAGGG GCTGGAGTGG GTGGCAGTTA TATCATATGA TGGAAGCAAT |
| 1021 AAATACTACG CAGACTCCGT GAAGGGCCGA TTCGCCATCT CCAGAGACAA TTCCAAGAAC |
| 1081 ACGCTGTATC TGCAAATGAA CAGCCTGAGA GCTGAGGACA CGGCTGTGTA TTACTGTGCG |
| 1141 AGAGCGCTGG GGAGCTGGGG GGGTTGGGAC CACTACATGG ACGTCTGGGG CAAAGGGACC |

| CysFc-044 DNA sequence (SEQ ID NO: 838) |
|---|

```
1201 ACGGTCACCG TCTCCTCAGG TGGCGGCGGA TCAGGTGGGG GTGGATCAGG TGGCGGTGGC
1261 TCCGGTGGCG GGGGATCAGT GGTGACTCAG CCACCCTCAG CGTCTGGGAC CCCCGGGCAG
1321 AGGGTCACCA TCTCTTGTTC TGGAAGCAGC TCCAACATCG GAAGTAATAC TGTAAACTGG
1381 TACCAGCAGC TCCCAGGAAC GGCCCCCAAA CTCCTCATCT ATAGTAATAA TCAGCGGCCC
1441 TCAGGGGTCC CTGACCGATT CTCTGGCTCC AAGTCTGGCA CCTCAGCCTC CCTGGCCATC
1501 AGTGGGCTCC AGTCTGAGGA TGAGGCTGAT TATTACTGTG CAGCATGGGA TGACAGCCTG
1561 AATGGTTGGG TGTTCGGCGG AGGGACCAAG CTGACCGTCC TAGGTCAGCC CGGTGGCGGT
1621 GGCTCCGGCG GAGGTGGGTC CGGTGGCGGC GGATCAGGTG GGGGTGGATC AGGCGGTGGA
1681 GGTTCCGGTG GCGGGGATC AGACAAAACT CACACATGCC CACCGTGCCC AGCACCGGAA
1741 CTACTGGGCG GACCGTCAGT CTTCCTCTTC CCCCCAAAAC CCAAGGACAC CCTCATGATC
1801 TCCCGGACCC CTGAGGTCAC ATGCGTGGTG GTGGACGTGA GCCACGAAGA CCCTGAGGTC
1861 AAGTTCAACT GGTACGTGGA CGGCGTGGAG GTGCATAATG CCAAGACAAA GCCGCGGGAG
1921 GAGCAGTACA ACAGCACGTA CCGTGTGGTC AGCGTCCTCA CCGTCCTGCA CCAGGACTGG
1981 CTGAATGGCA AGGAGTACAA GTGCAAGGTC TCCAACAAAG CCCTCCCAGC CCCCATCGAG
2041 AAAACCATCT CCAAAGCCAA AGGGCAGCCC CGAGAACCAC AGGTGTACAC CCTGCCCCCA
2101 TCCCGGGATG AGCTGACCAA GAACCAGGTC AGCCTGACCT GCCTGGTCAA AGGCTTCTAT
2161 CCCAGCGACA TCGCCGTGGA GTGGGAGAGC AATGGGCAGC CGGAGAACAA CTACAAGACC
2221 ACGCCTCCCG TGTTGGACTC CGACGGCTCC TTCTTCCTCT ACAGCAAGCT CACCGTGGAC
2281 AAGAGCAGGT GGCAGCAGGG GAACGTCTTC TCATGCTCCG TGATGCATGA GGCTCTGCAC
2341 AACCACTACA CGCAGAAGAG CCTCTCCCTG TCTCCGGGTA AATGA
```

CysFc-044 amino acid sequence (SEQ ID NO: 839):
Signal sequence is underlined, furin cleavage site separating truncated Fc and linker is in thick underline, furin cleavage site separating linker and PDG13 scFv is dotted underline and linker region connecting PDG-13 scFv to Fc region is in dashed underline.

```
  1 METDTLLLWV LLLWVPGSTG CPPCPAPELL GGPSVFLFPP KPKDTLMISR TPEVTCVVVD
 61 VSHEDPEVKF NWYVDGVEVH NAKTKPREEQ YNSTYRVVSV LTVLHQDWLN GKEYKCKVSN
121 KALPAPIEKT ISKAKGQPRE PQVYTLPPSR DELTKNQVSL TCLVKGFYPS DIAVEWESNG
181 QPENNYKTTP PVLDSDGSFF LYSKLTVDKS RWQQGNVFSC SVMHEALHNH YTQKSLSLSP
241 GKRRRSGGG GSGGGGSGGG GSGGGGSGGG GSGGGGSRKR RKRQVKLLES GGGVVQPGRS
301 LRLSCAASGF TFSSYAMHWV RQAPGKGLEW VAVISYDGSN KYYADSVKGR FAISRDNSKN
361 TLYLQMNSLR AEDTAVYYCA RALGSWGGWD HYMDVWGKGT TVTVSSGGGG SGGGGSGGGG
421 SGGGGSVVTQ PPSASGTPGQ RVTISCSGSS SNIGSNTVNW YQQLPGTAPK LLIYSNNQRP
481 SGVPDRFSGS KSGTSASLAI SGLQSEDEAD YYCAAWDDSL NGWVFGGGTK LTVLGQPGGG
541 GSGGGGSGGG GSGGGGSGGG GSGGGGSDKT HTCPPCPAPE LLGGPSVFLF PPKPKDTLMI
601 SRTPEVTCVV VDVSHEDPEV KFNWYVDGVE VHNAKTKPRE EQYNSTYRVV SVLTVLHQDW
661 LNGKEYKCKV SNKALPAPIE KTISKAKGQP REPQVYTLPP SRDELTKNQV SLTCLVKGFY
```

| | |
|---|---|
| 721 | PSDIAVEWES NGQPENNYKT TPPVLDSDGS FFLYSKLTVD KSRWQQGNVF SCSVMHEALH |
| 781 | NHYTQKSLSL SPGK |

EXAMPLE 19

Preparation of Compounds With a Cleavable Linker (a) Synthesis of Compounds Incorporating a Self-Immolative Linker Outlined below is the preparation for a conjugate (conjugate A) in which compound 5 is covalently connected to a linker comprising the self-immolative moiety p-aniline carbamate (PABC) and a thrombin substrate moiety. In a similar fashion conjugates incorporating other thrombin substrate moieties were prepared and tested for cleavability in the presence of thrombin.

Fmoc-Cys(Acm)-Gly-Gly-Gly-Gly-Dphe-Pip-Arg(Pbf) (SEQ ID NO: 866)

The fully protected peptide was cleaved from the NovaPEG TGT resin by 30% HFIP/DCM and filtered into a round bottom reaction flask. The solvents were removed in vacuo, and the concentrate containing the peptide was precipitated and further triturated with ice cold diethyl ether (Et$_2$O). This material was directly used without further purification. ESI-MS m/z: 1309.51 (MH)$^+$.

Fmoc-Cys(Acm)-Gly-Gly-Gly-Gly-Dphe-Pip-Arg(Pff)-PABOH (p-aniline Benzyl Alcohol) (SEQ ID NO: 867)

A stirred solution of Fmoc-Cys(Acm)-Gly-Gly-Gly-Gly-Dphe-Pip-Arg(Pbf) (SEQ ID NO: 875) (268 mg, 0.2 mmol) and p-aniline benzyl alcohol (28 mg, 1.1 equiv) in THF (2 mL) at room temperature was treated with EEDQ (55.6 mg, 1.1 equiv). After 16 h, the mixture was evaporated to dryness, and the residue was triturated with ether. The resulting white solid product was collected by centrifugation and dried in vacuo (200 mg, 70%). ESI-MS m/z: 1414.61 (MH)$^+$.

Fmoc-Cys(Acm)-Gly-Gly-Gly-Gly-Gly-Dphe-Pip-Arg(Pbf)-PABC-PNP (SEQ ID NO: 868)

A stirred solution of Fmoc-Cys(Acm)-Gly-Gly-Gly-Gly-Dphe-Pip-Arg(Pbf)-PABOH) (SEQ ID NO: 876) (180 mg, 0.127 mmol) in dry THF (4 mL) and DCM (4 mL) at room temperature was treated with PNP chloroformate (38.5 mg, 1.5 equiv) and dry pyridine (15 mg, 1.5 equiv). After 16 h, the mixture was concentrated to 1 mL, and the product was precipitated and triturated with cold ether. The resulting white solid product was collected by centrifugation and dried in vacuo (150 mg, 75%). ESI-MS m/z: 1579.61 (MH)$^+$.

rRAPGK(Alloc)LTCLASYCWLFWTGIA-NH$_2$ (Disulfide) (SEQ ID NO: 869)

Linear alloc-protected compound 5 was synthesized on NovaPEG Rink Amide resin (0.2 mmol) as described in the general method. The Cys-Cys disulfidic bond was formed by stirring the crude peptide in 50% DMSO/H$_2$O overnight at 37° C. 35 mg of peptide was obtained after purification by preparative HPLC. ESI-MS m/z : 1298.17 (MH$_2$)$^{2+}$, 865.78 (MH$_3$)$^{3+}$.

Fmoc-Cys(Acm)-Gly-Gly-Gly-Gly-Dphe-Pip-Arg(Pbf)-PABC rRAPGK(Alloc)LTCLA SYCWLFWTGIA-NH$_2$ (Disulfide) (SEQ ID NO: 870)

Fmoc-Cys(Acm)-Gly-Gly-Gly-Gly-Dphe-Pip-Arg(Pbf)-PABC-PNP) (SEQ ID NO: 877) (12.5 mg, 0.008 mmol) and rRAPGK(Alloc)LTCLA SYCWLFWTGIA) (SEQ ID NO: 878) (30 mg, 0.011 mmol) in DMF (1 mL) at room temperature were treated with DIPEA (6.5 µL, 5 equiv). The mixture was allowed to stand in the dark overnight. The crude product was precipitated, and triturated with cold ether. The resulting crude product was collect by centrifugation, dried in vacuo, and used for the next step without further purification. ESI-MS m/z: 2018.32 (MH$_2$)$^{2+}$, 1345.86 (MH$_3$)$^{3+}$.

Fmoc-Cys(Acm)-Gly-Gly-Gly-Gly-Dphe-Pip-Arg-PABC-rRAPGK(Alloc)LTCLASYCWLFWTGIA-NH$_2$ (Disulfide) (SEQ ID NO: 871)

Pbf deprotection of Fmoc-Cys(Acm)-Gly-Gly-Gly-Gly-Dphe-Pip-Arg(Pbf)-PABC-rRAPGK(Alloc)LTCLA SYCWLFWTGIA) (SEQ ID NO: 879) from the previous step was carried out in 1 mL of solvent mixture (72% TFA, 5% DMF, 5% H$_2$O, 18% DCM) for 75 min. Since the PABC linker was unstable under this condition, aliquots were taken at various time points to monitor progress of the reaction. At 75 min, cold ether (50 mL) was added to stop the reaction. The resulting solid was purified by preparative HPLC, to give a white powder (8 mg, 25% for 2 steps), ESI-MS m/z : 1261.83 (MH$_3$)$^{3+}$.

Fmoc-Cys(Acm)-Gly-Gly-Gly-Gly-Dphe-Pip-Arg-PABC-rRAPGKLTCLA SYCWLFWTGIA-NH$_2$ (Disulfide) (SEQ ID NO: 872)

Fmoc-Cys(Acm)-Gly-Gly-Gly-Gly-Dphe-Pip-Arg-PABC-rRAPGL(Alloc)LTCLASYCWLFWTGIA (SEQ ID NO: 880) (8 mg, 0.002 mmol) in MeOH/Dioxane (1:1, 180 µL) under N$_2$ at room temperature was treated with Pd(PPh$_3$)$_4$ (0.0002 mmol, 0.1 equiv, 20 µL of a THF solution of Pd(PPh$_3$)$_4$ (23 mg/mL), followed by PhSiH$_3$ (0.01 mmol, 5 equiv). After 20 min, the crude mixture was precipitated and triturated with cold ether. The resulting crude product was used for the next step without purification. ESI-MS m/z: 1233.82 (MH$_3$)$^{3+}$.

Cys(Acm)-Gly-Gly-Gly-Gly-Dphe-Pip-Arg-PABC-rRAPGKLTCLASYCWLFWTGIA-NH$_2$ (Disulfide) (SEQ ID NO: 873)

Fmoc deprotection of Fmoc-Cys(Acm)-Gly-Gly-Gly-Gly-Dphe-Pip-Arg-PABC-rRAPGKLTCLA SYCWLFWTGIA) (SEQ ID NO: 881) from the previous step was carried out in DMSO (200 µL) with Et$_2$NH (50 µL, excess). After 20 min, the reaction was complete and the mixture was purified by preparative HPLC, to give conjugate A a white powder (0.83 mg, 12% over 2 steps). ESI-MS m/z: 1159.80 (MH$_3$)$^{3+}$, 1159.80 (MH$_4$)$^{4+}$.

The above procedures can be used to synthesize conjugates comprising other compounds of the present disclosure.

(b) Thrombin Cleavage of Conjugate A

Conjugate A (21 µL, 0.24 mM) in water was added to 476.5 µL PBS. The mixture was incubated at 37° C. for 30 min, followed by 2.5 µL of thrombin (278 nM, 10 µg/mL), giving the following approximate initial concentrations: thrombin (1.4 nM, physiological concentration), conjugate A (10 µM). The mixture was incubated at 37° C. Aliquots (60 µL) at various time points were quenched with 1 µL of hirudin (10 µM) and injected into the HPLC (C-18 column, CH$_3$CN/H$_2$O, 0 to 70% over 12 minutes, 60° C. 0.5 mL/min, λ =280 nm). Under these conditions, conjugate A was cleaved rapidly by 1.4 nM thrombin to release the active procoagulant compound 5 (i.e., the conjugate was fully cleaved after about 60 min of incubation).

EXAMPLE 20

Preparation of FC-Compound Conjugates by Copper-Catalyzed Azide-Alkyne Cycloaddition A semi-synthetic method to prepare conjugates in which a compound of the present disclosure is linked to Fc is outlined below. This method allows linkage of Fc with a compound containing an unnatural amino acid. Incorporation of an unnatural amino acids may increase biological activity and/or stability. This method is an alternative approach to the native chemical ligation with a N-terminal Cys on Fc and a peptide-thioester directly.
$NH_2$-$PEG_{27}$-COSBn A stirred solution of Boc-NH-$PEG_{27}$—COOH (500 mg, 0.35 mmol) and benzyl mercaptan (174 mg, 4 equiv) in DMF (2 mL) at room temperature was treated with DIC (53 mg, 1.2 equiv) and DMAP (4.3 mg, 0.1 equiv). After 16 h, the crude product was precipitated, triturated with cold ether, and collected by centrifugation. The Boc group was cleaved by addition of 10 mL of 95% TFA/TIPS into the resulting white pellet. After 30 min, the mixture was concentrated to 1 mL, and the product was precipitated and triturated with cold ether. The resulting off-white oil product was collected by centrifugation, dried in vacuo, and used for next step without further purification (550 mg), ESI-MS m/z: 142.83 $(MH)^+$.
$N_3PEG_{27}$-COSBn:

A stirred solution of $NH_2$-$PEG_{27}$-COSBn (300 mg, 0.21 mmol) and 5-Azidopentanoic acid (60 mg, 2 equiv) in DMF (1 mL) at room temperature was treated with PyBOP (164 mg, 1.5 equiv) and DIEA (136 mg, 5 equiv). After 16 h, the crude product was precipitated, triturated with cold ether, and collected by centrifugation. The resulting solid was purified by preparative HPLC, to give a white powder (120 mg, 37%). ESI-MS m/z: 1553.77 $(MH)^+$.
Fc-$PEG_{27}$-$N_3$ Dimer Conjugate Cys-Fc (2580 µL, 8 mg/mL in PBS, pH 7.4) was treated with 2-mercaptoethanesulfonic acid, sodium salt (MESNA) (300 µL, 100 mM in PBS) and $N_3$-$PEG_{27}$-COSBn (120 µL, 50 mM in water) such that the final concentration of Cys-Fc, MESNA, and $N_3$-$PEG_{27}$-COSBn were 6.9 mg/mL, 10 mM, and 2 mM respectively. The reaction mixture was allowed to stand at room temperature for 16 h. The crude reaction mixture was dialyzed exhaustively against PBS (pH 7.4) (7 changes over 24 hours). SDS-PAGE gel and LC/MS showed greater than 90% conversion. MW observed (reduced): 27707.02.
Fc-$PEG_{27}$-Procoagulant Peptide Conjugate (Copper-Catalyzed Azide-Alkyne Cycloaddition Fc-PEG27-N3 dinner conjugate (20 µL, 13 mg/mL in PBS pH 7.4) was treated with premixed solution of CuSO4 and Tris(3-hydroxypropyltriazolylmethyl)amine (THPTA) (10 µL, 1:1 ratio, 10 mM in water), and Pra-PEG4-PRIRTVG-PGSRSASGKLTCLASYCWLFWTGIA-NH2 (SEQ ID NO: 904) (30 µL, 2.15 mM) (Pra=L-propargylglycine). The pH was adjusted to 5.5 by addition of MES buffer (40 µL, 1 M pH 5.5) and water (90 µL). Reducing agent sodium ascorbate (10 µL, 100 mM) was added to initiate the reaction. Final concentrations of Fc-PEG27-N3 dimer conjugate, CuSO4, THPTA, and SYN4002 were 49 µM, 500 µM, 500 µM, and 322.5 µM, respectively. After 2 h, LC/MS showed greater than 90% conversion. MW observed (reduced): 31501.96.

EXAMPLE A

Hemophilia A/B In Vivo Studies

The pro-coagulant compounds and conjugates of the present disclosure can be tested using hemophilia A and/or B animals. In one example, the animal is a hemophilia A mouse. In another example, the test animal is a hemophilia A dog (e.g., in-bred colony maintained at the Francis Owen Blood Research Laboratory at the University of North Carolina, Chapel Hill). These dogs have a severe hemophilic phenotype comparable to the severe form of the human disease (Graham, J B, et al., *J. Exp. Med.* 1949;90:97-111; Lozier, J N, et al., *Proc. Natl. Acad. Sci.* 2002;99:12991-12996, each of which is incorporated by reference herein in its entirety).

In one example, pro-coagulant compounds and/or conjugates of the present disclosure are injected, e.g. IV or SC, into hemophilia A mice. Blood is collected by vena cava puncture at different time points, e.g. 2, 15, 30, 60, 120, 240 and 480 min (3-5 mice per time point) and citrated immediately. In another example blood is collected at 2 min, 1 h, 6 h, 12 h, 24 h, 48 h and 96 h. Activity is measured by ex vivo Rotem, and remaining blood is centrifuged at 5000 rpm for 2×10 min to generate plasma for PK analysis.

In one example, pro-coagulant compounds and/or conjugates of the present disclosure are injected, e.g. IV or SC, into hemophilia A dogs. Blood samples are drawn at different time points, e.g. 2, 15, 30, 60, 120, 240 and 480 min. In another example blood is drawn at 2 min, 1 h, 6 h, 12 h, 24 h, 48 h and 96 h. Activity is measured by ex vivo WBCT, and remaining blood is centrifuged at 5000 rpm for 2=10 min to generate plasma for PK analysis (Dumont, J A, et al. *Blood* 2012, 119, 3024-3030 which is incorporated by reference herein in its entirety).

In one example, pro-coagulant compounds and/or conjugates of the present disclosure are injected, e.g. IV or SC, into hemophilia A mice and acute efficacy is tested by a tail clip model. Shortly after injection, e.g. 5 min, mice are injured by tail clip and blood loss is measured for 30 min (10-15 mice per dose) and compared to vehicle and FVIII treated mice (Dumont, J A, et al. *Blood* 2012, 119, 3024-3030 which is incorporated by reference herein in its entirety).

In one example, pro-coagulant compounds and/or conjugates of the present disclosure are injected, e.g. IV or SC, into hemophilia A mice and prophylactic efficacy is tested by a tail vein transection (TVT) model. Following the injection, e.g. after 24 hours, mice are injured by TVT and the survival rate is measured at different time points, e.g. hourly up to 24 hours (10-15 mice per dose) and compared to vehicle and FVIII treated mice. (Dumont, J A, et al. *Blood* 2012, 119, 3024-3030 which is incorporated by reference herein in its entirety).

Additional bleeding and thrombogenicity models can be used such as described in Tranholm, M, et al, *Blood* 2003, 102, 3615-3620; Tranholm, M, et al, *Thrombosis Research* 2003, 109, 217-223; Lauritzen, B, et al, *Journal of Thrombosis and Hemostasis* 2009, 7, 651-657.

Having now fully described this invention, it will be understood by those of ordinary skill in the art that the same can be performed within a wide and equivalent range of conditions, formulations and other parameters without affecting the scope of the invention or any embodiment thereof.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

All patents and publications cited herein are incorporated by reference herein in their entirety.

What is claimed is:

1. A compound comprising at least one amino acid sequence selected from SEQ ID NOS: 4, 9, 10-54, 59-99, 104-183, 200-208, 214-216, 219-233, 238-247, 259, 260, 264-272, 282-293, 296, 307, 309-311, 315, 316, 326, 327, 336, 337, 339, 340, 346-348, 352, 360-362, 364, 367-375, 380, 383-386, 389, 392, 400-406, 409-415, 417, 419-421, 423-463, 471-489, 491-496, 526-533, 536, 537, 543-548, 550-555, 840-843, 861, 869, 873, 874, 878, 880, 892, and 895-898, or the retro-, inverso- or the retro-inverso peptide thereof, or the pharmaceutically acceptable salt or solvate thereof.

2. The compound of claim 1, wherein the compound is covalently linked to a half-life extending moiety.

3. The compound of claim 2, wherein the half-life extending moiety is selected from Fc, FcRn binding ligand, albumin, albumin-binding ligand, transferrin, a polyethylene glycol (PEG) moiety, a polypropylene glycol (PPG) moiety, a PAS moiety, and a hydroxyethyl starch (HES) moiety.

4. A pharmaceutical composition comprising the compound of claim 1, and a pharmaceutically acceptable carrier.

5. The compound of claim 1, which comprises at least one amino acid sequence selected from SEQ ID NOS: 29, 48-51, 59-86, 91-96, 104-148, 149-152, 153-183, 200-205, 214-216, 219-230, 238-240, 242-244, 264, 282-293, 296, 307, 346, 360-361, 367, 369-370, 374-375, 383, 385, 389, 411-413, 414, 417, 419-420, 423, 424-440, 450-460, 462, 471-489, 491, 492, 494, 496, 526-533, 536-537, 545-548, 550-555, 840-843, 861, 869, 873, 874, 878, 880, 892, and 895-898.

6. The pharmaceutical composition of claim 4, wherein the compound comprises at least one amino acid sequence selected from SEQ ID NOS: 29, 48-51, 59-86, 91-96, 104-148, 149-152, 153-183, 200-205, 214-216, 219-230, 238-240, 242-244, 264, 282-293, 296, 307, 346, 360-361, 367, 369-370, 374-375, 383, 385, 389, 411-413, 414, 417, 419-420, 423, 424-440, 450-460, 462, 471-489, 491, 492, 494, 496, 526-533, 536-537, 545-548, 550-555, 840-843, 861, 869, 873, 874, 878, 880, and 895-898.

7. A conjugate comprising the compound of claim 1 and a first heterologous moiety which are linked to each other via a first optional linker.

8. The conjugate of claim 7, which comprises a structure according to Formula (A1) or (A2):

Het1-(L$_1$)$_m$-Pep　　　　(A1)

Pep-(L$_1$)$_m$-Het1　　　　(A2)

wherein
Het1 is the first heterologous moiety;
m is an integer selected from 0 and 1;
$L_1$ is either absent (m=0) or present (m=1), and when present is a linker;
Pep is a compound according to claim 1; and
(—) is a covalent bond.

9. A pharmaceutical composition comprising the conjugate of claim 7 and a pharmaceutically acceptable carrier.

10. The conjugate of claim 7, wherein the compound comprises at least one amino acid sequence selected from SEQ ID NOS: 29, 48-51, 59-86, 91-96, 104-148, 149-152, 153-183, 200-205, 214-216, 219-230, 238-240, 242-244, 264, 282-293, 296, 307, 346, 360-361, 367, 369-370, 374-375, 383, 385, 389, 411-413, 414, 417, 419-420, 423, 424-440, 450-460, 462, 471-489, 491, 492, 494, 496, 526-533, 536-537, 545-548, 550-555, 840-843, 861, 869, 873, 874, 878, 880, and 895-898.

11. A pharmaceutical composition comprising the conjugate of claim 10 and a pharmaceutically acceptable carrier.

12. A nucleic acid molecule encoding the conjugate of claim 7.

13. A vector or a set of vectors comprising the nucleic acid molecule of claim 12.

14. A host cell comprising the vector of claim 13.

15. A method of increasing the catalytic activity ($k_{cat}$) of a blood coagulation factor, comprising contacting the blood coagulation factor with the compound of claim 1.

16. A method for treating bleeding diathesis in a mammalian subject, the method comprising administering to the subject a therapeutically effective amount of the compound of claim 1.

17. A method of treating a mammalian subject having a deficiency in at least one blood coagulation factor selected from FV, FVII, FVIIa, FVIII, FIX, FX, FXI, and vWF, the method comprising administering to the subject a therapeutically effective amount of the compound of claim 1.

18. A method for making the compound of claim 1, the method comprising forming a peptide having the amino acid sequence, or the retro-, inverso- or retro-inverso peptide thereof using solid-phase peptide synthesis.

19. A method for treating or ameliorating a bleeding disease or disorder in a subject in need thereof, comprising administering to the subject an effective amount of the conjugate of claim 7.

20. A method of treating or ameliorating a coagulation factor deficiency in a mammalian subject comprising administering to the subject an effective amount of the conjugate of claim 7, wherein the coagulation factor is selected from FVII, FVIIa, FVIII, FIX, and FXI.

21. A method for producing a conjugate comprising culturing the host cell of claim 14 in culture medium and recovering the conjugate from the culture medium.

* * * * *